US011486002B2

(12) United States Patent
Barany et al.

(10) Patent No.: US 11,486,002 B2
(45) Date of Patent: *Nov. 1, 2022

(54) METHOD FOR IDENTIFICATION AND ENUMERATION OF NUCLEIC ACID SEQUENCE, EXPRESSION, COPY, OR DNA METHYLATION CHANGES, USING COMBINED NUCLEASE, LIGASE, POLYMERASE, AND SEQUENCING REACTIONS

(71) Applicant: Cornell University, Ithaca, NY (US)

(72) Inventors: Francis Barany, New York, NY (US); John William Efcavitch, San Carlos, CA (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/524,527

(22) Filed: Jul. 29, 2019

(65) Prior Publication Data

US 2019/0345552 A1 Nov. 14, 2019

Related U.S. Application Data

(62) Division of application No. 15/316,778, filed as application No. PCT/US2015/034724 on Jun. 8, 2015, now Pat. No. 10,407,722.

(60) Provisional application No. 62/009,047, filed on Jun. 6, 2014, provisional application No. 62/136,093, filed on Mar. 20, 2015.

(51) Int. Cl.
| C12Q 1/6874 | (2018.01) |
| C12Q 1/6806 | (2018.01) |
| C12Q 1/6809 | (2018.01) |
| C12Q 1/6816 | (2018.01) |
| C12Q 1/6844 | (2018.01) |
| C12Q 1/6848 | (2018.01) |
| C12Q 1/6855 | (2018.01) |
| C12Q 1/6869 | (2018.01) |
| C12N 15/10 | (2006.01) |

(52) U.S. Cl.
CPC ....... *C12Q 1/6874* (2013.01); *C12N 15/1068* (2013.01); *C12Q 1/6806* (2013.01); *C12Q 1/6809* (2013.01); *C12Q 1/6816* (2013.01); *C12Q 1/6844* (2013.01); *C12Q 1/6848* (2013.01); *C12Q 1/6855* (2013.01); *C12Q 1/6869* (2013.01)

(58) Field of Classification Search
CPC .. C12Q 1/6874; C12Q 1/6806; C12Q 1/6809; C12Q 1/6816; C12Q 1/6844; C12Q 1/6848; C12Q 1/6855; C12Q 1/6869; C12Q 2525/307; C12Q 2531/125; C12N 15/1068
See application file for complete search history.

(56) References Cited

U.S. PATENT DOCUMENTS

| 5,736,373 A | 4/1998 | Hamilton |
| 8,093,030 B2 | 1/2012 | Schoenfeld et al. |
| 8,497,069 B2 | 7/2013 | Hutchison, III |
| 10,202,629 B2 * | 2/2019 | Arnold ................. C12Q 1/6844 |
| 10,407,722 B2 * | 9/2019 | Barany ................. C12Q 1/6809 |
| 2008/0311626 A1 | 12/2008 | Hjorleifsdottir et al. |
| 2009/0099041 A1 | 4/2009 | Church et al. |
| 2012/0003657 A1 | 1/2012 | Myllykangas et al. |
| 2012/0083018 A1 | 4/2012 | Schoenfeld et al. |

(Continued)

FOREIGN PATENT DOCUMENTS

| CN | 101213311 A | 7/2008 |
| CN | 103582887 A | 2/2014 |

(Continued)

OTHER PUBLICATIONS

Nallur et al. Signal amplification by rolling circle amplification on DNA microarrays. Nucleic Acids Research (2001) vol. 29, No. 23, e118, pp. 1-9.*

(Continued)

*Primary Examiner* — David C Thomas

(74) *Attorney, Agent, or Firm* — Troutman Pepper Hamilton Sanders LLP (Rochester)

(57) ABSTRACT

The present invention relates to a method for the highly specific, targeted capture of regions of human genomes and transcriptomes from the blood, i.e. from cell free circulating DNA, exosomes, microRNA, circulating tumor cells, or total blood cells, to allow for the highly sensitive detection of mutation, expression, copy number, translocation, alternative splicing, and methylation changes using combined nuclease, ligation, polymerase, and massively parallel sequencing reactions. The method generates a collection of different circular chimeric single-stranded nucleic acid constructs, suitable for sequencing on multiple platforms. In some embodiments, each construct of the collection comprised a first single stranded segment of original genomic DNA from a host organism and a second single stranded synthetic nucleic acid segment that is linked to the first single stranded segment and comprises a nucleotide sequence that is exogenous to the host organism. These chimeric constructs are suitable for identifying and enumerating mutations, copy changes, translocations, and methylation changes. In other embodiments, input mRNA, lncRNA, or miRNA is used to generate circular DNA products that reflect the presence and copy number of specific mRNA's, lncRNA's splice-site variants, translocations, and miRNA.

19 Claims, 129 Drawing Sheets
Specification includes a Sequence Listing.

(56) References Cited

U.S. PATENT DOCUMENTS

| | | |
|---|---|---|
| 2012/0115145 A1 | 5/2012 | Fu |
| 2012/0270272 A1 | 10/2012 | Barany et al. |
| 2013/0157870 A1 | 6/2013 | Pushkarev |
| 2013/0315944 A1 | 11/2013 | Meng et al. |

FOREIGN PATENT DOCUMENTS

| | | |
|---|---|---|
| JP | 2006-507014 | 3/2006 |
| JP | 2007-300921 | 11/2007 |
| JP | 2008-054589 | 3/2008 |
| JP | 2008-527979 | 7/2008 |
| JP | 2014-506788 | 3/2014 |
| WO | 2006/030455 A1 | 3/2006 |
| WO | 2007/076461 A1 | 7/2007 |
| WO | 2007092538 A2 | 8/2007 |
| WO | 2010120803 A2 | 10/2010 |
| WO | 2010126614 A2 | 11/2010 |
| WO | 2011054936 A1 | 5/2011 |
| WO | 2012/003374 A2 | 1/2012 |
| WO | 2013/036929 A1 | 3/2013 |
| WO | 2013036929 A1 | 3/2013 |
| WO | 2013/188840 A1 | 12/2013 |
| WO | 2013188840 A1 | 12/2013 |
| WO | 2014/047561 A1 | 3/2014 |
| WO | 2014047561 A1 | 3/2014 |
| WO | 2014137328 A1 | 9/2014 |
| WO | 2014/161712 A1 | 10/2014 |
| WO | 2015/089333 A1 | 6/2015 |

OTHER PUBLICATIONS

Examination Report for Australian Application No. 2015269103 (dated Dec. 21, 2020).
Hamzeh-Mivehroud et al., "Phage Display as a Technology Delivering on the Promise of Peptide Drug Discovery," Drug Discovery Today 18(23/24):1 144-1157 (2013).
Myllykangas et al., "Targeted Sequencing Library Preparation by Genomic DNA Circularization," BMC Biotechnology 11:122(2011).
Supplementary Partial European Search Report and Partial Opinion Accompanying the Partial Search Report for corresponding European Patent Application No. EP 15802743.3 (Jan. 8, 2018).
Extended European Search Report and opinion for European Application No. 15802743.3 dated Apr. 9, 2018.
Translation and Office Action for Israel Application No. 219126, dated Aug. 28, 2019.
PCT International Search Report and Written Opinion corresponding to PCT/US2015/034724, filed Jun. 8, 2015 (dated Mar. 31, 2016).
Lin et al., "A Molecular Inversion Probe Assay for Detecting Alternative Splicing," BMC Genomics 11:712 (2010).
Akhras et al., "Connector Inversion Probe Technology: A Powerful One-primer Multiplex DNA Amplification System for Numerous Scientific Applications," PLoS One 2(9):e915 (2007).
Lou et al., "High-throughput DNA Sequencing Errors are Reduced by Orders of Magnitude Using Circle Sequencing," Proc Natl Acad Sci USA 110(49):19872-7 (2013).
Ignatov et al., "A Strong Strand Displacement Activity of Thermostable DNA Polymerase Markedly Improves the Results of DNA Amplification," Bio Techniques 57:81-87 (2014).
Schmitt et al., "Detection of Ultra-rare Mutations by Next-generation Sequencing," Proc Natl Acad Sci USA 109 (36):14508-13 (2012).
Forshew et al., "Noninvasive Identification and Monitoring of Cancer Mutations by Targeted Deep Sequencing of Plasma DNA," Sci Transl Med 4(136):136ra68 (2012).
Frampton et al., "Development and Validation of a Clinical Cancer Genomic Profiling Test Based on Massively Parallel DNA Sequencing," Nat Biotechnol 31(11):1023-31 (2013).
Flusberg et al., "Direct Detection of DNA Methylation During Single-molecule, Real-time Sequencing," Nat Methods 7(6):461-5 (2010).
Li et al., "Sensitive Digital Quantification of DNA Methylation in Clinical Samples," Nat Biotechnol 27(9):858-63 (2009).
Kadam et al., "Quantitative Measurement of Cell-free Plasma DNA and Applications for Detecting Tumor Genetic Variation and Promoter Methylation in a Clinical Setting," J Mol Diagn 14(4):346-56 (2012).
Chimonidou et al., "SOX17 Promoter Methylation in Circulating Tumor Cells and Matched Cell-free DNA Isolated from Plasma of Patients with Breast Cancer," Clin Chem 59(1):270-9 (2013).
Bhattacharyya et al., "Genome-wide Hydroxymethylation Tested Using the HELP-GT Assay Shows Redistribution n Cancer," Nucleic Acids Res41(16):e157 (2013).
Rand et al., "Headloop Suppression PCR and its Application to Selective Amplification of Methylated DNA Sequences," Nucleic Acids Res 33(14):e127 (2005).
Fleischhacker et al., "Methods for Isolation of Cell-free Plasma DNA Strongly Affect DNA Yield," Clin Chim Acta 412(23-24):2085-8 (2011).
Li et al., "Genome-wide Methylated CpG Island Profiles of Melanoma Cells Reveal a Melanoma Coregulation Network," Sci Rep 3:2962 (2013).
Kinde et al., "Detection and Quantification of Rare Mutations with Massively Parallel Sequencing," Proc Natl Acad Sci USA 108(23):9530-5 (2011).
Hiatt et al., "Single Molecule Molecular Inversion Probes for Targeted, High-accuracy Detection of Low-frequency Variation," Genome Res 23(5):843-54 (2013).
Narayan et al., "Ultrasensitive Measurement of Hotspot Mutations in Tumor DNA in Blood Using Error-suppressed Multiplexed Deep Sequencing," Cancer Res 72(14):3492-8 (2012).
Peters et al., "Accurate Whole-genome Sequencing and Haplotyping from 10 to 20 Human Cells," Nature 487 (7406):190-5 (2012).
Na et al., "A Robust and Simple-to-design Multiplex DNA Methylation Assay Based on MS-MLPA-CE-SSCP," Analyst 138(22):6969-76 (2013).
Toth et al., "Novel Dedicator of Cytokinesis 8 Mutations Identified by Multiplex Ligation-dependent Probe Amplification," Eur J Haematol 91(4):369-75 (2013).
Selvaraj et al., "Whole-genome Haplotype Reconstruction Using Proximity-ligation and Shotgun Sequencing," Nat Biotechnol 31(12):1111-8 (2013).
Misale et al., "Blockade of EGFR and MEK Intercepts Heterogeneous Mechanisms of Acquired Resistance to Anti-EGFR Therapies in Colorectal Cancer," Sci Transl Med 6(224):224ra26 (2014).
Bettegowda et al., "Detection of Circulating Tumor DNA in Farly- and Late-stage Human Malignancies," Sci Transl Med 6(224):224ra24 (2014).
Bidard et al., "Going with the Flow: From Circulating Tumor Cells to DNA," Sci Transl Med 5(207):207ps14 (2013).
Diaz and Bardelli, "Liquid Biopsies: Genotyping Circulating Tumor Dna," J Clin Oncol 32(6):579-86 (2014).
Schiffman et al., "Molecular Inversion Probes Reveal Patterns of 9p21 Deletion and Copy number Aberrations in Childhood Leukemia," Cancer Genet Cytogenet 193(1):9-18 (2009).
Dobosy et al., "RNase H-dependent PCR (rhPCR): Improved Specificity and Single Nucleotide Polymorphism Detection Using Blocked Cleavable Primers," BMC Biotechnol 11:80 (2011).
White et al., "Evaluation of a Novel Assay for Detection of the Fetal Marker RASSF1A: Facilitating Improved Diagnostic Reliability of Noninvasive Prenatal Diagnosis," PLoS One 7(9):e45073 (2012).
Gao et al., "Hypermethylation of IGSF4 Gene for Noninvasive Prenatal Diagnosis of Thalassemia," Med Sci Monit 18 (1):BR33-40 (2012).
Lim et al., "Non-invasive Epigenetic Detection of Fetal Trisomy 21 in First Trimester Maternal Plasma," PLoS One 6 (11):e27709 (2011).
Papageorgiou and Patsalis, "Non-invasive Prenatal Diagnosis of Aneuploidies: New Technologies and Clinical Applications," Genome Med 4(5):46 (2012).
Patsalis et al., "A New Non-invasive Prenatal Diagnosis of Down Syndrome Through Epigenetic Markers and Realtime qPCR," Expert Opin Biol Ther 12(Suppl 1):S155-61 (2012).

(56) References Cited

OTHER PUBLICATIONS

Sparks et al., "Selective Analysis of Cell-free DNA in Maternal Blood for Evaluation of Fetal Trisomy," Prenat Diagn 32(1):3-9 (2012).
Kawase et al., "Studies on Nucleic Acid Interactions. I. Stabilities of Mini-duplexes (dG2A4XA4G2-dC2T4YT4C2) and Self-complementary d(GGGAAXYTTCCC) Containing Deoxyinosine and Other Mismatched Bases," Nucleic Acids Res 14(19):7727-36 (1986).
Koos et al., "Analysis of Protein Interactions In Situ by Proximity Ligation Assays," Curr Top Microbiol Immunol 377:111-26(2014).
Ke et al., "Improving Precision of Proximity Ligation Assay by Amplified Single Molecule Detection," PLoS One 8(7): e69813(2013).
Flanigon et al., "Multiplex Protein Detection with DNA Readout Via Mass Spectrometry," N Biotechnol 30(2):153-8 (2013).
Nong et al., "Solid-phase Proximity Ligation Assays for Individual or Parallel Protein Analyses with Readout Via Real-time PCR or Sequencing," Nat Protoc 8(6):1234-48 (2013).
Larsson et al., "In Situ Genotyping Individual DNA Molecules by Target-primed Rolling-circle Amplification of Padlock Probes," Nat Methods 1(3):227-32 (2004).
Lizardi et al., "Mutation Detection and Single-molecule Counting Using Isothermal Rolling-circle Amplification," Nat Genet 19(3):225-32 (1998).
Baner et al., "Signal Amplification of Padlock Probes by Rolling Circle Replication," Nucleic Acids Res 26(22):5073-8 (1998).
Liu et al., "High Specific and Ultrasensitive Isothermal Detection of MicroRNA by Padlock Probe-based Exponential Rolling Circle Amplification," Anal Chem 85(16):7941-7 (2013).
"TaqMan Small RNA Assays,"Applied Biosystems by Life Technologies, Publication Parts No. 4364031 Rev. E (2011).
"Design Pipiline for TaqMan Small RNA Assays," TechNotes Newsletter 16(3).
"Protocol for Creating Custom RT and Preamplification Pools Using TaqMan MicroRNA Assays," Applied Biosystems by Life Technologies, User Bulletin, Publication Part No. 4465407 Rev. C (2013).
Zhang et al., "Highly Sensitive and Specific Multiplexed MicroRNA Quantification Using Size-coded Ligation Chain Reaction," Anal Chem 86(2):1076-82 (2014).
Drmanac et al., "Human Genome Sequencing Using Unchained Base Reads on Self-assembling DNA Nanoarrays," Science 327(5961):78-81 (2010).
International Preliminary Report on Patentability for Corresponding International Application No. PCT/US2015/034724 (Dec. 15, 2016).
English Translation and First Office Action for China Application No. 201580042765.4 (dated Dec. 23, 2019).
Extended European Search Report European Application No. 19178828.0 dated Oct. 10, 2019.
Extended European Search Report European Patent Application No. 21157460.3 (dated Jul. 28, 2021).
Notice for Reasons for Rejection for Japanese Patent Application No. 2016-571229 (dated May 20, 2019) with English Translation.
Office Action for Canadian Application No. 2950295 (dated May 10, 2021).
Notice for Reasons for Rejection for Japanese Patent Application No. 2016-571229 (dated May 28, 2020) with English Translation.
Decision of Rejection for Japanese Patent Application No. 2016-571229 (dated Apr. 28, 2021) with English Translation.
Notice Prior to Notice of Allowance for Israel Patent Application No. IL249126 with English Translation (dated Apr. 28, 2021).

* cited by examiner

A. Amplification of circular target with random hexamers. Using either primer or random hexamers, Phi29 DNA polymerase extends on circle template.

B. As polymerase continues to extend, it displaces original primer to form a single-stranded tail. Additional hexamers start extending on the tail.

C. Rolling circle amplification with random priming generates long single strands which allow for additional priming, and eventually resolve as double stranded fragments of varying length.

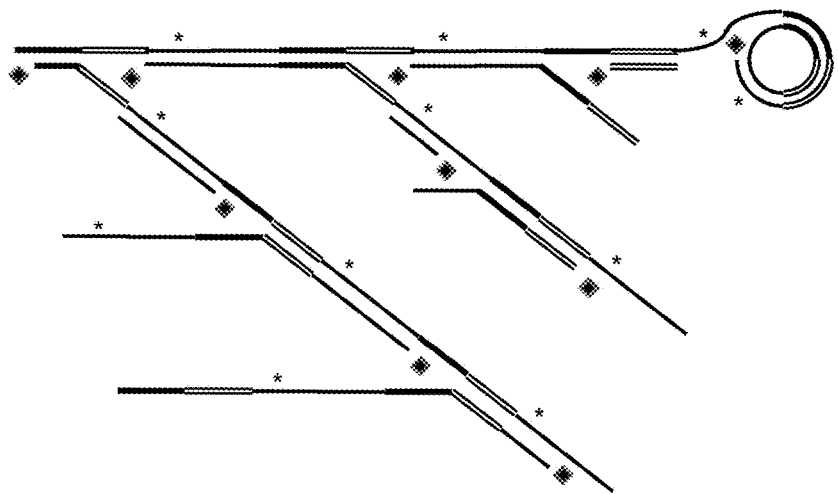

D. For next generation sequencing protocols, the double-stranded DNA is fragmented such that tandem copies of the target DNA are within a single fragment. Linkers are appended to allow for standard cluster or bead amplification and paired end reads. True mutation (*) will be present 2 or 3 times, and thus distinguished from polymerase error.

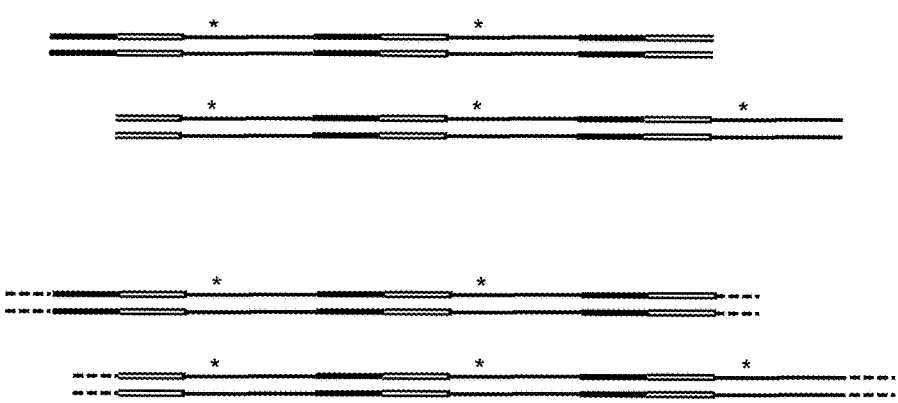

Figure 1

A. Amplification of single stranded circle containing mutated target with defined primer.

B. Phi29 or Bst DNA polymerase extends primer on circle template to generate single-stranded tail.

C. The extension product is denatured from the circle. A mix of unmethylated / methylated primer is hybridized to the long single strand, and polymerase lacking 5' nuclease, 3' nuclease, and strand-displacement activity, ligase, and a 2nd restriction enzyme are added to generate tandem copies of target DNA within a single fragment. For NGS sequencing, Linkers are appended to allow for standard cluster or bead amplification and paired end reads. True mutation (*) will be present 2 or more times, and thus distinguished from polymerase error.

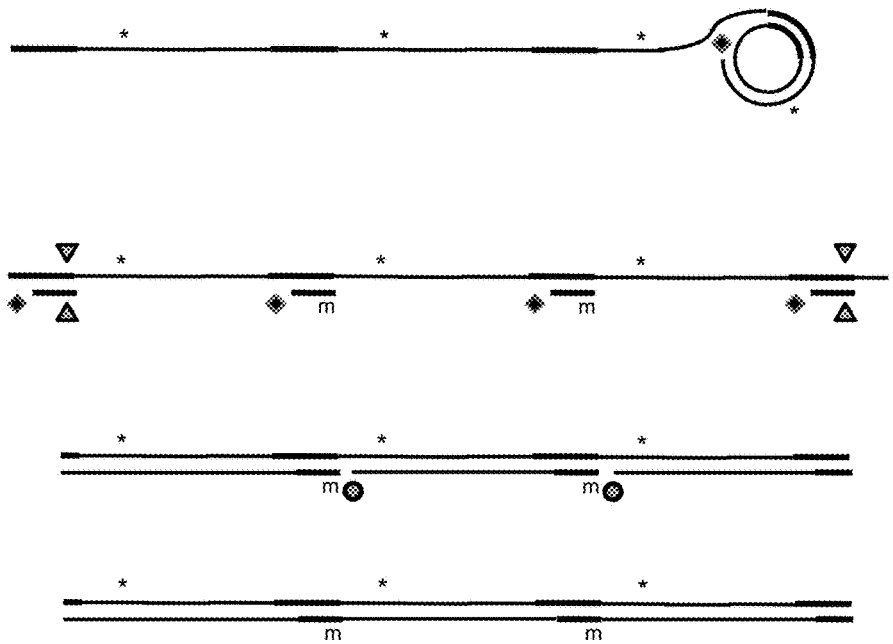

Figure 2

A. Amplification of single stranded circle containing methylated target with defined primer.

B. Bst DNA polymerase extends primer on circle template to generate single-stranded tail. BstU1 (CG^CG) will cleave dsDNA if unmethylated, but not hybrid methyl/unmethyl DNA, nor unmethylated ssDNA.

C. The extension product is denatured from the circle (and polymerase, BstUI heat inactivated). A mix of unmethylated / methylated primer is hybridized to the long single strand, and polymerase lacking 5' nuclease, 3' nuclease, and strand-displacement activity, ligase, and a 2nd restriction enzyme are added to generate tandem copies of target DNA within a single fragment. For NGS sequencing, Linkers are appended to allow for standard cluster or bead amplification and paired end reads.

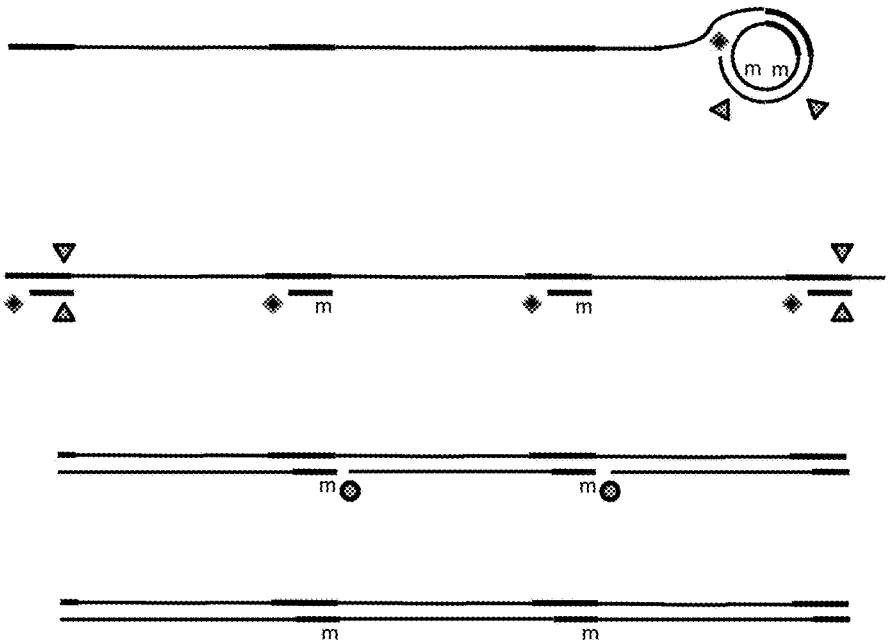

Figure 3

A. Amplification of circular target with defined primer. Initial template is either primer hybridized to single-stranded circle, similar, but with hybridized coupled oligonucleotide, or double-stranded circle, that is specifically nicked.

B. Phi29 DNA polymerase extends on circle template to generate single-stranded tail.

C. The extension product is hybridized to primers on a solid support. As rolling circle amplification generates long single stranded tail, it gets captured locally by hybridizing to adjacent primers on the surface, creating a carpet-like structure.

D. Alternatively, an additional sequence, suitable for capture on the solid support is already appended on the coupled oligonucleotide hybridized to the circular target. Under such conditions, the composite target / oligo may be first hybridized to the solid support, and then extended using Phi29 DNA polymerase.

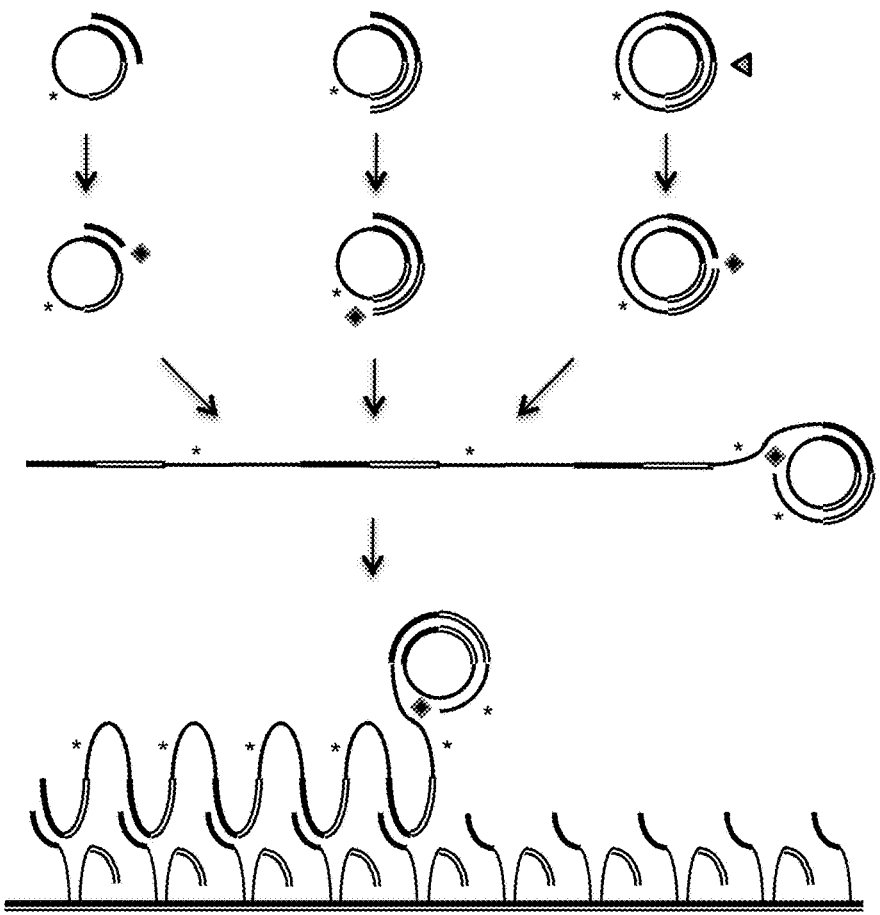

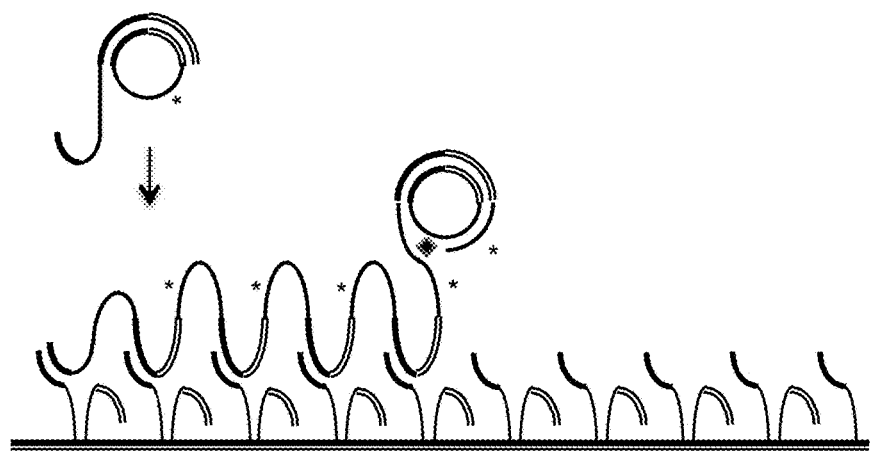

Figure 4

A. Amplification of circular target with primer to form condensed structures. Phi29-DNA polymerase extends around circular target.

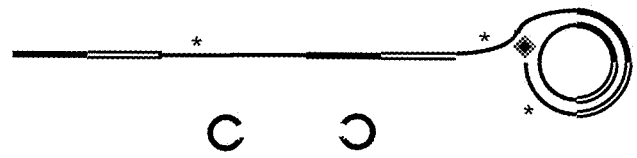

B. As polymerase continues to extend, oligonucleotides containing tandem repeats of complementary sequences condense the single-stranded tail into condensed structures.

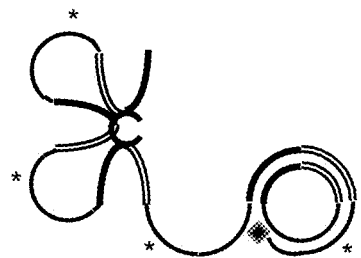

C. Rolling circle amplification can thus generate hundreds to thousands of tandem copies of target DNA in a condensed structure.

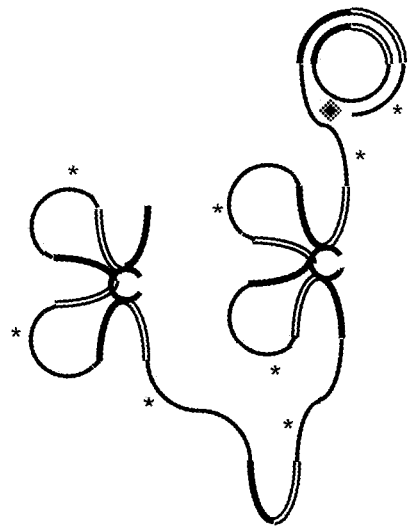

D. By varying the number of oligonucleotides with different complementary sequences, and the number of tandem repeats within a given oligonucleotide, the number of loops or "crosslinking nodes" can be varied, providing the opportunity to control the "compactness" of the structure.

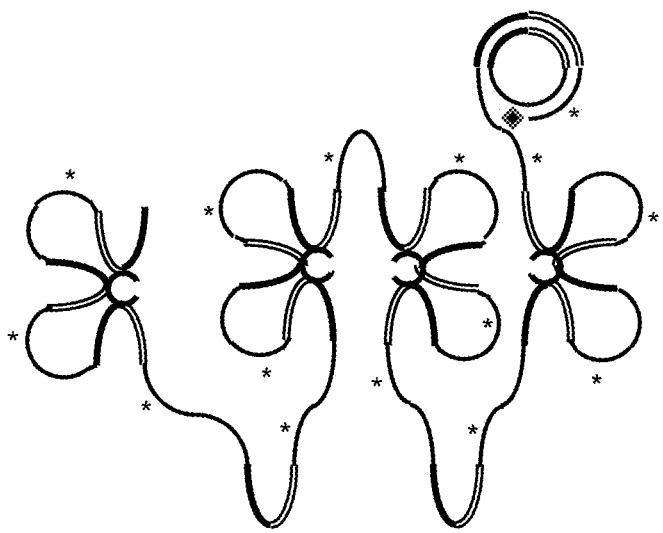

Figure 5

E. Capture of condensed rolling circle structures on a solid support. The structures hybridize to complementary primers at a few positions. The tandem repeat complementary oligonucleotides contain cleavable linkages, that are then cleaved.

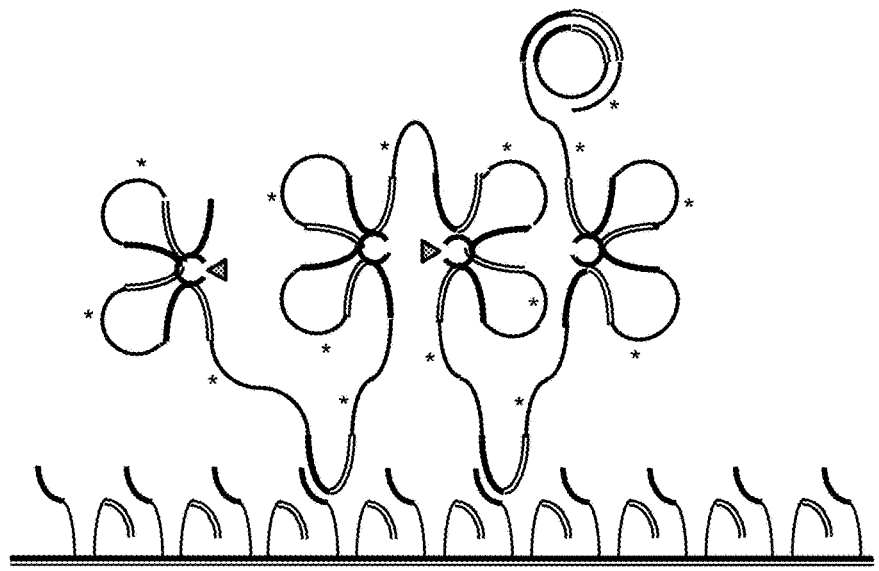

F. As the condensed structure starts to come apart, individual loops are captured locally by hybridizing to adjacent primers on the surface, creating a carpet-like structure.

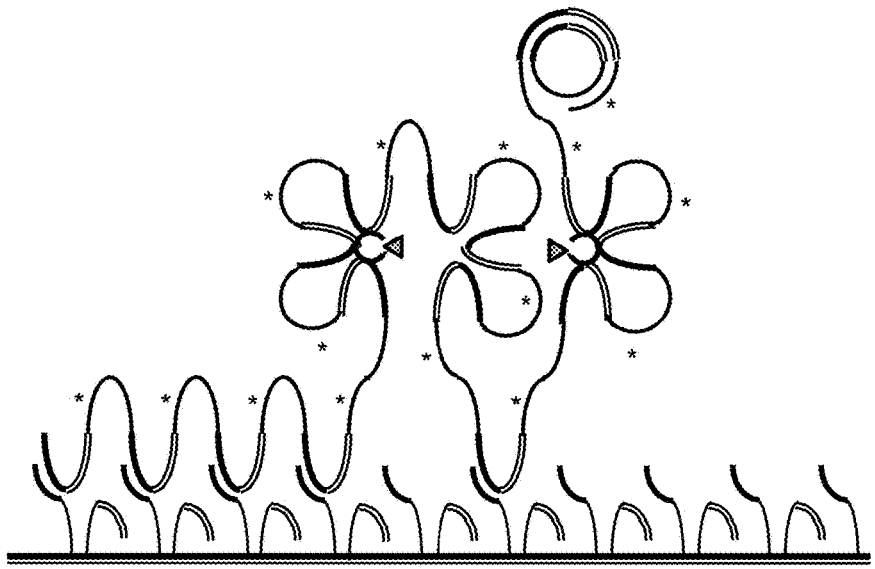

G. This approach assures that the hundreds to thousands of tandem copies of the target are captured next to each other, and suitable for subsequent sequencing.

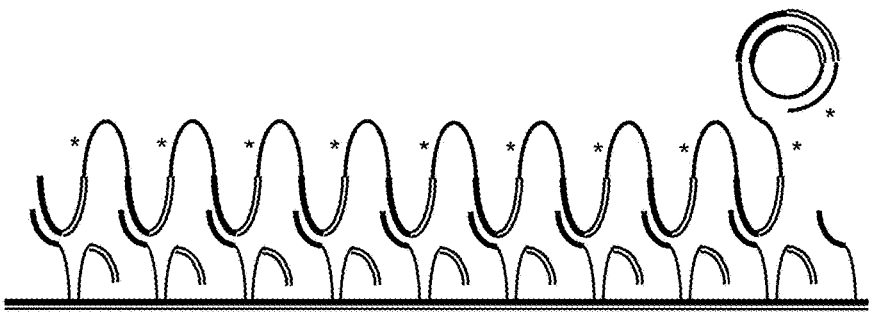

Figure 5 (continued)

A. Amplification of circular target for capture on a solid support with a single primer. Phi29 DNA polymerase extends on circle template to generate single-stranded primary extension product.

B. The extension product is hybridized to first primers on a solid support.

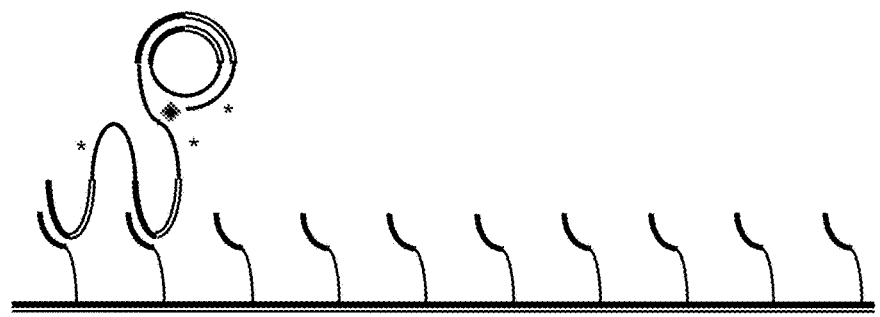

C. As rolling circle amplification generates a primary extension product, it is captured locally by hybridizing to adjacent first primers on the surface, creating a carpet-like structure.

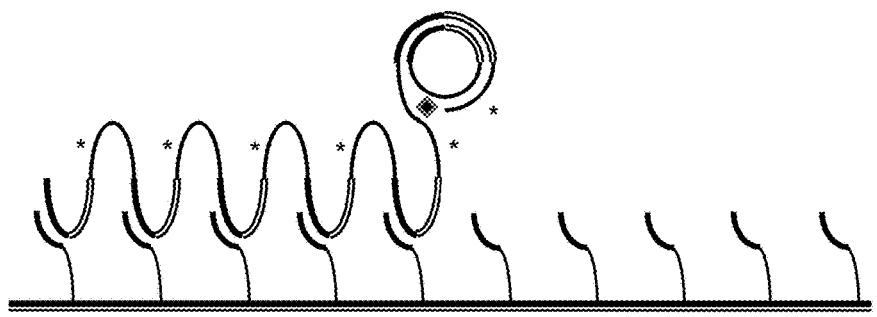

D. This approach assures that the hundreds to thousands of tandem complementary copies of the target are captured next to each other, and suitable for subsequent sequencing.

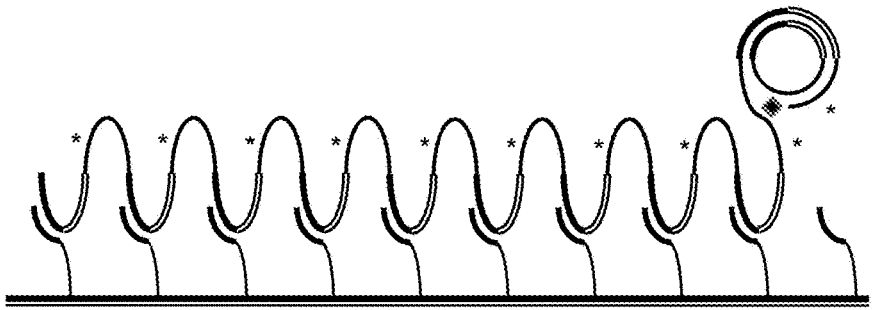

Figure 6

E. Hybridize sequencing primer adjacent to 3' end of first oligonucleotide primer on the support, and PNA or blocking oligonucleotide adjacent to 5' end.

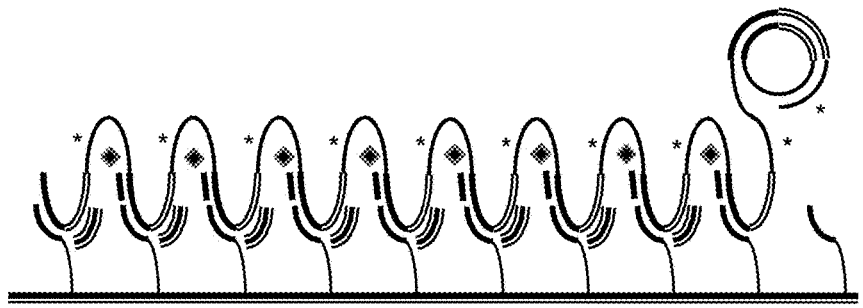

F. Sequence primary extension product (complement of genomic DNA sequence) using sequencing by synthesis.

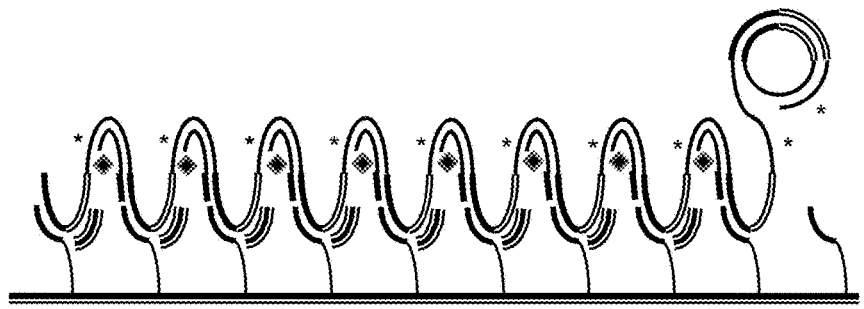

G. Sequencing continues until extension products are unable to extend due to PNA or blocking oligonucleotide.

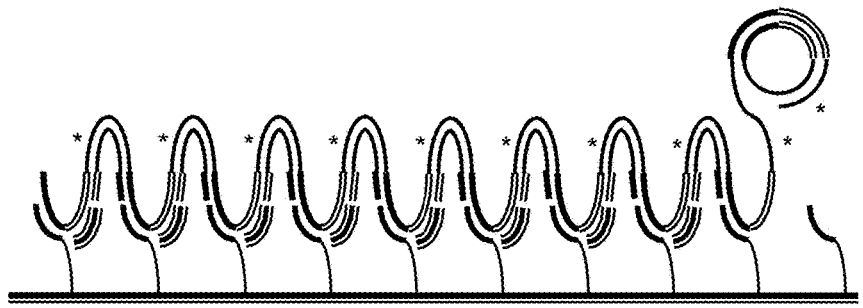

Figure 6 (continued)

H. Unblock primer on solid support. Using polymerase with 5'-3' nuclease activity, extend tethered primer on solid support, while digesting product from sequencing by synthesis.

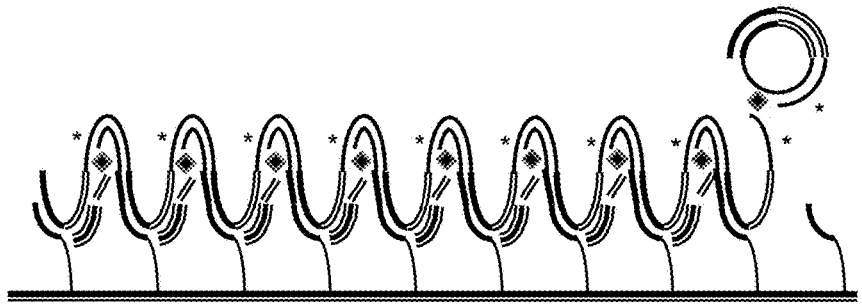

I. Polymerase extends strands to form secondary extension products. Extension continues until blocked by PNA or blocking oligonucleotide. This generates uni-length copies of the template.

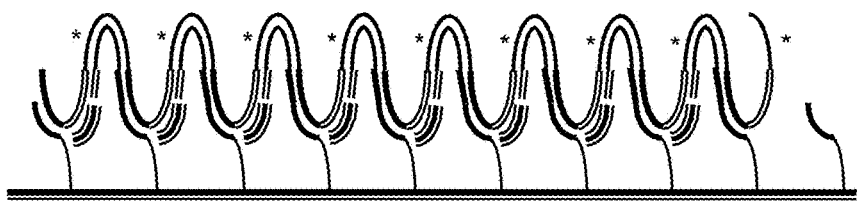

J. The primary extension product and circular template are denatured and washed away. The resultant copies of the template are suitable sequencing of the template strand.

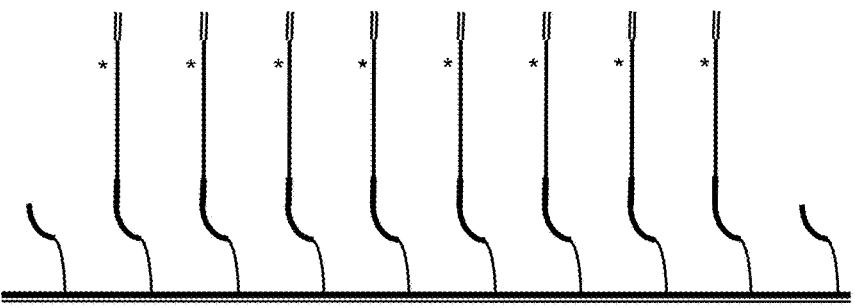

Figure 6 (continued)

K. Hybridize sequencing primer to uni-length template strands.
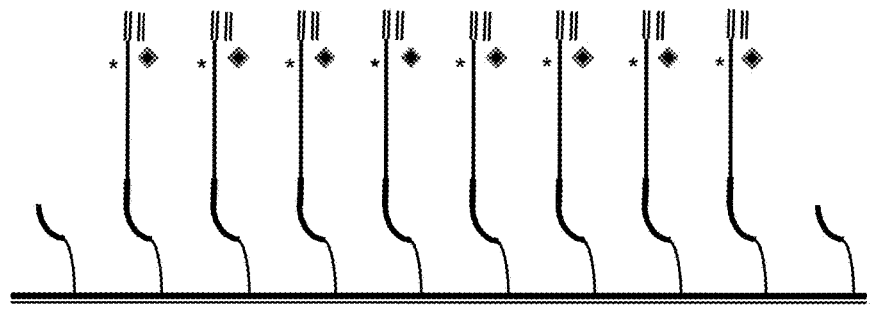
L. Sequence secondary extension product (i.e., genomic DNA strand) using sequencing by synthesis to identify mutation.
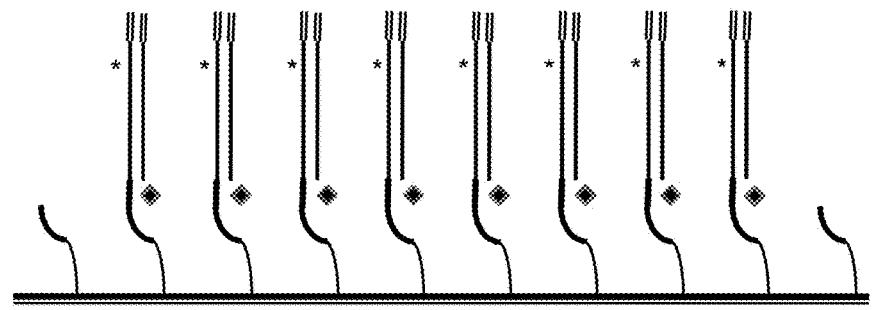
M. Sequencing continues until extension products reach end of tethered primers.
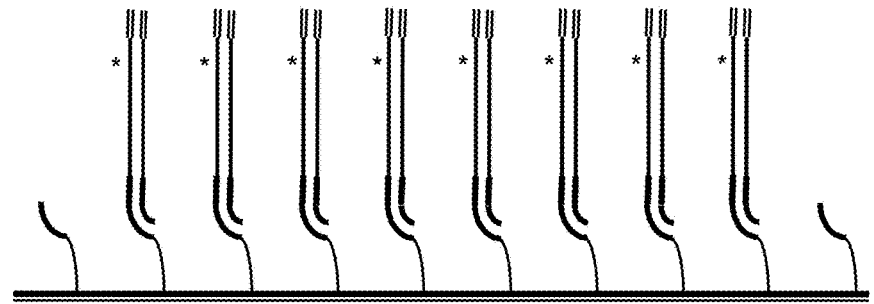
Figure 6 (continued)

A. Amplification of circular target for capture on a solid support with dual primers. Phi29 DNA polymerase extends on circle template to generate primary extension products.

B. The primary extension product is hybridized to 3' blocked first primers on a solid support.

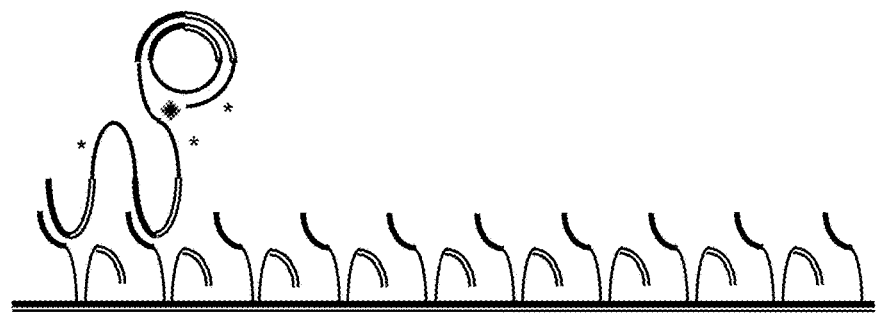

C. As rolling circle amplification generates a growing primary extension product, it gets captured locally by hybridizing to adjacent first primers on the surface, creating a carpet-like structure.

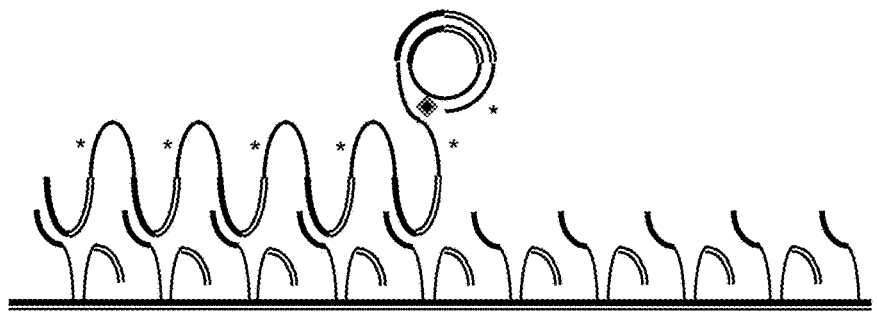

D. This approach assures that the hundreds to thousands of tandem complementary copies of the target are captured next to each other.

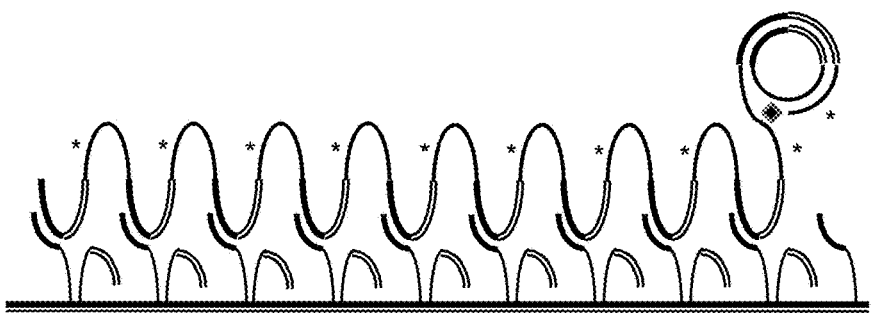

Figure 7

E. The blocking group is removed from the first primers hybridized to template.

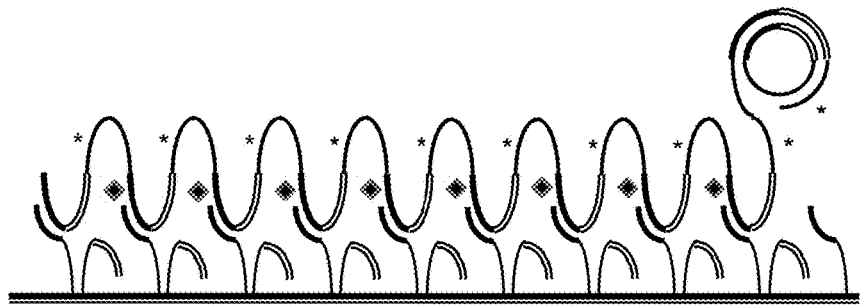

F. The extension product is copied at hundreds to thousands of positions using polymerase lacking 5' - 3' nuclease activity. This generates uni-length secondary extension products.

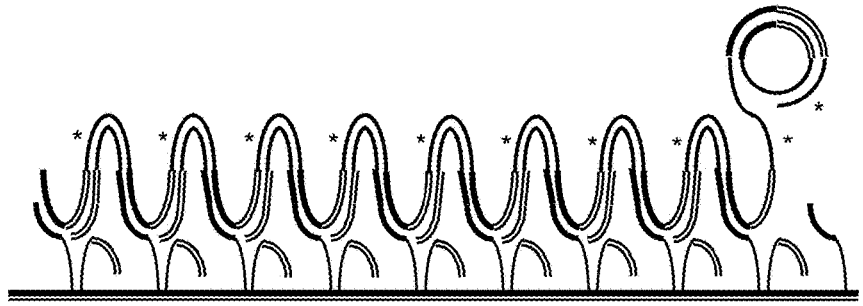

G. The primary extension product and circular template is denatured and washed away. The resultant secondary extension products are suitable for subsequent sequencing, as described in Figure 8.

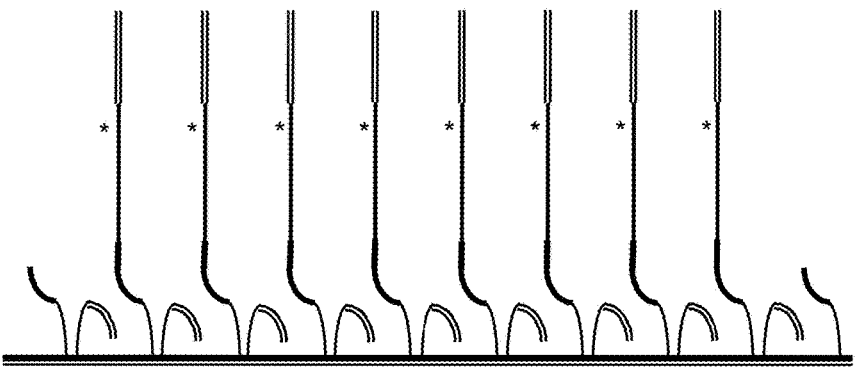

Figure 7 (continued)

A. Sequencing of rolling circle amplified target captured on a solid support with dual primers. Hybridize sequencing primer to uni-length template strands.
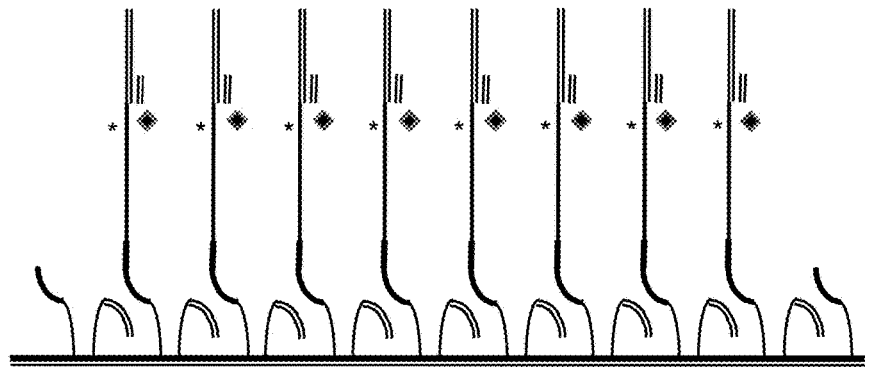
B. Sequence target DNA strand using sequencing by synthesis to identify mutation.
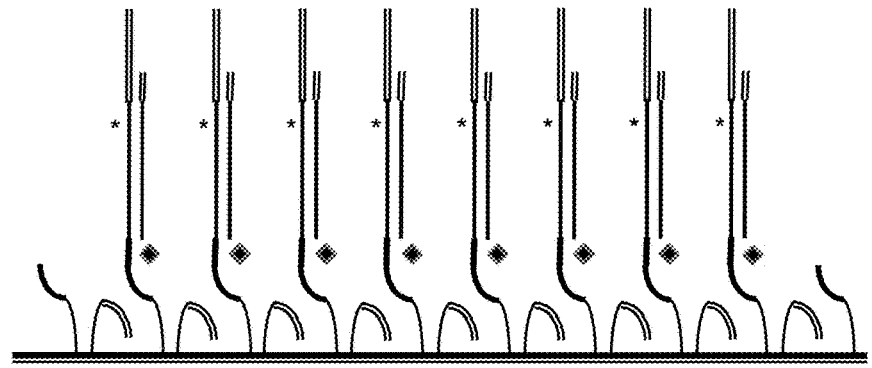
C. Sequencing continues until extension products reach end of tethered primers.
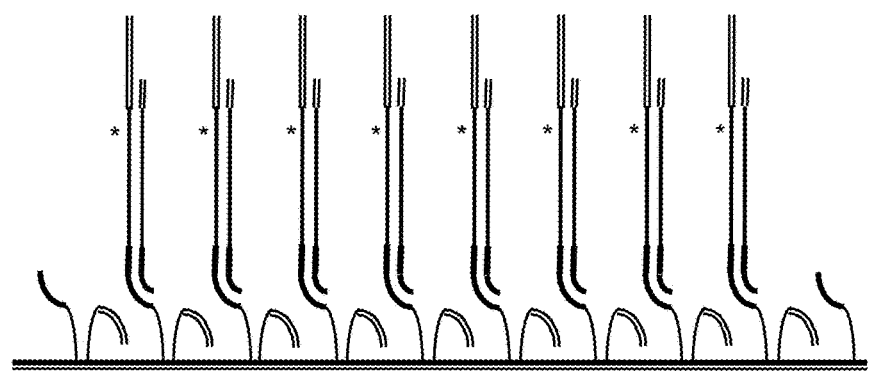
Figure 8

D. Sequence-by-synthesis products are denatured from the tethered extension products. Single-stranded secondary extension products hybridize to the second primers on the solid support.

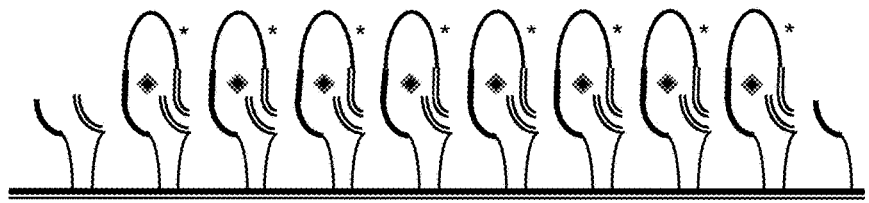

E. The secondary extension products are copied by extending the second primers to generate full-length copies of the secondary extension products. The secondary extension products are cleaved.

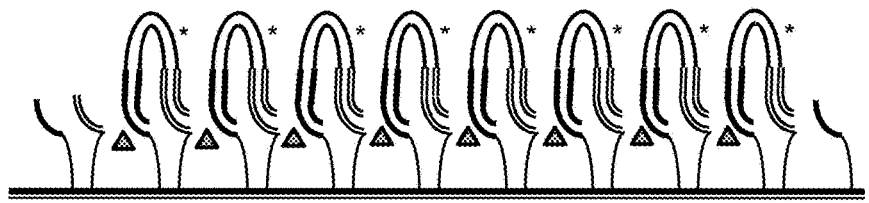

F. The cleaved secondary extension products are denatured and washed away. The resultant copies (tertiary extension products) are suitable for subsequent sequencing.

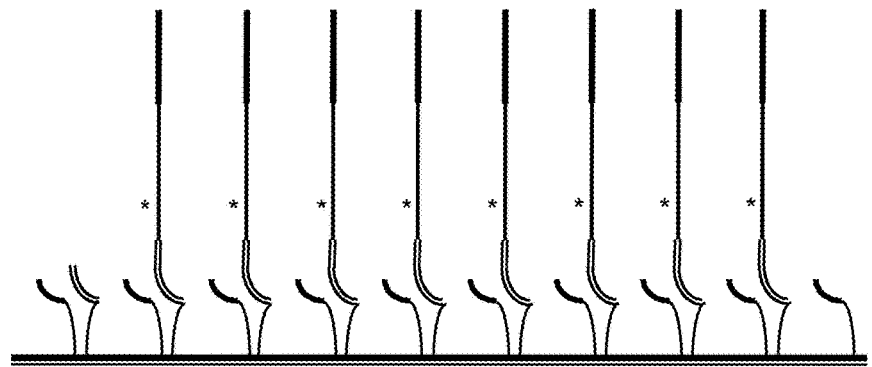

Figure 8 (continued)

G. Sequencing of rolling circle amplified target captured on a solid support with dual primers (continued). Hybridize sequencing primer to uni-length complementary template strands.

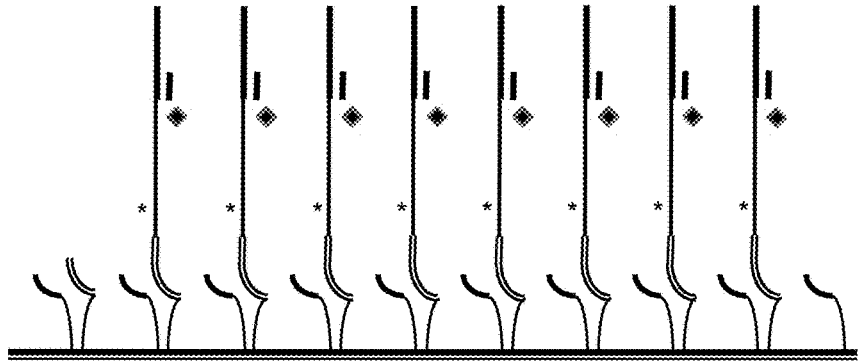

H. Sequence complementary target DNA strand using sequencing by synthesis to identify mutation.

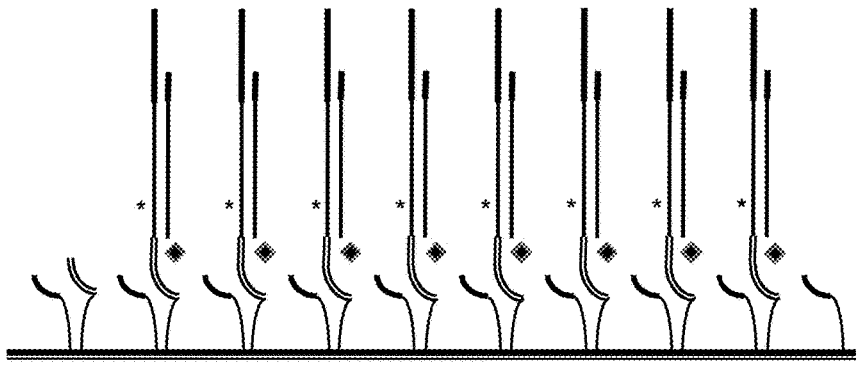

I. Sequencing continues until extension products reach end of tethered primers.

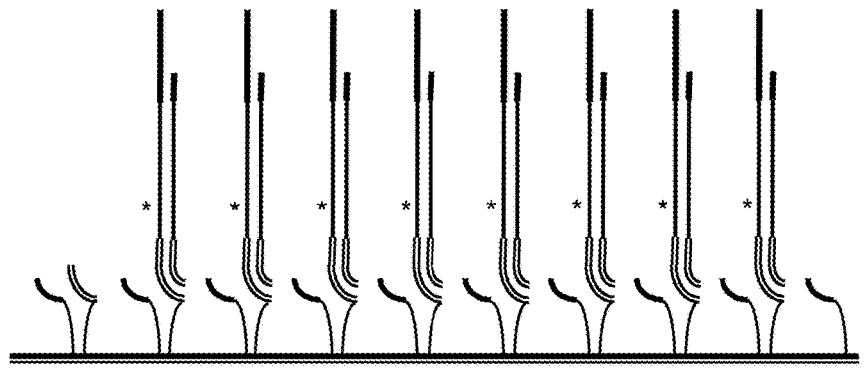

Figure 8 (continued)

A. The circular target is hybridized to an unblocked second oligonucleotide primer, which is extended by Phi29 DNA polymerase to generate a tethered primary extension product.

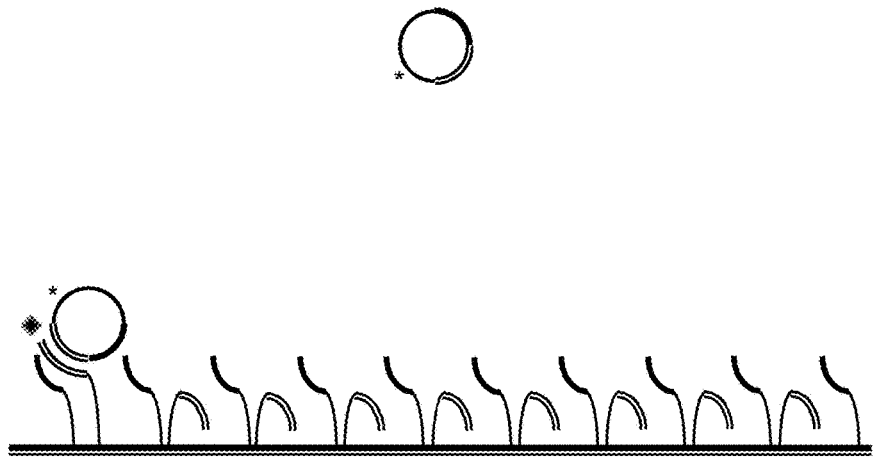

B. The single-stranded primary extension product generated by rolling circle amplification is captured locally by hybridization to adjacent first oligonucleotide primers on the surface, creating a carpet-like structure.

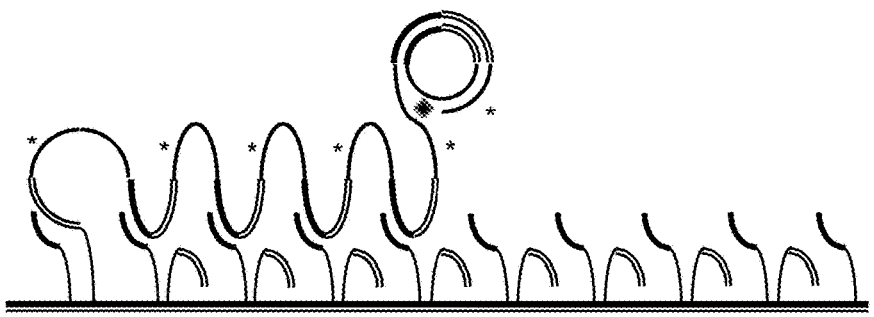

C. This approach assures that the hundreds to thousands of tandem complementary copies of the target genomic sequence are captured next to each other.

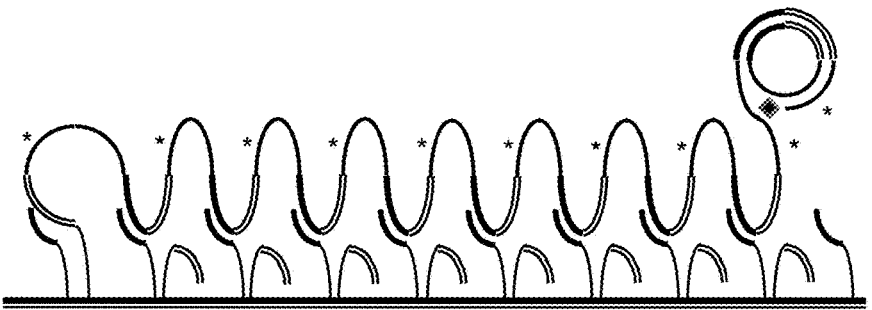

Figure 9

D. The 3' blocking group on the first oligonucleotide primer is removed.

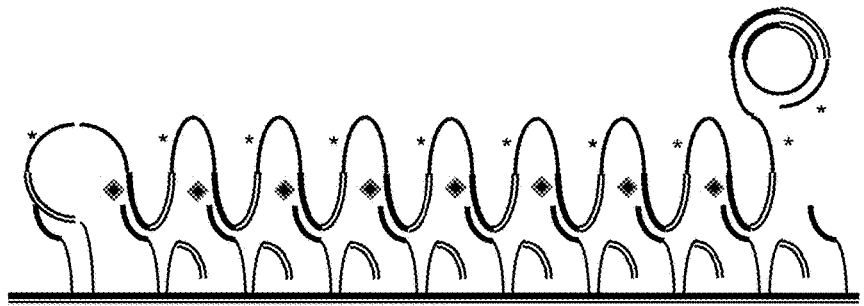

E. The primary extension product is copied at hundreds to thousands of positions using polymerase lacking 5' → 3' nuclease activity. This generates uni-length secondary extension products. The primary extension product is cleaved from the solid support.

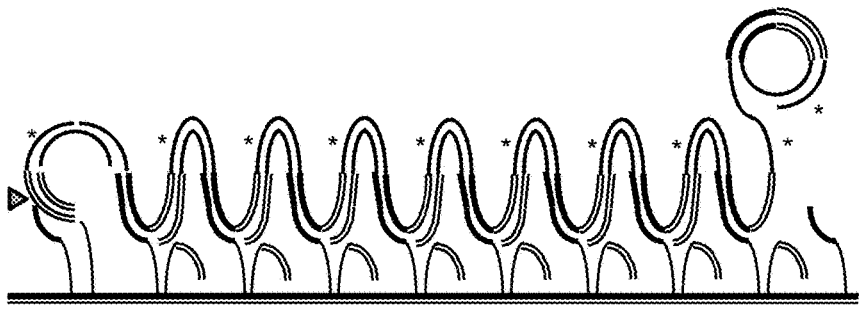

F. The primary extension product and circular template is denatured and washed away. The resultant copies of the template are suitable for subsequent sequencing, as described in Figure 8.

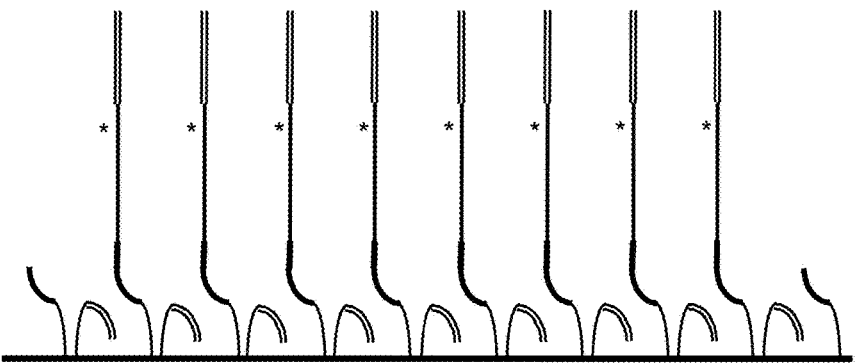

Figure 9 (continued)

A. Amplification of circular target for capture on a solid support with dual primers. The amplification primer hybridized to the circular construct contains a further portion, that in this case, is capable of hybridizing to a 3' blocked first primer on the solid support.

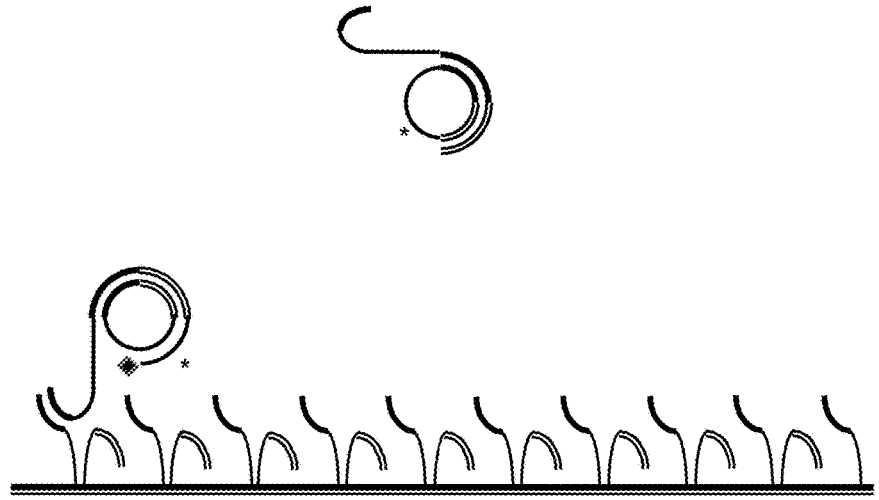

B. As rolling circle amplification of the tethered circular construct generates a single stranded primary extension product that is captured locally by hybridizing to adjacent first primers on the surface, creating a carpet-like structure.

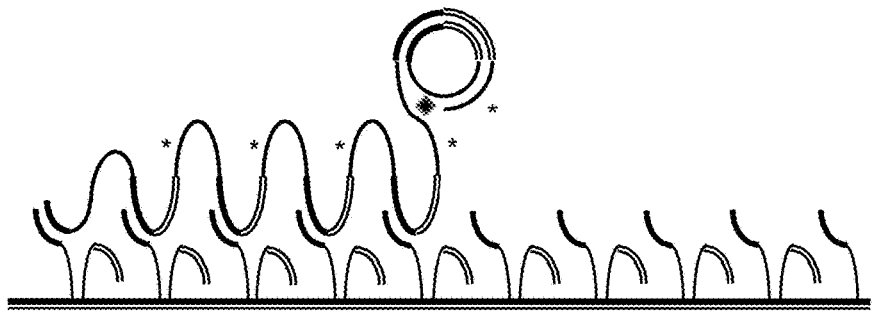

C. This approach assures that the hundreds to thousands of tandem copies of the target are captured next to each other.

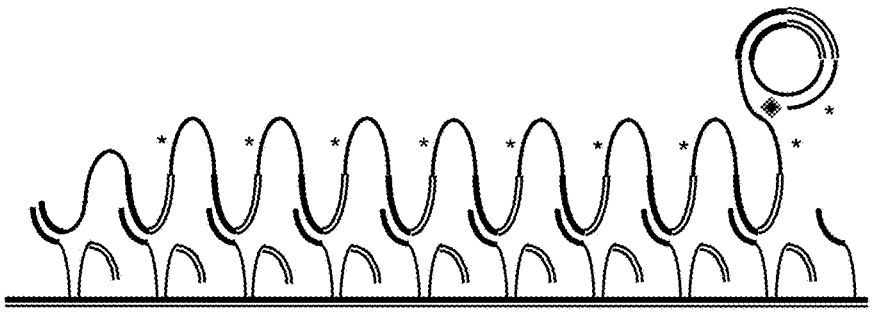

Figure 10

D. The blocking group is removed from primers hybridized to template.

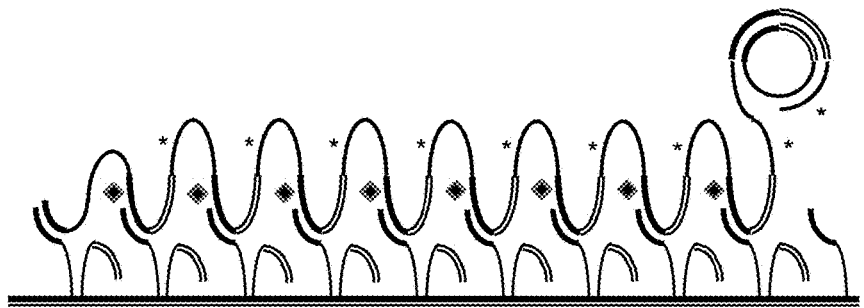

E. The extension product is copied at hundreds to thousands of positions using polymerase lacking 5' - 3' nuclease activity. This generates uni-length copies of the template.

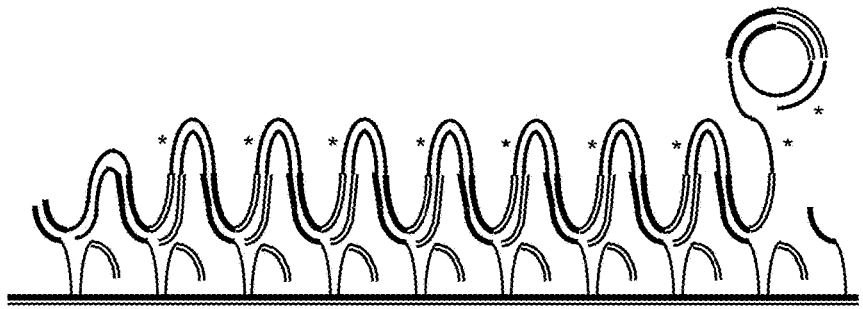

F. The original extension product and circular template is denatured and washed away. The resultant copies of the template are suitable for subsequent sequencing, as described in Figure 8.

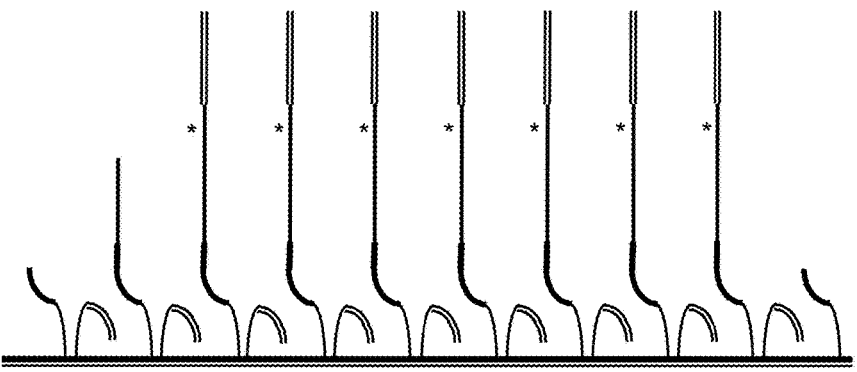

Figure 10 (continued)

A. Amplification of circular target for capture on a solid support with dual primers. DNA polymerase extends amplification primer on circle template to generate short primary extension product. Polymerase and extension product are denatured from circular template.

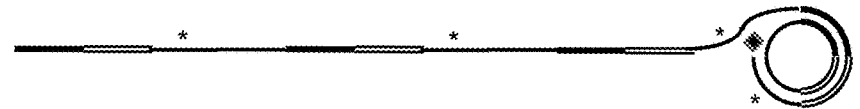

B. The extension product is hybridized to the first primers on a solid support.

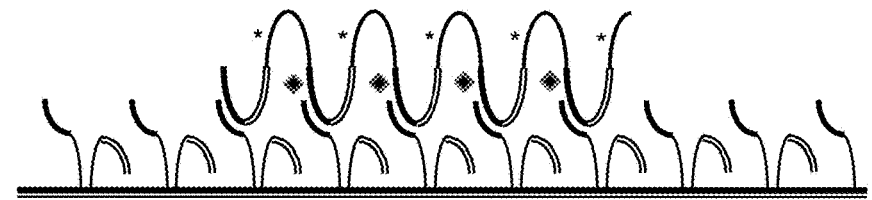

C. The extension product is copied multiple positions using polymerase lacking 5'-3' nuclease activity. This generates secondary extension products.

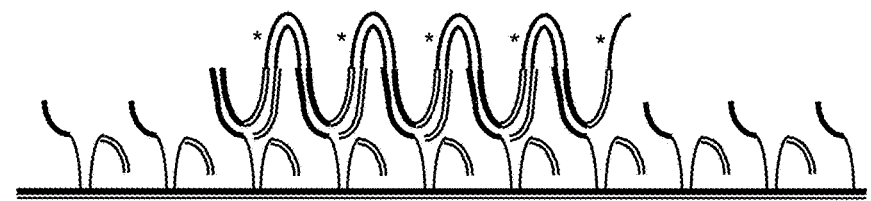

D. The primary extension product is denatured and washed away. The secondary extension products are templates suitable for subsequent amplification.

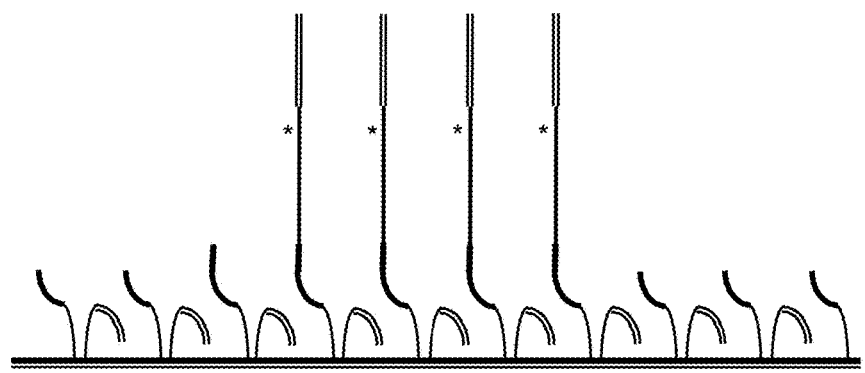

Figure 11

E. Single-stranded secondary extension products hybridize to the second primer on the solid support.
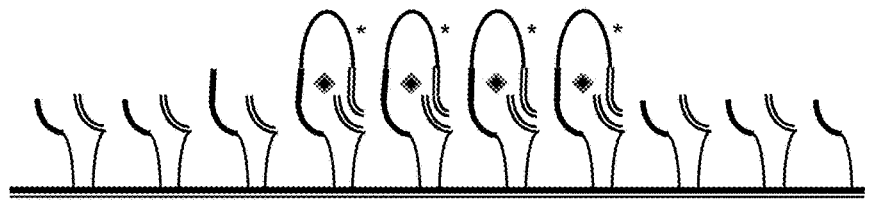
F. The second primers are polymerase extended to generates uni-length tertiary extension products.
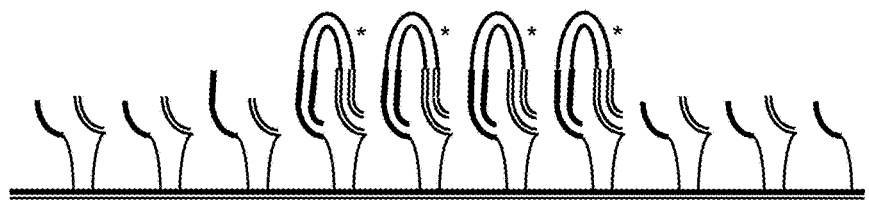
G. The extension products are denatured.
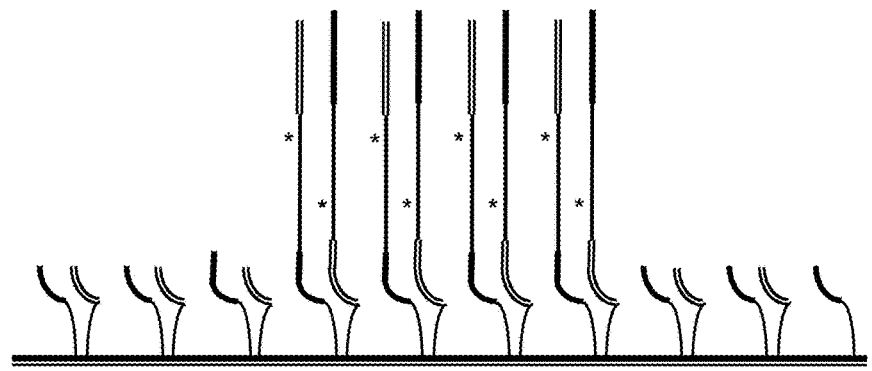
Figure 11 (continued)

H. Newly denatured single-stranded extension products hybridize to complementary primers on the solid support.

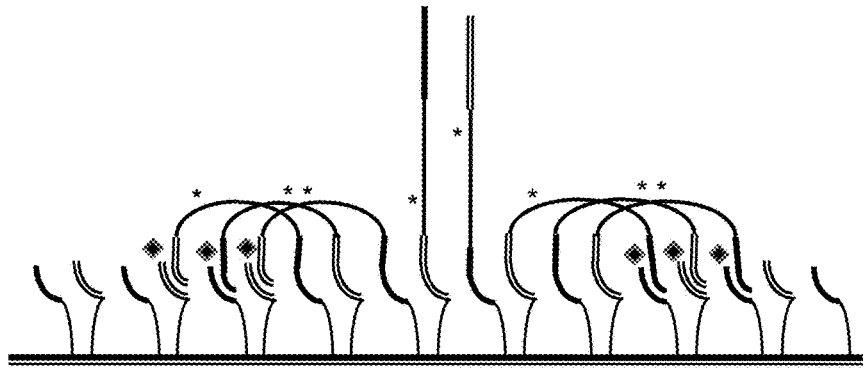

I. The first and second primers on the solid support are polymerase extended generating copies of the secondary and tertiary extension products.

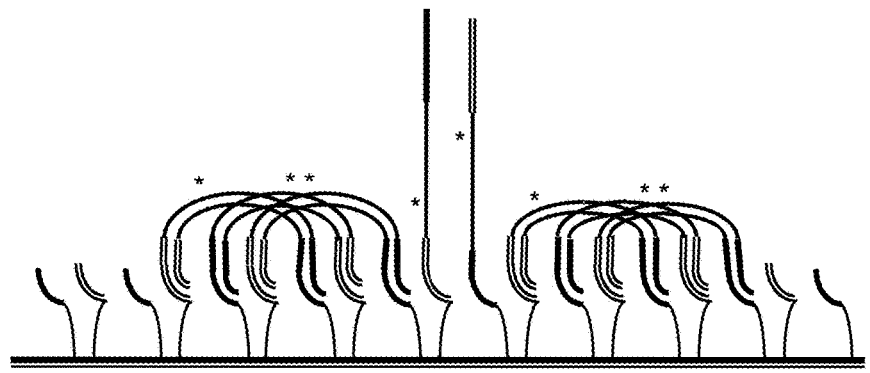

J. The extension products are denatured, and the process is repeated to generate enough template for sequencing by cleaving away template strands of one orientation, and proceeding as in Figure 8.

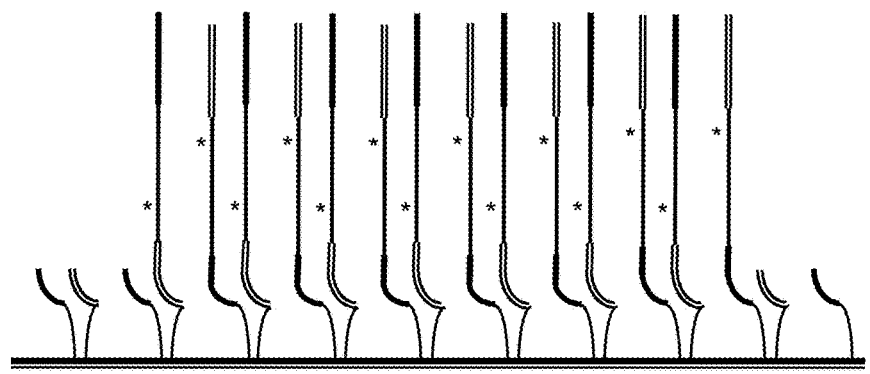

Figure 11 (continued)

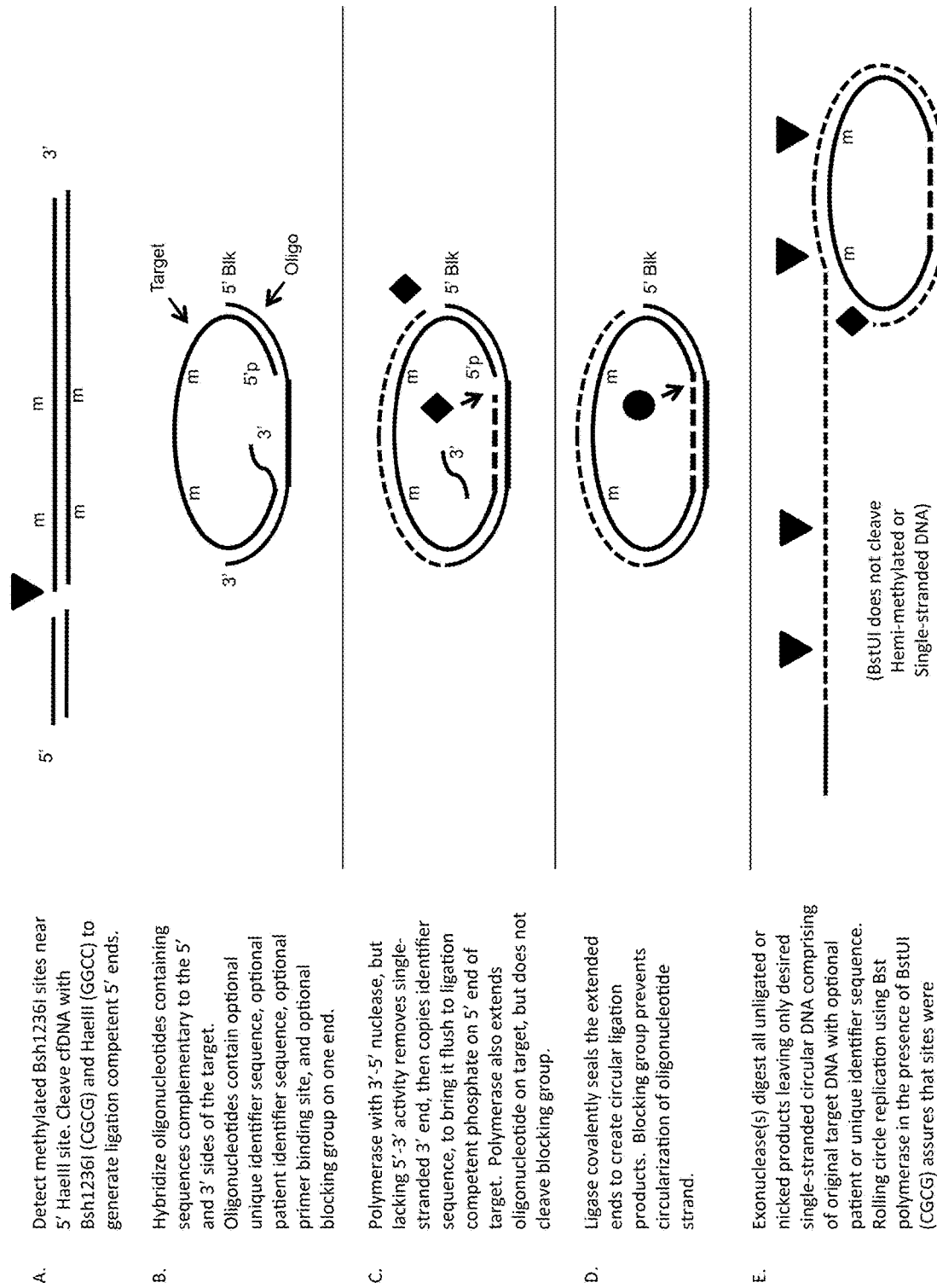

Figure 41

A. Detect methylated Bsh1236I sites near 5' HaeIII site. Cleave cfDNA with Bsh1236I (CGCG) and HaeIII (GGCC) to generate ligation competent 5' ends.

B. Hybridize oligonucleotides containing sequences complementary to the 5' and 3' sides of the target. Oligonucleotides contain optional unique identifier sequence, optional patient identifier sequence, optional primer binding site, and optional blocking group on one end.

C. Polymerase with 3'-5' nuclease, but lacking 5'-3' activity removes single-stranded 3' end, then copies identifier sequence, to bring it flush to ligation competent phosphate on 5' end of target. Polymerase also extends oligonucleotide on target, but does not cleave blocking group.

D. Ligase covalently seals the extended ends to create circular ligation products. Blocking group prevents circularization of oligonucleotide strand.

E. Exonuclease(s) digest all unligated or nicked products leaving only desired single-stranded circular DNA comprising of original target DNA with optional patient or unique identifier sequence. Rolling circle replication using Bst polymerase in the presence of BstUI (CGCG) assures that sites were methylated in the original sample.

A. Detect unmethylated adjacent HinP1I sites (GCGC) throughout genome. Ligate on short linkers with blocked 5' end. Cleave DNA with HinP1I (GCGC). Only adjacent HinP1I sites (GCGC) unmethylated in original target generate unblocked fragments when cleaved with HinP1I.

B. Ligate on longer linkers containing optional unique identifier sequence, optional patient identifier sequence, with either blocked 3' end (not shown), or thiophosphate containing backbone to inhibit subsequent digestion with 3' exonuclease. Only fragments with linker ligated to both sides will remain double-stranded.

C. Free end of linkers are rendered competent for ligation, either by, or in combination (i) phosphorylating 5' end, (ii) removing blocked 3' group, or (iii) using 5'-nuclease activity to cleave off matching 5'-overlapping base or flap, leaving ligation-competent 5'-phosphate. Ligation conditions are designed to favor multimerization.

D. Ligated products comprise of adjacent HinP1I sequences originally unmethylated in target DNA with optional unique identifier and/or patient identifier sequence. This product is suitable for optional additional steps and subsequent sequencing.

Figure 51

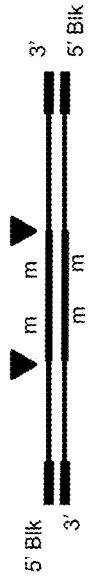

A. Detect methylated adjacent AciI sites (GCGG) throughout genome. Cleave with AciI. Ligate on short linkers with blocked 5' end. Cleave DNA with HaeIII (GGCC). Only adjacent HaeIII sites (GGCC) with methylated AciI sites in original target generate unblocked fragments when cleaved with HaeIII.

B. Ligate on longer linkers containing optional unique identifier sequence, optional patient identifier sequence, with either blocked 3' end (not shown), or thiophosphate containing backbone to inhibit subsequent digestion with 3' exonuclease. Only fragments with linker ligated to both sides will remain double-stranded.

C. Free end of linkers are rendered competent for ligation, either by, or in combination (i) phosphorylating 5' end, (ii) removing blocked 3' group, or (iii) using 5'-nuclease activity to cleave off matching 5'-overlapping base or flap, leaving ligation-competent 5'-phosphate. Ligation conditions are designed to favor multimerization.

D. Ligated products comprise of adjacent HaeIII sequences originally methylated at AciI sites in target DNA with optional unique identifier and/or patient identifier sequence. This product is suitable for optional additional steps and subsequent sequencing.

Figure 52

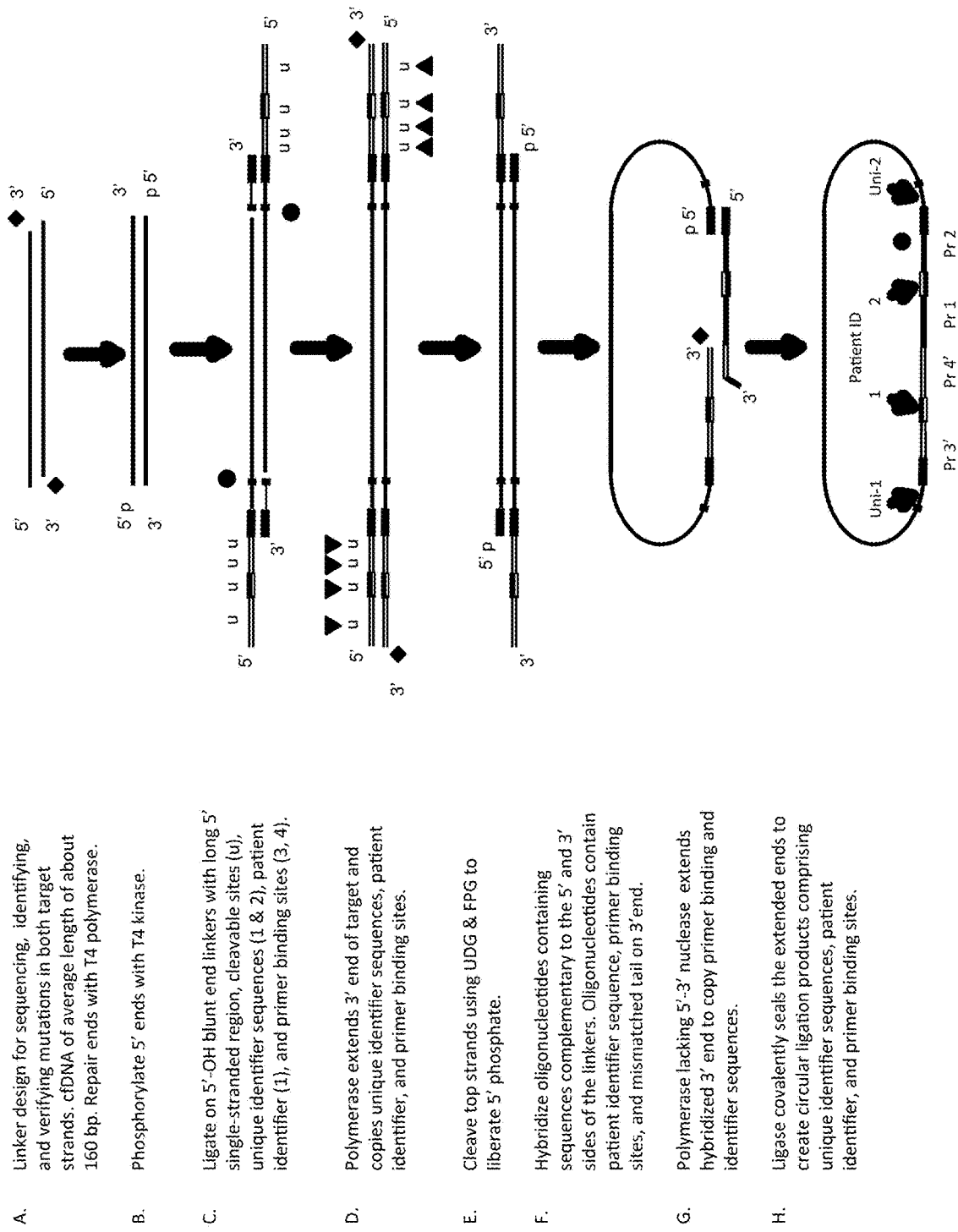

A. Linker design for sequencing, identifying, and verifying mutations in both target strands. cfDNA of average length of about 160 bp. Repair ends with T4 polymerase.

B. Phosphorylate 5' ends with T4 kinase.

C. Ligate on 5'-OH blunt end linkers with long 5' single-stranded region, cleavable sites (u), unique identifier sequences (1 & 2), patient identifier (1), and primer binding sites (3, 4).

D. Polymerase extends 3' end of target and copies unique identifier sequences, patient identifier, and primer binding sites.

E. Cleave top strands using UDG & FPG to liberate 5' phosphate.

F. Hybridize oligonucleotides containing sequences complementary to the 5' and 3' sides of the linkers. Oligonucleotides contain patient identifier sequence, primer binding sites, and mismatched tail on 3' end.

G. Polymerase lacking 5'-3' nuclease extends hybridized 3' end to copy primer binding and identifier sequences.

H. Ligase covalently seals the extended ends to create circular ligation products comprising unique identifier sequences, patient identifier, and primer binding sites.

Figure 64

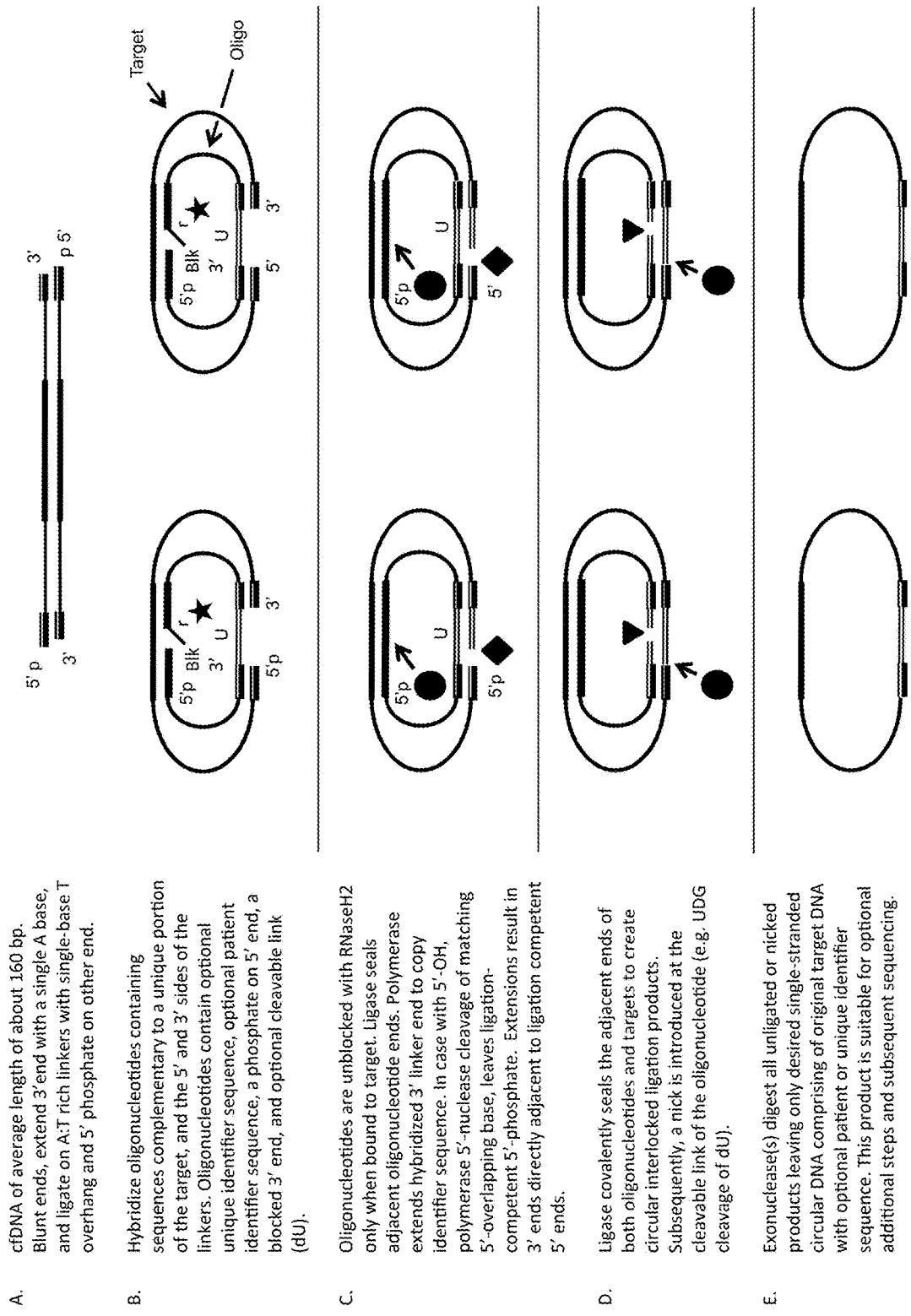

A. cfDNA of average length of about 160 bp. Blunt ends, extend 3' end with a single A base, and ligate on A:T rich linkers with single-base T overhang and 5' phosphate on other end.

B. Hybridize oligonucleotides containing sequences complementary to a unique portion of the target, and the 5' and 3' sides of the linkers. Oligonucleotides contain optional unique identifier sequence, optional patient identifier sequence, a phosphate on 5' end, a blocked 3' end, and optional cleavable link (dU).

C. Oligonucleotides are unblocked with RNaseH2 only when bound to target. Ligase seals adjacent oligonucleotide ends. Polymerase extends hybridized 3' linker end to copy identifier sequence. In case with 5'-OH, polymerase 5'-nuclease cleavage of matching 5'-overlapping base, leaves ligation-competent 5'-phosphate. Extensions result in 3' ends directly adjacent to ligation competent 5' ends.

D. Ligase covalently seals the adjacent ends of both oligonucleotides and targets to create circular interlocked ligation products. Subsequently, a nick is introduced at the cleavable link of the oligonucleotide (e.g. UDG cleavage of dU).

E. Exonuclease(s) digest all unligated or nicked products leaving only desired single-stranded circular DNA comprising of original target DNA with optional patient or unique identifier sequence. This product is suitable for optional additional steps and subsequent sequencing.

Figure 72

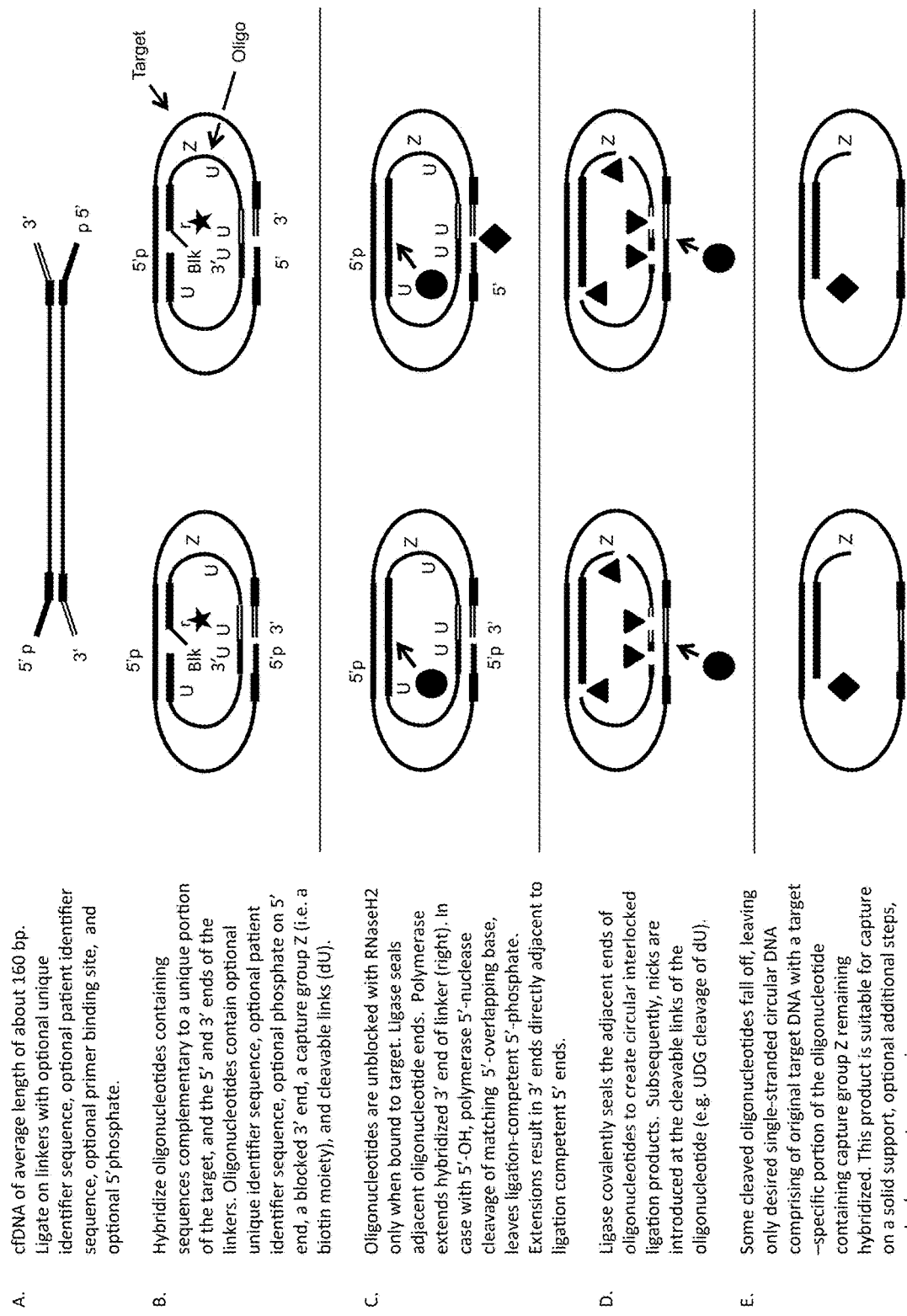

Figure 76

A. cfDNA of average length of about 160 bp. Ligate on linkers with optional unique identifier sequence, optional patient identifier sequence, optional primer binding site, and optional 5' phosphate.

B. Hybridize oligonucleotides containing sequences complementary to a unique portion of the target, and the 5' and 3' ends of the linkers. Oligonucleotides contain optional unique identifier sequence, optional patient identifier sequence, optional phosphate on 5' end, a blocked 3' end, a capture group Z (i.e. a biotin moiety), and cleavable links (dU).

C. Oligonucleotides are unblocked with RNaseH2 only when bound to target. Ligase seals adjacent oligonucleotide ends. Polymerase extends hybridized 3' end of linker (right). In case with 5'-OH, polymerase 5'-nuclease cleavage of matching 5'-overlapping base, leaves ligation-competent 5'-phosphate. Extensions result in 3' ends directly adjacent to ligation competent 5' ends.

D. Ligase covalently seals the adjacent ends of oligonucleotides to create circular interlocked ligation products. Subsequently, nicks are introduced at the cleavable links of the oligonucleotide (e.g. UDG cleavage of dU).

E. Some cleaved oligonucleotides fall off, leaving only desired single-stranded circular DNA comprising of original target DNA with a target-specific portion of the oligonucleotide containing capture group Z remaining hybridized. This product is suitable for capture on a solid support, optional additional steps, and subsequent sequencing.

A. Start with product comprising hybridized target-specific primer, or hybridize such primer to single-stranded circular DNA, comprising of original target DNA with optional unique identifier sequence, optional patient identifier sequence, optional primer binding site.

B. Hybridize oligonucleotides complementary to the target DNA. Oligonucleotides are optionally blocked or mismatched at the 3' end and contain capture group Z (i.e. a biotin moiety) on the 5' end. Capture target-containing circular DNA on solid support and wash away other nucleic acids.

C. Extend primer using strand-displacement polymerase to generate single strands of tandem copies of target DNA, and liberate extension product from the solid support. This extension product is suitable for sequencing.

Figure 84

A. Start with product comprising hybridized target-specific oligonucleotide, or hybridize such oligonucleotide to single-stranded circular DNA, comprising of original target DNA with optional unique identifier sequence, optional patient identifier sequence, optional primer binding site.

B. Oligonucleotides are optionally blocked or mismatched at the 3' end and contain capture group Z (i.e. a biotin moiety) on the 5' end. Capture target-containing circular DNA on solid support and wash away other nucleic acids. Hybridize target-specific primers either before or after capture.

C. Extend primer using strand-displacement polymerase to generate single strands of tandem copies of target DNA, and liberate extension product from the solid support. This extension product is suitable for sequencing.

Figure 85

A. Start with product comprising hybridized target-specific primer, or hybridize such primer to single-stranded circular DNA, comprising of original target DNA with optional unique identifier sequence, optional patient identifier sequence, optional primer binding site.

B. Hybridize oligonucleotide complementary to primer binding site. Oligonucleotide is optionally blocked or mismatched at the 3' end and contain capture group Z (i.e. a biotin moiety) on the 5' end. Capture target-containing circular DNA on solid support and wash away other nucleic acids.

C. Extend target-specific primer using strand-displacement polymerase to generate single strands of tandem copies of target DNA, and liberate extension product from the solid support. This extension product is suitable for sequencing.

Figure 88

A. Start with product comprising oligonucleotide hybridized to primer binding site, or hybridize such oligonucleotide to single-stranded circular DNA, comprising of original target DNA with optional unique identifier sequence, optional patient identifier sequence, and primer binding site.

B. Oligonucleotides are optionally blocked or mismatched at the 3' end and contain capture group Z (i.e. a biotin moiety) on the 5' end. Capture target-containing circular DNA on solid support and wash away other nucleic acids. Hybridize target-specific primers either before or after capture.

C. Extend target-specific primer using strand-displacement polymerase to generate single strands of tandem copies of target DNA, and liberate extension product from the solid support. This extension product is suitable for sequencing.

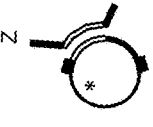

Figure 89

SEQUENCE LISTING

<160> NUMBER OF SEQ ID NOS: 154

<210> SEQ ID NO 1
<211> LENGTH: 33
<212> TYPE: DNA
<213> ORGANISM: Artificial
<220> FEATURE:
<223> OTHER INFORMATION: Primer

<400> SEQUENCE: 1
acactctttc cctacacgac gctcttccga tct                                33

<210> SEQ ID NO 2
<211> LENGTH: 33
<212> TYPE: DNA
<213> ORGANISM: Artificial
<220> FEATURE:
<223> OTHER INFORMATION: Primer

<400> SEQUENCE: 2
gatcggaaga gcacacgtct gaactccagt cac                                33

<210> SEQ ID NO 3
<211> LENGTH: 29
<212> TYPE: DNA
<213> ORGANISM: Artificial

```
<220> FEATURE:
<223> OTHER INFORMATION: Primer

<400> SEQUENCE: 3
aatgatacgg cgaccaccga gatctacac                                    29

<210> SEQ ID NO 4
<211> LENGTH: 34
<212> TYPE: DNA
<213> ORGANISM: Artificial
<220> FEATURE:
<223> OTHER INFORMATION: Primer

<400> SEQUENCE: 4
gtgactggag ttcagacgtg tgctcttccg atct                              34

<210> SEQ ID NO 5
<211> LENGTH: 30
<212> TYPE: DNA
<213> ORGANISM: Artificial
<220> FEATURE:
<223> OTHER INFORMATION: Primer

<400> SEQUENCE: 5
aaaaaaaaaa aaaaaaaaaa aaaaaaaaaa                                   30

<210> SEQ ID NO 6
<211> LENGTH: 14
<212> TYPE: DNA
<213> ORGANISM: Artificial
<220> FEATURE:
<223> OTHER INFORMATION: Short linker T Overhang

<400> SEQUENCE: 6
tgctcttccg atct                                                    14

<210> SEQ ID NO 7
<211> LENGTH: 12
<212> TYPE: DNA
<213> ORGANISM: Artificial
<220> FEATURE:
<223> OTHER INFORMATION: Bottom linker T overhang

<400> SEQUENCE: 7
gatcggaaga gc                                                      12

<210> SEQ ID NO 8
<211> LENGTH: 13
<212> TYPE: DNA
<213> ORGANISM: Artificial
<220> FEATURE:
<223> OTHER INFORMATION: Short linker blunt end

<400> SEQUENCE: 8
agatcggaag agc                                                     13

<210> SEQ ID NO 9
<211> LENGTH: 18
<212> TYPE: DNA
<213> ORGANISM: Artificial
<220> FEATURE:
<223> OTHER INFORMATION: Medium linker T overhang

<400> SEQUENCE: 9
tcgacgctct tccgatct                                                18
```

<210> SEQ ID NO 10
<211> LENGTH: 16
<212> TYPE: DNA
<213> ORGANISM: Artificial
<220> FEATURE:
<223> OTHER INFORMATION: Medium linker T overhang

<400> SEQUENCE: 10
gatcggaaga gcacac                                                  16

<210> SEQ ID NO 11
<211> LENGTH: 29
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (10)..(10)
<223> OTHER INFORMATION: N at position 10 is Deoxyuridine
<220> FEATURE:
<221> NAME/KEY: misc_feature
<222> LOCATION: (15)..(15)
<223> OTHER INFORMATION: N at position 15 is Deoxyuridine

<400> SEQUENCE: 11
aggcaagagn gcctngacga tacagctaa                                    29

<210> SEQ ID NO 12
<211> LENGTH: 59
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (40)..(40)
<223> OTHER INFORMATION: N at position 40 is Deoxyuridine
<220> FEATURE:
<221> NAME/KEY: misc_feature
<222> LOCATION: (45)..(45)
<223> OTHER INFORMATION: N at position 45 is Deoxyuridine

<400> SEQUENCE: 12
aaaaaaaaaa aaaaaaaaaa aaaaaaaaaa aggcaagagn gcctngacga tacagctaa   59

<210> SEQ ID NO 13
<211> LENGTH: 84
<212> TYPE: DNA
<213> ORGANISM: Artificial
<220> FEATURE:
<223> OTHER INFORMATION: Primer

<400> SEQUENCE: 13
aggcaagagt gccttgacga tacagctaat tcagaatcat tttgtggacg agatcggaag   60
agcacacgtc tgaactccag tcac                                         84

<210> SEQ ID NO 14
<211> LENGTH: 77
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature

```
<222> LOCATION: (50)..(50)
<223> OTHER INFORMATION: N at position 50 is Deoxyuridine
<220> FEATURE:
<221> NAME/KEY: misc_feature
<222> LOCATION: (64)..(64)
<223> OTHER INFORMATION: N at position 64 is Deoxyuridine
<220> FEATURE:
<221> NAME/KEY: misc_feature
<222> LOCATION: (73)..(73)
<223> OTHER INFORMATION: N at position 73 is Deoxyuridine

<400> SEQUENCE: 14
gagcacacgt ctgaactcca gtcaccgagt aatatctcgt angccgtctn ctgcttgaca      60
cacncgcaat ganacgg                                                    77

<210> SEQ ID NO 15
<211> LENGTH: 78
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (55)..(55)
<223> OTHER INFORMATION: N at position 55 is Deoxyuridine
<220> FEATURE:
<221> NAME/KEY: misc_feature
<222> LOCATION: (67)..(67)
<223> OTHER INFORMATION: N at position 67 is Deoxyuridine

<400> SEQUENCE: 15
gagcgtcgtg tagggaaaga gtgtaggcta tagtgtagat cncggtggtc gccgnatcat      60
tgcgagngtg tcaagcag                                                   78

<210> SEQ ID NO 16
<211> LENGTH: 83
<212> TYPE: DNA
<213> ORGANISM: Artificial
<220> FEATURE:
<223> OTHER INFORMATION: Primer

<400> SEQUENCE: 16
acactctttc cctacacgac gctcttccga tctttattat aaggcctgct gaaaatgact      60
gaatataaac ttgtggtagt tgg                                             83

<210> SEQ ID NO 17
<211> LENGTH: 37
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: N at position 15 is Deoxyuridine
<220> FEATURE:
<221> NAME/KEY: misc_feature
<222> LOCATION: (22)..(22)
<223> OTHER INFORMATION: N at position 22 is Deoxyuridine

<400> SEQUENCE: 17
ccaactacca caagnttata tncagtcatt ttcagca                              37

<210> SEQ ID NO 18
```

```
<211> LENGTH: 67
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (45)..(45)
<223> OTHER INFORMATION: N at position 45 is Deoxyuridine
<220> FEATURE:
<221> NAME/KEY: misc_feature
<222> LOCATION: (52)..(52)
<223> OTHER INFORMATION: N at position 52 is Deoxyuridine

<400> SEQUENCE: 18
aaaaaaaaaa aaaaaaaaaa aaaaaaaaaa ccaactacca caagnttata tncagtcatt     60
ttcagca                                                               67

<210> SEQ ID NO 19
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: N at position 11 is Deoxyuridine
<220> FEATURE:
<221> NAME/KEY: misc_feature
<222> LOCATION: (20)..(20)
<223> OTHER INFORMATION: N at position 20 is Deoxyuridine

<400> SEQUENCE: 19
ctcgatggag ngggtcccan cagtttgaac                                      30

<210> SEQ ID NO 20
<211> LENGTH: 60
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is Deoxyuridine
<220> FEATURE:
<221> NAME/KEY: misc_feature
<222> LOCATION: (50)..(50)
<223> OTHER INFORMATION: N at position 50 is Deoxyuridine

<400> SEQUENCE: 20
aaaaaaaaaa aaaaaaaaaa aaaaaaaaaa ctcgatggag ngggtcccan cagtttgaac     60

<210> SEQ ID NO 21
<211> LENGTH: 84
<212> TYPE: DNA
<213> ORGANISM: Artificial
<220> FEATURE:
<223> OTHER INFORMATION: Primer

<400> SEQUENCE: 21
ctcgatggag tgggtcccat cagtttgaac agttgtctgg atccattttg agatcggaag     60
agcacacgtc tgaactccag tcac                                            84

<210> SEQ ID NO 22
<211> LENGTH: 83
<212> TYPE: DNA
<213> ORGANISM: Artificial
```

```
<220> FEATURE:
<223> OTHER INFORMATION: Primer

<400> SEQUENCE: 22
acactctttc cctacacgac gctcttccga tctttctc atgaagacct cacagtaaaa    60
ataggtgatt ttggtctagc tac                                          83

<210> SEQ ID NO 23
<211> LENGTH: 41
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is Deoxyuridine
<220> FEATURE:
<221> NAME/KEY: misc_feature
<222> LOCATION: (27)..(27)
<223> OTHER INFORMATION: N at position 27 is Deoxyuridine

<400> SEQUENCE: 23
gtagctagac caaaancacc tattttnact gtgaggtctt c                      41

<210> SEQ ID NO 24
<211> LENGTH: 71
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (46)..(46)
<223> OTHER INFORMATION: N at position 46 is Deoxyuridine
<220> FEATURE:
<221> NAME/KEY: misc_feature
<222> LOCATION: (57)..(57)
<223> OTHER INFORMATION: N at position 57 is Deoxyuridine

<400> SEQUENCE: 24
aaaaaaaaaa aaaaaaaaaa aaaaaaaaaa gtagctagac caaaancacc tattttnact    60
gtgaggtctt c                                                        71

<210> SEQ ID NO 25
<211> LENGTH: 25
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (10)..(10)
<223> OTHER INFORMATION: N at position 10 is Deoxyuridine
<220> FEATURE:
<221> NAME/KEY: misc_feature
<222> LOCATION: (18)..(18)
<223> OTHER INFORMATION: N at position 18 is Deoxyuridine

<400> SEQUENCE: 25
gtgcagctgn gggttgantc cacac                                         25

<210> SEQ ID NO 26
<211> LENGTH: 55
<212> TYPE: DNA
<213> ORGANISM: Artificial
<220> FEATURE:
<223> OTHER INFORMATION: Primer
<220> FEATURE:
```

```
<221> NAME/KEY: misc_feature
<222> LOCATION: (40)..(40)
<223> OTHER INFORMATION: N at position 40 is Deoxyuridine
<220> FEATURE:
<221> NAME/KEY: misc_feature
<222> LOCATION: (48)..(48)
<223> OTHER INFORMATION: N at position 48 is Deoxyuridine

<400> SEQUENCE: 26
aaaaaaaaaa aaaaaaaaaa aaaaaaaaaa gtgcagctgn gggttgantc cacac      55

<210> SEQ ID NO 27
<211> LENGTH: 83
<212> TYPE: DNA
<213> ORGANISM: Artificial
<220> FEATURE:
<223> OTHER INFORMATION: Primer

<400> SEQUENCE: 27
gtgcagctgt gggttgattc cacacccccg cccggcaccc gcgtccgcga gatcggaaga   60
gcacacgtct gaactccagt cac                                          83

<210> SEQ ID NO 28
<211> LENGTH: 83
<212> TYPE: DNA
<213> ORGANISM: Artificial
<220> FEATURE:
<223> OTHER INFORMATION: Primer

<400> SEQUENCE: 28
acactctttc cctacacgac gctcttccga tcttcctaca gtactcccct gccctcaaca   60
agatgttttg ccaactggcc aag                                          83

<210> SEQ ID NO 29
<211> LENGTH: 29
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: N at position 11 is Deoxyuridine
<220> FEATURE:
<221> NAME/KEY: misc_feature
<222> LOCATION: (21)..(21)
<223> OTHER INFORMATION: N at position 21 is Deoxyuridine

<400> SEQUENCE: 29
cttggccagt nggcaaaaca ncttgttga                                    29

<210> SEQ ID NO 30
<211> LENGTH: 59
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is Deoxyuridine
<220> FEATURE:
<221> NAME/KEY: misc_feature
<222> LOCATION: (51)..(51)
<223> OTHER INFORMATION: N at position 51 is Deoxyuridine

<400> SEQUENCE: 30
aaaaaaaaaa aaaaaaaaaa aaaaaaaaaa cttggccagt nggcaaaaca ncttgttga   59
```

```
<210> SEQ ID NO 31
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (10)..(10)
<223> OTHER INFORMATION: N at position 10 is Deoxyuridine
<220> FEATURE:
<221> NAME/KEY: misc_feature
<222> LOCATION: (15)..(15)
<223> OTHER INFORMATION: N at position 15 is Deoxyuridine

<400> SEQUENCE: 31
gagcgctgcn caganagcga tggtga                                         26

<210> SEQ ID NO 32
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (40)..(40)
<223> OTHER INFORMATION: N at position 40 is Deoxyuridine
<220> FEATURE:
<221> NAME/KEY: misc_feature
<222> LOCATION: (45)..(45)
<223> OTHER INFORMATION: N at position 45 is Deoxyuridine

<400> SEQUENCE: 32
aaaaaaaaaa aaaaaaaaaa aaaaaaaaaa gagcgctgcn caganagcga tggtga        56

<210> SEQ ID NO 33
<211> LENGTH: 84
<212> TYPE: DNA
<213> ORGANISM: Artificial
<220> FEATURE:
<223> OTHER INFORMATION: Primer

<400> SEQUENCE: 33
gagcgctgct cagatagcga tggtgagcag ctggagctgg agagacgaca agatcggaag    60
agcacacgtc tgaactccag tcac                                           84

<210> SEQ ID NO 34
<211> LENGTH: 83
<212> TYPE: DNA
<213> ORGANISM: Artificial
<220> FEATURE:
<223> OTHER INFORMATION: Primer

<400> SEQUENCE: 34
acactctttc cctacacgac gctcttccga tcttccgcgc catggccatc tacaagcagt    60
cacagcacat gacggaggtt gtg                                            83

<210> SEQ ID NO 35
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (12)..(12)
```

<223> OTHER INFORMATION: N at position 12 is Deoxyuridine
<220> FEATURE:
<221> NAME/KEY: misc_feature
<222> LOCATION: (20)..(20)
<223> OTHER INFORMATION: N at position 20 is Deoxyuridine

<400> SEQUENCE: 35
cacaacctcc gncatgtgcn gtgactg         27

<210> SEQ ID NO 36
<211> LENGTH: 57
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (50)..(50)
<223> OTHER INFORMATION: N at position 50 is Deoxyuridine

<400> SEQUENCE: 36
aaaaaaaaaa aaaaaaaaaa aaaaaaaaaa cacaacctcc gncatgtgcn gtgactg         57

<210> SEQ ID NO 37
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: N at position 11 is Deoxyuridine
<220> FEATURE:
<221> NAME/KEY: misc_feature
<222> LOCATION: (22)..(22)
<223> OTHER INFORMATION: N at position 22 is Deoxyuridine

<400> SEQUENCE: 37
gaaacacttt ncgacatagt gnggtggtgc c         31

<210> SEQ ID NO 38
<211> LENGTH: 61
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is Deoxyuridine
<220> FEATURE:
<221> NAME/KEY: misc_feature
<222> LOCATION: (52)..(52)
<223> OTHER INFORMATION: N at position 52 is Deoxyuridine

<400> SEQUENCE: 38
aaaaaaaaaa aaaaaaaaaa aaaaaaaaaa gaaacacttt ncgacatagt gnggtggtgc         60
c         61

<210> SEQ ID NO 39
<211> LENGTH: 84
<212> TYPE: DNA
<213> ORGANISM: Artificial
<220> FEATURE:
<223> OTHER INFORMATION: Primer

<400> SEQUENCE: 39
gaaacacttt tcgacatagt gtggtggtgc cctatgagcc gcctgaggtc agatcggaag    60
agcacacgtc tgaactccag tcac                                          84

<210> SEQ ID NO 40
<211> LENGTH: 83
<212> TYPE: DNA
<213> ORGANISM: Artificial
<220> FEATURE:
<223> OTHER INFORMATION: Primer

<400> SEQUENCE: 40
acactctttc cctacacgac gctcttccga tctggcccct cctcagcatc ttatccgagt    60
ggaaggaaat ttgcgtgtgg agt                                           83

<210> SEQ ID NO 41
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: N at position 15 is Deoxyuridine
<220> FEATURE:
<221> NAME/KEY: misc_feature
<222> LOCATION: (20)..(20)
<223> OTHER INFORMATION: N at position 20 is Deoxyuridine

<400> SEQUENCE: 41
actccacacg caaanttccn tccactc                                       27

<210> SEQ ID NO 42
<211> LENGTH: 57
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (45)..(45)
<223> OTHER INFORMATION: N at position 45 is Deoxyuridine
<220> FEATURE:
<221> NAME/KEY: misc_feature
<222> LOCATION: (50)..(50)
<223> OTHER INFORMATION: N at position 50 is Deoxyuridine

<400> SEQUENCE: 42
aaaaaaaaaa aaaaaaaaaa aaaaaaaaaa actccacacg caaanttccn tccactc      57

<210> SEQ ID NO 43
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (12)..(12)
<223> OTHER INFORMATION: N at position 12 is Deoxyuridine
<220> FEATURE:
<221> NAME/KEY: misc_feature
<222> LOCATION: (18)..(18)
<223> OTHER INFORMATION: N at position 18 is Deoxyuridine

<400> SEQUENCE: 43

```
cctcaccatc ancacacngg aagactcc                                          28
```

<210> SEQ ID NO 44
<211> LENGTH: 58
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (48)..(48)
<223> OTHER INFORMATION: N at position 48 is Deoxyuridine

<400> SEQUENCE: 44

```
aaaaaaaaaa aaaaaaaaa aaaaaaaaa cctcaccatc ancacacngg aagactcc          58
```

<210> SEQ ID NO 45
<211> LENGTH: 84
<212> TYPE: DNA
<213> ORGANISM: Artificial
<220> FEATURE:
<223> OTHER INFORMATION: Primer

<400> SEQUENCE: 45

```
cctcaccatc atcacactgg aagactccag gtcaggagcc acttgccacc agatcggaag      60
agcacacgtc tgaactccag tcac                                              84
```

<210> SEQ ID NO 46
<211> LENGTH: 83
<212> TYPE: DNA
<213> ORGANISM: Artificial
<220> FEATURE:
<223> OTHER INFORMATION: Primer

<400> SEQUENCE: 46

```
acactctttc cctacacgac gctcttccga tctgctctga ctgtaccacc atccactaca      60
actacatgtg taacagttcc tgc                                               83
```

<210> SEQ ID NO 47
<211> LENGTH: 34
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (12)..(12)
<223> OTHER INFORMATION: N at position 12 is Deoxyuridine
<220> FEATURE:
<221> NAME/KEY: misc_feature
<222> LOCATION: (20)..(20)
<223> OTHER INFORMATION: N at position 20 is Deoxyuridine

<400> SEQUENCE: 47

```
gcaggaactg tnacacatgn agttgtagtg gatg                                   34
```

<210> SEQ ID NO 48
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (50)..(50)
<223> OTHER INFORMATION: N at position 50 is Deoxyuridine

<400> SEQUENCE: 48
aaaaaaaaaa aaaaaaaaaa aaaaaaaaaa gcaggaactg tnacacatgn agttgtagtg   60
gatg   64

<210> SEQ ID NO 49
<211> LENGTH: 24
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: N at position 15 is Deoxyuridine

<400> SEQUENCE: 49
gggagagacc ggcgnacaga ggaa   24

<210> SEQ ID NO 50
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (45)..(45)
<223> OTHER INFORMATION: N at position 45 is Deoxyuridine

<400> SEQUENCE: 50
aaaaaaaaaa aaaaaaaaaa aaaaaaaaaa gggagagacc ggcgnacaga ggaa   54

<210> SEQ ID NO 51
<211> LENGTH: 84
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: N at position 15 is Deoxyuridine

<400> SEQUENCE: 51
gggagagacc ggcgnacaga ggaagagaat ctccgcaaga aaggagagcc agatcggaag   60
agcacacgtc tgaactccag tcac   84

<210> SEQ ID NO 52
<211> LENGTH: 83
<212> TYPE: DNA
<213> ORGANISM: Artificial
<220> FEATURE:
<223> OTHER INFORMATION: Primer

<400> SEQUENCE: 52
acactctttc cctacacgac gctcttccga tctctctttt cctatcctga gtagtggtaa   60
tctactggga cggaacagct ttg   83

<210> SEQ ID NO 53

-continued

```
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (7)..(7)
<223> OTHER INFORMATION: N at position 7 is Deoxyuridine
<220> FEATURE:
<221> NAME/KEY: misc_feature
<222> LOCATION: (14)..(14)
<223> OTHER INFORMATION: N at position 14 is Deoxyuridine

<400> SEQUENCE: 53
caaagcngtt ccgncccagt agattacc                                          28

<210> SEQ ID NO 54
<211> LENGTH: 58
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (37)..(37)
<223> OTHER INFORMATION: N at position 37 is Deoxyuridine
<220> FEATURE:
<221> NAME/KEY: misc_feature
<222> LOCATION: (44)..(44)
<223> OTHER INFORMATION: N at position 44 is Deoxyuridine

<400> SEQUENCE: 54
aaaaaaaaaa aaaaaaaaaa aaaaaaaaaa caaagcngtt ccgncccagt agattacc         58

<210> SEQ ID NO 55
<211> LENGTH: 25
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (12)..(12)
<223> OTHER INFORMATION: N at position 12 is Deoxyuridine
<220> FEATURE:
<221> NAME/KEY: misc_feature
<222> LOCATION: (17)..(17)
<223> OTHER INFORMATION: N at position 17 is Deoxyuridine

<400> SEQUENCE: 55
gtaggcaaga gngcttngac gatac                                             25

<210> SEQ ID NO 56
<211> LENGTH: 55
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (47)..(47)
<223> OTHER INFORMATION: N at position 47 is Deoxyuridine

<400> SEQUENCE: 56
aaaaaaaaaa aaaaaaaaaa aaaaaaaaaa gtaggcaaga gngcttngac gatac            55
```

```
<210> SEQ ID NO 57
<211> LENGTH: 119
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (81)..(85)
<223> OTHER INFORMATION: n is a, c, g, or t

<400> SEQUENCE: 57
gtaggcaaga gtgctttgac gatacagctg attcagaatc atttcgtgga cgaatatgac      60
ccaacaatag aggtagatct nnnnnagatc ggaagagcac acgtctgaac tccagtcac     119

<210> SEQ ID NO 58
<211> LENGTH: 77
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (50)..(50)
<223> OTHER INFORMATION: N at position 50 is Deoxyuridine
<220> FEATURE:
<221> NAME/KEY: misc_feature
<222> LOCATION: (64)..(64)
<223> OTHER INFORMATION: N at position 64 is Deoxyuridine
<220> FEATURE:
<221> NAME/KEY: misc_feature
<222> LOCATION: (73)..(73)
<223> OTHER INFORMATION: N at position 73 is Deoxyuridine

<400> SEQUENCE: 58
gagcacacgt ctgaactcca gtcacttctg aatatctcgt angccgtctn ctgcttgaca      60
cacncgcaat ganacgg                                                    77

<210> SEQ ID NO 59
<211> LENGTH: 78
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (55)..(55)
<223> OTHER INFORMATION: N at position 55 is Deoxyuridine
<220> FEATURE:
<221> NAME/KEY: misc_feature
<222> LOCATION: (67)..(67)
<223> OTHER INFORMATION: N at position 67 is Deoxyuridine

<400> SEQUENCE: 59
gagcgtcgtg tagggaaaga gtgtgcctct atgtgtagat cncggtggtc gccgnatcat      60
tgcgagngtg tcaagcag                                                   78

<210> SEQ ID NO 60
<211> LENGTH: 118
<212> TYPE: DNA
<213> ORGANISM: Artificial
<220> FEATURE:
```

<223> OTHER INFORMATION: Primer
<220> FEATURE:
<221> NAME/KEY: misc_feature
<222> LOCATION: (34)..(38)
<223> OTHER INFORMATION: n is a, c, g, or t

<400> SEQUENCE: 60
acactctttc cctacacgac gctcttccga tctnnnnnct aatatggtca cattttcatt    60
gtttttatta taaggtctgc tgaaaatgac cgaatataaa cttgtagtag ttggagct    118

<210> SEQ ID NO 61
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (10)..(10)
<223> OTHER INFORMATION: N at position 10 is Deoxyuridine
<220> FEATURE:
<221> NAME/KEY: misc_feature
<222> LOCATION: (20)..(20)
<223> OTHER INFORMATION: N at position 20 is Deoxyuridine

<400> SEQUENCE: 61
agctccaacn actacaagtn tatattcggt c    31

<210> SEQ ID NO 62
<211> LENGTH: 61
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (40)..(40)
<223> OTHER INFORMATION: N at position 40 is Deoxyuridine
<220> FEATURE:
<221> NAME/KEY: misc_feature
<222> LOCATION: (50)..(50)
<223> OTHER INFORMATION: N at position 50 is Deoxyuridine

<400> SEQUENCE: 62
aaaaaaaaaa aaaaaaaaaa aaaaaaaaaa agctccaacn actacaagtn tatattcggt    60
c    61

<210> SEQ ID NO 63
<211> LENGTH: 21
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (4)..(4)
<223> OTHER INFORMATION: N at position 4 is Deoxyuridine
<220> FEATURE:
<221> NAME/KEY: misc_feature
<222> LOCATION: (10)..(10)
<223> OTHER INFORMATION: N at position 10 is Deoxyuridine

<400> SEQUENCE: 63
aaanctcgan ggagcgggtc c    21

<210> SEQ ID NO 64
<211> LENGTH: 51
<212> TYPE: DNA
<213> ORGANISM: Artificial

```
<220> FEATURE:
<223> OTHER INFORMATION: Primer
<220> FEATURE:
<221> NAME/KEY: misc_feature
<222> LOCATION: (34)..(34)
<223> OTHER INFORMATION: N at position 34 is Deoxyuridine
<220> FEATURE:
<221> NAME/KEY: misc_feature
<222> LOCATION: (40)..(40)
<223> OTHER INFORMATION: N at position 40 is Deoxyuridine

<400> SEQUENCE: 64
aaaaaaaaaa aaaaaaaaaa aaaaaaaaaa aaanctcgan ggagcgggtc c          51

<210> SEQ ID NO 65
<211> LENGTH: 119
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (81)..(85)
<223> OTHER INFORMATION: n is a, c, g, or t

<400> SEQUENCE: 65
aaatctcgat ggagcgggtc ccatcagttc gaacagttgt ctgggtccat tttgtggata    60
gtaagaattg aggctgtttt nnnnnagatc ggaagagcac acgtctgaac tccagtcac   119

<210> SEQ ID NO 66
<211> LENGTH: 118
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (34)..(38)
<223> OTHER INFORMATION: n is a, c, g, or t

<400> SEQUENCE: 66
acactctttc cctacacgac gctcttccga tctnnnnntt tccttcactt actacacctc    60
ggatatattt cttcacgaag acctcacagt gaaaataggt gatttcggtc tagctaca    118

<210> SEQ ID NO 67
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (7)..(7)
<223> OTHER INFORMATION: N at position 7 is Deoxyuridine
<220> FEATURE:
<221> NAME/KEY: misc_feature
<222> LOCATION: (17)..(17)
<223> OTHER INFORMATION: N at position 17 is Deoxyuridine

<400> SEQUENCE: 67
tgtagcnaga ccgaaancac ctattttcac                                    30

<210> SEQ ID NO 68
<211> LENGTH: 60
<212> TYPE: DNA
<213> ORGANISM: Artificial
<220> FEATURE:
<223> OTHER INFORMATION: Primer
<220> FEATURE:
```

```
<221> NAME/KEY: misc_feature
<222> LOCATION: (37)..(37)
<223> OTHER INFORMATION: N at position 37 is Deoxyuridine
<220> FEATURE:
<221> NAME/KEY: misc_feature
<222> LOCATION: (47)..(47)
<223> OTHER INFORMATION: N at position 47 is Deoxyuridine

<400> SEQUENCE: 68
aaaaaaaaaa aaaaaaaaaa aaaaaaaaaa tgtagcnaga ccgaaancac ctattttcac    60

<210> SEQ ID NO 69
<211> LENGTH: 18
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (7)..(7)
<223> OTHER INFORMATION: N at position 7 is Deoxyuridine
<220> FEATURE:
<221> NAME/KEY: misc_feature
<222> LOCATION: (15)..(15)
<223> OTHER INFORMATION: N at position 15 is Deoxyuridine

<400> SEQUENCE: 69
aggcgcngcc cccancat                                                  18

<210> SEQ ID NO 70
<211> LENGTH: 48
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (37)..(37)
<223> OTHER INFORMATION: N at position 37 is Deoxyuridine
<220> FEATURE:
<221> NAME/KEY: misc_feature
<222> LOCATION: (45)..(45)
<223> OTHER INFORMATION: N at position 45 is Deoxyuridine

<400> SEQUENCE: 70
aaaaaaaaaa aaaaaaaaaa aaaaaaaaaa aggcgcngcc cccancat                 48

<210> SEQ ID NO 71
<211> LENGTH: 119
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (81)..(85)
<223> OTHER INFORMATION: n is a, c, g, or t

<400> SEQUENCE: 71
aggcgctgcc cccatcatga gcgctgctcg gatagcgatg gtgaacagct ggagctggaa    60
agacgacagg gctggctgcc nnnnnagatc ggaagagcac acgtctgaac tccagtcac   119

<210> SEQ ID NO 72
<211> LENGTH: 118
<212> TYPE: DNA
<213> ORGANISM: Artificial
<220> FEATURE:
<223> OTHER INFORMATION: Primer
<220> FEATURE:
<221> NAME/KEY: misc_feature
```

```
<222> LOCATION: (34)..(38)
<223> OTHER INFORMATION: n is a, c, g, or t

<400> SEQUENCE: 72
acactctttc cctacacgac gctcttccga tctnnnnntg tgggtcgatt ccacaccccc    60
acccggcacc cgcgttcgcg ccatggccat ttacaagcag tcacaacaca tgacggag    118

<210> SEQ ID NO 73
<211> LENGTH: 29
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: N at position 11 is Deoxyuridine
<220> FEATURE:
<221> NAME/KEY: misc_feature
<222> LOCATION: (20)..(20)
<223> OTHER INFORMATION: N at position 20 is Deoxyuridine

<400> SEQUENCE: 73
ctccgtcatg ngttgtgacn gcttgtaaa                                      29

<210> SEQ ID NO 74
<211> LENGTH: 59
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is Deoxyuridine
<220> FEATURE:
<221> NAME/KEY: misc_feature
<222> LOCATION: (50)..(50)
<223> OTHER INFORMATION: N at position 50 is Deoxyuridine

<400> SEQUENCE: 74
aaaaaaaaaa aaaaaaaaaa aaaaaaaaaa ctccgtcatg ngttgtgacn gcttgtaaa    59

<210> SEQ ID NO 75
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (8)..(8)
<223> OTHER INFORMATION: N at position 8 is Deoxyuridine
<220> FEATURE:
<221> NAME/KEY: misc_feature
<222> LOCATION: (18)..(18)
<223> OTHER INFORMATION: N at position 18 is Deoxyuridine

<400> SEQUENCE: 75
aacacttntc gacacagngt ggtggt                                         26

<210> SEQ ID NO 76
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(38)
```

```
<223> OTHER INFORMATION: N at position 38 is Deoxyuridine
<220> FEATURE:
<221> NAME/KEY: misc_feature
<222> LOCATION: (48)..(48)
<223> OTHER INFORMATION: N at position 48 is Deoxyuridine

<400> SEQUENCE: 76
aaaaaaaaaa aaaaaaaaaa aaaaaaaaaa aacacttntc gacacagngt ggtggt        56

<210> SEQ ID NO 77
<211> LENGTH: 119
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (81)..(85)
<223> OTHER INFORMATION: n is a, c, g, or t

<400> SEQUENCE: 77 aacactttc gacacagtgt ggtggtgcct tatgagccgc ctgaagtctg gtttgcaacc      60
ggagtctctg ggaggaaggg nnnnnagatc ggaagagcac acgtctgaac tccagtcac    119

<210> SEQ ID NO 78
<211> LENGTH: 118
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (34)..(38)
<223> OTHER INFORMATION: n is a, c, g, or t

<400> SEQUENCE: 78
acactctttc cctacacgac gctcttccga tctnnnnnct cactgactgc tcttaggtct    60
agcccctcct cagcaccttn tccgagtgga gggaaatttg cgtgtagagt atttggat    118

<210> SEQ ID NO 79
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: N at position 11 is Deoxyuridine
<220> FEATURE:
<221> NAME/KEY: misc_feature
<222> LOCATION: (23)..(23)
<223> OTHER INFORMATION: N at position 23 is Deoxyuridine

<400> SEQUENCE: 79
atccaaatac nctacacgca aanttccctc c                                    31

<210> SEQ ID NO 80
<211> LENGTH: 61
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is Deoxyuridine
<220> FEATURE:
<221> NAME/KEY: misc_feature
```

<222> LOCATION: (53)..(53)
<223> OTHER INFORMATION: N at position 53 is Deoxyuridine

<400> SEQUENCE: 80

```
aaaaaaaaaa aaaaaaaaaa aaaaaaaaaa atccaaatac nctacacgca aanttccctc    60
c                                                                     61
```

<210> SEQ ID NO 81
<211> LENGTH: 21
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (8)..(8)
<223> OTHER INFORMATION: N at position 8 is Deoxyuridine

<400> SEQUENCE: 81

```
ggcggcanga accgaagacc c                                               21
```

<210> SEQ ID NO 82
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (38)..(38)
<223> OTHER INFORMATION: N at position 38 is Deoxyuridine

<400> SEQUENCE: 82

```
aaaaaaaaaa aaaaaaaaaa aaaaaaaaaa ggcggcanga accgaagacc c              51
```

<210> SEQ ID NO 83
<211> LENGTH: 119
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (81)..(85)
<223> OTHER INFORMATION: n is a, c, g, or t

<400> SEQUENCE: 83

```
ggcggcatga accgaaggcc catcctcact atcatcacac tggaggactc caggtcagga    60
accacttgcc accctgtaca nnnnnagatc ggaagagcac acgtctgaac tccagtcac    119
```

<210> SEQ ID NO 84
<211> LENGTH: 118
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (34)..(38)
<223> OTHER INFORMATION: n is a, c, g, or t

<400> SEQUENCE: 84

```
acactctttc cctacacgac gctcttccga tctnnnnntg gcctcacctt gggcctgtgt    60
catctcctag gttggttctg actgtaccac tatccactac aactatatgt gtaacagt     118
```

<210> SEQ ID NO 85

```
<211> LENGTH: 35
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (12)..(12)
<223> OTHER INFORMATION: N at position 12 is Deoxyuridine
<220> FEATURE:
<221> NAME/KEY: misc_feature
<222> LOCATION: (23)..(23)
<223> OTHER INFORMATION: N at position 23 is Deoxyuridine

<400> SEQUENCE: 85
actgttacac anatagttgt agnggatagt ggtac                           35

<210> SEQ ID NO 86
<211> LENGTH: 65
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (53)..(53)
<223> OTHER INFORMATION: N at position 53 is Deoxyuridine

<400> SEQUENCE: 86
aaaaaaaaaa aaaaaaaaaa aaaaaaaaaa actgttacac anatagttgt agnggatagt    60
ggtac                                                                65

<210> SEQ ID NO 87
<211> LENGTH: 21
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (9)..(9)
<223> OTHER INFORMATION: N at position 9 is Deoxyuridine

<400> SEQUENCE: 87
agagaccgnc gcacggagga a                                         21

<210> SEQ ID NO 88
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (39)..(39)
<223> OTHER INFORMATION: N at position 39 is Deoxyuridine

<400> SEQUENCE: 88
aaaaaaaaaa aaaaaaaaaa aaaaaaaaaa agagaccgnc gcacggagga a         51

<210> SEQ ID NO 89
<211> LENGTH: 119
<212> TYPE: DNA
<213> ORGANISM: Artificial
<220> FEATURE:
<223> OTHER INFORMATION: Primer
```

```
<220> FEATURE:
<221> NAME/KEY: misc_feature
<222> LOCATION: (9)..(9)
<223> OTHER INFORMATION: N at position 9 is Deoxyuridine
<220> FEATURE:
<221> NAME/KEY: misc_feature
<222> LOCATION: (81)..(85)
<223> OTHER INFORMATION: n is a, c, g, or t

<400> SEQUENCE: 89
agagaccgnc gcacggagga agagaatctt cgcaagaaag gagaacctca ccacgagcta    60
cccccaggga gcaccaagcg nnnnnagatc ggaagagcac acgtctgaac tccagtcac   119

<210> SEQ ID NO 90
<211> LENGTH: 118
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (34)..(38)
<223> OTHER INFORMATION: n is a, c, g, or t

<400> SEQUENCE: 90
acactctttc cctacacgac gctcttccga tctnnnnntt actgcttctt gcttctcttc    60
tcctatcctg agtaatggta atctactgga acggaacagc tttgaagtgc gtgtttgt    118

<210> SEQ ID NO 91
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (13)..(13)
<223> OTHER INFORMATION: N at position 13 is Deoxyuridine
<220> FEATURE:
<221> NAME/KEY: misc_feature
<222> LOCATION: (21)..(21)
<223> OTHER INFORMATION: N at position 21 is Deoxyuridine

<400> SEQUENCE: 91
acaaacacgc acntcaaagc ngttcc                                         26

<210> SEQ ID NO 92
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (43)..(43)
<223> OTHER INFORMATION: N at position 43 is Deoxyuridine
<220> FEATURE:
<221> NAME/KEY: misc_feature
<222> LOCATION: (51)..(51)
<223> OTHER INFORMATION: N at position 51 is Deoxyuridine

<400> SEQUENCE: 92
aaaaaaaaaa aaaaaaaaa aaaaaaaaaa acaaacacgc acntcaaagc ngttcc         56

<210> SEQ ID NO 93
<211> LENGTH: 34
<212> TYPE: DNA
<213> ORGANISM: Artificial
<220> FEATURE:
```

```
<223> OTHER INFORMATION: Primer
<220> FEATURE:
<221> NAME/KEY: misc_feature
<222> LOCATION: (30)..(30)
<223> OTHER INFORMATION: N at position 30 is ribouridine

<400> SEQUENCE: 93
aaggcctgct gaaaatgctg aatataaacn tgta                                   34

<210> SEQ ID NO 94
<211> LENGTH: 36
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (32)..(32)
<223> OTHER INFORMATION: N at position 32 is riboguanosine

<400> SEQUENCE: 94
cgtccacaaa atgattcgaa ttagctgtat cntcag                                 36

<210> SEQ ID NO 95
<211> LENGTH: 39
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (35)..(35)
<223> OTHER INFORMATION: N at position 35 is riboadenosine

<400> SEQUENCE: 95
tcagatatat ttcttcatga gacctcacag taaanataa                              39

<210> SEQ ID NO 96
<211> LENGTH: 33
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is ribouridine

<400> SEQUENCE: 96
acaaaatgga tccagcaact gttcaaacng ata                                    33

<210> SEQ ID NO 97
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (26)..(26)
<223> OTHER INFORMATION: N at position 26 is riboadenosine

<400> SEQUENCE: 97
cgccatggcc atcacaagca gtcacngcat                                        30

<210> SEQ ID NO 98
<211> LENGTH: 29
<212> TYPE: DNA
<213> ORGANISM: Artificial
```

<220> FEATURE:
<223> OTHER INFORMATION: Primer
<220> FEATURE:
<221> NAME/KEY: misc_feature
<222> LOCATION: (25)..(25)
<223> OTHER INFORMATION: N at position 25 is riboguanosine

<400> SEQUENCE: 98
gctgctcacc atcctatctg agcancgca                29

<210> SEQ ID NO 99
<211> LENGTH: 32
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (28)..(28)
<223> OTHER INFORMATION: N at position 28 is riboadenosine

<400> SEQUENCE: 99
cttcctacag tactccctgc cctcaacnag ac             32

<210> SEQ ID NO 100
<211> LENGTH: 29
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (25)..(25)
<223> OTHER INFORMATION: N at position 25 is riboguanosine

<400> SEQUENCE: 100
ggcggaggtg tgaatcaacc cacanctgt                 29

<210> SEQ ID NO 101
<211> LENGTH: 33
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is ribouridine

<400> SEQUENCE: 101
cctcagcatc ttatcgagtg gaaggaaant tgt            33

<210> SEQ ID NO 102
<211> LENGTH: 24
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: N at position 20 is ribocytosine

<400> SEQUENCE: 102
cggctcatag ggaccaccan actg                      24

<210> SEQ ID NO 103
<211> LENGTH: 35
<212> TYPE: DNA

<213> ORGANISM: Artificial
<220> FEATURE:
<223> OTHER INFORMATION: Primer
<220> FEATURE:
<221> NAME/KEY: misc_feature
<222> LOCATION: (31)..(31)
<223> OTHER INFORMATION: N at position 31 is riboadenosine

<400> SEQUENCE: 103
ctctgactgt accaccacca ctacaactac ntgta                          35

<210> SEQ ID NO 104
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (27)..(27)
<223> OTHER INFORMATION: N at position 27 is ribouridine

<400> SEQUENCE: 104
ctgacctgga gtcttcagtg tgatganggt a                              31

<210> SEQ ID NO 105
<211> LENGTH: 33
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is riboadenosine

<400> SEQUENCE: 105
tgagtagtgg taatctactg gacggaacng ctc                            33

<210> SEQ ID NO 106
<211> LENGTH: 32
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (28)..(28)
<223> OTHER INFORMATION: N at position 28 is ribocytosine

<400> SEQUENCE: 106
gctccccttt cttgggagat tctcttcntc ta                             32

<210> SEQ ID NO 107
<211> LENGTH: 70
<212> TYPE: DNA
<213> ORGANISM: Artificial
<220> FEATURE:
<223> OTHER INFORMATION: KRAS top strand capture oligo

<400> SEQUENCE: 107
tttttttttt gctggtggcg taggcaagag tgccttgacg atacagctaa ttcagaatca      60
ttttgtggac                                                            70

<210> SEQ ID NO 108
<211> LENGTH: 70
<212> TYPE: DNA
<213> ORGANISM: Artificial

```
<220> FEATURE:
<223> OTHER INFORMATION: KRAS bottom strand capture oligo

<400> SEQUENCE: 108 ttttttttttt acgccaccag ctccaactac cacaagttta tattcagtca ttttcagcag    60
gccttataat                                                            70

<210> SEQ ID NO 109
<211> LENGTH: 70
<212> TYPE: DNA
<213> ORGANISM: Artificial
<220> FEATURE:
<223> OTHER INFORMATION: BRAF top strand capture oligo

<400> SEQUENCE: 109 ttttttttttt gctacagtga aatctcgatg gagtgggtcc catcagtttg aacagttgtc    60
tggatccatt                                                            70

<210> SEQ ID NO 110
<211> LENGTH: 70
<212> TYPE: DNA
<213> ORGANISM: Artificial
<220> FEATURE:
<223> OTHER INFORMATION: BRAF bottom strand capture oligo

<400> SEQUENCE: 110 ttttttttttt gatttcactg tagctagacc aaaatcacct atttttactg tgaggtcttc    60
atgaagaaat                                                            70

<210> SEQ ID NO 111
<211> LENGTH: 70
<212> TYPE: DNA
<213> ORGANISM: Artificial
<220> FEATURE:
<223> OTHER INFORMATION: TP53 Exon 5.1 top strand capture oligo

<400> SEQUENCE: 111 ttttttttttt aagacctgcc ctgtgcagct gtgggttgat tccacacccc cgcccggcac    60
ccgcgtccgc                                                            70

<210> SEQ ID NO 112
<211> LENGTH: 70
<212> TYPE: DNA
<213> ORGANISM: Artificial
<220> FEATURE:
<223> OTHER INFORMATION: TP53 Exon 5.1 bottom strand capture oligo

<400> SEQUENCE: 112 ttttttttttt cacagggcag gtcttggcca gttggcaaaa catcttgttg agggcaggag    60
agtactgtag                                                            70

<210> SEQ ID NO 113
<211> LENGTH: 70
<212> TYPE: DNA
<213> ORGANISM: Artificial
<220> FEATURE:
<223> OTHER INFORMATION: TP53 Exon 5.2 top strand capture oligo

<400> SEQUENCE: 113 ttttttttttt aggcgctgcc cccaccatga gcgctgctca gatagcgatg gtgagcagct    60
ggagctggag                                                            70
```

<210> SEQ ID NO 114
<211> LENGTH: 70
<212> TYPE: DNA
<213> ORGANISM: Artificial
<220> FEATURE:
<223> OTHER INFORMATION: TP53 Exon 5.2 bottom strand capture oligo

<400> SEQUENCE: 114
tttttttttt gggcagcgcc tcacaacctc cgtcatgtgc tgtgactgct tgtagatggc    60
catggcgcgg    70

<210> SEQ ID NO 115
<211> LENGTH: 70
<212> TYPE: DNA
<213> ORGANISM: Artificial
<220> FEATURE:
<223> OTHER INFORMATION: TP53 Exon 6 top strand capture oligo

<400> SEQUENCE: 115
tttttttttt ttggatgaca gaaacacttt tcgacatagt gtggtggtgc cctatgagcc    60
gcctgaggtc    70

<210> SEQ ID NO 116
<211> LENGTH: 70
<212> TYPE: DNA
<213> ORGANISM: Artificial
<220> FEATURE:
<223> OTHER INFORMATION: TP53 Exon 6 bottom strand capture oligo

<400> SEQUENCE: 116
tttttttttt gtcatccaaa tactccacac gcaaatttcc ttccactcgg ataagatgct    60
gaggaggagc    70

<210> SEQ ID NO 117
<211> LENGTH: 70
<212> TYPE: DNA
<213> ORGANISM: Artificial
<220> FEATURE:
<223> OTHER INFORMATION: TP53 Exon 7 top strand capture oligo

<400> SEQUENCE: 117
tttttttttt ggcggcatga accggaggcc catcctcacc atcatcacac tggaagactc    60
caggtcagga    70

<210> SEQ ID NO 118
<211> LENGTH: 70
<212> TYPE: DNA
<213> ORGANISM: Artificial
<220> FEATURE:
<223> OTHER INFORMATION: TP53 Exon 7 bottom strand capture oligo

<400> SEQUENCE: 118
tttttttttt catgccgccc atgcaggaac tgttacacat gtagttgtag tggatggtgg    60
tacagtcaga    70

<210> SEQ ID NO 119
<211> LENGTH: 70
<212> TYPE: DNA
<213> ORGANISM: Artificial
<220> FEATURE:
<223> OTHER INFORMATION: TP53 Exon 8 top strand capture oligo

<400> SEQUENCE: 119

```
tttttttttt tgtcctggga gagaccgacg cacagaggaa gagaatctcc gcaagaaagg    60
agagcctcac                                                           70

<210> SEQ ID NO 120
<211> LENGTH: 70
<212> TYPE: DNA
<213> ORGANISM: Artificial
<220> FEATURE:
<223> OTHER INFORMATION: TP53 Exon 8 bottom strand capture oligo

<400> SEQUENCE: 120
tttttttttt cccaggacat gcacaaacac gcacctcaaa gctgttccgt cccagtagat    60
taccactact                                                           70

<210> SEQ ID NO 121
<211> LENGTH: 42
<212> TYPE: DNA
<213> ORGANISM: Artificial
<220> FEATURE:
<223> OTHER INFORMATION: Blunt end linker
<220> FEATURE:
<221> NAME/KEY: misc_feature
<222> LOCATION: (6)..(6)
<223> OTHER INFORMATION: N at position 6 is Deoxyuridine
<220> FEATURE:
<221> NAME/KEY: misc_feature
<222> LOCATION: (12)..(12)
<223> OTHER INFORMATION: N at position 12 is Deoxyuridine
<220> FEATURE:
<221> NAME/KEY: misc_feature
<222> LOCATION: (21)..(21)
<223> OTHER INFORMATION: N at position 21 is Deoxyuridine
<220> FEATURE:
<221> NAME/KEY: misc_feature
<222> LOCATION: (35)..(39)
<223> OTHER INFORMATION: n is a, c, g, or t

<400> SEQUENCE: 121
gtgacnggag tncagacgtg ngctcttccg atctnnnnng cc                       42

<210> SEQ ID NO 122
<211> LENGTH: 21
<212> TYPE: DNA
<213> ORGANISM: Artificial
<220> FEATURE:
<223> OTHER INFORMATION: Blunt end linker
<220> FEATURE:
<221> NAME/KEY: misc_feature
<222> LOCATION: (4)..(8)
<223> OTHER INFORMATION: N at positions 4-8 is 5' nitroindole
<220> FEATURE:
<221> NAME/KEY: misc_feature
<222> LOCATION: (12)..(12)
<223> OTHER INFORMATION: N at position 12 is Deoxyuridine

<400> SEQUENCE: 122
ggcnnnnnag ancggaagag c                                              21

<210> SEQ ID NO 123
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (4)..(4)
<223> OTHER INFORMATION: N at position 4 is Deoxyuridine
<220> FEATURE:
```

```
<221> NAME/KEY: misc_feature
<222> LOCATION: (15)..(15)
<223> OTHER INFORMATION: N at position 15 is Deoxyuridine

<400> SEQUENCE: 123
agancggaag agcgncgtgt agggaaa                                              27

<210> SEQ ID NO 124
<211> LENGTH: 57
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (34)..(34)
<223> OTHER INFORMATION: N at position 34 is Deoxyuridine
<220> FEATURE:
<221> NAME/KEY: misc_feature
<222> LOCATION: (45)..(45)
<223> OTHER INFORMATION: N at position 45 is Deoxyuridine

<400> SEQUENCE: 124
aaaaaaaaaa aaaaaaaaaa aaaaaaaaaa agancggaag agcgncgtgt agggaaa             57

<210> SEQ ID NO 125
<211> LENGTH: 92
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (4)..(4)
<223> OTHER INFORMATION: N at position 4 is Deoxyuridine
<220> FEATURE:
<221> NAME/KEY: misc_feature
<222> LOCATION: (15)..(15)
<223> OTHER INFORMATION: N at position 15 is Deoxyuridine
<220> FEATURE:
<221> NAME/KEY: misc_feature
<222> LOCATION: (31)..(31)
<223> OTHER INFORMATION: N at position 31 is Deoxyuridine
<220> FEATURE:
<221> NAME/KEY: misc_feature
<222> LOCATION: (49)..(49)
<223> OTHER INFORMATION: N at position 49 is Deoxyuridine
<220> FEATURE:
<221> NAME/KEY: misc_feature
<222> LOCATION: (64)..(64)
<223> OTHER INFORMATION: N at position 64 is Deoxyuridine
<220> FEATURE:
<221> NAME/KEY: misc_feature
<222> LOCATION: (80)..(80)
<223> OTHER INFORMATION: N at position 80 is Deoxyuridine

<400> SEQUENCE: 125
agancggaag agcgncgtgt agggaaagag ngtaggatag ggtgtaganc tcggtggtcg          60
ccgnatcatt gcgagtgtgn caagcagaag ac                                       92

<210> SEQ ID NO 126
<211> LENGTH: 82
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (19)..(19)
<223> OTHER INFORMATION: N a position 19 is Deoxyuridine
<220> FEATURE:
<221> NAME/KEY: misc_feature
```

```
<222> LOCATION: (31)..(31)
<223> OTHER INFORMATION: N a position 31 is Deoxyuridine
<220> FEATURE:
<221> NAME/KEY: misc_feature
<222> LOCATION: (49)..(49)
<223> OTHER INFORMATION: N a position 49 is Deoxyuridine
<220> FEATURE:
<221> NAME/KEY: misc_feature
<222> LOCATION: (65)..(65)
<223> OTHER INFORMATION: N a position 65 is Deoxyuridine

<400> SEQUENCE: 126
aaaaaggaag agcacacgnc tgaactccag ncaccgagta atatctcgna tgccgtcttc    60
tgctngacac actcgcaatg at                                             82

<210> SEQ ID NO 127
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (19)..(19)
<223> OTHER INFORMATION: N at position 19 is Deoxyuridine

<400> SEQUENCE: 127
aaaaaggaag agcacacgnc tgaactc                                        27

<210> SEQ ID NO 128
<211> LENGTH: 52
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (44)..(44)
<223> OTHER INFORMATION: N at position 44 is Deoxyuridine

<400> SEQUENCE: 128
aaaaaaaaaa aaaaaaaaaa aaaaaaaaaa ggaagagcac acgnctgaac tc            52

<210> SEQ ID NO 129
<211> LENGTH: 84
<212> TYPE: DNA
<213> ORGANISM: Artificial
<220> FEATURE:
<223> OTHER INFORMATION: Long D702 blunt end Linker
<220> FEATURE:
<221> NAME/KEY: misc_feature
<222> LOCATION: (10)..(10)
<223> OTHER INFORMATION: N at position 10 is Deoxyuridine
<220> FEATURE:
<221> NAME/KEY: misc_feature
<222> LOCATION: (27)..(27)
<223> OTHER INFORMATION: N at position 27 is Deoxyuridine
<220> FEATURE:
<221> NAME/KEY: misc_feature
<222> LOCATION: (35)..(35)
<223> OTHER INFORMATION: N at position 35 is Deoxyuridine
<220> FEATURE:
<221> NAME/KEY: misc_feature
<222> LOCATION: (48)..(48)
<223> OTHER INFORMATION: N at position 48 is Deoxyuridine
<220> FEATURE:
<221> NAME/KEY: misc_feature
<222> LOCATION: (54)..(54)
<223> OTHER INFORMATION: N at position 54 is Deoxyuridine
<220> FEATURE:
<221> NAME/KEY: misc_feature
<222> LOCATION: (63)..(63)
```

<223> OTHER INFORMATION: N at position 63 is Deoxyuridine
<220> FEATURE:
<221> NAME/KEY: misc_feature
<222> LOCATION: (77)..(81)
<223> OTHER INFORMATION: n is a, c, g, or t

<400> SEQUENCE: 129
gcgagtgtgn caagcagaag acggcanacg agatnccgga gagtgacngg agtncagacg    60
tgngctcttc cgatctnnnn ngcc    84

<210> SEQ ID NO 130
<211> LENGTH: 100
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (18)..(18)
<223> OTHER INFORMATION: N at position 18 is Deoxyuridine
<220> FEATURE:
<221> NAME/KEY: misc_feature
<222> LOCATION: (33)..(33)
<223> OTHER INFORMATION: N at position 33 is Deoxyuridine
<220> FEATURE:
<221> NAME/KEY: misc_feature
<222> LOCATION: (51)..(51)
<223> OTHER INFORMATION: N at position 51 is Deoxyuridine
<220> FEATURE:
<221> NAME/KEY: misc_feature
<222> LOCATION: (64)..(64)
<223> OTHER INFORMATION: N at position 64 is Deoxyuridine
<220> FEATURE:
<221> NAME/KEY: misc_feature
<222> LOCATION: (80)..(80)
<223> OTHER INFORMATION: N at position 80 is Deoxyuridine
<220> FEATURE:
<221> NAME/KEY: misc_feature
<222> LOCATION: (96)..(96)
<223> OTHER INFORMATION: N at position 96 is Deoxyuridine

<400> SEQUENCE: 130
agatcggaag agcgtcgngt agggaaagag tgnaggatag ggtgtagatc ncggtggtcg    60
ccgnatcatt gcgagtgtgn caagcagaag acggcntttt    100

<210> SEQ ID NO 131
<211> LENGTH: 70
<212> TYPE: DNA
<213> ORGANISM: Artificial
<220> FEATURE:
<223> OTHER INFORMATION: D503 thiophosphate Linker

<400> SEQUENCE: 131
aatgatacgg cgaccaccga gatctacacc ctatcctaca ctctttccct acacgacgct    60
cttccgatct    70

<210> SEQ ID NO 132
<211> LENGTH: 65
<212> TYPE: DNA
<213> ORGANISM: Artificial
<220> FEATURE:
<223> OTHER INFORMATION: D707 Linker

<400> SEQUENCE: 132
gatcggaaga gcacacgtct gaactccagt cacagcttca gatctcgtat gccgtcttct    60
gcttg    65

```
<210> SEQ ID NO 133
<211> LENGTH: 67
<212> TYPE: DNA
<213> ORGANISM: Artificial
<220> FEATURE:
<223> OTHER INFORMATION: Universal reverse linker bridge
<220> FEATURE:
<221> NAME/KEY: misc_feature
<222> LOCATION: (9)..(9)
<223> OTHER INFORMATION: N at position 9 is Deoxyuridine
<220> FEATURE:
<221> NAME/KEY: misc_feature
<222> LOCATION: (22)..(22)
<223> OTHER INFORMATION: N at position 22 is Deoxyuridine
<220> FEATURE:
<221> NAME/KEY: misc_feature
<222> LOCATION: (38)..(38)
<223> OTHER INFORMATION: N at position 38 is Deoxyuridine
<220> FEATURE:
<221> NAME/KEY: misc_feature
<222> LOCATION: (55)..(55)
<223> OTHER INFORMATION: N at position 55 is Deoxyuridine

<400> SEQUENCE: 133
tgtagatcnc ggtggtcgcc gnatcattgc gagtgtgnca agcagaagac ggcanacgag    60
atttttt                                                              67

<210> SEQ ID NO 134
<211> LENGTH: 70
<212> TYPE: DNA
<213> ORGANISM: Artificial
<220> FEATURE:
<223> OTHER INFORMATION: D504 thiophosphate Linker

<400> SEQUENCE: 134
aatgatacgg cgaccaccga gatctacacg gctctgaaca ctctttccct acacgacgct    60
cttccgatct                                                           70

<210> SEQ ID NO 135
<211> LENGTH: 11
<212> TYPE: DNA
<213> ORGANISM: Artificial
<220> FEATURE:
<223> OTHER INFORMATION: Small 5'-phos Linker

<400> SEQUENCE: 135
cctccgaccg t                                                         11

<210> SEQ ID NO 136
<211> LENGTH: 82
<212> TYPE: DNA
<213> ORGANISM: Artificial
<220> FEATURE:
<223> OTHER INFORMATION: D708 modified Linker
<220> FEATURE:
<221> NAME/KEY: misc_feature
<222> LOCATION: (11)..(16)
<223> OTHER INFORMATION: n is a, c, g, or t

<400> SEQUENCE: 136
cggtcggagg nnnnnnagat cggaagagca cacgtctgaa ctccagtcac gcgcattaat    60
ctcgtatgcc gtcttctgct tg                                             82

<210> SEQ ID NO 137
<211> LENGTH: 70
<212> TYPE: DNA
<213> ORGANISM: Artificial
<220> FEATURE:
```

-continued

<223> OTHER INFORMATION: D505 thiophosphate Linker

<400> SEQUENCE: 137
aatgatacgg cgaccaccga gatctacaca ggcgaagaca ctctttccct acacgacgct    60
cttccgatct                                                          70

<210> SEQ ID NO 138
<211> LENGTH: 9
<212> TYPE: DNA
<213> ORGANISM: Artificial
<220> FEATURE:
<223> OTHER INFORMATION: Primer

<400> SEQUENCE: 138 ctccgaccg                                                            9

<210> SEQ ID NO 139
<211> LENGTH: 79
<212> TYPE: DNA
<213> ORGANISM: Artificial
<220> FEATURE:
<223> OTHER INFORMATION: D506 - 2rG-LNA Linker
<220> FEATURE:
<221> NAME/KEY: misc_feature
<222> LOCATION: (71)..(76)
<223> OTHER INFORMATION: n is a, c, g, or t
<220> FEATURE:
<221> NAME/KEY: misc_feature
<222> LOCATION: (77)..(78)
<223> OTHER INFORMATION: N at positions 77-78 is riboguanosine
<220> FEATURE:
<221> NAME/KEY: misc_feature
<222> LOCATION: (79)..(79)
<223> OTHER INFORMATION: N at positions 79 is locked nucleic acid
      guanosine

<400> SEQUENCE: 139
aatgatacgg cgaccaccga gatctacact aatcttaaca ctctttccct acacgacgct    60
cttccgatct nnnnnnnnn                                                 79

<210> SEQ ID NO 140
<211> LENGTH: 65
<212> TYPE: DNA
<213> ORGANISM: Artificial
<220> FEATURE:
<223> OTHER INFORMATION: D709 Linker

<400> SEQUENCE: 140
gatcggaaga gcacacgtct gaactccagt caccatagcc gatctcgtat gccgtcttct    60
gcttg                                                               65

<210> SEQ ID NO 141
<211> LENGTH: 107
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: N at position 20 is Deoxyuridine
<220> FEATURE:
<221> NAME/KEY: misc_feature
<222> LOCATION: (40)..(40)
<223> OTHER INFORMATION: N at position 40 is Deoxyuridine
<220> FEATURE:
<221> NAME/KEY: misc_feature
<222> LOCATION: (50)..(50)

<223> OTHER INFORMATION: N at position 50 is Deoxyuridine
<220> FEATURE:
<221> NAME/KEY: misc_feature
<222> LOCATION: (66)..(66)
<223> OTHER INFORMATION: N at position 66 is Deoxyuridine
<220> FEATURE:
<221> NAME/KEY: misc_feature
<222> LOCATION: (80)..(80)
<223> OTHER INFORMATION: N at position 80 is Deoxyuridine
<220> FEATURE:
<221> NAME/KEY: misc_feature
<222> LOCATION: (96)..(96)
<223> OTHER INFORMATION: N at position 96 is Deoxyuridine

<400> SEQUENCE: 141
cgatacagct aattcagaan cattttgtgg acgaattttn aggtcgccgn atcattgcga      60
gtgtgncaag cagaagacgn tttttgctgg tggcgnaggc aagagtg                  107

<210> SEQ ID NO 142
<211> LENGTH: 115
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (27)..(27)
<223> OTHER INFORMATION: N at position 27 is Deoxyuridine
<220> FEATURE:
<221> NAME/KEY: misc_feature
<222> LOCATION: (49)..(49)
<223> OTHER INFORMATION: N at position 49 is Deoxyuridine
<220> FEATURE:
<221> NAME/KEY: misc_feature
<222> LOCATION: (59)..(59)
<223> OTHER INFORMATION: N at position 59 is Deoxyuridine
<220> FEATURE:
<221> NAME/KEY: misc_feature
<222> LOCATION: (75)..(75)
<223> OTHER INFORMATION: N at position 75 is Deoxyuridine
<220> FEATURE:
<221> NAME/KEY: misc_feature
<222> LOCATION: (89)..(89)
<223> OTHER INFORMATION: N at position 89 is Deoxyuridine
<220> FEATURE:
<221> NAME/KEY: misc_feature
<222> LOCATION: (106)..(106)
<223> OTHER INFORMATION: N at position 106 is Deoxyuridine

<400> SEQUENCE: 142
ttatattcag tcattttcag caggccntat aataaaaata atgattttna ggtcgccgna      60
tcattgcgag tgtgncaagc agaagacgnt ttttacgcca ccagcnccaa ctacc         115

<210> SEQ ID NO 143
<211> LENGTH: 110
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (14)..(14)
<223> OTHER INFORMATION: N at position 14 is Deoxyuridine
<220> FEATURE:
<221> NAME/KEY: misc_feature
<222> LOCATION: (20)..(20)
<223> OTHER INFORMATION: N at position 20 is Deoxyuridine
<220> FEATURE:
<221> NAME/KEY: misc_feature
<222> LOCATION: (36)..(36)
<223> OTHER INFORMATION: N at position 36 is Deoxyuridine
<220> FEATURE:
<221> NAME/KEY: misc_feature
<222> LOCATION: (46)..(46)
<223> OTHER INFORMATION: N at position 46 is Deoxyuridine
<220> FEATURE:
<221> NAME/KEY: misc_feature
<222> LOCATION: (62)..(62)
<223> OTHER INFORMATION: N at position 62 is Deoxyuridine
<220> FEATURE:
<221> NAME/KEY: misc_feature
<222> LOCATION: (76)..(76)
<223> OTHER INFORMATION: N at position 76 is Deoxyuridine
<220> FEATURE:
<221> NAME/KEY: misc_feature
<222> LOCATION: (94)..(94)
<223> OTHER INFORMATION: N at position 94 is Deoxyuridine
<220> FEATURE:
<221> NAME/KEY: misc_feature
<222> LOCATION: (100)..(100)
<223> OTHER INFORMATION: N at position 100 is Deoxyuridine

<400> SEQUENCE: 143
gtttgaacag ttgnctggan ccattttgtg gttttnaggt cgccgnatca ttgcgagtgt      60
gncaagcaga agacgntttt tgctacagtg aaanctcgan ggagtgggtc                110

<210> SEQ ID NO 144
<211> LENGTH: 130
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is Deoxyuridine
<220> FEATURE:
<221> NAME/KEY: misc_feature
<222> LOCATION: (29)..(29)
<223> OTHER INFORMATION: N at position 29 is Deoxyuridine
<220> FEATURE:
<221> NAME/KEY: misc_feature
<222> LOCATION: (47)..(47)
<223> OTHER INFORMATION: N at position 47 is Deoxyuridine
<220> FEATURE:
<221> NAME/KEY: misc_feature
<222> LOCATION: (57)..(57)
<223> OTHER INFORMATION: N at position 57 is Deoxyuridine
<220> FEATURE:
<221> NAME/KEY: misc_feature
<222> LOCATION: (73)..(73)
<223> OTHER INFORMATION: N at position 73 is Deoxyuridine
<220> FEATURE:
<221> NAME/KEY: misc_feature
<222> LOCATION: (87)..(87)
<223> OTHER INFORMATION: N at position 87 is Deoxyuridine
<220> FEATURE:
<221> NAME/KEY: misc_feature
<222> LOCATION: (107)..(107)
<223> OTHER INFORMATION: N at position 107 is Deoxyuridine

<400> SEQUENCE: 144
gtcttcatga agaaanatat ctgaggtgna gtaagtaaag gattttnagg tcgccgnatc      60
attgcgagtg tgncaagcag aagacgnttt tgatttcac tgtagcnaga ccaaaatcac     120
ctatttttac                                                            130

<210> SEQ ID NO 145
<211> LENGTH: 92
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (13)..(13)

```
<223> OTHER INFORMATION: N at position 13 is Deoxyuridine
<220> FEATURE:
<221> NAME/KEY: misc_feature
<222> LOCATION: (24)..(24)
<223> OTHER INFORMATION: N at position 24 is Deoxyuridine
<220> FEATURE:
<221> NAME/KEY: misc_feature
<222> LOCATION: (34)..(34)
<223> OTHER INFORMATION: N at position 34 is Deoxyuridine
<220> FEATURE:
<221> NAME/KEY: misc_feature
<222> LOCATION: (50)..(50)
<223> OTHER INFORMATION: N at position 50 is Deoxyuridine
<220> FEATURE:
<221> NAME/KEY: misc_feature
<222> LOCATION: (64)..(64)
<223> OTHER INFORMATION: N at position 64 is Deoxyuridine
<220> FEATURE:
<221> NAME/KEY: misc_feature
<222> LOCATION: (76)..(76)
<223> OTHER INFORMATION: N at position 76 is Deoxyuridine

<400> SEQUENCE: 145
tgattccaca ccnccgccct tttnaggtcg ccgnatcatt gcgagtgtgn caagcagaag      60 acgntttta agaccngccc tgtgcagctg tg                                    92

<210> SEQ ID NO 146
<211> LENGTH: 104
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: N at position 15 is Deoxyuridine
<220> FEATURE:
<221> NAME/KEY: misc_feature
<222> LOCATION: (35)..(35)
<223> OTHER INFORMATION: N at position 35 is Deoxyuridine
<220> FEATURE:
<221> NAME/KEY: misc_feature
<222> LOCATION: (45)..(45)
<223> OTHER INFORMATION: N at position 45 is Deoxyuridine
<220> FEATURE:
<221> NAME/KEY: misc_feature
<222> LOCATION: (61)..(61)
<223> OTHER INFORMATION: N at position 61 is Deoxyuridine
<220> FEATURE:
<221> NAME/KEY: misc_feature
<222> LOCATION: (75)..(75)
<223> OTHER INFORMATION: N at position 75 is Deoxyuridine
<220> FEATURE:
<221> NAME/KEY: misc_feature
<222> LOCATION: (88)..(88)
<223> OTHER INFORMATION: N at position 88 is Deoxyuridine

<400> SEQUENCE: 146
catcttgttg agggnaggag agtactgtag ttttnaggtc gccgnatcat tgcgagtgtg      60
ncaagcagaa gacgntttttt cacagggnag gtcttggcca gttg                     104

<210> SEQ ID NO 147
<211> LENGTH: 95
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (17)..(17)
<223> OTHER INFORMATION: N at position 17 is Deoxyuridine
<220> FEATURE:
<221> NAME/KEY: misc_feature
```

```
<222> LOCATION: (31)..(31)
<223> OTHER INFORMATION: N at position 31 is Deoxyuridine
<220> FEATURE:
<221> NAME/KEY: misc_feature
<222> LOCATION: (41)..(41)
<223> OTHER INFORMATION: N at position 41 is Deoxyuridine
<220> FEATURE:
<221> NAME/KEY: misc_feature
<222> LOCATION: (57)..(57)
<223> OTHER INFORMATION: N at position 57 is Deoxyuridine
<220> FEATURE:
<221> NAME/KEY: misc_feature
<222> LOCATION: (71)..(71)
<223> OTHER INFORMATION: N at position 71 is Deoxyuridine
<220> FEATURE:
<221> NAME/KEY: misc_feature
<222> LOCATION: (83)..(83)
<223> OTHER INFORMATION: N at position 83 is Deoxyuridine

<400> SEQUENCE: 147
gctcagatag cgatggngag cagctgtttt naggtcgccg natcattgcg agtgtgncaa      60
gcagaagacg nttttttaggc gcngccccca ccatg                                95

<210> SEQ ID NO 148
<211> LENGTH: 96
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is Deoxyuridine
<220> FEATURE:
<221> NAME/KEY: misc_feature
<222> LOCATION: (31)..(31)
<223> OTHER INFORMATION: N at position 31 is Deoxyuridine
<220> FEATURE:
<221> NAME/KEY: misc_feature
<222> LOCATION: (41)..(41)
<223> OTHER INFORMATION: N at position 41 is Deoxyuridine
<220> FEATURE:
<221> NAME/KEY: misc_feature
<222> LOCATION: (57)..(57)
<223> OTHER INFORMATION: N at position 57 is Deoxyuridine
<220> FEATURE:
<221> NAME/KEY: misc_feature
<222> LOCATION: (71)..(71)
<223> OTHER INFORMATION: N at position 71 is Deoxyuridine
<220> FEATURE:
<221> NAME/KEY: misc_feature
<222> LOCATION: (80)..(80)
<223> OTHER INFORMATION: N at position 80 is Deoxyuridine

<400> SEQUENCE: 148
gtgctgtgac tgcttgtaga nggccatttt naggtcgccg natcattgcg agtgtgncaa      60
gcagaagacg nttttttgggn agcgcctcac aacctc                               96

<210> SEQ ID NO 149
<211> LENGTH: 105
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: 'N at position 15 is Deoxyuridine
<220> FEATURE:
<221> NAME/KEY: misc_feature
<222> LOCATION: (27)..(27)
<223> OTHER INFORMATION: 'N at position 27 is Deoxyuridine
<220> FEATURE:
```

<221> NAME/KEY: misc_feature
<222> LOCATION: (37)..(37)
<223> OTHER INFORMATION: 'N at position 37 is Deoxyuridine
<220> FEATURE:
<221> NAME/KEY: misc_feature
<222> LOCATION: (53)..(53)
<223> OTHER INFORMATION: 'N at position 53 is Deoxyuridine
<220> FEATURE:
<221> NAME/KEY: misc_feature
<222> LOCATION: (67)..(67)
<223> OTHER INFORMATION: 'N at position 67 is Deoxyuridine
<220> FEATURE:
<221> NAME/KEY: misc_feature
<222> LOCATION: (78)..(78)
<223> OTHER INFORMATION: 'N at position 78 is Deoxyuridine

<400> SEQUENCE: 149
ccctatgagc cgccngaggt cttttttnagg tcgccgnatc attgcgagtg tgncaagcag    60
aagacgnttt ttttgganga cagaaacact tttcgacata gtgtg    105

<210> SEQ ID NO 150
<211> LENGTH: 107
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (22)..(22)
<223> OTHER INFORMATION: N at position 22 is Deoxyuridine
<220> FEATURE:
<221> NAME/KEY: misc_feature
<222> LOCATION: (32)..(32)
<223> OTHER INFORMATION: N at position 32 is Deoxyuridine
<220> FEATURE:
<221> NAME/KEY: misc_feature
<222> LOCATION: (42)..(42)
<223> OTHER INFORMATION: N at position 42 is Deoxyuridine
<220> FEATURE:
<221> NAME/KEY: misc_feature
<222> LOCATION: (58)..(58)
<223> OTHER INFORMATION: N at position 58 is Deoxyuridine
<220> FEATURE:
<221> NAME/KEY: misc_feature
<222> LOCATION: (72)..(72)
<223> OTHER INFORMATION: N at position 72 is Deoxyuridine
<220> FEATURE:
<221> NAME/KEY: misc_feature
<222> LOCATION: (88)..(88)
<223> OTHER INFORMATION: N at position 88 is Deoxyuridine

<400> SEQUENCE: 150
tcggataaga tgctgaggag gngccagttt tnaggtcgcc gnatcattgc gagtgtgnca    60
agcagaagac gnttttttgtc atccaaanac tccacacgca aatttcc    107

<210> SEQ ID NO 151
<211> LENGTH: 98
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (22)..(22)
<223> OTHER INFORMATION: N at position 22 is Deoxyuridine
<220> FEATURE:
<221> NAME/KEY: misc_feature
<222> LOCATION: (32)..(32)
<223> OTHER INFORMATION: N at position 32 is Deoxyuridine
<220> FEATURE:
<221> NAME/KEY: misc_feature
<222> LOCATION: (42)..(42)
<223> OTHER INFORMATION: N at position 42 is Deoxyuridine

```
<220> FEATURE:
<221> NAME/KEY: misc_feature
<222> LOCATION: (58)..(58)
<223> OTHER INFORMATION: N at position 58 is Deoxyuridine
<220> FEATURE:
<221> NAME/KEY: misc_feature
<222> LOCATION: (72)..(72)
<223> OTHER INFORMATION: N at position 72 is Deoxyuridine
<220> FEATURE:
<221> NAME/KEY: misc_feature
<222> LOCATION: (85)..(85)
<223> OTHER INFORMATION: N at position 85 is Deoxyuridine

<400> SEQUENCE: 151
accatcatca cactggaaga cnccaggttt tnaggtcgcc gnatcattgc gagtgtgnca     60
agcagaagac gnttttggc ggcangaacc ggagaccc                             98

<210> SEQ ID NO 152
<211> LENGTH: 103
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (23)..(23)
<223> OTHER INFORMATION: N at position 23 is Deoxyuridine
<220> FEATURE:
<221> NAME/KEY: misc_feature
<222> LOCATION: (36)..(36)
<223> OTHER INFORMATION: N at position 36 is Deoxyuridine
<220> FEATURE:
<221> NAME/KEY: misc_feature
<222> LOCATION: (46)..(46)
<223> OTHER INFORMATION: N at position 46 is Deoxyuridine
<220> FEATURE:
<221> NAME/KEY: misc_feature
<222> LOCATION: (62)..(62)
<223> OTHER INFORMATION: N at position 62 is Deoxyuridine
<220> FEATURE:
<221> NAME/KEY: misc_feature
<222> LOCATION: (76)..(76)
<223> OTHER INFORMATION: N at position 76 is Deoxyuridine
<220> FEATURE:
<221> NAME/KEY: misc_feature
<222> LOCATION: (86)..(86)
<223> OTHER INFORMATION: N at position 86 is Deoxyuridine

<400> SEQUENCE: 152
atgtagttgt agtggatggt ggnacagtca gttttnaggt cgccgnatca ttgcgagtgt    60
gncaagcaga agacgntttt tcatgncgcc catgcaggaa ctg                     103

<210> SEQ ID NO 153
<211> LENGTH: 99
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (25)..(25)
<223> OTHER INFORMATION: N at position 25 is Deoxyuridine
<220> FEATURE:
<221> NAME/KEY: misc_feature
<222> LOCATION: (34)..(34)
<223> OTHER INFORMATION: N at position 34 is Deoxyuridine
<220> FEATURE:
<221> NAME/KEY: misc_feature
<222> LOCATION: (44)..(44)
<223> OTHER INFORMATION: N at position 44 is Deoxyuridine
<220> FEATURE:
<221> NAME/KEY: misc_feature
<222> LOCATION: (60)..(60)
```

```
<223> OTHER INFORMATION: N at position 60 is Deoxyuridine
<220> FEATURE:
<221> NAME/KEY: misc_feature
<222> LOCATION: (74)..(74)
<223> OTHER INFORMATION: N at position 74 is Deoxyuridine
<220> FEATURE:
<221> NAME/KEY: misc_feature
<222> LOCATION: (85)..(85)
<223> OTHER INFORMATION: N at position 85 is Deoxyuridine

<400> SEQUENCE: 153
ggaagagaat ctccgcaaga aaggngagct tttnaggtcg ccgnatcatt gcgagtgtgn      60
caagcagaag acgnttttt gtccngggag agaccggcg                              99

<210> SEQ ID NO 154
<211> LENGTH: 107
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (17)..(17)
<223> OTHER INFORMATION: N at position 17 is Deoxyuridine
<220> FEATURE:
<221> NAME/KEY: misc_feature
<222> LOCATION: (35)..(35)
<223> OTHER INFORMATION: N at position 35 is Deoxyuridine
<220> FEATURE:
<221> NAME/KEY: misc_feature
<222> LOCATION: (45)..(45)
<223> OTHER INFORMATION: N at position 45 is Deoxyuridine
<220> FEATURE:
<221> NAME/KEY: misc_feature
<222> LOCATION: (61)..(61)
<223> OTHER INFORMATION: N at position 61 is Deoxyuridine
<220> FEATURE:
<221> NAME/KEY: misc_feature
<222> LOCATION: (75)..(75)
<223> OTHER INFORMATION: N at position 75 is Deoxyuridine
<220> FEATURE:
<221> NAME/KEY: misc_feature
<222> LOCATION: (90)..(90)
<223> OTHER INFORMATION: N at position 90 is Deoxyuridine

<400> SEQUENCE: 154
gttccgtccc agtagantac cactactcag ttttnaggtc gccgnatcat tgcgagtgtg      60
ncaagcagaa gacgnttttt cccaggacan gcacaaacac gcacctc                   107
```

METHOD FOR IDENTIFICATION AND ENUMERATION OF NUCLEIC ACID SEQUENCE, EXPRESSION, COPY, OR DNA METHYLATION CHANGES, USING COMBINED NUCLEASE, LIGASE, POLYMERASE, AND SEQUENCING REACTIONS

This application is a division of U.S. patent application Ser. No. 15/316,778, which is a national stage application under 35 U.S.C. § 371 of PCT Application No. PCT/US2015/034724, filed Jun. 8, 2015, which claims the benefit of U.S. Provisional Patent Application Ser. No. 62/009,047, filed Jun. 6, 2014, and 62/136,093, filed Mar. 20, 2015, each of which is hereby incorporated by reference in its entirety.

FIELD OF THE INVENTION

The present invention relates to a method for the highly specific, targeted capture of regions of human genomes and transcriptomes from the blood, i.e. from cell free circulating DNA, exosomes, microRNA, circulating tumor cells, or total blood cells, to allow for the highly sensitive detection of mutation, expression, copy number, translocation, alternative splicing, and methylation changes using combined nuclease, ligation, polymerase, and sequencing reactions.

BACKGROUND OF THE INVENTION

Advances in DNA sequencing hold the promise to standardize and develop non-invasive molecular diagnosis to improve prenatal care, transplantation efficacy, cancer and other disease detection and individualized treatment. Currently, patients with predisposing or early disease are not identified, and those with disease are not given the best treatment—all because of failures at the diagnostic level.

In the cancer field, there is a need to develop such technology for early detection, guiding therapy, and monitoring for recurrence—all from a blood sample. This includes the need to develop: (i) high sensitivity detection of single base mutation, small insertion, and small deletion mutations in known genes (when present at 1% to 0.01% of cell-free DNA); (ii) high sensitivity detection of promoter hypermethylation and hypomethylation (when present at 1% to 0.01% of cell-free DNA); (iii) accurate quantification of tumor-specific mRNA, lncRNA, and miRNA isolated from tumor-derived exosomes or RISC complex, or circulating tumor cells in blood; (iv) accurate quantification of tumor-specific copy changes in DNA isolated from circulating tumor cells; (v) accurate quantification of mutations, promoter hypermethylation and hypomethylation in DNA isolated from circulating tumor cells. All these (except quantification of tumor-specific copy changes in DNA isolated from circulating tumor cells) require focusing the sequencing on targeted genes or regions of the genome. Further, determination of the sequence information or methylation status from both strands of the original fragment provides critically needed confirmation of rare events.

Normal plasma contains nucleic acids released from normal cells undergoing normal physiological processes (i.e. exosomes, apoptosis). There may be additional release of nucleic acids under conditions of stress, inflammation, infection, or injury. In general, DNA released from apoptotic cells in an average of 160 bp in length, while DNA from fetal cells is an average of about 140 bp. Plasma from a cancer patient contains nucleic acids released from cancer cells undergoing abnormal physiological processes, as well as within circulating tumor cells (CTCs). Likewise, plasma from a pregnant woman contains nucleic acids released from fetal cells.

There are a number of challenges for developing reliable diagnostic and screening tests. The first challenge is to distinguish those markers emanating from the tumor or fetus that are indicative of disease (i.e. early cancer) vs. presence of the same markers emanating from normal tissue. There is also a need to balance the number of markers examined and the cost of the test, with the specificity and sensitivity of the assay. This is a challenge that needs to address the biological variation in diseases such as cancer. In many cases the assay should serve as a screening tool, requiring the availability of secondary diagnostic follow-up (i.e. colonoscopy, amniocentesis). Compounding the biological problem is the need to reliably detect nucleic acid sequence mutation or promoter methylation differences, or reliably quantify DNA or RNA copy number from either a very small number of initial cells (i.e. from CTCs), or when the cancer or fetus-specific signal is in the presence of a majority of nucleic acid emanating from normal cells. Finally, there is the technical challenge to distinguish true signal resulting from detecting the desired disease-specific nucleic acid differences vs. false signal generated from normal nucleic acids present in the sample vs. false signal generated in the absence of the disease-specific nucleic acid differences.

By way of an example, consider the challenge of detecting, in plasma, the presence of circulating tumor DNA harboring a mutation in the p53 gene or a methylated promoter region. Such a sample will contain a majority of cell-free DNA arising from normal cells, where the tumor DNA may only comprise 0.01% of the total cell-free DNA. Thus, if one were to attempt to find the presence of such mutant DNA by total sequencing, one would need to sequence 100,000 genomes to identify 10 genomes harboring the mutations. This would require sequencing 300,000 GB of DNA, a task beyond the reach of current sequencing technology, not to mention the enormous data-management issues. To circumvent this problem, many groups have attempted to capture specific target regions or to PCR amplify the regions in question. Sequence capture has suffered from dropout, such that maybe 90-95% of the desired sequences are captured, but desired fragments are missing. Alternatively, PCR amplification provides the risk of introducing a rare error that is indistinguishable from a true mutation. Further, PCR loses methylation information. While bisulfite treatment has been traditionally used to determine the presence of promoter methylation, it is also destructive of the DNA sample and lacks the ability to identify multiple methylation changes in cell-free DNA.

There are a number of different approaches for reducing error rate and improving the accuracy of sequencing runs. A consensus accuracy may be achieved in the presence of high error rates by sequencing the same region of DNA over and over again. However, a high error rate makes it extremely difficult to identify a sequence variant in low abundance, for example when trying to identify a cancer mutation in the presence of normal DNA. Therefore, a low error rate is required to detect a mutation in relatively low abundance.

The first approach termed tagged-amplicon deep sequencing (TAm-Seq) method (Forshew et al., "Noninvasive Identification and Monitoring of Cancer Mutations by Targeted Deep Sequencing of Plasma DNA," Sci Transl Med. 4(136): 136 (2012)) is based on designing primers to amplify 5995 bases that covered select regions of cancer-related genes, including TP53, EGFR, BRAF, and KRAS. This approach is able identify mutations in the p53 gene at frequencies of 2% to 65%. In this approach, primers are designed to preamplify the DNA (for 15 cycles) in a multiplexed reaction with many PCR primers. This creates both desired and undesired products, so it is followed with single-plex PCR to further amplify each of the desired products. The fragments subject to a final barcoding PCR prior to standard next-generation sequencing. The advantage of this approach is it uses the time tested multiplexed PCR-PCR, which is unparalleled for amplification of low numbers of starting nucleic acids. The disadvantage is that this approach is unable to distinguish a true mutation from a PCR error in the early rounds of amplification. Thus while the sensitivity of 2% (i.e. detecting one mutant allele in 50 wt alleles) is sufficient for evaluating late-stage cancers prior to making a treatment decision, it is not sensitive enough for early detection.

A variation of the first approach is termed Safe-Sequencing System "Safe-SeqS" (Kinde et al., "Detection and Quantification of Rare Mutations with Massively Parallel Sequencing," *Proc Natl Acad Sci USA* 108(23):9530-5 (2011)), where randomly sheared genomic DNA is appended onto the ends of linkers ligated to genomic DNA. The approach demonstrated that the vast majority of mutations described from genomic sequencing are actually errors, and reduced presumptive sequencing errors by at least 70-fold. Likewise, an approach called ultrasensitive deep sequencing (Narayan et al., "Ultrasensitive Measurement of Hotspot Mutations in Tumor DNA in Blood Using Error-suppressed Multiplexed Deep Sequencing," *Cancer Res.* 72(14):3492-8 (2012)) appends bar codes onto primers for a nested PCR amplification. Presumably, a similar system of appending barcodes was developed to detect rare mutations and copy number variations that depends on bioinformatics tools (Talasaz, A.; Systems and Methods to Detect Rare Mutations and Copy Number Variation, US Patent Application US 2014/0066317 A1, Mar. 6, 2014). Paired-end reads are used to cover the region containing the presumptive mutation. This method was used to track known mutations in plasma of patients with late stage cancer. These approaches require many reads to establish consensus sequences. Both of these methods requires extending across the target DNA, and thus it would be impossible to distinguish true mutation, from polymerase generated error, especially when copying across a damaged base, such as deaminated cytosine. Finally, these methods do not provide information on methylation status of CpG sites within the fragment.

The second approach termed Duplex sequencing (Schmitt et al., "Detection of Ultra-Rare Mutations by Next-Generation Sequencing," *Proc Natl Acad Sci USA* 109(36):14508-13 (2012)) is based on using duplex linkers containing 12 base randomized tags. By amplifying both top and bottom strands of input target DNA, a given fragment obtains a unique identifier (comprised of 12 bases on each end) such that it may be tracked via sequencing. Sequence reads sharing a unique set of tags are grouped into paired families with members having strand identifiers in either the top-strand or bottom-strand orientation. Each family pair reflects the amplification of one double-stranded DNA fragment. Mutations present in only one or a few family members represent sequencing mistakes or PCR-introduced errors occurring late in amplification. Mutations occurring in many or all members of one family in a pair arise from PCR errors during the first round of amplification such as might occur when copying across sites of mutagenic DNA damage. On the other hand, true mutations present on both strands of a DNA fragment appear in all members of a family pair. Whereas artifactual mutations may co-occur in a family pair with a true mutation, all except those arising during the first round of PCR amplification can be independently identified and discounted when producing an error-corrected single-strand consensus sequence. The sequences obtained from each of the two strands of an individual DNA duplex can then be compared to obtain the duplex consensus sequence, which eliminates remaining errors that occurred during the first round of PCR. The advantage of this approach is that it unambiguously distinguishes true mutations from PCR errors or from mutagenic DNA damage, and achieves an extraordinarily low error rate of $3.8 \times 10^{-10}$. The disadvantage of this approach is that many fragments need to be sequenced in order to get at least five members of each strand in a family pair (i.e. minimum of 10 sequence reads per original fragment, but often requiring far more due to fluctuations). Further, the method has not been tested on cfDNA, which tend to be smaller then fragments generated from intact genomic DNA, and thus would require sequencing more fragments to cover all potential mutations. Finally, the method does not provide information on methylation status of CpG sites within the fragment.

The third approach, termed smMIP for Single molecule molecular inversion probes (Hiatt et al., "Single Molecule Molecular Inversion Probes for Targeted, High-Accuracy Detection of Low-Frequency Variation," *Genome Res.* 23(5):843-54 (2013) combines single molecule tagging with multiplex capture to enable highly sensitive detection of low-frequency subclonal variation. The method claims an error rate of $2.6 \times 10^{-5}$ in clinical specimens. The disadvantage of this approach is that many fragments need to be sequenced in order to get at least five members of each strand in a family pair (i.e. minimum of 10 sequence reads per original fragment, but often requiring far more due to fluctuations). Also, the method requires extending across the target DNA, and thus it would be impossible to distinguish true mutation, from polymerase-generated error, especially when copying across a damaged base, such as deaminated cytosine. Further, the method has not been tested on cfDNA, which tend to be smaller then fragments generated from intact genomic DNA, and thus would require sequencing more fragments to cover all potential mutations. Finally, the method does not provide information on methylation status of CpG sites within the fragment.

The fourth approach, termed circle sequencing (Lou et al., "High-throughput DNA Sequencing Errors are Reduced by Orders of Magnitude Using Circle Sequencing," *Proc Natl Acad Sci USA* 110(49):19872-7 (2013), see also Mutational and fitness landscapes of an RNA virus revealed through population sequencing. Acevedo A, Brodsky L, Andino R., Nature. 2014 Jan. 30; 505(7485):686-90; and Library preparation for highly accurate population sequencing of RNA viruses. Acevedo A, Andino R. Nat Protoc. 2014 July; 9(7):1760-9.) is based on shearing DNA or RNA to about 150 bases, denaturing to form single strands, circularizing those single strands, using random hexamer primers and phi29 DNA polymerase for rolling circle amplification (in the presence of Uracil-DNA glycosylase and Formamidopyrimidine-DNA glycosylase), re-shearing the products to about 500 bases, and then proceeding with standard next generation sequencing. The advantage of this approach is that the rolling circle amplification makes multiple tandem copies off the original target DNA, such that a polymerase error may appear in only one copy, but a true mutation appears in all copies. The read families average 3 copies in size because the copies are physically linked to each other. The method also uses Uracil-DNA glycosylase and Formamidopyrimidine-DNA glycosylase to remove targets containing damaged bases, to eliminate such errors. The advantage of this technology is that it takes the sequencing error rate from a current level of about 0.1 to $1\times10^{-2}$, to a rate as low as $7.6\times10^{-6}$. The latter error rate is now sufficient to distinguish cancer mutations in plasma in the presence of 100 to 10,000-fold excess of wild-type DNA. A further advantage is that 2-3 copies of the same sequence are physically linked, allowing for verification of a true mutation from sequence data generated from a single fragment, as opposed to at least 10 fragments using the Duplex sequencing approach. However, the method does not provide the ability to determine copy number changes, nor provide information on methylation status of CpG sites within the fragment.

The fifth approach, developed by Complete Genomics (Drmanac et al., "Human Genome Sequencing Using Unchained Base Reads on Self-Assembling DNA Nanoarrays," *Science* 327(5961):78-81 (2010)) is based on using ligation reads on nanoball arrays. About 400 nucleotides of genomic DNA are circularized with linkers, cleaved, recircularized with additional linkers, and ultimately recircularized to contain about four linkers. The DNA undergoes rolling circle amplification using phi 29 DNA polymerase to generate nanoballs. These are then placed onto an array, and sequenced using a ligation-based approach. The salient point of this approach, of relevance herein, is that multiple tandem copies of the same sequence may be generated and subsequently sequenced off a single rolling circle amplification product. Since the same sequence is interrogated multiple times by either ligase or polymerase (by combining rolling circle with other sequencing by synthesis approaches), the error rate per base may be significantly reduced. As such, sequencing directly off a rolling circle product provides many of the same advantages of the circle sequencing approach described above.

The sixth approach, termed SMRT—single molecule real time-sequencing (Flusberg et al., "Direct Detection of DNA Methylation During Single-Molecule, Real-Time Sequencing," *Nat Methods* 7(6):461-5 (2010)) is based on adding hairpin loops onto the ends of a DNA fragment, and allowing a DNA polymerase with strand-displacement activity to extend around the covalently closed loop, providing sequence information on the two complementary strands. Specifically, single molecules of polymerase catalyze the incorporation of fluorescently labeled nucleotides into complementary nucleic acid strands. The polymerase slows down or "stutters" when incorporating a nucleotide opposite a methylated base, and the resulting fluorescence pulses allow direct detection of modified nucleotides in the DNA template, including N6-methyladenine, 5-methylcytosine and 5-hydroxymethylcytosine. The accuracy of the approach has improved, especially as the polymerase may traverse around the closed loop several times, allowing for determination of a consensus sequence. Although the technique is designed to provide sequence information on "dumbbell" shaped substrates (containing mostly the two complementary sequences of a linear fragment of DNA), it may also be applied to single-stranded circular substrates.

The present invention is directed at overcoming these and other deficiencies in the art.

SUMMARY OF THE INVENTION

A first aspect of the present invention is directed to a collection of different circular chimeric single-stranded nucleic acid constructs. Each construct of the collection comprised a first single stranded segment of original genomic DNA from a host organism and a second single stranded synthetic nucleic acid segment that is linked to the first single stranded segment and comprises a nucleotide sequence that is exogenous to the host organism. The second single stranded synthetic nucleic acid segment comprises a unique identifier portion, wherein the nucleotide sequence of both the unique identifier portion and the segment of original genomic DNA distinguishes one chimeric single-stranded nucleic acid construct in the collection from every other chimeric single-stranded nucleic acid construct in the collection. The chimeric single-stranded nucleic acid constructs of the collection are circularized and suitable for rolling circle amplification and/or sequencing.

Another aspect of the present invention is directed to a system comprising a collection of different circular chimeric single-stranded nucleic acid constructs. Each construct of the collection comprises a first single stranded segment of original genomic DNA from a host organism and a second single stranded nucleic acid segment that is linked to the first single stranded segment and comprises a nucleotide sequence that is exogenous to the host organism. The nucleotide sequence of the second single stranded nucleic acid segment comprises a first solid support primer-specific portion, a second solid support primer-specific portion, and a patient identifier sequence. The chimeric single-stranded nucleic acid constructs of the collection are circularized and suitable for rolling circle amplification and/or sequencing. The system further comprises a collection of extension products, each extension product comprising two or more tandem linear sequences complementary to the chimeric single-stranded nucleic acid construct from the collection. Each extension product in the collection is hybridized to its complementary circular chimeric single-stranded nucleic acid construct of the collection.

Another aspect of the present invention is directed to a system comprising a collection of different circular chimeric single-stranded nucleic acid constructs. Each construct comprises a first single stranded segment of original genomic DNA from a host organism and a second single stranded nucleic acid segment that is linked to the first single stranded segment and comprises a nucleotide sequence that is exogenous to the host organism. The nucleotide sequence of the second single stranded nucleic acid segment comprises a first solid support primer-specific portion, a second solid support primer-specific portion, and a patient identifier sequence. The chimeric single-stranded nucleic acid constructs of the collection are suitable for rolling circle amplification and/or sequencing. The system further comprises one or more oligonucleotide amplification primers, each primer comprising at least a first nucleotide sequence portion that is complementary to the first solid support primer-specific portion or the second solid support primer-specific portion of the chimeric single-stranded nucleic acid constructs of the collection; and a polymerase suitable for rolling circle amplification.

Other aspects of the present invention are directed to methods of sequencing a plurality of nucleic acid molecules in a sample using the collection and systems of the present invention.

Another aspect of the present invention is directed to a method for identifying, in a sample, one or more target ribonucleic acid molecules differing from other nucleic acid molecules in the sample by one or more bases. This method involves providing a sample containing one or more target ribonucleic acid molecules potentially containing one or more base differences and generating, in the sample, cDNA of the one or more target ribonucleic acid molecules, if present in the sample. The method further involves providing one or more first oligonucleotide probes, each first oligonucleotide probe comprising (a) a 3' cDNA target-specific sequence portion, (b) a 5'cDNA target specific portion, and a further portion, said further portion comprising (i) a unique identifier sequence, (ii) a patient identifier sequence, (iii) one or more primer binding sequences, or any combination of (i), (ii), and (iii), and contacting the sample and the one or more first oligonucleotide probes under conditions effective for 3' and 5' target specific portions of the first oligonucleotide probes to hybridize in a base specific manner to complementary regions of the cDNA. One or more ligation competent junctions suitable for coupling 3' and 5' ends of a first oligonucleotide probe hybridized to its complementary cDNA is generated and the one or more first oligonucleotide probes at the one or more ligation junctions is ligated to form circular ligated products comprising a deoxyribonucleic acid copy of the target ribonucleic acid sequence coupled to the further portion of the first oligonucleotide probe. The method further involves detecting and distinguishing the circular ligated products in the sample to identify the presence of one or more target ribonucleic acid molecules differing from other ribonucleic acid molecules in the sample by one or more bases.

Another aspect of the present invention is directed to a method for identifying, in a sample, one or more nucleic acid molecules potentially comprising distinct first target and second target regions coupled to each other. This method involves providing a sample potentially containing one or more nucleic acid molecules comprising distinct first target and second target regions coupled to each other, and providing one or more oligonucleotide probe sets, each probe set comprising (i) a first oligonucleotide probe comprising a 5' first target-specific portion, a 3' second target specific portion, and a further portion, and (ii) a second oligonucleotide probe comprising a 5' second target specific portion, a 3' first target specific portion, and a further portion, wherein the further portion of the first or second oligonucleotide probes of a probe set comprises (i) a unique identifier sequence, (ii) a patient identifier sequence, (iii) one or more primer binding sequences, or any combination of (i), (ii), and (iii). This method further involves contacting the sample and the one or more oligonucleotide probe sets under conditions effective for first and second oligonucleotide probes of a probe set to hybridize in a base specific manner to their corresponding first and second target regions of the nucleic acid molecule, if present in the sample, and generating one or more ligation competent junctions suitable for coupling 3' ends of first oligonucleotide probes to 5' ends of second oligonucleotide probes of a probe set and for coupling 5' ends of first oligonucleotide probes to 3' ends of second oligonucleotide probes of a probe set when said probe sets are hybridized to complementary first and second target regions of a nucleic acid molecule. The first and second oligonucleotides of a probe set are ligated at the one or more ligation competent junctions to form circular ligated products comprising a nucleotide sequence corresponding to the first and second distinct target regions of a nucleic acid molecule coupled to a further portion, and the circular ligated products are detected and distinguished in the sample thereby identifying the presence, if any, of one or more nucleic acid molecules comprising distinct first target and second target regions coupled to each other in the sample.

Another aspect of the present invention is directed to a method for identifying, in a sample, one or more target ribonucleic acid molecules differing from other nucleic acid molecules in the sample by one or more bases. This method involves providing a sample containing one or more target ribonucleic acid molecules potentially containing one or more base differences, and appending nucleotide linkers to 3' and 5' ends of the target ribonucleic acid molecules in the sample. This method further involves providing one or more oligonucleotide probes, each oligonucleotide probe comprising (a) a 3' portion complementary to the 3' nucleotide linker of the target ribonucleic acid molecule, (b) a 5' portion complementary to the 5' nucleotide linker of the target ribonucleic acid molecules, and (c) a further portion, said further portion comprising (i) a unique identifier sequence, (ii) a patient identifier sequence, (iii) one or more primer binding sequences, or any combination of (i), (ii), and (iii). The sample is contacted with the one or more oligonucleotide probes under conditions effective for the 3' and 5' portions of the oligonucleotide probes to hybridize in a base specific manner to complementary nucleotide linkers on the target ribonucleic acid molecules, if present in the sample. The 3' end of the hybridized oligonucleotide probe is extended to generate a complement of the one or more target ribonucleic acid molecules, and the 3' extended end of the oligonucleotide probe is ligated to the 5' end of the oligonucleotide probe to form a circular ligated product comprising a sequence complementary to the 3' nucleotide linker of the target ribonucleic acid molecule, a sequence complementary to the 5' nucleotide linker of the target ribonucleic acid molecule, the complement of the one or more target ribonucleic acid molecules, and the further portion of the oligonucleotide probe. This method further involves detecting and distinguishing the circular ligated products in the sample thereby identifying the presence of one or more target ribonucleic acid molecules differing from other nucleic acid molecules in the sample by one or more bases.

Another aspect of the present invention is directed to a method for identifying, in a sample, one or more target ribonucleic acid molecules differing from other nucleic acid molecules in the sample by one or more bases. This method involves providing a sample containing one or more target ribonucleic acid molecules potentially containing one or more base differences, and ligating nucleotide linkers to 3' and 5' ends of the target ribonucleic acid molecules in the sample, wherein said nucleotide linkers are coupled to each other by a further portion, said further portion comprising (i) a unique identifier sequence, (ii) a patient identifier sequence, (iii) one or more primer binding sequences, or any combination of (i), (ii), and (iii), whereby said ligating forms a circular ligation product comprising the target ribonucleic acid molecule, the 3' and 5' nucleotide linker sequences, and the further portion. This method further involves providing one or more first oligonucleotide primers comprising a nucleotide sequence that is complementary to a 3' or 5' nucleotide linker sequence of the circular ligation product, and hybridizing the one or more first oligonucleotide primers to the circular ligation product in a base specific manner. The 3' end of the first oligonucleotide primer is extended to generate a complement of the circular ligation product, and the circular ligation product complements in the sample are detected and distinguished, thereby identifying the presence of one or more target ribonucleic acid molecules differing from other nucleic acid molecules in the sample by one or more bases.

Another aspect of the present invention is directed to a method for identifying, in a sample, one or more target ribonucleic acid molecules differing from other nucleic acid molecules in the sample by one or more bases. This method involves providing a sample containing one or more target ribonucleic acid molecules potentially containing one or more base differences, and providing one or more oligonucleotide probe sets, each set comprising (a) a first oligonucleotide probe having a 5' stem-loop portion and a 3' portion complementary to a 3' portion of the target ribonucleic acid molecule, (b) a second oligonucleotide probe having a 3' portion complementary to a copy of the 5' end of the target ribonucleic acid molecule, a 5' portion complementary to the 5' stem-loop portion of the first oligonucleotide probe, and a further portion comprising (i) a unique target identifier sequence, (ii) a patient identifier sequence, (iii) a primer binding sequence, or any combination of (i), (ii), and (iii). The method further involves blending the sample, the one or more first oligonucleotide probes from a probe set, and a reverse transcriptase to form a reverse transcriptase reaction, and extending the 3' end of the first oligonucleotide probe hybridized to its complementary target ribonucleic acid molecule to generate a complement of the target ribonucleotide molecule, if present in the sample. The one or more second oligonucleotide probes of a probe set are hybridized to the extended first oligonucleotide probes comprising a complement of the target ribonucleotide sequences, and one or more ligation competent junctions are generated between 3' and 5' ends of each second oligonucleotide probe hybridized to an extended first oligonucleotide probe. The method further involves ligating the 3' and 5' ends of each second oligonucleotide probe to form circular ligated products comprising a deoxyribonucleic acid copy of the target ribonucleic acid sequence coupled to the further portion of the second oligonucleotide probe. The circular ligated products in the sample are detected and distinguished, thereby identifying the presence of one or more target ribonucleic acid molecules differing from other nucleic acid molecules in the sample by one or more bases.

The significance of the invention is that it teaches a method for the highly specific, targeted capture of regions of human genomes and transcriptomes from the blood, i.e. from cell free circulating DNA, exosomes, microRNA, circulating tumor cells, or total blood cells, to allow for the highly sensitive detection of mutation, expression, copy number, translocation, alternative splicing, and methylation changes suitable for use in a high-throughput diagnostics mode. The single-stranded constructs of the invention are suitable for readout by a number of different technologies including Next Generation Sequencing and are designed to be readout technology agnostic. In order to maximize the sensitivity of capture, the invention utilizes not just hybridization but polymerase extension and ligation to decrease false positives. In order to maximize specificity, the unligated probes are exonuclease digested preserving the circularized target sequences. Additional specificity can be obtained by the sequencing of tandem repeats of the original genomic sequence produced by rolling circle amplification. Finally, the invention teaches a method of capturing tandem repeats produced from the original genomic sequence, generated by rolling circle amplification on a surface and then subjecting them to sequencing by synthesis thereby allowing highly accurate mutation detection, methylation status and transcriptome enumeration. The method is especially suited for identifying cancer-specific markers directly from the blood, for cancer screening as well as monitoring treatment efficacy and recurrence. The method is also suited for prenatal diagnosis of copy abnormalities and Mendelian diseases directly from the maternal blood.

BRIEF DESCRIPTION OF THE DRAWINGS

FIG. 1 shows one approach for amplifying the circular chimeric single-stranded nucleic acid constructs of the present invention in preparation for next generation sequencing. This approach uses rolling circle amplification (RCA) or rolling circle replication (RCR) with random hexamers.

FIG. 2 shows a method for generating tandem linear copies of double stranded nucleic acid molecules, suitable for sequencing, from a RCA product.

FIG. 3 shows a method for generating tandem linear copies of nucleic acid molecules, suitable for sequencing. This process specifically selects for fragments that were methylated at all BstU1 sites in the initial target DNA.

FIG. 4 shows alternative approaches for amplifying the circular chimeric single-stranded nucleic acid constructs of the present invention in preparation for next generation sequencing. This approach uses RCA with a single specific primer either in solution or on a surface.

FIG. 5 illustrates one approach for condensing linear DNA amplicons generated in RCA or RCR into a compact structure prior to capture onto a sequencing flow cell surface.

FIG. 6 depicts a method of sequencing a plurality of nucleic acid molecules in a sample using the system and methods of the present invention.

FIG. 7 depicts a method for a amplifying nucleic acid molecules and capturing the resulting amplicons on a solid support suitable for next generation sequencing.

FIG. 8 shows the process of sequencing amplicons prepared in accordance with the methods of the present invention on a solid support surface.

FIG. 9 depicts a method for amplifying nucleic acid molecules and capturing the resulting amplicons on a solid support suitable for next generation sequencing. Sequencing the immobilized amplicons is carried out in accordance with the methods shown in FIG. 8.

FIG. 10 depicts another method for a amplifying nucleic acid molecules and capturing the resulting amplicons on a solid support suitable for next generation sequencing. Sequencing the immobilized amplicons is carried out in accordance with the methods shown in FIG. 8.

FIG. 11 depicts another method for a amplifying nucleic acid molecules and capturing the resulting amplicons on a solid support suitable for next generation sequencing. Sequencing the immobilized amplicons is carried out in accordance with the methods shown in FIG. 8.

FIG. 41 shows a process for producing chimeric circular single stranded nucleic acid constructs suitable for detecting methylated Bsh1236I sites near a 5'-HaeIII site in known regions of genomic DNA.

FIG. 51 depicts a process for detecting methylated adjacent HinP1I sites in known genomic regions.

FIG. 52 depicts a process for detecting unmethylated adjacent AciI sites in known genomic regions.

FIG. 64 shows a process for producing chimeric circular single stranded nucleic acid target constructs from cfDNA or sheared genomic DNA suitable for sequencing.

FIG. 72 shows another exemplary process for producing chimeric circular single stranded nucleic acid target constructs from cfDNA that involves activation with RNase H2.

FIG. 76 shows the generation of single-stranded circular DNA comprising original target cfDNA with a hybridized primer containing a capture group, using RNaseH2 unblocking of target specific primer.

FIG. 84 shows a process to generate and enrich for genomic target specific single stranded tandem repeat extension products suitable for sequencing.

FIG. 85 shows a process to generate and enrich for genomic target specific single stranded tandem repeat extension products suitable for sequencing.

FIG. 88 shows a process to generate and enrich for genomic target specific single stranded tandem repeat extension products suitable for sequencing.

FIG. 89 shows a process to generate and enrich for genomic target specific single stranded tandem repeat extension products suitable for sequencing.

DETAILED DESCRIPTION OF THE INVENTION

Figure 12:
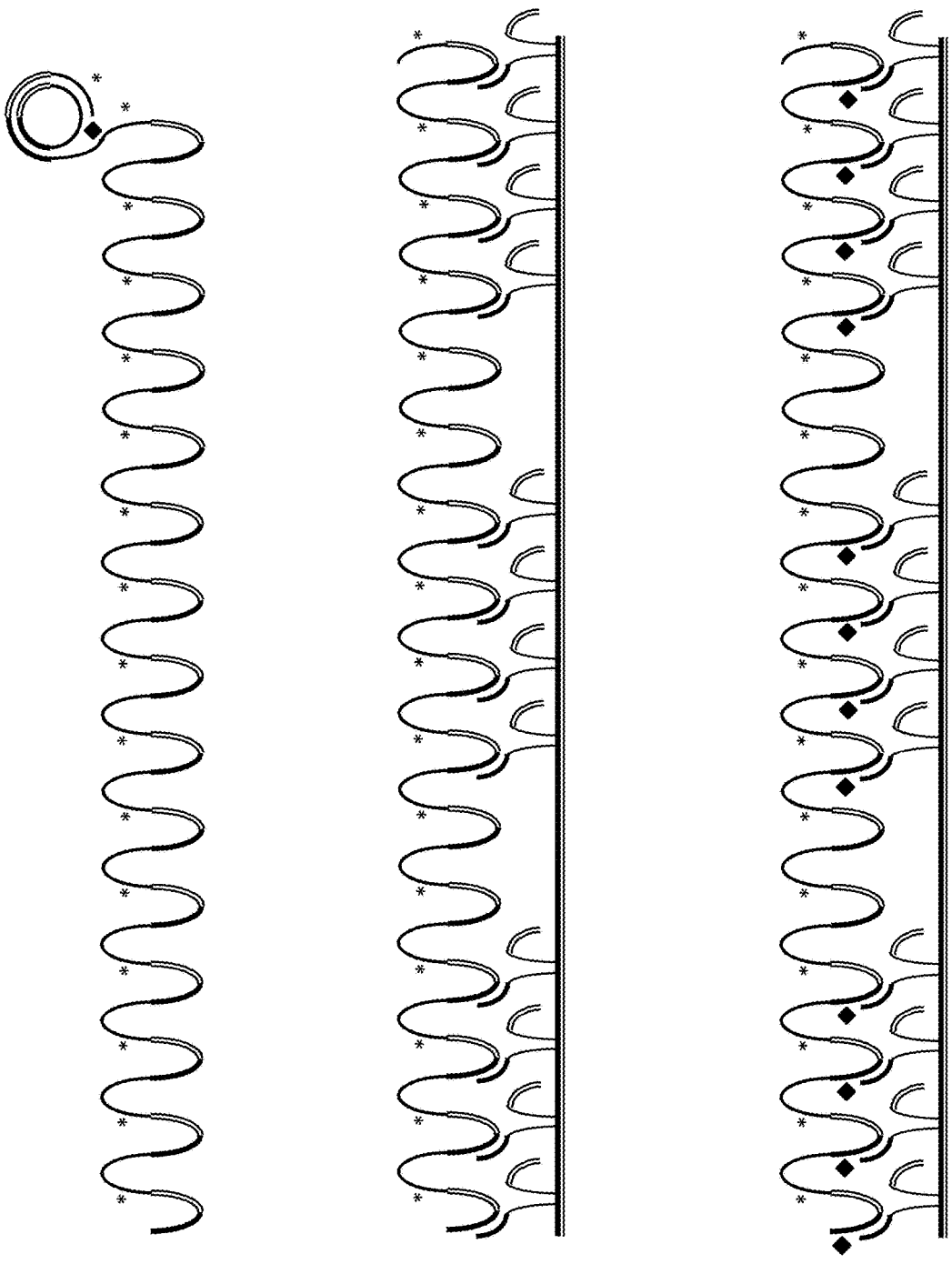
FIG. 12 depicts rolling circle amplification of a circular target to generate single stranded tandem repeat template DNA for capture on a solid support comprising dual primers.
Figure 12:
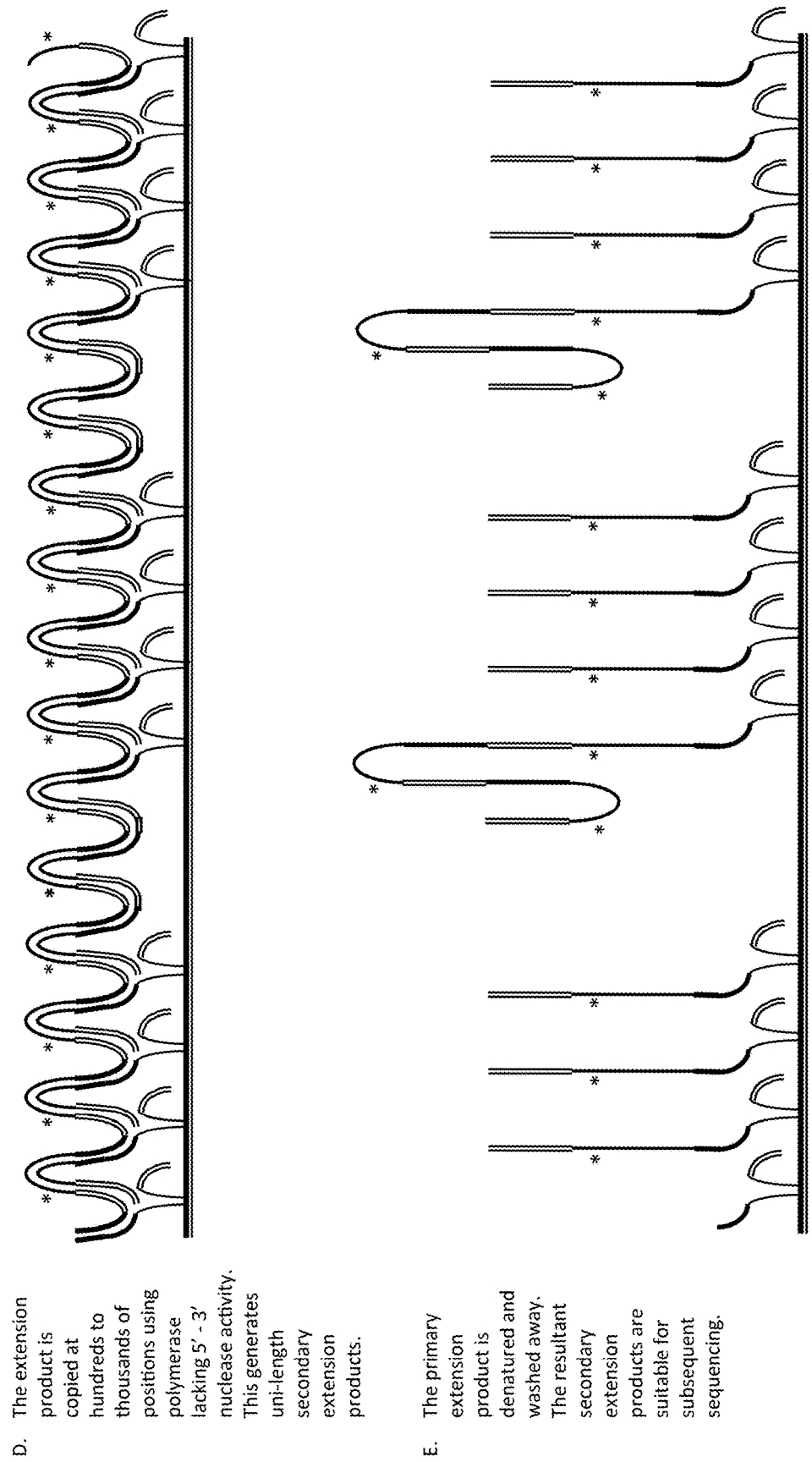

A first aspect of the present invention is directed to a collection of different circular chimeric single-stranded nucleic acid constructs. Each construct of the collection comprises a first single stranded segment of original genomic DNA from a host organism and a second single stranded synthetic nucleic acid segment that is linked to the first single stranded segment and comprises a nucleotide sequence that is exogenous to the host organism. The second single stranded synthetic nucleic acid segment comprises a unique identifier portion, wherein the nucleotide sequence of both the unique identifier portion and the segment of original genomic DNA distinguishes one chimeric single-stranded nucleic acid construct in the collection from every other chimeric single-stranded nucleic acid construct in the collection. The chimeric single-stranded nucleic acid constructs of the collection are circularized and suitable for rolling circle amplification and/or sequencing.

In accordance with this aspect of the present invention, the collection generally contains between 1,000 and 4,000,000,000 circular chimeric single-stranded nucleic acid constructs. Methods of making the circular chimeric single-stranded nucleic acid constructs of the collection are described in detail infra.

The first single stranded segment of the chimeric nucleic acid construct comprises a segment of original genomic DNA from a host. This segment of original genomic DNA may be a nucleic acid fragment that is a direct product of fragmentation of genomic DNA (i.e., without addition of one or more linker portions to the ends of the fragment), or a nucleic acid fragment of genomic DNA to which linkers have been added. The original genomic DNA segment may be derived from any genome, e.g., an animal, plant, protozoa, fungus, bacteria, or virus genome such as the genome of a human, apple tree, giardia, yeast, *Staphylococcus aureus*, or papillomavirus. The segment of DNA can be isolated from any fresh, frozen, or fixed (e.g., formalin-fixed and paraffin embedded) biological source, including, without limitation, tissue, cells, serum, plasma, blood, or exosomes.

The second single stranded synthetic nucleic acid segment of the nucleic acid constructs of the collection is covalently linked to the first single stranded segment, e.g., via a phosphodiester bond. The second single stranded synthetic nucleic acid segment contains an identifier sequence. In one embodiment, the identifier sequence is a barcode. The barcode is generally an 8-12 nucleotide base sequence that is used in conjunction with the sequence of the original genomic DNA segment to distinguish each nucleic acid construct from another in the collection. When the fragments of genomic DNA are of similar sequence, it is important that the identifier or barcode sequence is sufficiently divergent, such that no two nucleic acid constructs are the same. For collections comprising about 10,000 genome equivalents (the approximate genomes in 1 ml of cell-free DNA), unique identifier sequences of 8 nucleotides contain sufficient diversity (65,536) to assure each circular construct is unique. For collections comprising about 1,000,000 genome equivalents (the approximate genomes from total cells in 10 mls of blood), unique identifier sequences of 12 nucleotides contain sufficient diversity (16,777,216) to assure each circular construct is unique. In addition, when the genomic DNA is either randomly fragmented, or biologically fragmented (i.e. as in cell-free DNA), the junctions between the genomic DNA and the synthetic nucleic acid will provide additional unique sequences to assist in distinguishing each circular construct.

In another embodiment, the identifier sequence comprises one or more primer binding sites and/or patient identifier sequences as described infra. The primer binding sites are used not only to facilitate amplification, but alone or in combination with the patient identifier sequence can serve as an identifying sequence segment for purposes of distinguishing individual circular constructs within the collection. Accordingly, the identifier sequence of the second single stranded segment of the nucleic acid constructs of the collection may comprise a barcode sequence, one or more primer sequences, a patient identifier sequence, or any combination thereof.

The chimeric nucleic acid constructs of the collection are circularized, i.e., covalently closed circularized nucleic acid molecules. In accordance with this aspect of the present invention, the circularized constructs are completely single-stranded. In other aspects of the present invention, the circularized constructs may be partially double stranded or completely double-stranded.

Another aspect of the present invention is directed to a method for amplifying nucleic acid molecules. This method involves providing the collection of different circular chimeric single-stranded nucleic acid constructs of the present invention as described supra, and blending the collection with a polymerase and a plurality of short primers (6 to 10 nucleotides wherein a portion of said sequence comprises random bases and/or nucleotide analogues; e.g. random hexamers, heptamers, octamers), to form an amplification reaction. The one or more of short primers is complementary to a portion of one or more circular chimeric single stranded nucleic acid constructs of the collection. The amplification reaction mixture is subjected to one or more hybridization and extension treatments, wherein the one or more short primers hybridize to the circular chimeric single-stranded nucleic acid constructs and the polymerase extends the hybridized primers to produce a plurality of extension products. Each extension product comprises two or more tandem linear sequences that are complementary to a chimeric single-stranded nucleic acid construct from the collection.

FIG. 1 (steps A-D) provides an exemplary illustration of the above-described method of amplifying nucleic acid molecules. FIG. 1, step A shows a circular chimeric single-stranded nucleic acid construct of a collection and a plurality of random hexamer primers. The first single stranded segment of original genomic DNA in the circular construct is shown as a single thin black line. A mutation within the original genomic DNA segment is denoted with an (*). The unique identifier sequence of the circular construct is shown as a double line. Continuous extension of a hybridized hexamer primer to amplify the circular target is achieved using a polymerase capable of strand displacement, e.g. Phi29 DNA polymerase or the like (depicted as a diamond in FIG. 1). As shown in FIG. 1, step B, polymerase extension of a hybridized primer will eventually displace the original primer, creating a single-stranded tail. One or more of the hexamer primers may subsequently hybridize to the single stranded tail, and polymerase mediated extension of those hybridized primers continues as shown in FIG. 1, steps C and 1D to form double stranded extension products of varying length, each extension product containing two or more tandem linear sequences that are complementary to the circular construct.

The collection of double stranded extension products formed via this amplification method are suitable for any one of a broad range of next generation sequencing (NGS) protocols (e.g., 454 Pyrosequencing, Ion Torrent™ sequencing by synthesis, SOLiD™ sequencing by ligation, or MiSeq™ or HiSeq™ sequencing by synthesis systems). In accordance with NGS protocols, the double-stranded extension products are fragmented such that one or more tandem complementary copies of the target DNA is within a single fragment. Linkers are appended to the 5' and 3' ends of the fragmented DNA to allow for standard library preparation and template generation using cluster or bead amplification.

A consensus sequence of all physically linked complementary copies of the original DNA molecule within the circular target is generated during sequencing. Because true mutations (*) will be present 2 or 3 times within a fragment, they are easily distinguishable from polymerase error.

In accordance with this and all aspects of the present invention, sequencing of the chimeric circular nucleic acid constructs of the present invention and extension products thereof can be carried out using any sequencing method known in the art, including, without limitation, sequencing by fluorescent primer hybridization, molecular beacon hybridization, primer extension, ligase detection reaction, ligase chain reaction, pyrosequencing, exonuclease-based sequencing, fluorescence-based sequencing-by-synthesis, fluorescence-based sequencing-by-ligation, nanopore and nanotube based sequencing, ion-based sequencing-by-synthesis, and ion-based sequencing-by-ligation. As used herein, "sequencing" encompasses a method by which the identity of at least 10 consecutive nucleotides of a polynucleotide target or template is obtained.

In another aspect of the present invention, each circular nucleic acid construct of the collection comprises a first single stranded segment of original genomic DNA from a host organism and a second single stranded synthetic nucleic acid segment that is linked to the first single stranded segment and comprises a nucleotide sequence that is exogenous to the host organism. The second single stranded synthetic nucleic acid segment comprises a unique identifier portion and a primary primer binding site, wherein the nucleotide sequence of the unique identifier portion, the primary primer binding site and the segment of original genomic DNA distinguishes one chimeric single-stranded nucleic acid construct in the collection from every other chimeric single-stranded nucleic acid construct in the collection. The chimeric single-stranded nucleic acid constructs of the collection are circularized and suitable for rolling circle amplification and/or sequencing.

Another aspect of the present invention is directed to a method for generating tandem linear copies of nucleic acid molecules that are suitable for sequencing. This method involves providing the collection of different circular chimeric single-stranded nucleic acid constructs of the present invention as described supra, and blending the collection with a polymerase with strand displacement activity, and one or more primary primers, to form a rolling circle extension reaction. The one or more primary primers are complementary to a portion of one or more circular chimeric single stranded nucleic acid constructs of the collection. The rolling circle extension reaction mixture is subjected to one or more hybridization and extension treatments, wherein the one or more primers hybridize to the circular chimeric single-stranded nucleic acid constructs and the polymerase extends the hybridized primers to produce a plurality of extension products. Each extension product comprises two or more tandem linear sequences that are complementary to a chimeric single-stranded nucleic acid construct from the collection.

FIG. 2, steps A-C provide an exemplary illustration of the above-described method of amplifying nucleic acid molecules. FIG. 2, step A shows a circular chimeric single-stranded nucleic acid construct of a collection and a hybridized primary primer. The first single stranded segment of original genomic DNA in the circular construct is shown as a single thin black line. A mutation within the original genomic DNA segment is denoted with an (*). The unique identifier sequence and primary primer binding site of the circular construct are shown as a slightly thicker line.

Continuous extension of a hybridized primer to amplify the circular target is achieved using a polymerase capable of strand displacement, e.g. Phi29 or Bst DNA polymerase or the like (depicted as a diamond in FIG. 2). As shown in FIG. 2, step B, polymerase extension of a hybridized primer will eventually displace the original primer, creating a single-stranded tail. The extension product is denatured from the circle (see FIG. 2, step C). One or more secondary primer sets are provided, where each primer set comprises (a) a first secondary unmethylated primer having a nucleotide sequence that is complementary to a first portion of the single-stranded extension product formed from the primary primer, and (b) a second secondary methylated primer having a nucleotide sequence that is complementary to a second portion of the single-stranded extension product. The single-stranded extension products are blended with the secondary primer sets, a polymerase lacking strand displacement activity, a ligase and an endonuclease that cleaves both the single-stranded extension product and the first secondary primer when they are hybridized to each other (i.e., the endonuclease cleaves at an unmethylated double-stranded recognition sequence).

The first and second secondary primers hybridize to complementary regions of the single-stranded extension products as shown in FIG. 2, step C. The polymerase extends the hybridized primers to form ligation junctions with downstream hybridized secondary primers. The ligase ligates the extended secondary primers together to form double-stranded extension products as shown in FIG. 2, step C. The endonuclease cleaves both the extension product and first secondary primer where they are hybridized to form double-stranded fragments containing tandem linear copies of target genomic DNA sequences. The number of tandem linear sequences in the double-stranded extension product fragments reflects the ratio of first and second secondary primers utilized in the aforementioned method. These tandem copy fragments are suitable for sequencing using any sequencing method known in the art as described supra. For NGS sequencing, linkers are appended to allow for standard cluster or bead amplification and paired end reads. True mutation (*) will be present 2 or 3 times, and thus distinguished from polymerase error.

Another aspect of the present invention is directed to a method for generating tandem linear copies of nucleic acid molecules, if the target was methylated in the original genomic DNA (methylated base is depicted as "m", see FIG. 3). The process is essentially the same as described above, with Bst polymerase being used for continuous extension of the hybridized primary primer in the presence of BstU1 (CG^CG) restriction endonuclease (FIG. 3, step B). BstU1 will cleave double-stranded DNA if unmethylated, but not hybrid methylated/unmethylated DNA, nor unmethylated single-stranded DNA (FIG. 3, step B). (See Zierhut & Diffley, "Break Dosage, Cell Cycle Stage and DNA Replication Influence DNA Double Strand Break Response," EMBO J. 27(13):1875-85 (2008), which is hereby incorporated by reference in its entirety.) Since polymerase generates several copies of the target during rolling circle amplification, and since an unmethylated CGCG sites are cleaved by BstU1 in the double-stranded form, this process specifically selects for fragments that are methylated at all BstU1 sites in the initial target DNA. While FIG. 3 illustrates this method with the BstUI restriction endonuclease, other endonucleases that cleave double-stranded DNA if unmethylated, but not hybrid methylated/unmethylated DNA, nor unmethylated single-stranded DNA can be utilized to selectively amplify methylated genomic DNA. These endonucleases include but are not limited to the thermophilic enzymes BstHHI (recognizes GCGC; an isoschizomer of HhaI), BsiSI (recognizes CCGG; an isoschizomer of HpaII), and TaiI (recognizes ACGT; an isoschizomer of MaeII). All these enzymes are sensitive to methylation of the internal CpG sequence. The last enzyme in this series, TaqI restriction enzyme, is insensitive to methylation at the CpG site, so would not be suitable for the above technique.

In another aspect of the present invention, each circular nucleic acid construct of the collection comprises a first single stranded segment of original genomic DNA from a host organism linked to the second single stranded synthetic nucleic acid segment, where the second single stranded segment comprises one or more primer-specific sequences (e.g., a first and/or second solid support primer-specific portions), and optionally, a patient identifier sequence. In accordance with this aspect of the present invention, the second single stranded segment may or may not contain a unique identifier portion. The chimeric single-stranded nucleic acid constructs of the collection are circularized and suitable for rolling circle amplification and/or sequencing as described herein.

The patient identifier sequence of the second single stranded segment serves to identify the patient source of the original genomic DNA. The patient identifier sequence generally comprises about 5 to 8 nucleotides in length and is designed to distinguish sequences arising from different patients. In the preferred embodiment, the patient identifier sequences differ from each other in at least 3 positions, such that a single base error in sequencing still allows for positive identification of the correct patient identifier sequence. In current clinical laboratory practice, batch workup of samples is usually designed to be compatible with 96 and 384 well plate formats, such that 8, 16, 24, 48, 96, or 384 samples are processed simultaneously.

Another aspect of the present invention is directed to a system comprising a collection of different circular chimeric single-stranded nucleic acid constructs. Each construct of the collection comprises a first single stranded segment of original genomic DNA from a host organism and a second single stranded nucleic acid segment that is linked to the first single stranded segment and comprises a nucleotide sequence that is exogenous to the host organism. The nucleotide sequence of the second single stranded nucleic acid segment comprises a first solid support primer-specific portion, a second solid support primer-specific portion, and a patient identifier sequence. The chimeric single-stranded nucleic acid constructs of the collection are circularized and suitable for rolling circle amplification and/or sequencing. The system further comprises a collection of extension products, each extension product comprising two or more tandem linear sequences that are complementary to the chimeric single-stranded nucleic acid construct from the collection. Each extension product in the collection is hybridized to its complementary circular chimeric single-stranded nucleic acid construct of the collection. FIG. 4 at step B provides an exemplary depiction of this system of the present invention.

This system of the present invention may further comprise a solid support having a plurality of immobilized first oligonucleotide primers. Each first oligonucleotide primer on the solid support has a nucleotide sequence that is the same as the nucleotide sequence of the first solid support primer-specific portion of the chimeric single stranded nucleic acid constructs of the collection, and that is complementary to the first solid support primer-specific portion of the extension products. Accordingly, one or more of the first oligonucleotide primers on the solid support can hybridize to an extension product of the collection of extension products via the first solid support primer-specific portions. FIG. 4, step C provides an exemplary depiction of this system of the present invention.

The solid support can be made from a wide variety of materials. The substrate may be biological, nonbiological, organic, inorganic, or a combination of any of these, existing as particles, strands, precipitates, gels, sheets, tubing, spheres, beads, containers, capillaries, pads, slices, films, plates, slides, discs, membranes, etc. The substrate may have any convenient shape, such as a disc, square, circle, etc. The substrate is preferably flat but may take on a variety of alternative surface configurations. For example, the substrate may contain raised or depressed regions on which the hybridization takes place. The substrate and its surface preferably form a rigid support on which to carry out sequencing reactions described herein.

Commercially available next generation sequencing solid support platforms used for template preparation can be utilized in the system and methods of the present invention. For example, the Illumina® Flow Cell, Life Technologies® IonSphere™ and emulsion PCR beads, and 454 emulsion PCR beads can be used in the system and methods of the present invention. Accordingly, the first solid support primer-specific portion of the circular chimeric single stranded nucleic acid constructs is designed to be the same as the primers immobilized on a commercially available NGS solid support. Therefore, the extension products containing the complement of the first solid support primer-specific portion are capable of hybridizing to primers on the NGS solid support surface.

This system of the present invention may further comprise a collection of crosslinking oligonucleotides as shown in FIG. 5, step A. A crosslinking oligonucleotide is an oligonucleotide having two or more repeats of a nucleotide sequence, where the repeated nucleotide sequence has the same sequence as at least a portion of the second single stranded nucleic acid segment of the chimeric single-stranded nucleic acid constructs in the collection. Accordingly, the repeated nucleotide sequence of the crosslinking oligonucleotide is complementary to at least a portion of the nucleotide sequence of the extension product of the chimeric nucleic acid construct (i.e., a portion of the extension product corresponding to the second single stranded segment). The repeated nucleotide sequence may be about 10-25 nucleotides in length. One or more of the nucleotide sequence repeats of each crosslinking oligonucleotide hybridizes to a tandem linear sequence of an extension product of the collection of extension products as depicted in FIG. 5, steps B-D to form a condensed structure.

As shown in FIG. 5, steps E-H, the condensed extension product, bound to one or more crosslinking oligonucleotides, can be captured on a solid support having a plurality of immobilized first oligonucleotide primers. As described supra, the first oligonucleotide primers on the solid support have a nucleotide sequence that is complementary to the first solid support primer specific portion of the extension products (i.e., a nucleotide sequence that is the same as the nucleotide sequence of the first solid support primer-specific portion of the chimeric single stranded nucleic acid constructs). As shown in FIG. 5, step E, one or more tandem linear sequences of a condense extension product structure may hybridize to one or more first oligonucleotide primers on the solid support, thereby immobilizing the condensed structure. The crosslinking oligonucleotides can be designed to contain cleavable linkages that are enzymatically cleaved (depicted as triangles in FIG. 5, steps E and F). Suitable cleavable linkages include, without limitation, ribo-nucleotides, deoxy-Uracil, an apurinic site, and 8-oxoguanine. For example, the crosslinking oligonucleotide may contain an apurinic site that is cleaved by APE 1 endonuclease, Endo III, Endo IV, Endo VIII, Fpg, or hOGG1. Cleavage of the crosslinking oligonucleotides allows the condensed structure to fall apart and individual tandem sequences of the extension product are captured locally by hybridizing to adjacent primers on the solid support surface, creating a carpet-like structure (FIG. 5, step F). As shown in FIG. 5, step G, this approach assures that the hundreds to thousands of tandem complementary copies of the original target genomic DNA sequence are captured next to each other, and are suitable for subsequent sequencing.

Another aspect of the present invention is directed to a system comprising a collection of different circular chimeric single-stranded nucleic acid constructs. Each construct comprises a first single stranded segment of original genomic DNA from a host organism and a second single stranded nucleic acid segment that is linked to the first single stranded segment and comprises a nucleotide sequence that is exogenous to the host organism. The nucleotide sequence of the second single stranded nucleic acid segment comprises a first solid support primer-specific portion, a second solid support primer-specific portion, and a patient identifier sequence. The chimeric single-stranded nucleic acid constructs of the collection are suitable for rolling circle amplification and/or sequencing. The system further comprises one or more oligonucleotide amplification primers, each primer comprises at least a first nucleotide sequence portion that is complementary to the first solid support primer-specific portion or the second solid support primer-specific portion of the chimeric single-stranded nucleic acid constructs of the collection. Finally, this system also has a polymerase suitable for rolling circle amplification.

Exemplary depictions of this system of the present invention are shown in FIG. 4, step A. The circularized chimeric nucleic acid constructs contain the original genomic DNA segment (thin black line), a single base substitution or mutation of interest within the original DNA segment is denoted by the asterisk (*). The second single-stranded segment of the constructs contain a first solid support primer-specific portion of the chimeric construct (depicted as a thick black line) and a second solid support primer specific portion (depicted as a double black line). Amplification primers suitable for priming rolling circle amplification of the chimeric constructs can be complementary to a segment of the first solid support primer-specific portion of the construct as shown in the left-hand panel of FIG. 4, step A; complementary to a segment of both the first and second solid support primer specific portions of the chimeric construct as shown in the middle and right panels of FIG. 4, step A; or complementary to a portion of the second solid support primer-specific portion of the construct as shown in FIG. 9, step A. In this latter embodiment, the amplification primer complementary to the second solid support primer-specific portion of the chimeric construct is immobilized on a solid support, which tethers the extension product formed during rolling circle amplification directly to the solid support. In an alternative embodiment, the amplification primers may comprise a further portion that is capable of being tethered to a solid support as shown in FIG. 4, step D and FIG. 10, step A. In one embodiment, the further portion comprises a unique nucleotide sequence that is complementary to the nucleotide sequence of a capture oligonucleotide immobilized on the solid support. In another embodiment, the further portion comprises a nucleotide sequence that is complementary to a first or second solid oligonucleotide primer immobilized on the solid support. In another embodiment, the further portion is a capture moiety that is captured by a capture binding partner immobilized on the solid support. The capture moiety and capture binding partner need not be nucleic acid in nature. For example, the capture moiety may be a biotin group or a His-Tag, which would be captured by immobilized streptavidin or NTA matrix respectively.

In another embodiment, the one or more oligonucleotide amplification primers comprise (i) a first nucleotide sequence that is complementary to the original genomic DNA segment of the chimeric single stranded nucleic acid constructs of the collection, (ii) a 3' portion comprising a cleavable nucleotide or nucleotide analogue and a blocking group that blocks 3' polymerase extension of said oligonucleotide amplification primer, and (iii) a 5' portion comprising a cleavable nucleotide or nucleotide analogue and a capture group, where the capture group is capable of being immobilized to a solid support.

In another embodiment, the one or more oligonucleotide amplification primers comprise (a) a first oligonucleotide amplification primer having (i) a first nucleotide sequence that is complementary to a first portion of the original genomic DNA segment of the chimeric single stranded nucleic acid constructs of the collection, and (ii) a 3' portion comprising a cleavable nucleotide or nucleotide analogue and a blocking group that blocks 3' polymerase extension of said first oligonucleotide amplification primer, and (b) a second oligonucleotide amplification primer having (i) a first nucleotide sequence that is complementary to a second portion of the original genomic DNA segment of the chimeric single stranded nucleic acid constructs of the collection, and (ii) a 5' portion comprising a cleavable nucleotide or nucleotide analogue and a capture group, where the capture group is capable of being immobilized to a solid support.

In accordance with this aspect of the present invention, the system may further comprise a solid support having a plurality of immobilized first oligonucleotide primers. The first oligonucleotide primers on the solid support have a nucleotide sequence that is the same as the nucleotide sequence of the first solid support primer-specific portion of the chimeric single stranded nucleic acid constructs of the collection (see e.g., FIG. 6, step B). The solid support of this system may further comprise a plurality of immobilized second oligonucleotide primers having a nucleotide sequence that is complementary to the nucleotide sequence of the second solid support primer-specific portion of the chimeric single stranded nucleic acid constructs of the collection (see e.g., FIG. 5, step B). As described supra, commercially available NGS solid support platforms used for template preparation (e.g. Illumina® Flow Cell, Life Technologies IonSphere®, etc.) are suitable for the systems of the present invention.

The system of the present invention may also comprise a collection of crosslinking oligonucleotides as described supra (i.e., an oligonucleotide having two or more repeats of a nucleotide sequence, where the repeated nucleotide sequence has the same sequence as at least a portion of the second single stranded nucleic acid segment of the chimeric single-stranded nucleic acid constructs in the collection).

In accordance with this aspect of the present invention, the polymerase of this system is a strand-displacing polymerase that is suitable for rolling circle amplification. Exemplary strand-displacing polymerases include, without limitation, phi29 DNA polymerase, Bst DNA polymerase (large fragment or 5'→3' exo-), Bsu DNA Polymerase (large fragment or 5'→3' exo-), DeepVent$_R$® (exo-) polymerase, Klenow Fragment (3'→5' exo-), DNA Polymerase I (5'→3' exo-), M-MuLV Reverse Transcriptase, Vent$_R$® (exo-) DNA Polymerase, and PyroPhage 3173 DNA Polymerase. Other exemplary strand-displacing polymerases include those having thermostability and strand-displacing activity, such as SD DNA polymerase (a mutant Taq DNA polymerase) (see U.S. Patent Application Publication No. 2012/0115145 to Fu, WO2014/161712 to Ignatov et al., and Ignatov et al., "A Strong Stand Displacement Activity of Thermostable DNA Polymerase Markedly Improves the Results of DNA Amplification," *BioTechniques* 57:81087 (2014), which are hereby incorporated by reference in their entirety); AptaHotTaq Polymerase (thermostable 5'→3' polymerase activity with a 5' flap endonuclease activity); polymerases derived from thermophilic viruses and microbes (see U.S. Patent Application Publication 2012/0083018 to Schoenfeld et al., and U.S. Pat. No. 8,093,030 to Schoenfeld et al., which are hereby incorporated by reference in their entirety); polymerases derived from *Thermus antranikianii* and *Thermus brockianus* as disclosed in WO2006/030455 to Hjorleifsdottir et al., and U.S. Patent Application Publication No. 2008/0311626 to Hjorleifsdottir et al., which are hereby incorporated by reference in their entirety; the thermostable polymerase derived from *Thermus scotoductus* (see WO2007/076461 to Rech et al., which is hereby incorporated by reference in its entirety); and Type I DNA polymerase derived from *Bacillus pallidus* (see U.S. Pat. No. 5,736,373 to Hamilton, which is hereby incorporated by reference in its entirety). Other strand-displacing polymerases known in the art are also suitable for this system and related methods of the present invention.

Another aspect of the present invention is directed to a method of sequencing a plurality of nucleic acid molecules using this system. In accordance with this method, the oligonucleotide amplification primers hybridized to complementary circular chimeric single-stranded nucleic acid constructs of the collection are blended with the polymerase to form a rolling circle amplification reaction mixture. The rolling circle amplification reaction mixture is subject to an extension treatment where the polymerase extends the one or more hybridized oligonucleotide amplification primers to produce a plurality of primary extension products. Each primary extension product comprises one or more tandem linear sequences, each tandem linear sequence being complementary to a circular chimeric single-stranded nucleic acid construct in the collection. The circular chimeric single-stranded nucleic acid constructs can be sequenced directly, e.g., the circular chimeric construct is the template for sequence-by-synthesis. Alternatively, the primary extension products formed from the rolling circle amplification reaction are the templates used for sequencing. As noted above, any sequencing method known in the art can be utilized to sequence the circular nucleic acid constructs or the primary extension products thereof.

In one embodiment, the primary extension products are immobilized on a solid support prior to sequencing. A suitable solid support comprises at least a plurality of first oligonucleotide primers each having a nucleotide sequence that is the same as the nucleotide sequence of the first solid support primer-specific portion of the chimeric single stranded nucleic acid constructs of the collection (i.e., having a sequence complementary to the first solid support primer-specific portion of the primary extension products). Suitable solid supports include, without limitation, those that are commercially available and utilized for template preparation in next generation sequencing platforms, e.g., Illumina® flow cell, Life Technologies™ Ion Sphere™. The primary extension products hybridize to the first oligonucleotide primers on the solid support and are sequenced on the support as described in more detail below.

The solid support may further comprise a plurality of second oligonucleotide primers. The second primers have a nucleotide sequence that is complementary to the second solid support primer-specific primer portion of the chimeric single stranded nucleic acid constructs. As depicted in FIG. 9, step B and described in more detail herein, rolling circle amplification of the chimeric nucleic acid construct may be primed by a second oligonucleotide primer on the solid support. This approach can be used to tether the primary extension product directly to the solid support.

As depicted in FIG. 5, steps A-G crosslinking oligonucleotides can be utilized to condense the growing primary extension product formed from a rolling circle amplification reaction. As shown in FIG. 5, step A, DNA polymerase (filled diamonds) extends an amplification primer around the circular construct containing the original genomic segment. As polymerase continues to extend, the growing primary extension product condenses by hybridizing to complementary repeated regions of crosslinking oligonucleotides as shown in FIG. 5, step B. The process continues as shown in FIG. 5, steps C and D to generate hundreds to thousands of tandem complementary copies of target DNA in a condensed structure. By varying the number of oligonucleotides with different complementary sequences, and the number of tandem repeats within a given oligonucleotide, the number of loops or "crosslinking nodes" can be varied, providing the opportunity to control the "compactness" of the structure. As shown in FIG. 5, step E, the condensed primary extension product can be immobilized on a solid support via hybridization of the primary extension product to complementary first oligonucleotide primers. As shown in FIG. 5, step E, the condensed structure hybridizes to complementary primers at a few positions. The crosslinking oligonucleotides contain cleavable linkages, and upon cleavage the condensed structure starts to come apart (FIG. 5, step F). Individual loops of the primary extension product are captured locally by hybridizing to adjacent first primers on the surface of the solid support, creating a carpet-like structure (FIG. 5, step G). This approach assures that the hundreds to thousands of tandem copies of the target are captured next to each other, and suitable for subsequent sequencing.

FIG. 6 depicts an exemplary method of sequencing in accordance with the present invention. As shown in FIG. 6, step A, the process begins with DNA polymerase (e.g., Phi29 polymerase; filled diamonds) extending an amplification primer hybridized to a circular chimeric nucleic acid construct template to generate a primary extension product. The extension product hybridizes to first oligonucleotide primers on a solid support (FIG. 6, step B). As shown in FIG. 6, step C, the growing extension product formed from the rolling circle amplification reaction is captured locally on the solid support by hybridizing to adjacent first oligonucleotide primers on the surface, creating a carpet-like structure. As shown in FIG. 6, step D, this approach assures that hundreds to thousands of tandem complementary copies of the original genomic DNA segment are captured next to each other for subsequent sequencing.

Once the primary extension product is immobilized on the solid support (FIG. 6, step D), a sequencing primer is hybridized adjacent to the 3' end of first oligonucleotide primer on the solid support as shown in FIG. 6, step E.

Optionally, a PNA or blocking oligonucleotide can be hybridized adjacent to the 5' end of the first oligonucleotide primer as also depicted in FIG. 6, step E. The primary extension product is the template for sequencing-by-synthesis reaction that is primed by the sequencing primer as depicted in FIG. 6, step F. Sequencing continues until the secondary sequence-by-synthesis extension product being formed is unable to extend further due to the PNA or blocking oligonucleotide (FIG. 6, step G).

To sequence the opposite strand (i.e. to obtain the sequence of the primary extension products), the first oligonucleotide primer on solid support is unblocked. A polymerase (filled diamonds) with 5'-3' nuclease activity extends the tethered sequencing primer on the solid support while digesting product from the sequencing by synthesis reaction as shown in FIG. 6, step H. As shown in FIG. 6, step I, the polymerase (filled diamonds) extends strands until it is unable to go further due to PNA or blocking oligonucleotide (wide striped line). This generates uni-length copies of the template, each template comprising a copy of the original genomic DNA sequence. As shown in FIG. 6, step J, the original primary extension product and circular template is denatured and washed away. A second sequencing primer is hybridized to each uni-length template strands as shown in FIG. 6, step K, and sequence-by-synthesis is used to obtain the sequence of the immobilized template as shown in FIG. 6, steps L and M.

FIG. 7 depicts another exemplary method of sequencing in accordance with the present invention. This method involves the rolling circle amplification of a circular chimeric nucleic acid construct and capture of the primary extension product on a solid support having both first and second oligonucleotide primers. As shown in FIG. 7, step A, a strand-displacing DNA polymerase (filled diamond) extends an amplification primer on a circularized template to generate a single-stranded primary extension product. The first oligonucleotide primers on the solid support surface contain a removable blocking group at their 3' end rendering them incapable of extension during the rolling circle amplification process (FIG. 7, step B). A blocking group is a chemical moiety that prevents a polymerase or other enzyme from amplifying, extending or reacting with the oligonucleotide in a productive manner. In this example, the blocking group prevents polymerase extension of the 3' end. Suitable blocking groups include, without limitation, C3-spacers, C18-spacers, terminator nucleotides, 2'-O-methyl ribonucleotide derivatives, 3' phosphate, or other modifications of the 3' or 2' OH moieties. The blocking group itself may be cleavable, such as by use of reversible terminator nucleotides, or 3' phosphates, or the blocking group and optionally some additional nucleotides may be removed by cleaving at a cleavable linkage that then liberates a free 3' OH end. Suitable cleavable linkages include, without limitation, ribonucleotides, deoxy-Uracil, an apurinic site, and 8-oxoguanine. As shown in FIG. 7, step C, as rolling circle amplification continues to generate a growing primary extension product, the product is captured locally by hybridizing to adjacent first oligonucleotide primers on the solid support surface creating a carpet-like structure. This approach assures that the hundreds to thousands of tandem copies of the target are captured next to each other on the solid support surface (FIG. 7, step D).

As shown in FIG. 7, step E, the blocking group is removed from first oligonucleotide primers hybridized to primary extension product on the solid support. The blocking group may be removed by cleaving a cleavable linkage. Ribonucleotide cleavable linkages can be cleaved using RNaseH; deoxy-Uracil cleavable linkages can be cleaved using UDG and AP endonuclease, or using UDG, Endo VIII, and T4 kinase; apurinic site cleavable linkages can be cleaved using Tth Endo IV, Endo IV, or AP endonuclease; and 8-oxoguanine cleavable linkages can be cleaved with Fgp. Once the primer is unblocked, it is extended thereby copying the primary extension product at hundreds to thousands of positions on the solid support using polymerase (filled diamonds) lacking 5'→3' nuclease activity (FIG. 7, step F). This generates uni-length secondary extension products of the circularized template. As shown in FIG. 7, step G, the primary extension product and circular template are denatured and washed away to render the resultant secondary extension products of the template suitable for subsequent sequencing as depicted in FIG. 8, steps A-I.

FIG. 8 illustrates the sequencing of rolling circle amplified target (e.g. secondary extension products) captured on a solid support having both first and second oligonucleotide primers. FIG. 8, step A shows the uni-length secondary extension products generated from polymerase mediated extension of hybridized primary extension products as described in FIG. 7. The sequencing process begins with hybridization of sequencing primers to the secondary extension products as shown in FIG. 8, step A. Sequence-by-synthesis is used to obtain the sequence of the immobilized secondary extension products (FIG. 8, step B). Sequencing continues until extension products reach the end of the tethered first oligonucleotide primers (FIG. 8, step C). The sequence-by-synthesis products are denatured from the tethered secondary extension products and the single-stranded secondary extension products hybridize to the second oligonucleotide primers on the solid support as shown in FIG. 8, step D. The secondary extension products are copied by extending the hybridized second oligonucleotide primers to generate full-length copies of the secondary extension products, i.e., tertiary extension products (FIG. 8, step E). The secondary extension products are cleaved, denatured, and washed away (FIG. 8, steps E-F), leaving the tethered tertiary extension products suitable for subsequent sequencing. A sequencing primer is hybridized to the tertiary extension products (FIG. 8, step G) and sequence-by-synthesis is carried out to obtain the sequence of the tertiary products as shown in FIG. 8, steps H and I.

Sequencing of the secondary and tertiary extension products can be achieved using sequence-by-synthesis as described and depicted herein. Sequence-by-synthesis includes fluorescence-based sequencing-by-synthesis and ion-based sequencing-by-synthesis. Other suitable sequencing methods can also be employed, including, for example and without limitation, fluorescent primer hybridization, molecular beacon hybridization, primer extension, exonuclease-based sequencing, ligase detection reaction, ligase chain reaction, pyrosequencing, fluorescence-based sequencing-by-ligation, nanopore and nanotube based sequencing, and ion-based sequencing-by-ligation.

FIG. 9 depicts another exemplary method of sequencing in accordance with the present invention. As shown in FIG. 9, step A, this embodiment involves direct hybridization of the chimeric circular nucleic acid construct to an unblocked second oligonucleotide primer on the solid support. The second primer serves as an amplification primer, priming rolling circular amplification of the circular construct. The primary extension product that is generated is directly tethered to the solid support (FIG. 9, step A). The primary extension product generated by rolling circle amplification hybridizes to first oligonucleotide primers on the solid support containing a removable 3' blocking group as shown in FIG. 9, steps B and C, thereby generating multiple "carpet loop" structures. The 3'-blocking group of the first primers is removed (FIG. 9, step D), allowing the first primers to be extended by a suitable polymerase (e.g., a polymerase lacking 5'→3' nuclease activity) to generate a surface composed of hundreds to thousands of uni-length secondary extension products covalently attached to the solid support surface (FIG. 9, step E). As shown in FIG. 9, steps E-F, treatment of the surface with a site-specific cleavage reagent or enzyme that cleaves the first primer, followed by a denaturation step, releases the primary extension product, leaving the covalently attached secondary extension products, which are suitable for subsequent sequencing as shown and described in FIG. 8, steps A-I.

FIG. 10 depicts another exemplary method of sequencing in accordance with the present invention. In this embodiment, the amplification primer comprises a short single-stranded tail, i.e., a further portion that is captured on the solid support. As depicted in FIG. 10, step A, the further portion may comprise a nucleotide sequence that is complementary to the nucleotide sequence of a capture probe or primer on the solid support surface. Hybridization of the further portion to its complementary capture probe or primer directly tethers the primary extension product formed by rolling circle amplification to the solid support. As rolling circle amplification continues to generate a growing primary extension product comprising tandem complementary copies of the chimeric circular structure, the primary extension product is captured locally by hybridization to 3' blocked first oligonucleotide primers on the surface creating multiple carpet loop structures on the surface (FIG. 10, steps B and C). The first primers are deblocked (FIG. 10, step D), and extended with a polymerase lacking a 5'→3' nuclease activity to form multiple secondary extension products that are a uniform length (FIG. 10, step E). Denaturation releases the primary extension product and leaves behind covalently attached secondary extension products which are the same sense as the original circularized templates and all end with a defined sequencing primer binding sequence at their 3' ends. The covalently attached secondary extension products are suitable templates for sequencing as shown in FIG. 8.

FIG. 11 illustrates another exemplary method of sequencing in accordance with the present invention. In FIG. 11, step A, Phi29 DNA polymerase (filled diamonds) extends amplification primer on chimeric circle template to generate a short single stranded primary extension product. The polymerase and primary extension product are denatured from the circular template. As shown in FIG. 11, step B, the primary extension product is hybridized to first primers on a solid support. The primary extension product is copied by polymerase extension of the immobilized first oligonucleotide primers at multiple positions (filled diamonds). Suitable polymerases include polymerase lacking 5'→3' nuclease activity as described supra. This generates uni-length secondary extension products (FIG. 11, step C). The primary extension product is denatured and washed away as shown in FIG. 11, step D. The remaining single-stranded secondary extension products are amplified using a cluster amplification process where the secondary extension products hybridize to second oligonucleotide primers on the solid support as shown in FIG. 11, step E. The second primers are polymerase extended (FIG. 11, step F) to form tertiary extension products. After denaturation (FIG. 11, step G), the secondary and tertiary extension products hybridize to complementary first and second primers on the solid support (FIG. 11, step H). Hybridized primers are polymerase extended to form copies of the secondary and tertiary extension products as shown in FIG. 11I. The extension products are denatured, and the process is repeated to generate enough templates for sequencing (FIG. 11, step J) each strand using the method depicted in FIG. 8. Alternative means of forming surfaces with covalently attached identical copies of the limited (short) RCA amplicon includes Sequoia amplification (WO2013/012440 to Barany et al., which is hereby incorporated by reference in its entirety) and wildfire amplification (Ma et al., "Isothermal Amplification Method for Next-Generation Sequencing,". *Proc Natl Acad Sci USA* 10(35): 14320-3 (2013), which is hereby incorporated by reference in its entirety).

FIG. 12 illustrates another exemplary method of sequencing in accordance with the present invention, similar to that presented in FIG. 11. In FIG. 12, step A, Phi29 or Bst DNA polymerase (filled diamonds) extends amplification primer on chimeric circle template to generate a long single stranded primary extension product. The polymerase and primary extension product are denatured from the circular template. As shown in FIG. 12, step B, the primary extension product is hybridized to multiple first primers in more than one well or area on a solid support. Since the primary extension product is long, it may extend into multiple wells or discrete areas on the solid surface that have primers. The advantage of this property of long extension products is that the same target will be sequenced in multiple neighboring wells or areas, thus providing additional verification of a low-abundance mutation. The primary extension product is copied by polymerase extension of the immobilized first oligonucleotide primers at multiple positions (filled diamonds) as shown in FIG. 12, step C. Suitable polymerases include polymerase lacking 5'→3' nuclease activity as described supra. This generates uni-length secondary extension products, except when bridging between wells where tandem repeat extension products are generated (FIG. 12, steps C and D). The primary extension product is denatured and washed away as shown in FIG. 12, step E. The remaining single-stranded secondary extension products are amplified using a cluster amplification process where the secondary extension products hybridize to second oligonucleotide primers on the solid support as shown in FIG. 11, steps E-I. The extension products are denatured, and the process is repeated to generate enough template for sequencing (see FIG. 11, step J) each strand using the method depicted in FIG. 8.

Another aspect of the present invention is directed to methods of making the circular chimeric single stranded nucleic acid constructs that are a component of the systems and methods described herein. A number of exemplary methods are described below and depicted in the accompanying figures.

One suitable method for making the circular chimeric single stranded nucleic acid constructs involves providing a sample containing one or more target genomic DNA segments. The target genomic DNA segments may potentially contain one or more base differences or one or more methylated residues of interest for detection. The method further involves providing one or more first oligonucleotide probes, each first oligonucleotide probe comprising (a) a 5' target-specific portion, (b) a 3' target-specific portion, and (c) a further portion. The further portion is a nucleotide sequence comprising (i) a patient identifier sequence, (ii) a first solid support primer-specific portion, and (iii) a second solid support primer-specific portion. The sample and the one or more first oligonucleotide probes are contacted under conditions effective for the 3' target-specific portion of a first oligonucleotide probe to hybridize in a base specific manner to a complementary 3' end of a target genomic DNA segment, and for the 5' target-specific portion of the first oligonucleotide probe to hybridize in a base specific manner to a complementary 5' end of the target genomic DNA segment, if present in the sample. Following hybridization, one or more ligation competent junctions suitable for coupling the 3' and 5' ends of the target genomic DNA segment hybridized to the first oligonucleotide probe are generated and the target genomic DNA segment is ligated together at the one or more ligation junctions to form a circular chimeric single-stranded nucleic acid construct of the collection.

Figure 13:
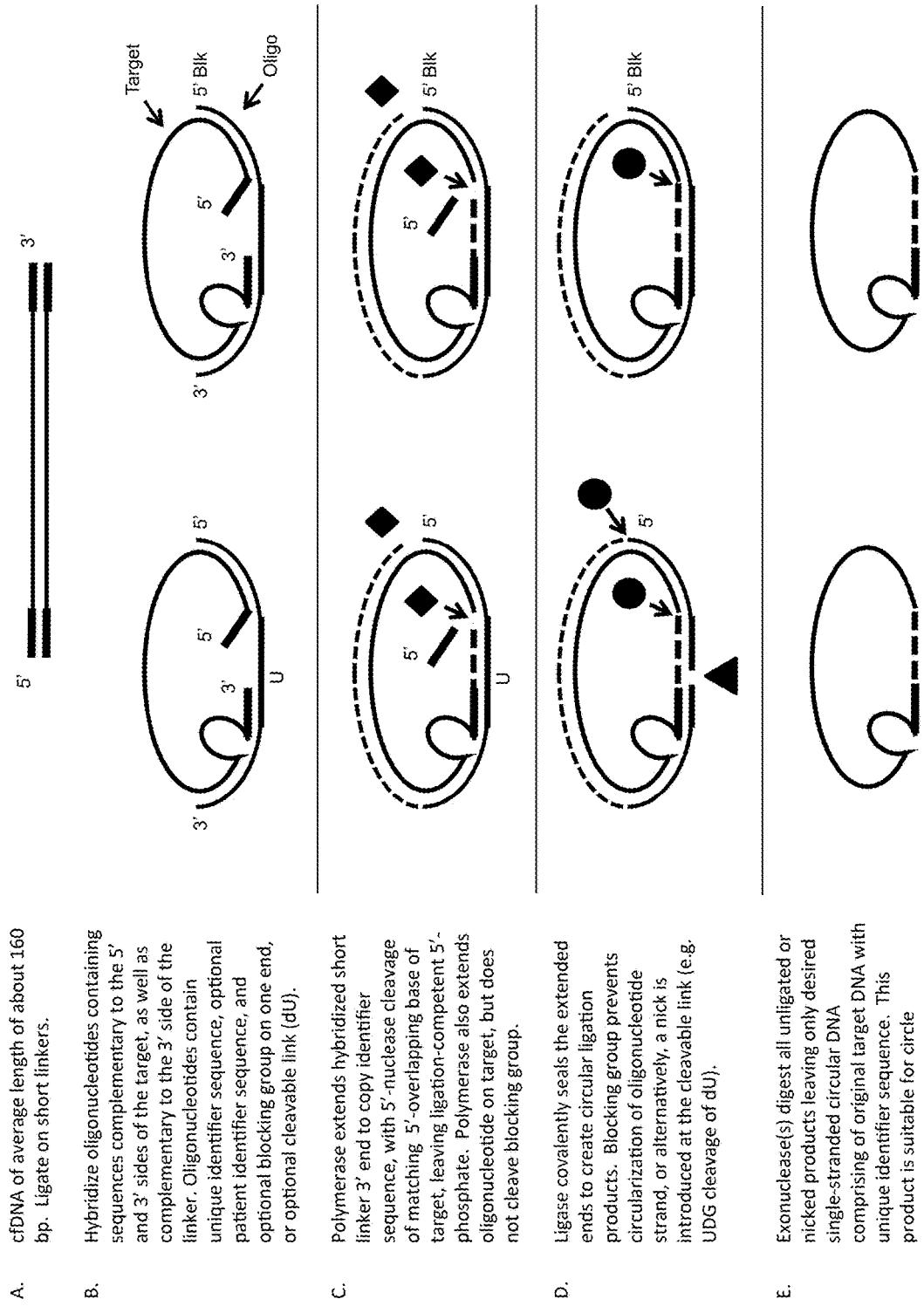
FIG. 13 depicts a method of generating circular chimeric single-stranded nucleic acid constructs of the present invention.

FIG. 13, steps A-E show one exemplary process for producing chimeric circular single stranded nucleic acid "target" constructs suitable for sequencing as described supra. In this embodiment, the original genomic segments comprise segments of cell free DNA (cfDNA) having an average length of 160 bp, or segments of genomic DNA sheared to about 160 bp fragments ("target oligonucleotide" or "DNA segment"). The process starts with the ligation of short linkers to the DNA segments (thick black bars, FIG. 13, step A). As shown in FIG. 13, step B, oligonucleotide probes containing sequences complementary to the 5' and 3' ends of the target DNA segment and complementary to the 3' linker are hybridized to the DNA segments. The looped region near the 3' end of the target DNA oligonucleotide in FIG. 13, step B is a region of the target oligonucleotide that is not complementary to the oligonucleotide probe. As shown in this Figure, small regions of non-complementarity between the target oligonucleotide segment and the oligonucleotide probe do not affect the process of forming the chimeric circular constructs.

The further portion of the oligonucleotide probe (shown as a thick black bar) may also contain a unique identifier sequence, a patient identifier sequence, a primer binding sequence, and/or a cleavable link (FIG. 13, step B, left panel, the cleavable link depicted within the thick bar labelled as "U"). The oligonucleotide probe may also contain a blocking group on one end (FIG. 13, step B, right panel, probe has a 5' blocking group). As shown in FIG. 13, step C, a polymerase (filled diamond) extends the hybridized short linker 3' end of the DNA segment to copy the further portion of the oligonucleotide probe. The polymerase used in this embodiment may comprise exonuclease activity, e.g., 5' to 3' exonuclease activity or 3' to 5' exonuclease activity. Following extension, a 5'-nuclease cleaves at a matching 5'-overlapping base of target DNA to remove the 5' linker region thereby leaving ligation-competent 5'-phosphate. Polymerase also extends the 3' end of the oligonucleotide probe using the target DNA segment as a template (FIG. 13, step C), but does not cleave blocking group (FIG. 13, step C, left side). In FIG. 13, step D (left panel), ligase (filled circle) covalently seals the ligation junction between the 3' and 5' ends of the extended target genomic DNA segment, and the 3' and 5' ends of the extended oligonucleotide probe to create circular ligation products. A nick is introduced at the cleavable link (e.g. UDG cleavage of dU, filled triangle) of the circularized oligonucleotide probe, to render the oligonucleotide probe susceptible to exonuclease digestions (FIG. 13, step E, left panel). As shown in FIG. 13, step D, right panel, ligase (filled circle) covalently seals the ligation junction between the 3' and 5' ends of the extended target genomic DNA segment; however, the 5' blocking group on the oligonucleotide probe prevents circularization of the oligonucleotide probe. As shown in FIG. 13, step E, exonuclease(s) digest all unligated or nicked oligonucleotide products (i.e., oligonucleotide probes) leaving only the desired single-stranded circular nucleic acid constructs comprising the original target DNA segment coupled to the further portion containing, e.g., a unique identifier sequence, primer binding sequence, or patient identifier sequence. As described supra, the resulting circularized product is suitable for rolling circle amplification and circle sequencing.

Figure 14:
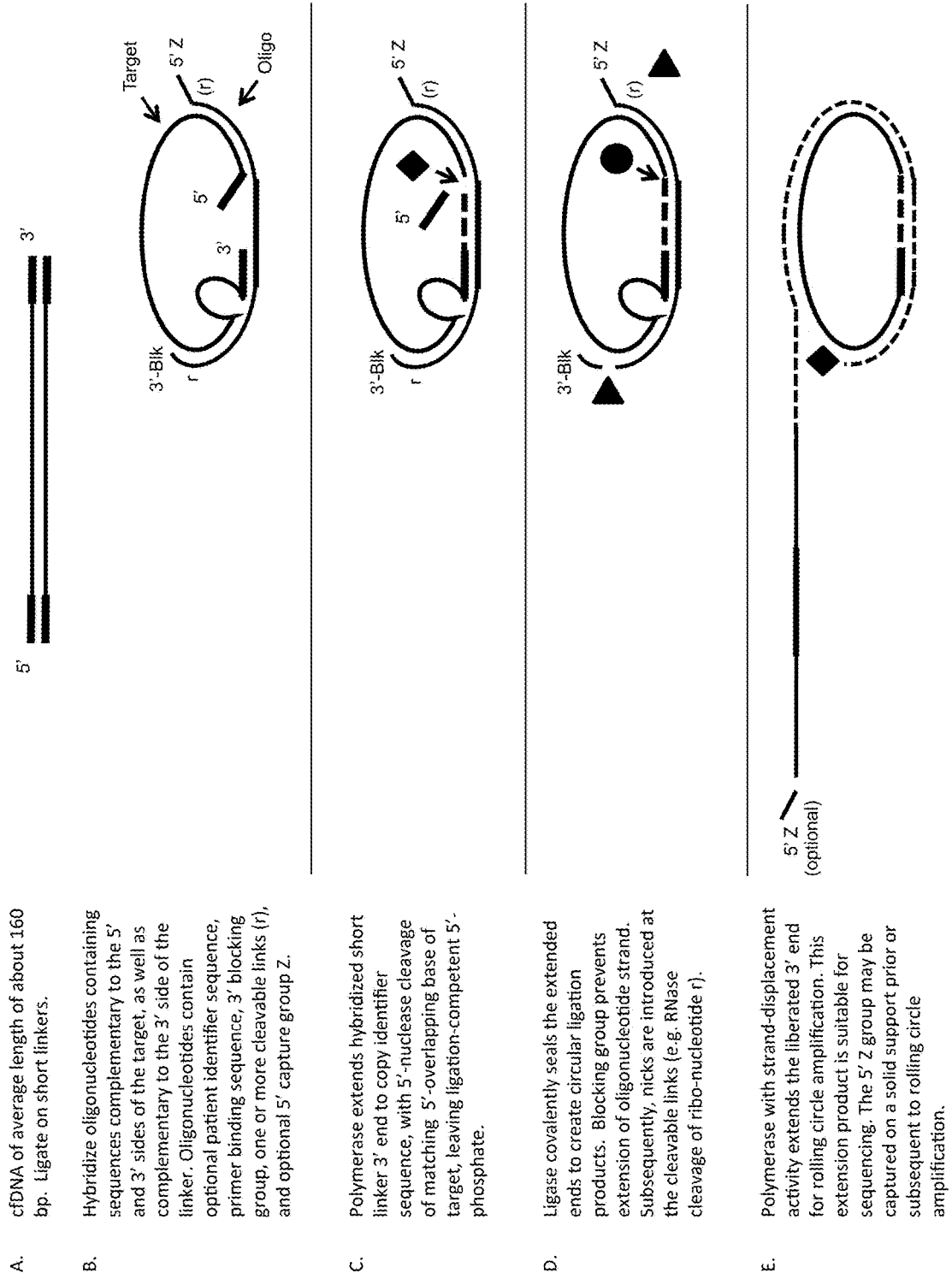
FIG. 14 depicts a method of generating and amplifying circular chimeric single-stranded nucleic acid constructs of the present invention.

The process depicted in FIG. 14, steps A-E is essentially the same as that shown in FIG. 13, steps A-E, however, the oligonucleotide probe comprises a blocking group (3'-Blk) on its 3' end, one or more cleavable link(s) ("r"), a primer binding sequence, and an optional 5' capture group ("Z") (See FIG. 14, step B). Polymerase (filled diamond) extends the hybridized short linker 3' end of the DNA segment to copy the further portion of the oligonucleotide probe. Nuclease cleavage of the 5' end of the DNA segment at an overlapping matching base generates a ligation-competent 5'-phosphate (FIG. 14, step C). In FIG. 14, step D, ligase (filled circle) covalently seals the extended end to create a circular target ligation product. The 3' blocking group of the oligonucleotide probe prevents extension of oligonucleotide probe. Subsequently, the blocking group is removed by cleavage at the cleavable link, e.g., RNase (filled triangle) cleavage of ribo-nucleotide "r" (FIG. 14, step D). As shown in FIG. 14, step E, polymerase (filled diamond) with strand-displacement activity extends the liberated 3' end of the oligonucleotide probe to initiate rolling circle amplification. The primary extension product formed by rolling circle amplification is suitable for sequencing. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 15:
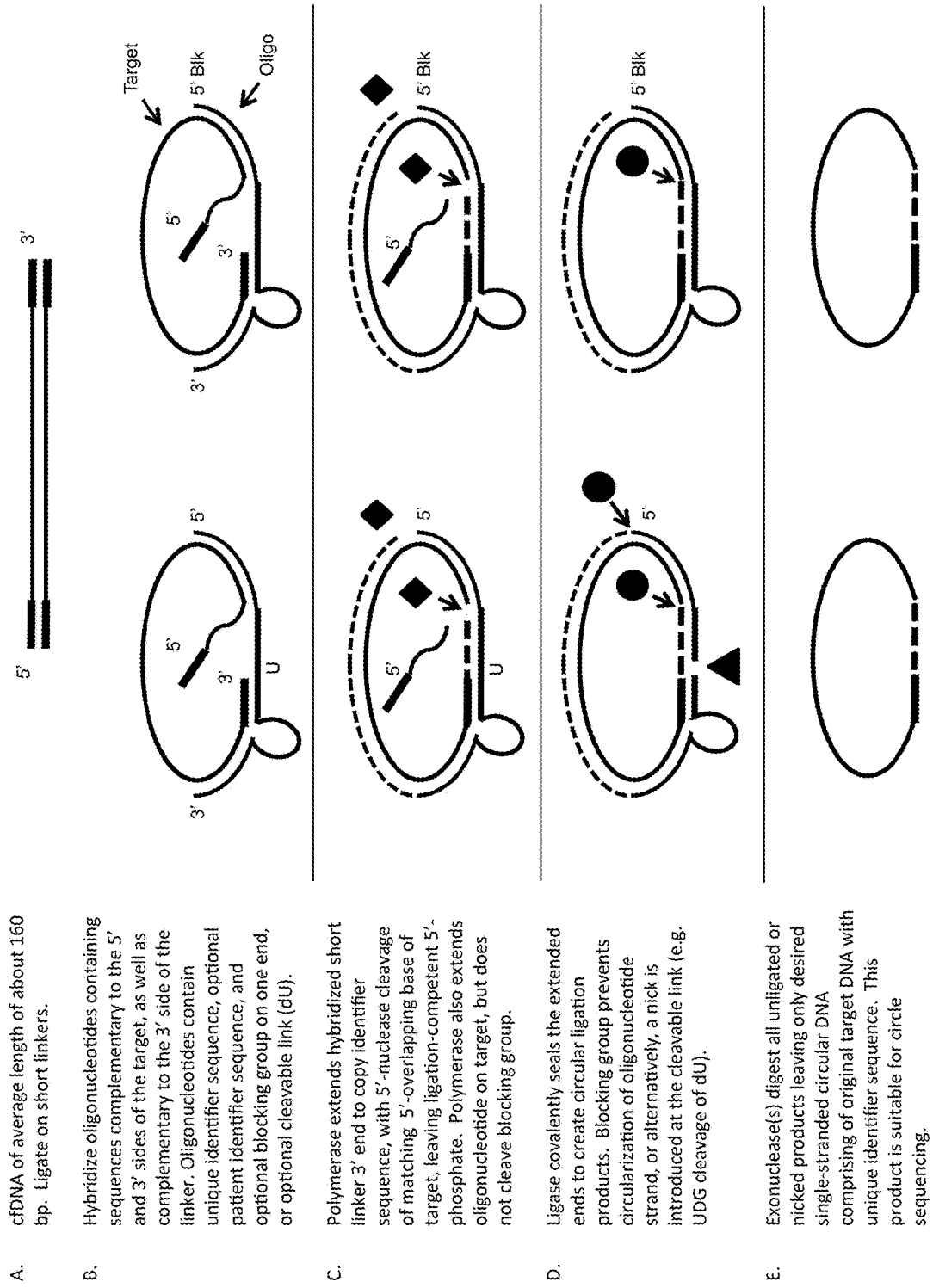
FIG. 15 depicts a method of generating circular chimeric single-stranded nucleic acid constructs of the present invention.
Figure 17:
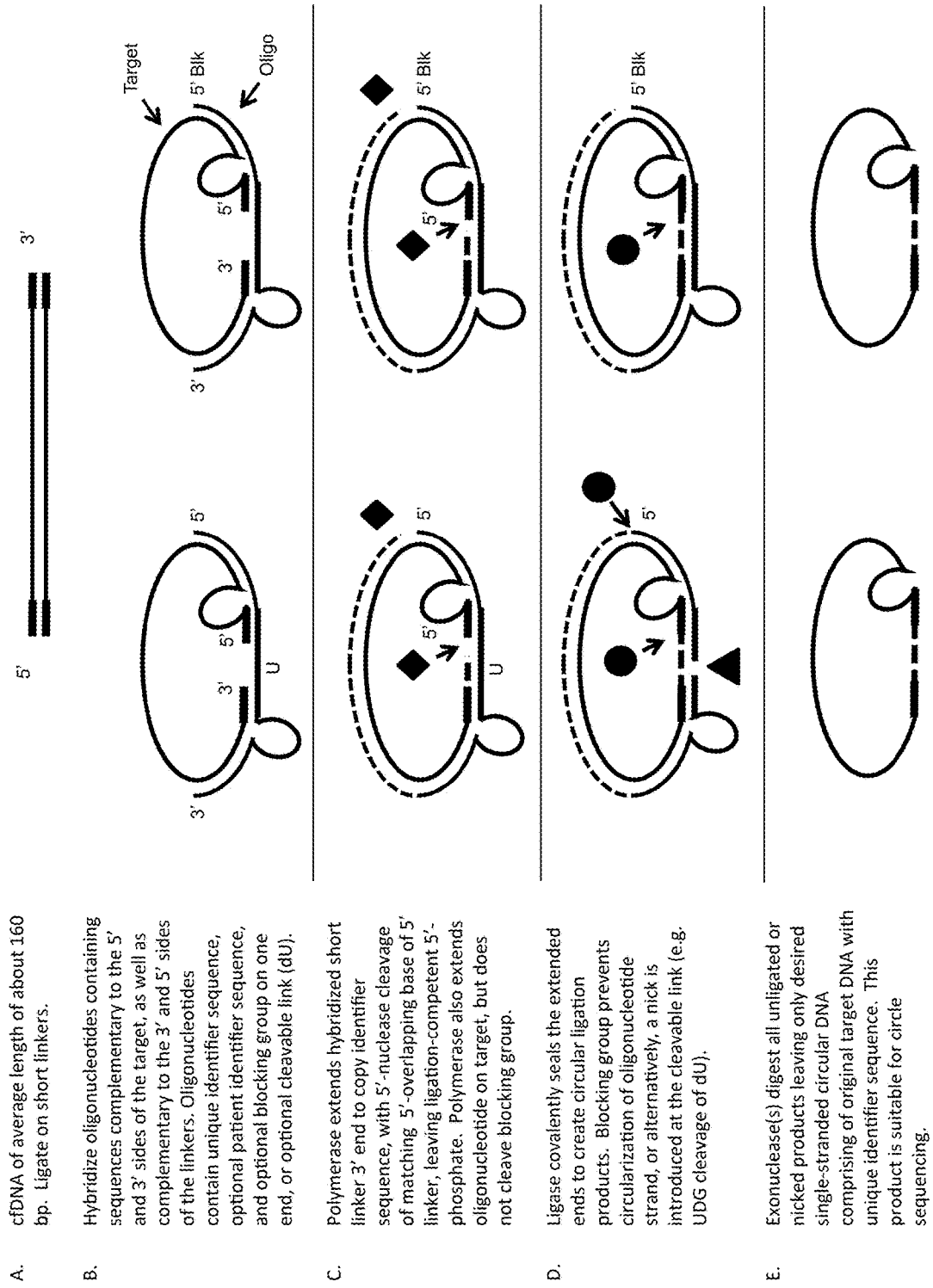
FIG. 17 depicts a method of generating circular chimeric single-stranded nucleic acid constructs of the present invention.

FIG. 15 and FIG. 17 show a similar process as depicted in FIG. 13 for producing chimeric circular single stranded nucleic acid "target" constructs suitable for sequencing. The target genomic DNA is derived from cfDNA of average length of 160 bp or genomic DNA sheared to about 160 bp fragments. The process starts with the ligation of short linkers to the DNA segments (thick black bars, FIG. 15, step A and FIG. 17, step A). As shown in FIG. 15, step B and FIG. 17, step B, oligonucleotide probes containing sequences complementary to the 5' and 3' ends of the DNA segment and complementary to the 3' linker of the DNA segment are hybridized to the target DNA segments. In the embodiment depicted in FIG. 15, step B, the oligonucleotide probe contains a region, i.e., a nucleotide sequence portion that is non-complementary to the 3' end of the target oligonucleotide (looped out portion near the 3' end of the oligonucleotide probe in FIG. 15, step B). In addition, the 5' end of the target oligonucleotide, including the linker, is not complementary to the oligonucleotide probe, thereby forming a flap. In the embodiment of FIG. 17, step B, both the oligonucleotide probe and the target oligonucleotide contain nucleotide sequence portions that are non-complementary to the target or probe oligonucleotide, respectively. These non-complementary regions are depicted as a looped region near the 3' end of the oligonucleotide probe and a looped region near the 5' end of the target oligonucleotide FIG. 17, step B). These regions do not affect the overall process of forming the circularized nucleic acid constructs.

The further portion of the oligonucleotide probes (shown as a thick black bar) may contain a unique identifier sequence, a patient identifier sequence, a primer binding sequence, and/or a cleavable link (depicted within the thick bar as "U" (FIG. 15, step B and 17, step B, left panel). The oligonucleotide probes may also contain a blocking group on one end (FIG. 15, step B and FIG. 17, step B, right panel; blocking group on 5' end of oligonucleotide probe). As shown in FIGS. 15, step C and 17, step C, polymerase (filled diamond) extends the hybridized short linker 3' end of the DNA segment to copy the further portion of the oligonucleotide probe. The polymerase used in this embodiment may comprise exonuclease activity, e.g., 5' to 3' exonuclease activity or 3' to 5' exonuclease activity. Following extension, a 5'-nuclease cleaves at a matching 5'-overlapping base of target DNA to remove the 5' linker region thereby leaving ligation-competent 5'-phosphate (FIG. 15, step C and FIG. 17, step C). Polymerase also extends the 3' end of the oligonucleotide probe using the target DNA segment as a template (FIG. 15, step C and FIG. 17, step C). The blocking group on the 5' of the probe (FIGS. 15, step C and 17, step C, left side) is not cleaved. In FIG. 15, step D and FIG. 17, step D (left panel), ligase (filled circle) covalently seals the ligation junction between the 3' and 5' ends of the extended target genomic DNA segment, and the 3' and 5' ends of the extended oligonucleotide probe to create circular ligation products. A nick is introduced at the cleavable link (e.g. UDG cleavage of dU, filled triangle) of the circularized oligonucleotide probe, to render the oligonucleotide probe susceptible to exonuclease digestions (FIG. 15, step E and FIG. 17, step E, left panel). As shown in FIGS. 15, step D and 17, step D, right panel, ligase (filled circle) covalently seals the ligation junction between the 3' and 5' ends of the extended target genomic DNA segment; however, the 5' blocking group on the oligonucleotide probe prevents circularization of the oligonucleotide probe. As shown in FIG. 15, step E and FIG. 17, step E, exonuclease(s) digest all unligated or nicked oligonucleotide products (i.e., oligonucleotide probes) leaving only the desired single-stranded circular nucleic acid constructs comprising the original target DNA segment coupled to the further portion containing, e.g., a unique identifier sequence, primer binding sequence, or patient identifier sequence. As described supra, the resulting circularized product is suitable for rolling circle amplification and circle sequencing.

Figure 16:
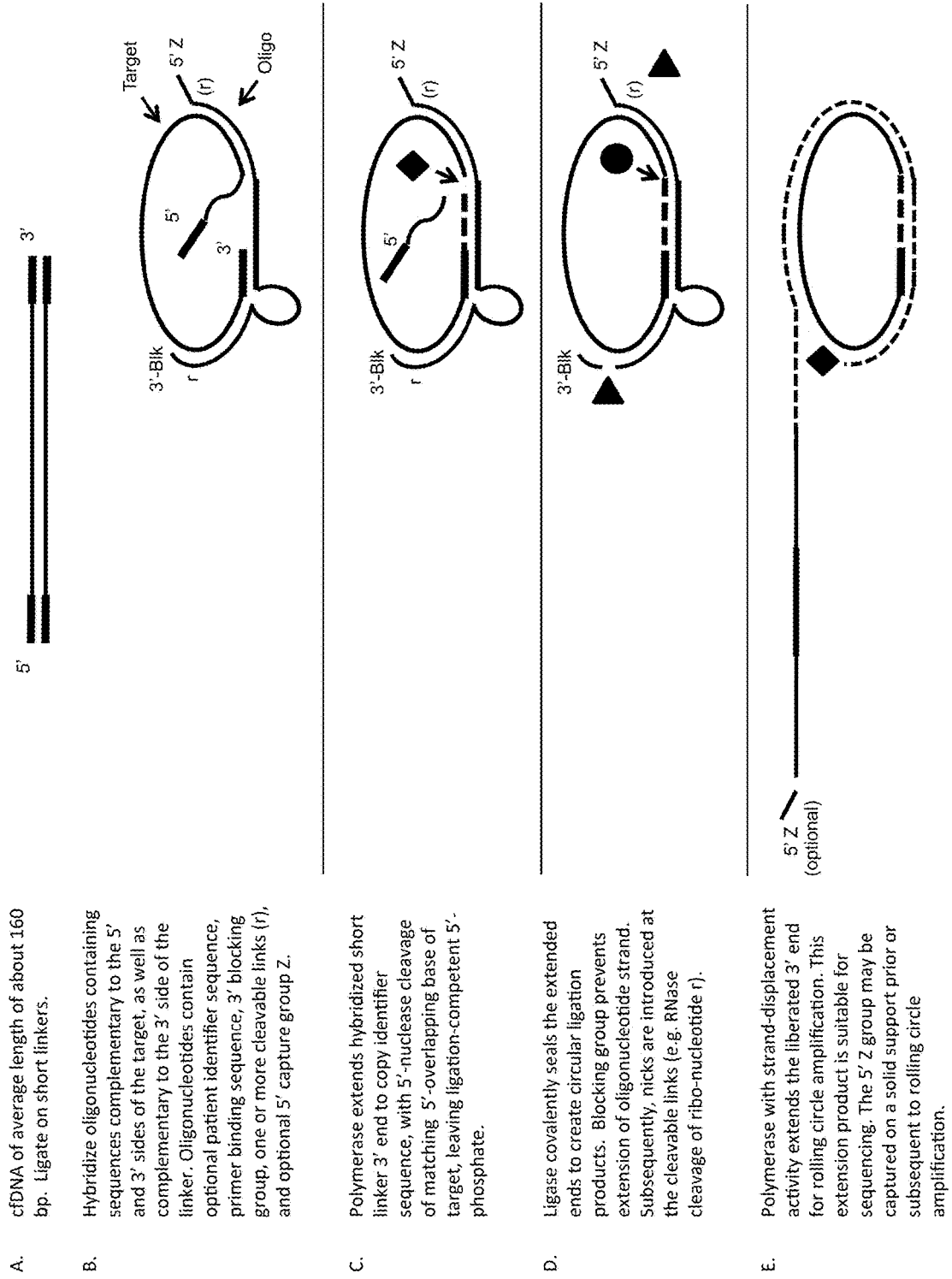
FIG. 16 depicts a method of generating and amplifying circular chimeric single-stranded nucleic acid constructs of the present invention.
Figure 18:
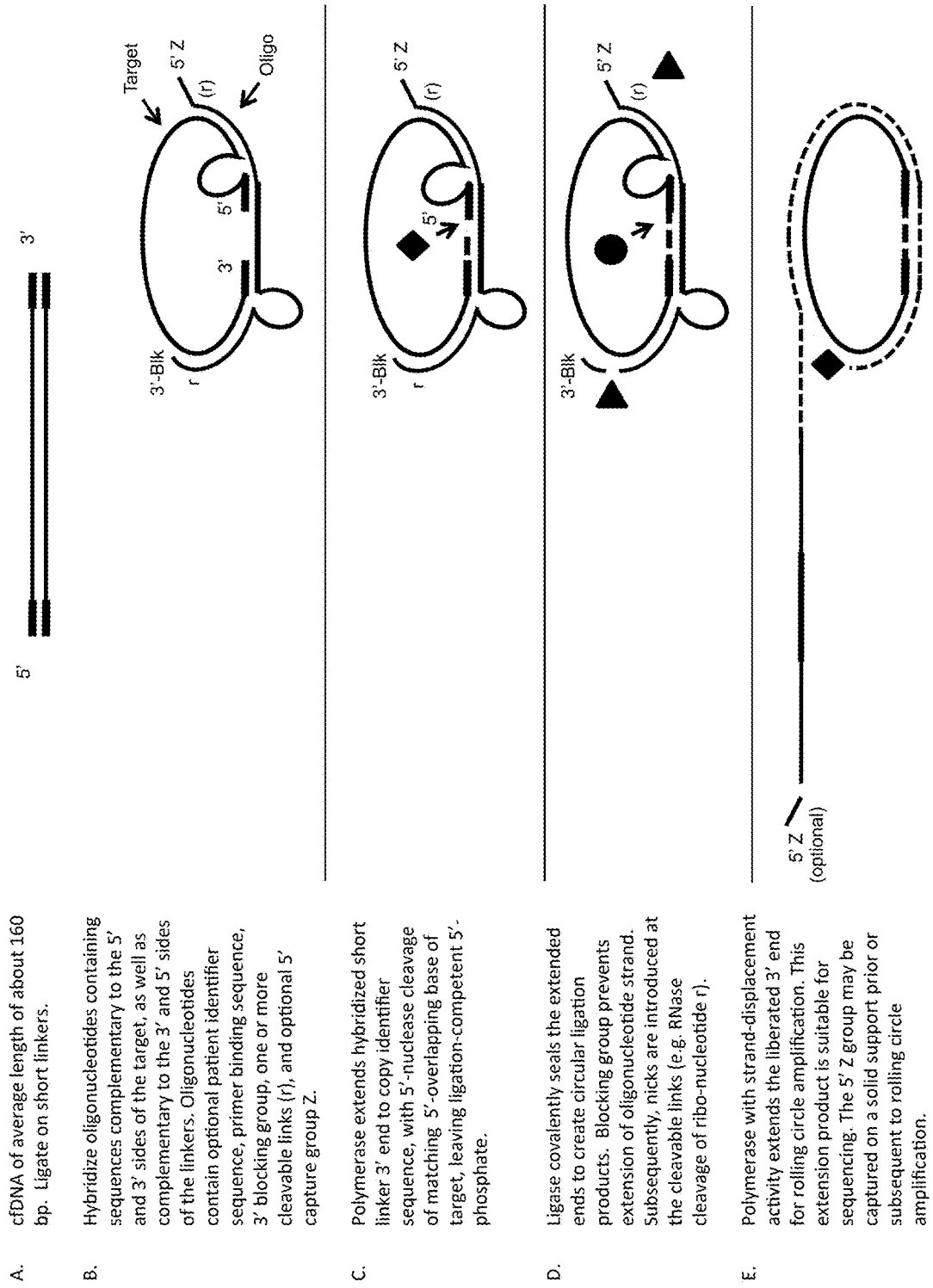
FIG. 18 depicts a method of generating and amplifying circular chimeric single-stranded nucleic acid constructs of the present invention.

The process depicted in FIGS. 16 and 18 is essentially the same as that shown in FIGS. 15 and 17, respectfully, however, the oligonucleotide probe comprises a blocking group (3'-Blk) on its 3' end, one or more cleavable link(s), a primer binding sequence, and an optional 5' capture group ("Z") (See FIG. 16, step B and FIG. 18, step B). Polymerase (filled diamond) extends the hybridized short linker 3' end of the DNA segment to copy the further portion of the oligonucleotide probe. Nuclease cleavage of the 5' end of the DNA segment at an overlapping matching base generates a ligation-competent 5'-phosphate (FIG. 16, step C and FIG. 18, step C). In FIG. 16, step D and FIG. 18, step D, ligase (filled circle) covalently seals the extended end to create a circular ligation product. The 3' blocking group of the oligonucleotide probe prevents extension of oligonucleotide probe. Subsequently, the blocking group is removed by cleavage at the cleavable link, e.g., RNase (filled triangle) cleavage of ribo-nucleotide "r". As shown in FIG. 16, step E and 18, step E, polymerase (filled diamond) with strand-displacement activity extends the liberated 3' end of the oligonucleotide probe to initiate rolling circle amplification. The primary extension product formed by rolling circle amplification is suitable for sequencing. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 19:
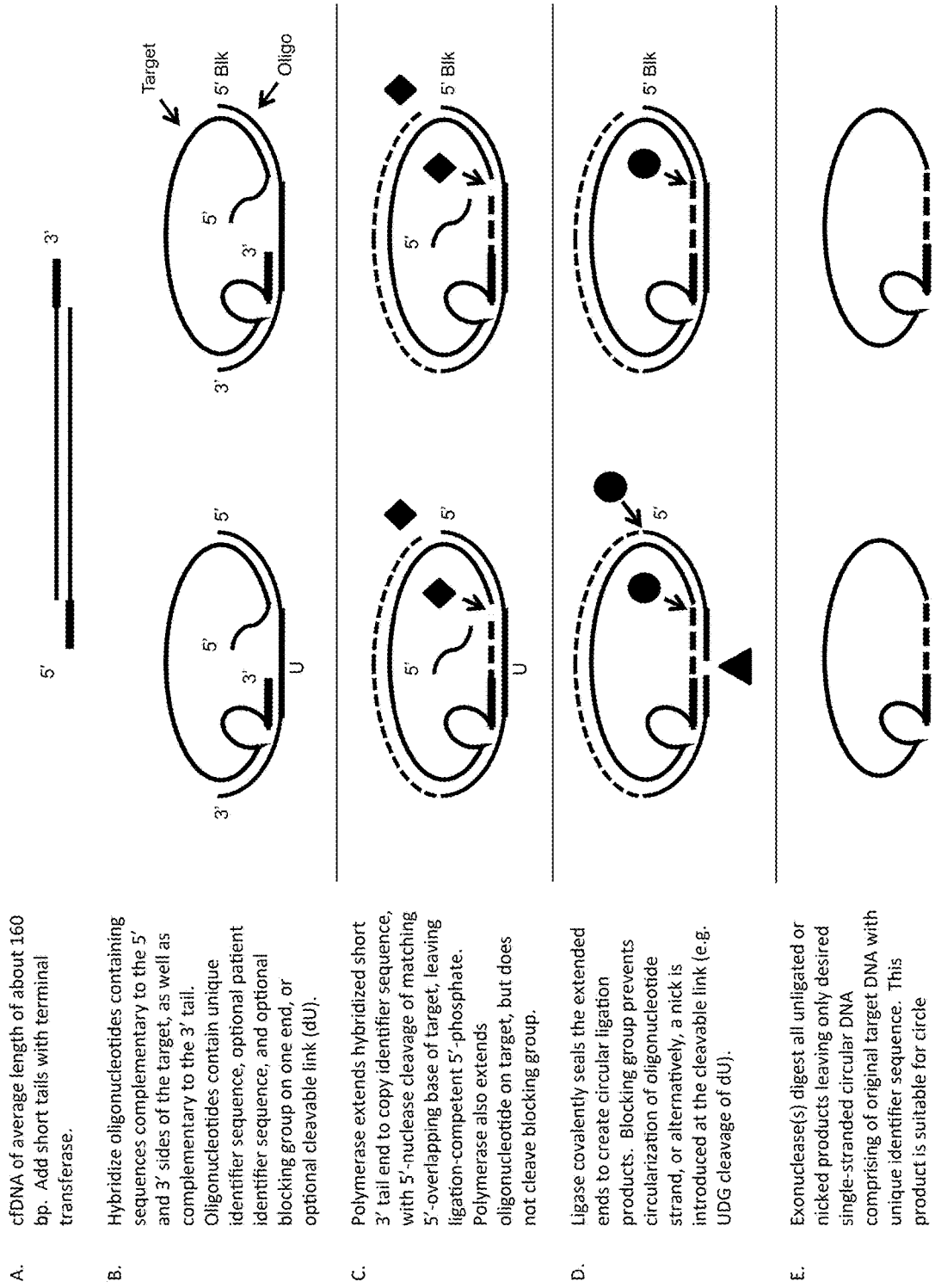
FIG. 19 depicts a method of generating circular chimeric single-stranded nucleic acid constructs of the present invention.
Figure 21:
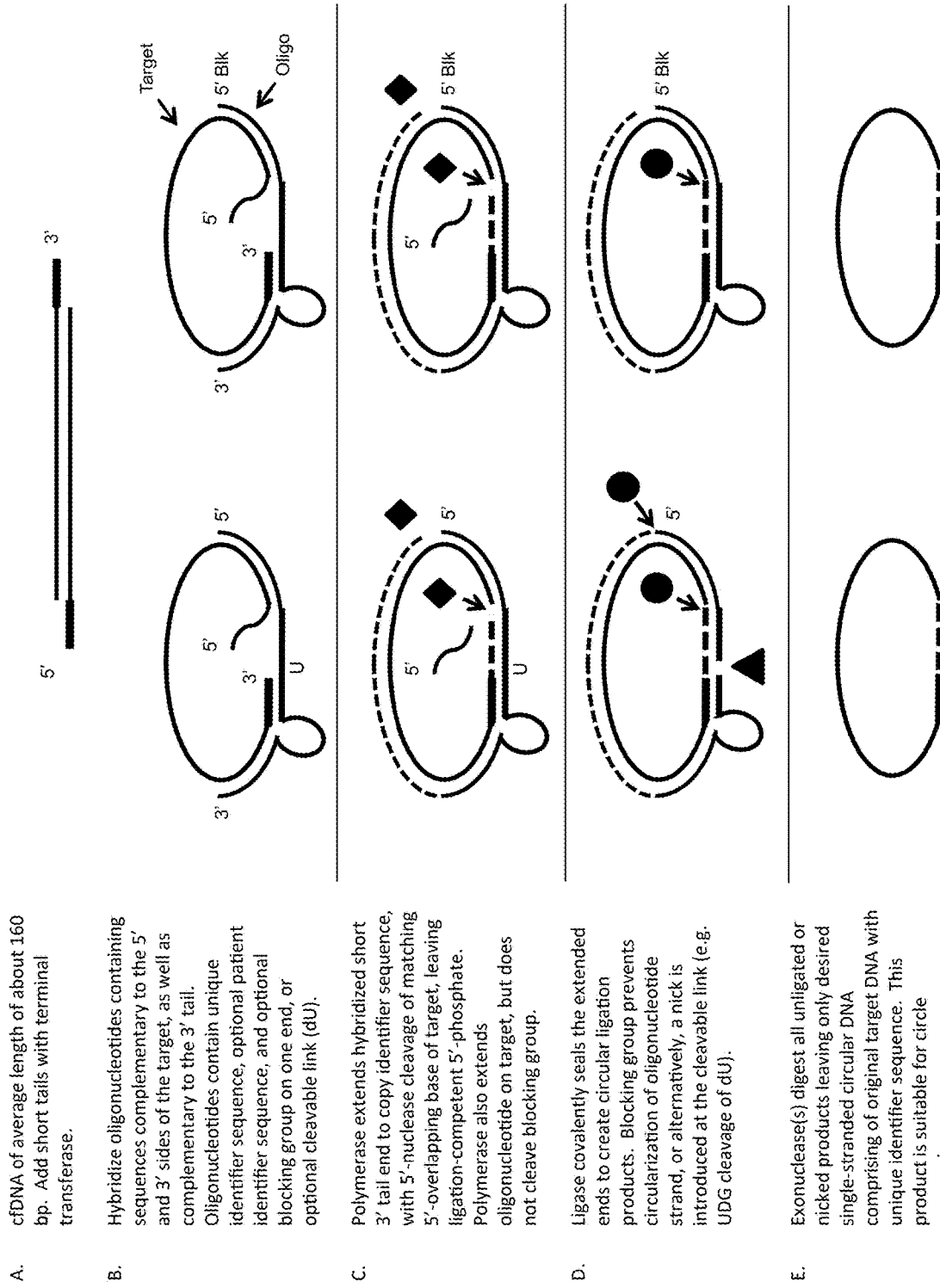
FIG. 21 depicts a method of generating circular chimeric single-stranded nucleic acid constructs of the present invention.

FIGS. 19 and 21 show a similar process for producing chimeric circular single stranded nucleic acid "target" constructs suitable for sequencing as described in reference to FIGS. 13, 15, and 17 supra. The target genomic DNA is derived from cfDNA of average length of 160 bp or genomic DNA sheared to about 160 bp fragments. In this embodiment, the process starts with terminal transferase mediated addition of short nucleotide sequence tails to the 3' end of the target oligonucleotide strands (thick black bars on the 3' ends of target oligonucleotides, FIGS. 19, step A and 21, step A). As shown in FIG. 19, step B and FIG. 21, step B, oligonucleotide probes containing sequences complementary to the 5' and 3' ends of the DNA segment and complementary to the 3' linker of the DNA segment are hybridized to the target DNA segments. In the embodiment depicted in FIG. 19, step B, the DNA oligonucleotide contains a region, i.e., a nucleotide sequence portion on its 3' end that is non-complementary to the probe oligonucleotide (looped out portion near the 3' end of the target oligonucleotide in FIG. 19, step B). In addition, the 5' end of the target oligonucleotide is not complementary to the oligonucleotide probe, thereby forming a flap. In the embodiment of FIG. 21, step B, the oligonucleotide probe contains nucleotide sequence portion that is non-complementary to the target oligonucleotide. This non-complementary region is depicted as a looped region near the 3' end of the oligonucleotide probe. The 5' end of the target oligonucleotide in FIG. 21, step B is not complementary to the oligonucleotide probe, forming a flap suitable for nuclease cleavage. These regions of non-complementarity between the target oligonucleotide and probe oligonucleotide do not affect the overall process of forming the circularized nucleic acid constructs.

The further portion of the oligonucleotide probes (shown as a thick black bar) may contain a unique identifier sequence, a patient identifier sequence, a primer binding sequence, and/or a cleavable link (within the thick bar labelled as "U") (FIGS. 19, step B and 21, step B, left panel). The oligonucleotide probes may also contain a blocking group on one end (e.g. FIGS. 19, step B and 21, step B, right panel show a blocking group on 5' end of oligonucleotide probe). As shown in FIG. 19, step C and FIG. 21, step C, polymerase (filled diamond) extends the hybridized short linker 3' end of the DNA segment to copy the further portion of the oligonucleotide probe. The polymerase used in this embodiment may comprise exonuclease activity, e.g., 5' to 3' exonuclease activity or 3' to 5' exonuclease activity. Following extension, a 5'-nuclease cleaves at a matching 5'-overlapping base of target DNA to remove the 5' linker region thereby leaving ligation-competent 5'-phosphate. Polymerase also extends the 3' end of the oligonucleotide probe using the target DNA segment as a template (FIGS. 19, step C and 21, step C). The blocking group on the 5' of the probe (FIGS. 19, step C and 21, step C, right side) is not cleaved. In FIG. 19, step D and FIG. 21, step D (left panel), ligase (filled circle) covalently seals the ligation junction between the 3' and 5' ends of the extended target genomic DNA segment, and the 3' and 5' ends of the extended oligonucleotide probe to create circular ligation products. A nick is introduced at the cleavable link (e.g. UDG cleavage of dU, filled triangle) of the circularized oligonucleotide probe to render the oligonucleotide probe susceptible to exonuclease digestion (FIGS. 19, step E and 21, step E, left panel). As shown in FIGS. 19, step D and 21, step D, right panel, ligase (filled circle) covalently seals the ligation junction between the 3' and 5' ends of the extended target genomic DNA segment; however, the 5' blocking group on the oligonucleotide probe prevents circularization of the oligonucleotide probe. As shown in FIGS. 19, step E and 21, step E, exonuclease(s) digest all unligated or nicked oligonucleotide products (i.e., oligonucleotide probes) leaving only the desired single-stranded circular nucleic acid constructs comprising the original target DNA segment coupled to the further portion containing, e.g., a unique identifier sequence, primer binding sequence, or patient identifier sequence. As described supra, the resulting circularized product is suitable for rolling circle amplification and circle sequencing.

Figure 20:
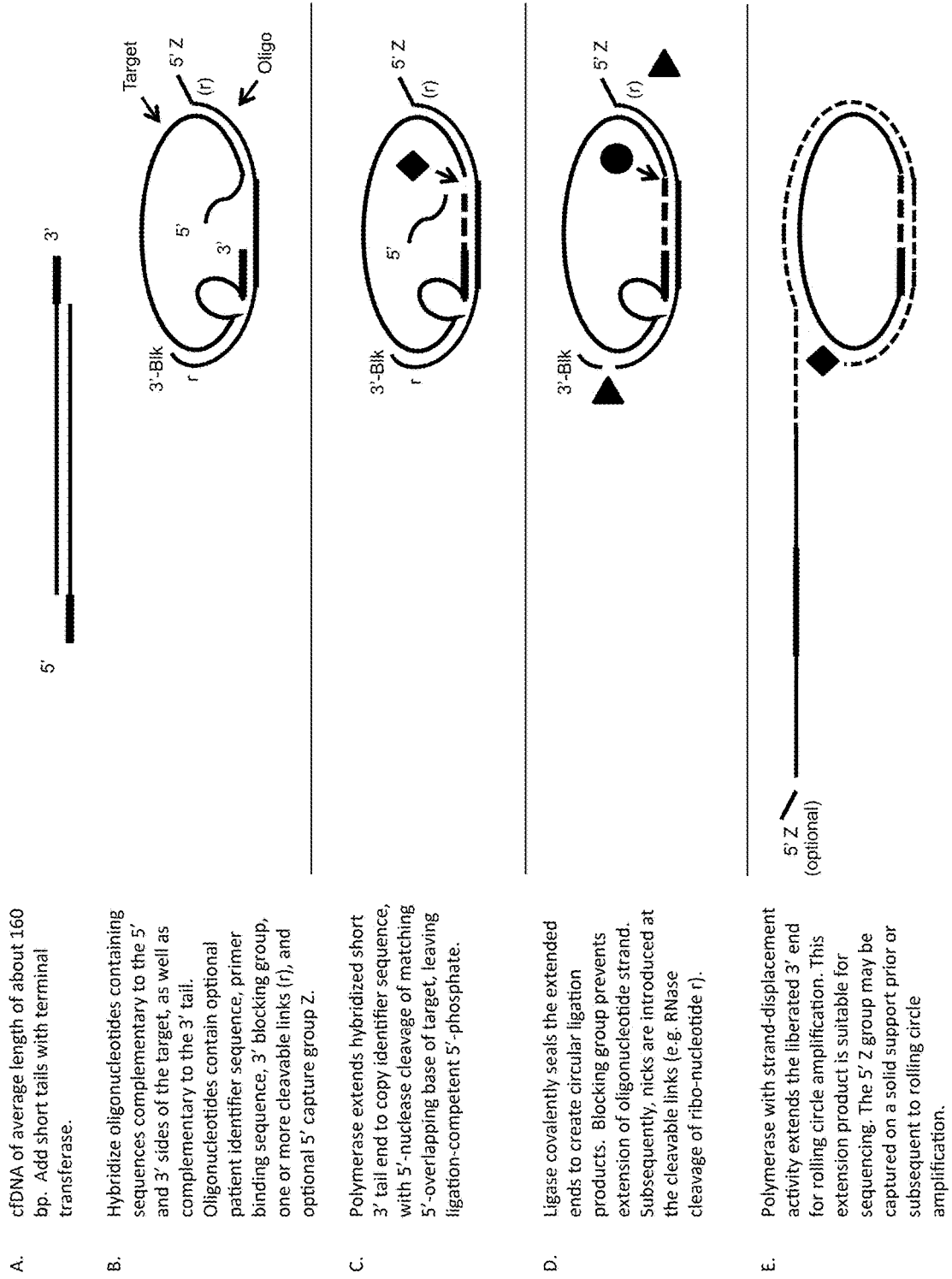
FIG. 20 depicts a method of generating and amplifying circular chimeric single-stranded nucleic acid constructs of the present invention.
Figure 22:
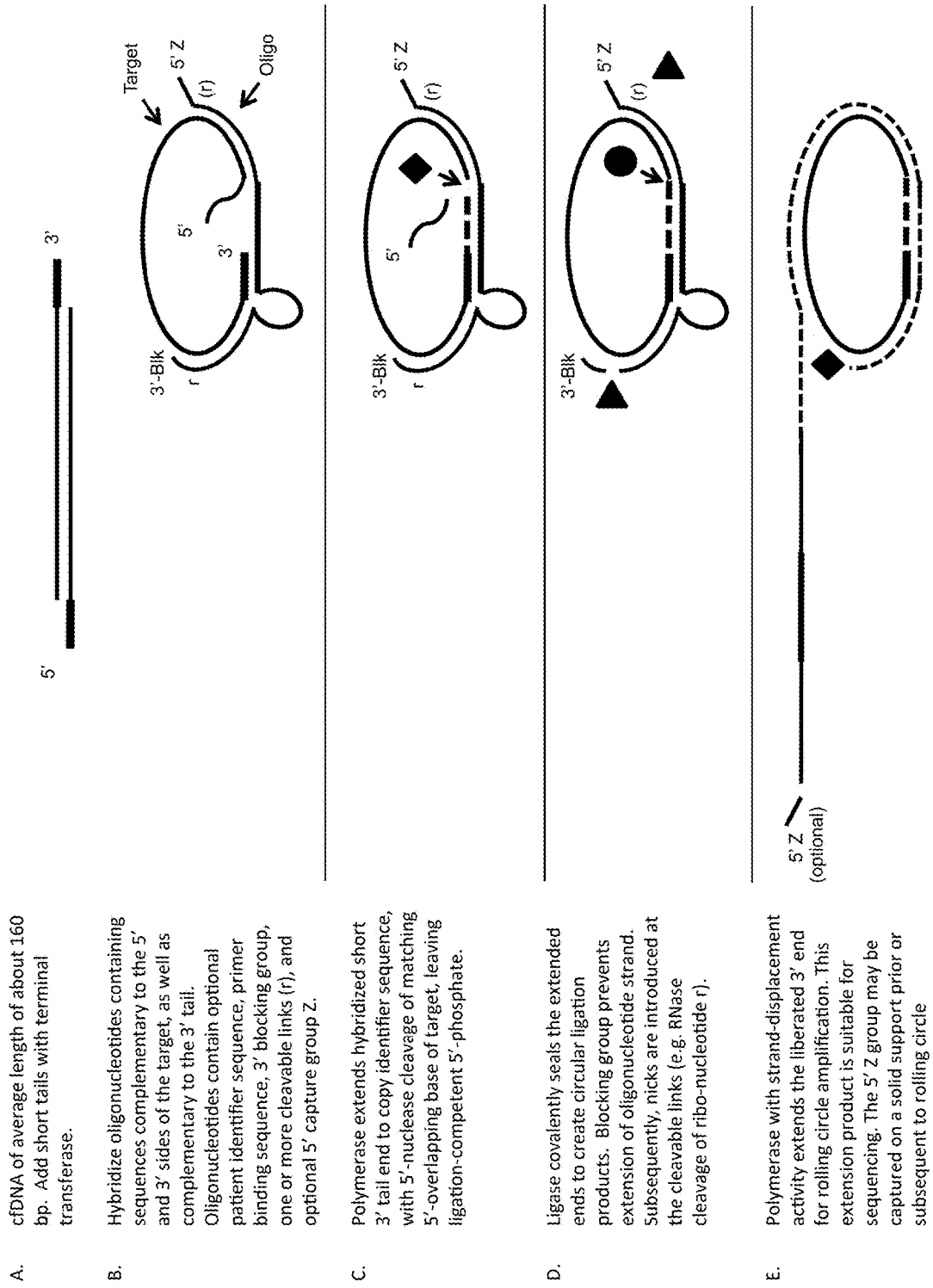
FIG. 22 depicts a method of generating and amplifying circular chimeric single-stranded nucleic acid constructs of the present invention.

The process depicted in FIGS. 20 and 22 is essentially the same as that shown in FIGS. 19 and 21, respectfully, however, the oligonucleotide probe comprises a blocking group (3'-Blk) on its 3' end, one or more cleavable link(s) ("r"), a primer binding sequence, and an optional 5' capture group ("Z") as shown in FIG. 20, step B and FIG. 22, step B). Polymerase (filled diamond) extends the hybridized short linker 3' end of the DNA segment to copy the further portion of the oligonucleotide probe. Nuclease cleavage of the 5' end of the DNA segment at an overlapping matching base generates a ligation-competent 5'-phosphate (FIG. 20, step C and FIG. 22, step C). In FIG. 20, step D and FIG. 22, step D, ligase (filled circle) covalently seals the extended 3' end of the target to its 5' end to create a circular ligation product. The 3' blocking group of the oligonucleotide probe prevents extension of oligonucleotide probe. Subsequently, the blocking group is removed by cleavage at the cleavable link, e.g., RNase (filled triangle) cleavage of ribo-nucleotide "r". As shown in FIGS. 20, step E and 22, step E, polymerase (filled diamond) with strand-displacement activity extends the liberated 3' end of the oligonucleotide probe to initiate rolling circle amplification. The primary extension product formed by rolling circle amplification is suitable for sequencing. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 23:
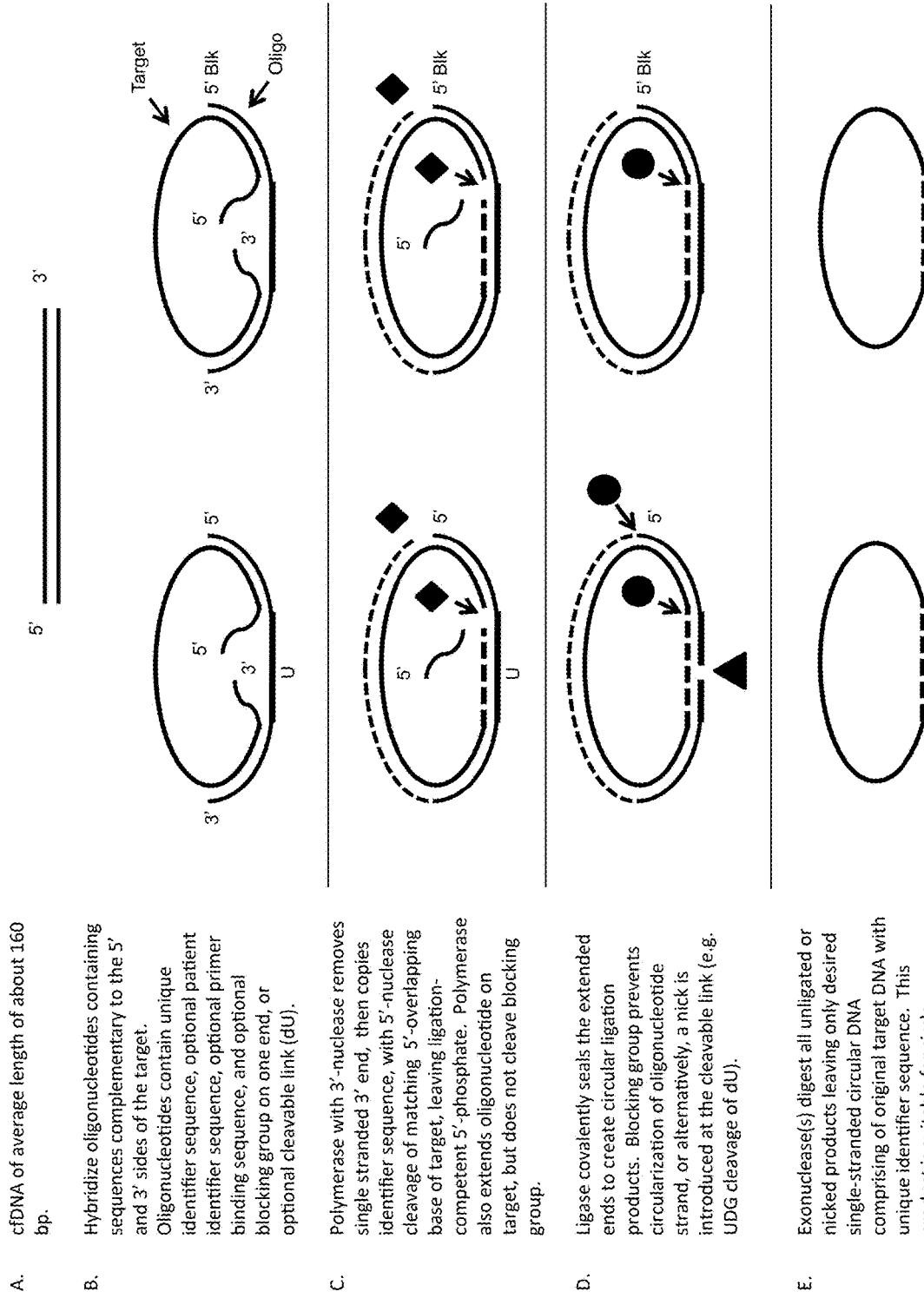
FIG. 23 depicts a method of generating circular chimeric single-stranded nucleic acid constructs of the present invention.
Figure 25:
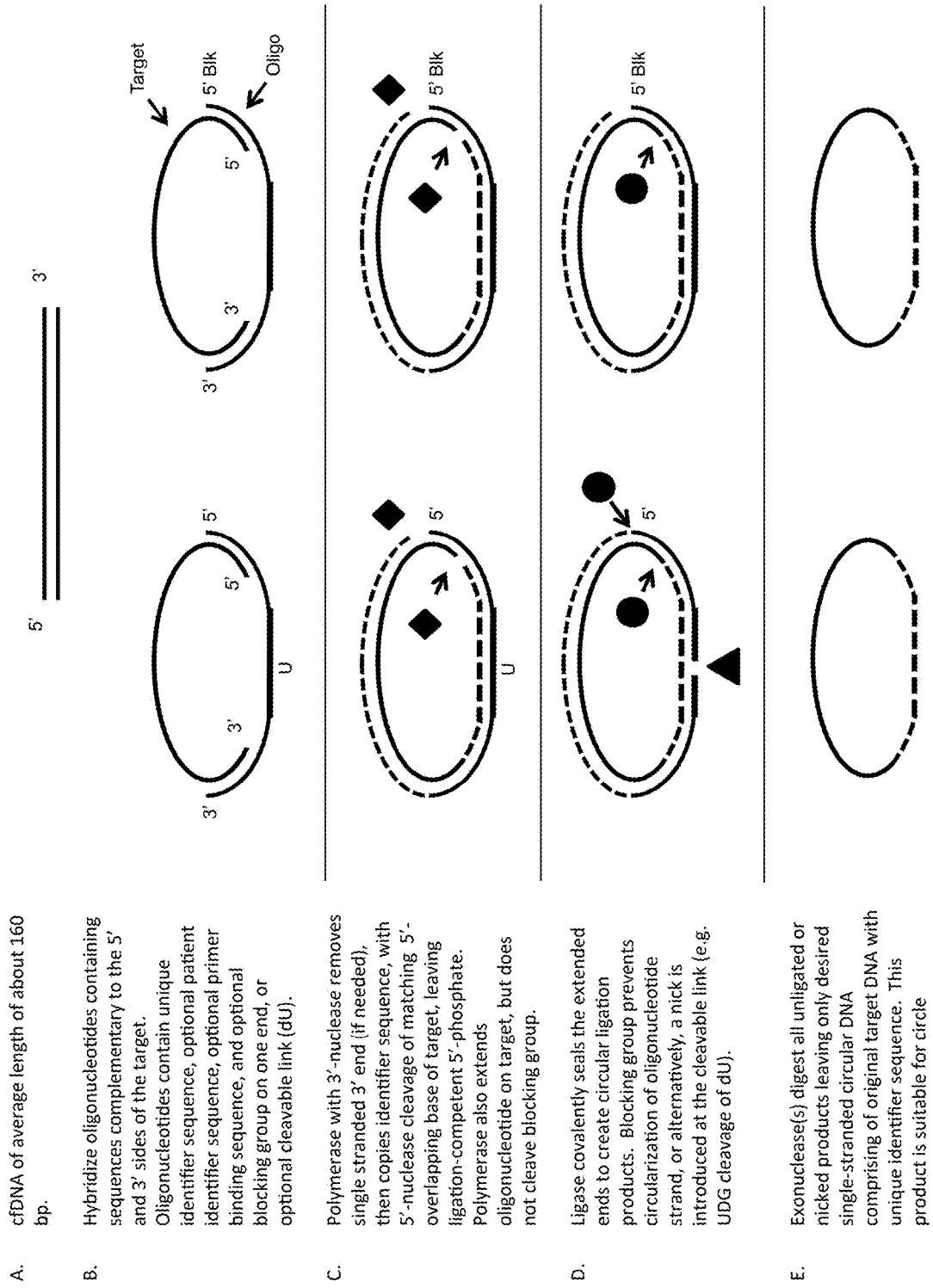
FIG. 25 depicts a method of generating circular chimeric single-stranded nucleic acid constructs of the present invention.

FIG. 23 and FIG. 25 show a similar process for producing chimeric circular single stranded nucleic acid "target" constructs suitable for sequencing as described in reference to FIGS. 13, 15, 17, 19 and 21 supra. The target genomic DNA is derived from cfDNA of average length of 160 bp or genomic DNA sheared to about 160 bp fragments. In the embodiments of FIGS. 23 and 25, no 3' or 5' linkers or tails are added to the genomic DNA segments. As shown in FIG. 23, step B and FIG. 25, step B, oligonucleotide probes containing sequences complementary to the 5' and 3' ends of the DNA segment are hybridized to the target DNA segments. In the embodiment depicted in FIG. 23, step B, the 3' and 5' ends of the DNA oligonucleotide are not complementary to the oligonucleotide probe, forming two non-hybridized flaps. In the embodiment of FIG. 25, step B, the 3' and 5' ends of the DNA oligonucleotide are complementary to the oligonucleotide probe.

The further portion of the oligonucleotide probes (shown as a thick black bar) may contain a unique identifier sequence, a patient identifier sequence, a primer binding sequence, and/or a cleavable link (within the thick bar labelled as "U" (FIGS. 23, step B and 25, step B, left panel). The oligonucleotide probes may also contain a blocking group on one end (e.g., FIGS. 23, step B and 25, step B, right panel; blocking group on 5' end of oligonucleotide probe).

As shown in FIG. 23, step C, a polymerase (filled diamond) having 3' nuclease activity removes the single stranded 3' end of the target oligonucleotide and then extends the 3' end of the DNA segment to copy the further portion of the oligonucleotide probe. Polymerase mediated extension of the 3' end of the target oligonucleotide also occurs in the process of FIG. 25, step B. Following extension in the processes of FIG. 23, step C and FIG. 25, step C, a 5'-nuclease cleaves at a matching 5'-overlapping base of target DNA to remove the 5' linker region thereby leaving ligation-competent 5'-phosphate. Polymerase also extends the 3' end of the oligonucleotide probe using the target DNA segment as a template (FIGS. 23, step C and 25, step C). The blocking group on the 5' of the probe (FIGS. 23, step C and 25, step C, right side) is not cleaved. In FIGS. 23, step D and 25, step D (left panel), ligase (filled circle) covalently seals the ligation junction between the 3' and 5' ends of the extended target genomic DNA segment, and the 3' and 5' ends of the extended oligonucleotide probe to create circular ligation products. A nick is introduced at the cleavable link (e.g. UDG cleavage of dU, filled triangle) of the circularized oligonucleotide probe, to render the oligonucleotide probe susceptible to exonuclease digestions (FIGS. 23, step E and 25, step E, left panel). As shown in FIGS. 23, step D and 25, step D, right panel, ligase (filled circle) covalently seals the ligation junction between the 3' and 5' ends of the extended target genomic DNA segment; however, the 5' blocking group on the oligonucleotide probe prevents circularization of the oligonucleotide probe. As shown in FIGS. 23, step E and 25, step E, exonuclease(s) digest all unligated or nicked oligonucleotide products (i.e., oligonucleotide probes) leaving only the desired single-stranded circular nucleic acid constructs comprising the original target DNA segment coupled to the further portion containing, e.g., a unique identifier sequence, primer binding sequence, or patient identifier sequence. As described supra, the resulting circularized product is suitable for rolling circle amplification and circle sequencing.

The 3' and 5' target specific portions of the oligonucleotide probes, e.g., the oligonucleotide probes used in the process depicted in FIG. 25, can be designed to contain one or more nucleotide mismatches with the target genomic DNA segment. This design feature ensures the target genomic DNA segment of the ligated circularized nucleic acid construct can be distinguished from the polymerase extended portion of the ligated circularize nucleic acid construct (i.e., the solid line of the circularized construct can be distinguished from the dashed line of the construct in FIG. 25E).

Figure 24:
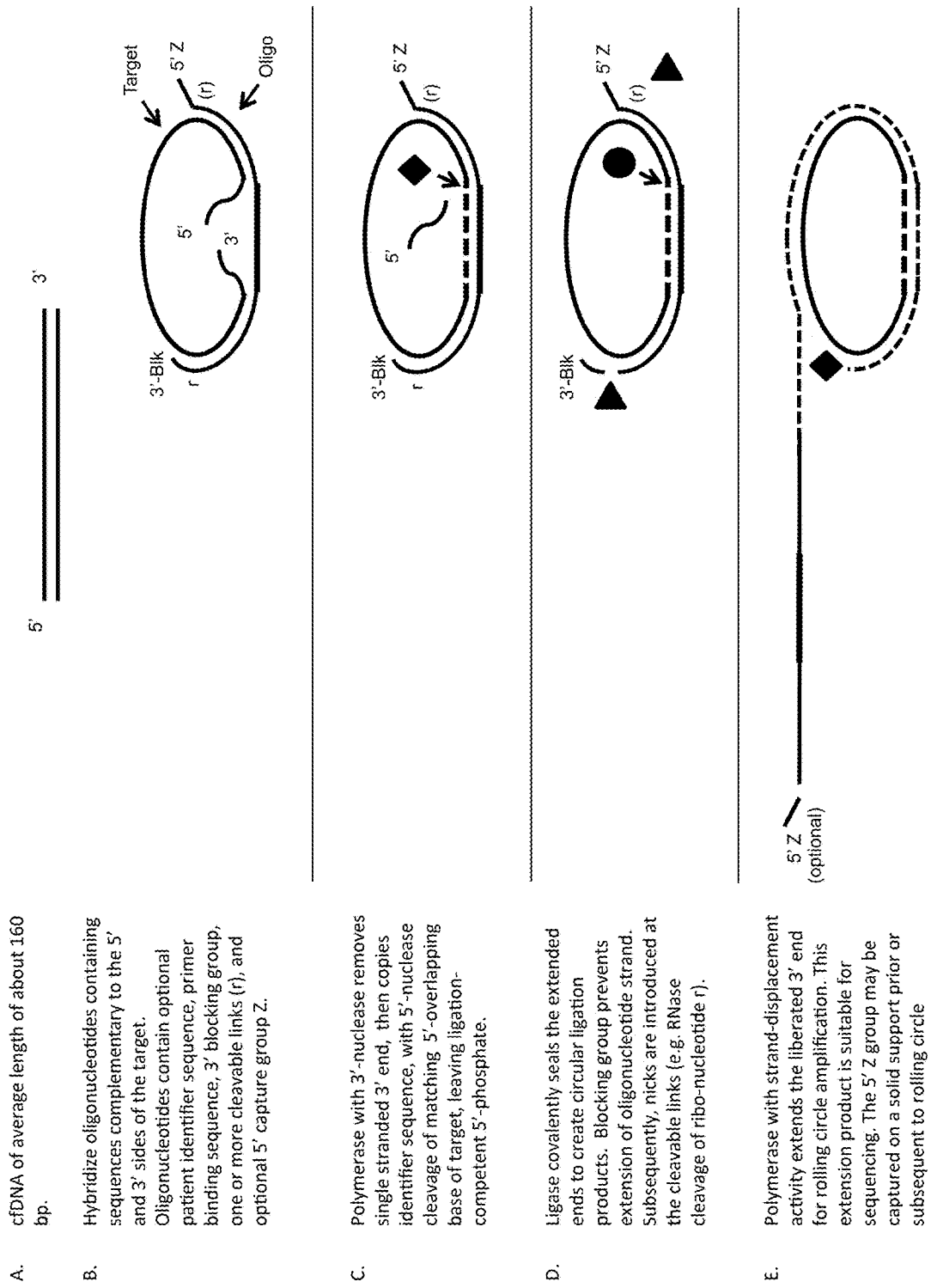
FIG. 24 depicts a method of generating and amplifying circular chimeric single-stranded nucleic acid constructs of the present invention.
Figure 26:
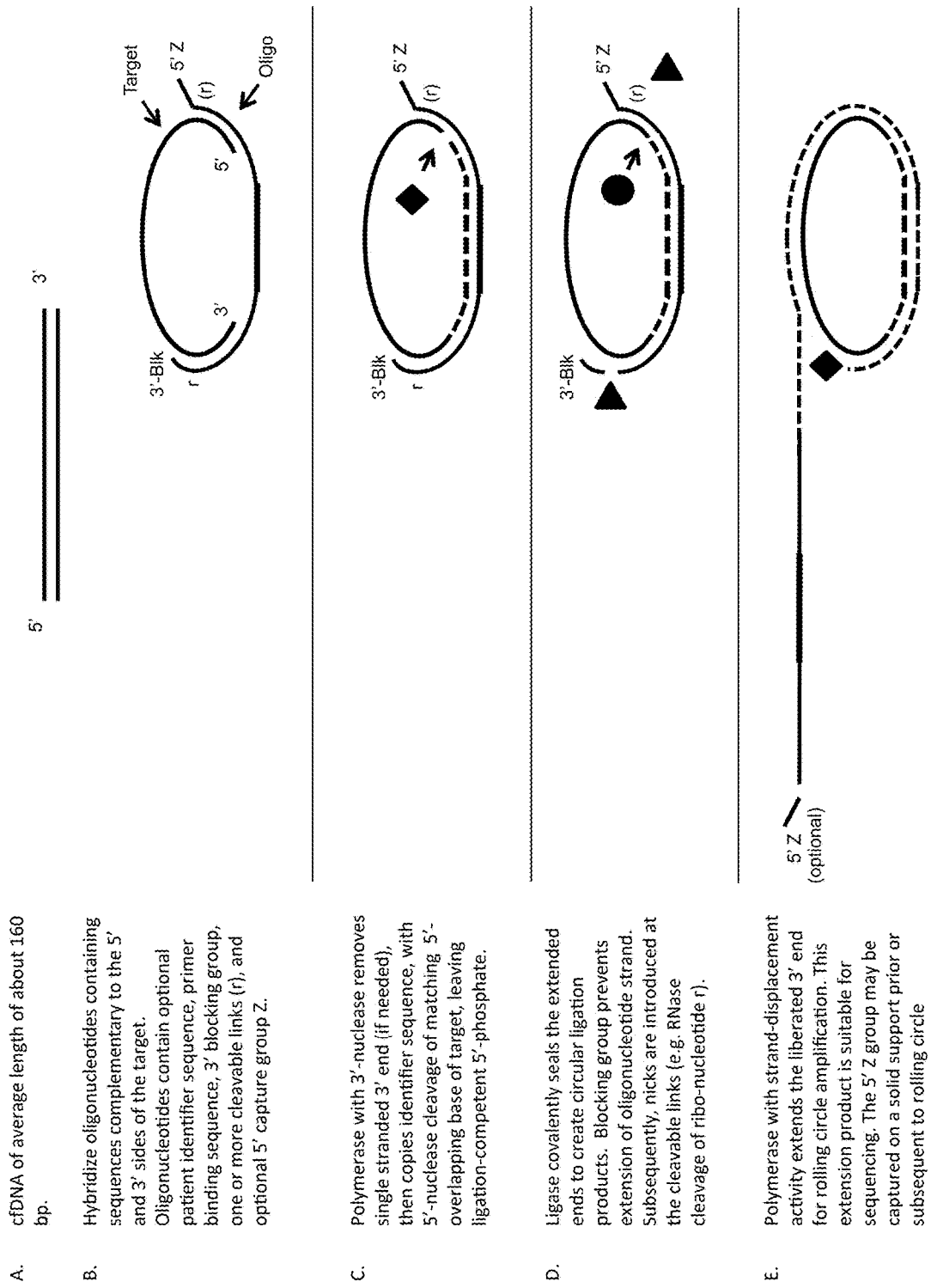
FIG. 26 depicts a method of generating and amplifying circular chimeric single-stranded nucleic acid constructs of the present invention.

The process depicted in FIGS. 24 and 26 is essentially the same as that shown in FIGS. 23 and 25, respectfully, however, the oligonucleotide probe comprises a blocking group (3'-Blk) on its 3' end, one or more cleavable link(s), a primer binding sequence, and an optional 5' capture group ("Z") (FIGS. 24, step B and 26, step B). Polymerase (filled diamond) extends the hybridized 3' end of the DNA segment to copy the further portion of the oligonucleotide probe. In the embodiment of FIG. 24, step C, the polymerase cleaves the 3' non-complementary flap of the target oligonucleotide prior to extension. Nuclease cleavage of the 5' end of the DNA segment at an overlapping matching base generates a ligation-competent 5'-phosphate (FIGS. 24, step C and 26, step C). In FIGS. 24, step D and 26, step D, ligase (filled circle) covalently seals the extended 3' end of the DNA segment to its 5' end to create a circular ligation product. The 3' blocking group of the oligonucleotide probe prevents extension of oligonucleotide probe. Subsequently, the blocking group is removed by cleavage at the cleavable link, e.g., RNase (filled triangle) cleavage of ribo-nucleotide "r". As shown in FIGS. 24, step E and 26, step E, polymerase (filled diamond) with strand-displacement activity extends the liberated 3' end of the oligonucleotide probe to initiate rolling circle amplification. The primary extension product formed by rolling circle amplification is suitable for sequencing. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 27:
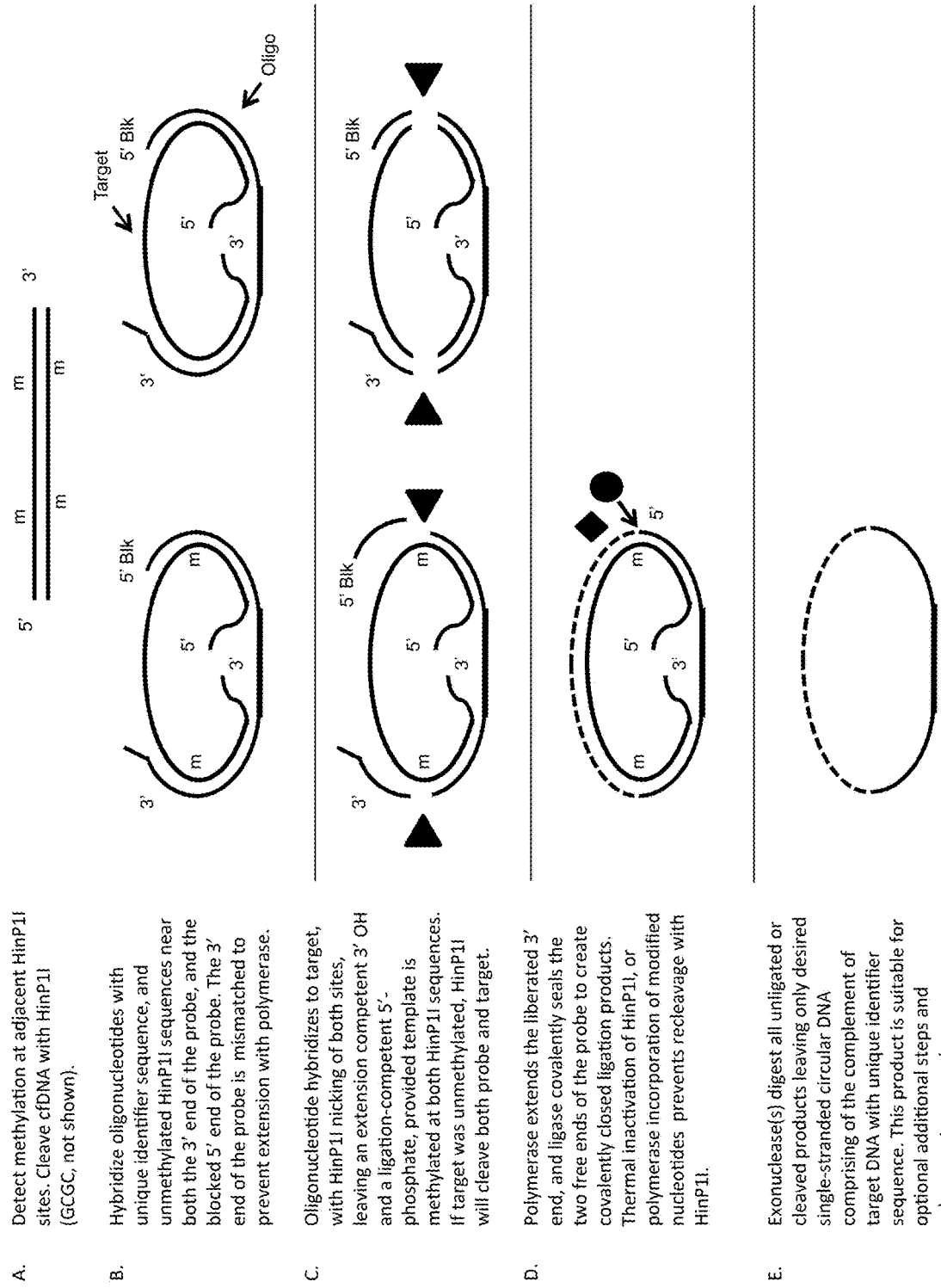
FIG. 27 show a method of detecting methylation at adjacent HinP1 sites in known genetic sequence.

FIG. 27 shows a process of forming single-stranded circularized nucleic acid constructs containing adjacent methylated HinP1I sites (GCGC). The circularized nucleic acid constructs are suitable for detection and/or sequencing of the methylated HinP1I sites. As shown in FIG. 27, step A, the process begins with cleaving cfDNA or genomic DNA with HinP1I at unmethylated HinP1I recognition sites to form genomic DNA segments of about 160 bp. Methylated HinP1I sites within the target oligonucleotide fragments are indicated by 'In'. As shown in FIG. 27, step B, oligonucleotide probes with unique identifier sequence (thick black line) and unmethylated HinP1I sequences near both the 3' and 5' ends of the oligonucleotide probe (i.e., complementary to the HinP1I sites of the cfDNA) hybridize to target cfDNA oligonucleotides having methylated HinP1I sites (left panel) or unmethylated HinP1I sites (right panel). The 5' end of the oligonucleotide probe contains a blocking group and the 3' end is mismatched to the target oligonucleotide to prevent polymerase extension. In FIG. 27, step C, the oligonucleotide probe hybridized to the genomic target segment is subject to HinP1I (filled triangles) cleavage. If both the probe and target oligonucleotides do not contain methylated HinP1I sites, HinP1I cleaves both the target and probe oligonucleotides, thus removing unmethylated target sequences from further analysis. If the target oligonucleotide contains methylated HinP1I sites, but the probe oligonucleotide does not contain methylated HinP1I sites as shown in FIG. 27, step C, left panel, HinP1I cleaves only the probe oligonucleotide, thereby generating an extension competent 3'-OH and a ligation-competent 5'-phosphate on the probe. Polymerase (filled diamond) extends the liberated 3' end of the oligonucleotide probe, and ligase (filled circle) covalently seals the 3' extended end and 5' end of the oligonucleotide probe to create a covalently closed ligation product (FIG. 27, step D). Thermal inactivation of HinP1I, or polymerase incorporation of modified nucleotides prevents re-cleavage with HinP1I. As shown in FIG. 27, step E, exonuclease digestion removes all unligated or cleaved products thereby leaving only desired single-stranded circular DNA constructs comprising the complement of the target DNA with unique identifier sequence. This circularized ligation product is suitable for rolling circle amplification and subsequent sequencing.

Figure 28:
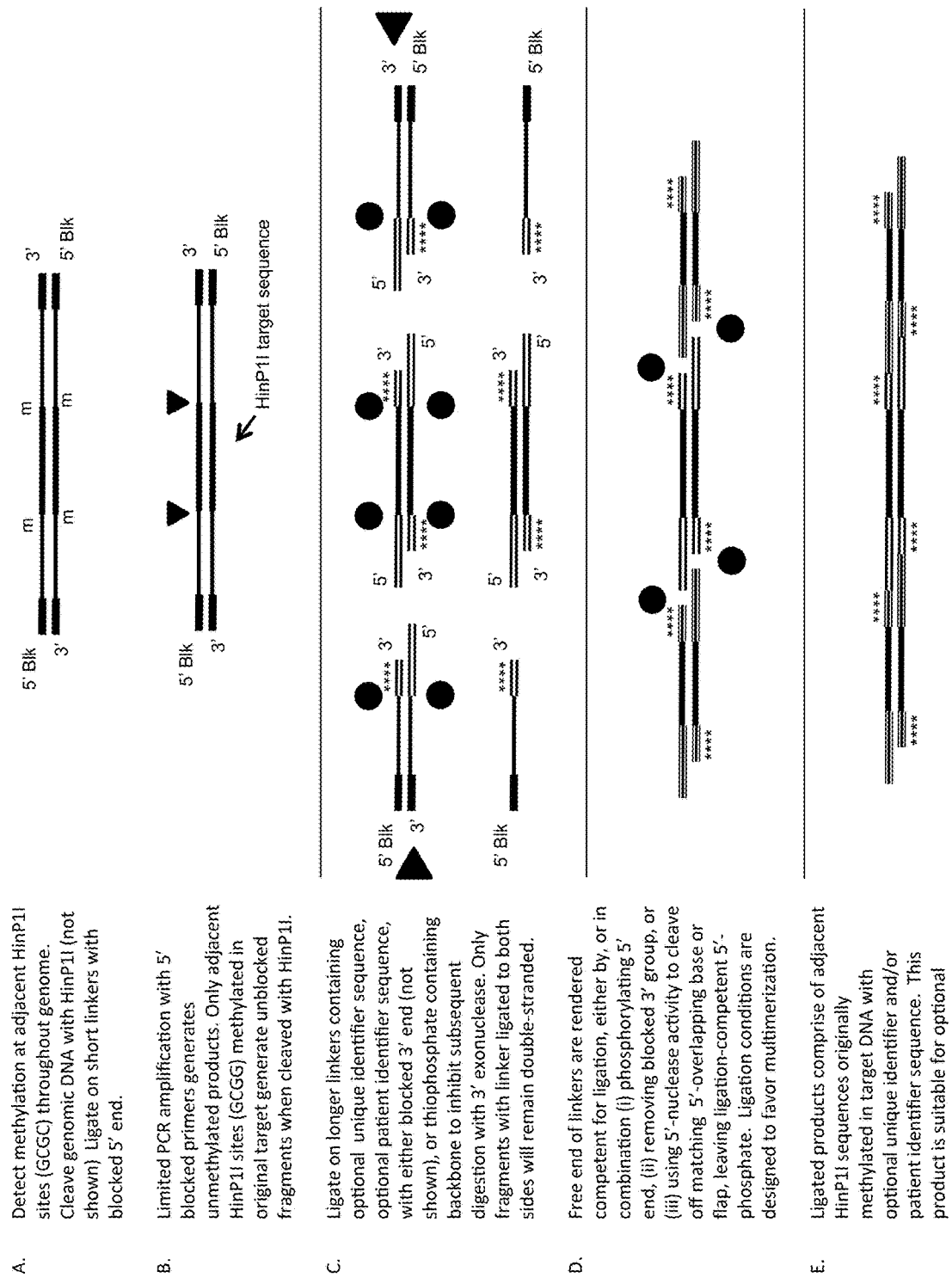
FIG. 28 depicts a process for detecting methylation at adjacent HinP1 sites throughout the genome.

FIG. 28 shows a process for the discovery of methylation at adjacent HinP1I sites (GCGC) throughout the genome. This process involves cleaving genomic DNA with HinP1I and ligating on short linkers (thick black lines) with blocked 5'-ends on to the cleaved genomic fragments as shown in FIG. 28, step A. "m" indicates methylated HinP1I sites. In FIG. 28, step B, limited PCR amplification with 5' blocked primers generates unmethylated products. Only adjacent HinP1I sites (GCGG) methylated in original target generate unblocked fragments when cleaved with HinP1I (filled triangles). As shown in FIG. 28, step C, ligate (filled circles) on linkers (double lines) containing optional unique identifier sequence (grey filled double lines), optional patient identifier sequence (grey filled double lines), with either blocked 3'-end or thiophosphate containing backbone (****) to inhibit subsequent digestion with 3' exonuclease (filled triangles). Only fragments with linkers ligated to both sides will remain double-stranded. In FIG. 28, step D, the free end of linkers are rendered competent for ligation, either by (i) phosphorylating 5'-end, (ii) removing blocked 3'-group, or (iii) using 5'-nuclease activity to cleave off matching 5'-overlapping base or flap, leaving ligation-competent 5'-phosphate, or any combination thereof. In FIG. 28, step E, ligation conditions are designed to favor oligomerization. Ligated products comprise of adjacent HinP1I sequences originally methylated in target DNA with optional unique identifier and/or patient identifier sequence. The final product is suitable for optional additional steps and subsequent sequencing.

Figure 29:
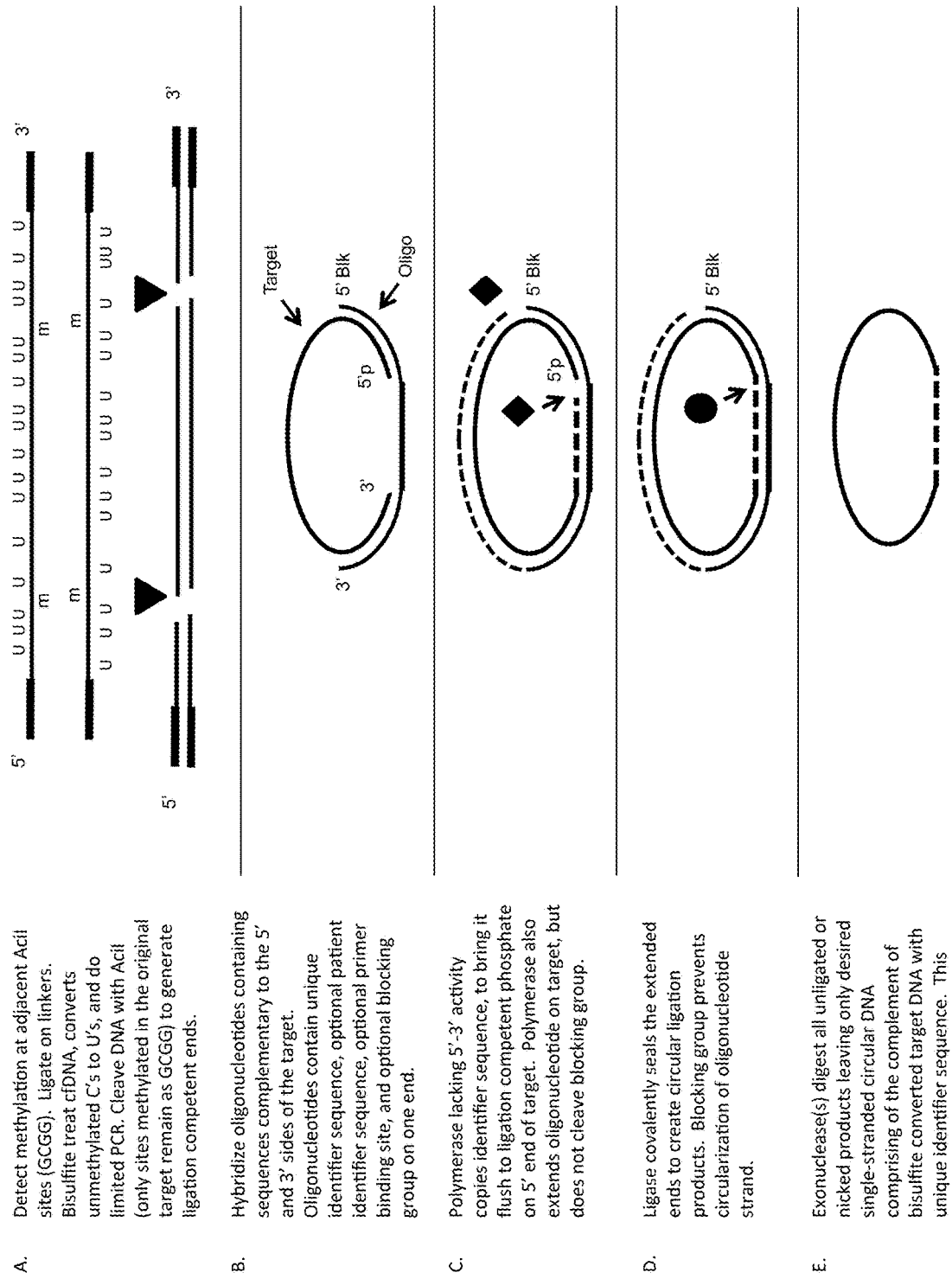
FIG. 29 depicts a method of generating circular chimeric single-stranded nucleic acid constructs of the present invention containing adjacent AciI methylation sites.

FIG. 29 shows a process for producing chimeric circular single stranded nucleic acid constructs suitable for detecting methylation at adjacent AciI sites (GCGG) in known genomic regions starting from cfDNA of average length of 160 bp or genomic DNA sheared to about 160 bp fragments ("target oligonucleotide" or "DNA segment"). As shown in FIG. 29, step A, the process starts with appending bisulfite resistant linkers (thick black lines) on the 3' and 5' ends of the genomic DNA segments (e.g., by ligation). Bisulfite treatment of the genomic DNA, converts unmethylated cytosines to uracils which results in single strand products ("m" in FIG. 29, step A represents methylated AciI sites). Limited PCR is performed to generate double-stranded products, and the resulting PCR product is cleaved with AciI (filled triangles). Only methylated sites in the original target segment remain as GCGG and are subject to AciI cleavage to generate ligation competent ends. As shown in FIG. 29, step B, oligonucleotide probes containing sequences complementary to the 5' and 3' sides of the cleaved target oligonucleotide, and, optionally, a 5'-blocking group, are hybridized to their respective complementary target oligonucleotides. In addition to the target-specific portions, the oligonucleotide probes also contain a further portion. This further portion is a nucleotide sequence portion that may contain a unique identifier sequence, a patient identifier sequence, and one or more primer binding sites. As shown in FIG. 29, step C, polymerase lacking 5'-3' activity (filled diamonds) extends the 3' end of the target oligonucleotide, copying the further portion of the probe and generating a ligation competent junction with the 5' end of target oligonucleotide. Polymerase also extends the oligonucleotide probe using the target oligonucleotide as template, but does not cleave the 5' blocking group of the probe if present. In FIG. 29, step D, ligase (filled circle) covalently seals the 3' and 5' ends of the target oligonucleotide to create circular ligation product containing the target (bisulfite treated and copied) DNA segment. The 5' blocking group on the oligonucleotide probe prevents circularization of the oligonucleotide probe strand. As shown in FIG. 29, step E, exonuclease(s) digest all unligated or nicked products leaving only desired single-stranded circular DNA comprising of the complement of bisulfite converted target DNA with unique identifier sequence. The final product is suitable for circle sequencing using any of the methods described supra.

Figure 30:
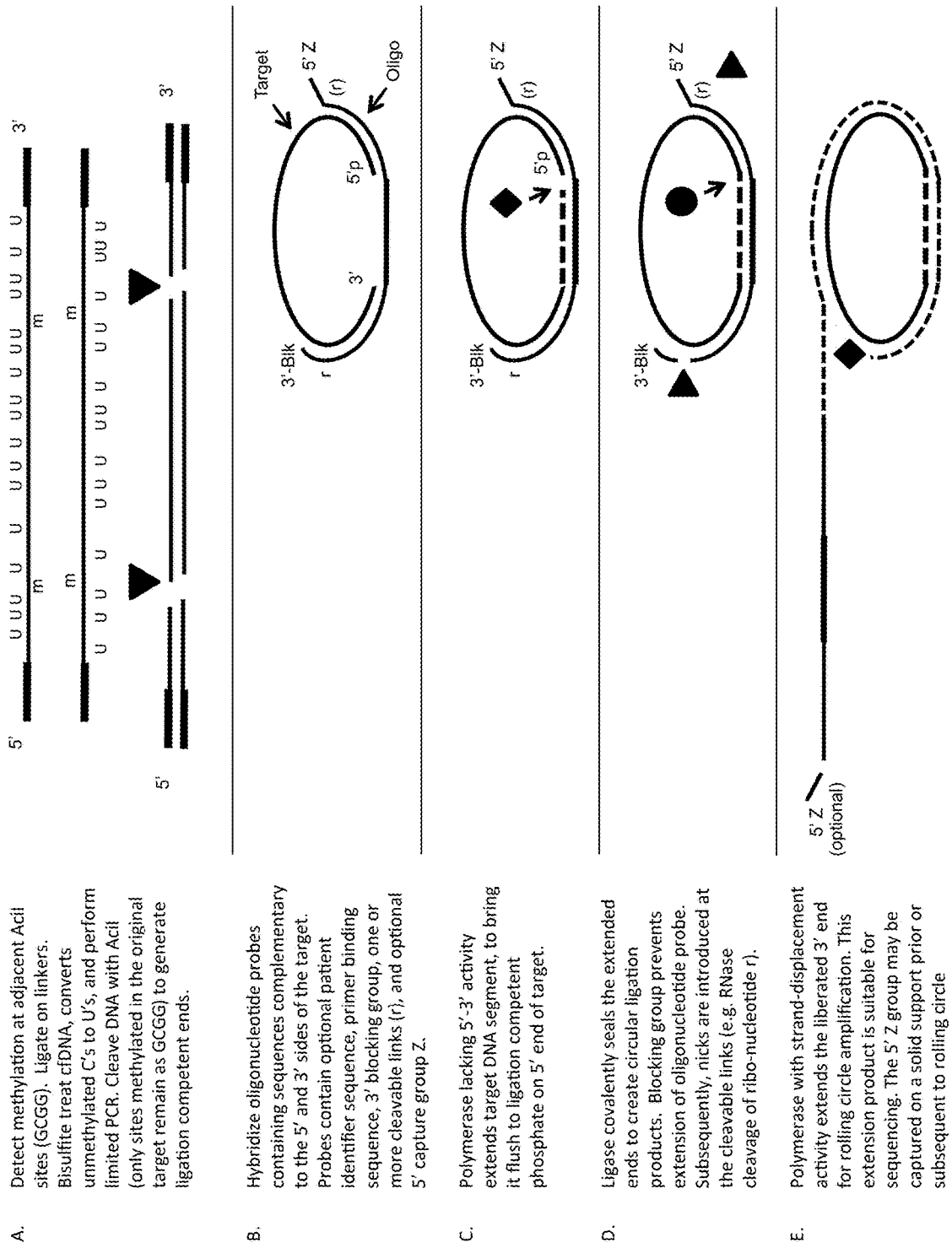
FIG. 30 depicts a method of generating and amplifying circular chimeric single-stranded nucleic acid constructs of the present invention containing adjacent AciI methylation sites.

FIG. 30 shows a process for producing chimeric circular single stranded nucleic acid constructs suitable for detecting methylation at adjacent AciI sites (GCGG) in known genomic regions starting from cfDNA of average length of 160 bp or genomic DNA sheared to about 160 bp fragments.

As shown in FIG. 30A, the process starts with appending bisulfite resistant linkers (thick black lines) to the 3' and 5' ends of the genomic DNA segments (e.g., by ligation). "m" in the genomic DNA segments represents methylated AciI sites. Bisulfite treatment of the cfDNA and/or genomic DNA segments, converts unmethylated C's to U's generating single strand products. Limited PCR is performed to generate double-stranded products, and the resulting PCR products are cleaved with AciI (filled triangles, only sites methylated in the original target remain as GCGG) to generate ligation competent ends. As shown in FIG. 30, step B, oligonucleotide probes containing sequences complementary to the 5' and 3' sides of the cleaved target PCR products are hybridized to their respective complementary target oligonucleotides. The oligonucleotide probe may have a blocking group (3'-Blk) on its 3' end, one or more cleavable link(s), and/or an optional 5' capture group ("Z"). In addition to the target-specific portions, the oligonucleotide probes also contain a further portion. This further portion is a nucleotide sequence portion that may contain a unique identifier sequence, a patient identifier sequence, and one or more primer binding sites. As shown in FIG. 30, step C, a polymerase lacking 5'-3' activity (filled diamonds) extends the 3' end of the target oligonucleotide, copying the further portion of the probe and generating a ligation competent junction with the 5' end of target oligonucleotide. In FIG. 30, step D, ligase (filled circle) covalently seals the 3' and 5' ends of the target oligonucleotide to create circular ligation product containing the target (bisulfite treated, copied) DNA segment. The 3' blocking group on the oligonucleotide probe prevents extension and circularization of the oligonucleotide probe strand. Subsequent removal of the 3' blocking group by nicking the cleavable link (e.g. RNase cleavage of ribonucleotide r) allows polymerase-mediated extension of the oligonucleotide probe (FIG. 30, step D). As shown in FIG. 30, step E, polymerase (filled diamond) with strand-displacement activity extends the liberated 3' end for rolling circle amplification. This extension product is suitable for sequencing using any of the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 31:
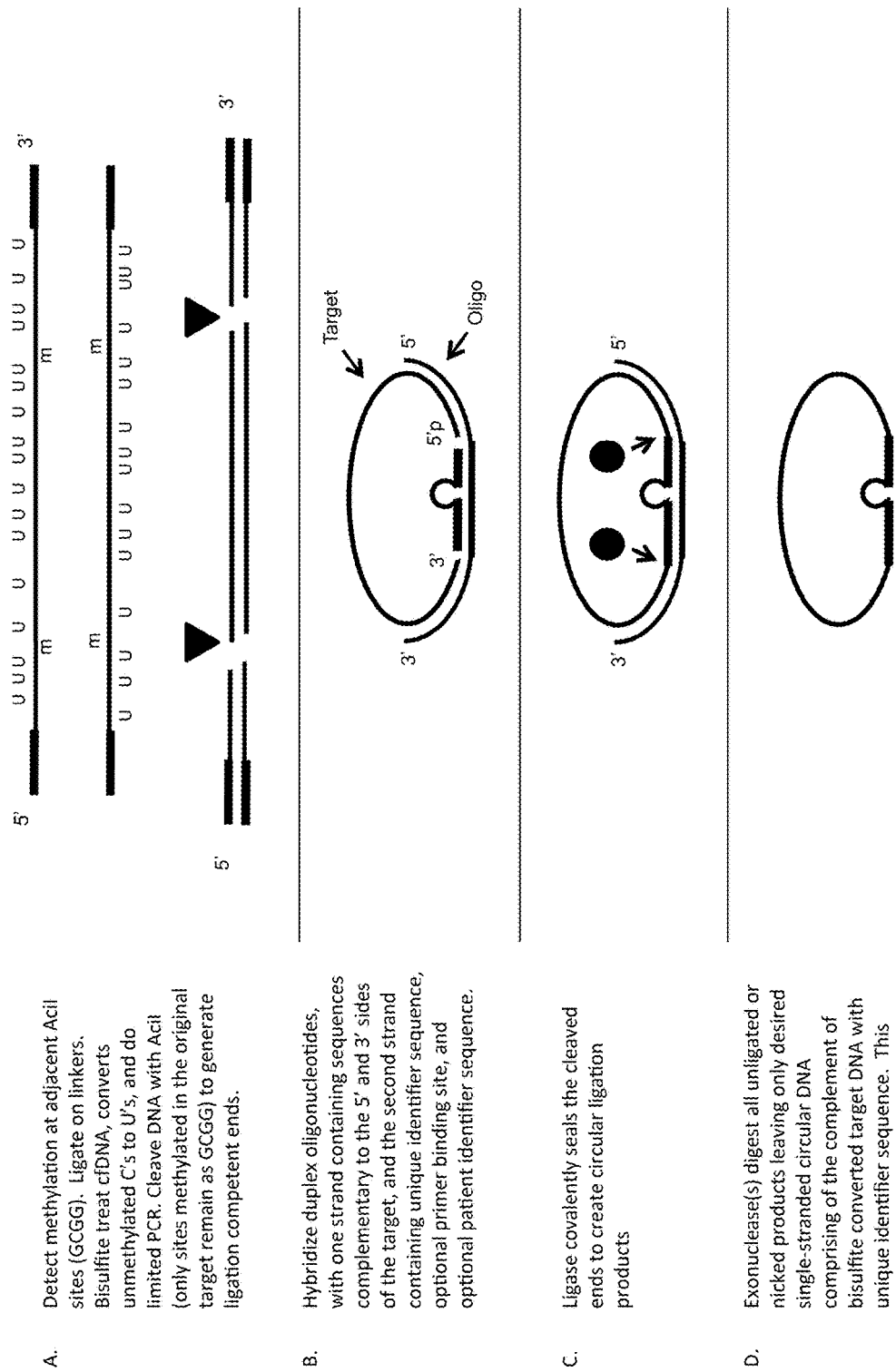
FIG. 31 depicts a method of generating circular chimeric single-stranded nucleic acid constructs of the present invention containing adjacent AciI methylation sites.

FIG. 31 shows a process for producing chimeric circular single stranded nucleic acid constructs suitable for detecting methylation at adjacent AciI sites (GCGG) in known genomic regions starting from cfDNA of average length of 160 bp or genomic DNA sheared to about 160 bp fragments (m represents methylated AciI sites). As shown in FIG. 31, step A, the process starts by appending bisulfite resistant linkers (thick black lines) onto the 3' and 5' ends of the genomic DNA segments (e.g., by ligation). Bisulfite treatment of the cfDNA and/or genomic DNA segments, converts unmethylated C's to U's generating single strand products. Limited PCR is performed to generate double-stranded products, and the resulting PCR products are cleaved with AciI (filled triangles). Only sites methylated in the original target remain as GCGG and are subject to cleavage by AciI to generate ligation competent ends. As shown in FIG. 31, step B, duplex oligonucleotide probes are hybridized to the cleaved target DNA segments. The duplex probes comprise a first oligonucleotide probe strand containing nucleotide sequences complementary to the 5' and 3' sides of the target DNA segments, which are separated from each other by a further portion. The further portion comprises a unique identifier portion, and/or a patient identifier portion, and/or one or more primer binding sequences. The second oligonucleotide probe of the duplex oligonucleotide probe (thick black line with loop) contains a sequence that is complementary to the further portion of the first oligonucleotide probe. The looped region of the second oligonucleotide probe represents a non-complementary region. As shown in FIG. 31, step C, hybridization of the duplex probes to the cleaved genomic DNA segments creates two ligation competent junctions, between the 3' end of the DNA segment and 5' end of the second oligonucleotide probe and between the 3' end of the second oligonucleotide probe and the 5' of the cleaved genomic segment. Ligase (filled circles) covalently seals the ligation junctions to create circular ligation products containing the target (bisulfite treated, copied) DNA segment (FIG. 31, step C). As shown in FIG. 31, step D, exonuclease digestion removes all unligated or nicked products leaving only desired single-stranded circular ligation products which are suitable for circle sequencing using any of the methods described herein.

Figure 32:
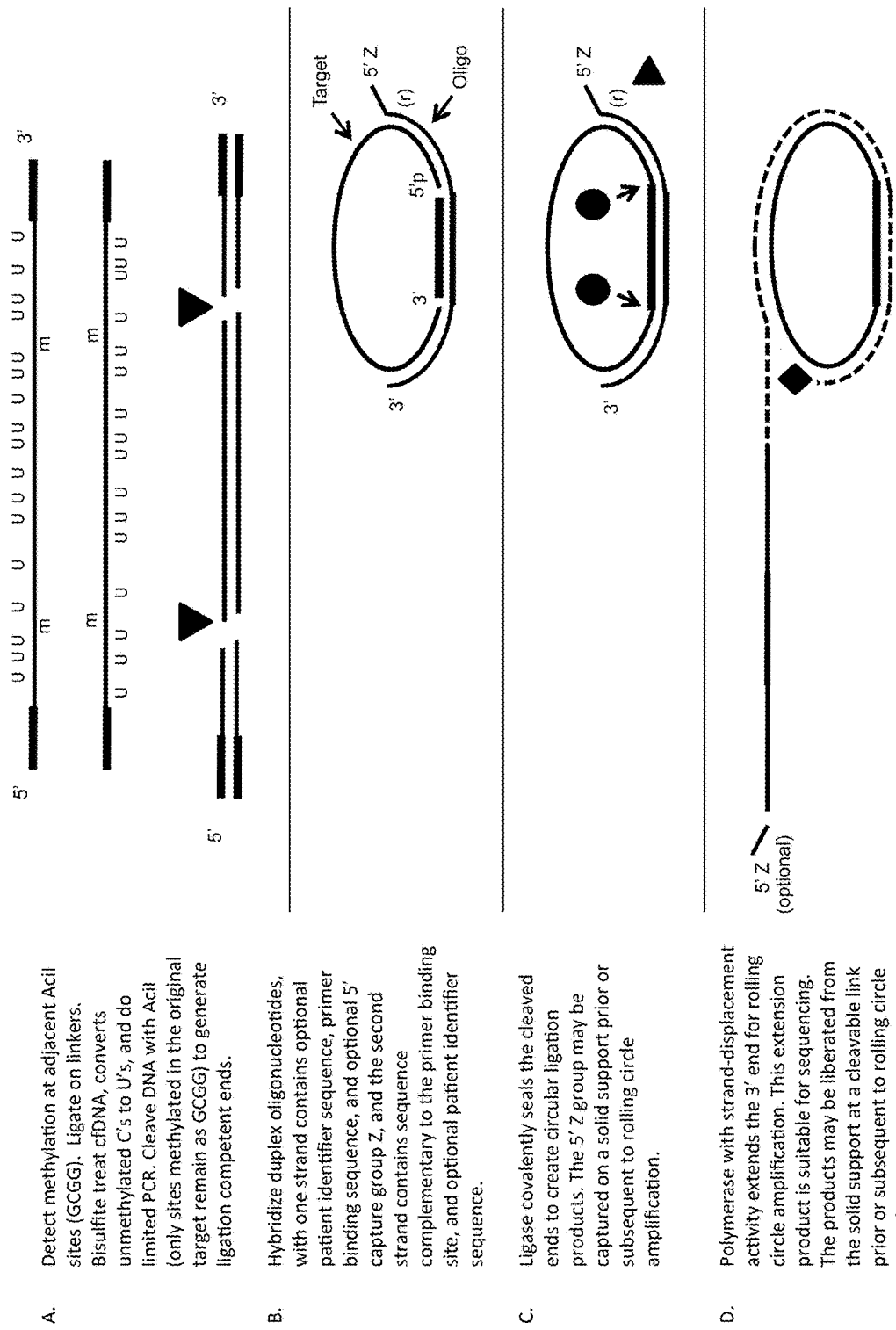
FIG. 32 depicts a method of generating and amplifying circular chimeric single-stranded nucleic acid constructs of the present invention containing adjacent AciI methylation sites.

FIG. 32 shows essentially the same process for producing chimeric circular single stranded nucleic acid constructs suitable for detecting methylation at adjacent AciI sites as shown and described in FIG. 31. In the embodiment depicted in FIG. 32, the first oligonucleotide probe of the duplex probe set has an optional 5' capture group ("Z") (FIG. 32, step B). After ligation of the second oligonucleotide probe and the target (bisulfite treated, copied) DNA segment to form a circularized ligation product (FIG. 32, step C), the 3' end of the first oligonucleotide probe is extended using a strand displacing polymerase. Rolling circular amplification generates a first primary extension product, containing tandem linear sequences that are complementary to the circularized ligation product (FIG. 32, step D) and suitable for sequencing using the methods described herein.

Figure 33:
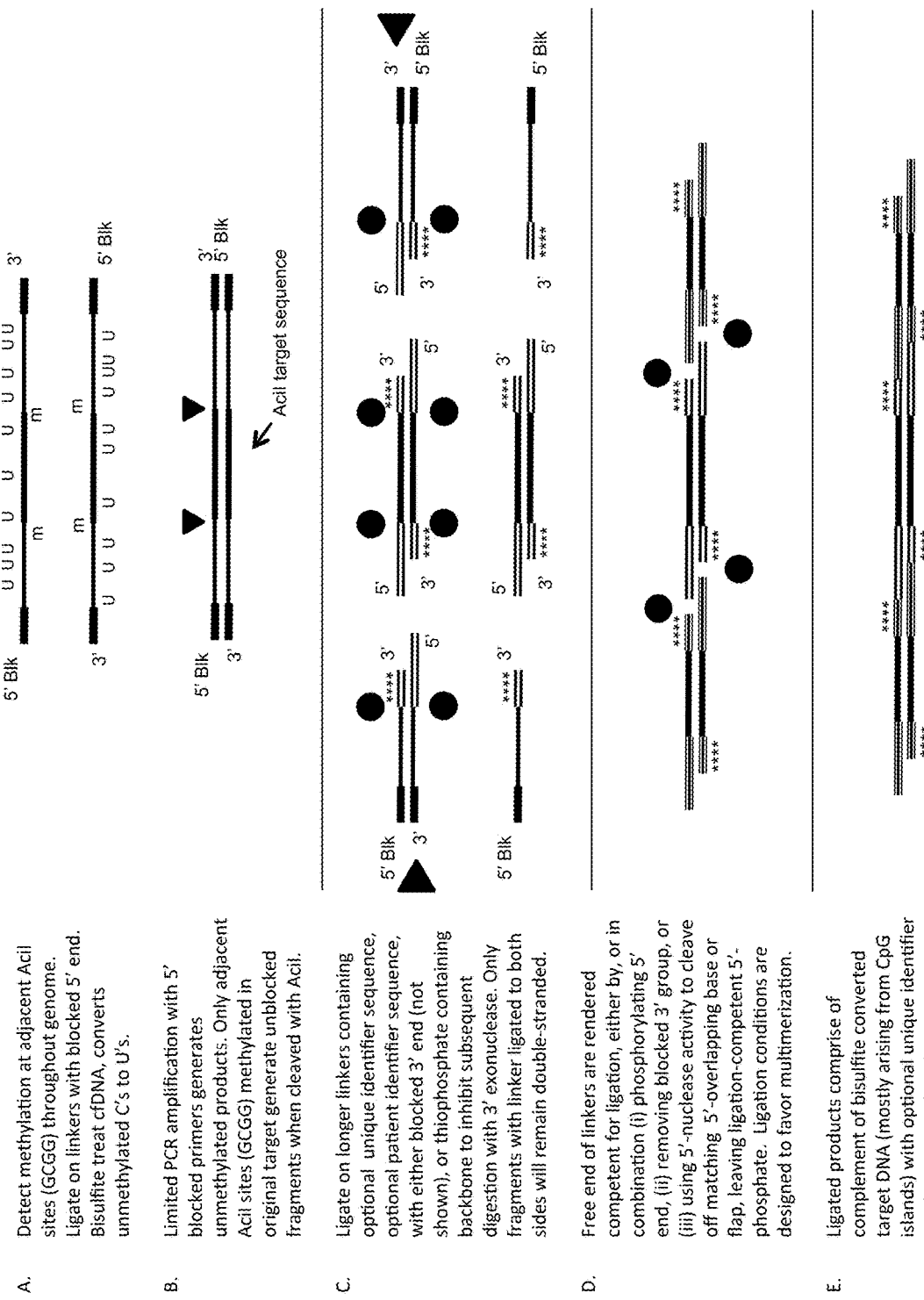
FIG. 33 show a process for detecting methylation at adjacent AciI sites throughout the genome.

FIG. 33 shows a process for the discovery of methylation at adjacent AciI sites (GCGG) throughout the genome starting from either genomic DNA that has been sheared to an average size of 150 bp or from cfDNA with an average size of 160 bp. As shown in FIG. 33, step A, the process begins by appending, e.g., via ligation, short linkers onto the 3' and 5' ends of the DNA segments (thick black lines). The 5' linker contains a blocking group. Bisulfite treatment of the genomic DNA converts unmethylated C's to U's resulting in single stranded products. As shown in FIG. 33, step B, limited PCR amplification with 5' blocked primers generates unmethylated products. Only adjacent AciI sites (GCGG) methylated in original target generate unblocked fragments when cleaved with AciI (filled triangles). As shown in FIG. 33, step C, linkers (grey double lines) containing a unique identifier sequence and/or a patient identifier sequence are appended (e.g., by ligation to AciI cleavage products). The linkers contain either a 3' blocking group or a thiophosphate containing backbone (****) to inhibit subsequent digestion with 3'-exonuclease (filled triangles). Only fragments with linkers appended to both sides remain double-stranded (FIG. 33, step C, lower panel). As shown in FIG. 33, step D, the linker ends are rendered competent for ligation (filled circles), either by (i) phosphorylating 5' ends, (ii) removing blocked 3' groups, or (iii) using 5'-nuclease activity to cleave off matching 5'-overlapping base or flap to generate ligation-competent 5'-phosphate, or (iv) any combination of these techniques. Ligation conditions are designed to favor oligomerization. FIG. 33, step E shows ligated products comprised of the complement of bisulfite converted target DNA (mostly arising from CpG islands) with optional unique identifier and/or patient identifier sequence. The final product is suitable for additional steps and subsequent sequencing.

Figure 34:
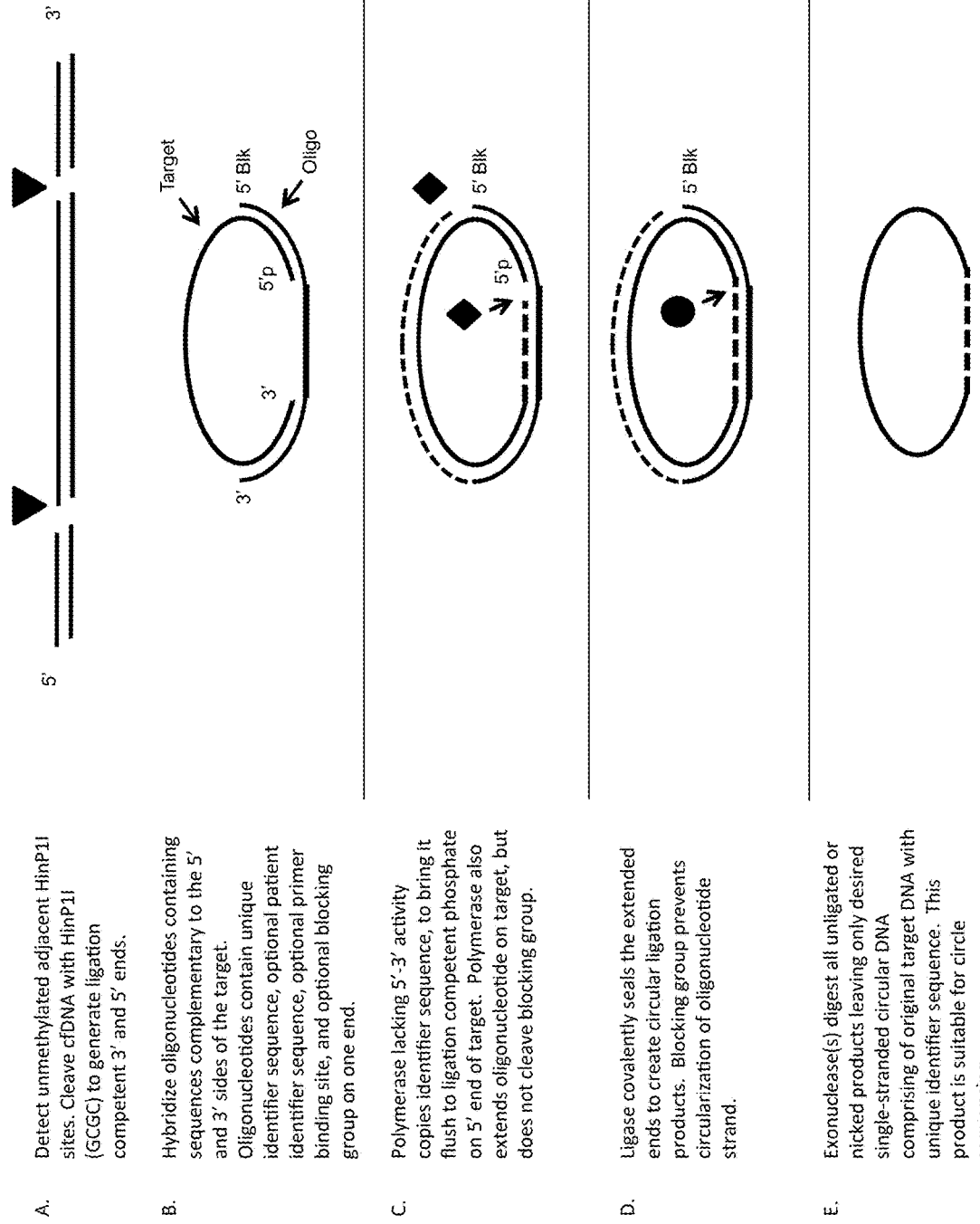
FIG. 34 depicts a method of generating circular chimeric single-stranded nucleic acid constructs of the present invention containing adjacent unmethylated HinP1I sites.

FIG. 34 shows a process for producing chimeric circular single stranded nucleic acid constructs suitable for detecting unmethylated adjacent HinP1I sites in defined regions of the genome starting from cfDNA of average length of 160 bp or genomic DNA sheared to about 160 bp fragments. As shown in FIG. 34, step A, the process starts with HinP1I cleavage of genomic DNA at GCGC recognition sites (filled triangles) to generate ligation competent 3' and 5' ends. As shown in FIG. 34, step B, oligonucleotide probes containing sequences complementary to the 5' and 3' sides of the cleaved target DNA segments are hybridized to their respective cleaved target DNA segments. The oligonucleotide probes also contain a further nucleotide portion that contains a unique identifier sequence and, optionally, a patient identifier sequence. In the embodiment of FIG. 34, the oligonucleotide probe also has a blocking group on one end, e.g., the 5' end. Polymerase (filled diamonds) lacking 5'-3' activity extends the 3' end of the hybridized target DNA segment, copying the further portion of the probe and creating a ligation junction with the ligation competent phosphate on 5' end of target (FIG. 34, step C). Polymerase also extends the oligonucleotide probe using the target DNA segment as a template, but does not cleave the blocking group on its 5' end. In FIG. 34, step D, ligase (filled circle) covalently seals the junction between the 3' extended end and the 5' end of the DNA segment to create circular ligation products. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 34, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification and circle sequencing.

Figure 35:
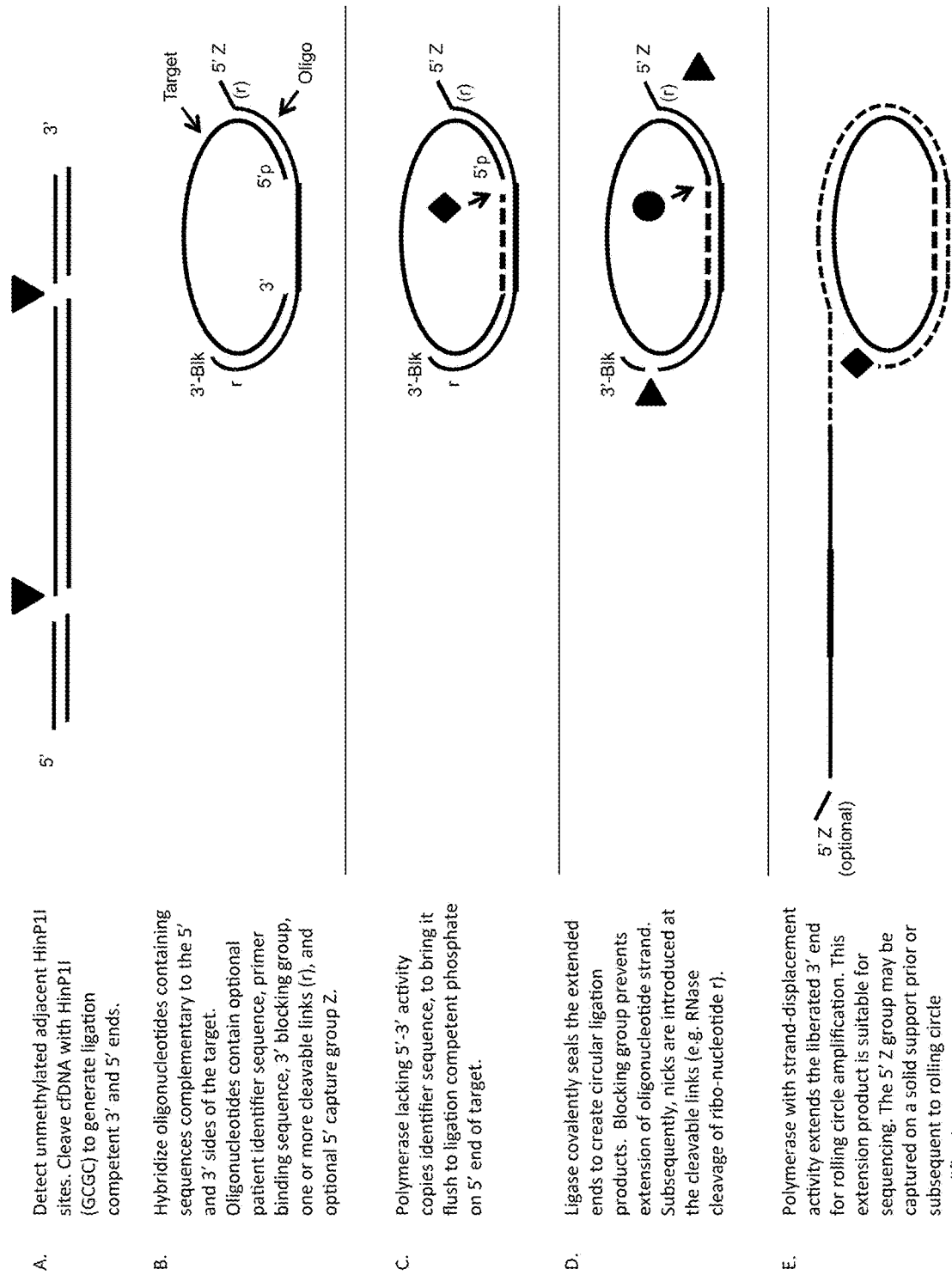
FIG. 35 depicts a method of generating and amplifying circular chimeric single-stranded nucleic acid constructs of the present invention containing adjacent unmethylated HinP1I sites.

FIG. 35 shows essentially the same process for producing chimeric circular single stranded nucleic acid constructs suitable for detecting unmethylated adjacent HinP1I sites in defined regions of the genome as shown and described in FIG. 34. In the embodiment depicted in FIG. 35, the oligonucleotide probe contains sequences complementary to the 5' and 3' sides of the target DNA segment that are separated by the further nucleotide portion. In addition, the oligonucleotide probe also has a blocking group (3'-Blk) on its 3' end, one or more cleavable link(s), where the cleavable link is depicted as "r", and an optional 5' capture group ("Z") (FIG. 35, step B). The 3' end of the hybridized target DNA segment is polymerase extended creating a ligation junction with the ligation competent phosphate on the 5' end of the target DNA segment. After ligation of the 3' extended end and 5' end of the target DNA segment to form a circularized ligation product (FIG. 35, step C), the 3'blocking group on the oligonucleotide probe is removed (e.g., RNase H cleavage of the ribonucleotide link) (FIG. 35, step D), and a polymerase (filled diamonds) lacking 5'-3' activity extends the oligonucleotide probe using the circularized DNA ligation product as a template (FIG. 35, step E). Rolling circular amplification generates a primary extension product containing tandem linear sequences that are complementary to the circularized ligation product (FIG. 35, step E). The primary extension product is suitable for sequencing using the methods described herein. The 5' optional Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 36:
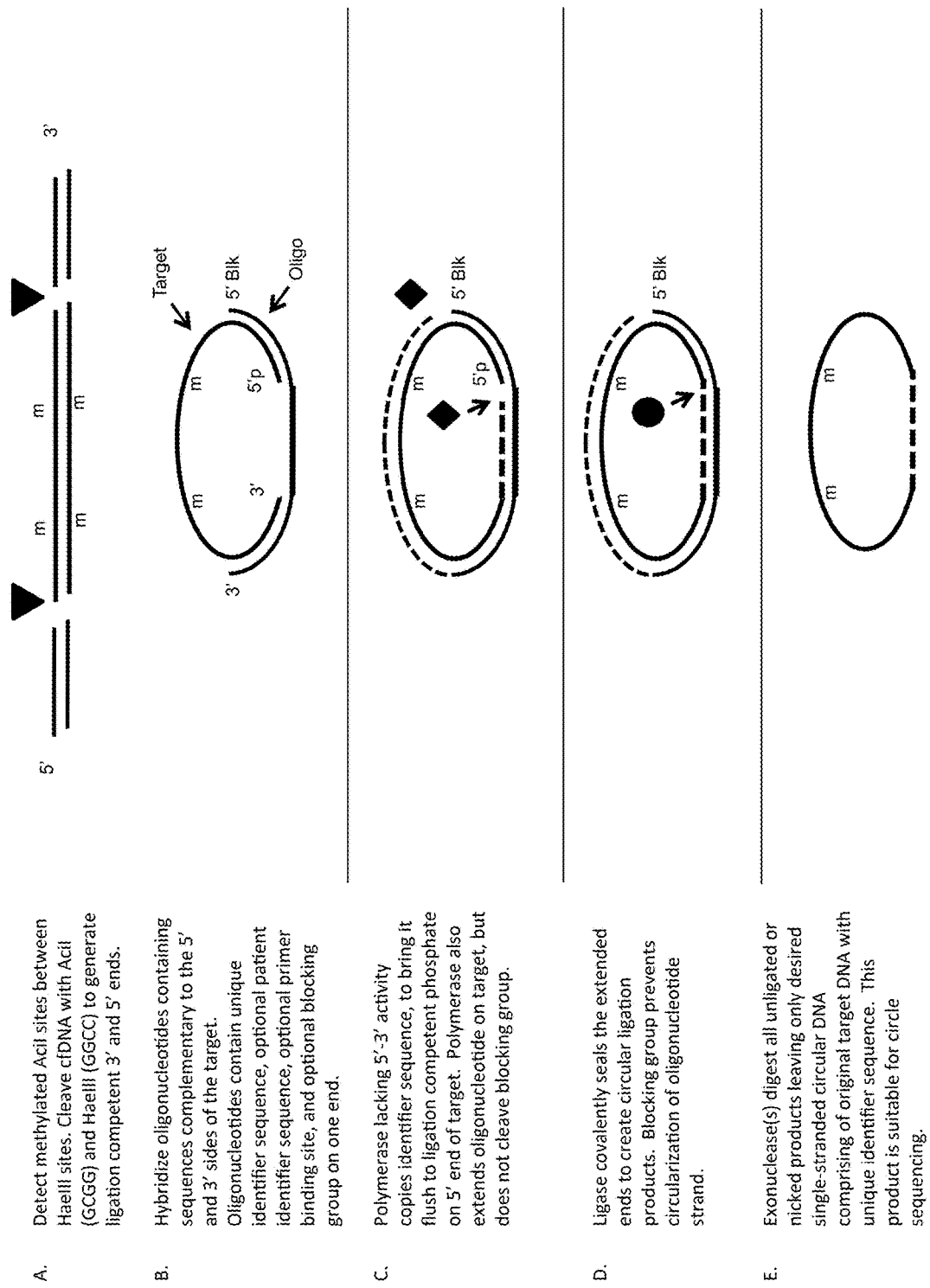
FIG. 36 depicts a method of generating circular chimeric single-stranded nucleic acid constructs of the present invention containing adjacent methylated AciI sites located between HaeIII restriction sites.
Figure 37:
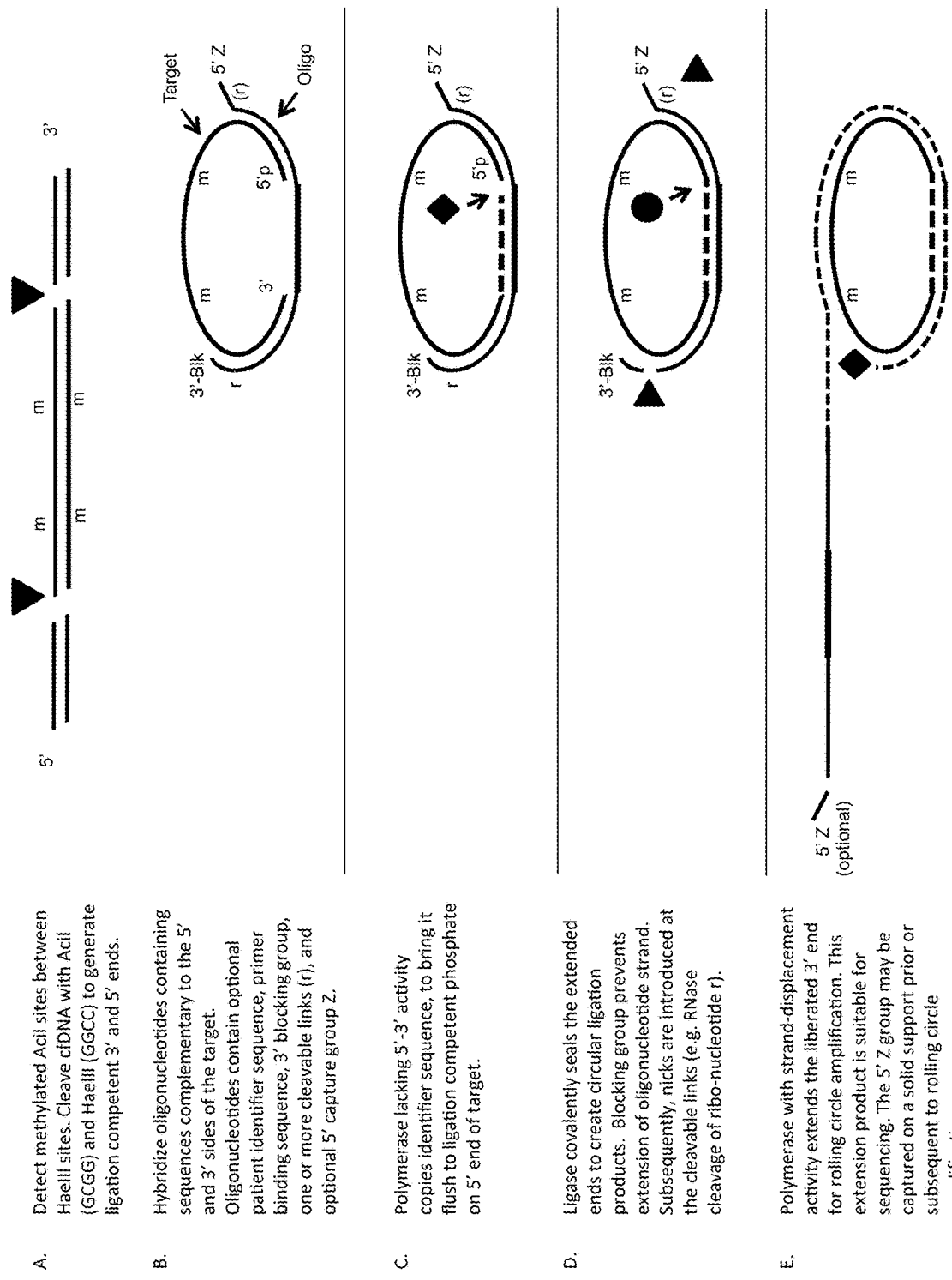
FIG. 37 depicts a method of generating and amplifying circular chimeric single-stranded nucleic acid constructs of the present invention containing adjacent methylated AciI sites located between HaeIII restriction sites.

FIGS. 36 and 37 show a process for producing chimeric circular single stranded nucleic acid constructs suitable for detecting methylated AciI sites between HaeIII sites in known genomic regions of cfDNA or sheared total genomic DNA. Genomic DNA is cleaved with AciI (filled triangles, GCGG) and HaeIII (filled triangles, GGCC) to generate ligation competent 3'- and 5'-ends; m represents methylated sites within the cleaved segments (FIGS. 36, step A and 37, step A). In the embodiment of FIG. 36, oligonucleotide probes containing 5' and 3' end sequences complementary to the 5' and 3' sides of the target DNA segments are hybridized to the cleaved DNA segments (FIG. 36, step B). The oligonucleotide probes also contain a further nucleotide portion that contains one or more of a unique identifier sequence, a patient identifier sequence, and/or one or more primer binding sites. The oligonucleotide probes may also have a blocking group on one end (e.g., a 5' blocking group as shown in FIG. 36, step B). Polymerase (filled diamonds) lacking 5'-3' activity extends the 3' end of the hybridized target DNA segment, copying the further portion of the probe and creating a ligation junction with the ligation competent phosphate on the 5' end of target (FIG. 36, step C). Polymerase also extends the oligonucleotide probe using the target DNA segment as a template, but does not cleave the blocking group on its 5' end. In FIG. 36, step D, ligase (filled circle) covalently seals the junction between the 3' extended end and the 5' end of the DNA segment to create circular ligation products. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 36, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification and circle sequencing.

In the embodiment depicted in FIG. 37 the oligonucleotide probe contains sequences complementary to the 5' and 3' sides of the target DNA segment that are separated by the further nucleotide portion. In addition, the oligonucleotide probe also has a blocking group (3'-Blk) on its 3' end, one or more cleavable link(s), where the cleavable link is depicted at "r", and an optional 5' capture group ("Z") (FIG. 37, step B). After ligation of the 3' extended end and 5' end of the target DNA segment to form a circularized ligation product (FIG. 37, step C), the 3'blocking group on the oligonucleotide probe is removed (e.g., RNase H cleavage of the ribonucleotide link) (FIG. 37, step D), and a polymerase (filled diamonds) lacking 5'-3' activity extends the oligonucleotide probe using the circularized DNA ligation product as a template (FIG. 37, step E). Rolling circular amplification generates a primary extension product containing tandem linear sequences that are complementary to the circularized ligation product (FIG. 37, step E). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 38:
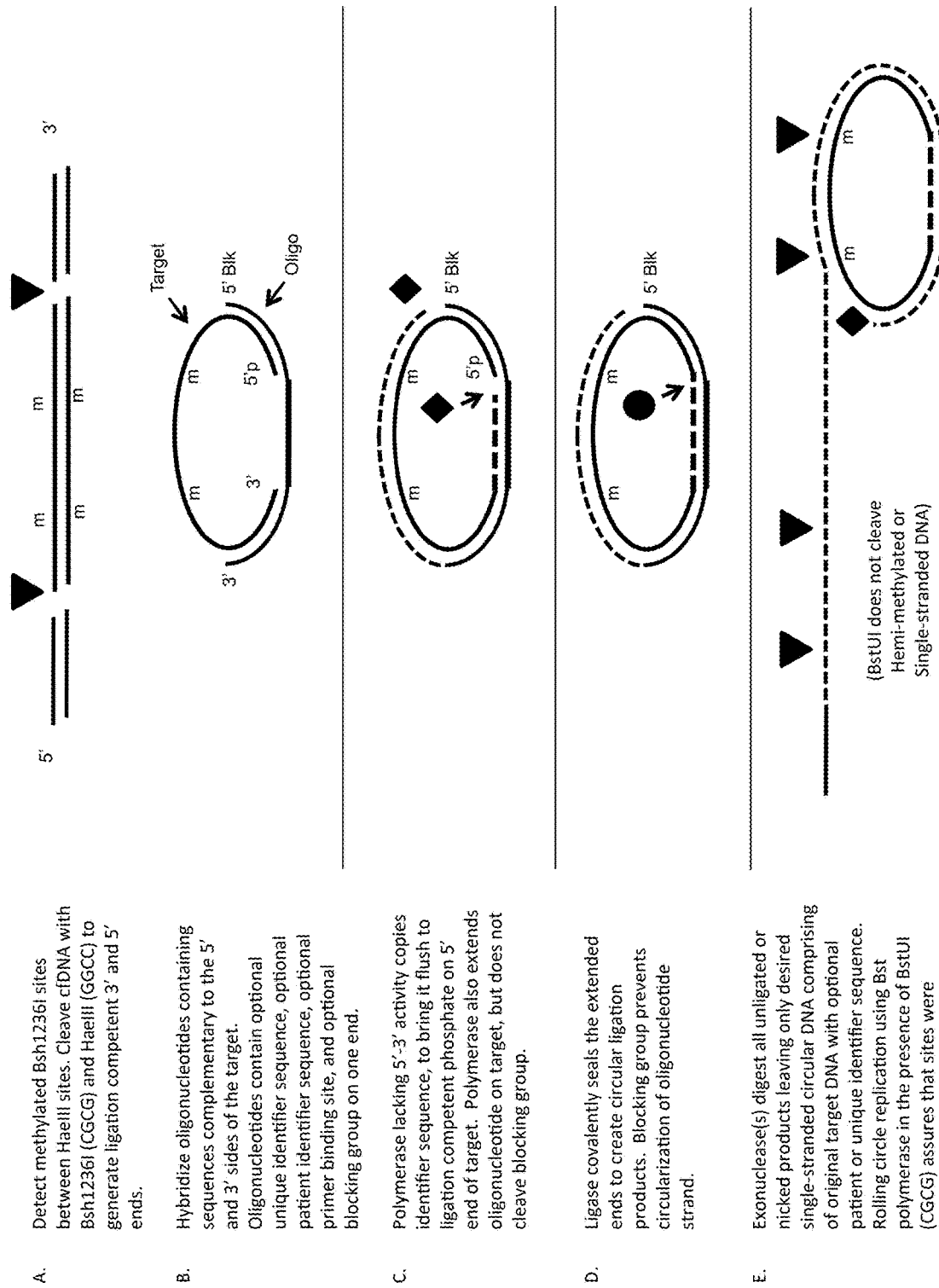
FIG. 38 shows a process for producing chimeric circular single stranded nucleic acid constructs of the present invention containing methylated Bsh1236I sites between HaeIII sites in known genomic regions of cfDNA or sheared total genomic DNA.

FIG. 38 shows a process for producing chimeric circular single stranded nucleic acid constructs suitable for detecting methylated Bsh1236I sites between HaeIII sites in known genomic regions of cfDNA or sheared total genomic DNA. Genomic DNA is cleaved with Bsh1236I (CGCG) and HaeIII (filled triangles, GGCC) to generate ligation competent 3'- and 5'-ends; m represents methylated sites within the cleaved segments (FIG. 38, step A). In the embodiment of FIG. 38, oligonucleotide probes containing 5' and 3' end sequences complementary to the 5' and 3' sides of the target DNA segments are hybridized to the cleaved DNA segments (FIG. 38, step B). The oligonucleotide probes also contain a further nucleotide portion that contains one or more of a unique identifier sequence, a patient identifier sequence, and/or one or more primer binding sites. The oligonucleotide probes may also have a blocking group on one end (e.g., a 5' blocking group as shown in FIG. 38, step B). Polymerase (filled diamonds) lacking 5'-3' activity extends the 3' end of the hybridized target DNA segment, copying the further portion of the probe and creating a ligation junction with the ligation competent phosphate on 5' end of target (FIG. 38, step C). Polymerase also extends the oligonucleotide probe using the target DNA segment as a template, but does not cleave the blocking group on its 5' end. In FIG. 38, step D, ligase (filled circle) covalently seals the junction between the 3' extended end and the 5' end of the DNA segment to create circular ligation products. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 38, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification using Bst polymerase in the presence of BstUI (CGCG) to assure that sites that were methylated in the original target are not cleaved, and subsequently are identified by sequencing. This example shows the utilization of BstUI restriction endonuclease. However, other endonucleases that cleave double-stranded DNA if unmethylated, but not hybrid methylated/unmethylated DNA, nor unmethylated single-stranded DNA can also be utilized in this method. These include but are not limited to the thermophilic enzymes BstHHI (recognizes GCGC; an isoschizomer of HhaI), BsiSI (recognizes CCGG; an isoschizomer of HpaII), and TaiI (recognizes ACGT; an isoschizomer of MaeII).

Figure 39:
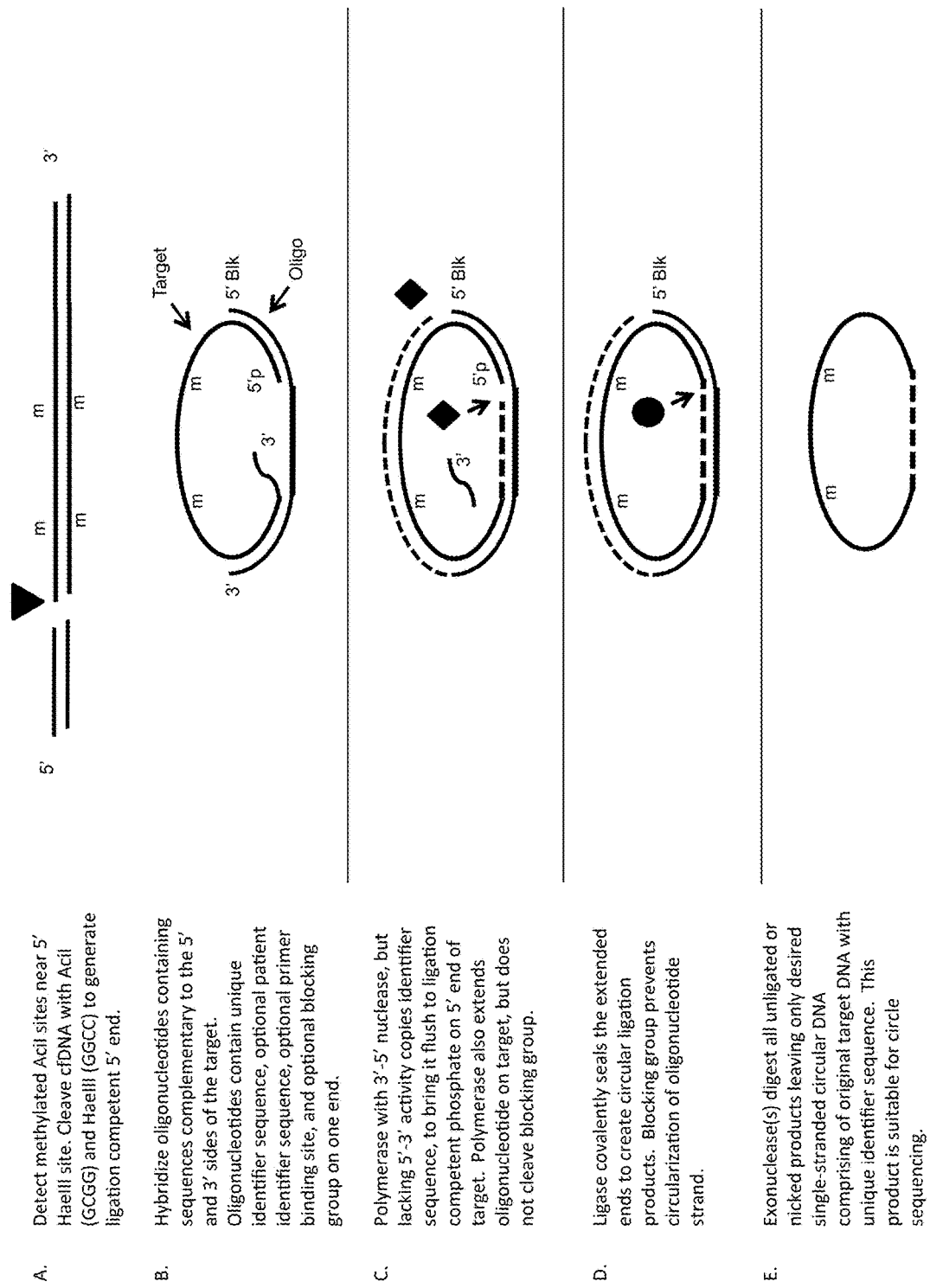
FIG. 39 depicts a method of generating circular chimeric single-stranded nucleic acid constructs of the present invention containing one or more methylated AciI sites near a 5' HaeIII restriction site.

FIG. 39 and FIG. 36 show a process for producing chimeric circular single stranded nucleic acid constructs suitable for detecting methylated AciI sites near a 5'-HaeIII site in known regions of genomic DNA. The method is suitable for detecting methylated AciI sites in genomic DNA sheared to an average size of 160 bp or cfDNA having an average size of 160 bp. Genomic DNA is cleaved with AciI (GCGG) and HaeIII (GGCC) to generate ligation competent 5' ends (FIGS. 39, step A and 40, step A). In the embodiment depicted in FIG. 39, oligonucleotide probes containing 5' and 3' end sequences complementary to the 5' and 3' sides of the target genomic DNA segments are hybridized to the cleaved DNA segments (FIG. 39, step B). The oligonucleotide probes also contain a further nucleotide portion that comprises one or more of a unique identifier sequence, a patient identifier sequence, and one or more primer binding sites. The oligonucleotide probes may also have a blocking group on one end (e.g., a 5' blocking group as shown in FIG. 39, step B). Polymerase with 3'-5' nuclease (filled diamonds), but lacking 5'-3' activity removes single-stranded 3' end, and then extends the 3' end of the hybridized target DNA segment, copying the further portion of the probe and creating a ligation junction with the ligation competent phosphate on 5' end of target (FIG. 39, step C). Polymerase also extends the oligonucleotide probe using the target DNA segment as a template, but does not cleave the blocking group on its 5' end. In FIG. 39, step D, ligase (filled circle) covalently seals the junction between the 3' extended end and the 5' end of the DNA segment to create circular ligation products. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 39, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification and circle sequencing.

Figure 40:
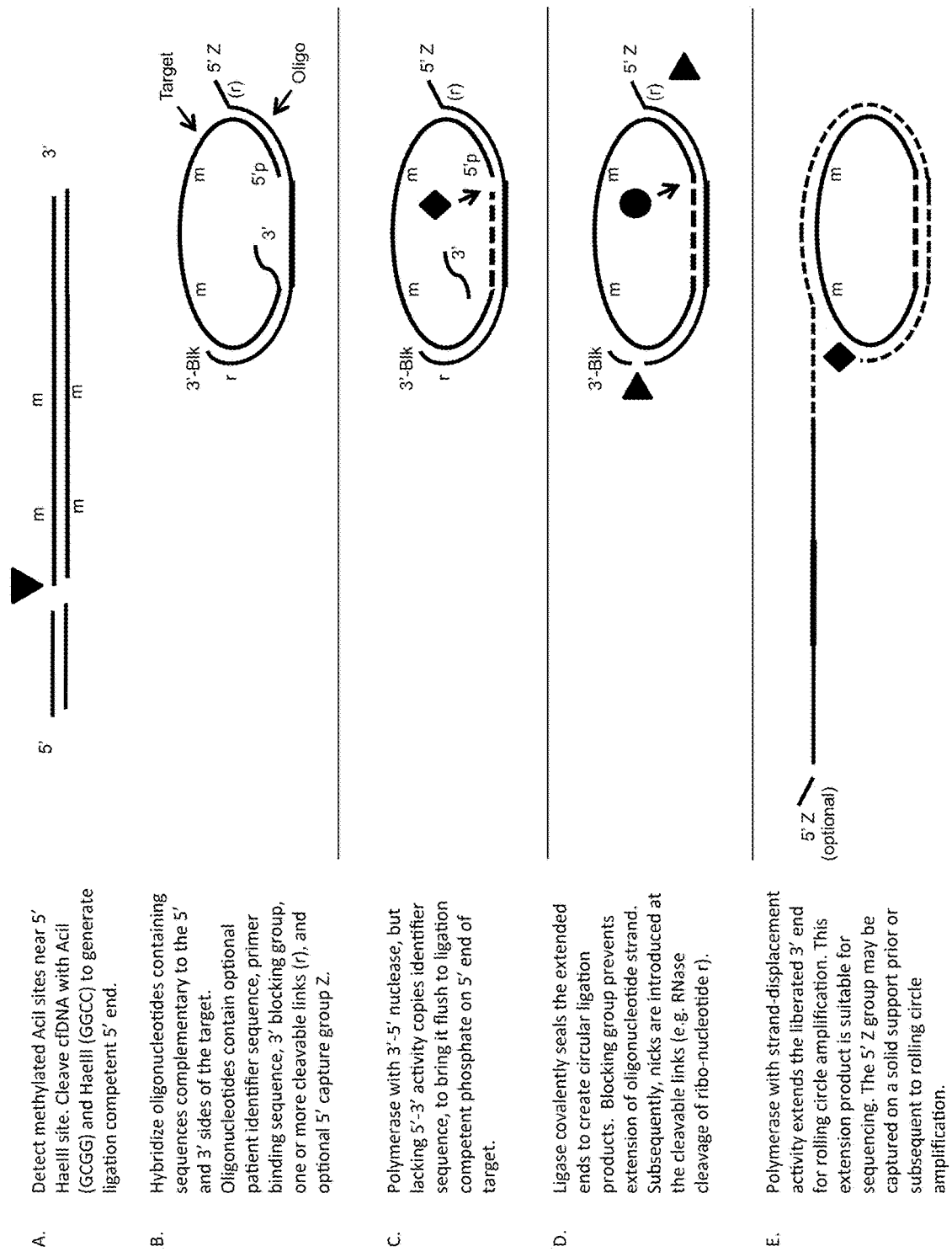
FIG. 40 depicts a method of generating and amplifying circular chimeric single-stranded nucleic acid constructs of the present invention containing one or more methylated AciI sites near a 5' HaeIII restriction site.

In the embodiment depicted in FIG. 40 the oligonucleotide probes contain 5' and 3' end sequences complementary to the 5' and 3' sides of the cleaved target DNA segment that are separated by the further nucleotide portion. In addition, the oligonucleotide probes also have a blocking group (3'-Blk) on its 3' end, one or more cleavable link(s), where the cleavable link is depicted at "r", and an optional 5' capture group ("Z") (FIG. 40, step A). After ligation of the 3' extended end and 5' end of the target DNA segment to form a circularized ligation product (FIG. 40, step C), the 3'blocking group on the oligonucleotide probe is removed (e.g., RNase H cleavage of the ribonucleotide link) (FIG. 40, step D), and a polymerase (filled diamonds) lacking 5'-3' activity extends the oligonucleotide probe using the circularized DNA ligation product as a template (FIG. 40, step E). Rolling circular amplification generates a primary extension product containing tandem linear sequences that are complementary to the circularized ligation product (FIG. 40, step E). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

FIG. 41 shows a process for producing chimeric circular single stranded nucleic acid constructs suitable for detecting methylated Bsh1236I sites near a 5'-HaeIII site in known regions of genomic DNA. The method is suitable for detecting methylated Bsh1236I sites in genomic DNA sheared to an average size of 150 bp or cfDNA having an average size of 160 bp. Genomic DNA is cleaved with Bsh1236I (CGCG) and HaeIII (GGCC) to generate ligation competent 5' ends (FIG. 41, step A). In the embodiment depicted in FIG. 41, oligonucleotide probes containing 5' and 3' end sequences complementary to the 5' and 3' sides of the target genomic DNA segments are hybridized to the cleaved DNA segments (FIG. 41, step B). The oligonucleotide probes also contain a further nucleotide portion that comprises one or more of a unique identifier sequence, a patient identifier sequence, and one or more primer binding sites. The oligonucleotide probes may also have a blocking group on one end (e.g., a 5' blocking group as shown in FIG. 41, step B). Polymerase with 3'-5' nuclease activity (filled diamonds), but lacking 5'-3' activity removes single-stranded 3' end of the target DNA segment, and then extends the cleaved 3' end of the hybridized target DNA segment, copying the further portion of the probe and creating a ligation junction with the ligation competent phosphate on 5' end of target (FIG. 41, step C). Polymerase also extends the oligonucleotide probe using the target DNA segment as a template, but does not cleave the blocking group on its 5' end. In FIG. 41, step D, ligase (filled circle) covalently seals the junction between the 3' extended end and the 5' end of the DNA segment to create circular ligation products. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 41, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification using Bst polymerase in the presence of BstUI (CGCG) to assure that sites that were methylated in the original target are subsequently identified by sequencing. This example shows the utilization of the BstUI restriction endonuclease. However, other endonucleases that cleave double-stranded DNA if unmethylated, but not hybrid methylated/unmethylated DNA, nor unmethylated single-stranded DNA can alternatively be utilized. These include but are not limited to the thermophilic enzymes BstHHI (recognizes GCGC; an isoschizomer of HhaI), BsiSI (recognizes CCGG; an isoschizomer of HpaII), and TaiI (recognizes ACGT; an isoschizomer of MaeII).

Figure 42:
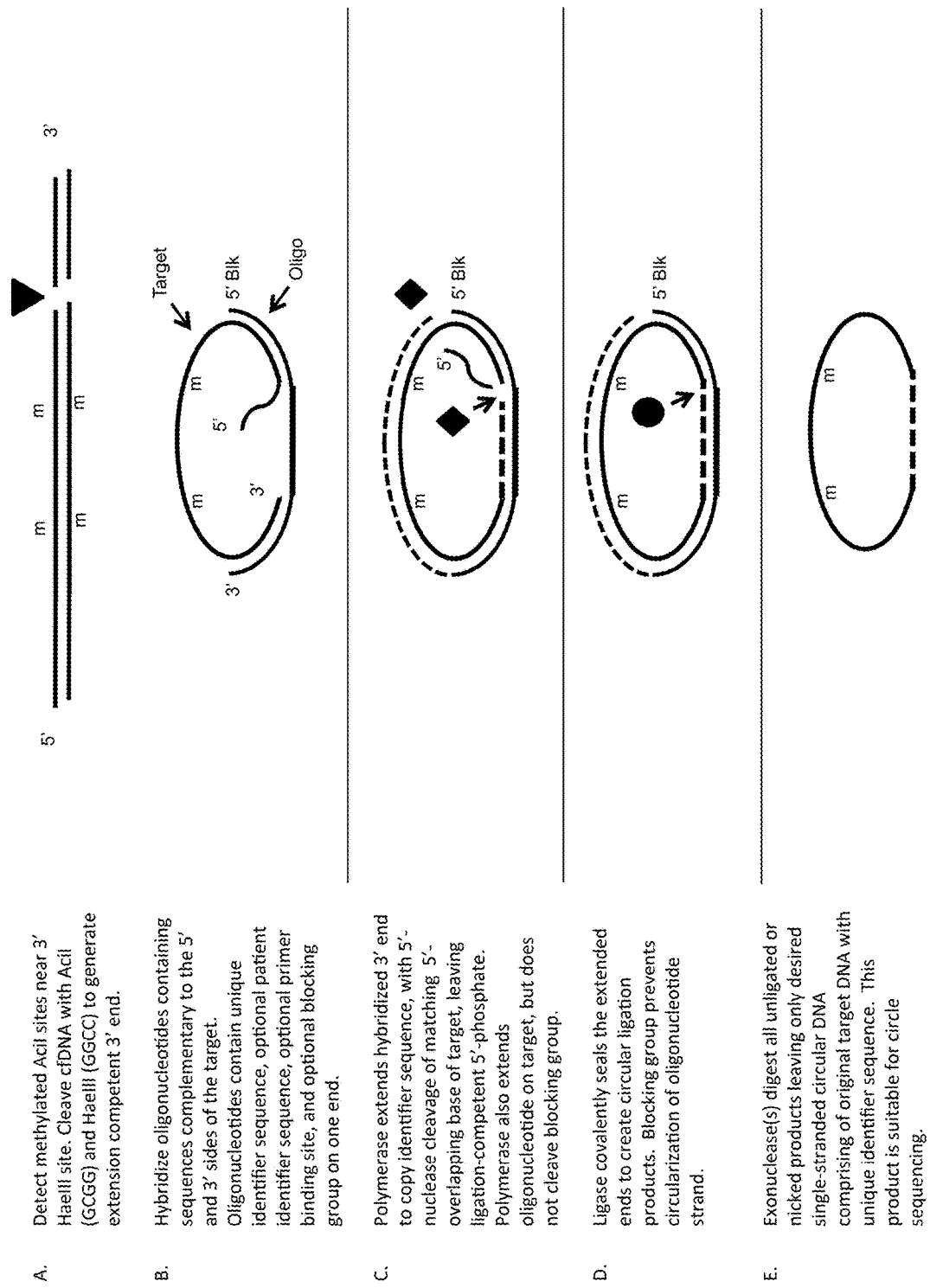
FIG. 42 depicts a method of generating circular chimeric single-stranded nucleic acid constructs of the present invention containing one or more methylated AciI sites near a 3' HaeIII restriction site.
Figure 43:
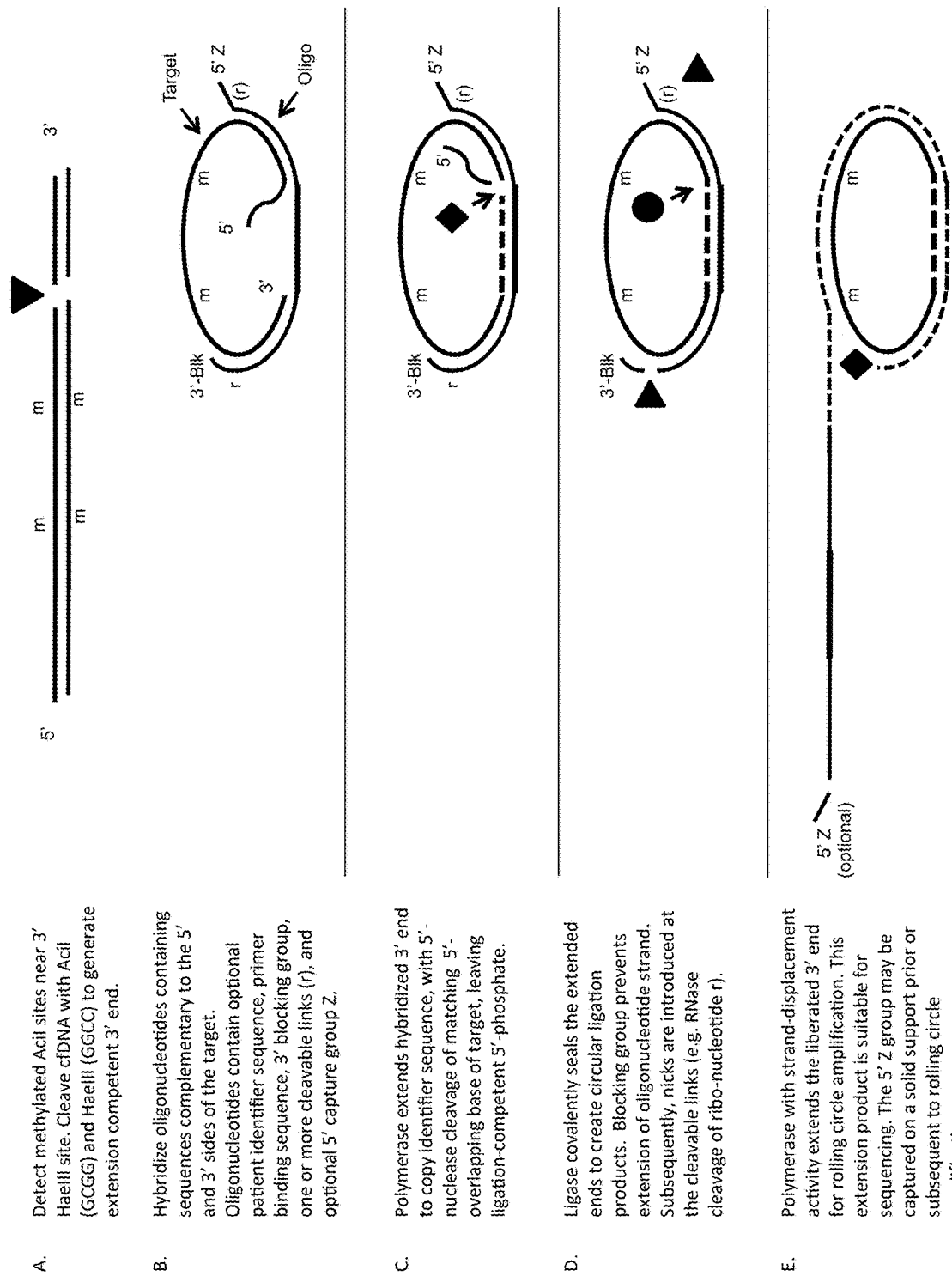
FIG. 43 depicts a method of generating and amplifying circular chimeric single-stranded nucleic acid constructs of the present invention containing one or more methylated AciI sites near a 3' HaeIII restriction site.

FIG. 42 and FIG. 43 show a process for producing chimeric circular single stranded nucleic acid constructs suitable for detecting methylated AciI sites near a 3'-HaeIII site in known genomic regions of cfDNA or sheared total genomic DNA. Genomic DNA is cleaved with AciI (GCGG) and HaeIII (GGCC) to generate extension competent 3' ends (FIGS. 42, step A and 43, step A). In the embodiment of FIG. 42, oligonucleotide probes containing 5' and 3' end sequences complementary to the 5' and 3' sides of the target DNA segments are hybridized to the cleaved DNA segments (FIG. 42, step B). The oligonucleotide probes also contain a further nucleotide portion that contains one or more of a unique identifier sequence, a patient identifier sequence, and/or one or more primer binding sites. The oligonucleotide probes may also have a blocking group on one end (e.g., a 5' blocking group as shown in FIG. 42B). Polymerase (filled diamonds) lacking 5'-3' activity extends the 3' end of the hybridized target DNA segment, copying the further portion of the probe. The 5' nuclease activity of the polymerase cleaves a matching 5' overlapping base of the target DNA segment thereby generating a ligation competent 5' phosphate (FIG. 42, step C). Polymerase also extends the oligonucleotide probe using the target DNA segment as a template, but does not cleave the blocking group on its 5' end. In FIG. 42, step D, ligase (filled circle) covalently seals the junction between the 3' extended end and the 5' end of the DNA segment to create circular ligation products containing an original genomic DNA segment. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 42, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification and circle sequencing.

In the embodiment of FIG. 43, the oligonucleotide probes contain sequences complementary to the 5' and 3' sides of the target DNA segment that are separated by the further nucleotide portion. In addition, the oligonucleotide probes also have a blocking group (3'-Blk) on the 3' end, one or more cleavable link(s), where the cleavable link is depicted at "r", and an optional 5' capture group ("Z") (FIG. 43, step B). After ligation of the 3' extended end and 5' end of the target DNA segment to form a circularized ligation product (FIG. 43, step C), the 3' blocking group on the oligonucleotide probe is removed (e.g., RNase H cleavage of the ribonucleotide link) (FIG. 43, step D), and a polymerase (filled diamonds) lacking 5'-3' activity extends the oligonucleotide probe using the circularized DNA ligation product as a template (FIG. 43, step E). Rolling circular amplification generates a primary extension product containing tandem linear sequences that are complementary to the circularized ligation product (FIG. 43, step E). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 44:
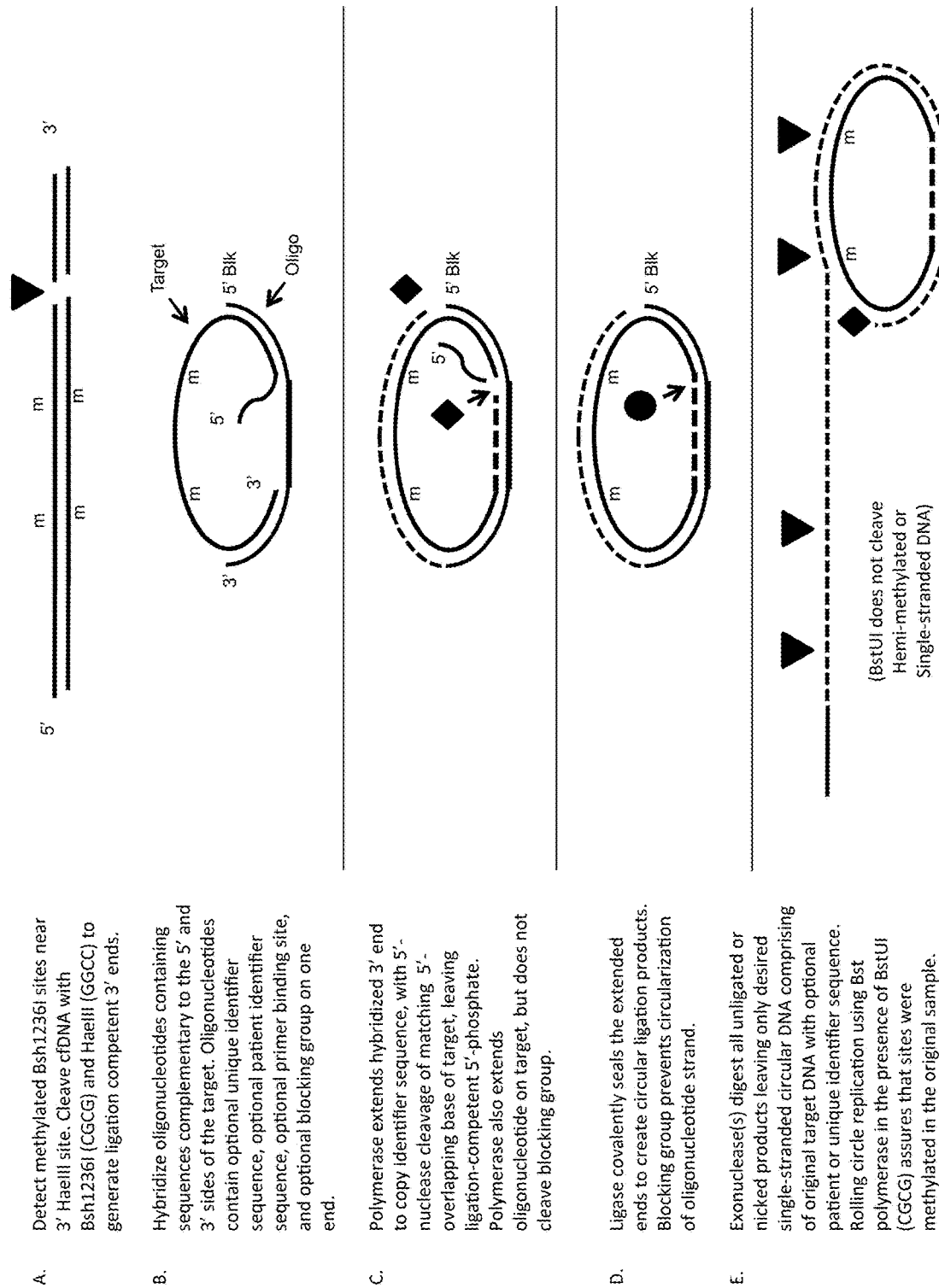
FIG. 44 shows a process for producing chimeric circular single stranded nucleic acid constructs suitable for detecting methylated Bsh1236I sites near a 3'-HaeIII site in known genomic regions of cfDNA or sheared total genomic DNA.

FIG. 44 shows a process for producing chimeric circular single stranded nucleic acid constructs suitable for detecting methylated Bsh1236I sites near a 3'-HaeIII site in known genomic regions of cfDNA or sheared total genomic DNA. Genomic DNA is cleaved with Bsh1236I (CGCG) and HaeIII (GGCC) to generate extension competent 3' ends (FIG. 44, step A). In the embodiment of FIG. 44, oligonucleotide probes containing 5' and 3' end sequences complementary to the 5' and 3' sides of the target DNA segments are hybridized to the cleaved DNA segments (FIG. 44, step B). The oligonucleotide probes also contain a further nucleotide portion that contains one or more of a unique identifier sequence, a patient identifier sequence, and/or one or more primer binding sites. The oligonucleotide probes may also have a blocking group on one end (e.g., a 5' blocking group as shown in FIG. 44, step B). Polymerase (filled diamonds) lacking 5'-3' activity extends the 3' end of the hybridized target DNA segment, copying the further portion of the probe. The 5' nuclease activity of the polymerase cleaves a matching 5' overlapping base of the target DNA segment thereby generating a ligation competent 5' phosphate (FIG. 44, step C). Polymerase also extends the oligonucleotide probe using the target DNA segment as a template, but does not cleave the blocking group on its 5' end. In FIG. 44, step D, ligase (filled circle) covalently seals the junction between the 3' extended end and the 5' end of the DNA segment to create circular ligation products containing an original genomic DNA segment. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 44, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification using Bst polymerase in the presence of BstUI (CGCG) to assure that sites that were methylated in the original target are subsequently identified by sequencing. This example shows the use of BstUI restriction endonuclease. However, other endonucleases that cleave double-stranded DNA if unmethylated, but not hybrid methylated/unmethylated DNA, nor unmethylated single-stranded DNA can be used. These include but are not limited to the thermophilic enzymes BstHHI (recognizes GCGC; an isoschizomer of HhaI), BsiSI (recognizes CCGG; an isoschizomer of HpaII), and TaiI (recognizes ACGT; an isoschizomer of MaeII).

Figure 45:
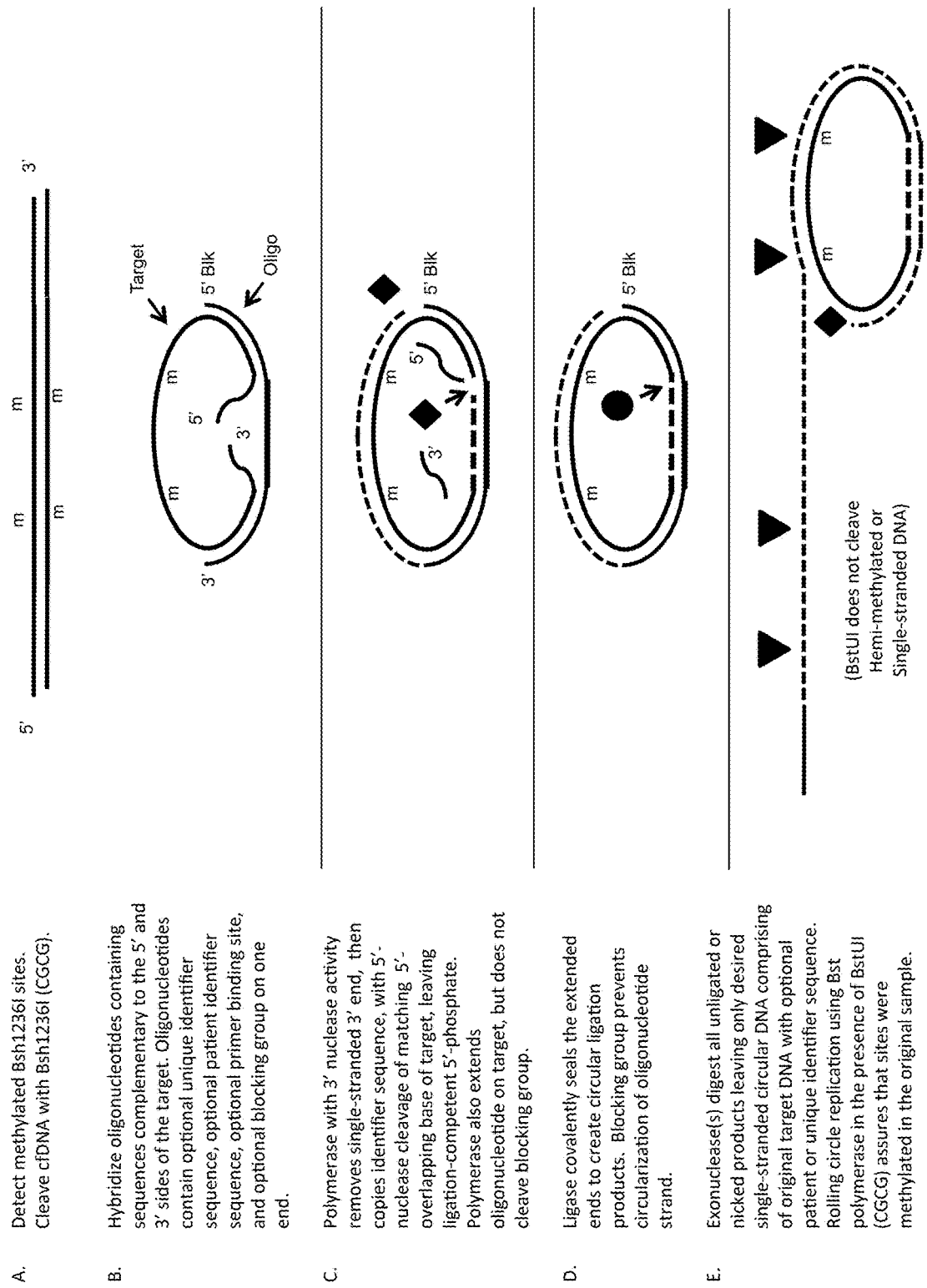
FIG. 45 shows a process for producing chimeric circular single stranded nucleic acid constructs suitable for detecting neighboring methylated Bsh1236I sites in known regions of genomic DNA.

FIG. 45 shows a process for producing chimeric circular single stranded nucleic acid constructs suitable for detecting neighboring methylated Bsh1236I sites in known regions of genomic DNA. The method is suitable for detecting methylated Bsh1236I sites in genomic DNA sheared to an average size of 150 bp or cfDNA having an average size of 160 bp. Genomic DNA is cleaved with Bsh1236I (CGCG) at unmethylated recognition sites in the target DNA (FIG. 45, step A). In the embodiment depicted in FIG. 45, oligonucleotide probes containing 5' and 3' end sequences complementary to the 5' and 3' sides of the target genomic DNA segments are hybridized to the DNA segments (FIG. 45, step B). The oligonucleotide probes also contain a further nucleotide portion that comprises one or more of a unique identifier sequence, a patient identifier sequence, and one or more primer binding sites. The oligonucleotide probes may also have a blocking group on one end (e.g., a 5' blocking group as shown in FIG. 44, step B). Polymerase (filled diamonds) with 3'-5 activity removes single-stranded 3' end of target, and then extends the 3' end of the hybridized target DNA segment, copying the further portion of the probe. The 5'-3' nuclease activity of the polymerase cleaves a matching 5' overlapping base of the target DNA segment thereby generating a ligation competent 5' phosphate (FIG. 45, step C). Polymerase also extends the oligonucleotide probe using the target DNA segment as a template, but does not cleave the blocking group on its 5' end. In FIG. 45, step D, ligase (filled circle) covalently seals the junction between the 3' extended end and the 5' end of the DNA segment to create circular ligation products. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 45, step E, exonuclease digestion of all unligated or nicked products leaves only desired single-stranded circular DNA comprising the original target DNA segment coupled to a further identifying nucleotide sequence, e.g., unique identifier sequence. The final product is suitable for rolling circle amplification using Bst polymerase in the presence of BstUI (CGCG). Thus, sites that were methylated in the original target are amplified and subsequently identified by sequencing. This example shows the utilization of the BstUI restriction endonuclease. However, other endonucleases that cleave double-stranded DNA if unmethylated, but not hybrid methylated/unmethylated DNA, nor unmethylated single-stranded DNA can be used. These include but are not limited to the thermophilic enzymes BstHHI (recognizes GCGC; an isoschizomer of HhaI), BsiSI (recognizes CCGG; an isoschizomer of HpaII), and TaiI (recognizes ACGT; an isoschizomer of MaeII).

Figure 46:
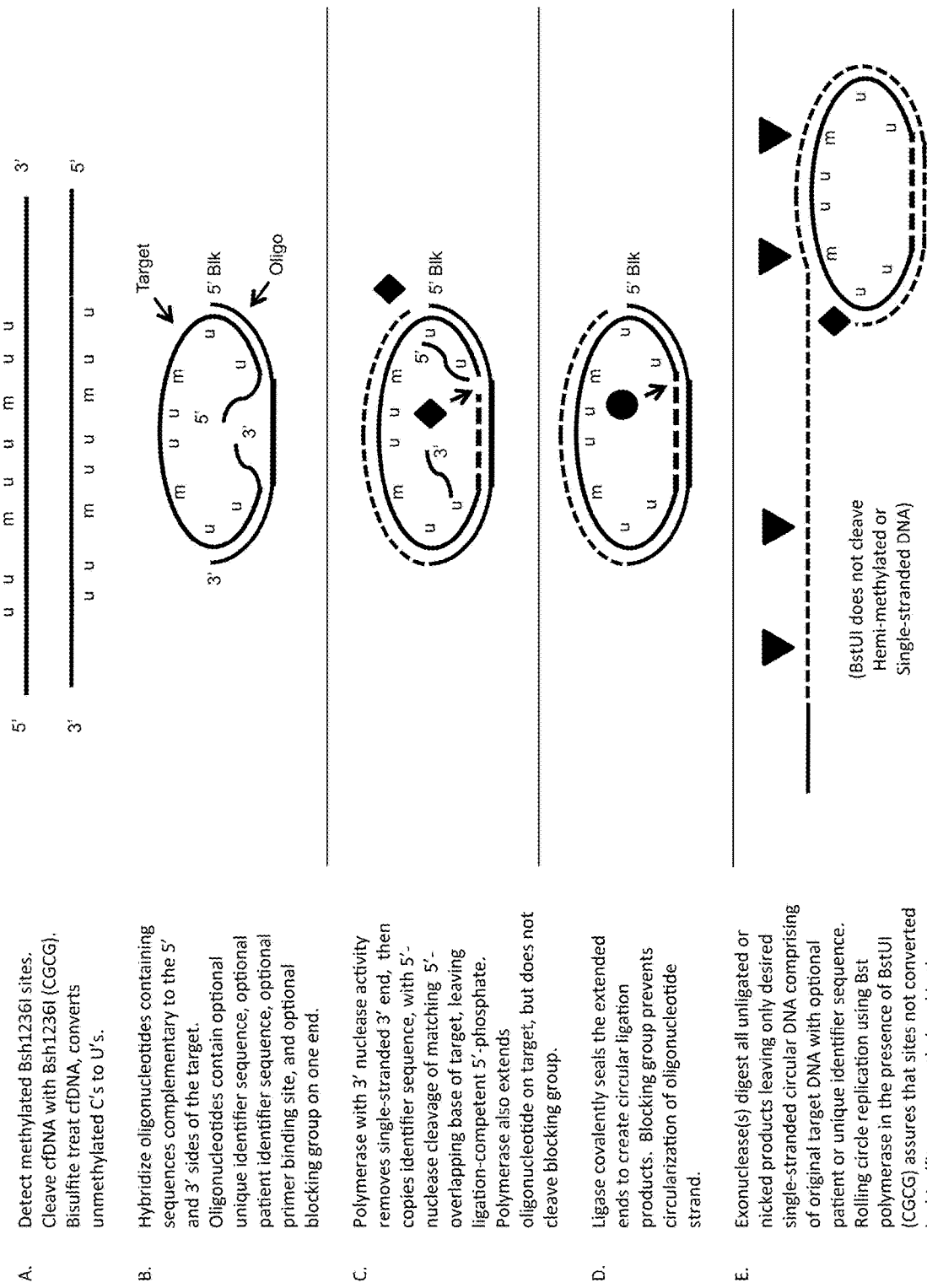
FIG. 46 shows a process for producing chimeric circular single stranded nucleic acid constructs suitable for detecting all methylated CpG sites near Bsh1236I sites in known regions of genomic DNA.

FIG. 46 shows a process for producing chimeric circular single stranded nucleic acid constructs suitable for detecting all methylated CpG sites near Bsh1236I sites in known regions of genomic DNA. The method is suitable for detecting all methylated CpG sites near methylated Bsh1236I sites in genomic DNA sheared to an average size of 150 bp or cfDNA having an average size of 160 bp. Genomic DNA is cleaved with Bsh1236I (CGCG) at unmethylated recognition sites (FIG. 46, step A). Bisulfite treatment converts unmethylated C's to U's and renders the strands non-complementary. In the embodiment depicted in FIG. 46, oligonucleotide probes containing 5' and 3' end sequences complementary to the 5' and 3' sides of the bisulfite-treated methylated target genomic DNA segments are hybridized to the DNA segments (FIG. 46, step B). The oligonucleotide probes also contain a further nucleotide portion that comprises one or more of a unique identifier sequence, a patient identifier sequence, and one or more primer binding sites. The oligonucleotide probes may also have a blocking group on one end (e.g., a 5' blocking group as shown in FIG. 46, step B). Polymerase (filled diamonds) with 3'-5' activity removes single-stranded 3' end of bisulfite-treated target, and then extends the 3' end of the hybridized target DNA segment to copy the further portion of the probe. The 5'-3' nuclease activity of the polymerase cleaves a matching 5' overlapping base of the bisulfite-treated target DNA segment thereby generating a ligation competent 5' phosphate (FIG. 46, step C). Polymerase also extends the oligonucleotide probe using the bisulfite-treated target DNA segment as a template, but does not cleave the blocking group on its 5' end. In FIG. 46, step D, ligase (filled circle) covalently seals the junction between the 3' extended end and the 5' end of the DNA segment to create circular ligation products. The 5' blocking group on the oligonucleotide probe prevents circularization of the oligonucleotide probe. As shown in FIG. 46, step E, exonuclease digestion of all unligated or nicked products leaves only desired single-stranded circular DNA comprising the original bisulfite-treated target DNA segment coupled to a further identifying nucleotide sequence, e.g., unique identifier sequence. The final product is suitable for rolling circle amplification using Bst polymerase in the presence of BstUI (CGCG) to assure that sites not converted by bisulfite were methylated in the original target, and all other methylated CpG sites are identified by sequencing. This example shows the use of BstUI restriction endonuclease. However, other endonucleases that cleave double-stranded DNA if unmethylated, but not hybrid methylated/unmethylated DNA, or unmethylated single-stranded DNA, and that retain restriction recognition of methylated sites after bisulfite treatment can be utilized. This includes but is not limited to the thermophilic enzyme TaiI (recognizes ACGT; an isoschizomer of MaeII).

Figure 47:
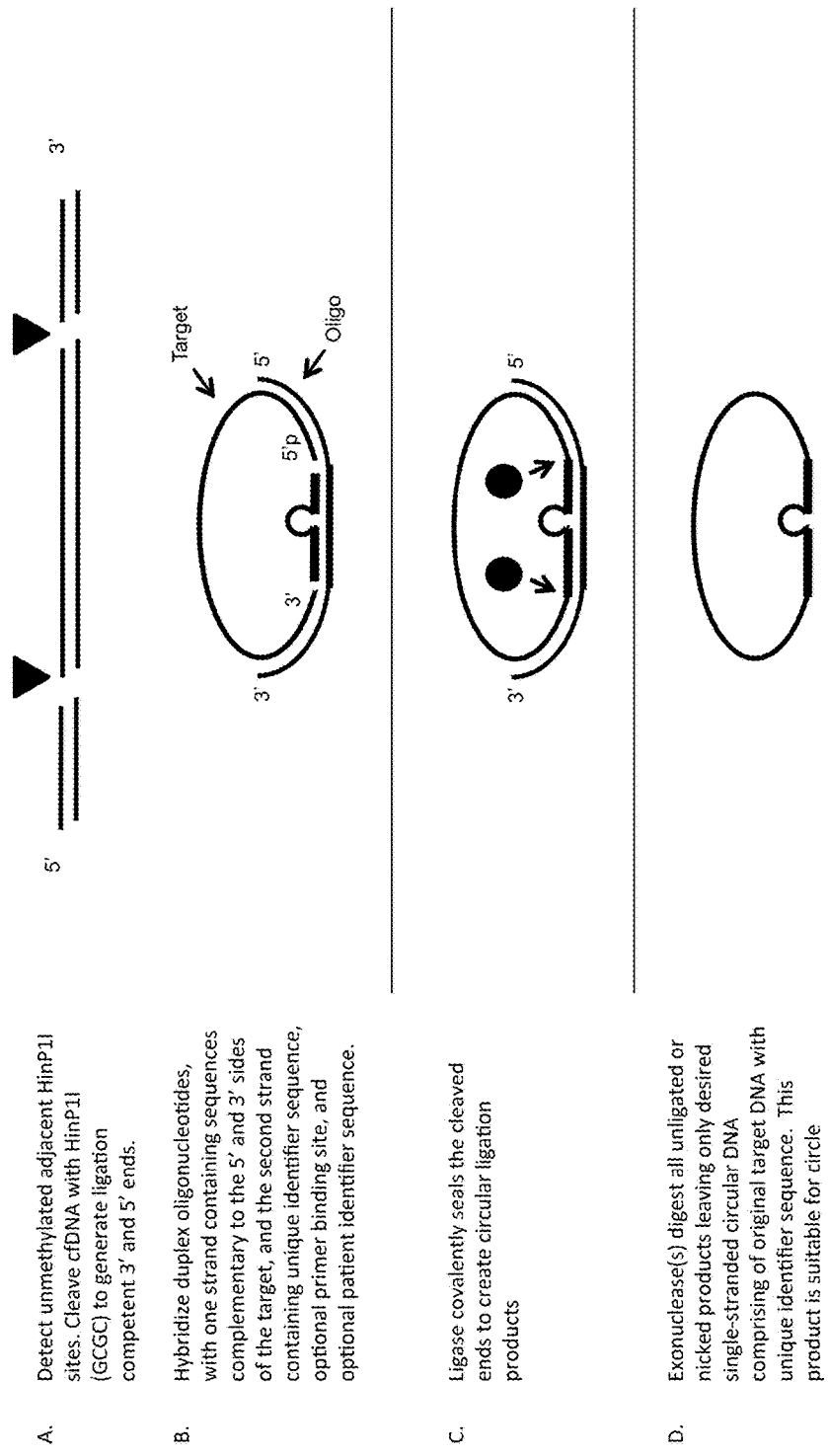
FIG. 47 depicts a method of generating circular chimeric single-stranded nucleic acid constructs of the present invention containing adjacent unmethylated HinP1I sites.
Figure 48:
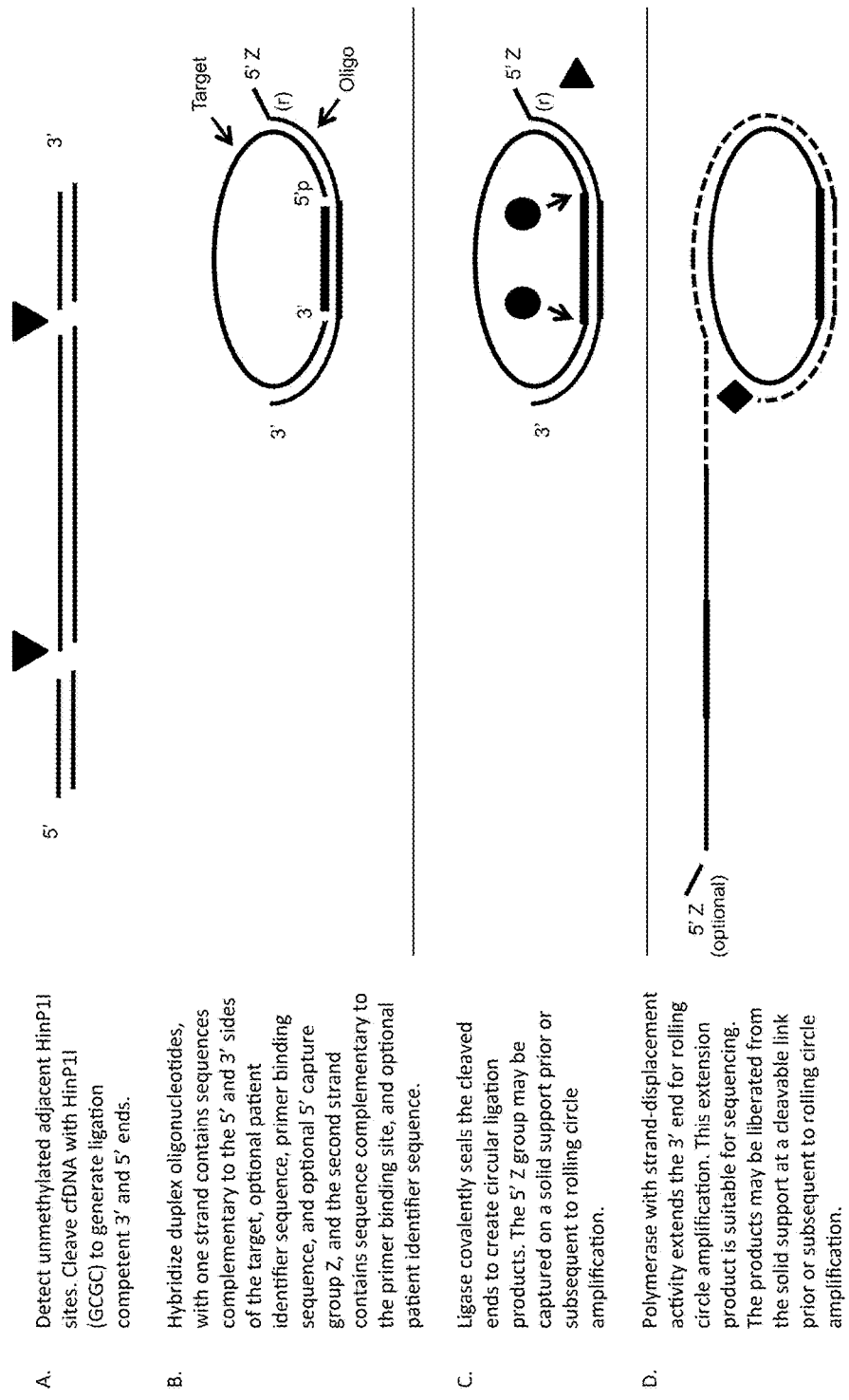
FIG. 48 depicts a method of generating and amplifying circular chimeric single-stranded nucleic acid constructs of the present invention containing adjacent unmethylated HinP1I sites.

FIG. 47 and FIG. 48 show a process for producing chimeric circular single stranded nucleic acid constructs suitable for detecting unmethylated adjacent HinP1I sites in known genomic regions of cfDNA or sheared total genomic DNA. Genomic DNA is cleaved with HinP1I (GCGC) (filled triangles) to generate ligation competent 3' and 5' ends (FIGS. 47, step A and 48, step A). As shown in FIG. 47, step B, duplex oligonucleotide probes are hybridized to the cleaved target DNA segments. The duplex probes comprise a first oligonucleotide probe strand containing nucleotide sequences complementary to the 5' and 3' sides of the target DNA segments, which are separated by a further portion. The further portion comprises a unique identifier portion, and/or a patient identifier portion, and/or one or more primer binding sequences. The second oligonucleotide probe of the duplex oligonucleotide probes (thick black line with loop) contains a sequence that is complementary to the further portion of the first oligonucleotide probe. The looped region of the second oligonucleotide probe represents a non-complementary region. As shown in FIG. 47, step C, hybridization of the duplex probes to the cleaved genomic DNA segments creates two ligation competent junctions, i.e., between the 3' end of the DNA segment and 5' end of the second oligonucleotide probe, and between the 3' end of the second oligonucleotide probe and the 5' of the cleaved genomic segment. Ligase (filled circles) covalently seals the ligation junctions to create circular ligation products containing the genomic DNA segments (FIG. 47, step C). As shown in FIG. 47, step D, exonuclease digestion removes all unligated or nicked products leaving only the desired single-stranded circular ligation products which are suitable for circle sequencing using any of the methods described herein.

In the embodiment depicted in FIG. 48 the first oligonucleotide probe of the duplex probe contains sequences complementary to the 5' and 3' sides of the target DNA segment that are separated by the further nucleotide portion. In addition, the first oligonucleotide probe also has an optional 5' capture group ("Z") (FIG. 48, step B). After ligation at the two ligation junctions between the target DNA segment and second oligonucleotide probe to form the circularized ligation product of FIG. 48, step C, a polymerase (filled diamonds) having strand displacing activity extends the first oligonucleotide probe using the circularized DNA containing ligation product as a template (FIG. 48, step D). Rolling circular amplification generates a primary extension product containing tandem linear sequences that are complementary to the circularized ligation product (FIG. 48, step D). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 49:
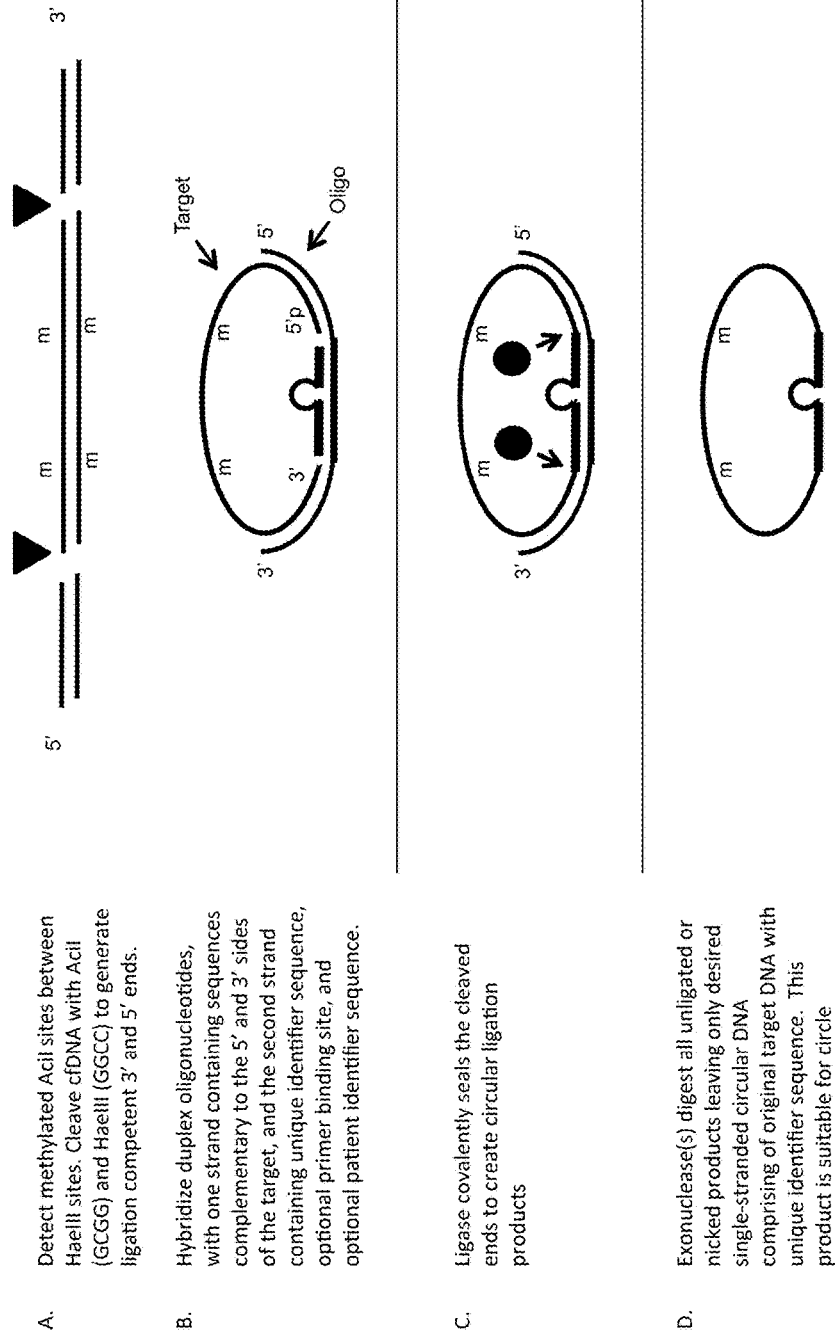
FIG. 49 depicts a method of generating circular chimeric single-stranded nucleic acid constructs of the present invention containing adjacent methylated AciI sites located between HaeIII restriction sites.
Figure 50:
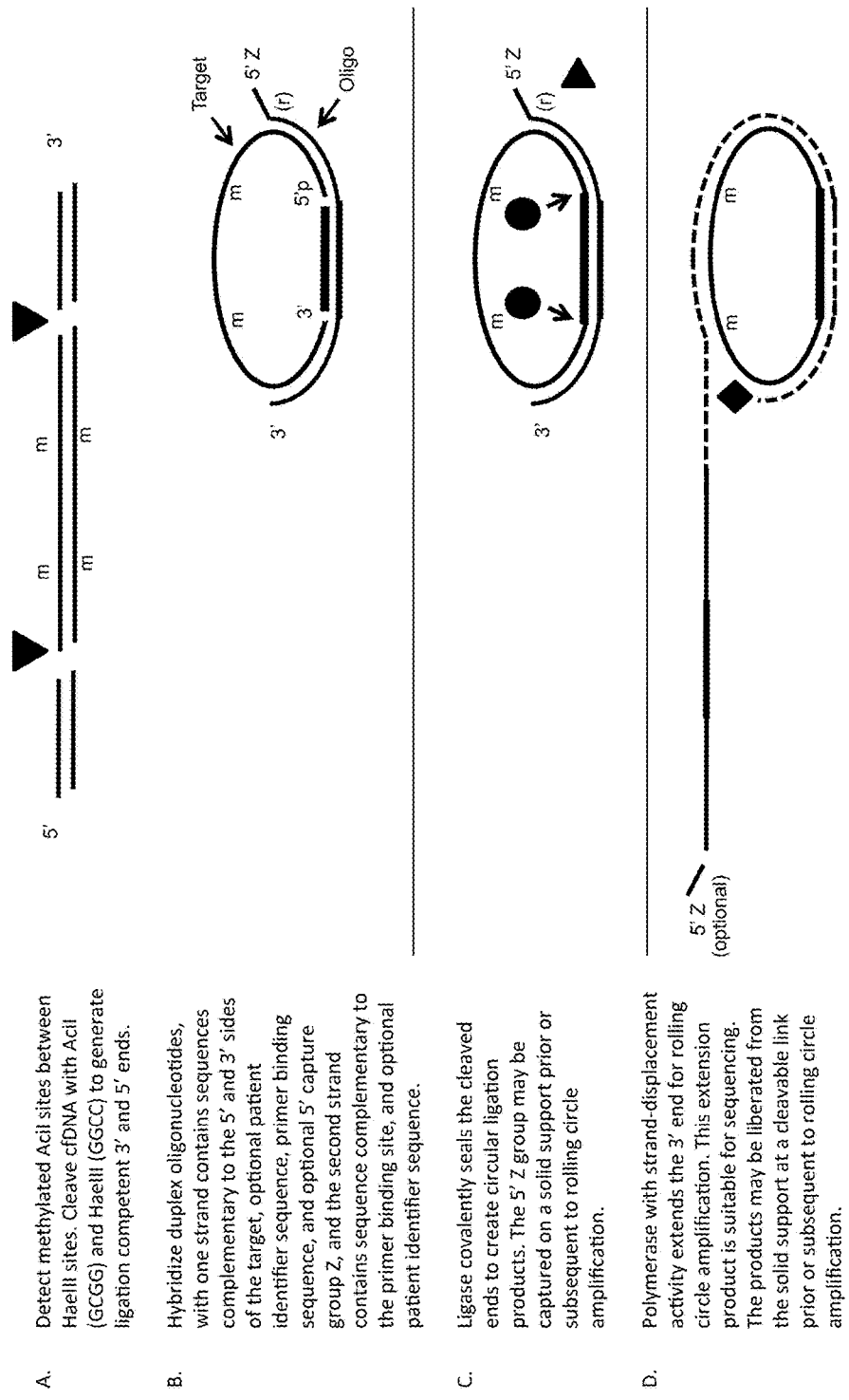
FIG. 50 depicts a method of generating and amplifying circular chimeric single-stranded nucleic acid constructs of the present invention containing adjacent methylated AciI sites located between HaeIII restriction sites.

FIG. 49 and FIG. 50 show a process for producing chimeric circular single stranded nucleic acid constructs suitable for detecting methylated ("m") AciI sites located between HaeIII sites in known genomic regions of cfDNA or sheared total genomic DNA. Genomic DNA is cleaved with AciI (filled triangles, GCGG) and HaeIII (filled triangles, GGCC) to generate ligation competent 3' and 5' ends (FIGS. 49, step A and 50, step A). As shown in FIGS. 49, step B and 50, step B, duplex oligonucleotide probes are hybridized to the cleaved target DNA segments. In the embodiment depicted in FIG. 49, the duplex probes comprise a first oligonucleotide probe strand containing nucleotide sequences complementary to the 5' and 3' sides of the target DNA segments, which are separated by a further portion. The further portion comprises a unique identifier portion, and/or a patient identifier portion, and/or one or more primer binding sequences (FIG. 49, step B). The second oligonucleotide probe of the duplex oligonucleotide probes (thick black line with loop) contains a sequence that is complementary to the further portion of the first oligonucleotide probe (FIG. 49, step B). The looped region of the second oligonucleotide probe represents a non-complementary region. As shown in FIG. 49, step C, hybridization of the duplex probes to the cleaved genomic DNA segments creates two ligation competent junctions, i.e., between the 3' end of the DNA segment and 5' end of the second oligonucleotide probe, and between the 3' end of the second oligonucleotide probe and the 5' of the cleaved genomic segment. Ligase (filled circles) covalently seals the ligation junctions to create circular ligation products containing the methylated genomic DNA segments (FIG. 49, step C). As shown in FIG. 49, step D, exonuclease digestion removes all unligated or nicked products leaving only the desired single-stranded circular ligation products which are suitable for circle sequencing using any of the methods described herein.

In the embodiment depicted in FIG. 50 the first oligonucleotide probe of the duplex probe contains sequences complementary to the 5' and 3' sides of the target DNA segment that are separated by the further nucleotide portion. In addition, the first oligonucleotide probe also has an optional 5' capture group ("Z") (FIG. 50, step B). After ligation at the two ligation junctions between the target DNA segment and second oligonucleotide probe to form a circularized methylated ligation product (FIG. 50, step C), a polymerase (filled diamonds) having strand displacing activity extends the first oligonucleotide probe using the circularized DNA containing ligation product as a template (FIG. 50, step D). Rolling circular amplification generates a primary extension product containing tandem linear sequences that are complementary to the circularized ligation product (FIG. 50, step D). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

FIG. 51 shows a process to discover unmethylated adjacent HinP1I sites (GCGC) in known regions of genomic DNA. Genomic DNA, whether isolated from whole cells, or as cfDNA in the plasma, contains ends through natural enzymatic processes or shearing. These need to be blocked from subsequent steps by appending short linkers to the 3' and 5' ends of the DNA ends (e.g., append linkers via ligation). The 5' end linkers contain a blocking group (thick black lines) as shown in FIG. 51, step A. Cleave linker appended DNA with HinP1I (GCGC) (filled triangles) (FIG. 51, step A). Only adjacent HinP1I sites (GCGG) unmethylated in original genomic DNA generate unblocked fragments when cleaved with HinP1I. As shown in FIG. 51, step B, long linkers (partially grey double lines) containing a unique identifier sequence and/or a patient identifier sequence are appended to the HinP1I cleaved DNA fragments. The long linkers contain either 3'-end blocking group or a thiophosphate containing backbone (****) to inhibit subsequent digestion with 3'-exonuclease (filled triangles). Only fragments with linkers appended to both sides will remain double-stranded. As shown in FIG. 51, step C, the free end of linkers are rendered competent for ligation, either by (i) phosphorylating 5'-end, (ii) removing 3'-blocking group, (iii) using 5'-nuclease activity to cleave off matching 5'-overlapping base or flap generating ligation-competent 5'-phosphate, or (iv) any combination of (i), (ii), (iii). Ligation (filled circles) conditions are designed to favor oligomerization. As shown in FIG. 51, step D, the ligated products are composed of adjacent HinP1I sequences originally unmethylated in genomic DNA coupled to a unique identifier sequence and/or patient identifier sequence. The final product is suitable for subsequent sequencing.

FIG. 52 shows a process for the discovery of methylated adjacent AciI sites (GCGG) in known regions throughout genome. Genomic DNA is cleaved with AciI (filled triangles); m represents methylated sites. As shown in FIG. 52, step A, short linkers with a 5' end blocking group (thick black lines) are appended, e.g., by ligation, to the AciI digested DNA. The linker appended DNA is cleaved with HaeIII (GGCC). Only adjacent HaeIII sites (GGCC) with methylated AciI sites in original genomic DNA generate unblocked fragments when cleaved with HaeIII. In FIG. 52, step B, long linkers (partially grey double lines) containing a unique identifier sequence and/or a patient identifier sequence are appended to the HaeIII cleaved DNA fragments. The long linkers contain either 3'-end blocking group or a thiophosphate containing backbone (**) to inhibit subsequent digestion with 3'-exonuclease (filled triangles). Only fragments with linkers appended to both sides will remain double-stranded. As shown in FIG. 52, step C, the free end of linkers are rendered competent for ligation, either by (i) phosphorylating 5'-end, (ii) removing 3'-blocking group, (iii) using 5'-nuclease activity to cleave off matching 5'-overlapping base or flap generating ligation-competent 5'-phosphate, or (iv) any combination of (i), (ii), (iii). Ligation (filled circles) conditions are designed to favor oligomerization. As shown in FIG. 52**, step D, the ligated products are composed of adjacent HaeIII sequences originally methylated at AciI sites in genomic DNA coupled to a unique identifier sequence and/or patient identifier sequence. The final product is suitable for subsequent sequencing.

Figure 53:
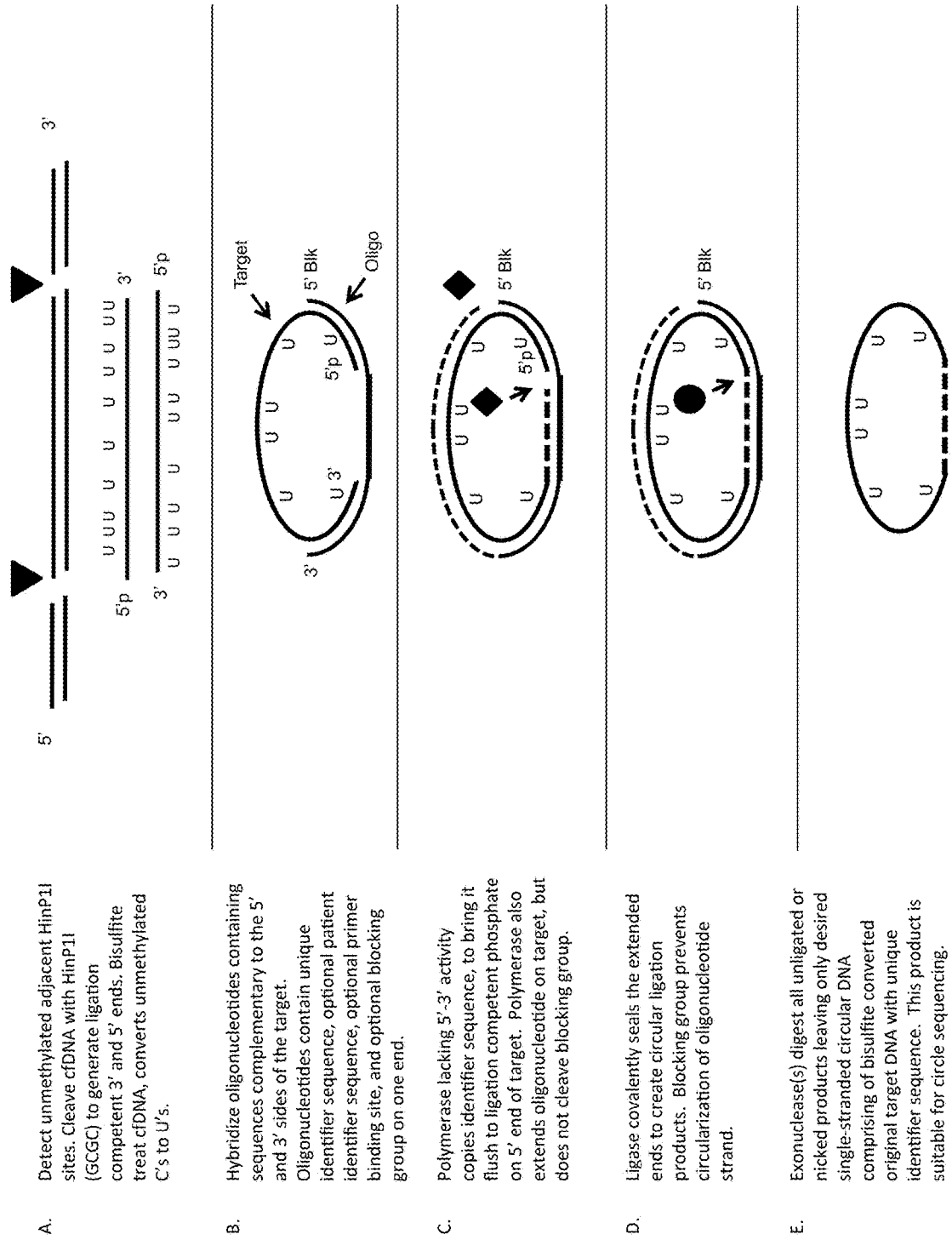
FIG. 53 depicts a method of generating circular chimeric single-stranded nucleic acid constructs of the present invention containing unmethylated adjacent HinP1I sites in known genomic regions.
Figure 54:
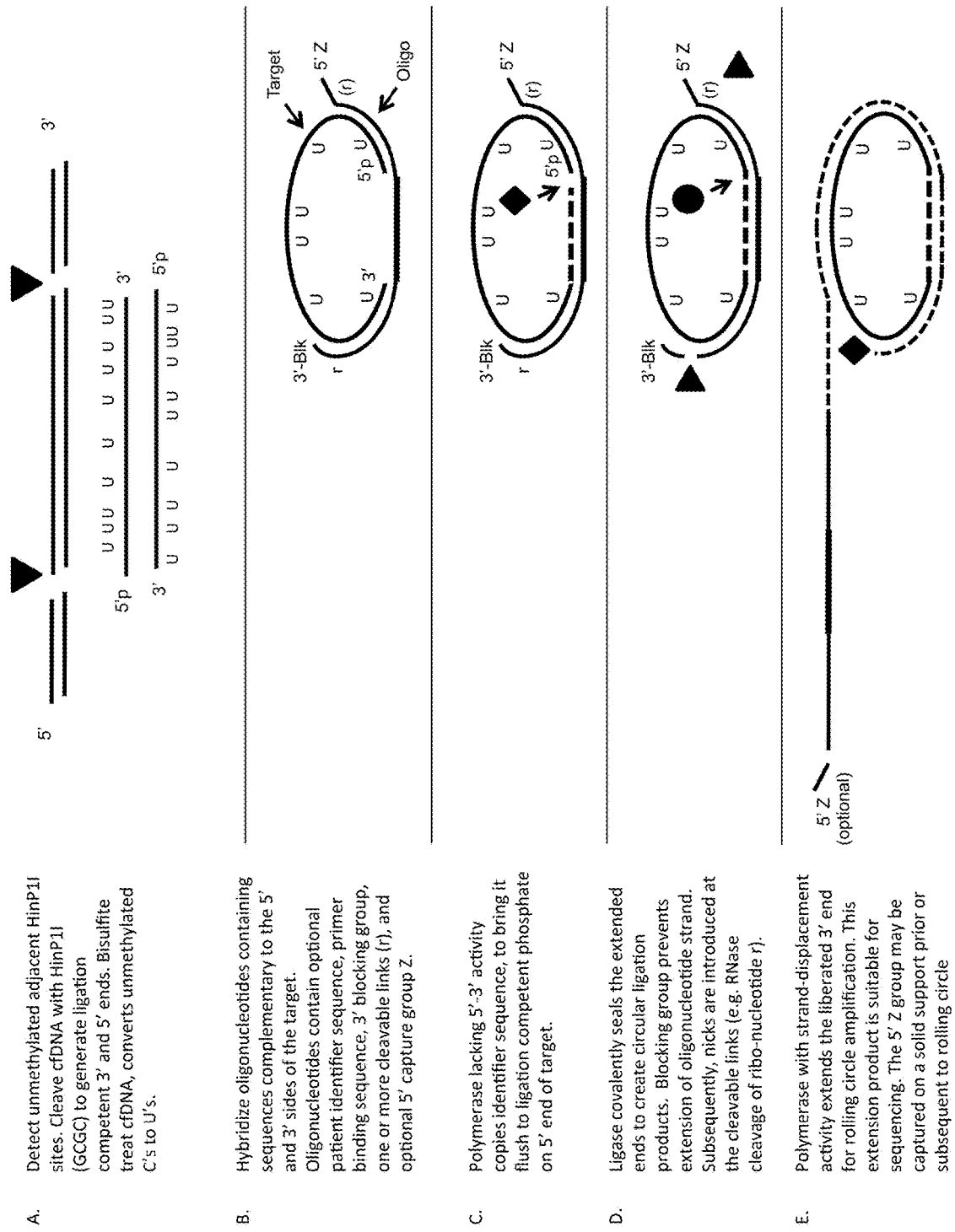
FIG. 54 depicts a method of generating and amplifying circular chimeric single-stranded nucleic acid constructs of the present invention containing unmethylated adjacent HinP1I sites in known genomic regions.

FIG. 53 and FIG. 54 show a process for producing chimeric circular single stranded nucleic acid constructs suitable for detecting unmethylated adjacent HinP1I sites in known genomic regions of cfDNA or sheared total genomic DNA. Genomic DNA is cleaved with HinP1I (GCGC) to generate ligation competent 3'- and 5'-ends as shown in FIGS. 53, step A and 54, step A. Bisulfite treatment of HinP1I digested DNA, converts unmethylated C's to U's. In the embodiment of FIG. 53, oligonucleotide probes containing 5' and 3' end sequences complementary to the 5' and 3' sides of the target DNA segments are hybridized to the cleaved DNA segments (FIG. 53, step B). The oligonucleotides contain unique identifier sequence, optional patient identifier sequence, and optional blocking group on one end. Polymerase (filled diamonds) lacking 5'-3' activity extends the 3' end of target DNA segment, to bring it flush to ligation competent phosphate on 5'-end of the target FIG. 53, step C. Polymerase also extends oligonucleotide probe on target, but does not cleave 5' blocking group. In FIG. 53, step D, ligase (filled circles) covalently seals the extended target DNA segment ends to create circular ligation products. Blocking group prevents circularization of oligonucleotide probe. As shown in FIG. 53, step E, exonuclease digestion removes all unligated or nicked products leaving only the desired single-stranded circular DNA comprising of bisulfite converted original target DNA with unique identifier sequence. The final product is suitable for rolling circle amplification and circle sequencing.

In the embodiment of FIG. 54 the oligonucleotide probes contain sequences complementary to the 5' and 3' sides of the target DNA segment that are separated by the further nucleotide portion. In addition, the oligonucleotide probes also have a blocking group (3'-Blk) on the 3' end, one or more cleavable link(s), where the cleavable link is depicted at "r", and an optional 5' capture group ("Z") (FIG. 54, step B). After ligation of the 3' extended end and 5' end of the target DNA segment to form a circularized ligation product (FIG. 54, step C), the 3'blocking group on the oligonucleotide probe is removed (e.g., RNase H cleavage of the ribonucleotide link) (FIG. 54, step D), and a polymerase (filled diamonds) lacking 5'-3' activity extends the oligonucleotide probe using the circularized DNA ligation product as a template (FIG. 54, step E). Rolling circular amplification generates a primary extension product containing tandem linear sequences that are complementary to the circularized ligation product (FIG. 54, step E). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 55:
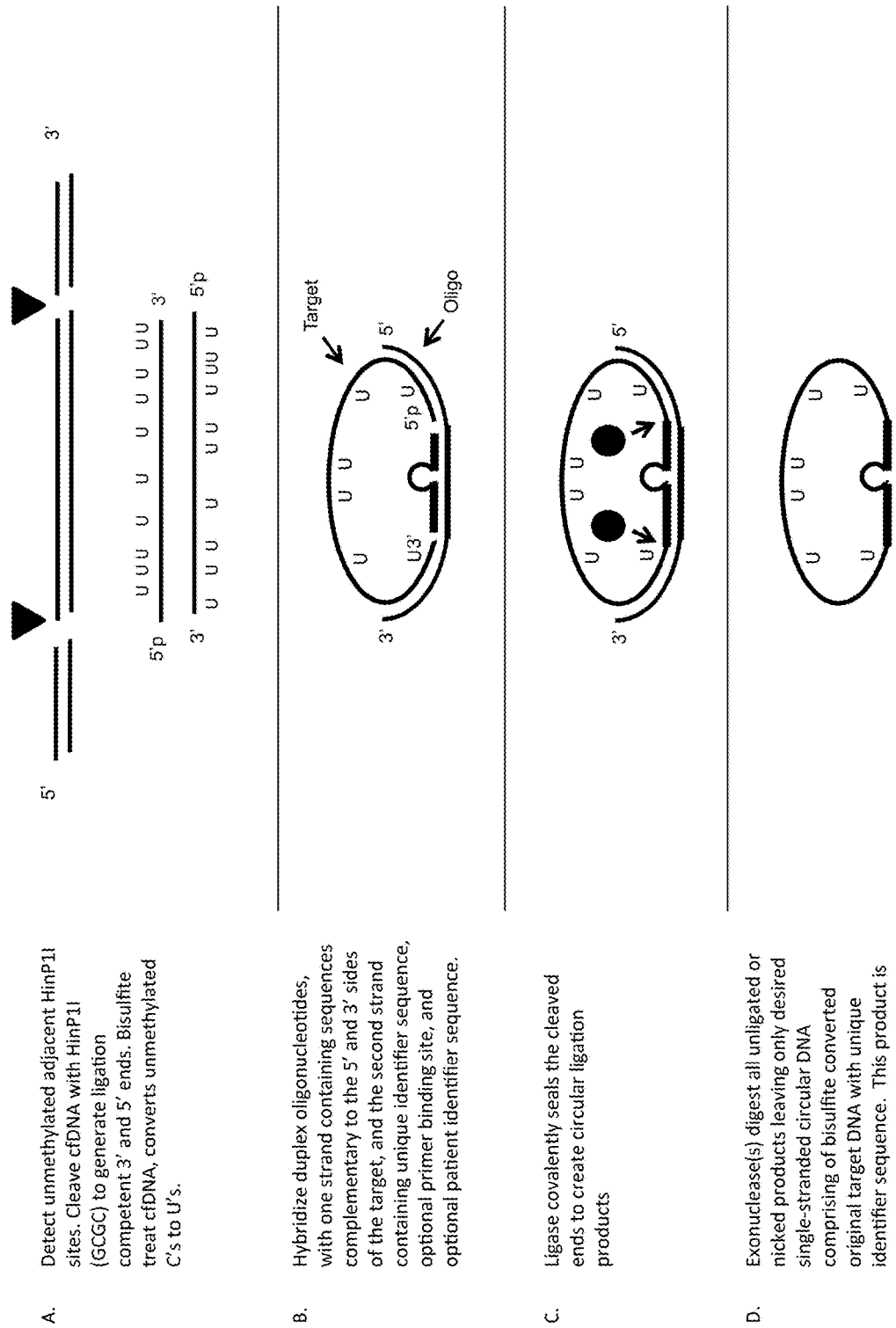
FIG. 55 depicts a method of generating circular chimeric single-stranded nucleic acid constructs of the present invention containing unmethylated adjacent HinP1I sites in known genomic regions.
Figure 56:
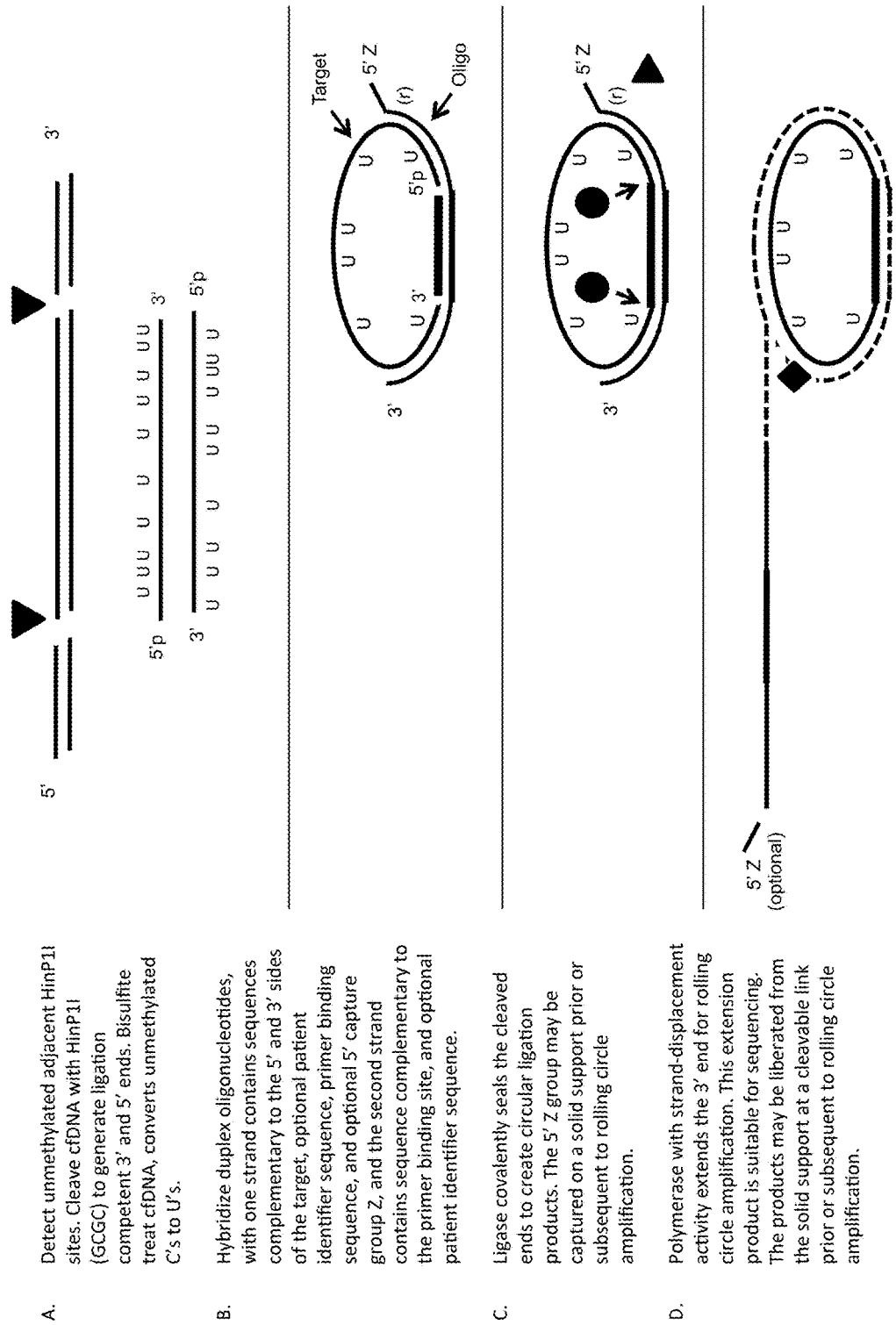
FIG. 56 depicts a method of generating and amplifying circular chimeric single-stranded nucleic acid constructs of the present invention containing unmethylated adjacent HinP1I sites in known genomic regions.

FIGS. 55 and 56 show a process for producing chimeric circular single stranded nucleic acid constructs suitable for detecting unmethylated adjacent HinP1I sites in known genomic regions of cfDNA or sheared total genomic DNA. As shown in FIGS. 55, step A and 56, step A, genomic DNA is cleaved with HinP1I (GCGC) (filled triangles) to generate ligation competent 3'- and 5'-ends. Bisulfite treatment of the HinP1I digested DNA, converts unmethylated C's to U's (FIGS. 55, step A and 56, step A). As shown in FIGS. 55, step B and 56, step B, duplex oligonucleotide probes are hybridized to the cleaved target DNA segments. In the embodiment depicted in FIG. 55, the duplex probes comprise a first oligonucleotide probe strand containing nucleotide sequences complementary to the 5' and 3' sides of the target DNA segments, which are separated by a further portion. The further portion comprises a unique identifier portion, and/or a patient identifier portion, and/or one or more primer binding sequences (FIG. 55, step B). The second oligonucleotide probe of the duplex oligonucleotide probes (thick black line with loop) contains a sequence that is complementary to the further portion of the first oligonucleotide probe (FIG. 55, step B). The looped region of the second oligonucleotide probe represents a non-complementary region. As shown in FIG. 55, step C, hybridization of the duplex probes to the HinP1I digested and bisulfite treated genomic DNA creates two ligation competent junctions, i.e., between the 3' end of the DNA segment and 5' end of the second oligonucleotide probe, and between the 3' end of the second oligonucleotide probe and the 5' of the DNA segment. Ligase (filled circles) covalently seals the ligation junctions to create circular ligation products containing the bisulfite treated genomic DNA segments (FIG. 55, step C). As shown in FIG. 55, step D, exonuclease digestion removes all unligated or nicked products leaving only the desired single-stranded circular ligation products which are suitable for circle sequencing using any of the methods described herein.

In the embodiment depicted in FIG. 56 the first oligonucleotide probe of the duplex probe contains sequences complementary to the 5' and 3' sides of the target DNA segment that are separated by the further nucleotide portion. In addition, the first oligonucleotide probe also has an optional 5' capture group ("Z") (FIG. 56, step B). After ligation at the two ligation junctions between the target DNA segment and second oligonucleotide probe to form a circularized ligation product (FIG. 56, step C), a polymerase (filled diamonds) having strand displacing activity extends the first oligonucleotide probe using the circularized DNA containing ligation product as a template (FIG. 56, step D). Rolling circular amplification generates a primary extension product containing tandem linear sequences that are complementary to the circularized ligation product (FIG. 56, step D). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 57:
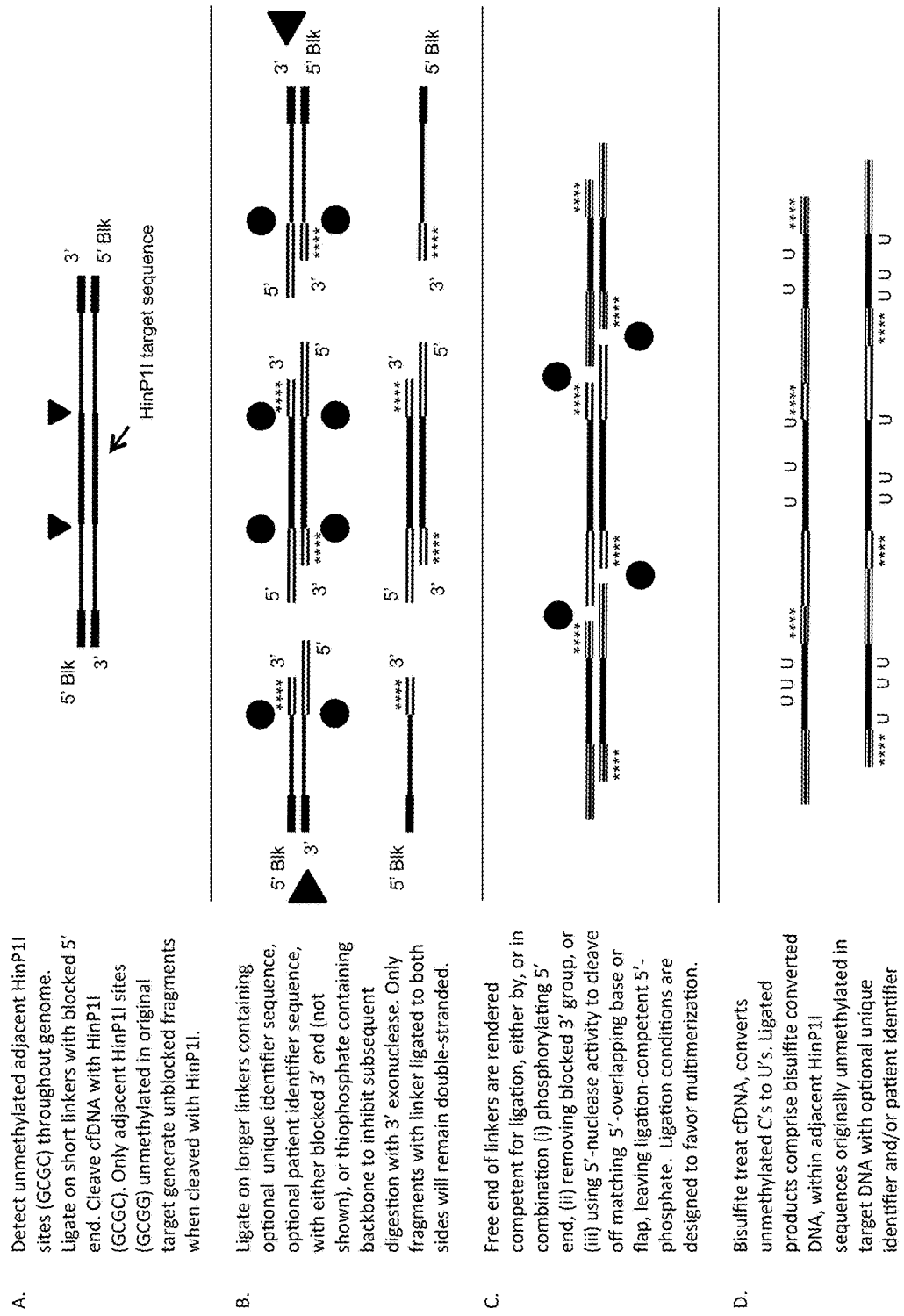
FIG. 57 shows a process for detecting unmethylated adjacent HinP1I sites in known genomic regions.

FIG. 57 shows a process for the discovery of unmethylated adjacent HinP1I sites (GCGC) in known genomic regions of cfDNA or sheared total genomic DNA. Genomic DNA, whether isolated from whole cells, or as cfDNA in the plasma, contains ends through natural enzymatic processes or shearing. These need to be blocked from subsequent steps by appending short linkers to the 3' and 5' ends of the DNA ends (e.g., append linkers via ligation). The 5' end linkers contain a blocking group (thick black lines) as shown in FIG. 57, step A. Cleave linker appended DNA with HinP1I (GCGC) (filled triangles) (FIG. 57, step A). Only adjacent HinP1I sites (GCGG) unmethylated in original genomic DNA generate unblocked fragments when cleaved with HinP1I. As shown in FIG. 57, step B, long linkers (partially grey double lines) containing a unique identifier sequence and/or a patient identifier sequence are appended to the HinP1I cleaved DNA fragments. The long linkers contain either 3'-end blocking group or a thiophosphate containing backbone (****) to inhibit subsequent digestion with 3'-exonuclease (filled triangles). Only fragments with linkers appended to both sides will remain double-stranded. As shown in FIG. 57, step C, the free end of linkers are rendered competent for ligation either by (i) phosphorylating 5'-end, (ii) removing 3'-blocking group, (iii) using 5'-nuclease activity to cleave off matching 5'-overlapping base or flap generating ligation-competent 5'-phosphate, or (iv) any combination of (i), (ii), (iii). Ligation (filled circles) conditions are designed to favor oligomerization. As shown in FIG. 57, step D, bisulfite treatment of the ligation products converts unmethylated C's to U's. Ligated products comprise bisulfite converted DNA, within adjacent HinP1I sequences originally unmethylated in target DNA coupled to a unique identifier and/or patient identifier sequence. The final product is suitable for additional steps and subsequent sequencing.

Figure 58:
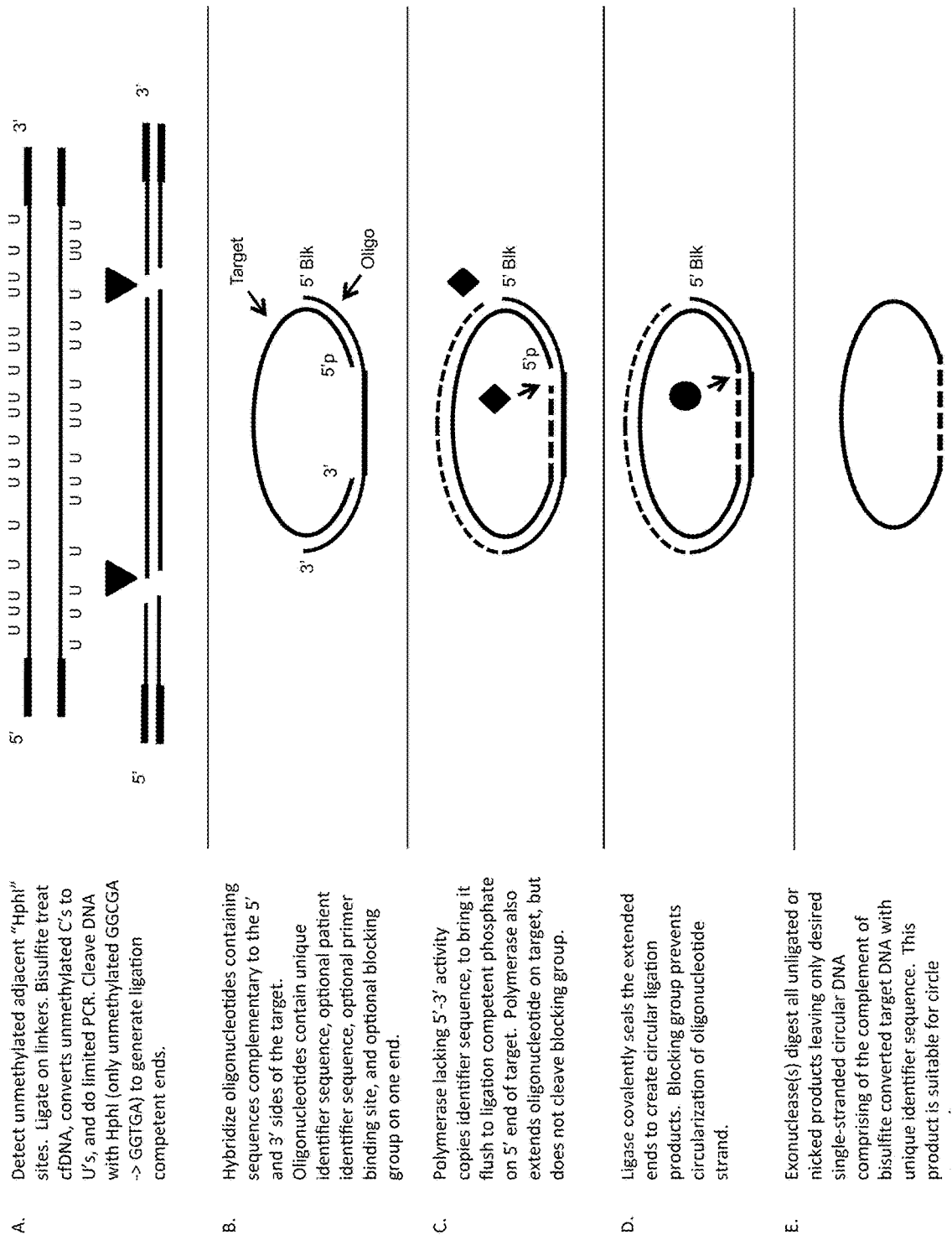
FIG. 58 depicts a method of generating circular chimeric single-stranded nucleic acid constructs of the present invention containing unmethylated adjacent Hph1 sites in known genomic regions.
Figure 59:
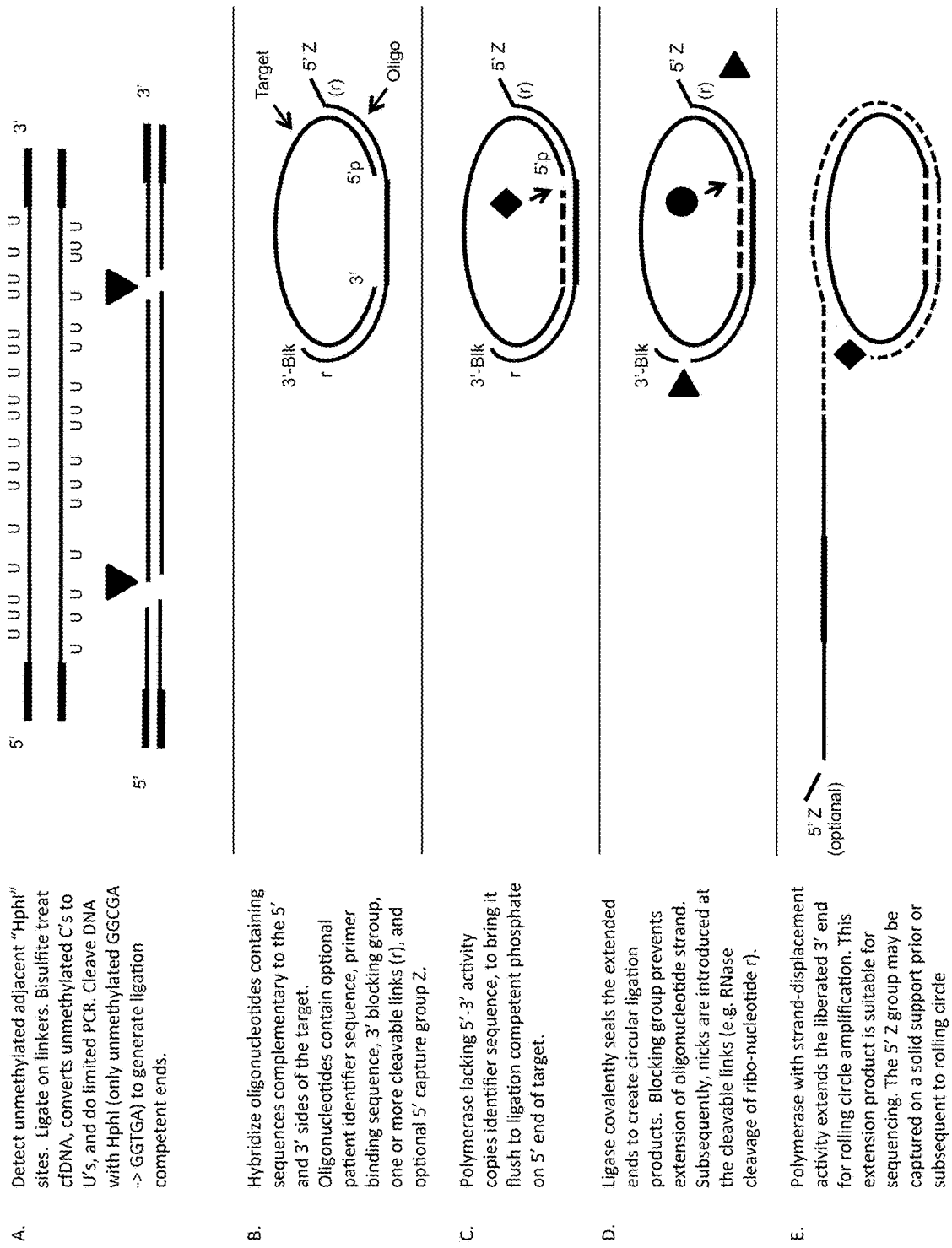
FIG. 59 depicts a method of generating and amplifying circular chimeric single-stranded nucleic acid constructs of the present invention containing unmethylated adjacent Hph1 sites in known genomic regions.

FIG. 58 and FIG. 59 show a process for producing chimeric circular single stranded nucleic acid constructs suitable for detecting unmethylated adjacent "Hph1" sites in known genomic regions of cfDNA or sheared total genomic DNA. As shown in FIGS. 58, step A and 59, step A, short linkers are appended (e.g., by ligation) to cfDNA fragments or sheared genomic DNA. The linker appended DNA is bisulfite treated to convert unmethylated C's to U's. Limited PCR is performed and the resulting PCR products are cleaved with Hph1 (only unmethylated GGCGA→GGTGA) to generate ligation competent ends (FIGS. 58, step A and 59, step A). In the embodiment of FIG. 58, oligonucleotide probes containing 5' and 3' end sequences complementary to the 5' and 3' sides of the digested target PCR segments are hybridized to the cleaved DNA segments (FIG. 58, step B). The oligonucleotide probes also contain a further nucleotide portion that contains one or more of a unique identifier sequence, a patient identifier sequence, and/or one or more primer binding sites. The oligonucleotide probes may also have a blocking group on one end (e.g., a 5' blocking group as shown in FIG. 58, step B). Polymerase (filled diamonds) lacking 5'-3' activity extends the 3' end of the hybridized target DNA segment, copying the further portion of the probe and forming a ligation junction with the 5' end of the hybridized target DNA segment (FIG. 58, step C). Polymerase also extends the oligonucleotide probe using the target DNA segment as a template, but does not cleave the blocking group on its 5' end. In FIG. 58, step D, ligase (filled circle) covalently seals the junction between the 3' extended end and the 5' end of the DNA segment to create circular ligation products containing the PCR generated HphI digested DNA segments. The 5' blocking group on the oligonucleotide probe prevents circularization of the oligonucleotide probe. Alternatively, a nick is introduced at a cleavable link contained in the further portion, e.g. the further portion contains a uracil nucleotide that is cleaved using UDG. As shown in FIG. 58, step E, exonuclease digestion of all unligated or nicked products leaves only desired single-stranded circular DNA comprising the PCR generated HphI digested DNA segment coupled to a further identifying nucleotide sequence, e.g., unique identifier sequence. The final product is suitable for rolling circle amplification and circle sequencing.

In the embodiment of FIG. 59 the oligonucleotide probes also contain sequences complementary to the 5' and 3' sides of the digested target PCR segments that are separated by the further nucleotide portion. In addition, the oligonucleotide probes also have a blocking group (3'-Blk) on its 3' end, one or more cleavable link(s), where the cleavable link is depicted at "r", and an optional 5' capture group ("Z") (FIG. 59, step B). After ligation of the 3' extended end and 5' end of the target PCR segment to form a circularized ligation product (FIG. 59, step C), the 3' blocking group on the oligonucleotide probe is removed (e.g., RNase H cleavage of the ribonucleotide link) (FIG. 59, step D), and a polymerase (filled diamonds) lacking 5'-3' activity extends the oligonucleotide probe using the circularized DNA ligation product as a template (FIG. 59, step E). Rolling circular amplification generates a primary extension product containing tandem linear sequences that are complementary to the circularized ligation product (FIG. 58, step E). The primary extension product is suitable for sequencing using the methods described herein. The optional 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 60:
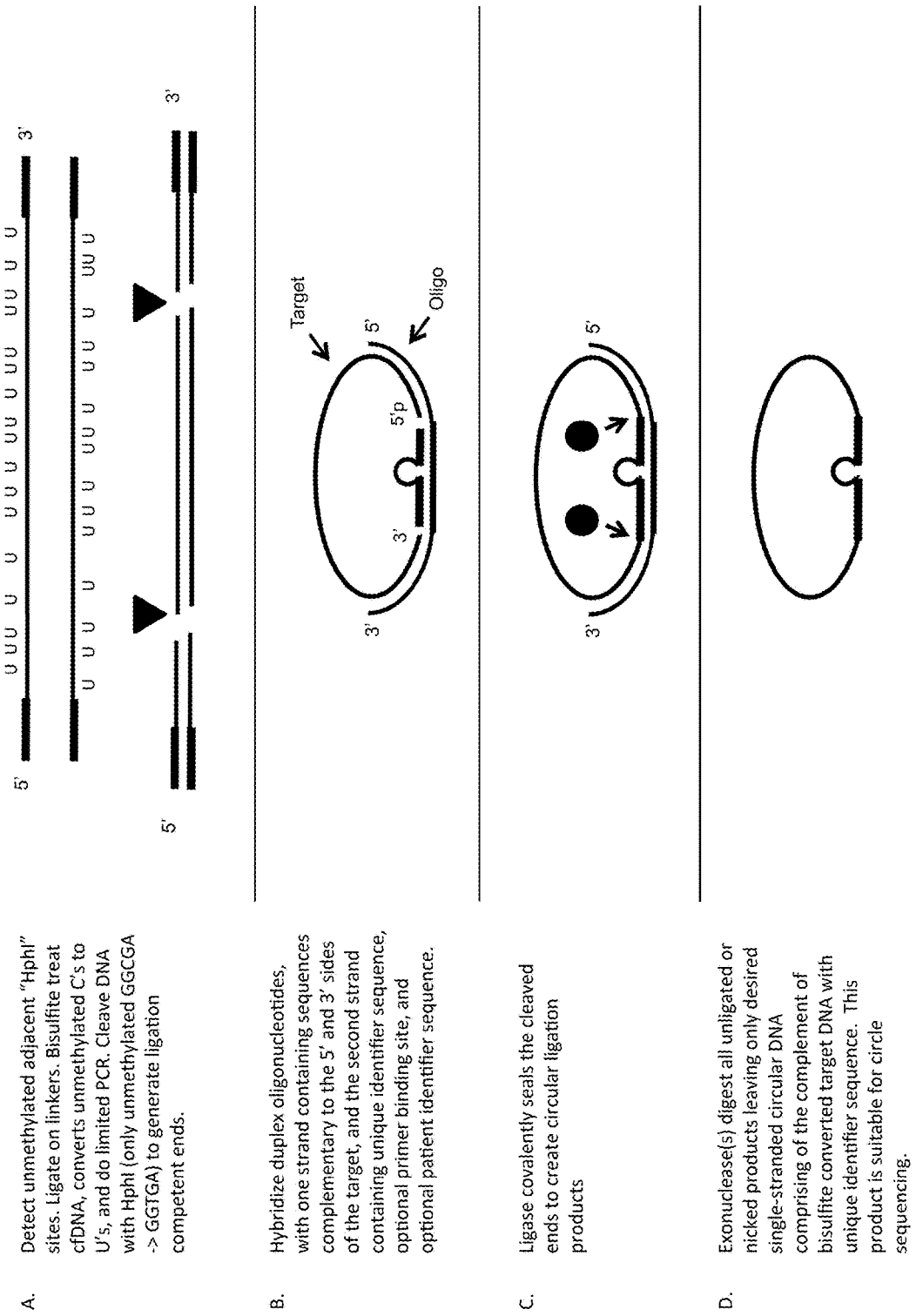
FIG. 60 depicts a method of generating circular chimeric single-stranded nucleic acid constructs of the present invention containing unmethylated adjacent Hph1 sites in known genomic regions.
Figure 61:
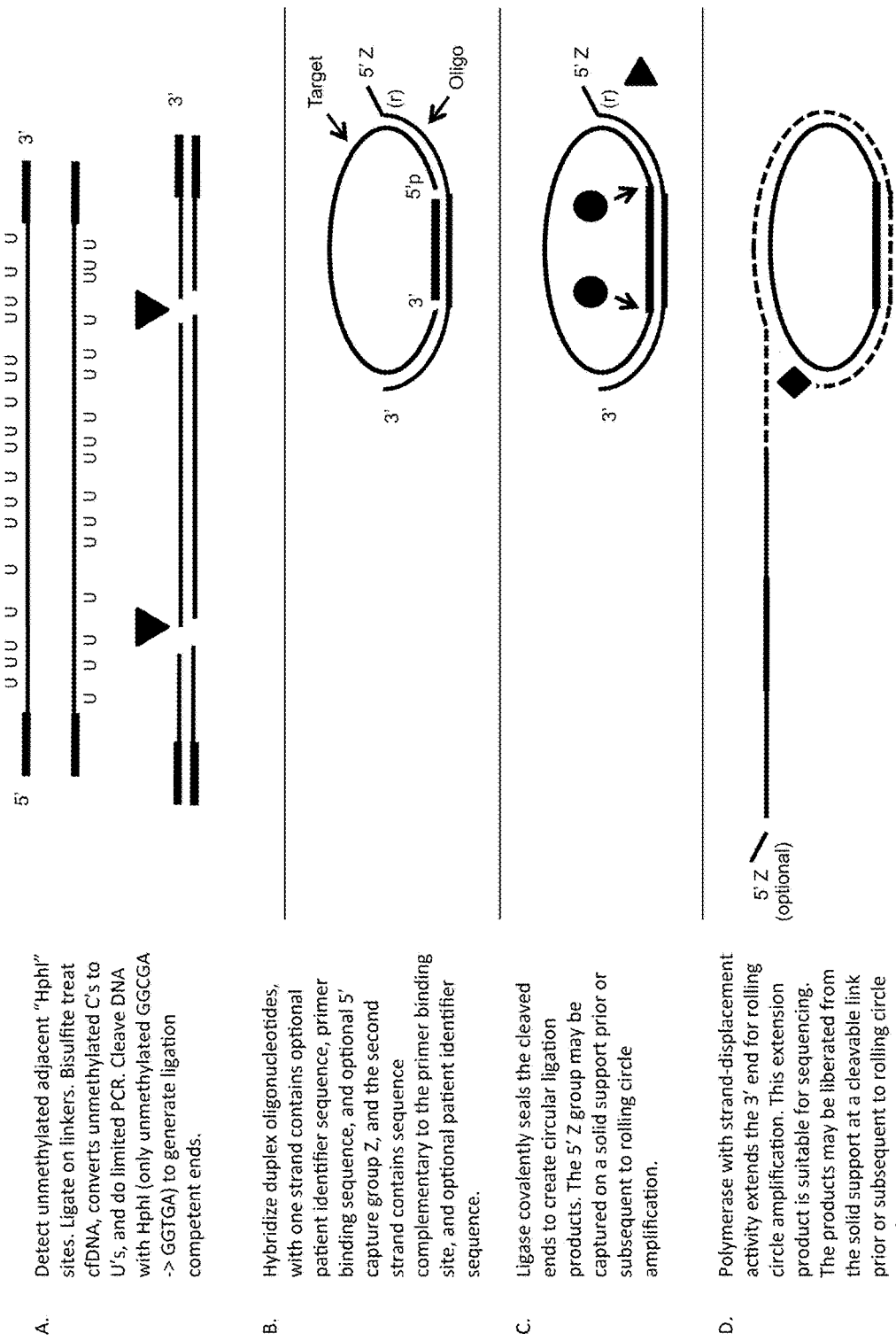
FIG. 61 depicts a method of generating and amplifying circular chimeric single-stranded nucleic acid constructs of the present invention containing unmethylated adjacent Hph1 sites in known genomic regions.

FIGS. 60 and 61 show a process for producing chimeric circular single stranded nucleic acid constructs suitable for detecting unmethylated adjacent "HphI" sites in known genomic regions of cfDNA or sheared total genomic DNA. As shown in FIGS. 60, step A and 61, step A, short linkers are appended (e.g., by ligation) to cfDNA fragments or sheared genomic DNA. The linker appended DNA is bisulfite treated to convert unmethylated C's to U's. Limited PCR is performed and the resulting PCR products are cleaved with Hph1 (only unmethylated GGCGA→GGTGA) to generate ligation competent ends (FIGS. 60, step A and 61, step A). As shown in FIGS. 60, step B and 61, step B, duplex oligonucleotide probes are hybridized to the cleaved target DNA segments. In the embodiment depicted in FIG. 60, the duplex probes comprise a first oligonucleotide probe strand containing nucleotide sequences complementary to the 5' and 3' sides of the target PCR segments. These target-specific portions of the first oligonucleotide probe are separated by a further portion comprising a unique identifier portion, and/or a patient identifier portion, and/or one or more primer binding sequences (FIG. 60, step B). The second oligonucleotide probe of the duplex oligonucleotide probes (thick black line with loop) contains a sequence that is complementary to the further portion of the first oligonucleotide probe (FIG. 60, step B). The looped region of the second oligonucleotide probe represents a non-complementary region. As shown in FIG. 60, step C, hybridization of the duplex probes to the Hph1 digested PCR products creates two ligation competent junctions, i.e., between the 3' end of the DNA segment and 5' end of the second oligonucleotide probe, and between the 3' end of the second oligonucleotide probe and the 5' of the DNA segment. Ligase (filled circles) covalently seals the ligation junctions to create circular ligation products containing the Hph1 digested segments (FIG. 60, step C). As shown in FIG. 60, step D, exonuclease digestion removes all unligated or nicked products leaving only the desired single-stranded circular ligation products which are suitable for circle sequencing using any of the methods described herein.

In the embodiment depicted in FIG. 61 the first oligonucleotide probe of the duplex probe contains sequences complementary to the 5' and 3' sides of the target DNA segment that are separated by the further nucleotide portion. In addition, the first oligonucleotide probe also has an optional 5' capture group ("Z") (FIG. 61, step B). After ligation at the two ligation junctions between the Hph1 digested PCR segment and second oligonucleotide probe to form a circularized ligation product (FIG. 61, step C), a polymerase (filled diamonds) having strand displacing activity extends the first oligonucleotide probe using the circularized ligation product as a template (FIG. 61, step D). Rolling circular amplification generates a primary extension product containing tandem linear sequences that are complementary to the circularized ligation product (FIG. 61, step D). The primary extension product is suitable for sequencing using the methods described herein. The 5' Z group may be captured on a solid support prior or subsequent to rolling circle amplification. Once captured, the primer-bound circular ligation product or extension thereof may be liberated from the solid support via cleavage at the cleavable link, either prior or subsequent to rolling circle amplification.

Figure 62:
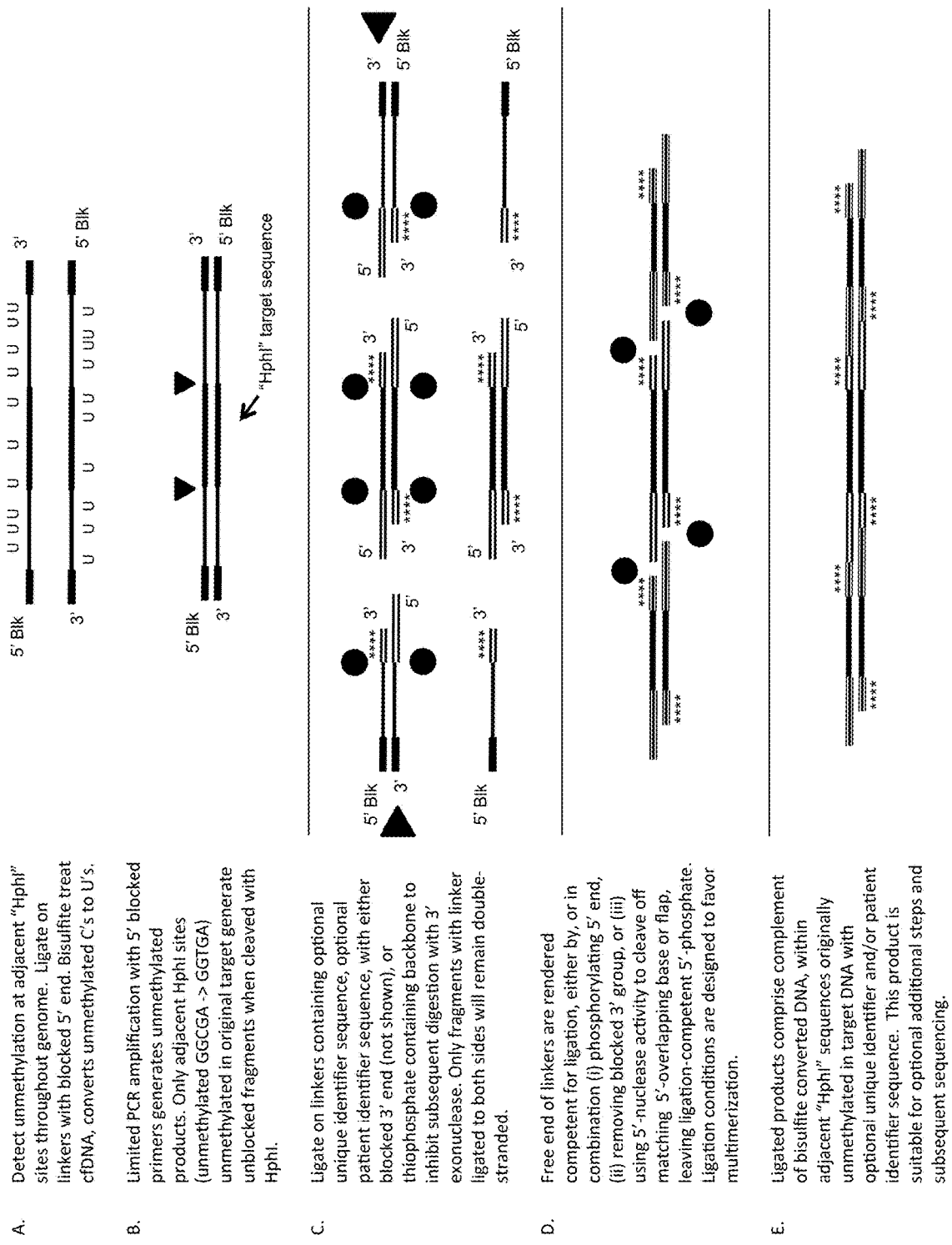
FIG. 62 shows a process for detecting unmethylated adjacent Hph1 sites in known genomic regions.

FIG. 62 shows a process for the discovery of unmethylated adjacent Hph1 sites in known genomic regions of cfDNA or sheared total genomic DNA. Genomic DNA, whether isolated from whole cells, or as cfDNA in the plasma, contains ends through natural enzymatic processes or shearing. These need to be blocked from subsequent steps by appending short linkers to the 3' and 5' ends of the DNA ends (e.g., append linkers via ligation). The 5' end linkers contain a blocking group (thick black lines) as shown in FIG. 62, step A. The linker appended DNA is bisulfite treated to convert unmethylated C's to U's. As shown in FIG. 62, step B, limited PCR amplification with 5' blocked primers generates unmethylated double stranded products. Only adjacent Hph1 sites (unmethylated GGCGA→GGTGA) that were unmethylated in original target generate unblocked fragments when cleaved with Hph1 (filled triangles). As shown in FIG. 62, step C, linkers (grey filled double lines) containing a unique identifier sequence and/or a patient identifier sequence are appended to the Hph1 cleaved DNA fragments. The linkers contain either 3'-end blocking group or a thiophosphate containing backbone (**) to inhibit subsequent digestion with 3'-exonuclease (filled triangles). Only fragments with linkers appended to both sides will remain double-stranded. As shown in FIG. 62, step D, the free end of linkers are rendered competent for ligation, either by (i) phosphorylating 5'-end, (ii) removing 3'-blocking group, (iii) using 5'-nuclease activity to cleave off matching 5'-overlapping base or flap generating ligation-competent 5'-phosphate, or (iv) any combination of (i), (ii), (iii). Ligation (filled circles) conditions are designed to favor oligomerization. As shown in FIG. 62**, step E, ligated products comprise complement of bisulfite converted DNA, within adjacent Hph1 sequences originally unmethylated in genomic DNA with optional unique identifier and/or patient identifier sequence. The final product is suitable for optional additional steps and subsequent sequencing.

Another suitable approach for generating the different circular chimeric single stranded nucleic acid constructs of the collection involves providing a sample containing one or more target genomic DNA segments potentially containing one or more base differences or one or more methylated residues and appending nucleotide linkers sequences to 3' and 5' ends of the target genomic DNA segments. The appended nucleotide linkers optionally comprise (i) the patient identifier sequence, (ii) the first solid support primer-specific portion, (iii) the second solid support primer-specific portion, and/or (iv) unique identifier sequence. One or more first oligonucleotide probes are provided where each first oligonucleotide probe comprises (a) a portion complementary to a 3' linker portion of the linker appended target genomic DNA segment, (b) a portion complementary to the 5' linker portion of the linker appended target genomic DNA segment, and (c) optionally a further portion. The further portion optionally comprises (i) the patient identifier sequence, (ii) the first solid support primer-specific portion, (iii) the second solid support primer-specific portion and/or (iv) unique identifier sequence. The sample and the one or more first oligonucleotide probes are contacted under conditions effective for the 3' and 5' portions of the first oligonucleotide probes to hybridize in a base specific manner to complementary linkers of the linker appended target genomic DNA segments, if present in the sample. One or more ligation competent junctions suitable for coupling the 3' and 5' ends of the linker appended target genomic DNA segment hybridized to the first oligonucleotide probe are generated. Ligation of the linker appended target genomic DNA segment at the one or more ligation junctions forms different circular chimeric single-stranded nucleic acid construct of the collection.

Figure 63:
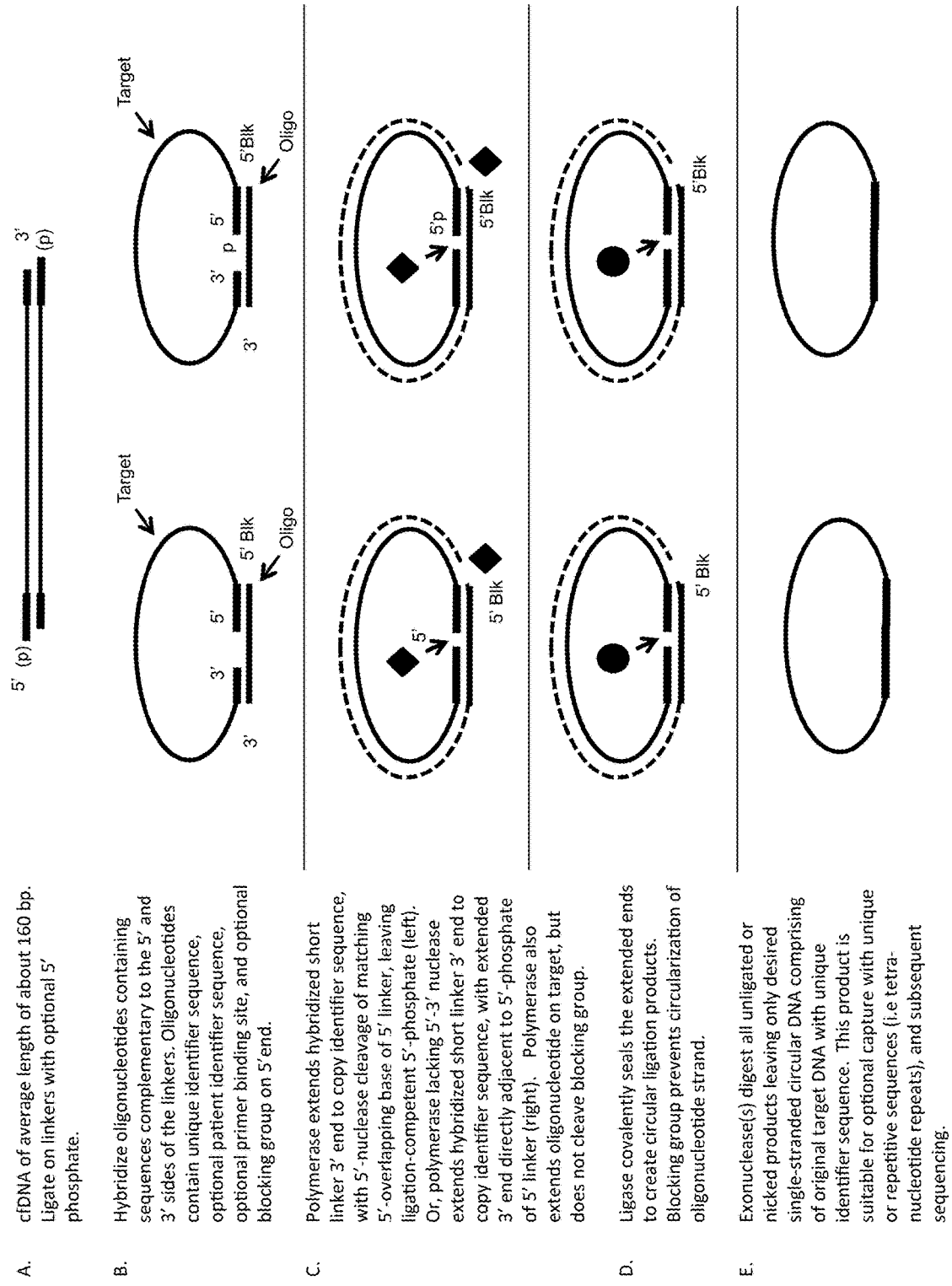
FIG. 63 shows a process for producing chimeric circular single stranded nucleic acid target constructs from cfDNA or sheared genomic DNA suitable for sequencing.

FIG. 63 shows exemplary related processes for producing chimeric circular single stranded nucleic acid target constructs suitable for sequencing as described supra. In these embodiments, the original genomic segments comprise segments of cfDNA (~160 bp) or segments of sheared genomic DNA (~160 bp) containing, e.g., tumor specific mutations, SNPs, or polymorphic repetitive sequences. The process starts with the ligation of short linkers onto the 3' and 5' ends of the DNA segments (thick black bars, FIG. 63, step A). The appended linkers of the process depicted in FIG. 63, right panel contain a ligation competent 5' phosphate group while the appended linkers of the process depicted in FIG. 63, left panel do not contain a ligation competent 5' phosphate group. Oligonucleotide probes (thick black line) containing nucleotide sequences complementary to the 5' and 3' linkers of the target DNA segments and a 5' blocking group are hybridized to their respective target DNA segments (FIG. 63, step A). The linker-specific portions of the oligonucleotide probe are separated by a further portion. This further portion comprises optional unique identifier portion, and/or a patient identifier portion, and/or one or more primer binding sequences. Polymerase (filled diamond) extends the 3' linker end of the hybridized target DNA segment to form a ligation junction with the 5' linker end of the target DNA segment (FIG. 63, step B). In the embodiment shown in FIG. 63, step C, a polymerase having 5'-nuclease activity cleaves a matching 5'-overlapping base on the 5' linker after extension to generate a ligation-competent 5'-phosphate. In the embodiment depicted in FIG. 63, step C, right panel a polymerase lacking 5'→3' nuclease activity can be utilized because the 5' linker of the target DNA segment contains a ligation competent 5' end. Polymerase also extends the 3' end of the oligonucleotide probe, using the hybridized circularized target DNA segment as a template until it reaches the 5' blocking group of the probe. As shown in FIG. 63, step D, ligase (filled circle) covalently seals the extended 3' end and 5' end of the DNA segments to create circular ligation products. The 5' blocking group on the oligonucleotide probe prevents circularization of the polymerase extended oligonucleotide probe. As shown in FIG. 63, step E, exonuclease digestion removes all unligated or nicked products leaving only the desired single-stranded circularized DNA ligation products. These circularized ligation products are suitable for optional capture with unique or repetitive sequences (e.g., tetra-nucleotide repeats), or rolling circle extension with unique targeted primers, and subsequent sequencing.

FIG. 64 shows another exemplary process for producing chimeric circular single stranded nucleic acid target constructs suitable for sequencing as described supra. In this embodiment, the target genomic DNA segment is a double-stranded target genomic DNA segment having 5' and 3' end suitable for ligation or extension (FIG. 64, step B). The target genomic DNA segment is appended with nucleotide linker sequences. In accordance with this embodiment, the nucleotide linkers comprise first and second linker oligonucleotides, wherein (i) the first linker oligonucleotide comprises a 5' single-stranded portion, one or more cleavable nucleotides or nucleotide analogues, a unique identifier sequence, a 3' end that is complementary to the second linker oligonucleotide, and a 3'-OH, and (ii) the second linker oligonucleotide comprises a 5'-OH end, a 5' portion that is complementary to the first linker oligonucleotide, and an optional 3'-blocked end. The second linker oligonucleotide hybridizes to its complementary portion of the first linker oligonucleotide to form composite linkers suitable for appending to the target genomic DNA segment.

As shown in FIG. 64, steps C-D, the double stranded target genomic DNA is blended with the composite linkers, a ligase, and a polymerase under conditions suitable for (i) ligation of the 3'-OH of the first linker oligonucleotide of the composite linker to the 5' end of the double-stranded target genomic DNA segments, (ii) polymerase extension of the 3' end of the double-stranded target genomic DNA segment to create a complementary copy of the first linker oligonucleotide of the composite linker, and (iii) cleaving the one or more cleavable nucleotides or nucleotide analogues to form the linker appended target genomic DNA segments. Oligonucleotide probes (thin black, and double line) containing nucleotide sequences complementary to the 5' and 3' single-stranded portions of the linkers of the target DNA segments are hybridized to their respective target DNA segments (FIG. 64, step F). The oligonucleotide probes contain the patient identifier sequence, primer binding sites, and a mismatched tail on the 3' end. Polymerase (filled diamond) extends the 3' linker end of the hybridized target DNA segment to form a ligation junction with the 5' linker end of the target DNA segment (FIG. 64, step G). As shown in FIG. 64, step H, ligase (filled circle) covalently seals the 3' and 5' ends of the linker appended DNA segment to create circular ligation products. These circularized ligation products are suitable for optional capture with unique or repetitive sequences (e.g., tetra-nucleotide repeats), or rolling circle extension with unique targeted primers, and subsequent sequencing.

Figure 65:
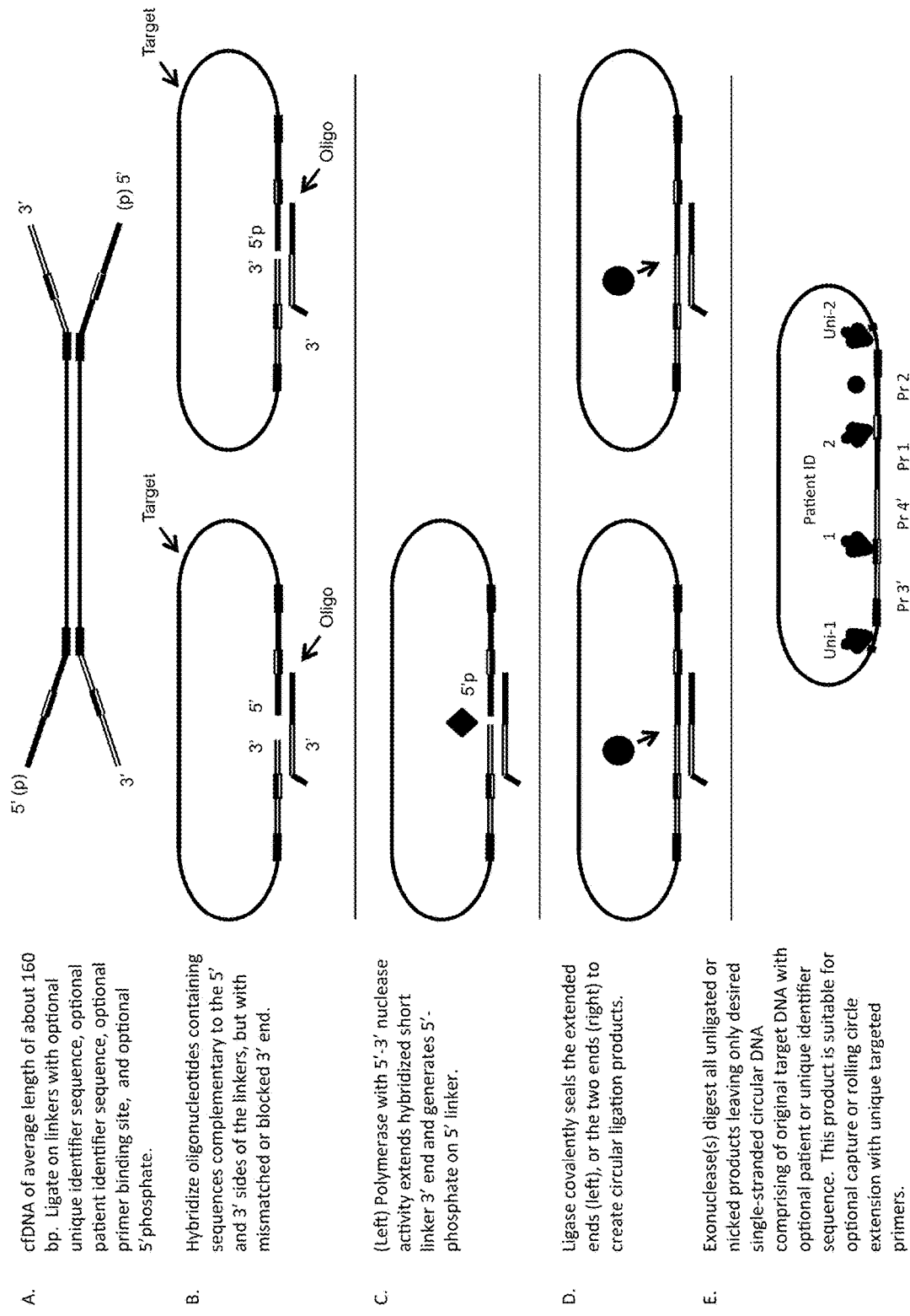
FIG. 65 shows a process for producing chimeric circular single stranded nucleic acid target constructs from cfDNA or sheared genomic DNA suitable for sequencing.

FIG. 65 shows exemplary related processes for producing chimeric circular single stranded nucleic acid target constructs suitable for sequencing as described supra. In these embodiments, the original genomic segments comprise segments of cfDNA (~160 bp) or segments of sheared genomic DNA (~160 bp) containing, e.g., tumor specific mutations, SNPs, or polymorphic repetitive sequences. The process starts with the ligation of composite linkers comprising both single-stranded (thinner black and double lines) and double stranded portions (thick black bars) onto the 3' and 5' ends of the DNA segments (FIG. 65, step A). The appended linkers of the process depicted in FIG. 65, step B, right panel contain a ligation competent 5' phosphate group while the appended linkers of the process depicted in FIG. 65, step B, left panel do not contain a ligation competent 5' phosphate group. Oligonucleotide probes (thin black, and double line) containing nucleotide sequences complementary to the 5' and 3' single-stranded portions of the linkers of the target DNA segments are hybridized to their respective target DNA segments. Polymerase (filled diamond) extends the 3' linker end of the hybridized target DNA segment to form a ligation junction with the 5' linker end of the target DNA segment (FIG. 65, step C). In the embodiment shown in FIG. 65, step C, a polymerase having 5'-nuclease activity cleaves a matching 5'-overlapping base on the 5' linker after extension to generate a ligation-competent 5'-phosphate. As shown in FIG. 65, step D, ligase (filled circle) covalently seals the 3' and 5' ends of the linker appended DNA segment to create circular ligation products. As shown in FIG. 65, step E, exonuclease digestion removes all unligated or nicked products leaving only the desired single-stranded circularized DNA ligation products. These circularized ligation products are suitable for optional capture with unique or repetitive sequences (e.g., tetra-nucleotide repeats), or rolling circle extension with unique targeted primers, and subsequent sequencing.

Figure 66:
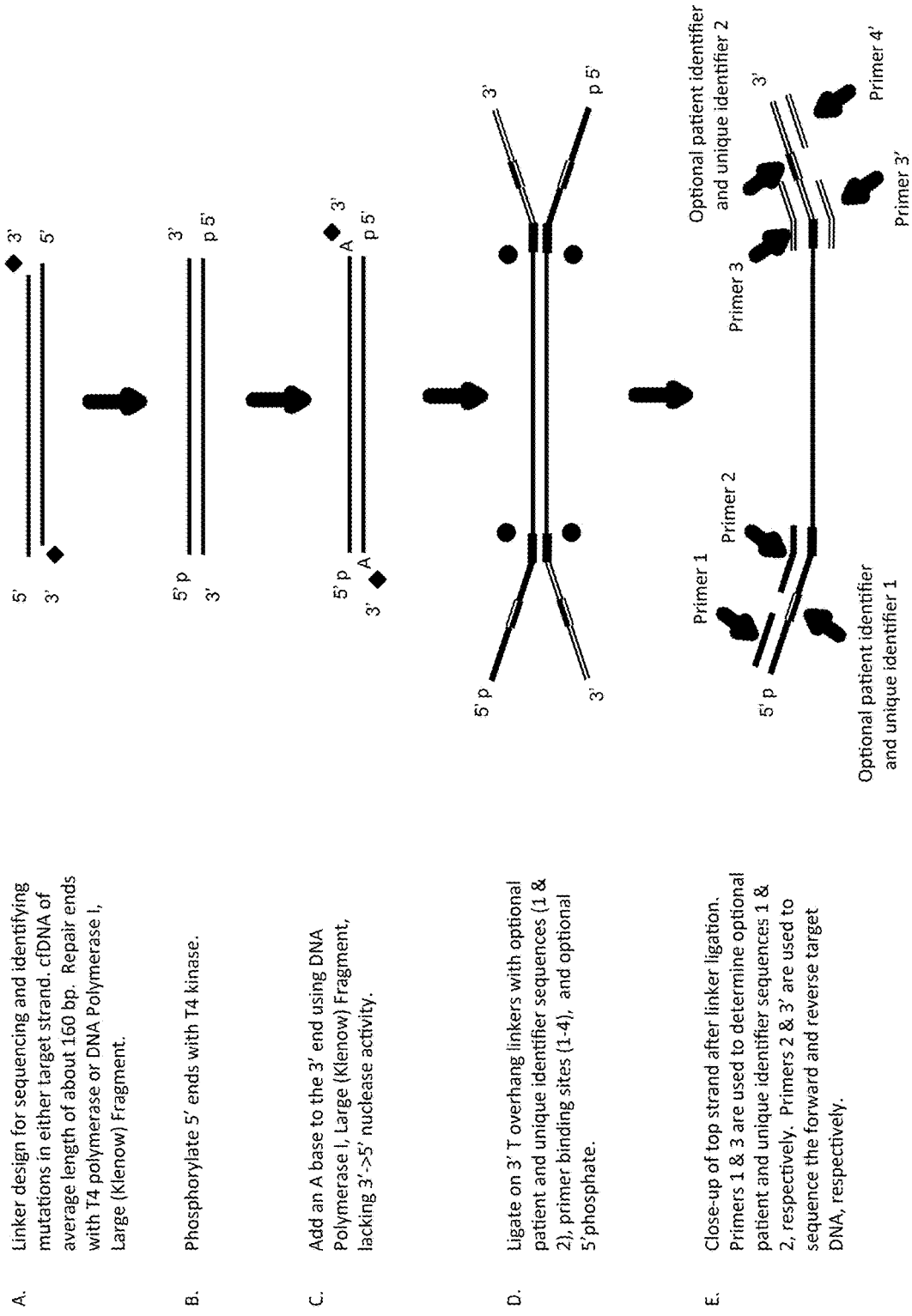
FIG. 66 shows linker design and ligation to generate sequencing ready templates from cfDNA.

The standard approach for appending linkers is illustrated in FIG. 66 and is well known by those skilled in the art. In these embodiments, the original genomic segments comprise segments of cfDNA (~160 bp) or segments of sheared genomic DNA (~160 bp) containing, e.g., tumor specific mutations, SNPs, or polymorphic repetitive sequences. The ends of fragmented DNA are repaired using a polymerase with 3'-5' exonuclease activity such as T4 polymerase or DNA Polymerase I, Large (Klenow) Fragment, which extends recessed 3' ends, or degrades 3' overhang ends till they are flush with the 5' end (FIG. 66, step A). The 5' ends are phosphorylated with T4 kinase, and an additional A base appended to the 3' end using DNA Polymerase I, Large (Klenow) Fragment, lacking 3'→5' nuclease activity (FIG. 66, steps B and C). Ligate on linkers with 3' T overhangs using T4 ligase (FIG. 66, step D). In this figure, primer portions 1 & 3 of the linkers are used to determine optional patient and unique identifier sequences 1 & 2, respectively. Primer portions 2 and 3' are used to sequence the forward and reverse target DNA, respectively. This product is suitable for circularization of top or bottom original target strand as illustrated in FIGS. 63 and 65 above.

Figure 67:
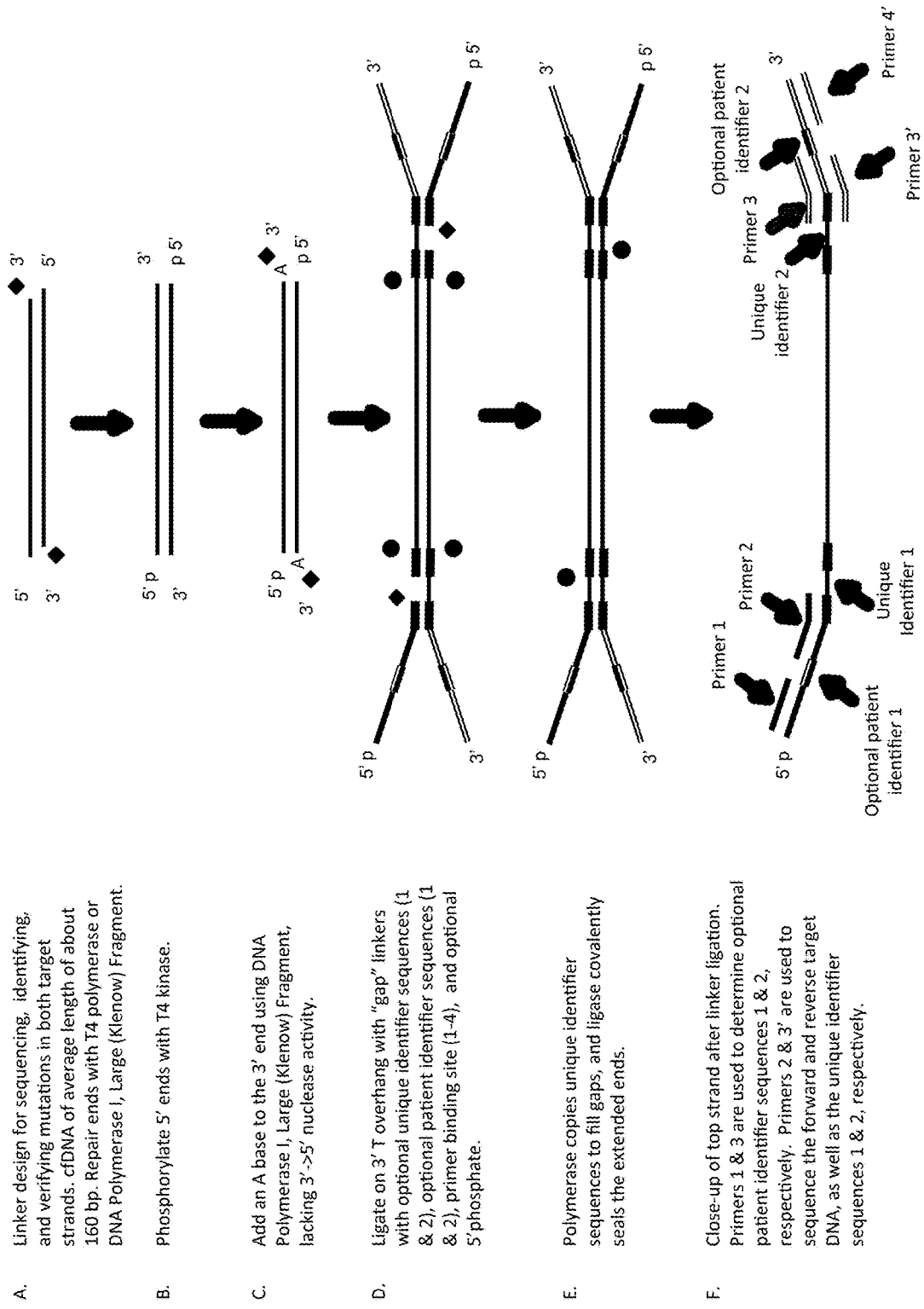
FIG. 67 shows "gapped" linker design for sequencing, identifying, and verifying mutations in both target strands of cfDNA.

While the standard approach provides the opportunity for introducing unique sequences on the single-stranded portions of the linkers, these sequences do not allow for unambiguous matching of a top strand sequence with a bottom strand sequence. To achieve this type of construct, the standard approach is modified as illustrated in FIG. 67. In these embodiments, the original genomic segments comprise segments of cfDNA (~160 bp) or segments of sheared genomic DNA (~160 bp) containing, e.g., tumor specific mutations, SNPs, or polymorphic repetitive sequences. The ends of fragmented DNA are repaired using a polymerase with 3'-5' exonuclease activity such as T4 polymerase or DNA Polymerase I, Large (Klenow) Fragment, which extends recessed 3' ends, or degrades 3' overhang ends till they are flush with the 5' end (FIG. 67, step A). The 5' ends are optionally phosphorylated with T4 kinase (FIG. 67, step B), and an A-base overhang is added to the 3' ends using DNA polymerase I, large (Klenow) Fragment, lacking 3'→5'nuclease activity.

In this embodiment, the linker sequence comprises a first, second and third oligonucleotide. The first oligonucleotide comprises the first solid support primer-specific portion, one or more first patient identifier sequences, a first sequencing primer binding site, and a 3' end that is complementary to the third oligonucleotide. The second oligonucleotide comprising a region complementary to the 5' end of the third oligonucleotide, and the third oligonucleotide comprises a 5' end that is complementary to the second oligonucleotide, a second sequencing primer binding site, a portion complementary to the 3' end of the first oligonucleotide, a second patient identifier sequence, and the second solid support primer-specific portion. The third oligonucleotide hybridizes to complementary portions of the first and second oligonucleotides to form composite linkers. As shown in FIG. 67, step D, the double stranded target genomic DNA segments are blended with the composite linkers, a ligase, and a polymerase under conditions suitable for ligation of the second and third oligonucleotides of the composite linkers to the 5' and 3' ends, respectively, of the double-stranded target genomic DNA segments. Polymerase extends the 3' end of the first oligonucleotide of the composite linker to create a ligation junction with the second oligonucleotide of the composite linker at its 5' end (FIG. 67, step E). If the 5' end of the second oligonucleotide of the composite linker is not phosphorylated, the polymerase should have 5'-3' nuclease activity to liberate a 5'phosphate suitable for ligation. If the second oligonucleotide is phosphorylated on the 5' end, the polymerase should lack 5'-3' nuclease activity, allowing it to extend up to the linker, followed by ligase sealing the nick. As shown in FIG. 67, step E, ligase covalently seals the first and second oligonucleotides of the composite linker at said ligation junction to form linker appended double-stranded target genomic DNA. In this embodiment, primer portions 1 and 3 of the linkers are used to determine optional patient identifier sequences 1 and 2, respectively (See FIG. 67, step F). Primer portions 2 and 3' of the linkers are used to sequence the forward and reverse target DNA, as well as the unique identifier sequences 1 and 2, respectively. This product is suitable for circularization of each of the original target strands as illustrated in FIGS. 63 and 65 above. Upon determining the sequences of these strands the unique identifier sequences 1 and 2 will enable unambiguous matching of a top strand sequence with a bottom strand sequence, thus allowing for independent verification of low-abundance mutation on both strands of the original target molecule.

Figure 68:
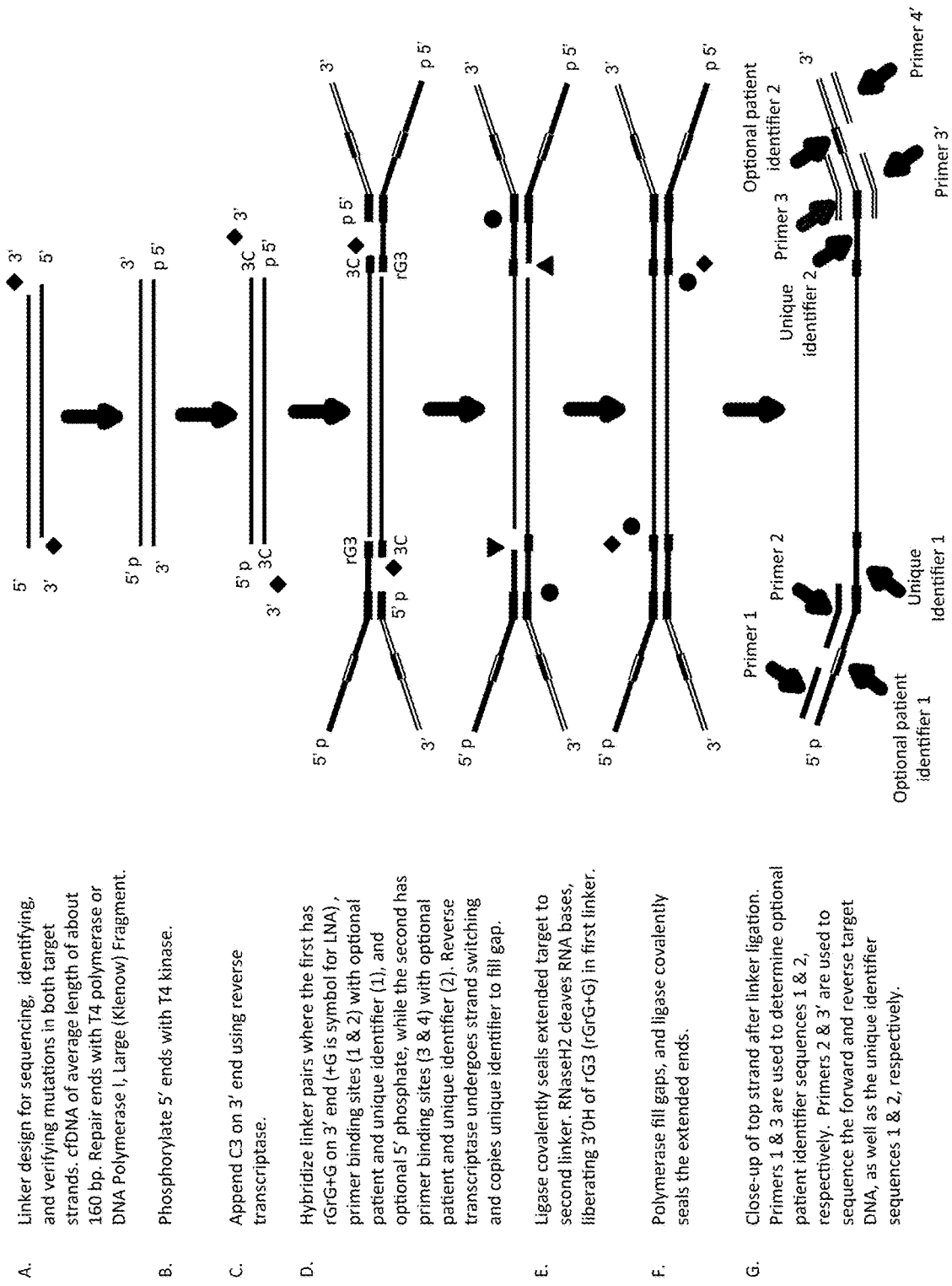
FIG. 68 shows linker design for sequencing, identifying, and verifying mutations in both target strands of cfDNA using $C_3$ tailing, ligation, activation of rG containing linkers with RNaseH2, gap filling, and ligation.

FIG. 68 exemplifies another approach for appending primer sequences to the ends of target DNA, such that it is suitable for producing chimeric circular single stranded nucleic acid target constructs, and allow for unambiguous matching of a top strand sequence with a bottom strand sequence. In these embodiments, the original genomic segments comprise segments of cfDNA (~160 bp) or segments of sheared genomic DNA (~160 bp) containing, e.g., tumor specific mutations, SNPs, or polymorphic repetitive sequences. The ends of fragmented DNA are repaired using a polymerase with 3'-5' exonuclease activity such as T4 polymerase or DNA Polymerase I, Large (Klenow) Fragment, which extends recessed 3' ends, or degrades 3' overhang ends till they are flush with the 5' end (FIG. 68, step A). The 5' ends are optionally phosphorylated with T4 kinase (FIG. 68, step B). A reverse transcriptase such as Moloney Murine Leukemia Virus Reverse Transcriptase (M-MLV RT, New England Biolabs), or Superscript II or III Reverse Transcriptase (Life Technologies) appends three C bases to the 3' end of each target (FIG. 68, step C).

In this embodiment, the linker sequences comprise (i) a first linker oligonucleotide comprising the first solid support primer-specific portion, one or more first patient identifier sequences, a first sequencing primer binding site, and riboguanosine bases on the 3' end, and (ii) a second linker oligonucleotide comprising a second sequencing primer binding site, a second patient identifier sequence, the second solid support primer-specific portion, and a 5' portion that is complementary to the first oligonucleotide. The double-stranded target genomic DNA segments are blended with the linker sequences, a reverse transcriptase, and a ligase to form a reverse-transcription-ligation reaction mixture. The riboguanosine bases of the first linker oligonucleotide hybridize to the 3' cytosine overhang of the double stranded target genomic DNA segment (FIG. 68, step D). The reverse transcriptase undergoes strand switching and the 3' hybridized end of the double stranded target genomic DNA segment is extended to generate a sequence complementary to the first patient identifier sequence of the first linker oligonucleotide and a ligation junction with the 5' end of the second linker oligonucleotide (FIG. 68, step D). The extended 3' ends of the double stranded target genomic DNA segments are ligated to the 5' end of the second oligonucleotide at the ligation junction. RNaseH2 cleaves the riboguanosine bases of the first linker oligonucleotide, liberating a 3'OH suitable for polymerase mediated extension (FIG. 68, step E). The 3' end of the first linker oligonucleotide is extended and ligated to the 5' end of the double-stranded target genomic DNA (FIG. 68, step F). If the second linker or target DNA is not phosphorylated on the 5' end, the polymerase should have 5'-3' nuclease activity to liberate a 5'phosphate suitable for ligation. If the second linker and target are phosphorylated, as shown in FIG. 68, the polymerase should lack 5'-3' nuclease activity, allowing it to extend up to the 5' end of the second primer or target respectively, followed by ligase sealing the nick. As shown in FIG. 68, step G, primer portions 1 and 3 of the linkers are used to determine optional patient identifier sequences 1 and 2, respectively. Primer portions 2 and 3' of the linkers are used to sequence the forward and reverse target DNA, as well as the unique identifier sequences 1 and 2, respectively. This product is suitable for circularization of each of the original target strands as illustrated in FIGS. 63 and 65 above. Upon determining the sequences of these strands the unique identifier sequences 1 and 2 will enable unambiguous matching of a top strand sequence with a bottom strand sequence, thus allowing for independent verification of low-abundance mutation on both strands of the original target molecule.

Figure 69:
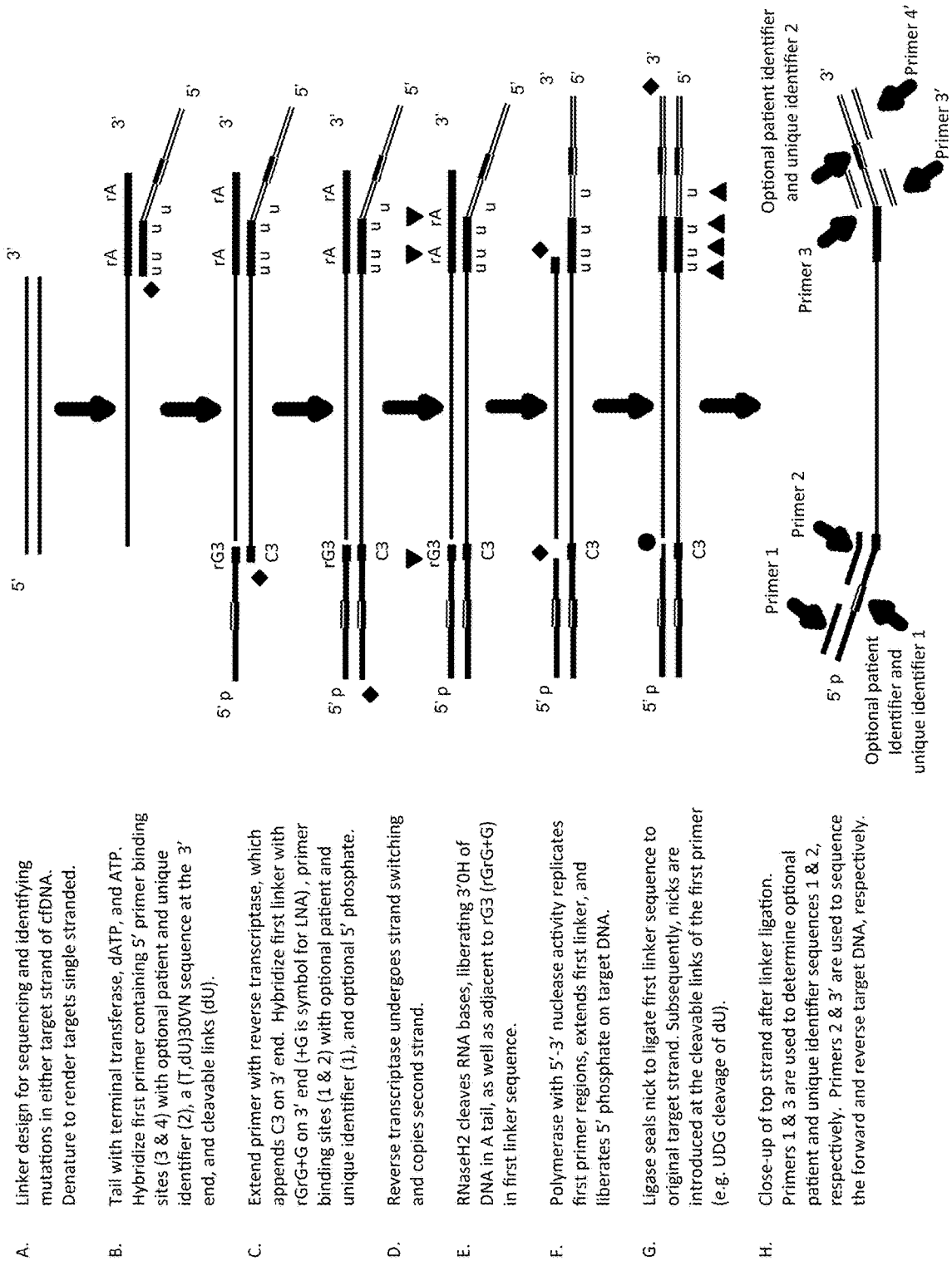
FIG. 69 shows linker design for sequencing and identifying mutations in either target strand of cfDNA using dA tailing with limited rA insertion, $C_3$ tailing, ligation, activation of rG containing linkers with RNaseH2, gap filling, and ligation.

FIG. 69 exemplifies another approach for appending primer sequences to the ends of target DNA, such that it is suitable for producing chimeric circular single stranded nucleic acid target constructs. In this embodiment, the original genomic segments comprise segments of cfDNA (~160 bp) or segments of sheared genomic DNA (~160 bp) containing, e.g., tumor specific mutations, SNPs, or polymorphic repetitive sequences. The fragments are denatured to render the targets single-stranded (FIG. 69, step A). The 3' ends are tailed with terminal transferase using a mixture of dATP and ATP, such that an average of 50-100 bases are added and there is at least one cleavable rATP incorporation in the first 30 bases (FIG. 69, step B). In accordance with this embodiment, one or more sets of oligonucleotides are provided, where each set comprises i) a primer oligonucleotide comprising the second solid support primer-specific portion, one or more patient identifier sequences, a sequencing primer binding site, and a mononucleotide repeat region comprising one or more cleavable nucleotides that is complementary to the extension region of the target genomic DNA segment, and (ii) a first linker oligonucleotide comprising the first solid support primer-specific portion, one or more patient identifier sequences, a sequencing primer binding site. The first linker oligonucleotide has two-riboguanosine bases and a locked-nucleic-acid guanosine base on its 3' (rGrG+G) As depicted in FIG. 69, step B, the process involves with hybridization of the primer oligonucleotide containing 5' primer binding sites (3 and 4) with optional patient and unique identifier (2), a (T,dU)$_{30}$VN sequence at the 3' end, and cleavable links (dU) to the terminal transferase extension region of the target genomic DNA (FIG. 69, step B). A reverse transcriptase such as Moloney Murine Leukemia Virus Reverse Transcriptase (M-MLV RT, New England Biolabs), or Superscript II or III Reverse Transcriptase (Life Technologies) extends the primer to make a full-length copy of the target, and appends three C bases to the 3' end of extended target sequence (FIG. 68, step C). The first linker oligonucleotide having the 3' rGrG+G hybridizes to the three C bases of the extended target sequence as shown in FIG. 68, step C. The reverse transcriptase undergoes strand switching and copies the first linker oligonucleotide (FIG. 69, step D). RNaseH2 cleaves the RNA bases, liberating the 3'OH of DNA in the A tail, as well as adjacent to the rGrG+G of the first linker oligonucleotide (FIG. 69, step D). Polymerase with 5'→3' nuclease activity replicates the primer oligonucleotide regions, extends first linker oligonucleotide, and liberates 5' phosphate on target DNA (FIG. 69, step F). Ligase seals nick of first linker oligonucleotide to ligate first linker to original target strand (FIG. 69, step G). Subsequently, nicks are introduced at the cleavable links of the primer oligonucleotide (e.g. UDG cleavage of dU), such that the copy of the target will not undergo further amplification, as it lacks the first primer-binding region. In this figure, primer portions 1 and 3 are used to determine optional patient and unique identifier sequences 1 and 2, respectively (FIG. 69, step H). Primer portions 2 and 3' are used to sequence the forward and reverse target DNA, respectively. When using primer 3', for the initial cycle TTP without terminator is used, such that the instrument does not waste time sequencing the T30 region. This product is suitable for circularization of top or bottom original target strand as illustrated in FIGS. 63 and 65 above.

Figure 70:
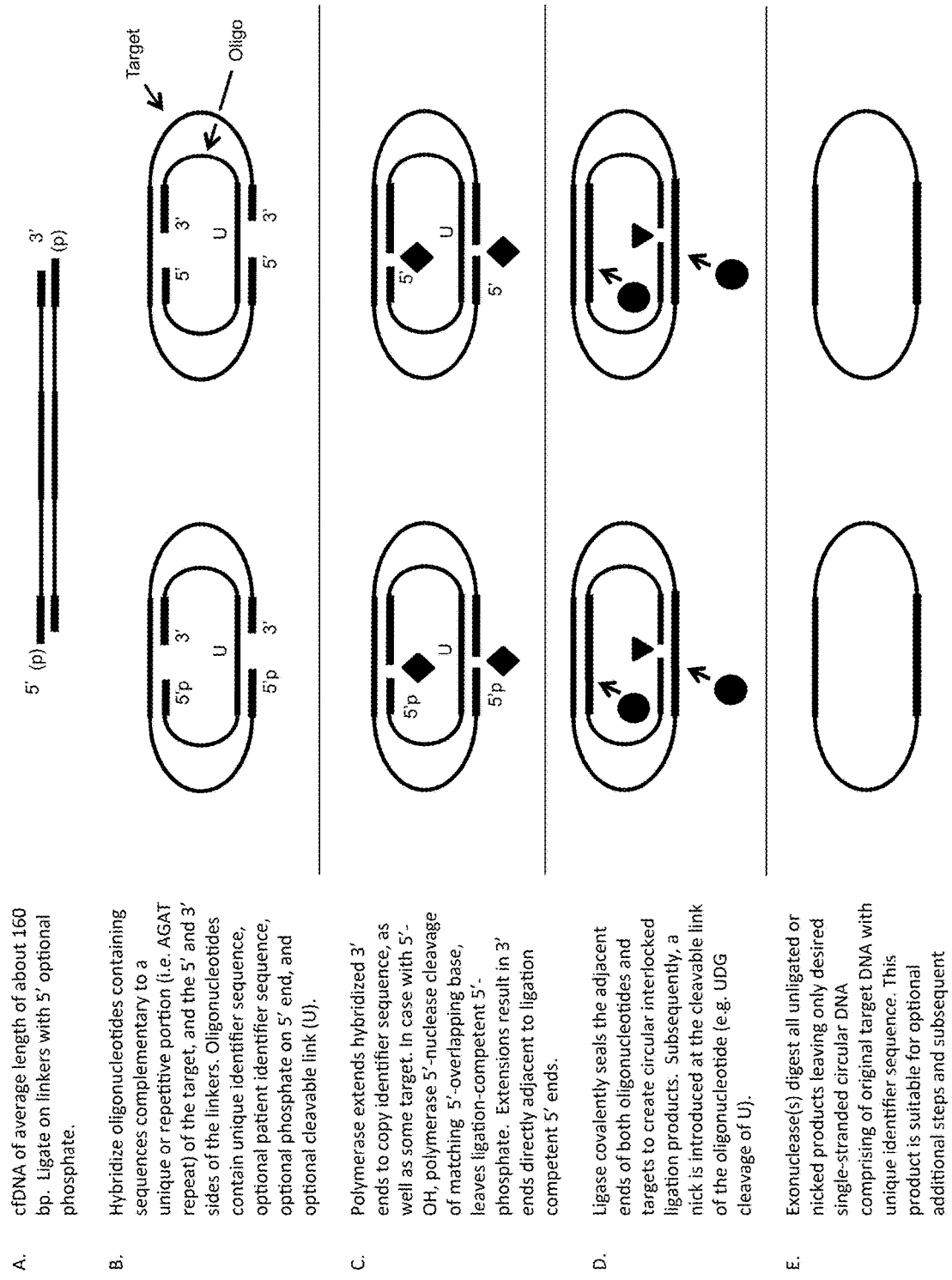
FIG. 70 shows a process for producing chimeric circular single stranded nucleic acid target constructs from cfDNA or sheared genomic DNA suitable for sequencing.

FIG. 70 shows another exemplary process for producing chimeric circular single stranded nucleic acid target constructs suitable for sequencing as described supra. In these embodiments, the original genomic segments comprise segments of cfDNA (~160 bp) or segments of sheared genomic DNA (~160 bp) containing, e.g., tumor specific mutations, SNPs, or polymorphic repetitive sequences. The process starts with the ligation of short linkers onto the 3' and 5' ends of the DNA segments (thick black bars, FIG. 70, step A). The 5' end of the appended linkers optionally contains a ligation competent phosphate. Oligonucleotide probes containing sequences complementary to a unique or repetitive portion (i.e. AGAT repeat) of the target DNA segment, and the 5' and 3' sides of the linkers are hybridized to their respective target DNA segments as shown in FIG. 70, step B. The oligonucleotides probes also contain a further portion that contains one or more of a unique identifier sequence, a patient identifier sequence, a ligation competent 5' phosphate, and a cleavable link (dU). Polymerase (filled diamonds) extends hybridized 3' ends of the target DNA segment and the oligonucleotide probe (FIG. 70, step C) to create ligation junctions with the corresponding 5' end of the target DNA segment and probe, respectively. In the absence of a ligation competent 5' phosphate on the target segment or probe, polymerase 5'-nuclease activity cleaves a matching 5'-overlapping base to generate a ligation-competent 5'-phosphate. As shown in FIG. 70, step D, ligase (filled circles) covalently seals the adjacent ends of the oligonucleotide probe and target segment to create circular interlocked ligation products. Subsequently, a nick is introduced at the cleavable link of the oligonucleotide probe (e.g. UDG cleavage of dU, filled triangles). As shown in FIG. 70, step E, exonuclease digestion removes all unligated or nicked products leaving only the desired single-stranded circular construct comprising an original target DNA segment coupled to a unique identifier sequence. The final product is suitable for optional additional steps and subsequent sequencing.

Figure 71:
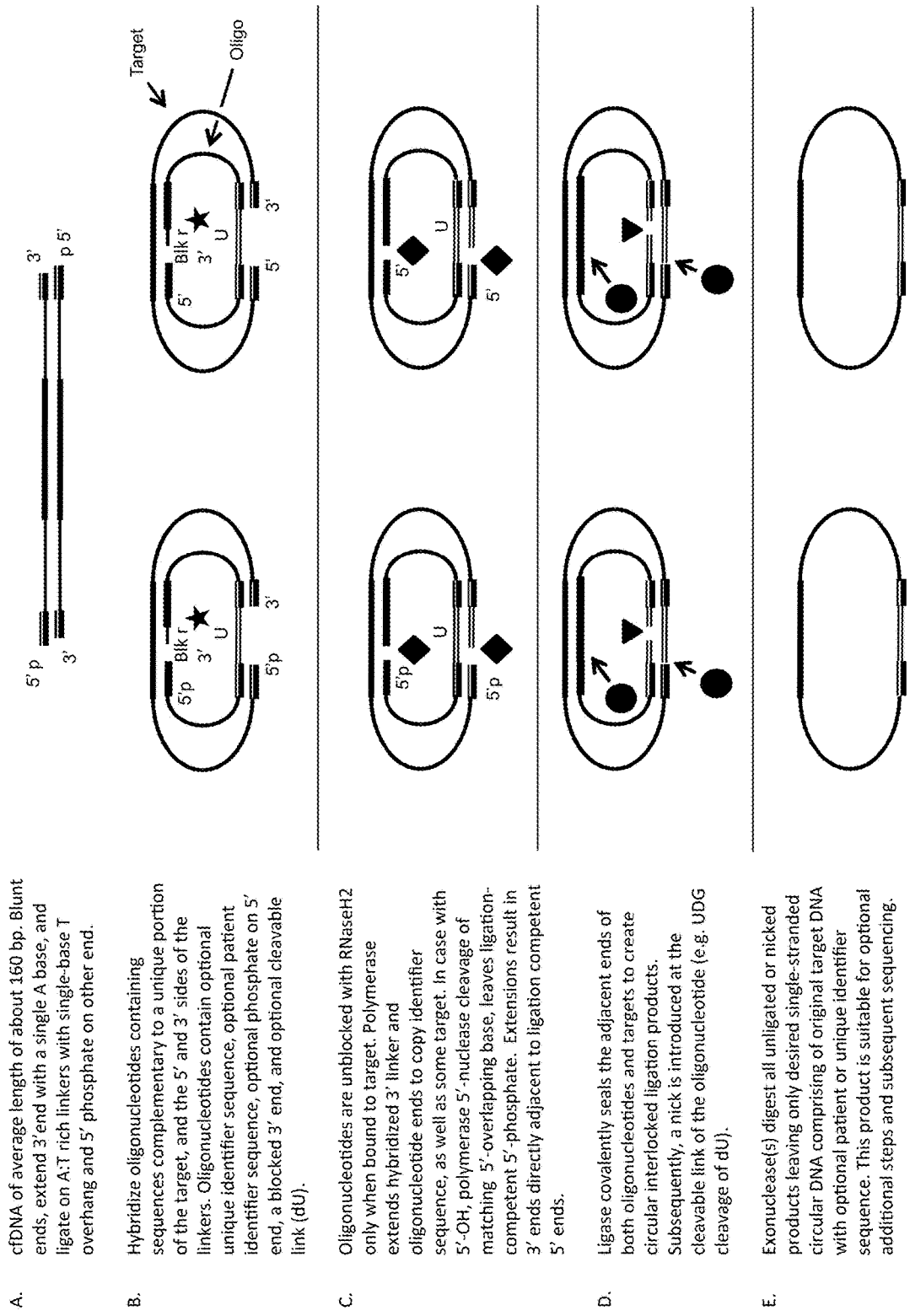
FIG. 71 shows a process for producing chimeric circular single stranded nucleic acid target constructs from cfDNA that involves activation with RNase H2.

FIG. 71 shows another exemplary process for producing chimeric circular single stranded nucleic acid target constructs suitable for sequencing as described supra. In these embodiments, the original genomic segments comprise segments of cfDNA (~160 bp) or segments of sheared genomic DNA (~160 bp) containing, e.g., tumor specific mutations, SNPs, or unique sequences. The process starts with the ligation of short linkers onto the 3' and 5' ends of the DNA segments (thick black/white bars, FIG. 71, step A). The 5' end of the appended linkers optionally contains a ligation competent phosphate. Oligonucleotide probes containing sequences complementary to a unique sequence of the target DNA segment, and the 5' and 3' sides of the linkers are hybridized to their respective target DNA segments as shown in FIG. 71, step B. The oligonucleotide probes also contain a further portion that contains one or more of a unique identifier sequence, a patient identifier sequence, an optional ligation competent 5' phosphate, and an optional cleavable link (dU). In one embodiment, the 3' end of the oligonucleotide probe further comprises a few extra bases and a blocking group, which is liberated to form a free 3'OH by cleavage with a nuclease only when hybridized to the target, e.g., a ribonucleotide base as the blocking group and RNase H2 (star) as the cleaving nuclease (FIG. 71, step C). Polymerase (filled diamonds) extends hybridized 3' ends of the target DNA segment and the oligonucleotide probe (FIG. 71, step C) to create ligation junctions with the corresponding 5' end of the target DNA segment and probe, respectively. In the absence of a ligation competent 5' phosphate on the target segment or probe, polymerase 5'-nuclease activity cleaves a matching 5'-overlapping base to generate a ligation-competent 5'-phosphate. As shown in FIG. 71, step D, ligase (filled circles) covalently seals the adjacent ends of the oligonucleotide probe and target segment to create circular interlocked ligation products. Subsequently, a nick is introduced at the cleavable link of the oligonucleotide probe (e.g. UDG cleavage of dU, filled triangles). As shown in FIG. 71, step E, exonuclease digestion removes all unligated or nicked products leaving only the desired single-stranded circular construct comprising an original target DNA segment coupled to an optional patient or unique identifier sequence. The final product is suitable for optional additional steps and subsequent sequencing.

FIG. 72 shows another exemplary process for producing chimeric circular single stranded nucleic acid target constructs suitable for sequencing as described supra. In these embodiments, the original genomic segments comprise segments of cfDNA (~160 bp) or segments of sheared genomic DNA (~160 bp) containing, e.g., tumor specific mutations, SNPs, or unique sequences. The process starts with the ligation of short linkers onto the 3' and 5' ends of the DNA segments (thick black/white bars, FIG. 72, step A). The 5' end of the appended linkers optionally contains a ligation competent phosphate. Oligonucleotide probes containing sequences complementary to a unique sequence of the target DNA segment, and the 5' and 3' sides of the linkers are hybridized to their respective target DNA segments as shown in FIG. 71, step B. The oligonucleotides probes also contain a further portion that contains one or more of a unique identifier sequence, a patient identifier sequence, a ligation competent 5' phosphate, and an optional cleavable link (dU). In one embodiment, the 3' end of the oligonucleotide probe further comprises a few extra bases and a blocking group, which is liberated to form a free 3'OH by cleavage with a nuclease only when hybridized to the target, e.g., a ribonucleotide base as the blocking group and RNase H2 (star) as the cleaving nuclease. The liberated 3'OH end is now suitable for direct ligation to the 5' phosphorylated end when the oligonucleotide probe is hybridized on the target (FIG. 72, step C). Polymerase (filled diamonds) extends hybridized 3' ends of the target DNA segment (FIG. 72, step C) to create ligation junctions with the corresponding 5' end of the target DNA segment. In the absence of a ligation competent 5' phosphate on the linker of the target segment, polymerase 5'-nuclease activity cleaves a matching 5'-overlapping base to generate a ligation-competent 5'-phosphate. As shown in FIG. 72, step D, ligase (filled circles) covalently seals the adjacent ends of the target segment to create circular interlocked ligation products. Subsequently, a nick is introduced at the cleavable link of the oligonucleotide probe (e.g. UDG cleavage of dU, filled triangles). As shown in FIG. 72, step E, exonuclease digestion removes all unligated or nicked products leaving only the desired single-stranded circular construct comprising an original target DNA segment coupled to an optional patient or unique identifier sequence. The final product is suitable for optional additional steps and subsequent sequencing.

Figure 73:
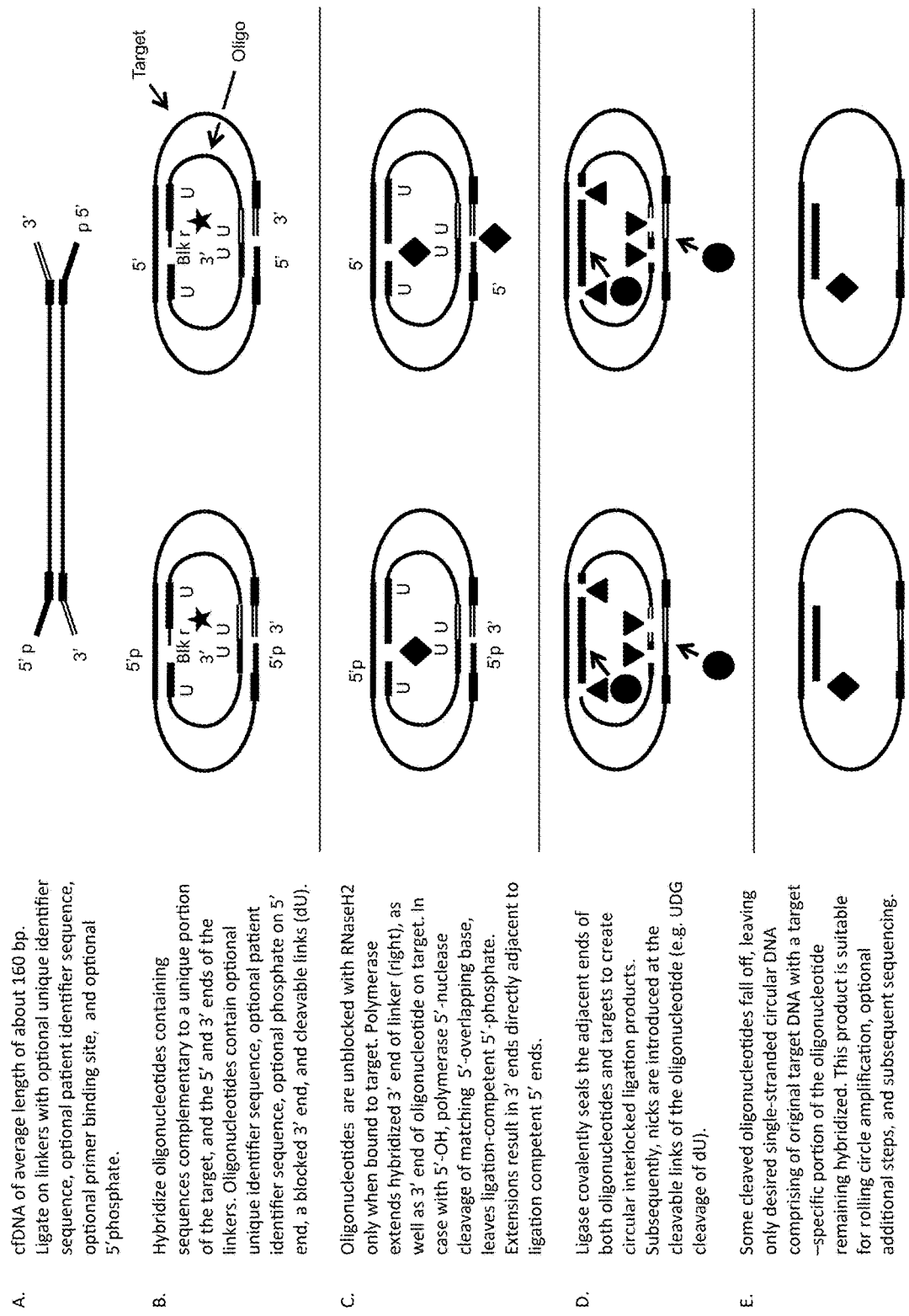
FIG. 73 shows the generation of single-stranded circular DNA comprising original target cfDNA with a hybridized primer.

FIG. 73 shows exemplary process for producing chimeric circular single stranded nucleic acid target constructs with a hybridized target-specific oligonucleotide that is suitable for priming rolling circle amplification and sequencing as described supra. In these embodiments, the original genomic segments comprise segments of cfDNA (~160 bp) or segments of sheared genomic DNA (~160 bp) containing, e.g., tumor specific mutations, SNPs, or unique sequences. The process starts with the ligation of composite linkers comprising both single-stranded (thinner black and double lines) and double stranded portions (thick black bars) onto the 3' and 5' ends of the DNA segments (FIG. 73, step A). The appended linkers of the process depicted in FIG. 73 left panel contain a ligation competent 5' phosphate group while the appended linkers of the process depicted in FIG. 73 right panel do not contain a ligation competent 5' phosphate group. Oligonucleotide probes containing nucleotide sequences complementary to a unique sequence of the target DNA segment (thicker black lines), and to the 5' and 3' single-stranded portions of the linkers (thin black, and double line) appended to the target DNA segments are hybridized to their respective target DNA segments as shown in FIG. 73, step B. The oligonucleotide probes also contain optional unique identifier sequence, optional patient identifier sequence, optional phosphate on 5' end, and one or more cleavable links (dU). In one embodiment, the 3' end of the oligonucleotide probe further comprises a few extra bases and a blocking group, which is liberated to form a free 3'OH by cleavage with a nuclease only when hybridized to the target, e.g., a ribonucleotide base as the blocking group and RNase H2 (star) as the cleaving nuclease. Polymerase (filled diamonds) extends hybridized 3' ends of the target DNA segment and the oligonucleotide probe (FIG. 73, step C) to create ligation junctions with the corresponding 5' end of the target DNA segment and probe, respectively. In the absence of a ligation competent 5' phosphate on the target segment or probe, polymerase 5'-nuclease activity cleaves a matching 5'-overlapping base to generate a ligation-competent 5'-phosphate. As shown in FIG. 73, step D, ligase (filled circles) covalently seals the adjacent ends of the oligonucleotide probe and target segment to create circular interlocked ligation products. Subsequently, one or more nicks are introduced at the cleavable links of the oligonucleotide probe (e.g. UDG cleavage of dU, filled triangles). As shown in FIG. 73, step E, the cleaved oligonucleotide fragments fall off the target DNA, leaving only the desired single-stranded circular construct comprising an original target DNA segment having a target-specific hybridized primer. The final product is suitable for rolling circle amplification, optional additional steps, and subsequent sequencing.

Figure 74:
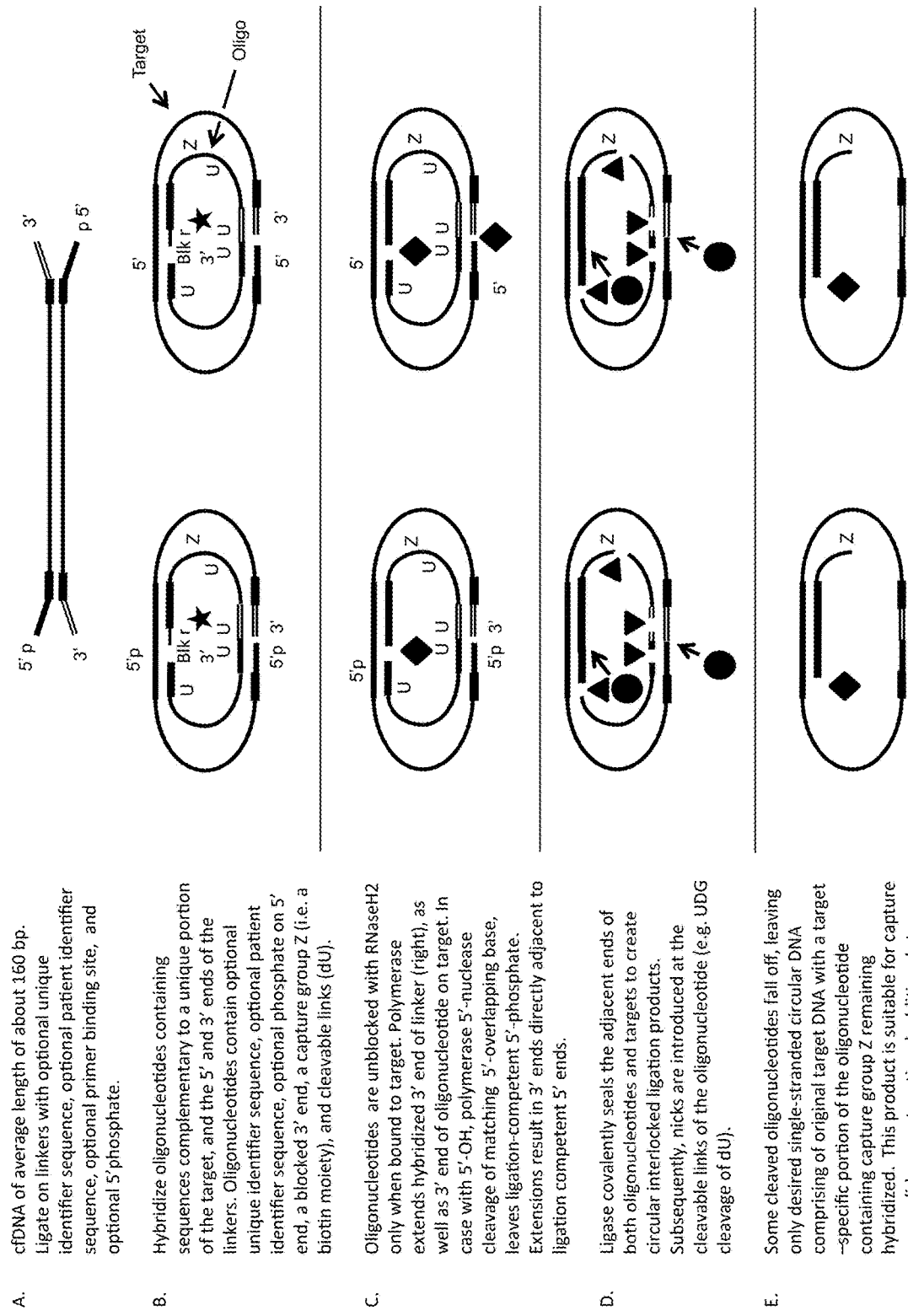
FIG. 74 shows the generation of single-stranded circular DNA comprising original target cfDNA with a hybridized primer containing a capture group.

FIG. 74 depicts another exemplary process for producing chimeric circular single stranded nucleic acid target constructs with hybridized a target-specific oligonucleotide that is suitable for priming rolling circle amplification and sequencing as described supra. The steps of this embodiment are similar to the embodiment shown in FIG. 73, steps A-E. However, in this embodiment the oligonucleotide probes also comprise a capture group (Z) (i.e. biotin) suitable for capture of products on a solid support (i.e. with Streptavidin coated solid support). As shown in FIG. 74, step E, the cleaved oligonucleotide fragments fall off the target DNA, leaving only the desired single-stranded circular construct comprising an original target DNA segment having a target-specific hybridized primer that also contains a capture group (Z) for a subsequent capture step. The final product is suitable for rolling circle amplification, optional additional steps, and subsequent sequencing.

Figure 75:
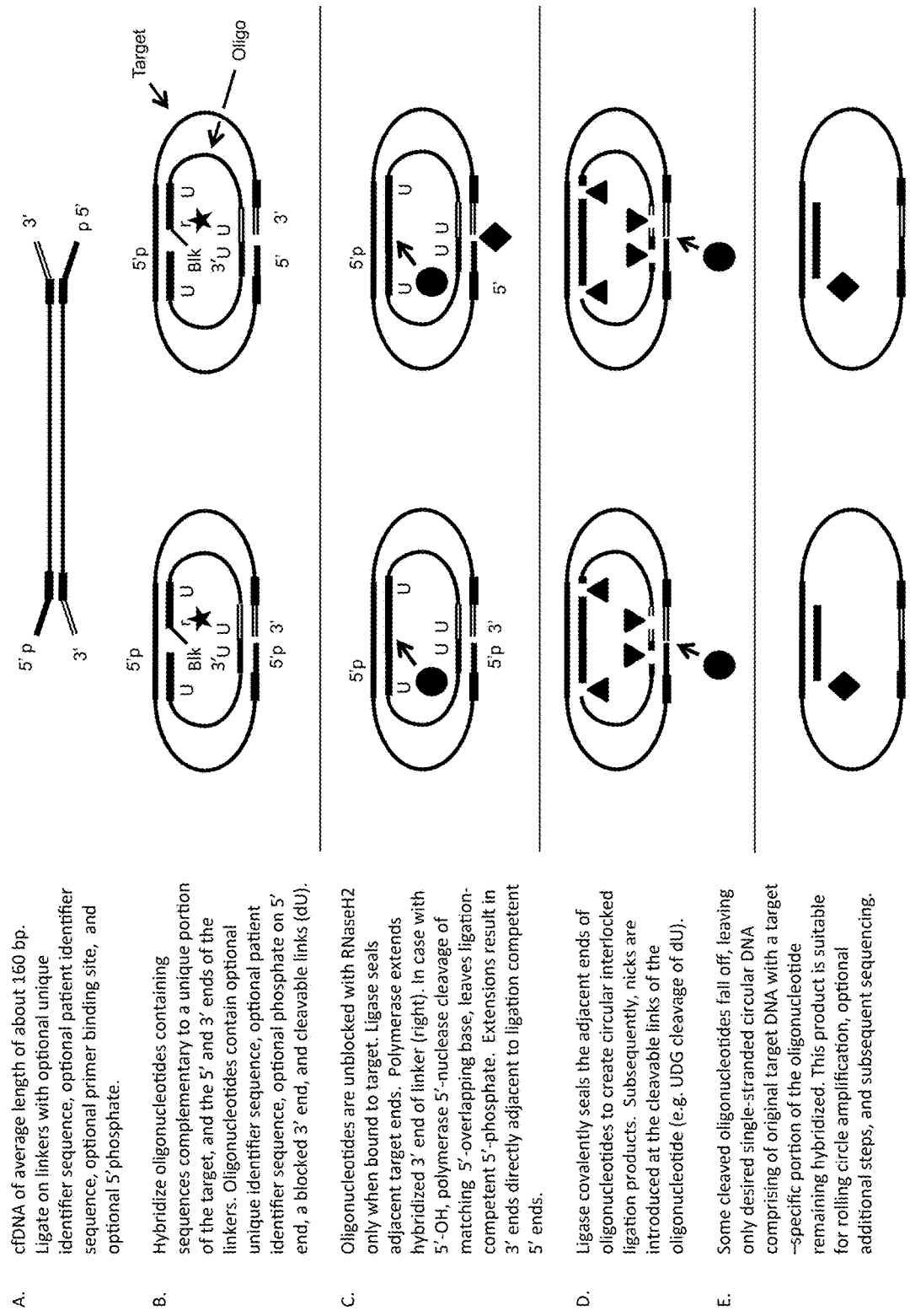
FIG. 75 shows the generation of single-stranded circular DNA comprising original target cfDNA with hybridized primer using RNaseH2 unblocking of target specific primer.

FIG. 75 shows another exemplary process for producing chimeric circular single stranded nucleic acid target constructs with a hybridized target-specific oligonucleotide that is suitable for priming rolling circle amplification and sequencing as described supra. In these embodiments, the original genomic segments comprise segments of cfDNA (~160 bp) or segments of sheared genomic DNA (~160 bp) containing, e.g., tumor specific mutations, SNPs, or unique sequences. The process starts with the ligation of composite linkers comprising both single-stranded (thinner black and double lines) and double stranded portions (thick black bars) onto the 3' and 5' ends of the DNA segments (FIG. 75, step A). The appended linkers of the process depicted in FIG. 75 left contain a ligation competent 5' phosphate group while the appended linkers of the process depicted in FIG. 75 right do not contain a ligation competent 5' phosphate group. Oligonucleotide probes containing nucleotide sequences complementary to a unique sequence of the target DNA segment (thicker black lines), and to the 5' and 3' single-stranded portions of the appended linkers (thin black, and double line) of the target DNA segments are hybridized to their respective target DNA segments as shown in FIG. 75, step B. The oligonucleotide probes also optionally contain a unique identifier sequence, optional patient identifier sequence, a phosphate on the 5' end, and one or more cleavable links (dU). In one embodiment, the 3' end of the oligonucleotide probe further comprises a few extra bases and a blocking group, which is liberated to form a free 3'OH by cleavage with a nuclease only when hybridized to the target, e.g., a ribonucleotide base as the blocking group and RNase H2 (star) as the cleaving nuclease. As the ends of the oligonucleotide probes are adjacent to each other after RNaseH2 cleavage, they are suitable for sealing with a ligase (FIG. 75, step C). Polymerase (filled diamonds) extends hybridized 3' ends of the target DNA segment (FIG. 75, step C, right) to create ligation junctions with the corresponding 5' end of the target DNA segment. In the absence of a ligation competent 5' phosphate on the target segment, polymerase 5'-nuclease activity cleaves a matching 5'-overlapping base to generate a ligation-competent 5'-phosphate. As shown in FIG. 75, step D, ligase (filled circles) covalently seals the adjacent ends of the target segment to create circular interlocked ligation products. Subsequently, one or more nicks are introduced at the cleavable links of the oligonucleotide probe (e.g. UDG cleavage of dU, filled triangles). As shown in FIG. 75, step E, the cleaved oligonucleotide fragments fall off the target DNA, leaving only the desired single-stranded circular construct comprising an original target DNA segment with a target-specific hybridized primer. The final product is suitable for rolling circle amplification, optional additional steps, and subsequent sequencing.

FIG. 76 is another exemplary process for producing chimeric circular single stranded nucleic acid target constructs with hybridized target-specific oligonucleotide suitable for rolling circle amplification and sequencing as described supra. The steps of this embodiment are similar to those depicted in FIG. 75, steps A-E. However, in this embodiment the oligonucleotide probe also comprises a capture group (Z) (i.e. biotin) suitable for capture of products on a solid support (i.e. with Streptavidin coated solid support). As shown in FIG. 76, step E, the cleaved oligonucleotide fragments fall off the target DNA, leaving only the desired single-stranded circular construct comprising an original target DNA segment with a target-specific hybridized primer that also contains a capture group (Z) for a subsequent capture step. The final product is suitable for rolling circle amplification, optional additional steps, and subsequent sequencing.

Figure 77:
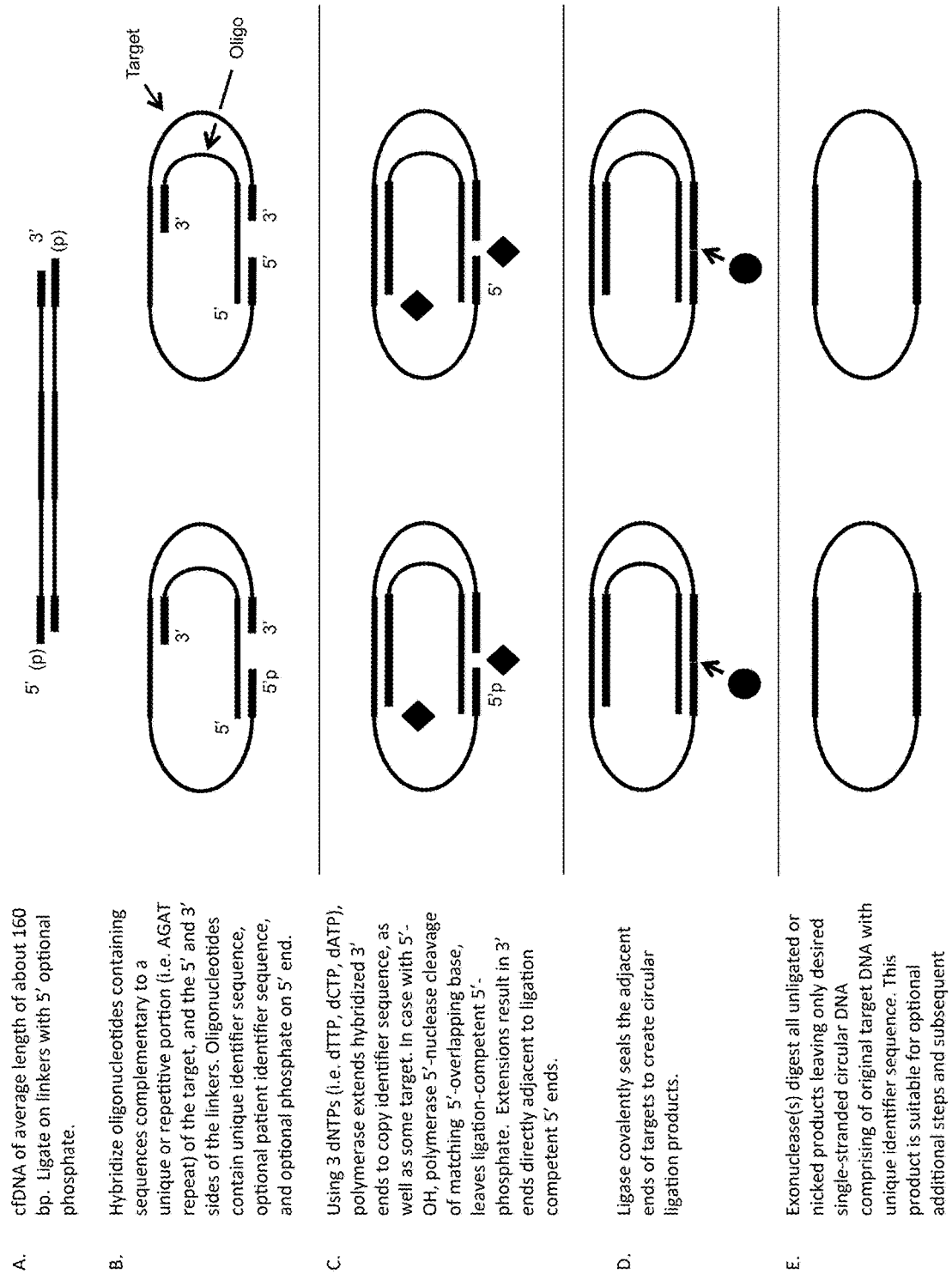
FIG. 77 shows a process for producing chimeric circular single stranded nucleic acid target constructs from cfDNA or sheared genomic DNA suitable for sequencing.

FIG. 77 shows another exemplary process for producing chimeric circular single stranded nucleic acid target constructs suitable for sequencing as described supra. In these embodiments, the original genomic segments comprise segments of cfDNA (~160 bp) or segments of sheared genomic DNA (~160 bp) containing, e.g., tumor specific mutations, SNPs, or polymorphic repetitive sequences. The process starts with the ligation of short linkers onto the 3' and 5' ends of the DNA segments (thick black bars, FIG. 77, step A). The 5' end of the appended linkers optionally contains a ligation competent phosphate (FIG. 77, step B, left panel). Oligonucleotide probes containing sequences complementary to a unique or repetitive portion (i.e. AGAT repeat) of the target DNA segment, and the 5' and 3' sides of the appended linkers are hybridized to their respective target DNA segments as shown in FIG. 77, step B. The oligonucleotide probes also contain a further portion that contains one or more of a unique identifier sequence, a patient identifier sequence, a ligation competent 5' phosphate, and a cleavable link (dU). FIG. 77, step C shows the use of 3 dNTPs (i.e. dTTP, dCTP, dATP) for polymerase (filled diamonds) mediated extension of the hybridized 3' ends of the target DNA segment and the oligonucleotide probe. Extension of the 3' end of the target DNA segment creates a ligation junction with the corresponding 5' end of the target DNA segment. In the absence of a ligation competent 5' phosphate on the target DNA segment (FIG. 77, step C), 5'-nuclease activity of the polymerase cleaves a matching 5'-overlapping base to generate a ligation-competent 5'-phosphate. In FIG. 77, step D, ligase (filled circles) covalently seals the adjacent ends of the target DNA segment to create a circular ligation product. Exonuclease digestion removes all unligated or nicked products leaving only the desired single-stranded circular construct comprising the original target DNA segment coupled to a unique identifier sequence. The final product is suitable for optional additional steps and subsequent sequencing.

Figure 78:
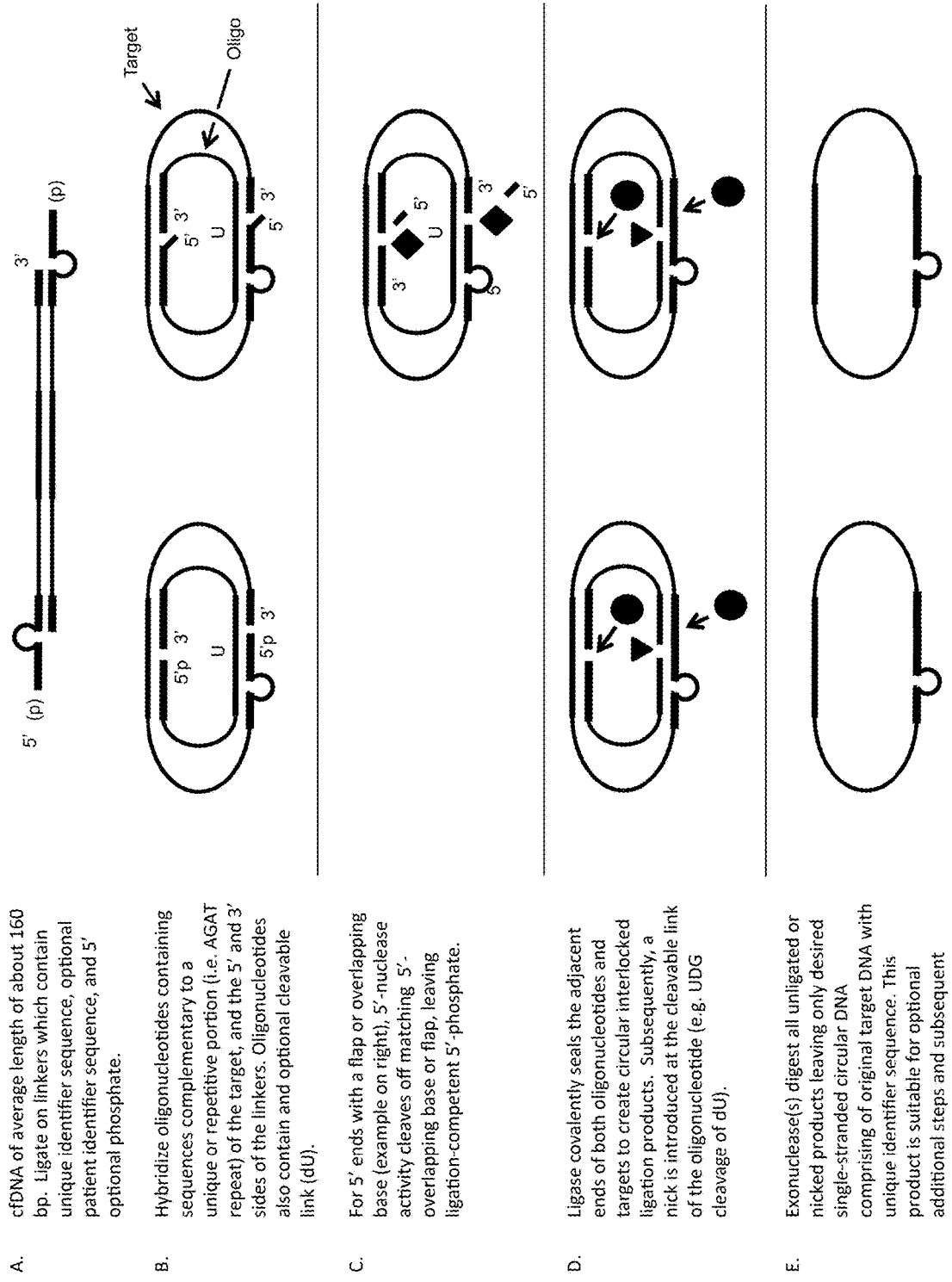
FIG. 78 shows a process for producing chimeric circular single stranded nucleic acid target constructs from cfDNA or sheared genomic DNA suitable for sequencing.

FIG. 78 shows another exemplary process for producing chimeric circular single stranded nucleic acid target constructs suitable for sequencing as described supra. In these embodiments, the original genomic segments comprise segments of cfDNA (~160 bp) or segments of sheared genomic DNA (~160 bp) containing, e.g., tumor specific mutations, SNPs, or polymorphic repetitive sequences. The process starts with the ligation of short linkers onto the 3' and 5' ends of the DNA segments (thick black bars, FIG. 78, step A). The appended linkers of the process contain a unique identifier sequence, and, optionally, a patient identifier sequence and a ligation competent 5' phosphate group. As shown in FIG. 78, step B, oligonucleotide probes containing sequences complementary to a unique or repetitive portion (i.e. AGAT repeat) of the target DNA segment and the 5' and 3' sides of the appended linkers are hybridized to their respective target DNA segments. The oligonucleotide probes also contain an optional cleavable link (dU) and 5' ligation competent phosphate group. When the 5' end of the linker appended target DNA segment and/or the 5' end of the oligonucleotide probe do not contain a ligation competent 5' end (FIG. 78, left panel), but rather contain a flap or overlapping base (FIG. 78, step B, right panel), 5'-nuclease activity (filled diamonds) cleaves at the matching 5'-overlapping base or flap, leaving a ligation-competent 5'-phosphate (FIG. 78, step C). As shown in FIG. 78, step D, ligase (filled circles) covalently seals the adjacent ends of the oligonucleotide probes and target DNA segments to create circular interlocked ligation products. Subsequently, a nick is introduced at the cleavable link of the oligonucleotide probe (e.g., UDG cleavage of dU, filled triangles), and exonuclease digestion removes all unligated or nicked products, leaving only desired single-stranded circular DNA comprising of original genomic target DNA coupled to a unique identifier sequence. The final product is suitable for optional additional steps and subsequent sequencing.

The procedures exemplified in FIGS. 63, 65, and 70-78 for producing chimeric circular single stranded nucleic acid target constructs suitable for sequencing, as well as the procedures exemplified in FIGS. 66, 67, 68, and 69 for appending linkers onto target DNA in the process of producing chimeric circular single stranded nucleic acid target constructs all have in common the capture of original target DNA into single stranded circles. In some embodiments the oligonucleotide probe provides some target selectivity (FIGS. 70-78), and in some cases the product comprises both the original target DNA in a single stranded circle with a target-specific hybridized primer suitable for rolling circle amplification or direct capture and subsequent sequencing (FIGS. 73-76). For those approaches where the final product is a chimeric circular single stranded nucleic acid target without a hybridized primer, FIGS. 79-81 exemplify three different approaches for hybridizing target-specific primer at very high specificity, followed by capture, washing away non-target nucleic acids, and subsequent rolling circle amplification.

Figure 79:
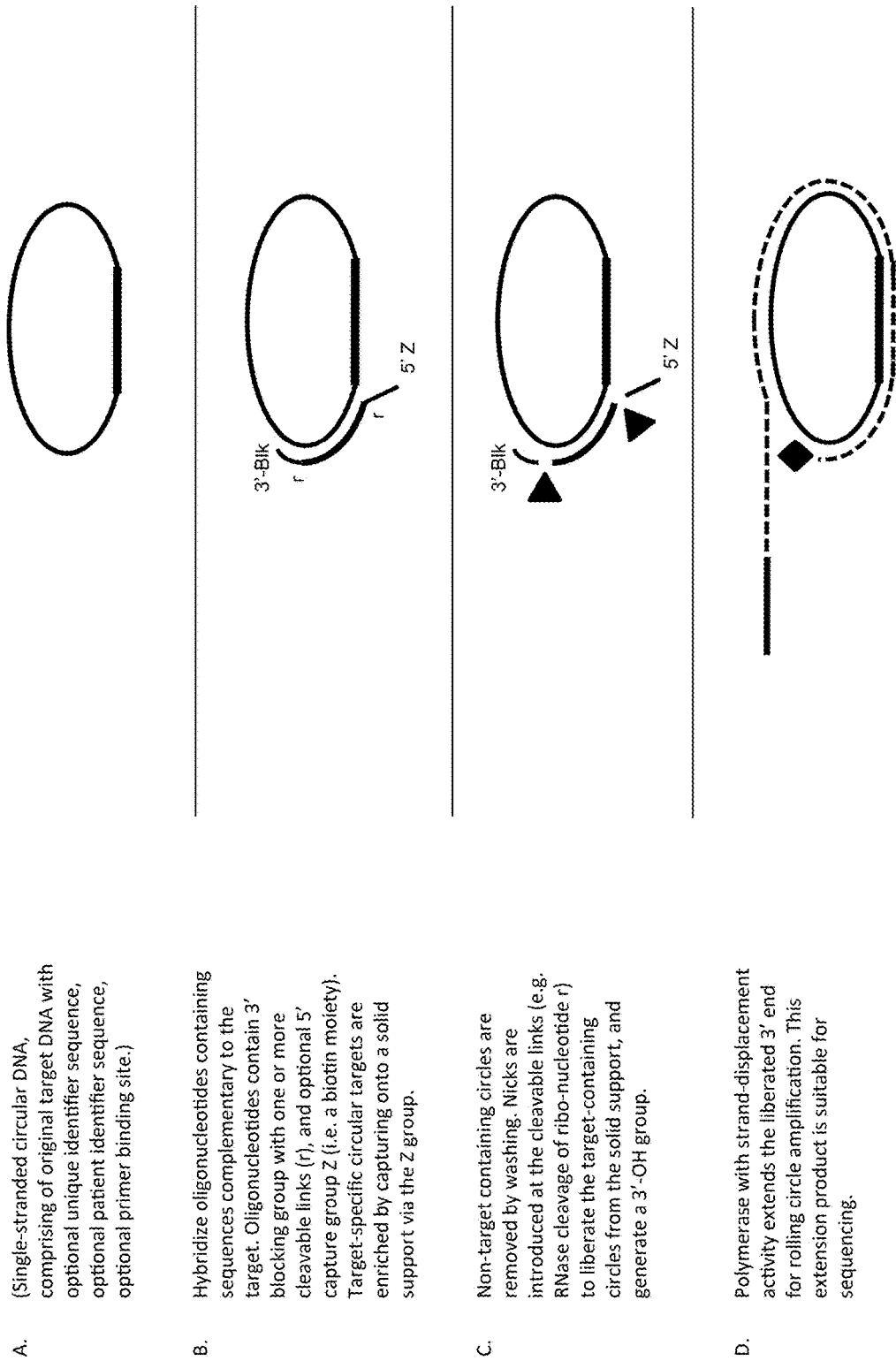
FIG. 79 shows a process for enriching target specific single strand circular DNA using capture by target specific primers which can subsequently be used for rolling circle amplification.

FIG. 79 shows an exemplary process for enriching for desired target-specific chimeric circular single stranded nucleic acid target constructs suitable for sequencing as described supra. A target-specific oligonucleotide primer is designed to contain a blocked 3' group that is liberated by RNaseH2 cleavage of a cleavable ribonucleotide link if and only if hybridized to the target (Dobosy et al., "RNase H-Dependent PCR (rhPCR): Improved Specificity and Single Nucleotide Polymorphism Detection Using Blocked Cleavable Primers," *BMC Biotechnol.* 11:80 (2011), which is hereby incorporated by reference in its entirety), as well as an optional 5' capture group (e.g., a biotin moiety) (see FIG. 79, step B). Circular DNA comprising the desired targets are enriched by capturing the hybridized primer/circle construct on a solid support via the capture group on the primer, for example, streptavidin capture of the biotin moiety. Non-target containing circles are removed by washing. Nicks are introduced at the cleavable links (e.g. RNase cleavage of ribo-nucleotide r) to liberate the target-containing circles from the solid support, and generate a 3'-OH group on the primer. Polymerase with strand-displacement activity extends the liberated 3' end of the primer for rolling circle amplification (see FIG. 80, step B). This extension product is suitable for subsequent sequencing.

Figure 80:
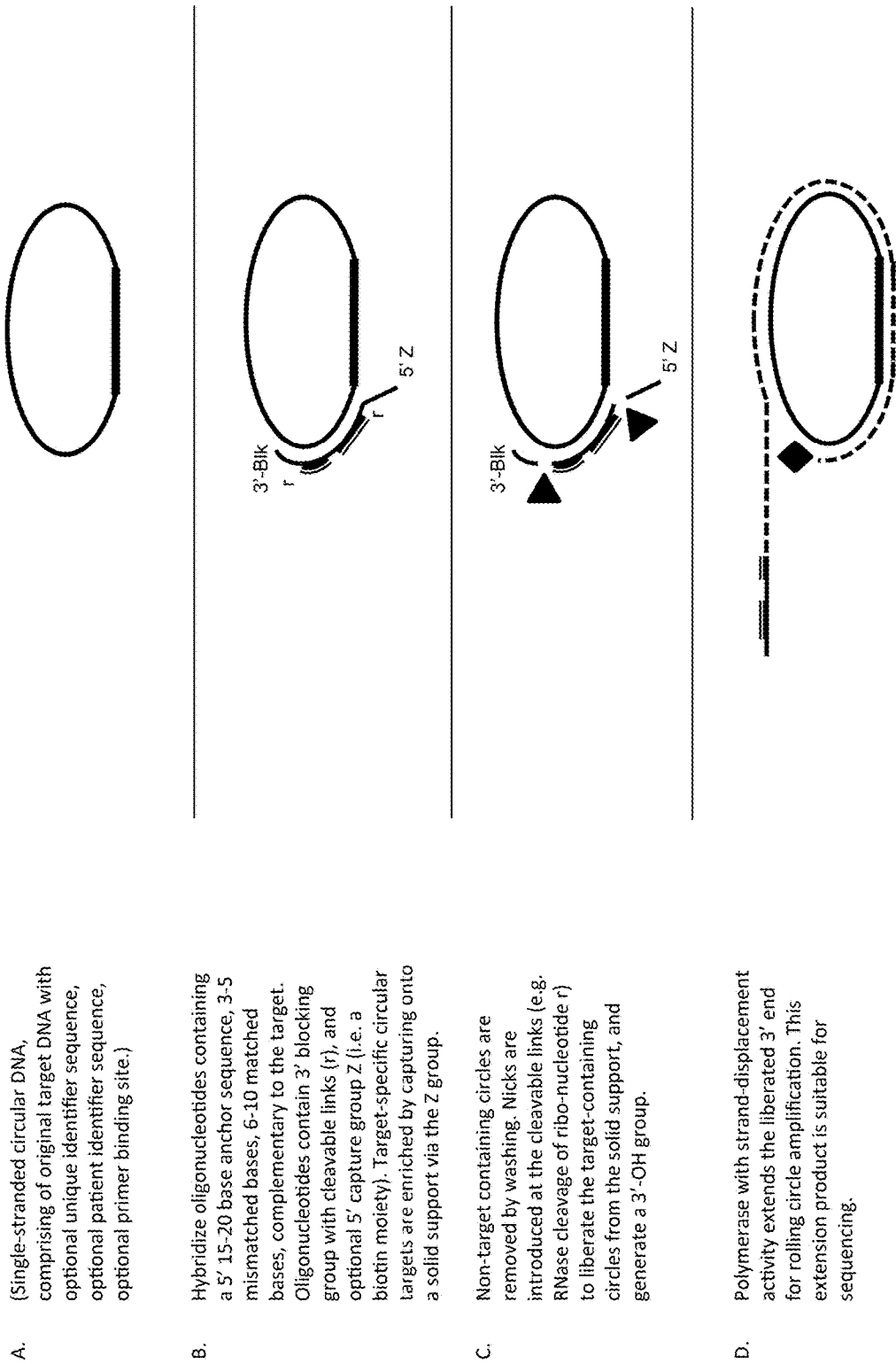
FIG. 80 shows a process for enriching target specific single strand circular DNA using capture by gapped tandem target specific primers which can subsequently be used for rolling circle amplification.

FIG. 80 shows another exemplary process for enriching for desired target-specific chimeric circular single stranded nucleic acid target constructs suitable for sequencing as described supra. In this embodiment a target-specific oligonucleotide primer is designed to contain a 5' 15-20 base anchor sequence, 3-5 mismatched bases, 6-10 matched bases, complementary to the target (Chun et al., "Dual Priming Oligonucleotide System for the Multiplex Detection of Respiratory Viruses and SNP Genotyping of CYP2C19 Gene," *Nucleic Acids Res.* 35(6):e40 (2007), which is hereby incorporated by reference in its entirety). As in FIG. 79, the oligonucleotide primer also contains a blocked 3' group that is liberated by RNaseH2 cleavage at a cleavable ribonucleotide link if and only if hybridized to the target, as well as an optional 5' capture group (i.e. a biotin moiety) (see FIG. 80, step B). Circular DNA comprising the desired targets are enriched by capturing the hybridized primer/circle construct on a solid support via the capture group, for example, streptavidin capture of the biotin moiety. Non-target containing circles are removed by washing. Nicks are introduced at the cleavable links (e.g. RNase cleavage of ribo-nucleotide r) to liberate the target-containing circles from the solid support, and generate a 3'-OH group on the primer (FIG. 80, step C). Polymerase with strand-displacement activity extends the liberated 3' end of the primer for rolling circle amplification (FIG. 80, step D). This extension product is suitable for subsequent sequencing.

Figure 81:
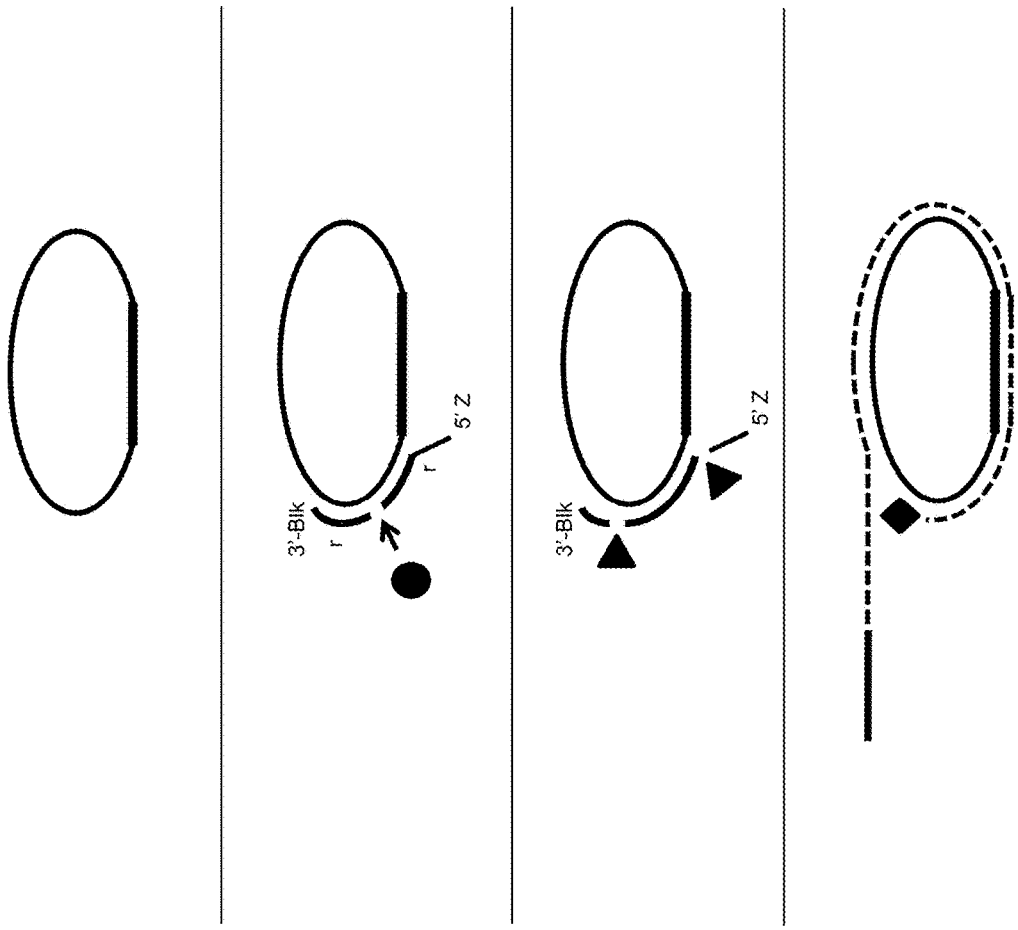
FIG. 81 shows a process for enriching target specific single strand circular DNA using target specific primers which can subsequently be used for rolling circle amplification.

FIG. 81 shows another exemplary process for enriching for desired target-specific chimeric circular single stranded nucleic acid target constructs suitable for sequencing as described supra. In this embodiment, two adjacent oligonucleotides are hybridized to the target-specific portion of the circular construct. The upstream oligonucleotide primer comprises an optional 5' capture group (e.g., a biotin moiety). The downstream oligonucleotide primer is designed to contain a 5' phosphate and a blocked 3' group that is liberated by RNaseH2 cleavage at a cleavable ribonucleotide link if and only if hybridized to the target (FIG. 81, step B). In the presence of target, ligase covalently links the two oligonucleotides to each other (FIG. 81, step B). Circular DNA comprising the desired targets may be enriched for by capturing the hybridized primer/circular constructs on a solid support via the capture group, for example, streptavidin capture of the biotin moiety. Non-target containing circles are removed by washing. Nicks are introduced at the cleavable links (e.g. RNase cleavage of ribo-nucleotide r) to liberate the target-containing circles from the solid support, and generate a 3'-OH group on the downstream oligonucleotide (FIG. 81, step C). Polymerase with strand-displacement activity extends the liberated 3' end for rolling circle amplification (FIG. 81, step D). This extension product is suitable for subsequent sequencing.

Thus, the procedures exemplified in FIGS. 55, 56, 65, 70, and 71-78 for producing chimeric circular single stranded nucleic acid target constructs suitable for sequencing, plus the procedures exemplified in FIGS. 79-81 provide examples for generating chimeric circular single stranded nucleic acid target constructs with target-specific or primer binding site primers hybridized and suitable for rolling circle amplification, followed by subsequent sequencing. FIGS. 82-89 exemplify different strategies for capturing or further enriching for the desired targets.

Figure 82:
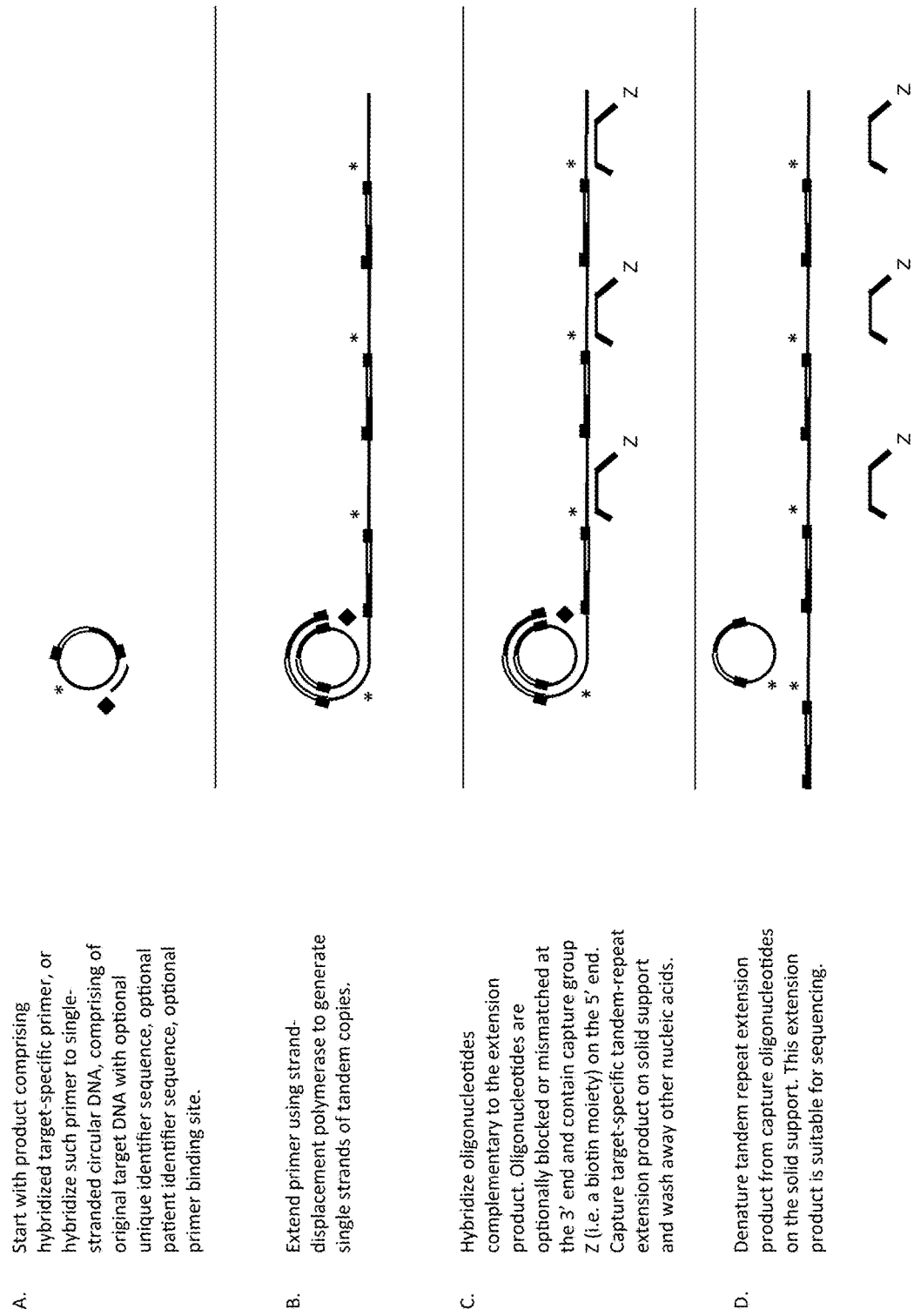
FIG. 82 shows a process to generate and enrich for genomic target specific single stranded tandem repeat extension products suitable for sequencing.

FIG. 82 shows an exemplary process for target enrichment. In this embodiment a target-specific primer hybridized to chimeric circular single stranded nucleic acid target constructs is extended using strand-displacement polymerase to generate single stranded extension product comprising two or more tandem copies of the chimeric circular single stranded construct of tandem copies (FIG. 82, step B). Oligonucleotides complementary to the extension product are hybridized. These oligonucleotides optionally contain a blocked or mismatched 3' end and contain a capture group Z (e.g., a biotin moiety) on the 5' end (FIG. 82, step C). Target-specific tandem-repeat extension product is captured on solid support and other nucleic acids are washed away. The tandem-repeat extension product is denatured from capture oligonucleotides on the solid support (FIG. 82, step C). This extension product is suitable for sequencing.

Figure 83:
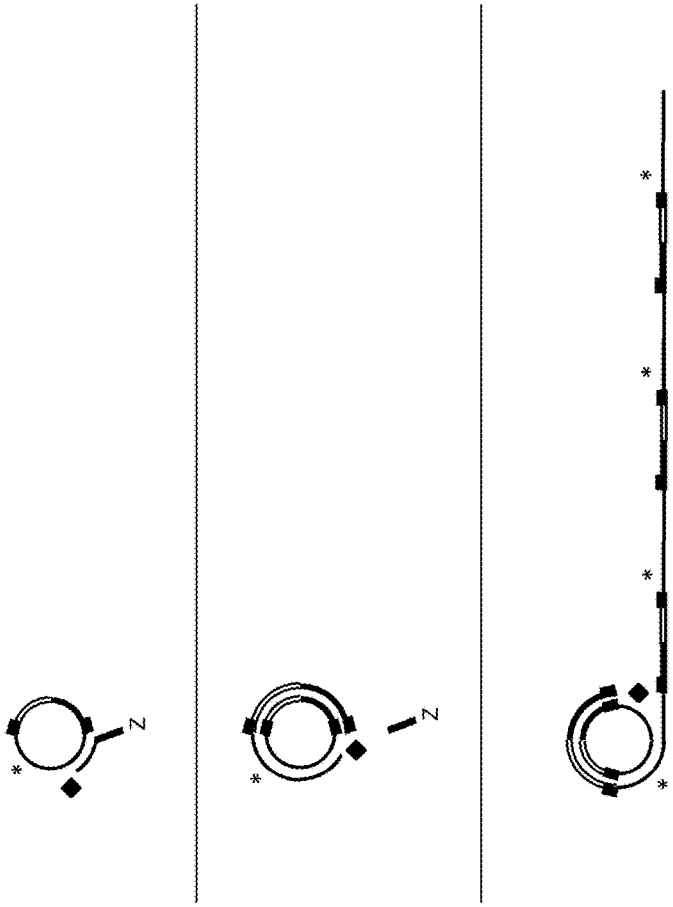
FIG. 83 shows a process to generate and enrich for genomic target specific single stranded tandem repeat extension products suitable for sequencing.

FIG. 83 shows another exemplary process for target-specific enrichment. In this embodiment, the target-specific oligonucleotide primer is hybridized to the chimeric circular single stranded nucleic acid target and contains a capture group Z (i.e. a biotin moiety) on the 5' end. The chimeric circular single stranded nucleic acid target construct is captured on a solid support and other nucleic acids are washed away (FIG. 83, step A). The original hybridized primer is extended using polymerase with 5'→3' nuclease activity to generate nicked circles that are liberated from the solid support as the polymerase cleaves the 5' portion of the hybridized oligonucleotide containing the capture group (FIG. 83, step B). The original polymerase is inactivated by either heat or protease. The 3' end of the nicked circle is extended with strand-displacement polymerase to generate single strands of tandem copies of target DNA (FIG. 83, step C). This extension product is suitable for sequencing.

FIG. 84 shows another exemplary process for target-specific enrichment. In this embodiment, two target-specific oligonucleotides are hybridized to the chimeric circular single stranded nucleic acid target as shown in FIG. 84, step B. Oligonucleotides are optionally blocked or mismatched at the 3' end and contain capture group Z (i.e. a biotin moiety) on the 5' end. The chimeric circular single stranded nucleic acid target construct is captured on a solid support and other nucleic acids are washed away. One of the hybridized primers is extended using polymerase with strand-displacement activity to generate single strands of tandem copies of target DNA, and liberate extension product from the solid support as shown in FIG. 84, step C. This extension product is suitable for sequencing.

FIG. 85 shows another exemplary process for target-specific enrichment. In this embodiment, a first target-specific oligonucleotide is hybridized to chimeric circular single stranded nucleic acid target. This oligonucleotide is optionally blocked or mismatched at the 3' end and contains a capture group Z (i.e. a biotin moiety) on the 5' end. The chimeric circular single stranded nucleic acid target construct is captured on a solid support and other nucleic acids are washed away. A second target-specific primer is hybridized to the captured circular constructs (FIG. 85, step B). A polymerase with strand-displacement activity is introduced to extend the second primer to generate single stranded extension product containing tandem copies of the target DNA and liberate extension product from the solid support (FIG. 85, step C). This extension product is suitable for sequencing.

Figure 86:
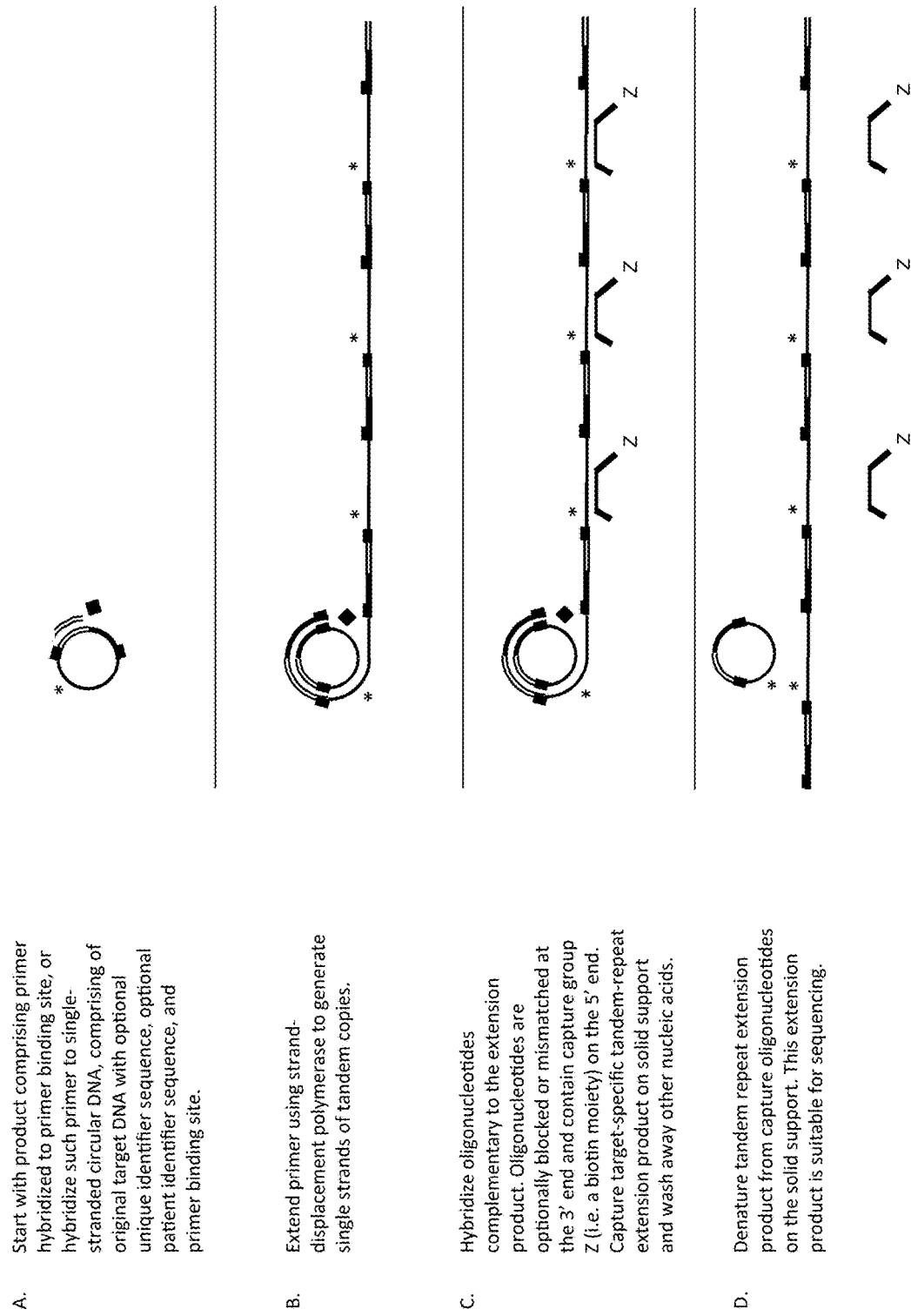
FIG. 86 shows a process to generate and enrich for genomic target specific single stranded tandem repeat extension products suitable for sequencing.
Figure 87:
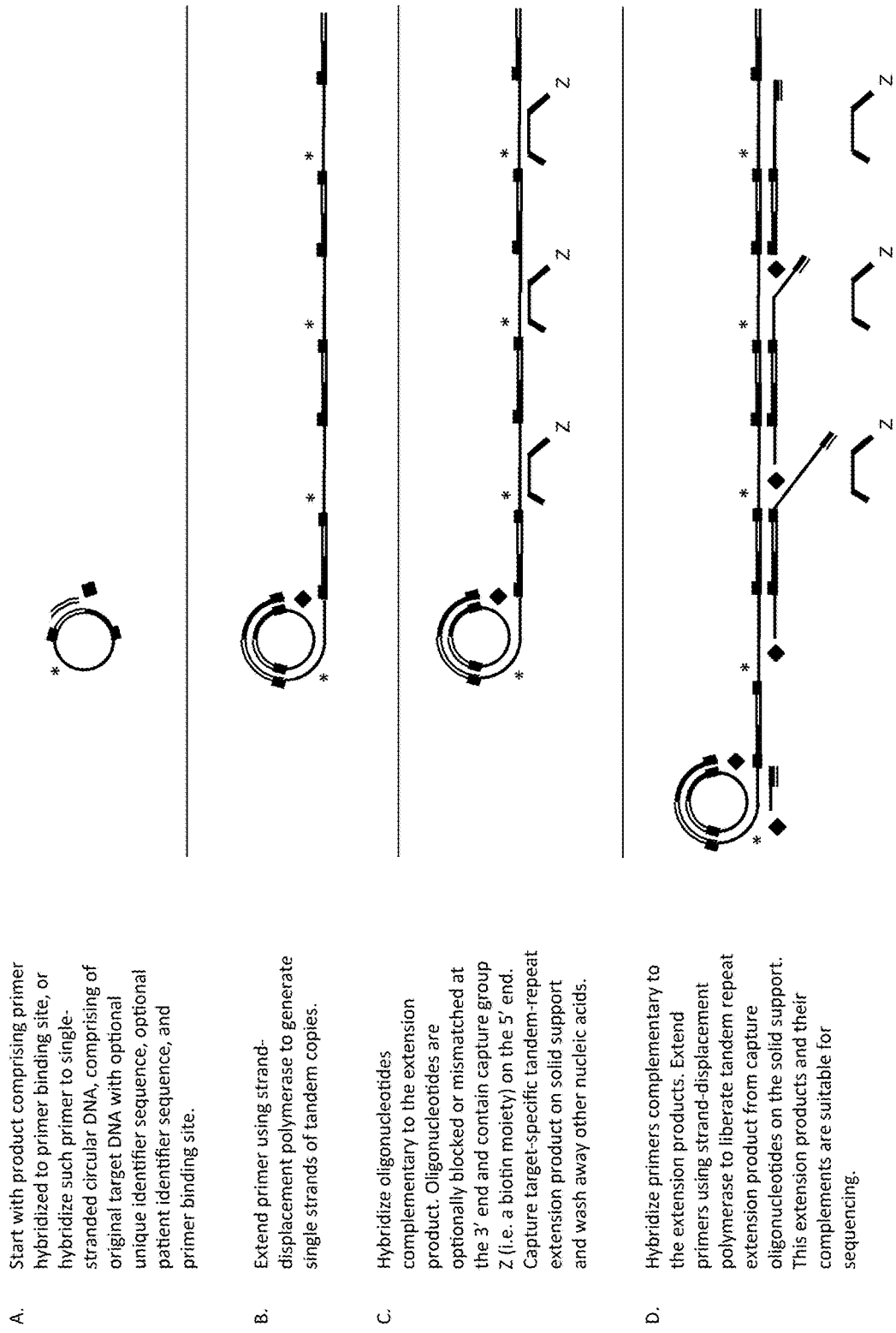
FIG. 87 shows a process to generate and enrich for genomic target specific single stranded tandem repeat extension products suitable for sequencing.

FIGS. 86 and 87 show exemplary processes for target-specific enrichment. In these embodiments, a primer binding site primer is hybridized to chimeric circular single stranded nucleic acid target and is extended using strand-displacement polymerase to generate single stranded extension product containing tandem copies of target DNA (FIG. 86, steps A-B and FIG. 87, steps A-B). Target-specific oligonucleotides complementary to the extension product are hybridized. The hybridized oligonucleotides are optionally blocked or mismatched at the 3' end and contain capture group Z (i.e. a biotin moiety) on the 5' end. Target-specific tandem-repeat extension product is captured on solid support and other nucleic acids are washed away (FIG. 86, step C and FIG. 87, step C). In FIG. 86, the tandem-repeat extension product is denatured from capture oligonucleotides on the solid support (FIG. 86, step D). This extension product is suitable for sequencing. In FIG. 87, additional target-specific primers complementary to the extension product are hybridized. Extension with strand-displacing polymerase liberates original extension product from the solid support, while making additional copies (FIG. 87, step D). The original extension product, and additional copies are suitable for sequencing.

FIG. 88 shows another exemplary process for target-specific enrichment. In this embodiment, a first target-specific primer and a second primer binding site-specific oligonucleotide are hybridized to the chimeric circular single stranded nucleic acid constructs (see FIG. 88, steps A-B). The second oligonucleotide is optionally blocked or mismatched at the 3' end and contains a capture group Z (i.e. a biotin moiety) on the 5' end. The chimeric circular single stranded nucleic acid target construct is captured on a solid support and other nucleic acids are washed away. The first target-specific hybridized primer is extended using polymerase with strand-displacement activity to generate single stranded extension product containing tandem copies of target DNA and liberate extension product from the solid support. This extension product is suitable for sequencing.

FIG. 89 shows another exemplary process for target-specific enrichment. In this embodiment, a primer binding site-specific oligonucleotide is initially hybridized to the chimeric circular single stranded nucleic acid target construct. This oligonucleotide is optionally blocked or mismatched at the 3' end and contains a capture group Z (i.e. a biotin moiety) on the 5' end. The chimeric circular single stranded nucleic acid target construct is captured on a solid support and other nucleic acids are washed away (FIG. 89, step A). A second target-specific primer is hybridized to the captured circular constructs. A polymerase with strand-displacement activity is used to generate single stranded extension products containing tandem copies of target DNA, and liberate said extension product from the solid support. This extension product is suitable for sequencing.

FIGS. 90-99 show the coverage effect of different oligonucleotide probe construction. The oligonucleotide probes in each Figure vary in their 5' (upstream) target specific portion, 3' (downstream) target-specific portions, gap lengths, and 3'-only or 5'- and 3'-anchoring ends to achieve coverage of a 160 nucleotide cfDNA target segment. The target genomic DNA segment is moved in 10 base increments simulating the "family" of all possible 160 nt targets produced by nucleosome protection.

Figure 90:
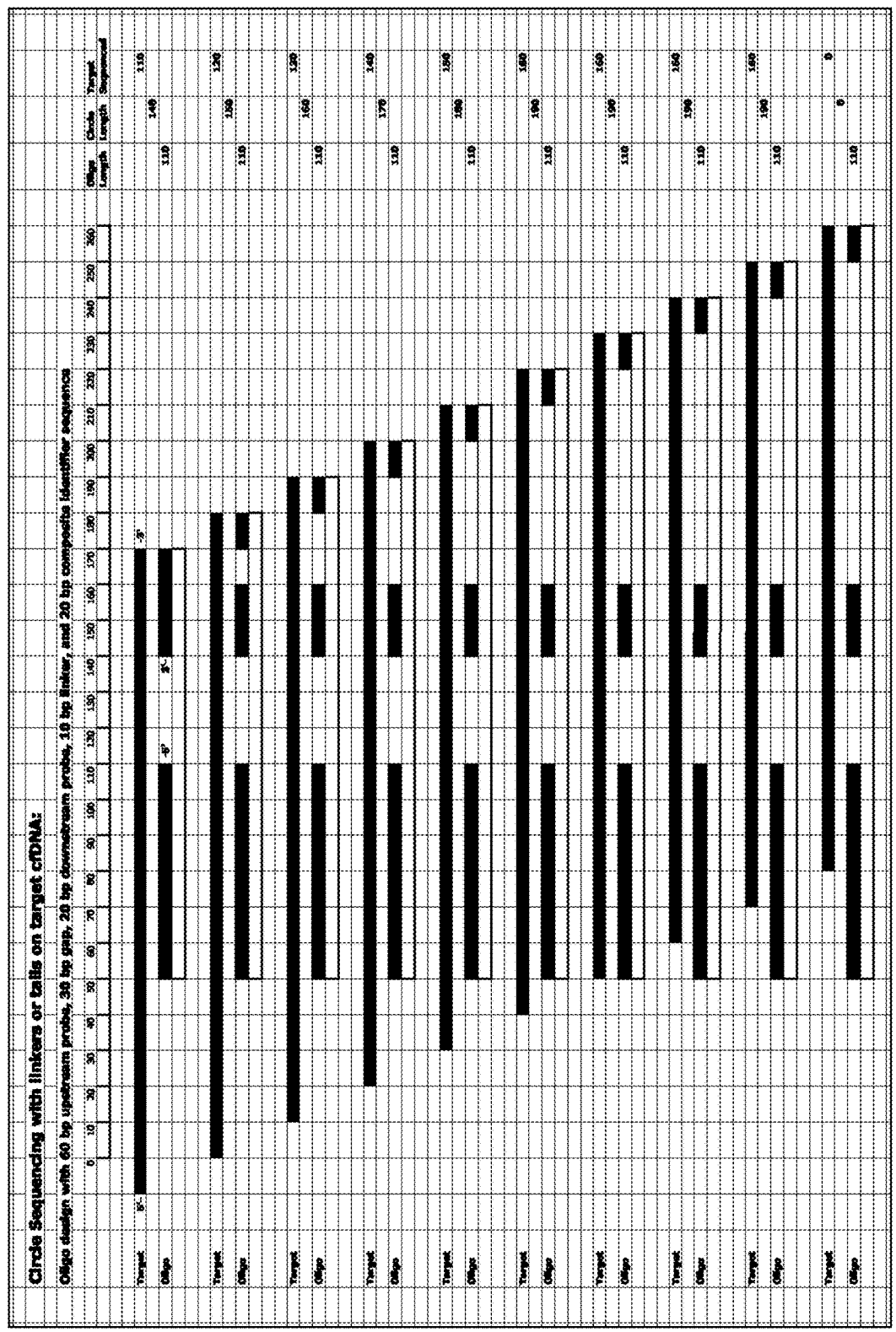
FIG. 90 shows the mapping of a family of oligonucleotide probes ("oligo") along a collection of cell free DNA (cfDNA) target fragments (160 nucleotides in length) in 10 nucleotide base increments. Each oligonucleotide probe contains a 20 base 3' target-specific portion, a 60 base 5' target-specific portion, a 10 base linker (black bar), and 20-160 base composite identifier sequence (thin line).

FIG. 90 shows oligonucleotide probe designs suitable for detection of all possible 160 nucleotide linker appended (black bars) fragments derived from cfDNA. In this embodiment, the oligonucleotide probe is anchored to the 3'-linker appended end of the family of cfDNA fragments shown, and contains a 60 base 5' or upstream target-specific portion (grey bar), a 20 base 3' or downstream target-specific portion (grey bar), a 10 base linker specific portion (black bar), and a 20 base identifier sequence (thin line between 5' target specific portion and linker portion that is illustrated below the upstream and downstream specific portions). The use of 20 bases as the identifier sequence is for illustrative purposes; it may contain a 12 base unique identifier sequence and an 8 base patient identifier sequence when amplifying and sequencing the chimeric circular DNA as illustrated in FIG. 1. Alternatively, the identifier portion can be in the range of 40 to 80 bases when using patient identifiers, first and second primer specific portions suitable for solid phase capture, and sequencing primer binding regions as illustrated in FIGS. 4-12. An illustration of the oligonucleotide probes of this Figure hybridized to their target cfDNA fragment is provided in FIG. 13. The very thin line of varying lengths between the 3' target specific portion and linker portion on the oligonucleotide probes shown in FIG. 90 corresponds to the length of the looped region near the 3' end of the target segment shown in FIGS. 13-16. It illustrates that the probe region and the region complementary to the linker region are physically coupled to each other.

Figure 91:
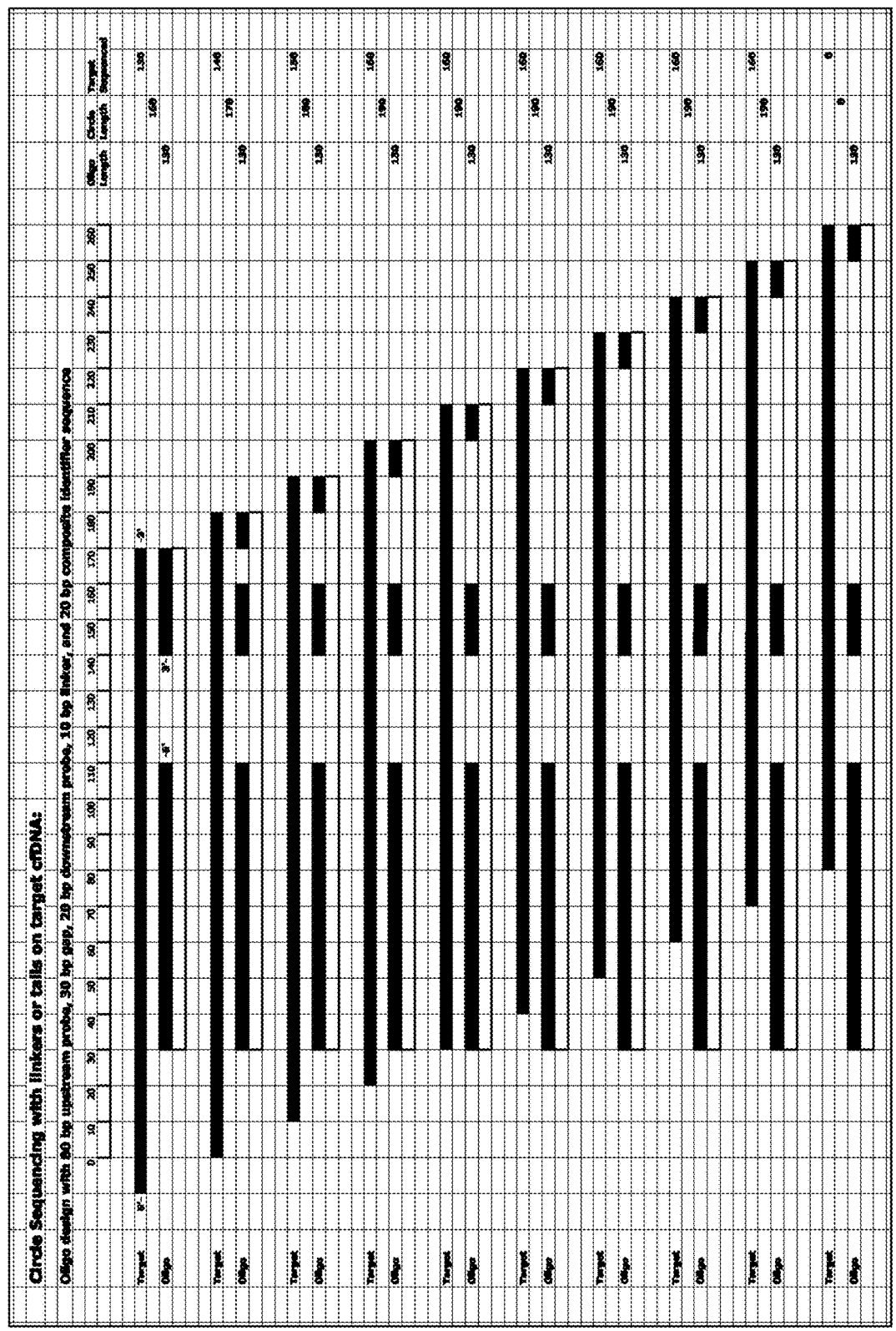
FIG. 91 shows the mapping of a family of oligonucleotide probes ("oligo"), along a collection of cfDNA target fragments (160 nucleotides in length) in 10 nucleotide base increments. Each oligonucleotide probe contains a 20 base 3' target-specific portion, a 80 base 5' target-specific portion, a 10 base linker (black bar), and 20-160 base composite identifier sequence (thin line).

The oligonucleotide probe design shown in FIG. 91 is similar to that shown in FIG. 90. In this embodiment, the oligonucleotide probe is anchored to the 3'-linker appended end of the family of cfDNA fragments shown, and contains an 80 base 5' or upstream target-specific portion, a 20 base 3' or downstream target-specific portion, a 10 base linker specific portion (thick black bar) and a 20-160 base identifier sequence. An illustration of the oligonucleotide probes of this Figure hybridized to their target cfDNA fragment is also provided in FIGS. 13-16.

Figure 92:
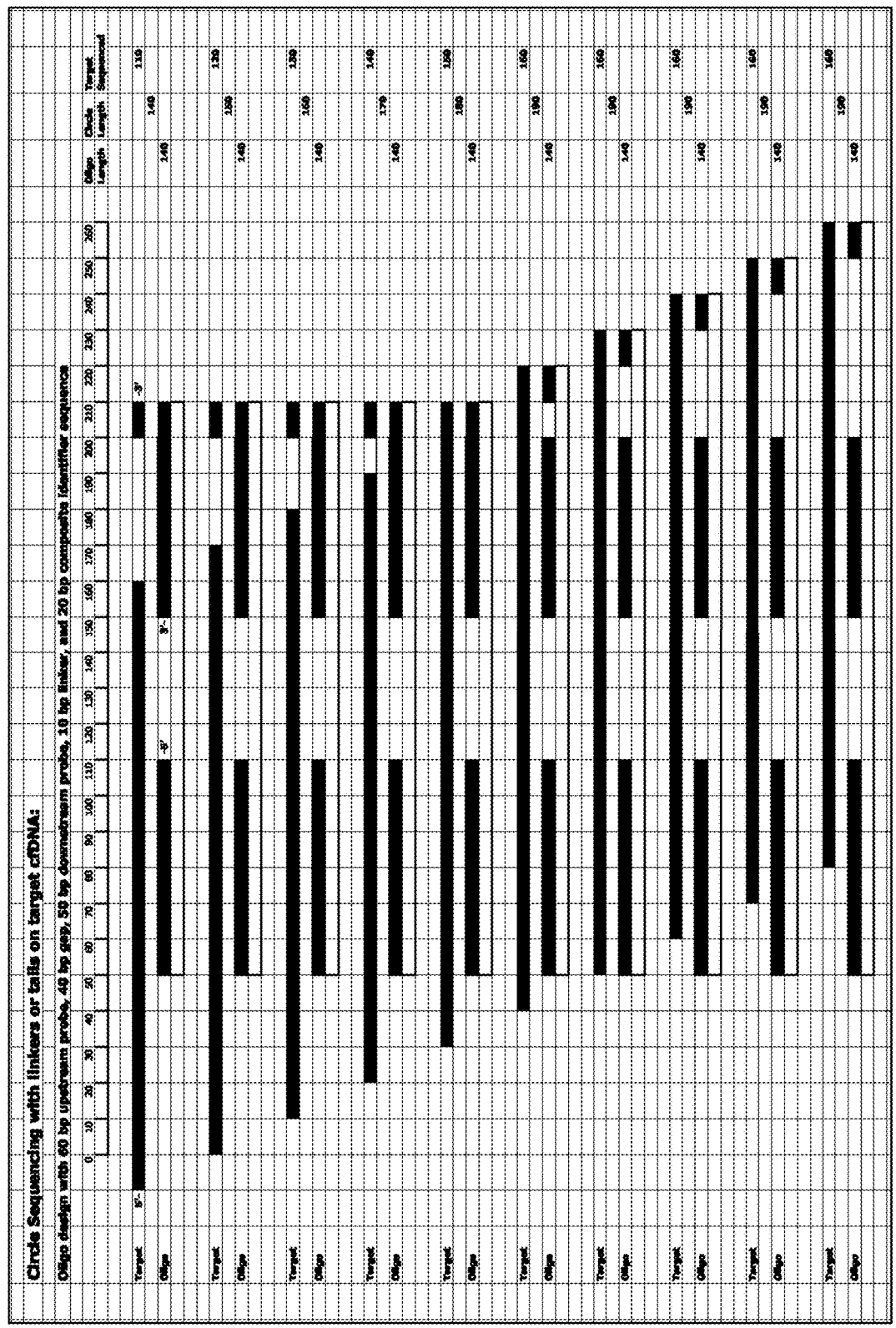
FIG. 92 shows the mapping of a family of oligonucleotide probes ("oligo"), along a collection of cfDNA target fragments (160 nucleotides in length) in 10 nucleotide base increments. Each oligonucleotide probe contains a 50 base 3' target-specific portion, a 60 base 5' target-specific portion, a 10 base linker (black bar), and 20-160 base composite identifier sequence (thin line).

FIG. 92 shows a variation of oligonucleotide probe design suitable for detection of all possible 160 nucleotide linker appended (black bars) fragments derived from cfDNA. In this embodiment, the oligonucleotide probe is anchored to the 3'-linker appended end of the family of cfDNA fragments shown, and contains a 60 base 5' or upstream target-specific portion (grey bar), a 50 base 3' or downstream target-specific portion (grey bar), a 10 base linker specific portion (black bar) and a 20-160 base identifier sequence (thin line between 5' target specific portion and linker portion). The use of 20 bases as the identifier sequence is for illustrative purposes only; alternative lengths as described above in reference to FIG. 90 are also suitable. An illustration of the oligonucleotide probes of this Figure hybridized to its target cfDNA fragment is provided in FIGS. 13 and 15. The very thin line of varying lengths between the 3' linker of the cfDNA segment and the 3' end of the cfDNA shown in FIG. 92 corresponds to the length of the looped region of the oligonucleotide probe shown in FIGS. 13-16. It illustrates that the probe region and the region complementary to the linker region are physically coupled to each other.

Figure 93:
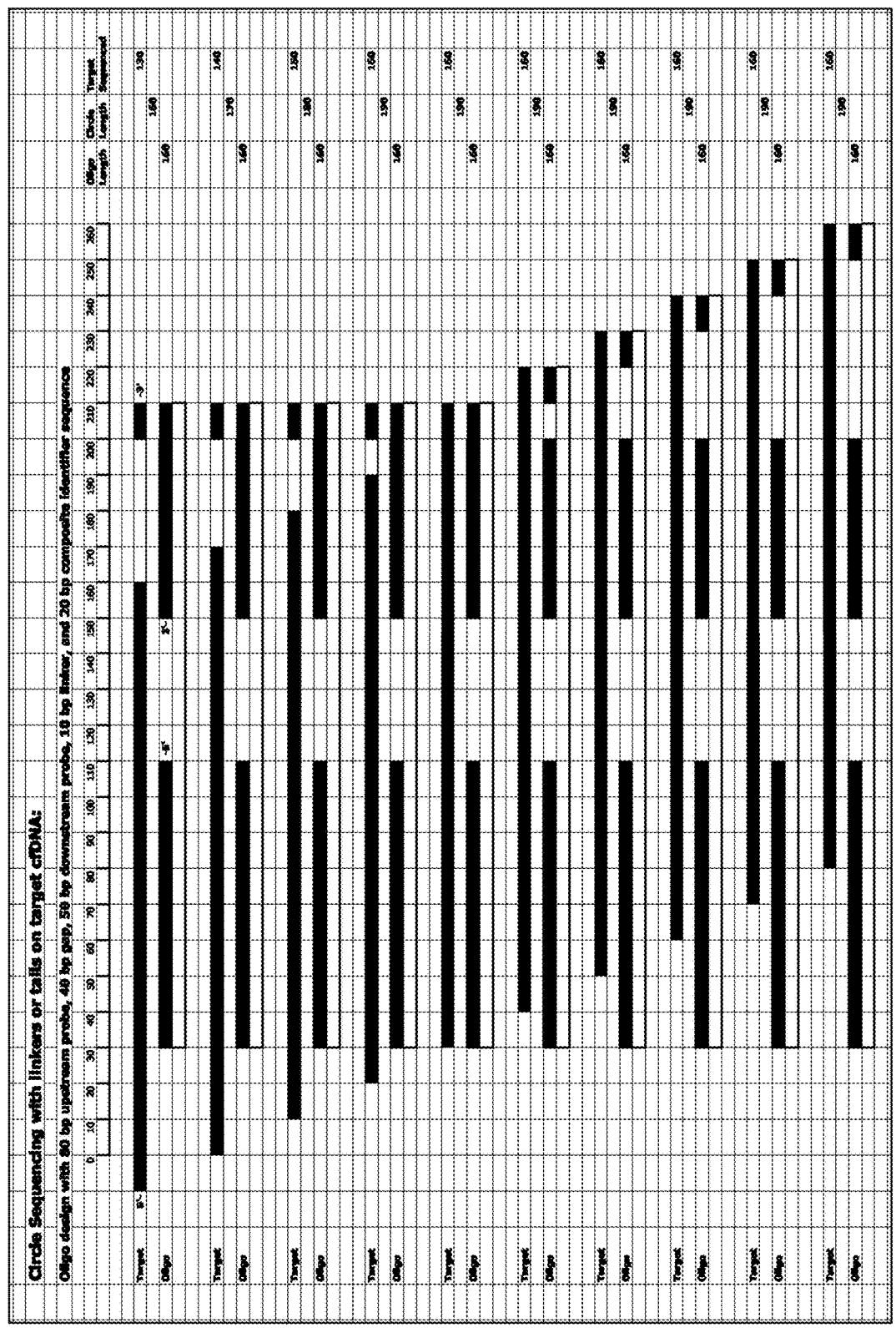
FIG. 93 shows the mapping of a family of oligonucleotide probes ("oligo"), along a collection of cfDNA target fragments (160 nucleotides in length) in 10 nucleotide base increments. Each oligonucleotide probe contains a 50 base 3' target-specific portion, a 80 base 5' target-specific portion, a 10 base linker (black bar), and 20-160 base composite identifier sequence (thin line).

The oligonucleotide probe design shown in FIG. 93 is similar to that shown in FIG. 92. In this embodiment, the oligonucleotide probe is anchored to the 3'-linker appended end of the family of cfDNA fragments shown, and contains an 80 base 5' or upstream target-specific portion, a 50 base 3' or downstream target-specific portion, a 10 base linker specific portion (thick black bar), a 40 base gap segment and a 20-160 base identifier sequence. An illustration of the oligonucleotide probes of this Figure hybridized to their target cfDNA fragment is provided in FIGS. 13-16.

Figure 94:
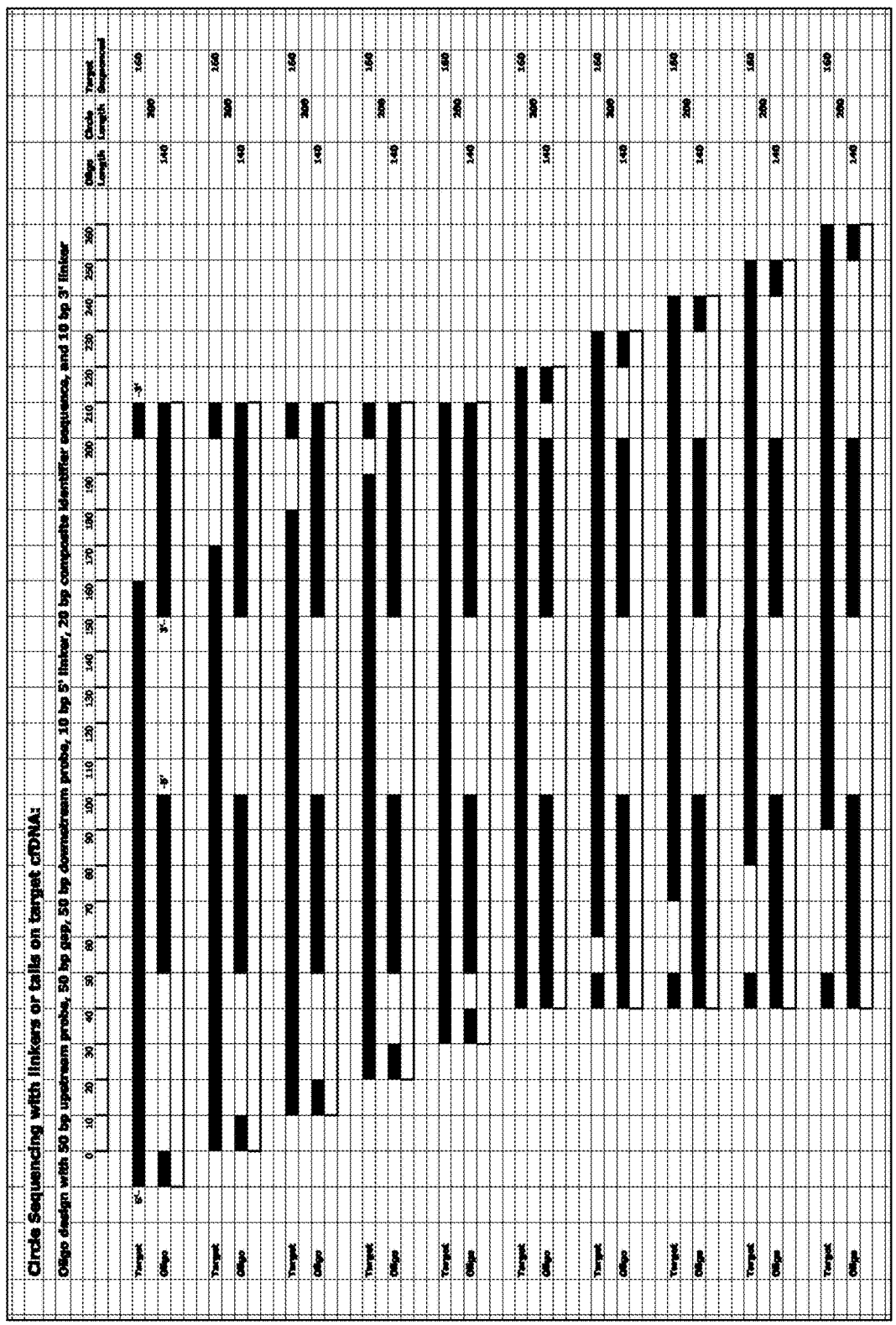
FIG. 94 shows the mapping of a family of oligonucleotide probes ("oligo"), along a collection of cfDNA target fragments (160 nucleotides in length) in 10 nucleotide base increments. Each oligonucleotide probe contains a 50 base 3' target-specific portion, a 50 base 5' target-specific portion, 3' and 5' 10 base linkers (black bar), and 20-160 base composite identifier sequence (thin line).

FIG. 94 shows a slight variation of oligonucleotide probe design suitable for detection of all possible 160 nucleotide linker appended (black bars) fragments derived from cfDNA. In this embodiment, the oligonucleotide probe is anchored to the 3'-linker appended end of the family of cfDNA fragments shown, and contains a 50 base 5' or upstream target-specific portion (grey bar), a 50 base 3' or downstream target-specific portion (grey bar), a 10 base 3' linker specific portion (black bar), 10 base 5' linker specific portion (black bar), and a 20-80 base identifier sequence (thin line between 5' and 3' target specific portions, that is illustrated below grey bars and linker portion). An illustration of an oligonucleotide probe of this Figure hybridized to its target cfDNA fragment is provided in FIG. 14. The very thin line of varying lengths in the target cfDNA segment shown in FIG. 94 corresponds to the looped region in the oligonucleotide probe of FIG. 14, and the very thin line of varying length in the oligonucleotide probes of FIG. 94 corresponds to the looped region of the target DNA segment of FIGS. 17 and 18. It illustrates that the probe region and the region complementary to the linker region are physically coupled to each other.

Figure 95:
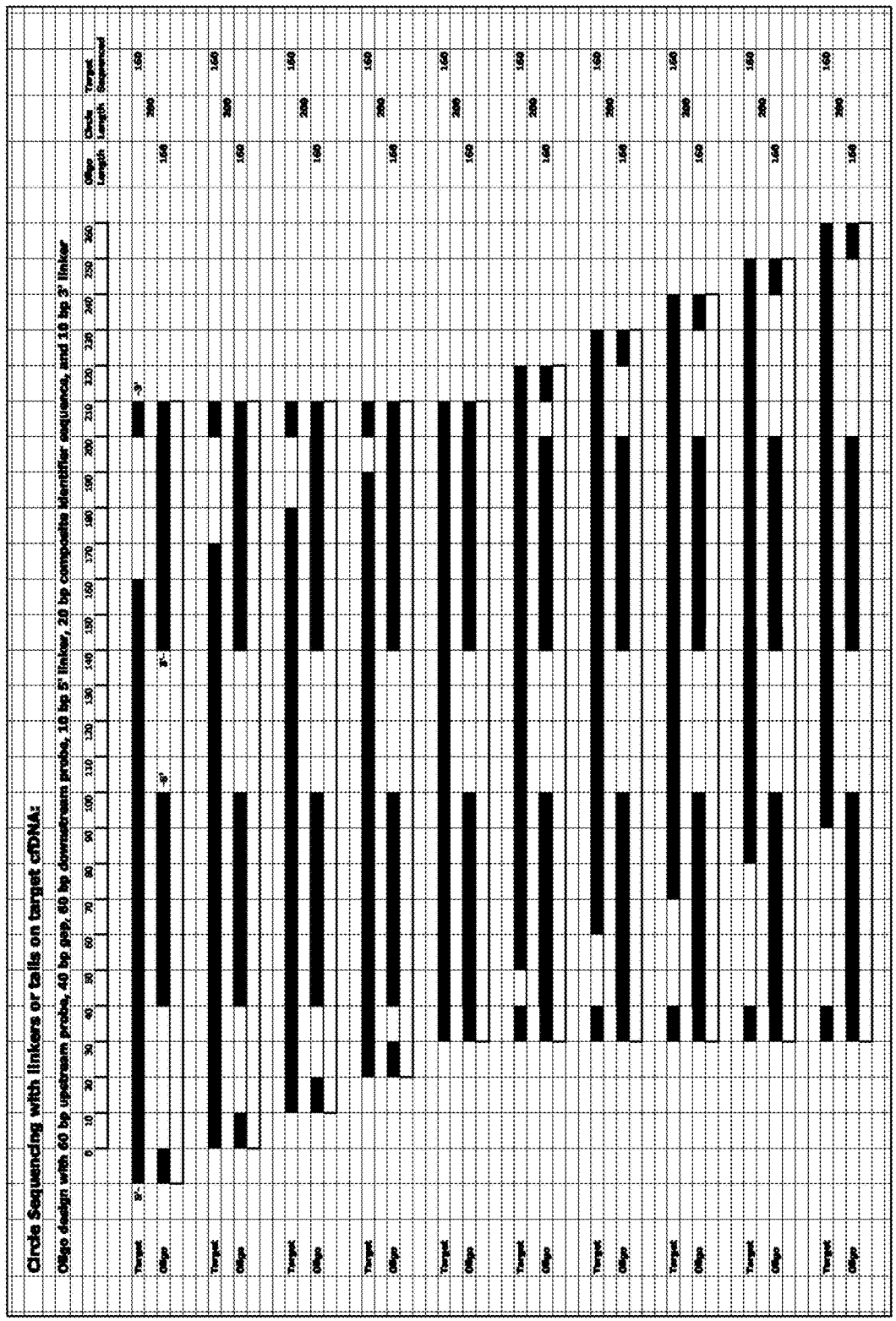
FIG. 95 shows the mapping of a family of oligonucleotide probes ("oligo"), along a collection of cfDNA target fragments (160 nucleotides in length) in 10 nucleotide base increments. Each oligonucleotide probe contains a 60 base 3' target-specific portion, a 60 base 5' target-specific portion, 3' and 5' 10 base linkers (black bar), and 20-160 base composite identifier sequence (thin line).

The oligonucleotide probe design shown in FIG. 95 is similar to that shown in FIG. 94. In this embodiment, the oligonucleotide probe is anchored to the 3'-linker and 5' linker appended ends of the family of cfDNA fragments shown. The probe contains a 60 base 5' or upstream target-specific portion, a 60 base 3' or downstream target-specific portion, a 10 base 3' linker specific portion, a 10 base 5' linker specific portion and a 20-80 base identifier sequence. An illustration of the oligonucleotide probes of this Figure hybridized to their target cfDNA fragment is also provided in FIGS. 17 and 18.

Figure 96:
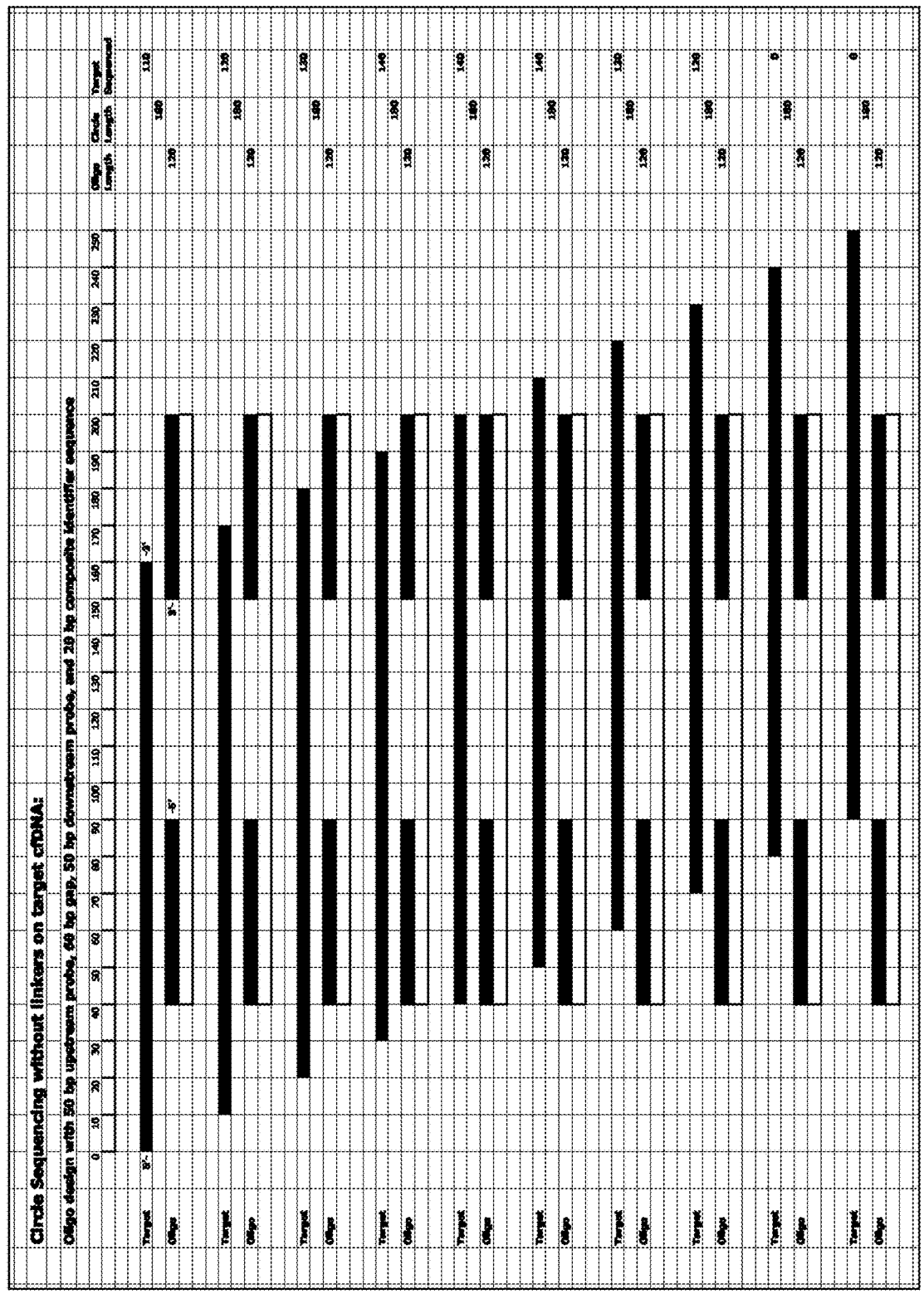
FIG. 96 shows the mapping of a family of oligonucleotide probes ("oligo"), along a collection of cfDNA target fragments (160 nucleotides in length) in 10 nucleotide base increments. Each oligonucleotide probe contains a 50 base 3' target-specific portion, a 50 base 5' target-specific portion, and 20-160 base composite identifier sequence (thin line).

FIG. 96 shows another variation of oligonucleotide probe design suitable for detection of all possible 160 nucleotide non-linker appended fragments derived from cfDNA (darker grey bars). In this embodiment, the oligonucleotide probe contains a 50 base 5' or upstream target-specific portion (grey bar with black lines), a 50 base 3' or downstream target-specific portion (grey bar with black lines) and a 20-80 base identifier sequence (thin line between 5' & 3' target specific portions and shown beneath the gray bars). The short vertical black lines within the grey probe regions symbolize single-base mismatches to the original target, such that the regions of authentic target DNA vs. copy of the probe may be readily identified. An illustration of an oligonucleotide probe of this Figure hybridized to its target cfDNA fragment is provided in FIGS. 23-26.

Figure 97:
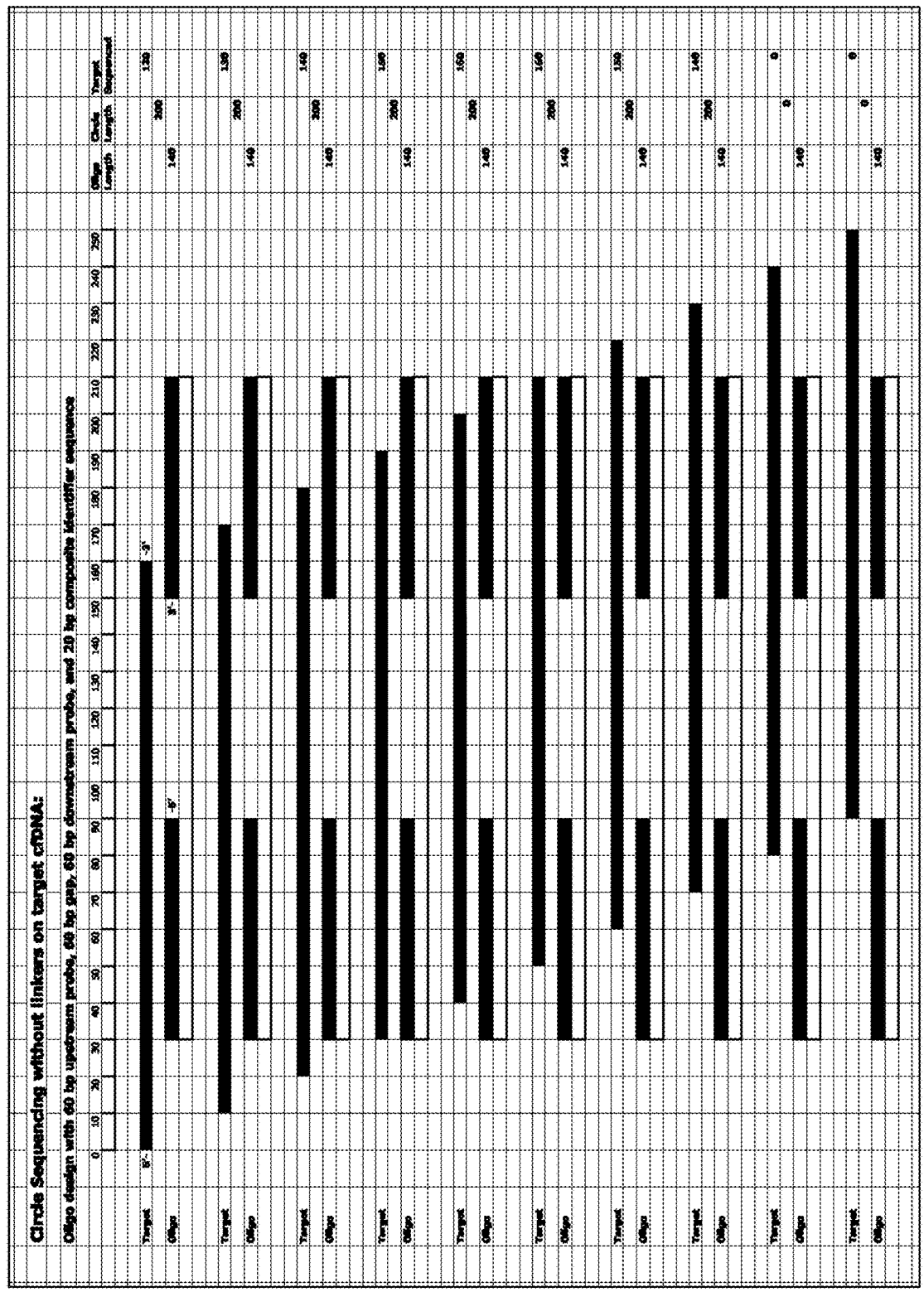
FIG. 97 shows the mapping of a family of oligonucleotide probes ("oligo"), along a collection of cfDNA target fragments (160 nucleotides in length) in 10 nucleotide base increments. Each oligonucleotide probe contains a 60 base 3' target-specific portion, a 60 base 5' target-specific portion, and 20-160 base composite identifier sequence (thin line).

The oligonucleotide probe design shown in FIG. 97 is similar to that shown in FIG. 96. In this embodiment, the oligonucleotide probe contains a 60 base 5' or upstream target-specific portion, a 60 base 3' or downstream target-specific portion and a 20-160 base identifier sequence. An illustration of the oligonucleotide probes of this Figure hybridized to their target cfDNA fragment is also provided in FIGS. 23, 24, 25 and 26.

Figure 98:
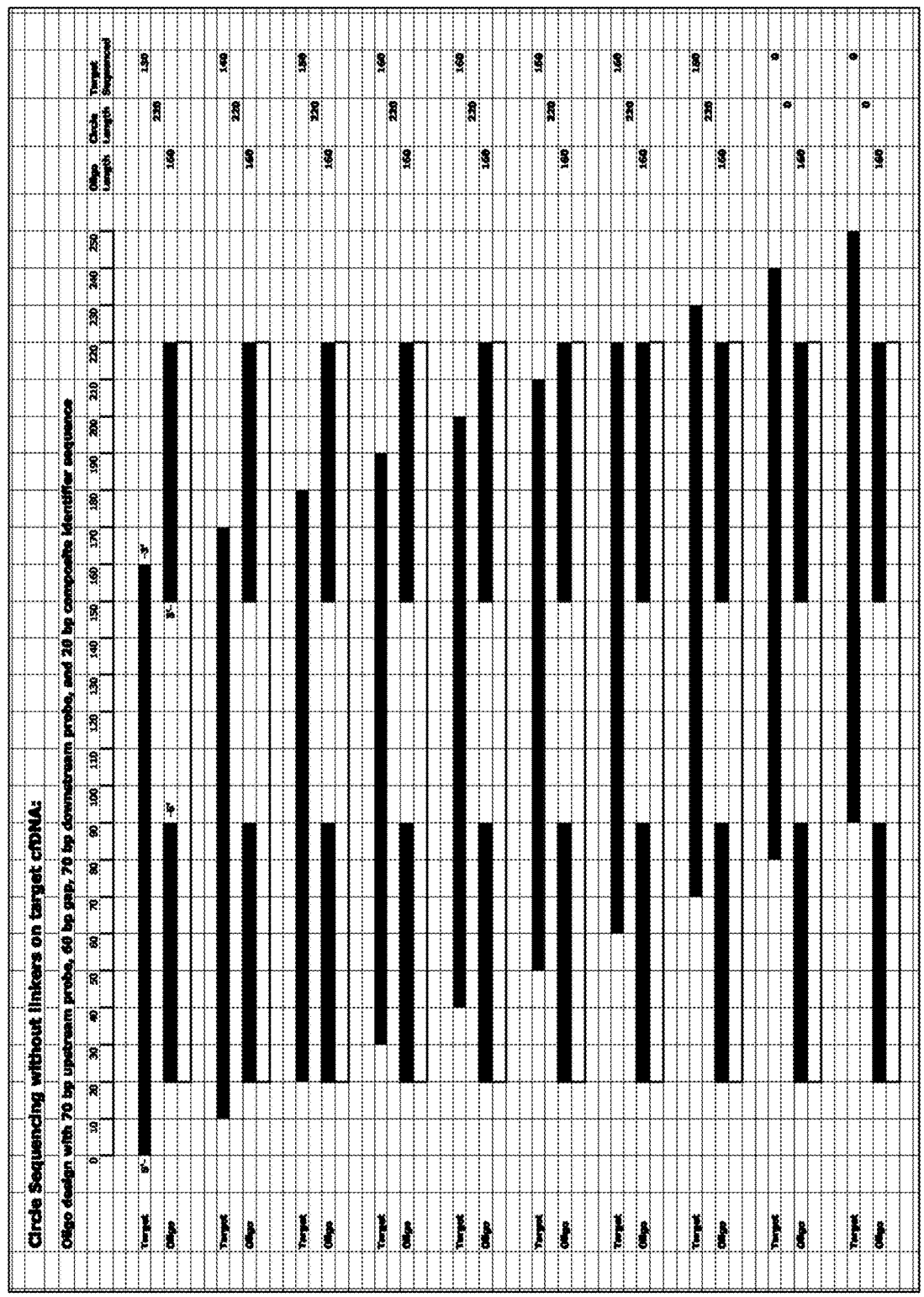
FIG. 98 shows the mapping of a family of oligonucleotide probes ("oligo"), along a collection of cfDNA target fragments (160 nucleotides in length) in 10 nucleotide base increments. Each oligonucleotide probe contains a 70 base 3' target-specific portion, a 70 base 5' target-specific portion, and 20-160 base composite identifier sequence (thin line).

The oligonucleotide probe design shown in FIG. 98 is similar to that shown in FIG. 96. In this embodiment, the oligonucleotide probe contains a 70 base 5' or upstream target-specific portion, a 70 base 3' or downstream target-specific portion and a 20-160 base identifier sequence. An illustration of the oligonucleotide probes of this Figure hybridized to their target cfDNA fragment is also provided in FIGS. 23, 24, 25 and 26.

Figure 99:
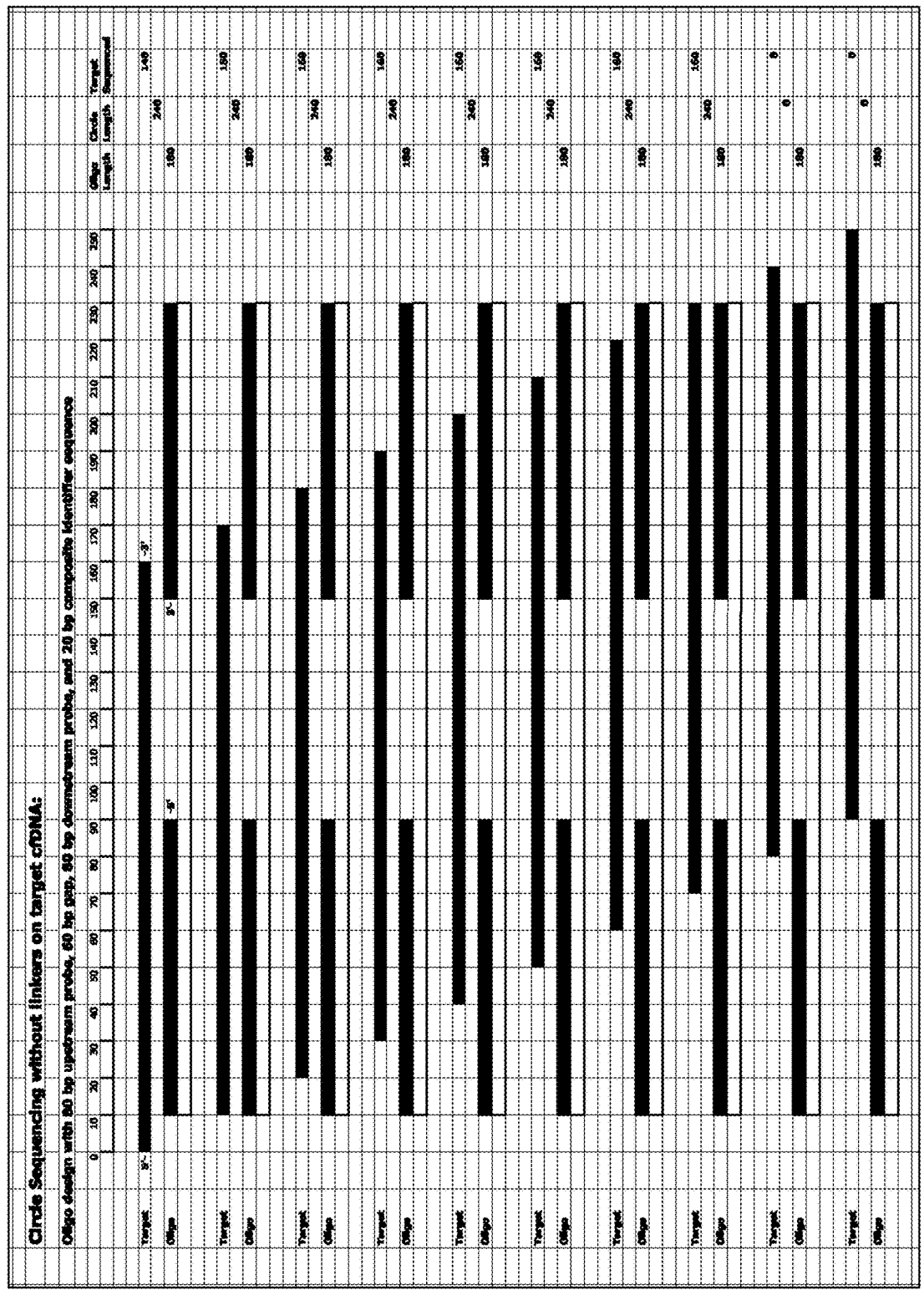
FIG. 99 shows the mapping of a family of oligonucleotide probes ("oligo"), along a collection of cfDNA target fragments (160 nucleotides in length) in 10 nucleotide base increments. Each oligonucleotide probe contains a 80 base 3' target-specific portion, a 80 base 5' target-specific portion, and 20-160 base composite identifier sequence (thin line).

The oligonucleotide probe design shown in FIG. 99 is similar to that shown in FIG. 96. In this embodiment, the oligonucleotide probe contains an 80 base 5' or upstream target-specific portion, an 80 base 3' or downstream target-specific portion and a 20-160 base identifier sequence. An illustration of the oligonucleotide probes of this Figure hybridized to their target cfDNA fragment is also provided in FIGS. 23-26.

Figure 100:
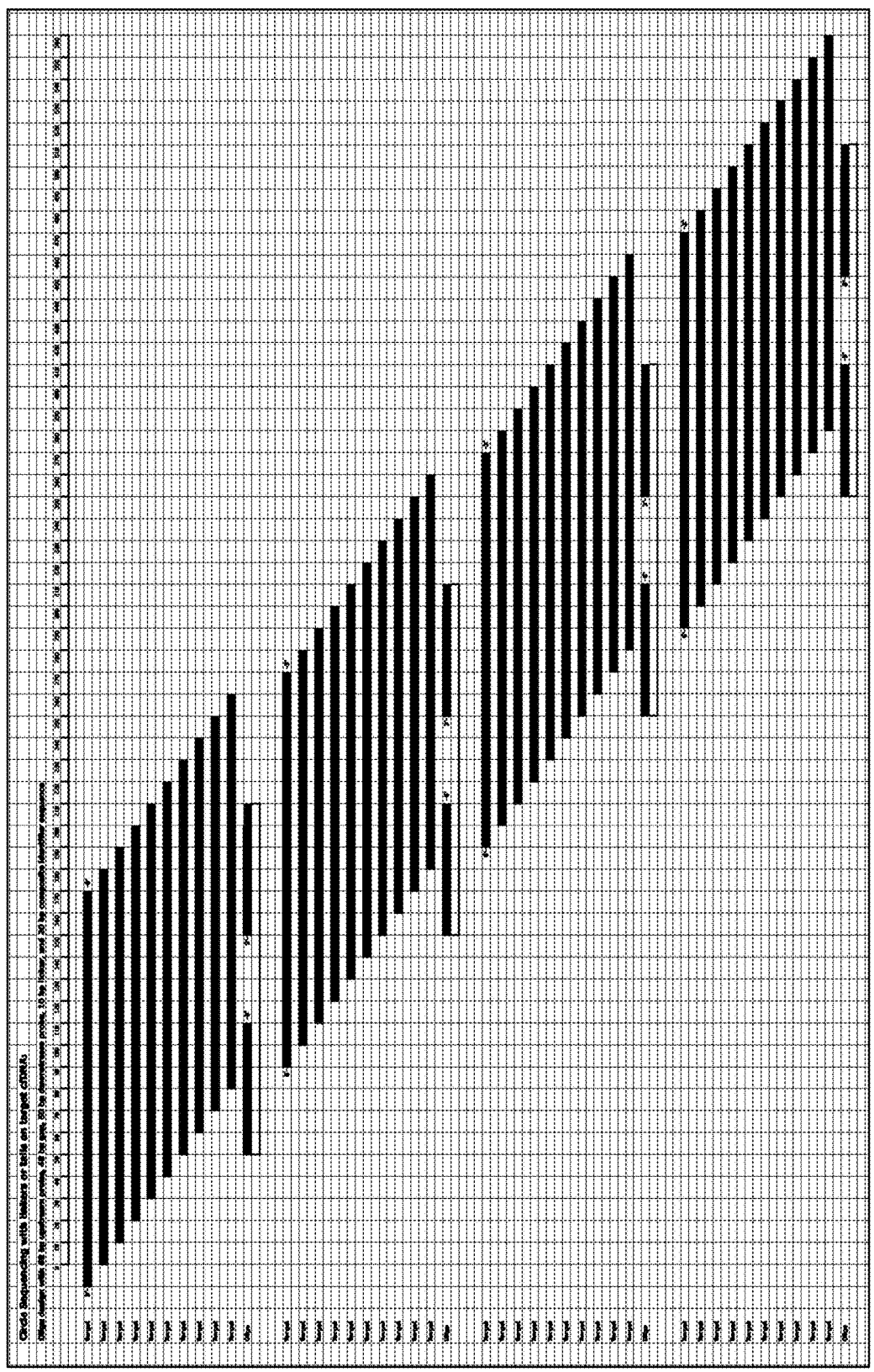
FIG. 100 illustrates how to design oligonucleotide probes with an overlapping tiling strategy to sequence larger contiguous target regions (about 500 bases shown as an example).

FIGS. 100 to 103 show the coverage of a target region by target specific oligonucleotide probes having 3' and/or 5' linker regions as it is tiled across adjacent 160 bp target regions. Specifically, FIG. 100 illustrates how to design oligonucleotide probes with an overlapping tiling strategy to sequence larger contiguous regions (about 500 bases shown as an example). The target region sequence that is detected is depicted by the dark grey portion. The target region sequence that is not detected is depicted as the light grey portion, and linkers are depicted as the black portion. Each successive vertical grouping in this Figure illustrates the probe coverage obtained by sliding the 160 bp target regions found in randomly generated cfDNA fragments (or randomly sheared fragments). The target region is successively slide by 10 base increments to demonstrate coverage of target region by a single probe. Each successive vertical grouping from left to right illustrates the target region coverage and probe overlap by a $2^{nd}$, $3^{rd}$ and $4^{th}$ different probe. The oligonucleotide probe structure shown here (below each vertical grouping) contains a 60 base 5' or upstream target specific probe portion, a 50 base 3' or downstream probe, a 10 base linker portion and a 20-160 bp identifier region (thin lines).

Figure 101:
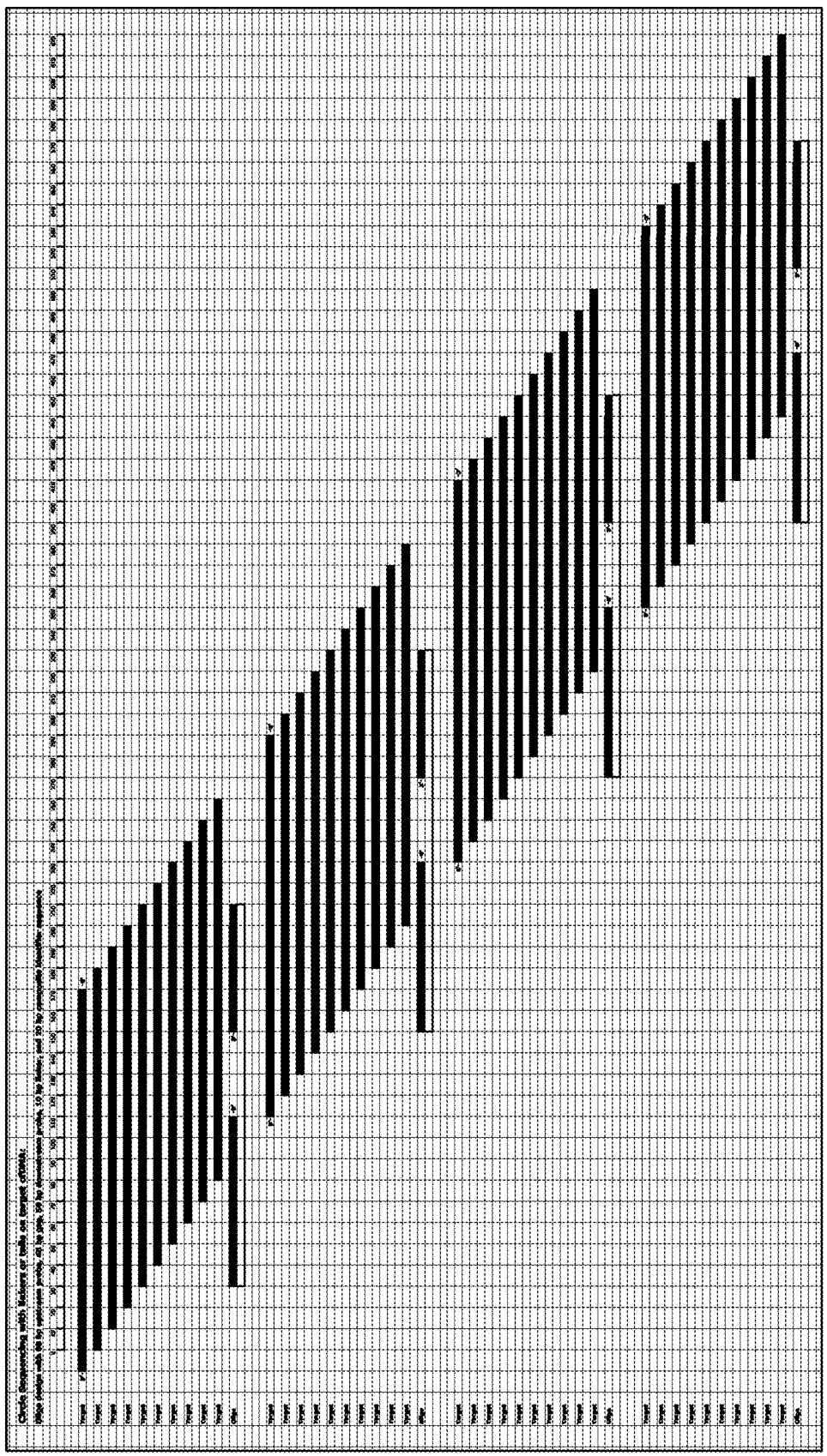
FIG. 101 illustrates how to design oligonucleotide probes with an overlapping tiling strategy to sequence larger contiguous target regions (about 500 bases shown as an example).

FIG. 101 shows a similar illustration of how to design oligonucleotide probes with an overlapping tiling strategy to sequence larger contiguous regions as shown in FIG. 100. The oligonucleotide probe structure shown here contains a 80 base 5' or upstream target specific probe portion, a 50 base 3' or downstream probe, a 10 base linker portion and a 20-160 bp identifier region (thin lines).

Figure 102:
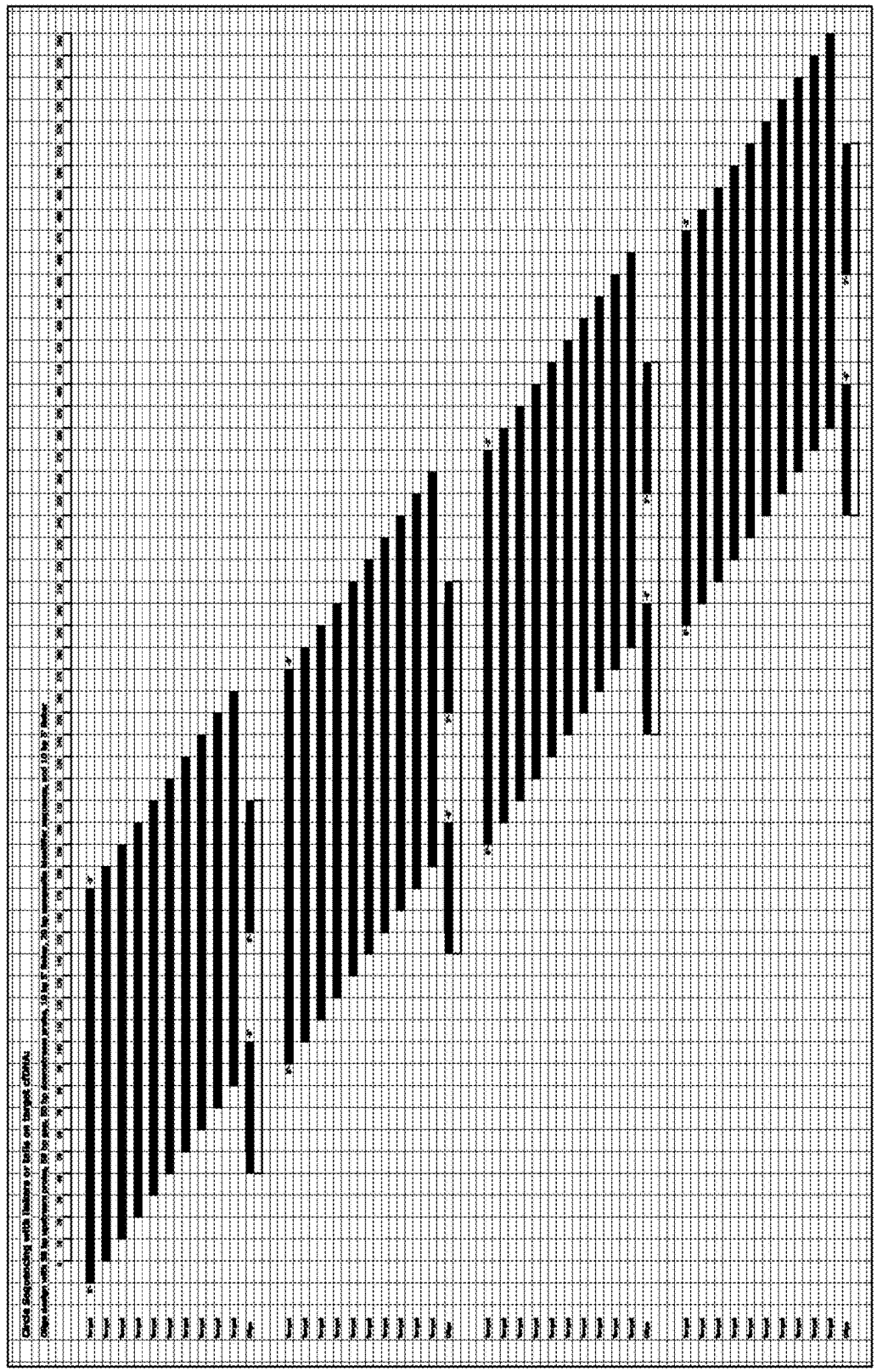
FIG. 102 illustrates how to design oligonucleotide probes with an overlapping tiling strategy to sequence larger contiguous target regions (about 500 bases shown as an example).

FIG. 102 shows a similar illustration of how to design oligonucleotide probes with an overlapping tiling strategy to sequence larger contiguous regions as shown in FIG. 100. The oligonucleotide probe structure shown here contains a 50 base 5' or upstream target specific probe portion, a 50 base 3' or downstream probe, a 10 base 5' and 3' linker portions and a 20-160 bp identifier region (thin lines).

Figure 103:
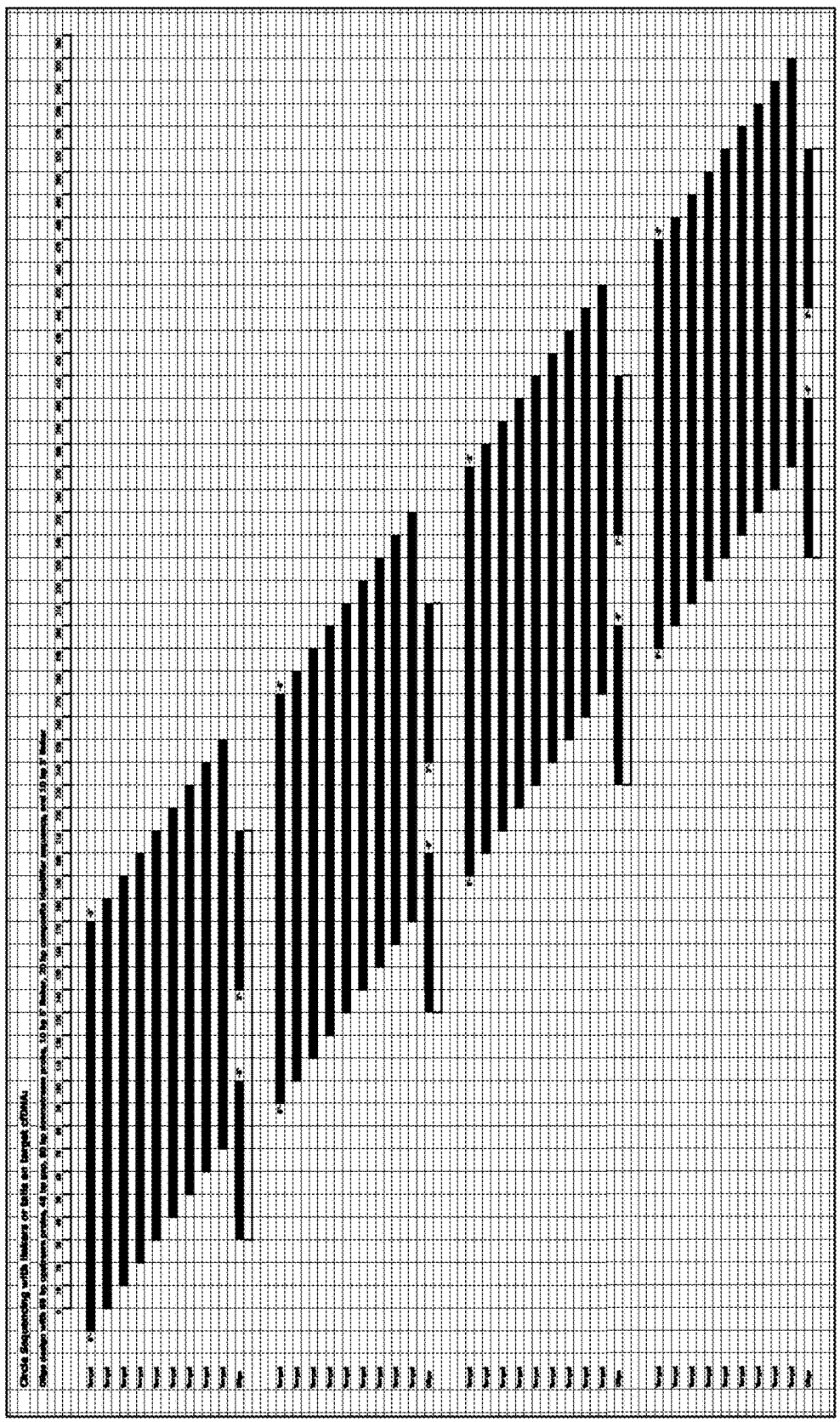
FIG. 103 illustrates how to design oligonucleotide probes with an overlapping tiling strategy to sequence larger contiguous target regions (about 500 bases shown as an example).

FIG. 103 shows a similar illustration of how to design oligonucleotide probes with an overlapping tiling strategy to sequence larger contiguous regions as shown in FIG. 100. The oligonucleotide probe structure shown here contains a 60 base 5' or upstream target specific probe portion, a 60 base 3' or downstream probe, a 10 base 5' and 3' linker portions and a 20-160 bp identifier region (thin lines).

Figure 104:
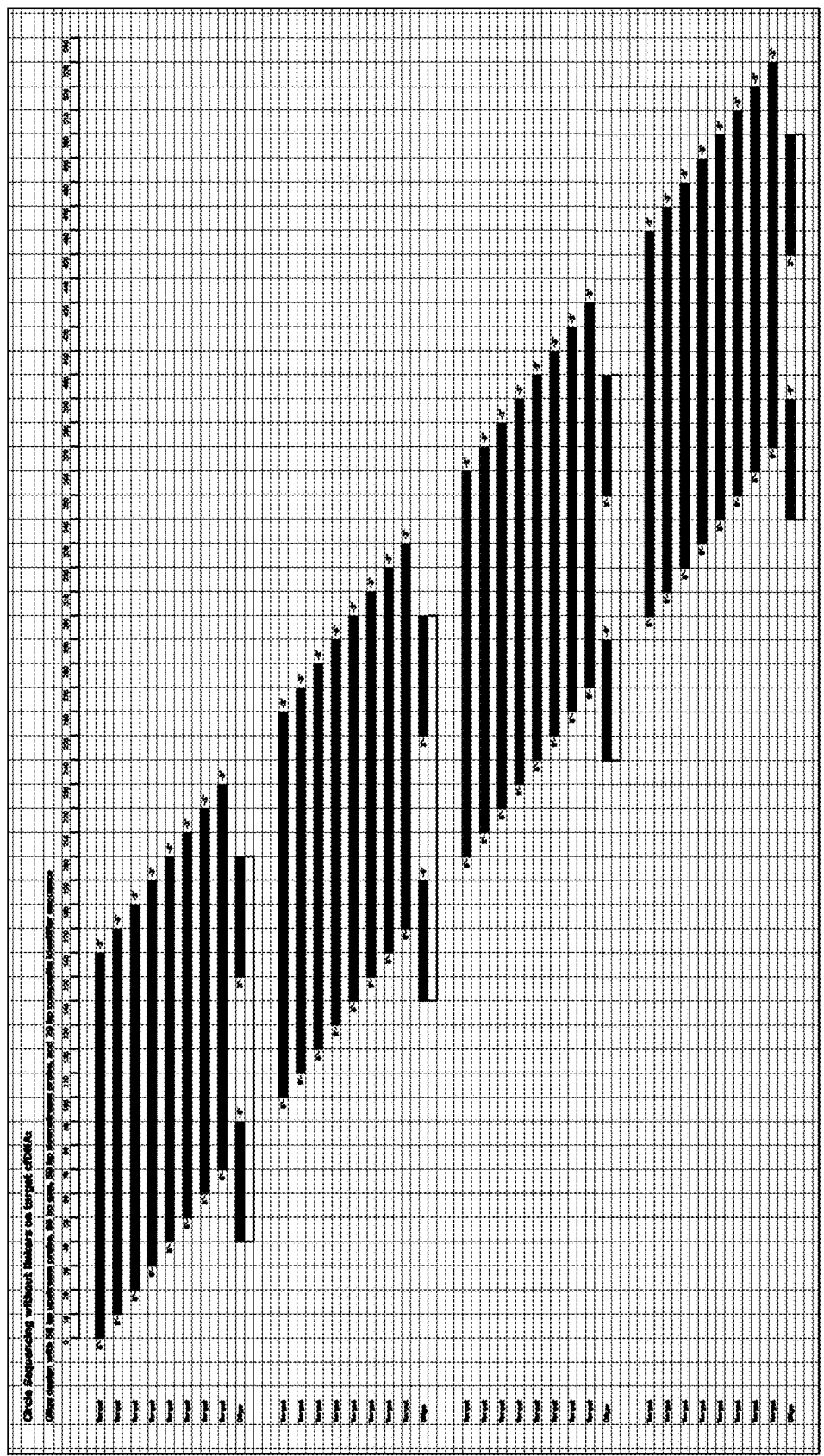
FIG. 104 shows target specific phased marked oligonucleotides tiled across adjacent 160 bp gene targets in a stretch of genomic DNA.

FIGS. 104 to 107 show the coverage of a target region by target specific phased marked oligonucleotides without 3' or 5' linkers as they are tiled across adjacent 160 bp target gene regions (represents process shown in FIGS. 20 and 22). The oligonucleotide probes having a 50 base 5'- and 3'-target specific regions contain a single base mismatch every 10 bases (vertical hash marks). Target region sequence which is detected (dark grey); target region sequence which is not detected (light grey). Specifically, FIG. 104 shows target specific phased marked oligonucleotides tiled across adjacent 160 bp gene targets (target segments are not appended with linkers) in a stretch of genomic DNA. 5'- and 3'-target specific probes have single base mismatch every 10 bases (vertical hash marks). Each successive grouping in the figure illustrates the simulation of probe coverage of sliding 160 bp target regions found in cfDNA. Target region is successively slid by 10 base increments to demonstrate coverage of target region by a single probe. Each successive grouping from left to right illustrates the target region coverage and probe overlap by a $2^{nd}$, $3^{rd}$ and $4^{th}$ different probe. The oligonucleotide probe structure shown in this figure contains a 50 base 5' or upstream target specific portion, a 50 base 3' or downstream target specific portion, and 20-160 base sequence identifier region.

Figure 105:
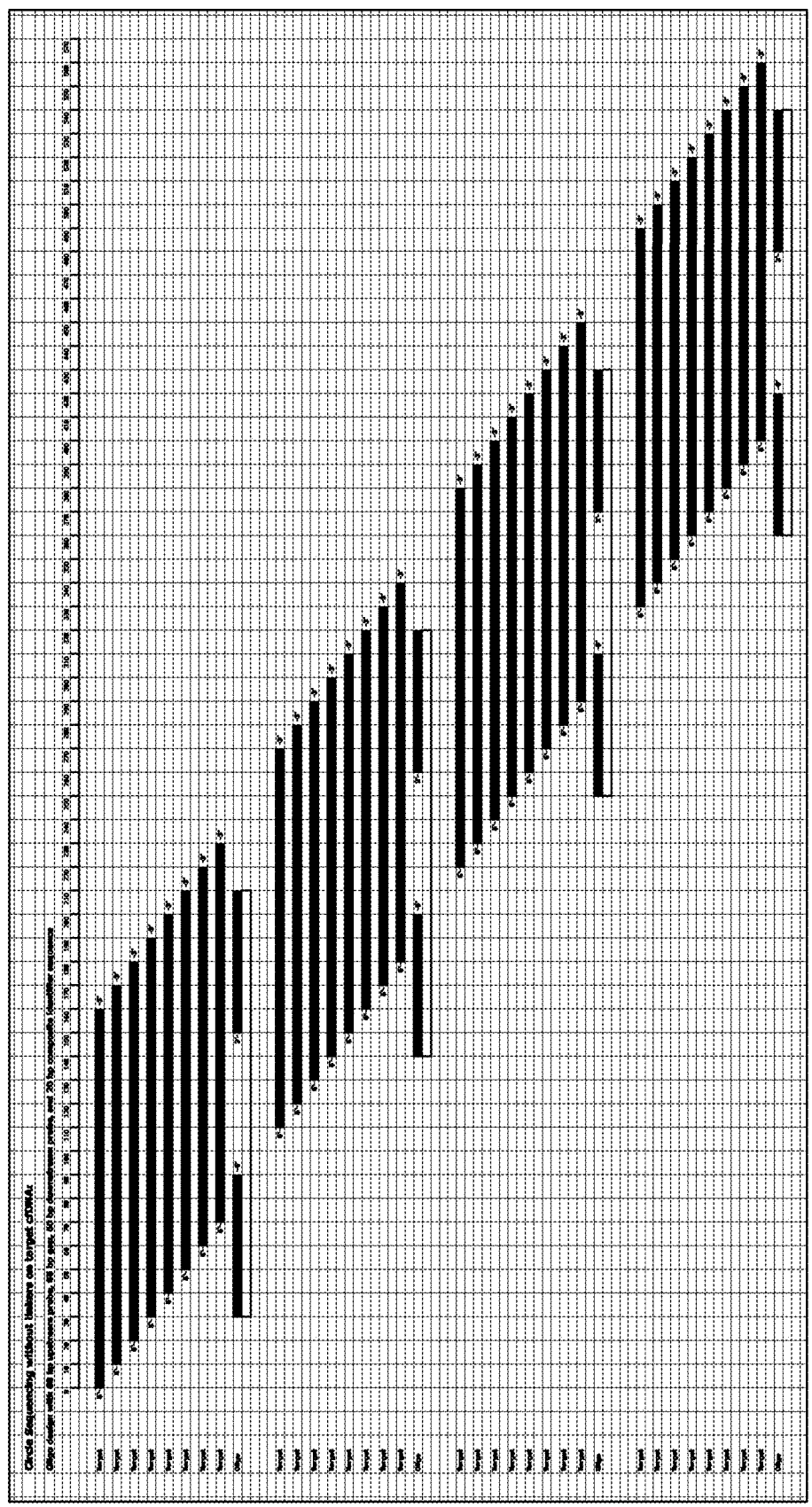
FIG. 105 shows target specific phased marked oligonucleotides tiled across adjacent 160 bp gene targets in a stretch of genomic DNA.

FIG. 105 shows a similar approach for target specific phased marked oligonucleotides tiled across adjacent 160 bp gene targets as shown in FIG. 104. The oligonucleotide probe structure shown in this figure contains a 60 base 5' or upstream target specific portion, a 60 base 3' or downstream target specific portion, and 20-160 base sequence identifier region.

Figure 106:
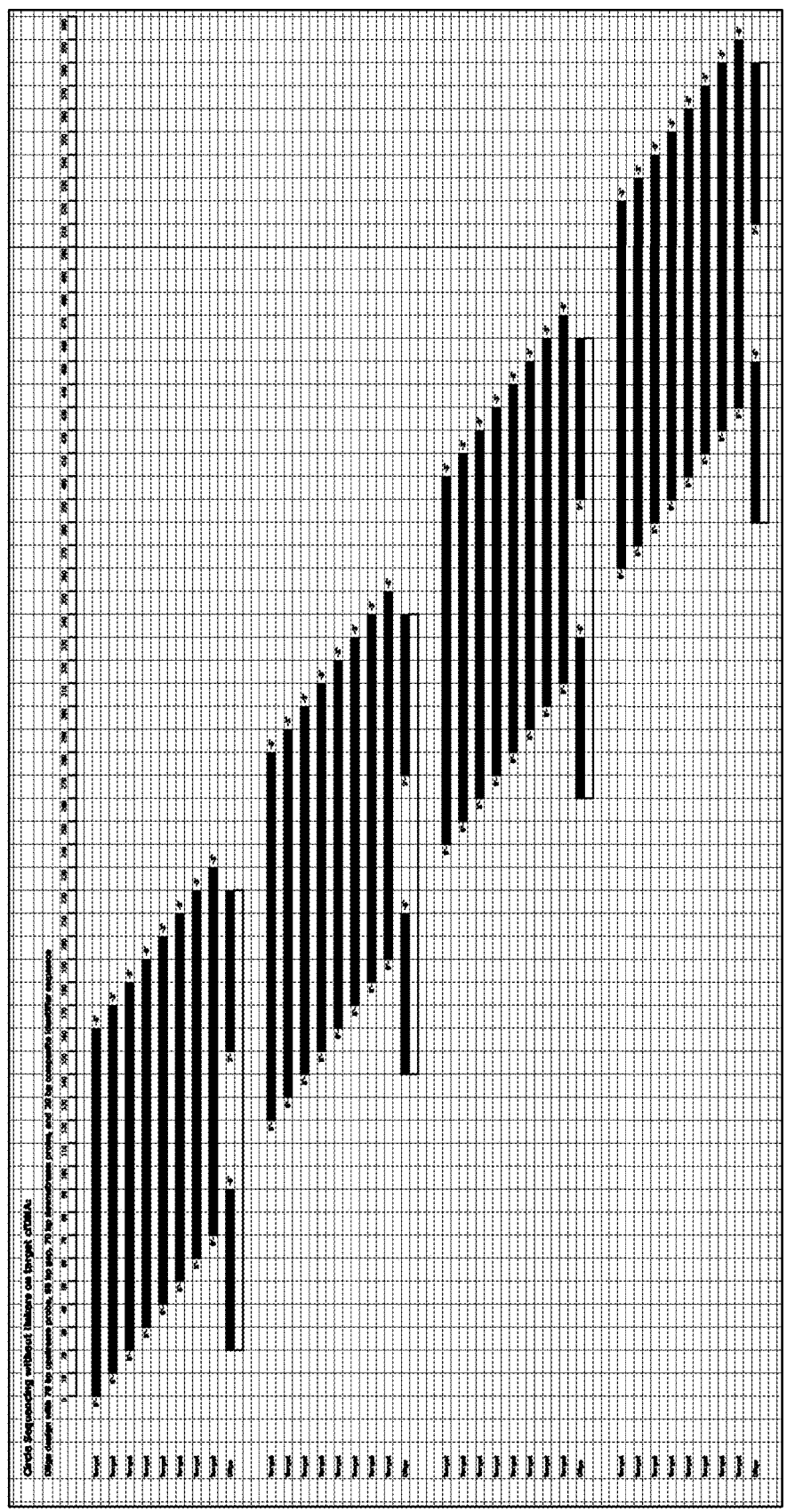
FIG. 106 shows target specific phased marked oligonucleotides tiled across adjacent 160 bp gene targets in a stretch of genomic DNA.

FIG. 106 shows a similar approach for target specific phased marked oligonucleotides tiled across adjacent 160 bp gene targets as shown in FIG. 104. The oligonucleotide probe structure shown in this figure contains a 70 base 5' or upstream target specific portion, a 70 base 3' or downstream target specific portion, and 20-160 base sequence identifier region.

Figure 107:
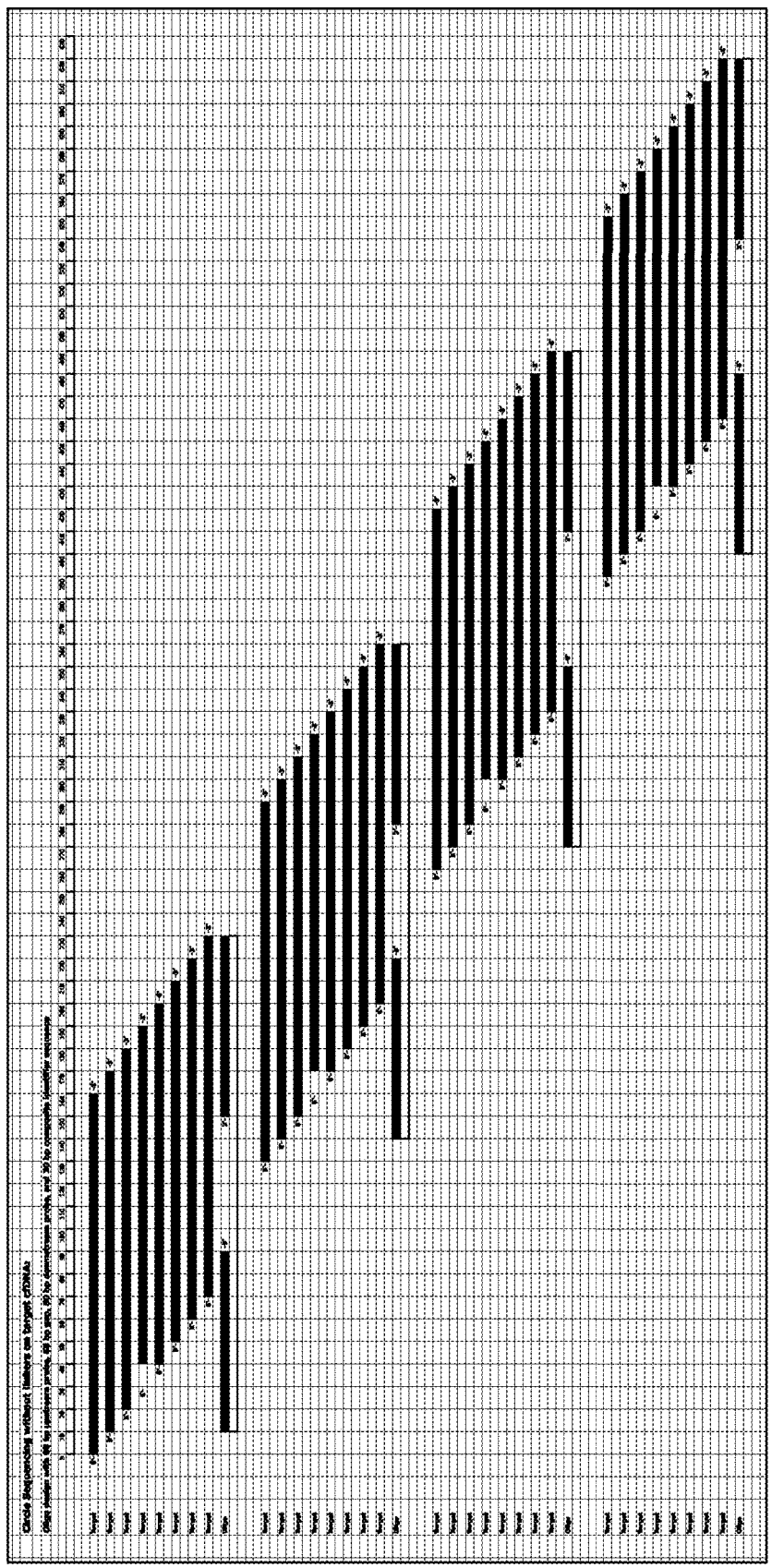
FIG. 107 shows target specific phased marked oligonucleotides tiled across adjacent 160 bp gene targets in a stretch of genomic DNA.

FIG. 107 shows a similar approach for target specific phased marked oligonucleotides tiled across adjacent 160 bp gene targets as shown in FIG. 104. The oligonucleotide probe structure shown in this figure contains an 80 base 5' or upstream target specific portion, an 80 base 3' or downstream target specific portion, and 20-160 base sequence identifier region.

Another aspect of the present invention is directed to a method for identifying, in a sample, one or more target ribonucleic acid molecules differing from other nucleic acid molecules in the sample by one or more bases. This method involves providing a sample containing one or more target ribonucleic acid molecules potentially containing one or more base differences and generating, in the sample, cDNA of the one or more target ribonucleic acid molecules, if present in the sample. The method further involves providing one or more first oligonucleotide probes, each first oligonucleotide probe comprising (a) a 3' cDNA target-specific sequence portion, (b) a 5'cDNA target specific portion, and a further portion, said further portion comprising (i) a unique identifier sequence, (ii) a patient identifier sequence, (iii) one or more primer binding sequences, or any combination of (i), (ii), and (iii). The sample is contacted with the one or more first oligonucleotide probes under conditions effective for 3' and 5' target specific portions of the first oligonucleotide probes to hybridize in a base specific manner to complementary regions of the cDNA. One or more ligation competent junctions suitable for coupling 3' and 5' ends of a first oligonucleotide probe hybridized to its complementary cDNA is generated and the first oligonucleotide probe, at the one or more ligation junctions, is ligated to form a ligated circular product comprising a deoxyribonucleic acid copy of the target ribonucleic acid sequence coupled to the further portion of the first oligonucleotide probe. The method further involves detecting and distinguishing the circular ligated products in the sample to identify the presence of one or more target ribonucleic acid molecules differing from other ribonucleic acid molecules in the sample by one or more bases.

Figure 108:
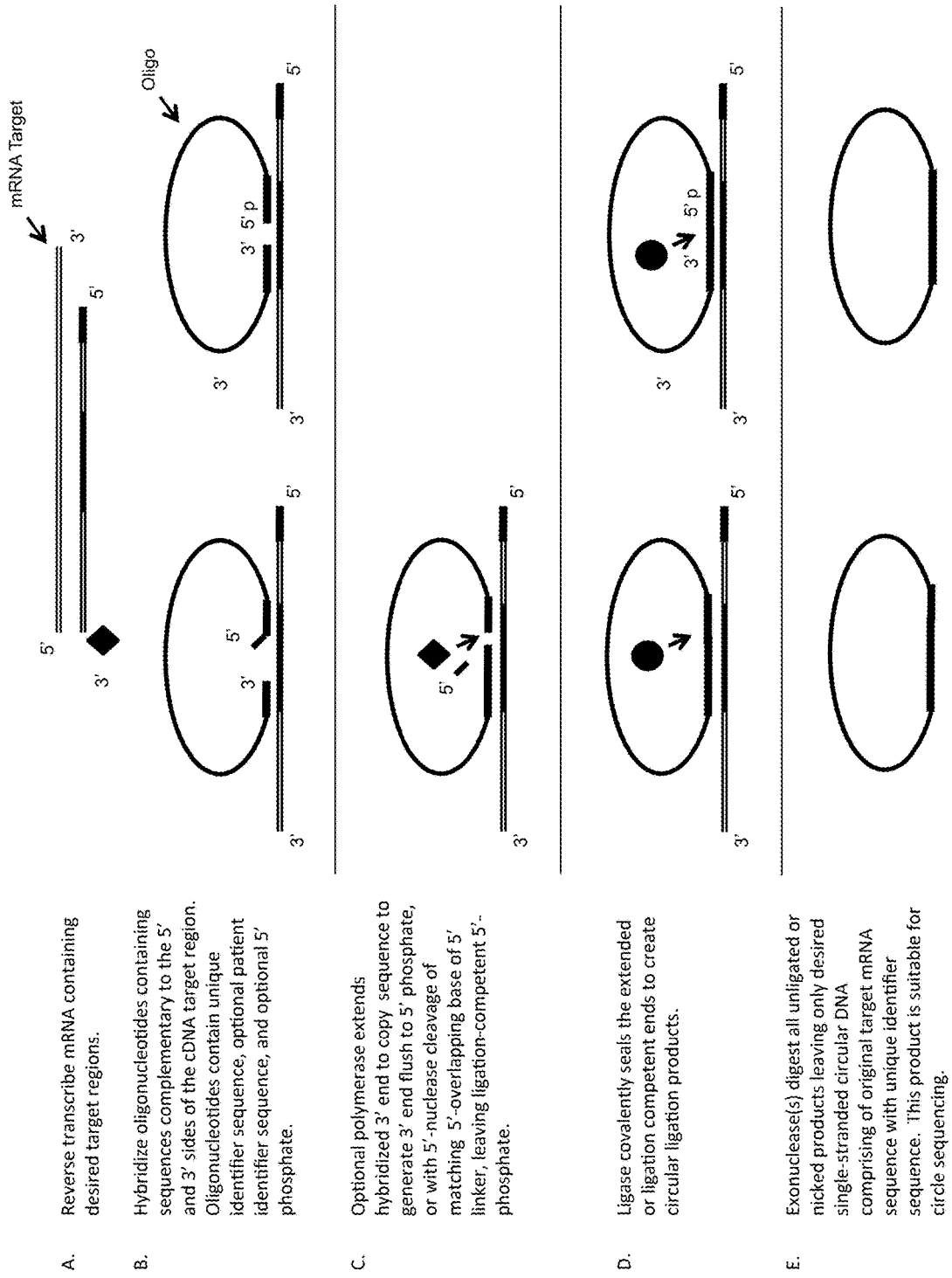
FIG. 108 depicts a method of generating circular chimeric single-stranded nucleic acid constructs that comprise a deoxyribonucleic sequence copy of a target ribonucleic acid molecule. The circular constructs are suitable for RCA and sequencing in accordance with the methods of the present invention.

In accordance with this aspect of the present invention, FIG. 108 shows a process for the target specific capture of mRNA or lncRNA transcripts for sequencing. As shown in FIG. 108, step A, mRNA or lncRNA containing the desired target regions is reverse transcribed (reverse transcription—filled diamond) to generate a complementary DNA (cDNA) molecule. As shown in FIG. 108, step B, an oligonucleotide probe containing 5' and 3' sequences complementary to the cDNA target region is hybridized to the cDNA molecule. The target-specific portions of the oligonucleotide probe are separated by a further portion. The further portion comprises a unique identifier portion, optionally a patient identifier portion, and optionally a 5' phosphate. If necessary, a polymerase (filled diamond) extends the hybridized 3' end of the oligonucleotide probe to generate a 3' end flush to the 5' end of the oligonucleotide probe (FIG. 108, step C). In the absence of a ligation competent phosphate on the 5' end, a polymerase having 5'-nuclease activity cleaves the matching 5'-overlapping base on the 5' end to generate a 5'-phosphate (left side of FIG. 108, step C). As shown in FIG. 108, step D, ligase (filled circles) covalently seals the extended or ligation competent ends to create circular ligation products. Finally, as shown in FIG. 108, step E, exonuclease digestion removes all unligated or nicked products leaving only the desired single-stranded circular construct comprising a cDNA copy of the target ribonucleic acid sequence coupled to a unique identifier sequence or patient identifier sequence. This product is suitable for rolling circle amplification and sequencing using any of the methods described herein.

Another aspect of the present invention is directed to a method for identifying, in a sample, one or more nucleic acid molecules potentially comprising distinct first target and second target regions coupled to each other (e.g., putative gene fusions). This method involves providing a sample potentially containing one or more nucleic acid molecules comprising distinct first target and second target regions coupled to each other, and providing one or more oligonucleotide probe sets, each probe set comprising (i) a first oligonucleotide probe comprising a 5' first target-specific portion, a 3' second target specific portion, and a further portion, and (ii) a second oligonucleotide probe comprising a 5' second target specific portion, a 3' first target specific portion, and a further portion, wherein the further portion of the first or second oligonucleotide probes of a probe set comprises (i) a unique identifier sequence, (ii) a patient identifier sequence, (iii) one or more primer binding sequences, or any combination of (i), (ii), and (iii). This method further involves contacting the sample and the one or more oligonucleotide probe sets under conditions effective for first and second oligonucleotide probes of a probe set to hybridize in a base specific manner to their corresponding first and second target regions of the nucleic acid molecule, if present in the sample, and generating one or more ligation competent junctions suitable for coupling 3' ends of first oligonucleotide probes to 5' ends of second oligonucleotide probes of a probe set and for coupling 5' ends of first oligonucleotide probes to 3' ends of second oligonucleotide probes of a probe set when said probe sets are hybridized to complementary first and second target regions of a nucleic acid molecule. The first and second oligonucleotides of a probe set are ligated at the one or more ligation competent junctions to form circular ligated products comprising a nucleotide sequence corresponding to the first and second distinct target regions of a nucleic acid molecule coupled to a further portion. The circular ligated products are detected and distinguished in the sample thereby identifying the presence, if any, of one or more nucleic acid molecules comprising distinct first target and second target regions coupled to each other in the sample.

Figure 109:
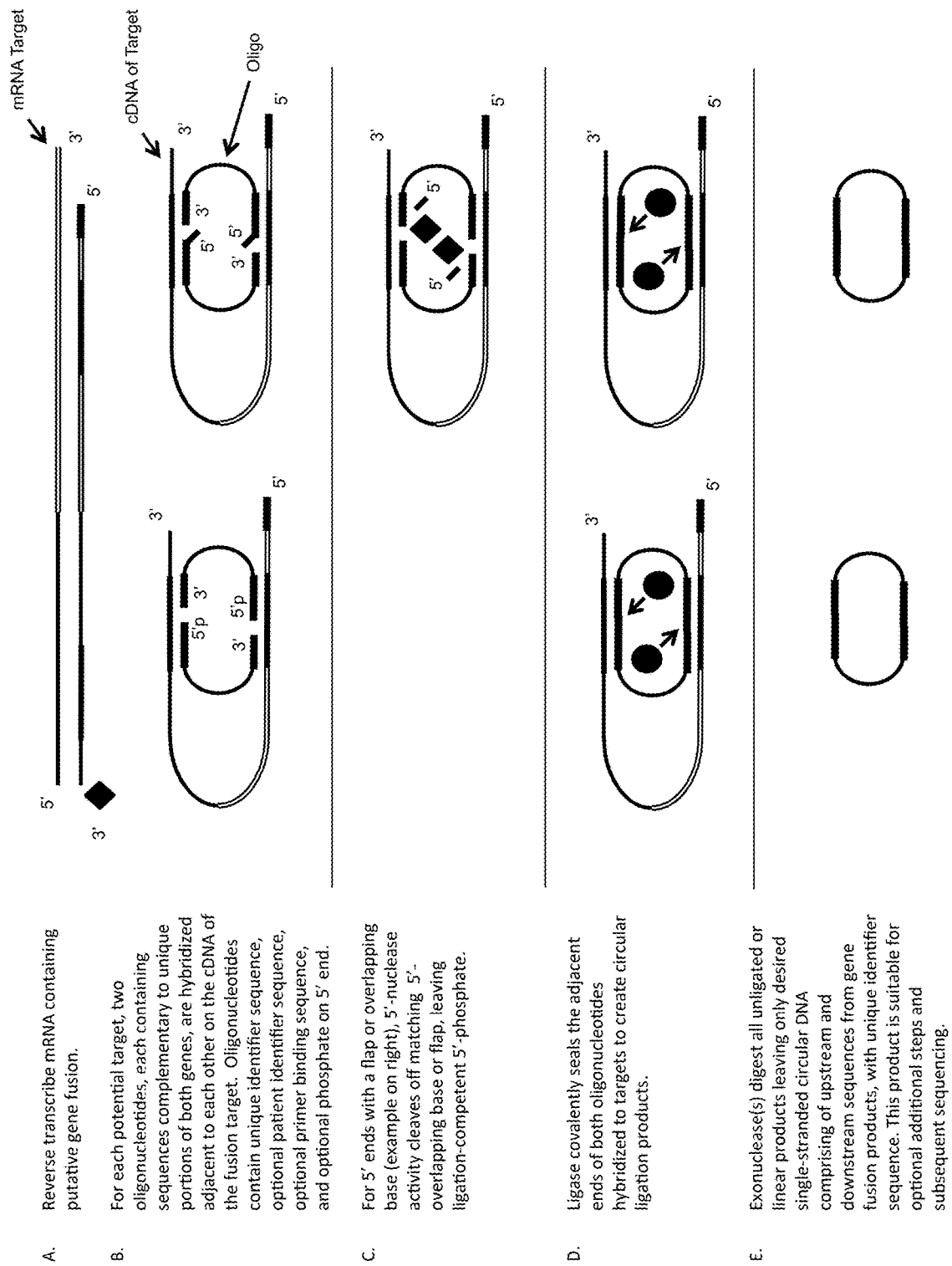
FIG. 109 depicts a method of generating circular chimeric single-stranded nucleic acid constructs that comprise a deoxyribonucleic sequence copy of a target ribonucleic acid molecule containing putative gene fusions. The circular constructs are suitable for RCA and sequencing in accordance with the methods of the present invention.

In accordance with this aspect of the present invention, FIG. 109, steps A-E show an exemplary process for detecting specific putative gene fusions in mRNAs. mRNA containing the putative gene fusion is reverse transcribed to generate a cDNA molecule (FIG. 109, step A). For each potential target, a probe set comprising a first and second oligonucleotide probe is provided. The first probe has a 5' first target-specific portion and a 3' second target specific portion, while the second probe has a 5' second target specific portion and a 3' first target specific portion. The target specific portions of each probe are separated by a nucleotide sequence that contains a unique identifier sequence, a patient identifier sequence, one or more primer binding sequences, or any combination thereof. The oligonucleotide probes hybridize to their respective complementary portions of the target cDNA molecule as shown in FIG. 109, step B. If the oligonucleotide probes contain ligation competent 5' ends, a ligase covalently seals the adjacent ends of the hybridized oligonucleotides to create a circular ligation product as shown in FIG. 109, step D (left panel). If the oligonucleotide probes contain a 5' flap or overlapping nucleotide base, a 5' nuclease cleaves the 5' end to generate a ligation-competent 5'-phosphate (FIG. 109, step C) prior to ligation (FIG. 109, step D, right panel). Exonuclease digestion removes all unligated or linear products leaving only the desired single-stranded circularized DNA constructs comprising the upstream and downstream sequences from gene fusion products coupled to a unique identifying, a patient identifying, and/or capture sequence (e.g., primer binding sequence). This product is suitable for rolling circle amplification and subsequent sequencing as described herein.

Figure 110:
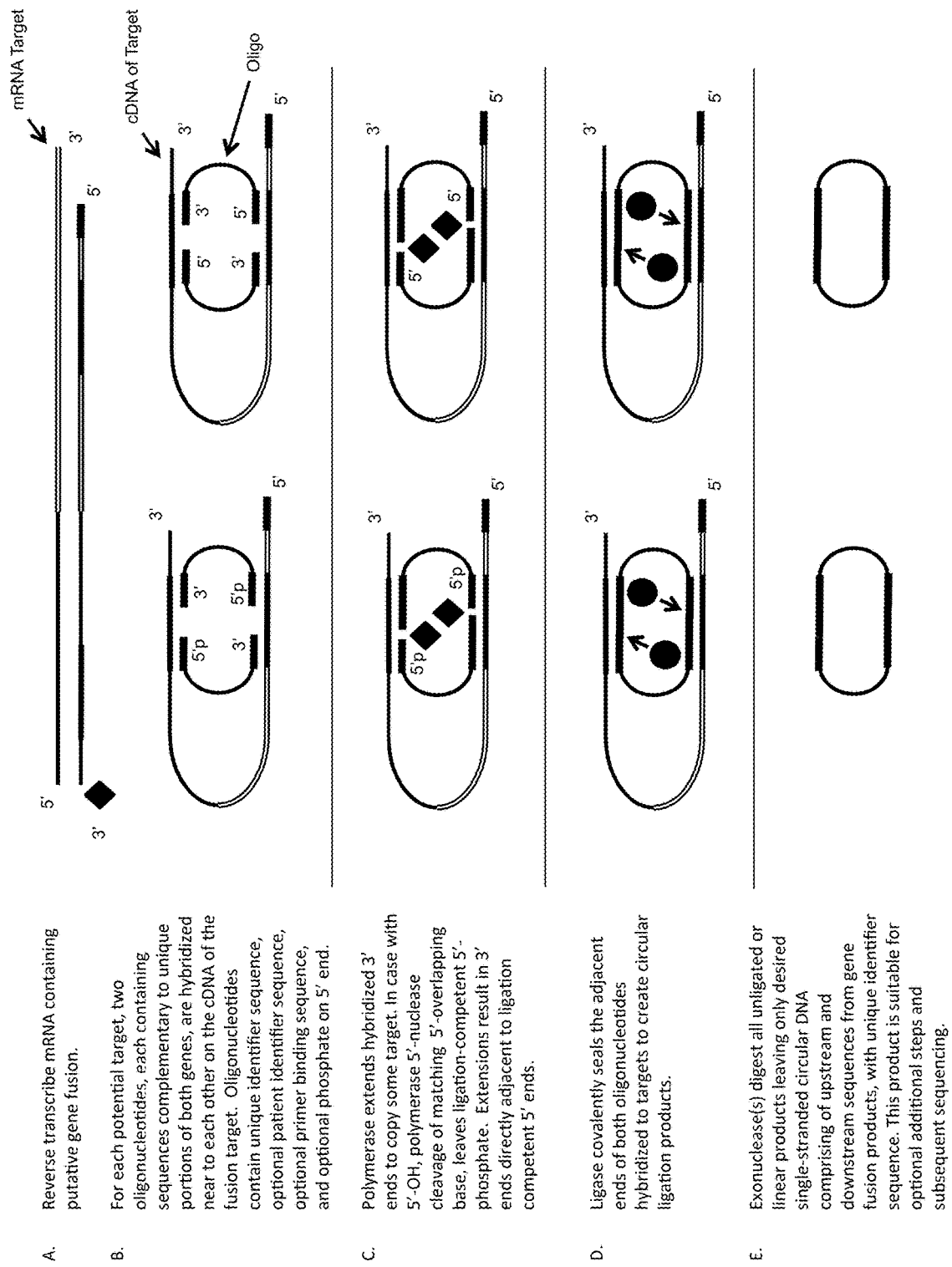
FIG. 110 depicts a method of generating circular chimeric single-stranded nucleic acid constructs that comprise a deoxyribonucleic sequence copy of a target ribonucleic acid molecule containing putative gene fusions. The circular constructs are suitable for RCA and sequencing in accordance with the methods of the present invention.

FIG. 110 shows a variation of the process depicted in FIG. 109 for detecting specific putative gene fusions in mRNAs. In this embodiment, the first and second oligonucleotide probes hybridize to their respective complementary regions of the cDNA molecule as shown in FIG. 110, step B. A polymerase extends the hybridized 3' ends of each first and second probe to form ligation junctions with the hybridized 5' ends of the second and first probes, respectively as shown in FIG. 110, step C. When the oligonucleotide probes have a 5'-OH (right side of FIG. 110, step C), 5'-nuclease activity of the polymerase cleaves the matching 5'-overlapping base, leaving a ligation-competent 5'-phosphate. Ligase (filled circles) covalently seals the adjacent ends of the hybridized first and second oligonucleotides probes to create circular ligation products (FIG. 110, step D). Exonuclease digestion removes unligated or linear products leaving only the desired single-stranded circular DNA constructs comprising the upstream and downstream sequences from gene fusion products coupled to a unique identifier sequence, a patient identifier sequence, and/or capture sequence (i.e., primer binding sequence). This product is suitable for rolling circle amplification and subsequent sequencing as described herein.

Figure 111:
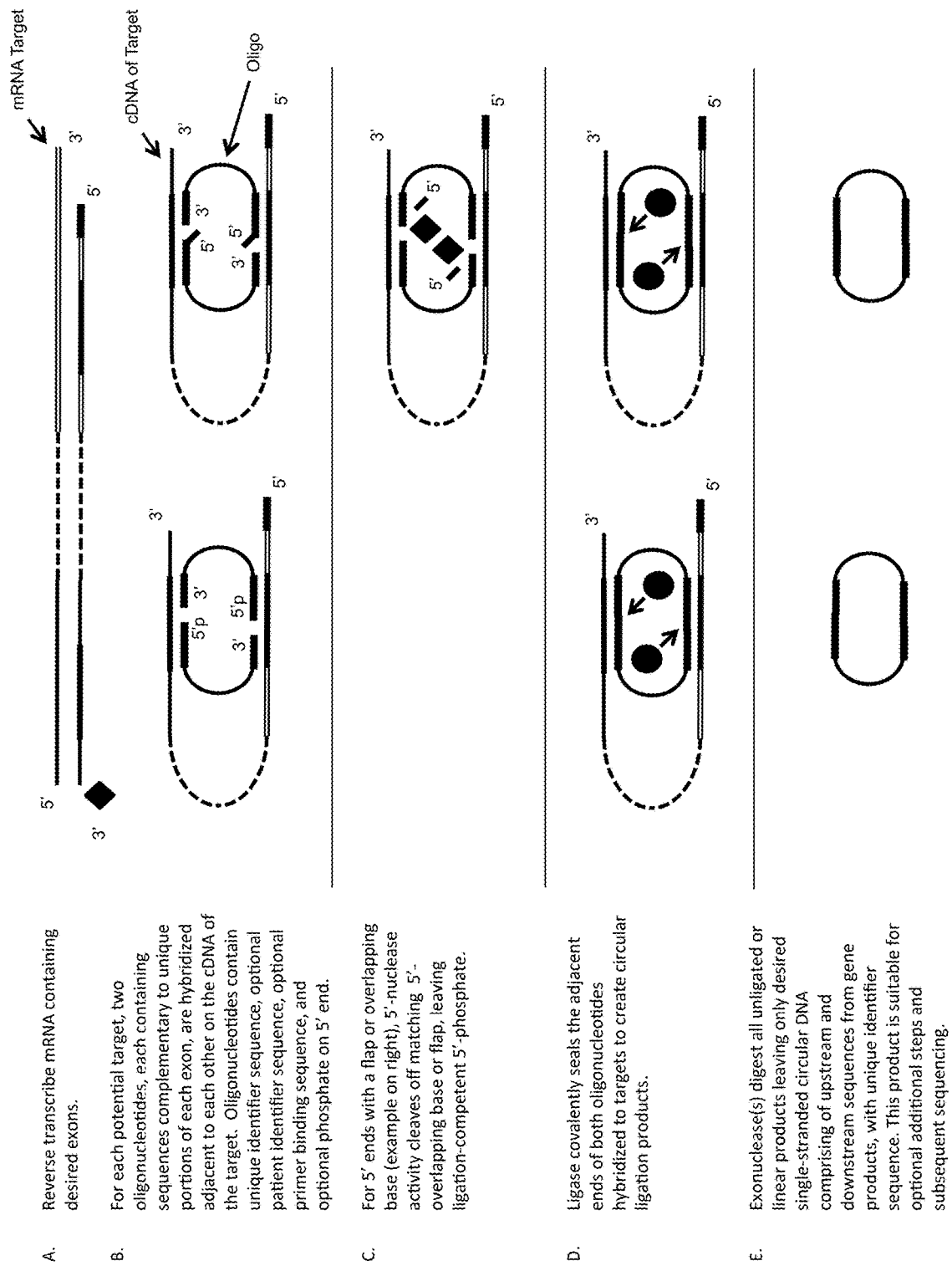
FIG. 111 depicts a method of generating circular chimeric single-stranded nucleic acid constructs that comprise a deoxyribonucleic sequence copy of a target ribonucleic acid molecule containing specific exons. The circular constructs are suitable for RCA and sequencing in accordance with the methods of the present invention.

FIG. 111 shows another process in accordance with this aspect of the invention that is suitable for the detection and quantitation of specific exons in mRNA or lncRNA. In this embodiment, mRNA or lncRNA containing the desired exons is reverse transcribed into cDNA (FIG. 111, step A). As shown in FIG. 111, step B, for each potential target, two oligonucleotide probes are provided, each probe containing 3' and 5' target-specific sequences complementary to unique portions of each exon of the cDNA molecule. The target specific portions of each probe are separated by a nucleotide sequence that contains a unique identifier sequence, a patient identifier sequence, one or more primer binding sequences, or any combination thereof. The probes are hybridized adjacent to each other on the cDNA of the target as shown in FIG. 111, step B. If the oligonucleotide probes contain ligation competent 5' ends, a ligase covalently seals the adjacent ends of the hybridized oligonucleotides to create a circular ligation product as shown in FIG. 111, step D (left panel). If the oligonucleotide probes contain a 5' flap or overlapping nucleotide base, a 5' nuclease cleaves the 5' end to generate a ligation-competent 5'-phosphate (FIG. 111, step C) prior to ligation (FIG. 111, step D, right panel). Exonuclease digestion removes all unligated or linear products leaving only the desired single-stranded circularized DNA constructs comprising the cDNA sequence of the desired exons coupled to a unique identifier sequence, a patient identifier sequence, and/or capture sequence (e.g., primer binding sequence). This product is suitable for rolling circle amplification and subsequent sequencing as described herein.

Figure 112:
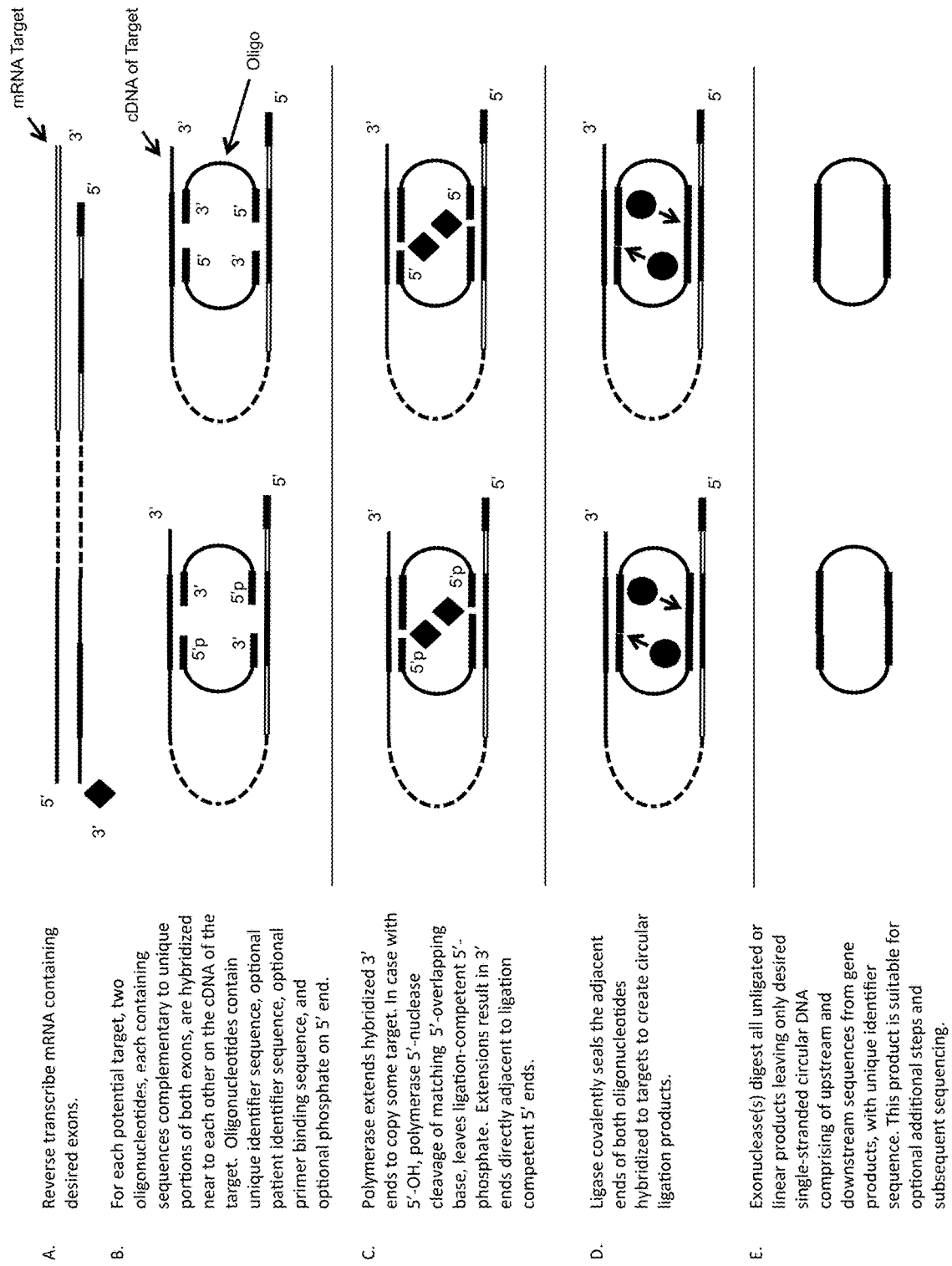
FIG. 112 depicts a method of generating circular chimeric single-stranded nucleic acid constructs that comprise a deoxyribonucleic sequence copy of a target ribonucleic acid molecule containing specific exons. The circular constructs are suitable for RCA and sequencing in accordance with the methods of the present invention.

FIG. 112 shows a variation of the process depicted in FIG. 111 for detecting and quantifying specific exons in mRNA or lncRNA. In this embodiment, the first and second oligonucleotide probes hybridize to their respective complementary region of the cDNA molecule as shown in FIG. 112, step B. A polymerase extends the hybridized 3' ends of each first and second probe to form ligation junctions with the hybridized 5' ends of the second and first probes, respectively as shown in FIG. 112, step C. When the oligonucleotide probes have a 5'-OH (right side of FIG. 110, step C), 5'-nuclease activity of the polymerase cleaves the matching 5'-overlapping base, leaving a ligation-competent 5'-phosphate. Ligase (filled circles) covalently seals the adjacent extended ends of the hybridized first and second oligonucleotides probes to create circular ligation products (FIG. 112, step D). Exonuclease digestion removes unligated or linear products leaving only the desired single-stranded circular DNA constructs comprising the cDNA sequence of the desired exons coupled to a unique identifier sequence, a patient identifier sequence, and/or capture sequence (i.e., primer binding sequence). This product is suitable for rolling circle amplification and subsequent sequencing as described herein.

Figure 113:
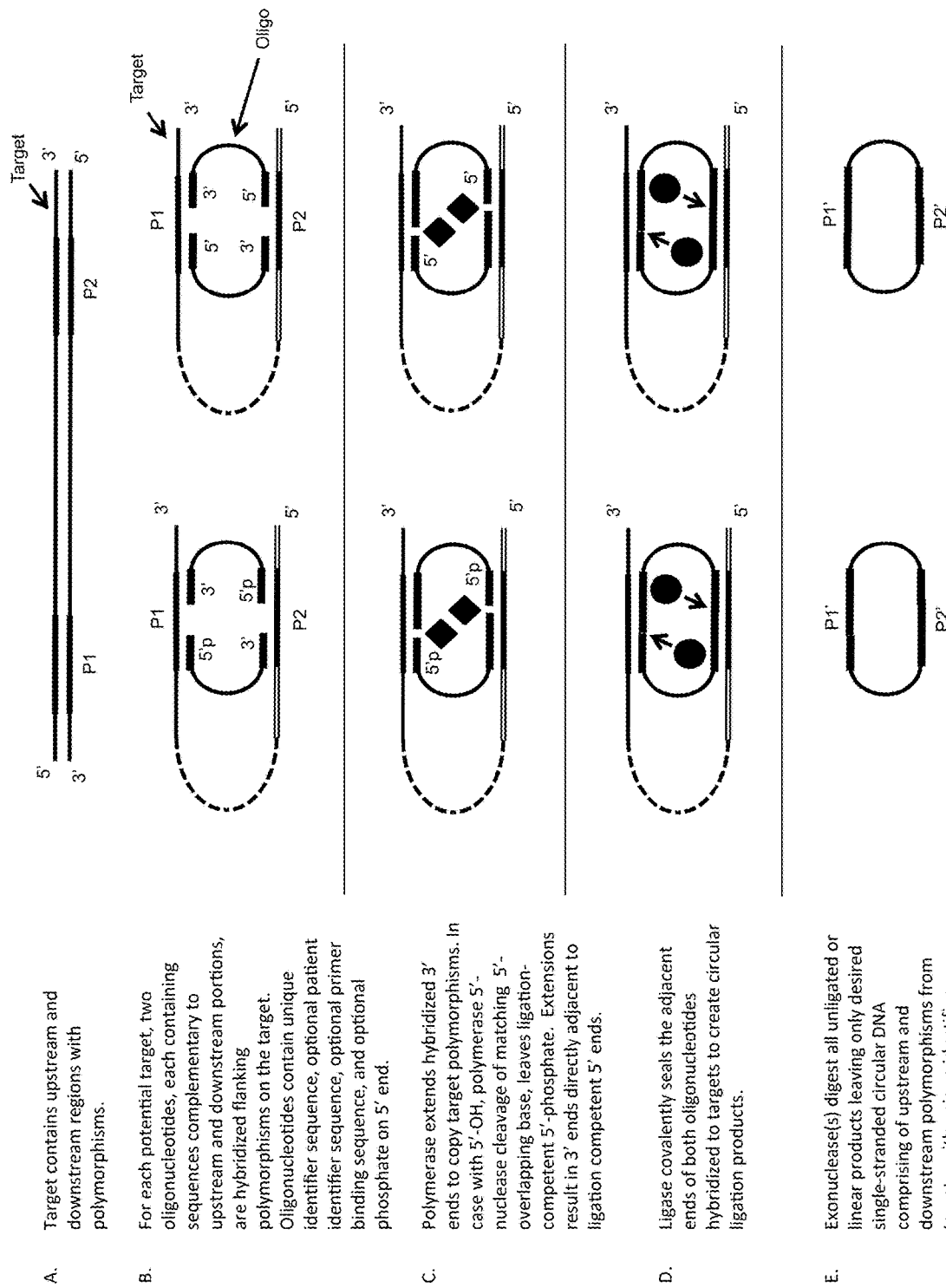
FIG. 113 depicts a method of generating circular chimeric single-stranded nucleic acid constructs that comprise a DNA segment containing polymorphisms. The circular constructs are suitable for RCA and sequencing in accordance with the methods of the present invention.

FIG. 113 shows another process in accordance with this aspect of the invention that is suitable for the detection of known polymorphisms on the same strand of genomic DNA. As shown in FIG. 113, step A, upstream and downstream regions of the target genomic DNA segment contain polymorphisms. As shown in FIG. 113, step B, for each potential target two oligonucleotide probes are provided, each probe containing 3' and 5' target-specific sequences that are complementary to the upstream and downstream portions of the DNA containing polymorphisms. The target specific portions of each probe are separated by a nucleotide sequence that contains a unique identifier sequence, a patient identifier sequence, one or more primer binding sequences, or any combination thereof. The probes hybridize adjacent to each other on the target genomic DNA sequences as shown in FIG. 113, step B. If the oligonucleotide probes contain ligation competent 5' ends, a ligase covalently seals the adjacent ends of the hybridized oligonucleotides to create a circular ligation product as shown in FIG. 113, step D (left panel). If the oligonucleotide probes contain a 5' flap or overlapping nucleotide base, a 5' nuclease cleaves the 5' end to generate a ligation-competent 5'-phosphate (FIG. 113, step C) prior to ligation (FIG. 113, step D, right panel). Exonuclease digestion removes all unligated or linear products leaving only the desired single-stranded circularized DNA constructs comprising the upstream and downstream sequences of genomic DNA containing polymorphisms coupled to a unique identifier sequence, a patient identifier sequence, and/or capture sequence (e.g., primer binding sequence). This product is suitable for rolling circle amplification and subsequent sequencing as described herein.

Another aspect of the present invention is directed to a method for identifying, in a sample, one or more target miRNA molecules differing from other nucleic acid molecules in the sample by one or more bases. This method involves providing a sample containing one or more target miRNA molecules potentially containing one or more base differences, and appending nucleotide linkers to 3' and 5' ends of the target miRNA molecules in the sample. This method further involves providing one or more oligonucleotide probes, each oligonucleotide probe comprising (a) a 3' portion complementary to the 3' nucleotide linker of the target miRNA molecule, (b) a 5' portion complementary to the 5' nucleotide linker of the target miRNA molecules, and (c) a further portion, said further portion comprising (i) a unique identifier sequence, (ii) a patient identifier sequence, (iii) one or more primer binding sequences, or any combination of (i), (ii), and (iii). The sample is contacted with the one or more oligonucleotide probes under conditions effective for the 3' and 5' portions of the oligonucleotide probes to hybridize in a base specific manner to complementary nucleotide linkers on the target miRNA molecules, if present in the sample. The 3' end of the hybridized oligonucleotide probe is extended to generate a complement of the one or more target miRNA molecules, and the 3' extended end of the oligonucleotide probe is ligated to the 5' end of the oligonucleotide probe to form a circular ligated product comprising a sequence complementary to the 3' nucleotide linker of the target miRNA molecule, a sequence complementary to the 5' nucleotide linker of the target miRNA molecule, the complement of the one or more target miRNA molecules, and the further portion of the oligonucleotide probe. This method further involves detecting and distinguishing the circular ligated products in the sample thereby identifying the presence of one or more target miRNA molecules differing from other nucleic acid molecules in the sample by one or more bases.

Figure 114:
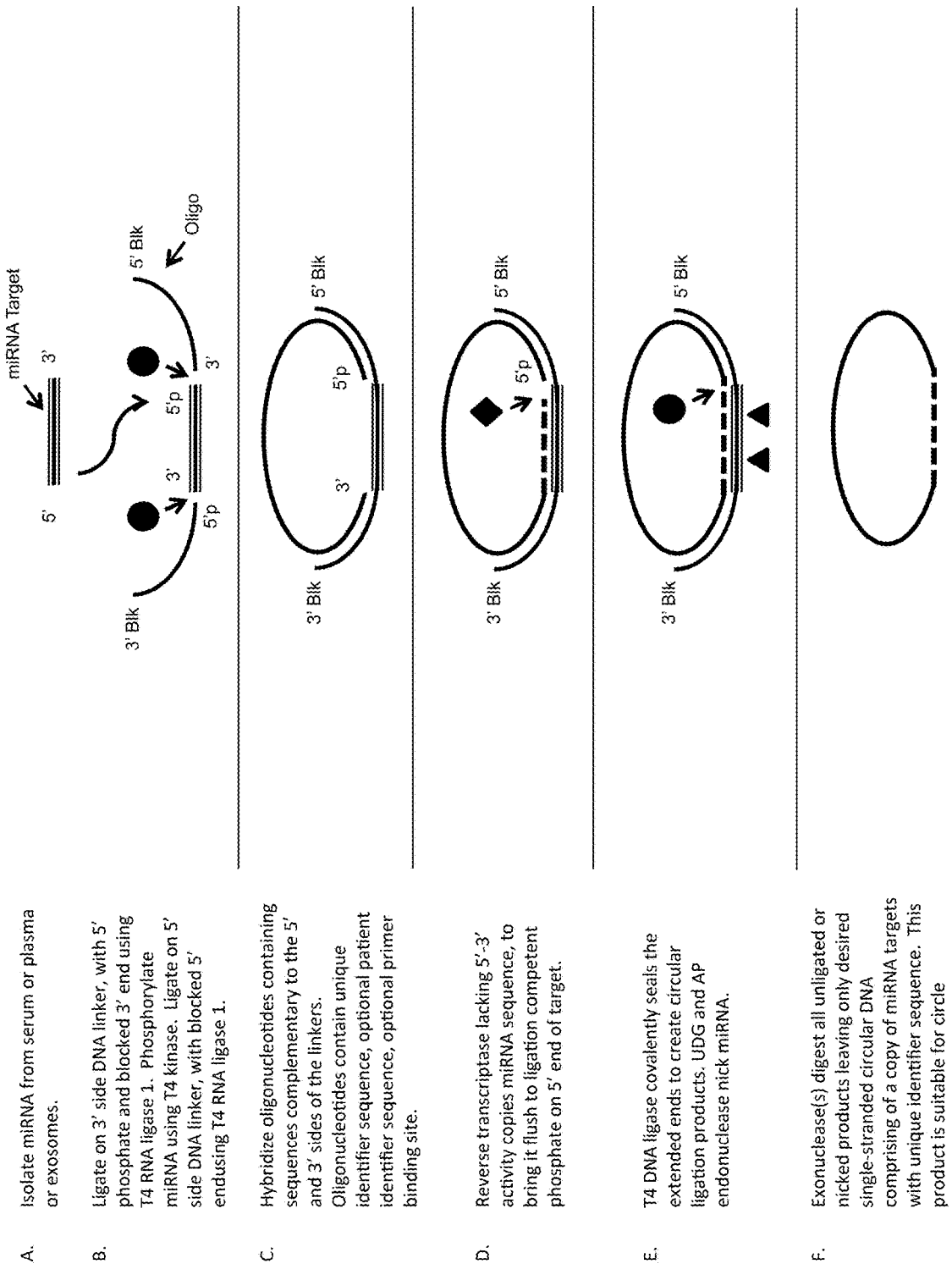
FIG. 114 depicts a method of generating circular chimeric single-stranded nucleic acid constructs that comprise a deoxyribonucleic sequence that is complementary to a target miRNA sequence. The circular constructs are suitable for RCA and sequencing in accordance with the methods of the present invention.

In accordance with this aspect of the present invention, FIG. 114 shows a process for detecting generic populations of miRNA. The starting material for this process is miRNA isolated from serum, or plasma, or exosomes (FIG. 114, step A). As shown in FIG. 114, step B, nucleotide linkers are appended to the 3' and 5' ends of the target ribonucleic acid molecules in the sample. As shown in FIG. 114, step B, the 3' linker contains a blocking group at its 3' end and a phosphate group at its 5' end to facilitate ligation using T4 RNA ligase (filled circles) to the 3' end of the target miRNA molecule. The 5' linker, also containing a blocking group on its 5' end is similarly ligated to the 5' end of the miRNA molecule using T4 RNA ligase. Oligonucleotide probes containing a 3' portion complementary to the 3' nucleotide linker of the target miRNA and a 5' portion complementary to the 5' nucleotide linker of the target miRNA are hybridized to their linker appended target miRNA molecule (FIG. 114, step C). The oligonucleotide probes also contain a nucleotide sequence comprising a unique identifier sequence, a patient identifier sequence, one or more primer binding sequences, or any combination thereof. Reverse transcriptase lacking 5'-3' activity (filled diamond) extends the 3' end of the hybridized oligonucleotide probe, copying the miRNA sequence, until it is adjacent to the ligation competent 5' end of the oligonucleotide probe (FIG. 114, step D). As shown in FIG. 114, step E, T4 DNA ligase (filled circles) covalently seals the extended 3' end of the oligonucleotide probe to a create circular ligation product. UDG and AP endonuclease (filled triangles) nick miRNA (FIG. 114, step E), and exonuclease digestion of all unligated or nicked products leaves only the desired single-stranded circular nucleic acid construct comprising a copy of the miRNA target coupled to a unique identifying sequence. This product is suitable for rolling circle amplification and circle sequencing as described herein.

Another aspect of the present invention is directed to a method for identifying, in a sample, one or more target miRNA molecules differing from other nucleic acid molecules in the sample by one or more bases. This method involves providing a sample containing one or more target miRNA molecules potentially containing one or more base differences, and ligating nucleotide linkers to 3' and 5' ends of the target miRNA molecules in the sample. The nucleotide linkers are coupled to each other by a further portion, said further portion comprising (i) a unique identifier sequence, (ii) a patient identifier sequence, (iii) one or more primer binding sequences, or any combination of (i), (ii), and (iii), whereby said ligating forms a circular ligation product comprising the target miRNA molecule, the 3' and 5' nucleotide linker sequences, and the further portion. This method further involves providing one or more first oligonucleotide primers comprising a nucleotide sequence that is complementary to a 3' or 5' nucleotide linker sequence of the circular ligation product, and hybridizing the one or more first oligonucleotide primers to the circular ligation product in a base specific manner. The 3' end of the first oligonucleotide primer is extended to generate a complement of the circular ligation product, and the circular ligation product complements in the sample are detected and distinguished, thereby identifying the presence of one or more target miRNA molecules differing from other nucleic acid molecules in the sample by one or more bases.

Figure 115:
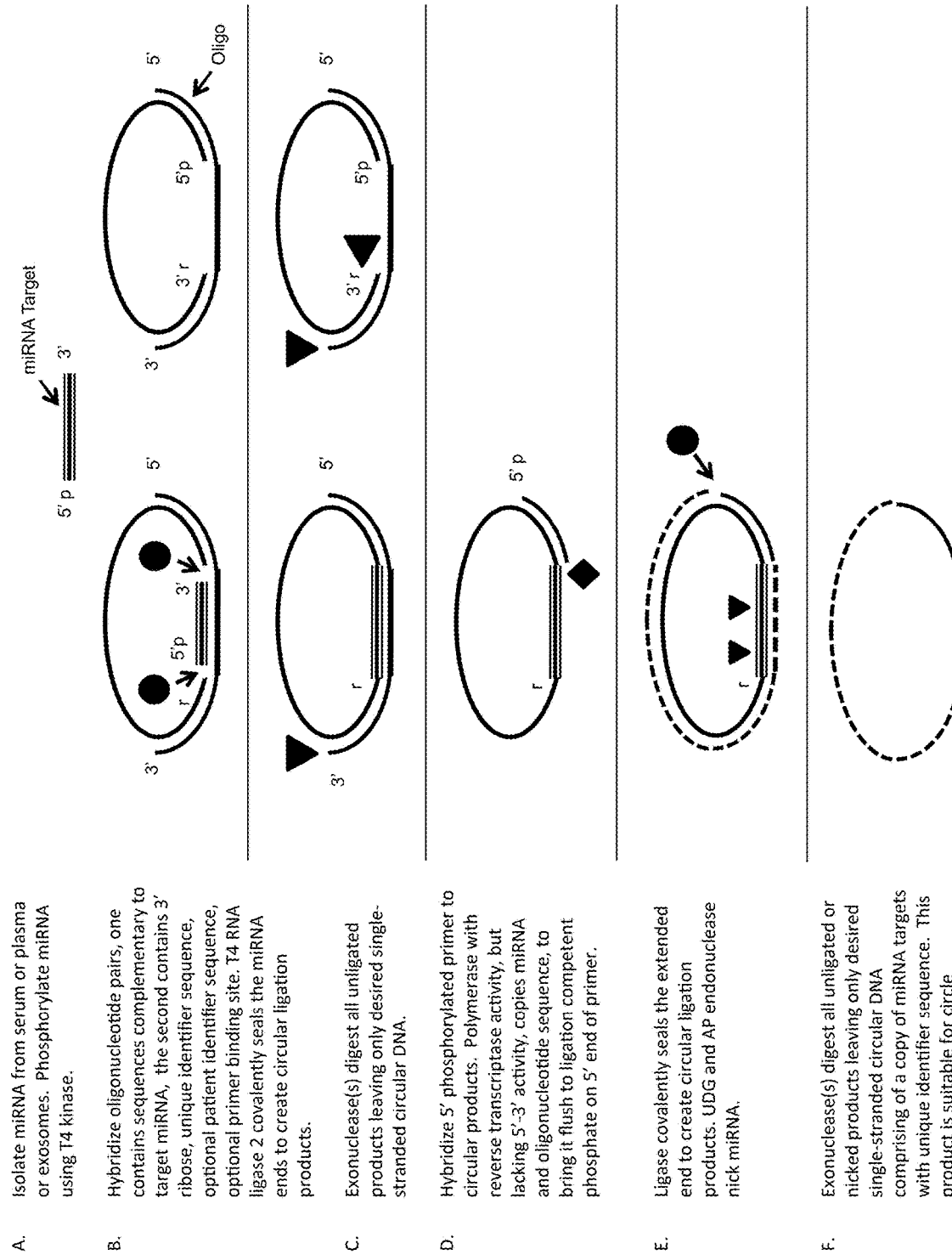
FIG. 115 depicts a method of generating circular chimeric single-stranded nucleic acid constructs that comprise a deoxyribonucleic sequence that is complementary to a target miRNA sequence. The circular constructs are suitable for RCA and sequencing in accordance with the methods of the present invention.

In accordance with this aspect of the present invention, FIG. 115 shows a process for detecting specific miRNA sequences. miRNA isolated from serum or exosomes (FIG. 115, step A), is phosphorylated at its 5'end. As shown in FIG. 115, step B, coupled nucleotide linkers are ligated onto the 3' and 5' ends of the target ribonucleic acid molecules in the sample. The nucleotide linkers are coupled by a nucleotide sequence containing a unique identifier sequence, a 3' ribonucleotide, a patient identifier sequence, one or more primer binding sequences, or any combination thereof. Ligation of the coupled nucleotide linkers is facilitated by an oligonucleotide probe having a 3' sequence complementary to the 3' end of the coupled linker, a 5' sequence complementary to the 5' end of the coupled linker, and a sequence complementary to the target miRNA as shown in FIG. 115, step B. Ligation of the nucleotide linkers to the miRNA molecule creates circularized ligation products containing the target miRNA molecule. As shown in FIG. 115, step C, exonuclease digestion removes all unligated products, e.g., the oligonucleotide probe, leaving only the desired single-stranded circularized construct containing the target miRNA. As shown in FIG. 115, step D, a 5' phosphorylated primer is hybridized to the circularized construct, and a polymerase having reverse transcriptase activity (diamond), but lacking 5'-3' activity, extends the hybridized primer around the circularized construct generating a complementary copy of the miRNA molecule. Ligase (filled circle) covalently seals the extended 3' end and phosphorylated 5' end of the primer to create a second circularized ligation product as shown FIG. 115, step E. UDG and AP endonuclease (filled triangle) nick the original miRNA molecule, and exonuclease digestion removes all unligated or nicked products leaving only the desired single-stranded circular nucleic acid constructs comprising a copy of the miRNA target coupled to a unique identifying sequence. This product is suitable for rolling circle amplification and circle sequencing as described herein.

Figure 116:
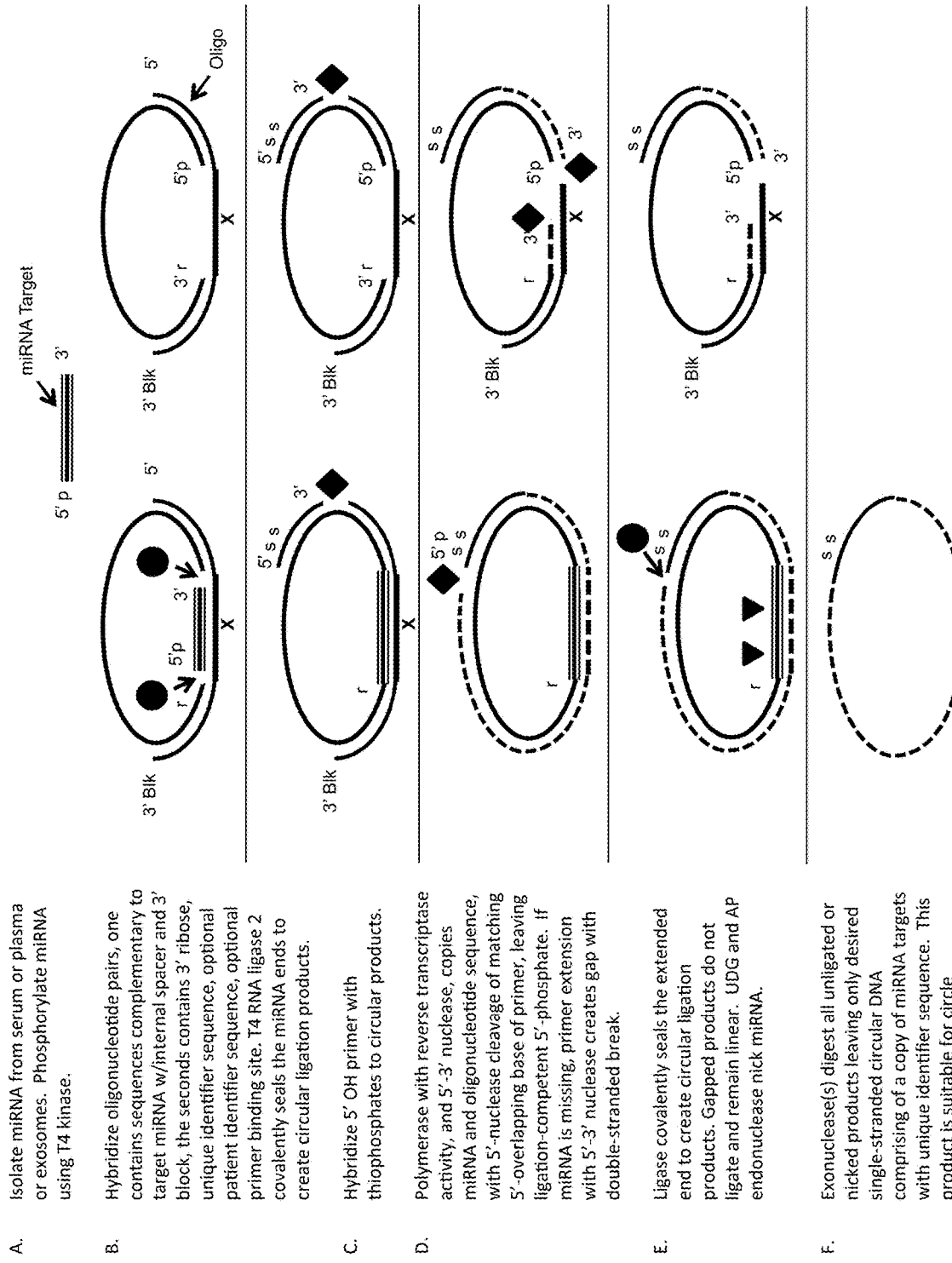
FIG. 116 depicts a method of generating circular chimeric single-stranded nucleic acid constructs that comprise a deoxyribonucleic sequence that is complementary to a target miRNA sequence. The circular constructs are suitable for RCA and sequencing in accordance with the methods of the present invention.

FIG. 116 shows a variation of the process depicted in FIG. 115 for detecting specific miRNA sequences. In this variation, ligation of the coupled nucleotide linkers to the target miRNA is facilitated using an oligonucleotide probe having a 3' blocking group and an internal spacer ("X") within the sequence that is complementary to the target miRNA sequence (FIG. 116, step B, left panel). Ligation of the coupled linkers to the target miRNA forms circularized ligation products as shown in FIG. 116, step B (left panel). A 5' OH primer containing thiophosphates is hybridized to the circularized ligation products as shown in FIG. 116, step C. A polymerase having reverse transcriptase activity and 5'-3' nuclease activity (filled diamonds) extends the 3' end of the hybridized primer to form a complementary copy of the circularized ligation product and the target miRNA molecule contained therein (FIGS. 116, step C and 116, step D, left panel). The 5'-nuclease activity of the polymerase cleaves the matching 5'-overlapping base of the primer, leaving a ligation-competent 5'-phosphate (FIG. 116, step D, left panel). Ligase (filled circle) covalently seals the extended end to create circular ligation products as shown in FIG. 116, step E. UDG and AP endonuclease (filled triangle) nick the original miRNA molecule (FIG. 116, step E, left panel), and exonuclease digestion removes all unligated or nicked products leaving only the desired single-stranded circular DNA comprising a copy of the miRNA target coupled to a unique identifying sequence (FIG. 116, step F, left panel). This product is suitable for rolling circle amplification and circle sequencing as described herein. In the absence of a target miRNA, as shown in FIG. 116, steps B-E, right panel, primer extension with 5'-3' nuclease creates gap with a double-stranded break. Gapped products do not ligate and remain linear (FIG. 116, step E, right panel). These linear products are removed from analysis by exonuclease digestion (FIG. 116, step F).

Another aspect of the present invention is directed to a method for identifying, in a sample, one or more target miRNA molecules differing from other nucleic acid molecules in the sample by one or more bases. This method involves providing a sample containing one or more target miRNA molecules potentially containing one or more base differences, and providing one or more oligonucleotide probe sets, each set comprising (a) a first oligonucleotide probe having a 5' stem-loop portion and a 3' portion complementary to a 3' portion of the target miRNA molecule, (b) a second oligonucleotide probe having a 3' portion complementary to a copy of the 5' end of the target miRNA molecule, a 5' portion complementary to the 5' stem-loop portion of the first oligonucleotide probe, and a further portion comprising (i) a unique target identifier sequence, (ii) a patient identifier sequence, (iii) a primer binding sequence, or any combination of (i), (ii), and (iii). The method further involves blending the sample, the one or more first oligonucleotide probes from a probe set, and a reverse transcriptase to form a reverse transcriptase reaction, and extending the 3' end of the first oligonucleotide probe hybridized to its complementary target miRNA molecule to generate a complement of the target miRNA molecule, if present in the sample. The one or more second oligonucleotide probes of a probe set are hybridized to the extended first oligonucleotide probes comprising a complement of the target miRNA sequences, and one or more ligation competent junctions are generated between 3' and 5' ends of each second oligonucleotide probe hybridized to an extended first oligonucleotide probe. The method further involves ligating the 3' and 5' ends of each second oligonucleotide probe to form circular ligated products, each product comprising a deoxyribonucleic acid copy of the target miRNA sequence coupled to the further portion of the second oligonucleotide probe. The circular ligated products in the sample are detected and distinguished, thereby identifying the presence of one or more target miRNA molecules differing from other nucleic acid molecules in the sample by one or more bases.

Figure 117:
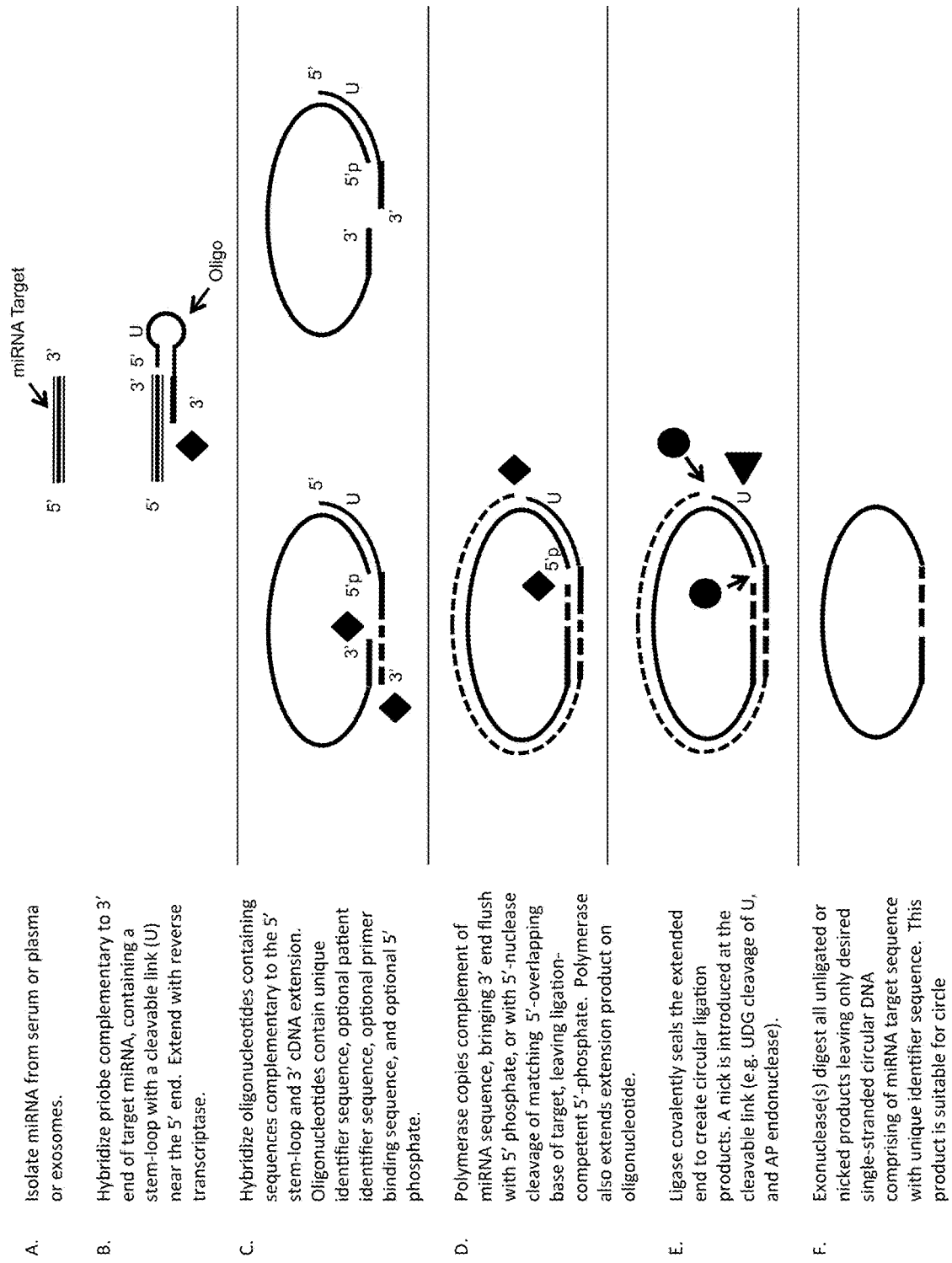
FIG. 117 depicts a method of generating circular chimeric single-stranded nucleic acid constructs that comprise a deoxyribonucleic sequence that is complementary to a target miRNA sequence. The circular constructs are suitable for RCA and sequencing in accordance with the methods of the present invention.

In accordance with this aspect of the present invention, FIG. 117 shows a method for detecting specific miRNA sequences. miRNA, isolated from serum, plasma, or exosomes is hybridized to a first oligonucleotide probe having a sequence that is complementary to the 3' end of target miRNA, and a stem-loop on its 5' end (FIG. 117, step B). The step loop region of the first oligonucleotide probe also contains a cleavable link (dU). The first oligonucleotide probe is extended using a reverse transcriptase (filled diamonds) thereby forming a complementary copy of the miRNA molecule. As shown in FIG. 117, step C, a second oligonucleotide probe containing a 3' sequence that is complementary to the 3' end of the extended first oligonucleotide probe, and a 5' sequence that is complementary to the 5' stem-loop of the first oligonucleotide probe is hybridized to complementary regions of the first oligonucleotide probe. The second oligonucleotide probes may also contain a unique identifier sequence, a patient identifier sequence, one or more primer binding sequences, a 5' phosphate, or any combination thereof. Polymerase (filled diamonds) extends the 3' end of the second oligonucleotide probe, producing a complementary copy of the miRNA sequence and bringing the 3' end of the probe adjacent its 5' end to form a ligation junction. (FIG. 117, step D). Polymerase also extends the 3' end of the first oligonucleotide probe (using the hybridized second oligonucleotide probe as a template) to create a ligation junction with its 5' end (FIG. 117, step D). As shown in FIG. 117, step E, ligase (filled circles) covalently seals the 3' and 5' ends of the first and second oligonucleotide probes at each respective ligation junction to create circularized ligation products. A nick is introduced at the cleavable link of the first oligonucleotide probe (e.g. UDG cleavage of dU, and AP endonuclease—filled triangle). As shown in FIG. 117, step E, exonuclease digestion removes all unligated or nicked products leaving only the desired single-stranded circularized nucleic acid construct (i.e., the second oligonucleotide probe) comprising a copy of the miRNA target sequence coupled to a unique identifying sequence. This product is suitable for rolling circle amplification and circle sequencing as described herein.

EXAMPLES

Prophetic Example 1—High Sensitivity Mutation Marker (when Present at 1% to 0.01%), Single Base Mutation, Small Insertion, and Small Deletion Mutations in Known Genes (e.g. Braf, K-Ras, p53)

Mutational changes in oncogenes are usually in discrete regions or positions and can often drive tumor progression.

A list of these genes and their mutations may be found in public databases such as the Sanger Genome Center "COSMIC" database. Presence of such mutations in serum is a strong indicator of some tumor tissue in the body. Traditionally such mutations have been identified using allele-specific PCR amplification. This approach is susceptible to an initial false-amplification, followed by amplification of the false product. Others have used digital PCR to try to quantify mutant DNA in the serum. However, mutational changes in tumor suppressor genes such as p53 and APC are too numerous to cover using allele-specific PCR approaches. Thus, the approach has shifted to deep sequencing across all exons of the protein. When input DNA is limiting, it is important to achieve equal amplification of different regions to assure the same general depth of coverage. There have been attempts to achieve equal amplifications using molecular inversion probes (MIP), see e.g., Akhras et al., "Connector Inversion Probe Technology: A Powerful One-Primer Multiplex DNA Amplification System for Numerous Scientific Applications," *PLoS One* 2(9):e915 (2007); Hiatt et al., "Single Molecule Molecular Inversion Probes for Targeted, High-Accuracy Detection of Low-Frequency Variation," *Genome Res.* 23(5):843-54 (2013), which are hereby incorporated by reference in their entirety. However these techniques depend on making a copy of genomic DNA, and thus risk introducing additional errors.

Overview of approach: The idea is to faithfully capture every fragment of target DNA that covers the regions or exons of interest, append a unique identifier sequence and an optional patient identifier, and circularize them for subsequent sequencing, such as circle sequencing. The original target DNA strand is circularized and sequenced. This avoids polymerase-induced errors that arise from extending (and circularizing) hybridized oligonucleotides, which would lead to false-positives. This approach provides the advantage of obtaining both copy number information when needed (i.e. viral load, chromosomal imbalance in tumors, detection of aneuploidy in non-invasive prenatal diagnosis), and mutational data with the minimum of sequencing required.

Variation 1.1: (FIGS. 13-16).

In this variation, short linkers are ligated to the DNA target (cfDNA of average length of about 160 bases). To capture the desired regions, oligonucleotide probes comprising a 5' probe region complementary to the sequences to the 5' side of the target, a unique identifier sequence, an optional patient identifier sequence, a sequence complementary to the 3' end of the linker, and a 3' probe region complementary to the sequences to the 3' side of the target, are hybridized to the target. The oligonucleotide may contain an optional blocking group on one end (5' end shown), or an optional cleavable linker. Depending on the probe design and the starting and ending bases of the target fragment, a portion of the target may loop out as a single stranded region between the 3'linker and the portion of the target complementary to the 3' probe (FIGS. 13 and 14), or a portion of the 5' end of the target sequence may not hybridize, or a portion of the 3' probe sequence from the oligonucleotide may loop out (FIGS. 15 and 16). Addition of a polymerase allows extension of the 3' end of the oligonucleotide on the target, as well as extension of the 3' end linker through the unique identifier sequence, and optional patient identifier sequence.

The hybridization conditions are chosen such that hybridization of the 3' probe region complementary to the sequence of the 3' side of the target brings the local concentration of the 3' end of the linker on the target to its complement, such that it hybridizes correctly and is readily extended by polymerase. However, if there is less than sufficient complementarity between the oligonucleotide probe and the target DNA, then the 3' end of the linker on the target will not hybridize to its complement, and rarely be extended by polymerase. Extension of the 3' end of the oligonucleotide on the target enhances association of the probe to the target, and thus increases the ability of the 3' end of the linker to hybridize correctly to its complement and be extended by polymerase. The 5'→3' nuclease cleavage activity of polymerase (or Fen nuclease) cleaves a matching 5'-overlapping base of target at or near the position where the 5' side of the target is complementary to the 5' portion of the probe, leaving ligation-competent 5'-phosphate from the authentic target. Polymerase also extends oligonucleotide on target, and either generates a ligation-competent 5'-phosphate (left side of FIGS. 13 and 15, step D), or does not cleave the blocking group on the 5' end of the oligonucleotide (right side of FIGS. 13 and 15, step D).

Ligase covalently seals the extended 3' ends to the ligation-competent 5'-phosphate to create circular ligation products. Blocking group prevents circularization of oligonucleotide probe (FIGS. 13 and 15, step D, right side), or alternatively, a nick is introduced at the cleavable link (e.g. UDG cleavage of dU, followed by cleavage of the apurinic backbone with AP endonuclease, FIGS. 13 and 15, step D, left side). Optional addition of Uracil-DNA glycosylase (UDG) and Formamidopyrimidine-DNA glycosylase (Fpg, also known as 8-oxoguanine DNA glycosylase, which acts both as a N-glycosylase and an AP-lyase) may be used to nick targets containing damaged bases. Exonuclease(s) are then added to digest all unligated or nicked products leaving only desired single-stranded circular DNA comprising of original target DNA with unique identifier sequence. This product is suitable for rolling circle amplification and circle sequencing, or direct SMRT sequencing.

This approach requires an enzyme with target-dependent 5'→3' nuclease activity such that the ligation-competent 5'-phosphate is generated only when there is proper hybridization and complementarity between the 5' probe region and the 5' target region. When using polymerase with 5'→3' nuclease cleavage activity, the challenge is to avoid having polymerase extend the short linker along the 5' probe region in such a way that it destroys the 5' target region (i.e. nick-translation) without a ligation step. Nick-translation that destroys original target DNA and replaces it with extended DNA may inadvertently introduce a polymerase error that would be propagated and miscalled as a mutation. This may be minimized by using a mixture of polymerases, both with and without 5'→3' nuclease cleavage activity (e.g. in a ratio of 1:20) under conditions of distributive extension in the presence of ligase such that most extension is by polymerase without nuclease activity until polymerase with nuclease activity is required to create the ligation competent junction, followed by polymerase dissociation, and a ligation event to generate the desired circular ligation product.

cfDNA, with sizes in the 140 to 170 nucleotide range, reflect cleavage of chromosomal DNA around nucleosome units. Such cleavage events may be somewhat phased, or more random, generating a number of fragments that may be evenly or unevenly distributed. Thus, there is a need to design oligonucleotide probes that will give coverage independent of where the fragment breaks.

FIGS. 90 through 93 provide some examples of different oligonucleotide probe design to cover fragments across a 250 base region. In these figures, the potential target fragment (shifted by 10 bases across a region) is represented by a dark gray bar, the linkers by a short black bar, the probe regions as light gray bars, the unique sequence identifier and optional patient identifier as a thicker black line, and connection between two sequences schematically drawn as a thinner line. FIGS. 100 and 101 illustrate how multiple probes would be designed to cover approximately a 500 base contiguous region.

In FIG. 90, the upstream 5' probe region (60 bases) is complementary to target bases 50-110, while the downstream 3' probe region (20 bases) is complementary to target bases 140-160. For the purposes of this example, the linker is 10 bases, and the composite identifier sequence is 20 bases (12 bases for sequence identifier and 8 bases for patient identifier). When the target is from position 1 to 160, this probe design will allow circularization of a 140 base product, of which 110 bases, i.e. from positions 50 to 160, provide target sequence information. When the target is from position 11 to 170, this probe design will allow circularization of a 150 base product, of which 120 bases, i.e. from positions 50 to 170, provide target sequence information. With this design, the maximum 160 bases of sequence information will be derived with target starting from positions 51 to 81, and ending at positions 210 to 240 respectively. In the figure, when target is from position 61 to 250, there is no circular product formation. Some product might form, however, due to the shorter region of complementarity between the 5' probe region and the 5' side of the target, there is concern that they will not always hybridize. In addition, with this design, there is concern the target "loop out" region of 90 bases on the 3' side may be too long to allow for efficient hybridization of the 3' end of the linker to its complement on the oligonucleotide (short black bars on the right side of the illustration).

In FIG. 91, the upstream 5' probe region (80 bases) is complementary to target bases 30-110, while the downstream 3' probe region (20 bases) is complementary to target bases 140-160. This figure is similar to FIG. 90, except the 5' probe region is longer. For the first 4 examples of targets, the longer oligonucleotide allows for capture of more target DNA, such that the resultant circles contain 20 additional bases of original target DNA.

FIGS. 100 and 101 illustrate how to design oligonucleotide probes with an overlapping tiling strategy to sequence larger contiguous regions (about 500 bases shown herein). FIG. 100 illustrates four "consecutive" probes using the design in FIG. 90, while FIG. 101 illustrates four "consecutive" probes using the design in FIG. 91. Potential 160 bp fragments that could be generated over the region (shifted by 10 bases) are illustrated. Underneath, the oligonucleotide that would cover all those fragments above it is shown. If the area in the target is in light grey, it will not provide reliable sequence information. If the area in the target is in dark grey, it should provide good sequence information. In this diagram, probes listed are sequentially designated as #1, #2, #3, #4 etc. For the multiplexed extension-ligation steps, odd probes #1, #3, #5 are pooled in a first oligonucleotide pool set, and then the even probes #2, #4, #6 are pooled into a second pool set. This approach avoids adjacent oligonucleotides (i.e. #1 and #2) competing for binding to the same target strand. Once the extension-circularization has taken place, the two pools may be combined and exonuclease and subsequent steps such as rolling circle amplification and circle sequencing, or direct SMRT sequencing may proceed.

Detailed Protocol (V1.1) for High Sensitivity Detection of Single Base Mutation, Small Insertion, or Small Deletion Mutations (when Present at 1% to 0.01%,) in Known Genes (e.g. Braf, K-Ras, p53):

1.1.a. Starting with cfDNA (or for example genomic DNA isolated from CTC, sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase appends linkers on both ends of the fragment. Optionally, purify target DNA from unligated linker.

1.1.b. Denature target DNA containing linkers on both ends (94° C. 1 minute) in the presence of oligonucleotide probes (comprising a 5' probe region complementary to the sequences to the 5' side of the targets, a unique identifier sequence, an optional patient identifier sequence, a sequence complementary to the 3' end of the linker, and a 3' probe region complementary to the sequences to the 3' side of the targets), and allow the oligonucleotides to hybridize to their complementary regions on the desired fragments by cooling to a desired temperature (e.g. 50° C. for 2 hours). Taq polymerase, and thermostable ligase (preferably from strain AK16D), dNTPs and optional KlenTaq (Taq polymerase lacking nuclease activity) are either added, subsequent to the annealing step, or at the start of the procedure. Allow for extension and ligation at the hybridization temperature, and optionally raise the temperature (e.g. 60° C.) to assure completion of extension and ligation, to generate circular products.

1.1.c. Optionally, cleave the oligonucleotide probe strand at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the linker sequence as a primer binding site.

Note 1: Oligonucleotide probe may contain an optional blocking group on the 5' side to interfere with subsequent 5'-3' nuclease activity of polymerase, such that the oligonucleotide probe does not circularize. Alternatively, a cleavable link may be included in the original oligonucleotide probe.

Note 2: Fen nuclease may be used instead of polymerase with 5'-3' nuclease activity to generate the ligation-competent 5' phosphate on the 5' side of the target.

Note 3: A 1:20 mixture of Taq polymerase (with 5'→3' nuclease activity) and KlenTaq (Taq polymerase without 5'→3' nuclease cleavage activity may be used under conditions of distributive extension (i.e. higher salt concentration) to minimize degradation of target DNA by nick translation.

Note 4: The ligation extension process may be carried out in two or more reaction tubes, one set containing "odd" numbered probes, the second set containing "even" numbered probes to avoid probes competing for the same target DNA strands. The separate reactions may be subsequently pooled.

Variation 1.2. (FIGS. 17-18).

In this variation, the aim is to capture all the target DNA sequence, independent of where the probe binds the target. As before, short linkers are ligated to the DNA target (cfDNA of average length of about 160 bases). To capture the desired regions, oligonucleotide probes comprising a 5' probe region complementary to the sequences to the 5' side of the target, a sequence complementary to the 5' end of the linker, a unique identifier sequence, an optional patient identifier sequence, a sequence complementary to the 3' end of the linker, and a 3' probe region complementary to the sequences to the 3' side of the target, are hybridized to the target. The oligonucleotide probe may contain an optional blocking group on one end (5' end shown), or an optional cleavable linker. Depending on the probe design and the starting and ending bases of the target fragment, a portion of the target or probe sequence may loop out as a single stranded region between the 3' linker and the portion of the target complementary to the 3' probe, as well as the 5' linker and the portion of the target complementary to the 5' probe (FIG. 17). Addition of a polymerase allows extension of the 3' end of the oligonucleotide on the target, as well as extension of the 3' end linker through the unique identifier sequence, and optional patient identifier sequence until it is adjacent to the 5' linker on the target.

The hybridization conditions are chosen such that hybridization of the 3' probe region complementary to the sequences of the 3' side of the target brings the local concentration of the 3' end of the linker on the target, such that it hybridizes correctly and is readily extended by polymerase. The 5' end of the linker may be designed to be slightly longer, such that once polymerase extends the 3' linker, it doesn't extend right through the 5' linker complementary sequence until it hits the 5' target portion that is hybridized to the 5' probe region. However, the "combined" hybridization effect of both the 3' linker and 5' linker regions to their complements on the oligonucleotide probe should still have a Tm below the hybridization temperature, such that random hybridization of incorrect target to oligonucleotide probe rarely if ever results in extension and ligation to give a circular product.

This variation requires that the oligonucleotide probe contain sequences complementary to both the 3' and 5' linker strands, with those sequences being separated by only about 20 bases. Since the sequences are complementary to the linker strands, which in turn are complementary to each other, self-pairing of the oligonucleotide probe needs to be avoided. One solution is to ligate linkers that contain an internal bubble, such that the two linkers retain double stranded character at the low temperature used for linker ligation (16° C. or even 4° C. with T4 ligase). In addition the 5' linker may be designed to be longer than the 3' linker. Finally, the regions of complementarity within the linker may be designed to have subtle mismatches or a nucleotide analogue (i.e. G:T and T:G; or I:A) which are more destabilizing in the complementary oligonucleotide probe (i.e. C:A and A:C; or C:T) such that the oligonucleotide probe is less likely to form the internal self-pairing with a loop at the overall hybridization temperature (i.e. 50° C.).

For example, an I:A mismatch in the middle of an A tract in a linker would lower the Tm by 2.4° C. compared to a T:A match, but the complementary mismatch in the oligonucleotide, C:T lowers the Tm by 10.1° C. (a difference of 7.7° C.). Likewise a G:T mismatch in the middle of an A tract in a linker would lower the Tm by 10.2° C. compared to a G:C match, but the complementary mismatch in the oligonucleotide, A:C lowers the Tm by 18.0° C. (a difference of 7.8° C.). See Kawase et al., "Studies on nucleic acid interactions. I. Stabilities of mini-duplexes (dG2A4XA4G2-dC2T4YT4C2) and self-complementary d(GG-GAAXYTTCCC) containing deoxyinosine and other mismatched bases," *Nucleic Acids Res.* 14(19):7727-36 (1986), which is hereby incorporated by reference in its entirety). Thus placing both such mismatches within the linker would be predicted to lower Tm of oligonucleotide self-pairing by about 15.5° C. compared to the linker self-pairing. The exact amount may vary based on sequence context, nevertheless, it should be apparent to those of skill in the art that use of I:A and G:T mismatch in a linker DNA duplex that remains double stranded at the ligation temperature of either 4° C. or 16° C., would be more than sufficient to assure that the complementary sequences, separated by about 20 bases within an oligonucleotide would not be self-pairing (i.e. hairpin with a 20 base loop) at the higher hybridization temperature of 50 C.

Extension of the 3' end of the oligonucleotide on the target enhances association of the probe to the target, and thus increases the ability of the 3' end of the linker to hybridize correctly to its complement and be extended by polymerase. The 5'→3' nuclease cleavage activity of polymerase (or Fen nuclease) cleaves a matching 5'-overlapping base of the 5' linker, leaving ligation-competent 5'-phosphate on the linker. Polymerase also extends oligonucleotide on target, and either generates a ligation-competent 5'-phosphate or does not cleave the blocking group on the 5' end of the oligonucleotide.

Ligase covalently seals the extended 3' ends to the ligation-competent 5'-phosphate to create circular ligation products. Blocking group prevents circularization of oligonucleotide probe, or alternatively, a nick is introduced at the cleavable link (e.g. UDG cleavage of dU, followed by cleavage of the apurinic backbone with AP endonuclease). Optional addition of Uracil-DNA glycosylase (UDG) and Formamidopyrimidine-DNA glycosylase (Fpg, also known as 8-oxoguanine DNA glycosylase, which acts both as a N-glycosylase and an AP-lyase) may be used to nick targets containing damaged bases. Exonuclease(s) are then added to digest all unligated or nicked products leaving only desired single-stranded circular DNA comprising of original target DNA with unique identifier sequence. This product is suitable for rolling circle amplification and circle sequencing, or direct SMRT sequencing.

The challenge here is to avoid having polymerase extend the 3' linker in such a way that it destroys the 5' linker without a ligation step (i.e. nick-translation). This may be accomplished by incorporating thiophosphate linkages in the $2^{nd}$ and $3^{rd}$ position from the 5' phosphate end, (which will be liberated by the 5'→3' nuclease activity of the polymerase). To minimize polymerase displacement of those bases as it extends one base too many (which would make it impossible to ligate to the downstream linker), the target bases at the ligation junction would preferentially be AT rich on the 3' side, and GC rich on the 5' side.

An alternative approach is to use a 5' linker containing an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the linker is bound to the target. The endonuclease also cleaves single-stranded linker, but with lower efficiency, and thus linker hybridized to template would be the preferred substrate. When using thermostable EndoIII, the PCR polymerase used would lack the 5'→3' exonuclease activity.

As mentioned above, the nick-translation problem may also be minimized by using a mixture of polymerases, both with and without 5'→3' nuclease cleavage activity (e.g. in a ratio of 1:20) under conditions of distributive extension in the presence of ligase such that most extension is by polymerase without nuclease activity until polymerase with nuclease activity is required to create the ligation competent junction, followed by polymerase dissociation, and a ligation event to generate the desired circular ligation product.

FIGS. 94 and 95 provide some examples of different oligonucleotide probe design to cover fragments across a 250 base region. In these figures, the potential target fragment (shifted by 10 bases across a region) is represented by a dark gray bar, the linkers by a short black bar, the probe regions as light gray bars, the unique sequence identifier and optional patient identifier as a thicker black line, and connection between two sequences schematically drawn as a thinner line. FIGS. 102 and 103 illustrate how multiple probes would be designed to cover approximately a 500 base contiguous region.

In FIG. 94, the upstream 5' probe region (50 bases) is complementary to target bases 50-100, while the downstream 3' probe region (50 bases) is complementary to target bases 150-200. For the purposes of this example, the 3' linker is 10 bases, and the composite identifier sequence is 20 bases (12 bases for sequence identifier and 8 bases for patient identifier) and the 5' linker is illustrated as 10 bases, although in another embodiment it would be somewhat longer, about 12 to 18 bases. When the target is from position 1 to 160, this probe design will allow circularization of a 200 base product, of which all 160 bases provide target sequence information. These probes are designed such that independent of where the target is, from 1 to 160 all the way from 91 to 250, they should still form extension products that circularize to form products of about 200 bases.

In FIG. 95, the upstream 5' probe region (60 bases) is complementary to target bases 40-100, while the downstream 3' probe region (60 bases) is complementary to target bases 140-200. This figure is similar to FIG. 94, except both the 3' and 5' probe regions are longer. This probe design may be more efficient at capturing targets at the ends (i.e. targets 1 to 160; 11 to 170; 81 to 240; and 91 to 250).

FIGS. 102 and 103 illustrate how to design oligonucleotide probes with an overlapping tiling strategy to sequence larger contiguous regions (about 500 bases shown herein). FIG. 102 illustrates four "consecutive" probes using the design in FIG. 94, while FIG. 103 illustrates four "consecutive" probes using the design in FIG. 95. Potential 160 bp fragments that could be generated over the region (shifted by 10 bases) are illustrated. Underneath, the oligonucleotide that would cover all those fragments above it is shown. In this diagram, probes listed are sequentially designated as #1, #2, #3, #4 etc. For the multiplexed extension-ligation steps, odd probes #1, #3, #5 are pooled in a first oligonucleotide pool set, and then the even probes #2, #4, #6 are pooled into a second pool set. This approach avoids adjacent oligonucleotides (i.e. #1 and #2) competing for binding to the same target strand. Once the extension-circularization has taken place, the two pools may be combined and exonuclease and subsequent steps such as rolling circle amplification and circle sequencing, or direct SMRT sequencing may proceed. Detailed Protocol (V1.2) for High Sensitivity Detection of Single Base Mutation, Small Insertion, or Small Deletion Mutations (when Present at 1% to 0.01%,) in Known Genes (e.g. Braf, K-Ras, p53):

1.2.a. Starting with cfDNA (or for example genomic DNA isolated from circulating tumor cells (CTC), sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Optionally, purify target DNA from unligated linker.

1.2.b. Denature target DNA containing linkers on both ends (94° C., 1 minute) in the presence of oligonucleotide probes (comprising a 5' probe region complementary to the sequences on the 5' side of the targets, a sequence complementary to the 5' end of the linker, a unique identifier sequence, an optional patient identifier sequence, a sequence complementary to the 3' end of the linker, and a 3' probe region complementary to the sequences to the 3' side of the targets), and allow the oligonucleotides to hybridize to their complementary regions on the desired fragments by cooling to a desired temperature (e.g. 50° C. for 2 hours). Taq polymerase and/or KlenTaq (Taq polymerase lacking nuclease activity), and thermostable ligase (preferably from strain AK16D), dNTPs are either added subsequent to the annealing step, or at the start of the procedure. Allow for extension and ligation at the hybridization temperature, and optionally raise the temperature (e.g. 60° C.) to assure completion of extension and ligation, to generate circular products.

1.2.c. Optionally, cleave the oligonucleotide probe at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the linker sequence as a primer binding site.

Note 1: Oligonucleotide may contain an optional blocking group on the 5' side to interfere with subsequent 5'-3' nuclease activity of polymerase, such that the oligonucleotide probe does not circularize. Alternatively, a cleavable link may be included in the original oligonucleotide.

Note 2: Fen nuclease may be used instead of polymerase with 5'-3' nuclease activity to generate the ligation-competent 5' phosphate on the 5' side of the target.

Note 3: The 5' end linker may be synthesized to contain thiophosphate linkages in the $2^{nd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream linker), the target bases at the ligation junction would preferentially be AT rich on the 3' side, and GC rich on the 5' side.

Note: 4: When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when bound to the target. The endonuclease also cleaves single-stranded oligonucleotide, but with lower efficiency, and thus linker hybridized to template would be the preferred substrate.

Note 5: When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

Note 6: A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Note 7: The ligation extension process may be carried out in two or more reaction tubes, one set containing "odd" numbered probes, the second set containing "even" numbered probes to avoid probes competing for the same target DNA strands. The separate reactions may be subsequently pooled.

Note 8: Example of linkers containing single-base 3' "T" overhangs is provided as oligonucleotides iSx-003-ShAdT (Top strand), and iSx-004-pShAdB (Bottom strand) (see Table 1). Example of slightly longer linkers, to enhance binding to the linker region, is provided as oligonucleotides iSx-006-MdAdT (Top strand), and iSx-007-pMdAdB (Bottom strand) (see Table 1). Linkers iSx-003-ShAdT and iSx-006-MdAdT (see Table 1) may contain optional thiophosphate groups near the 5' end to prevent nick-translation and facilitate circularization of targets with linker ends. Linkers iSx-004-pShAdB and iSx-007-pMdAdB (see Table 1) may contain optional thiophosphate groups near or at the 3' end to prevent degradation if using a polymerase with proofreading activity, and facilitate circularization of targets with linker ends.

Note 9: If an extra base is not added to the target DNA (i.e. skipping the Klenow step), then a blunt end ligation is used. To avoid linker-to-linker ligation, the blunt end of the linker is un-phosphorylated. Example of linkers containing blunt ends is provided as oligonucleotides iSx-003-ShAdT (Top strand), and iSx-005-ShAdB (Bottom strand) (see Table 1).

Note 10: When designing oligonucleotides for use with longer linker sequences, comprising "barcoding" or "indexing" sequences for use with commercial instruments, it may be necessary to assemble the oligonucleotide using PCR, strand-displacement amplification, or a combination thereof. During PCR, use of dUTP instead of TTP incorporates uracil, suitable for subsequent cleavage by UDG. The reverse-strand primer may be phosphorylated, allowing for its digestion using lambda exonuclease or a similar 5'→3' exonuclease. A dA30 sequence may be appended to the 5' end of the forward primer, enabling strand displacement amplification. Examples of oligonucleotides suitable for assembly amplification for sequencing regions of KRAS, BRAF, and TP53 exons 5-8 containing hotspot mutations are shown in Table 1 (below) and include the following: (i) KRAS forward and reverse target regions (iSx-001-bkA30, iSx-016-bkA30-KRSF11, iSx-017-pKRSF12, iSx-008-701F, iSx-009-501R, iSx-018-pKRSF13, and iSx-018-pKRSR14) and (iSx-015-pKRSF10, iSx-017-pKRSF12, iSx-008-701F, iSx-009-501R, iSx-018-pKRSF13, iSx-019-bkA30-KRSR15, and iSx-001-bkA30); (ii) BRAF forward and reverse target regions (iSx-001-bkA30, iSx-023-bkA30-BRF-F11, iSx-024-pBRF-F12, iSx-008-701F, iSx-009-501R, iSx-025-pBRF-F13, and iSx-026-pBRF-R14) and (iSx-022-pBRF-F10, iSx-024-pBRF-F12, iSx-008-701F, iSx-009-501R, iSx-025-pBRF-F13, iSx-027-bkA30-pBRF-R15, and iSx-001-bkA30); (iii) TP53 Exon 5 upstream forward and reverse target regions (iSx-001-bkA30, iSx-035-bkA30-pTP53e5F11, iSx-036-pTP53e5F12, iSx-008-701F, iSx-009-501R, iSx-037-pTP53e5F13, iSx-038-pTP53e5R14) and (iSx-034-pTP53e5F10, iSx-036-pTP53e5F12, iSx-008-701F, iSx-009-501R, iSx-037-pTP53e5F13, iSx-039-bkA30-pTP53e5R15, and iSx-001-bkA30); (iv) TP53 Exon 5 downstream forward and reverse target regions (iSx-001-bkA30, iSx-043-bkA30-TP53e5F21, iSx-044-pTP53e5F22, iSx-008-701F. iSx-009-501R, iSx-045-pTP53e5F23, and iSx-046-pTP53e5R24) and (iSx-042-pTP53e5F20, iSx-044-pTP53e5F22, iSx-008-701F. iSx-009-501R, iSx-045-pTP53e5F23, iSx-047-bkA30-TP53e5R25 and iSx-001-bkA30); (v) TP53 Exon 6 forward and reverse target regions (iSx-001-bkA30, iSx-053-bkA30-TP53e6F31, iSx-054-pTP53e6F32, iSx-008-701F, iSx-009-501R, iSx-055-pTP53e6F33, and iSx-056-pTP53e6R34) and (iSx-052-pTP53e6F30, iSx-054-pTP53e6F32, iSx-008-701F, iSx-009-501R, iSx-055-pTP53e6F33, iSx-057-bkA30-TP53e6R35, and iSx-001-bkA30); (vi) TP53 Exon 7 forward and reverse target regions (iSx-001-bkA30, iSx-063-bkA30-TP53e7F41, iSx-064-pTP53e7F42, iSx-008-701F, iSx-009-501R, iSx-065-pTP53e7F43, and iSx-066-pTP53e7R44) and (iSx-062-pTP53e7F40, iSx-064-pTP53e7F42, iSx-008-701F, iSx-009-501R, iSx-065-pTP53e7F43, iSx-067-pTP53e7R45, and iSx-001-bkA30); and (vii) TP53 Exon 8 forward and reverse target regions (iSx-001-bkA30, iSx-073-bkA30-TP53e8F51, iSx-074-pTP53e8F52, iSx-008-701F, iSx-009-501R, iSx-075-pTP53e8F53, and iSx-076-pTP53e8R54) and (iSx-072-pTP53e8F50, iSx-074-pTP53e8F52, iSx-008-701F, iSx-009-501R, iSx-075-pTP53e8F53, iSx-077-bkA30-TP53e8R55, and iSx-001-bkA30).

Note 11: After generating the circular products comprising target regions of KRAS, BRAF, and TP53 exons 5-8 containing hotspot mutations, these regions may be subject to rolling circle amplification using target-specific primers to generate tandem-repeat products. These products may be generated either prior to, or after capture of desired targets with target-specific oligonucleotides on a solid support (See note 12 below). Primers may contain an internal cleavable nucleotide base or abasic site such as 1',2'-Dideoxyribose (dSpacer), enabling incorporation of dUTP during rolling circle amplification for protection against carryover contamination. Examples of such primers are shown in Table 1 below and include the following: (i) KRAS forward and reverse primers (iSx-108-KRS-rcF26, iSx-109-KRS-rcR27); (ii) BRAF forward and reverse primers (iSx-118-BRF-rcF26, iSx-119-BRF-rcR27); (iii) TP53 Exon 5 forward and reverse primers (iSx-128-TP53e5-rcF66, iSx-129-TP53e5-rcR67; iSx-130-TP53e5-rcF68, iSx-131-TP53e5-rcR69); (iv) TP53 Exon 6 forward and reverse primers (iSx-138-TP53e6-rcF76, iSx-139-TP53e6-rcR77); (v) TP53 Exon 7 forward and reverse primers (iSx-148-TP53e7-rcF86, iSx-149-TP53e7-rcR87); and (vi) TP53 Exon 8 forward and reverse primers (iSx-158-TP53e8-rcF96, iSx-159-TP53e8-rcR97).

Note 12: After generating the circular products comprising target regions of KRAS, BRAF, and TP53 exons 5-8 containing hotspot mutations, and/or generating tandem-repeat products, these products may be captured by hybridizing to longer oligonucleotides, which contain a capture group suitable for subsequent capture on a solid support. Examples of such primers, containing biotin groups suitable for capture via streptavidin-coated solid surfaces are shown in Table 1 below and include the following: (i) KRAS forward and reverse capture oligonucleotides (iSx-013-KRS-bcF1, iSx-014-KRS-bcR2); (ii) BRAF forward and reverse capture oligonucleotides (iSx-020-BRF-bcF1, iSx-021-BRF-bcR2); (iii) TP53 Exon 5 forward and reverse capture oligonucleotides (iSx-030-TP53e5-bcF1, iSx-031-TP53e5-bcR2; iSx-032-TP53e5-bcF3, iSx-033-TP53e5-bcR4); (iv) TP53 Exon 6 forward and reverse capture oligonucleotides (iSx-050-TP53e6-bcF5, iSx-051-TP53e6-bcR6); (v) TP53 Exon 7 forward and reverse capture oligonucleotides (iSx-060-TP53e7-bcF7, iSx-061-TP53e7-bcR8); and (vi) TP53 Exon 8 forward and reverse capture oligonucleotides (iSx-070-TP53e8-bcF9, iSx-071-TP53e8-bcR10).

Note 13: With the aforementioned products generated using the above primer and linker designs, after cluster or bead amplification, or capture within a well, address, or surface of a flow cell on a commercial instrument, the following primers may be used to initiate sequencing reactions: (i) iLx-003-PEsqP1, Paired End sequencing primer 1; (ii) iLx-004-BrCdR1, Indexing primer, Barcode Read 1; (iii) iLx-001-P5-BrCdR2, Barcode Read 2; and (iv) iLx-005-PEsqP2, Paired End sequencing primer 2 (see Table 1 for primer sequences).

Variation 1.3: (See e.g., FIGS. 19-22).

In this variation, instead of ligating short linkers to the DNA target, a short mononucleotide tail is appended using terminal transferase (cfDNA of average length of about 160 bases). The remaining steps are the same as in FIGS. 13 and 15. It is difficult to control how many bases are appended by terminal transferase. Therefore, the length of the homonucleotide tract (i.e. polyA) within the oligonucleotide determines the hybridization Tm. It may be necessary to also use a polymerase with 3'→5' proofreading activity to remove some of the excess homonucleotide tract until it is flush with its complement, and suitable for extension with polymerase.

Variation 1.4: (See e.g., FIGS. 23-26).

In this variation, nothing is appended to the DNA target (cfDNA of average length of about 160 bases). To capture the desired regions, oligonucleotides comprising a 5' probe region complementary to the sequences to the 5' side of the target, a unique identifier sequence, an optional patient identifier sequence, an optional primer binding sequence, and a 3' probe region complementary to the sequences to the 3' side of the target, are hybridized to the target. The 5' and 3' probe regions contain optional mismatches at regular intervals (i.e. 10, 12, or 15 bases). The oligonucleotide probe may contain an optional blocking group on one end (5' end shown), or an optional cleavable linker. Depending on the probe design and the starting and ending bases of the target fragment, a portion of the 5' or 3' end of the target sequence may not hybridize (FIG. 23). Addition of a polymerase or set of polymerases containing both 3'→5' and 5'→3' nuclease activity allows extension of the 3' end of the oligonucleotide on the target, as well as optional digestion of the single-stranded 3' end of the target until it is flush with the 3' probe region of the oligonucleotide (FIG. 23), followed by extension of the 3' end of the target through the unique identifier sequence, and optional patient identifier sequence.

The hybridization conditions are chosen such that hybridization of the 3' probe region complementary to the sequence of the 3' side of the target and hybridization of the 5' probe region complementary to the sequence of the 5' side of the target are enriched over targets that hybridize to only one side (and would form an unproductive extension product that would not circularize). Extension of the 3' end of the oligonucleotide probe on the target enhances association of the probe to the target. The 5'→3' nuclease cleavage activity of polymerase (or Fen nuclease) cleaves a matching 5'-overlapping base of target at or near the position where the 5' side of the target is complementary to the 5' portion of the probe, leaving ligation-competent 5'-phosphate from the authentic target. Polymerase also extends oligonucleotide probe using target at template, and either generates a ligation-competent 5'-phosphate (left side of FIGS. 23 and 22), or does not cleave the blocking group on the 5' end of the oligonucleotide (right side of FIGS. 23 and 25).

Ligase covalently seals the extended 3' ends to the ligation-competent 5'-phosphate to create circular ligation products. Blocking group prevents circularization of oligonucleotide probe (right side), or alternatively, a nick is introduced at the cleavable link (e.g. UDG cleavage of dU, followed by cleavage of the apurinic backbone with AP endonuclease, left side). Optional addition of Uracil-DNA glycosylase (UDG) and Formamidopyrimidine-DNA glycosylase (Fpg, also known as 8-oxoguanine DNA glycosylase, which acts both as a N-glycosylase and an AP-lyase) may be used to nick targets containing damaged bases. Exonuclease(s) are then added to digest all unligated or nicked products leaving only desired single-stranded circular DNA comprising of original target DNA with unique identifier sequence. This product is suitable for rolling circle amplification and circle sequencing, or direct SMRT sequencing.

This approach requires an enzyme or set of enzymes with target-dependent 5'→3' and 3'→5' nuclease activity such that the ligation-competent 5'-phosphate is generated only when there is proper hybridization and complementarity between the 5' probe region and the 5' target region. When using polymerase with 5'→3' nuclease cleavage activity, the challenge is to avoid having polymerase extend the short linker along the 5' probe region in such a way that it destroys the 5' target region (i.e. nick-translation) without a ligation step. Nick-translation that destroys original target DNA and replaces it with extended DNA may inadvertently introduce a polymerase error that would be propagated and miscalled as a mutation. This may be minimized by using a mixture of polymerases, both with and without 5'→3' nuclease cleavage activity (e.g. in a ratio of 1:20) under conditions of distributive extension in the presence of ligase such that most extension is by polymerase without nuclease activity until polymerase with nuclease activity is required to create the ligation competent junction, followed by polymerase dissociation, and a ligation event to generate the desired circular ligation product. Use of oligonucleotide probe design as depicted in FIGS. 25 and 26 may obviate the need for polymerase with 3'→5' nuclease activity. Use of T4 kinase to append a phosphate on the 5' end of the target in an initial reaction, may also be used to create a ligation-competent 5' phosphate, and obviate the need for polymerase with 5'→3' nuclease activity.

FIGS. 96-99 provide some examples of different oligonucleotide probe design to cover fragments across a 250 base region. In these figures, the potential target fragment (shifted by 10 bases across a region) is represented by a dark gray bar, the probe regions as light gray bars with thin black lines within the gray bars indicating mismatched bases, and the unique sequence identifier and optional patient identifier as a thicker black line. FIGS. 104-107 illustrate how multiple probes would be designed to cover approximately a 500 base contiguous region.

In FIG. 96, the upstream 5' probe region (50 bases) is complementary to target bases 40-90, while the downstream 3' probe region (50 bases) is complementary to target bases 150-200. For the purposes of this example, there are mismatches every 10 bases, and the composite identifier sequence is 20 bases (12 bases for sequence identifier and 8 bases for patient identifier). When the target is from position 1 to 160, this probe design will allow circularization of a 180 base product, of which 110 bases, i.e. from positions 50 to 160, provide target sequence information. When the target is from position 11 to 170, this probe design will allow circularization of a 180 base product, of which 120 bases, i.e. from positions 50 to 170, provide target sequence information. With this design, the maximum 140 bases of sequence information will be derived with target starting from position 31 to 51, and ending at positions 190 to 210 respectively. In the figure, when target is from position 81 to 250, there is no circular product formation. Some product might form, however, due to the shorter region of complementarity between the 5' probe region and the 5' side of the target, there is concern that they will not always hybridize.

In FIG. 97, the upstream 5' probe region (60 bases) is complementary to target bases 30-90, while the downstream 3' probe region (60 bases) is complementary to target bases 150-210. This figure is similar to FIG. 96, except both 5' and 3' probe regions are longer. For the first 5 examples of targets, the longer oligonucleotide allows for capture of more target DNA, such that the resultant circles contain 20 additional bases of original target DNA.

FIGS. 98 and 99 extend the trends of FIGS. 96 and 97, with probe regions of 70 and 80 bases respectively. As before, the longer probe regions assure more of the target is covered. The mismatches help to distinguish authentic target from a polymerase copy of the probe. When the DNA in question contains the wild-type base, it originated from the target, as well as the DNA sequence adjacent to it. When the DNA contains the complement of the mismatched base on the probe, then it is known that the base was generated from the probe.

FIGS. 104-107 illustrate how to design oligonucleotide probes with an overlapping tiling strategy to sequence larger contiguous regions (about 500 bases shown herein). FIG. 104 illustrates four "consecutive" probes using the design in FIG. 96, while FIGS. 105-107 illustrates four "consecutive" probes using the design in FIG. 97-99, respectively. Potential 160 bp fragments that could be generated over the region (shifted by 10 bases) are illustrated. Underneath, the oligonucleotide that would cover all those fragments above it is shown. If the area in the target is in light grey, it will not provide reliable sequence information. If the area in the target is in dark grey, it should provide good sequence information. In this diagram, probes listed are sequentially designated as #1, #2, #3, #4 etc. For the multiplexed extension-ligation steps, odd probes #1, #3, #5 are pooled in a first oligonucleotide pool set, and then the even probes #2, #4, #6 are pooled into a second pool set. This approach avoids adjacent oligonucleotides (i.e. #1 and #2) competing for binding to the same target strand. Once the extension-circularization has taken place, the two pools may be combined and exonuclease and subsequent steps such as rolling circle amplification and circle sequencing may proceed, or alternatively, direct SMRT sequencing on the covalently closed template, using the optional primer binding sequence as a primer binding site.

Detailed Protocol for High Sensitivity Detection of Single Base Mutation, Small Insertion, or Small Deletion Mutations (when Present at 1% to 0.01%,) in Known Genes (e.g. Braf, K-Ras, p53)

1.4.a. Starting with cfDNA (or for example genomic DNA isolated from CTC, sheared to about 150 bp), denature target DNA (94° C. 1 minute) in the presence of oligonucleotides (comprising a 5' probe region complementary to the sequences to the 5' side of the targets, a unique identifier sequence, an optional patient identifier sequence, an optional primer binding sequence, and a 3' probe region complementary to the sequences to the 3' side of the targets), and allow the oligonucleotides to hybridize to their complementary regions on the desired fragments by cooling to a desired temperature (e.g. 40° C. or 45° C. for 2 hours). The reaction is lowered in temperature, and DNA polymerases (i.e. T4 polymerase has strong 3'→5' proofreading activity) and DNA polymerase 1 (has weak 3'→5' proofreading, but good 5'→3' activity), and optionally Klenow fragment (no 5'→3' activity)), DNA ligase (T4 ligase or *E. coli* ligase), and dNTPs are added subsequent to the annealing step. Allow for extension and ligation at 23° C. or 30° C., and optionally raise the temperature (e.g. 37° C.) to assure completion of extension and ligation, to generate circular products.

1.4.b. Optionally, cleave the oligonucleotide probe at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the linker sequence as a primer binding site.

Note 1: Oligonucleotide may contain an optional blocking group on the 5' side to interfere with subsequent 5'-3' nuclease activity of polymerase, such that the oligonucleotide probe does not circularize. Alternatively, a cleavable link may be included in the original oligonucleotide.

Note 2: Fen nuclease may be used instead of polymerase with 5'-3' nuclease activity to generate the ligation-competent 5' phosphate on the 5' side of the target.

Note 3: A 1:20 mixture of T4 polymerase (with 5'→3' nuclease activity), DNA polymerase I (weak 3'→5' proofreading, but good 5'→3' activity) and Klenow (DNA polymerase I without 5'→3' nuclease cleavage activity) may be used under conditions of distributive extension (i.e. higher salt concentration) to minimize degradation of target DNA by nick translation.

Note 4: The ligation extension process may be carried out in two or more reaction tubes, one set containing "odd" numbered probes, the second set containing "even" numbered probes to avoid probes competing for the same target DNA strands. The separate reactions may be subsequently pooled.

Note 5: Use of mismatch bases in the probe sequence at regular intervals (i.e. 10, 12, or 15 bases) allows for distinguishing authentic target DNA sequence from sequence generated by copying the probe strand. The oligonucleotides listed in Note 6 below contain mismatch bases approximately every 15 bases in the target sequence regions.

Note 6: When designing oligonucleotides for use with longer linker sequences, comprising "barcoding" or "indexing" sequences for use with commercial instruments, it may be necessary to assemble the oligonucleotide using PCR, strand-displacement amplification, or a combination thereof. During PCR, use of dUTP instead of TTP incorporates uracil, suitable for subsequent cleavage by UDG. The reverse-strand primer may be phosphorylated, allowing for its digestion using lambda exonuclease or a similar 5'→3' exonuclease. A dA30 sequence may be appended to the 5' end of the forward primer, enabling strand displacement amplification. Examples of oligonucleotides suitable for assembly amplification for sequencing regions of KRAS, BRAF, and TP53 exons 5-8 containing hotspot mutations are shown in Table 1 (below) and include the following: (i) KRAS forward and reverse target regions (iSx-001-bkA30, iSx-103-bkA30-KRSF21, iSx-104-pKRSF22, iSx-100-705F, iSx-101-502R, iSx-105-pKRSF23, and iSx-106-pKRSR24) and (iSx-102-pKRSF20, iSx-104-pKRSF22, iSx-100-705F, iSx-101-502R, iSx-105-pKRSF23, iSx-107-bkA30-KRSR25, and iSx-001-bkA30); (ii) BRAF forward and reverse target regions (iSx-001-bkA30, iSx-113-bkA30-BRF-F21, iSx-114-pBRF-F22, iSx-100-705F, iSx-101-502R, iSx-115-pBRF-F23, and iSx-116-pBRF-R24) and (iSx-112-pBRF-F20, iSx-114-pBRF-F22, iSx-100-705F, iSx-101-502R, iSx-115-pBRF-F23, iSx-117-bkA30-BRF-R25 and iSx-001-bkA30); (iii) TP53 Exon 5 forward and reverse target regions (iSx-001-bkA30, iSx-123-bkA30-TP53e5F61, iSx-124-pTP53e5F62, iSx-100-705F, iSx-101-502R, iSx-125-pTP53e5F63, and iSx-126-pTP53e5R64) and (iSx-122-pTP53e5F60, iSx-124-pTP53e5F62, iSx-100-705F, iSx-101-502R, iSx-125-pTP53e5F63, iSx-127-bkA30-TP53e5F65, and iSx-001-bkA30); (iv) TP53 Exon 6 forward and reverse target regions (iSx-001-bkA30, iSx-133-bkA30-TP53e6F71, iSx-134-pTP53e6F72, iSx-100-705F, iSx-101-502R, iSx-135-pTP53e6F73, and iSx-136-pTP53e6R74) and (iSx-132-pTP53e6F70, iSx-134-pTP53e6F72, iSx-100-705F, iSx-101-502R, iSx-135-pTP53e6F73, iSx-137-bkA30-TP53e6F75, and iSx-001-bkA30); (v) TP53 Exon 7 forward and reverse target regions (iSx-001-bkA30, iSx-143-bkA30-TP53e7F81, iSx-144-pTP53e7F82, iSx-100-705F, iSx-101-502R, iSx-145-pTP53e7F83, and iSx-146-pTP53e7F84) and (iSx-142-pTP53e7F80, iSx-144-pTP53e7F82, iSx-100-705F, iSx-101-502R, iSx-145-pTP53e7F83, iSx-147-bkA30-TP53e7R85, and iSx-001-bkA30); and (vi) TP53 Exon 8 forward and reverse target regions (iSx-001-bkA30, iSx-153-bkA30-TP53e8F91, iSx-154-pTP53e8F92, iSx-100-705F, iSx-101-502R, iSx-155-pTP53e8F93, and iSx-156-pTP53e8R94) and (iSx-152-pTP53e8F90, iSx-154-pTP53e8F92, iSx-100-705F, iSx-101-502R, iSx-155-pTP53e8F93, iSx-157-bkA30-TP53e8R95 and iSx-001-bkA30).

Note 7: After generating the circular products comprising target regions of KRAS, BRAF, and TP53 exons 5-8 containing hotspot mutations, these regions may be subject to rolling circle amplification using target-specific primers to generate tandem-repeat products. These products may be generated either prior to, or after capture of desired targets with target-specific oligonucleotides on a solid support (See note 8 below). Primers may contain an internal cleavable nucleotide base or abasic site such as 1',2'-Dideoxyribose (dSpacer), enabling incorporation of dUTP during rolling circle amplification for protection against carryover contamination. Examples of such primers are shown in Table 1 (below) and include the following: (i) KRAS forward and reverse primers (iSx-108-KRS-rcF26, iSx-109-KRS-rcR27); (ii) BRAF forward and reverse primers (iSx-118-BRF-rcF26, iSx-119-BRF-rcR27); (iii) TP53 Exon 5 forward and reverse primers (iSx-128-TP53e5-rcF66, iSx-129-TP53e5-rcR67; iSx-130-TP53e5-rcF68, iSx-131-TP53e5-rcR69); (iv) TP53 Exon 6 forward and reverse primers (iSx-138-TP53e6-rcF76, iSx-139-TP53e6-rcR77); (v) TP53 Exon 7 forward and reverse primers (iSx-148-TP53e7-rcF86, iSx-149-TP53e7-rcR87); and (vi) TP53 Exon 8 forward and reverse primers (iSx-158-TP53e8-rcF96, iSx-159-TP53e8-rcR97).

Note 8: After generating the circular products comprising target regions of KRAS, BRAF, and TP53 exons 5-8 containing hotspot mutations, and/or generating tandem-repeat products, these products may be captured by hybridizing to longer oligonucleotides, which contain a capture group suitable for subsequent capture on a solid support. Examples of such capture oligonucleotides, containing biotin groups suitable for capture via streptavidin-coated solid surfaces are shown in Table 1 (below) and include the following: (i) KRAS forward and reverse capture oligonucleotides (iSx-013-KRS-bcF1, iSx-014-KRS-bcR2); (ii) BRAF forward and reverse capture oligonucleotides (iSx-020-BRF-bcF1, iSx-021-BRF-bcR2); (iii) TP53 Exon 5 forward and reverse capture oligonucleotides (iSx-030-TP53e5-bcF1, iSx-031-TP53e5-bcR2; iSx-032-TP53e5-bcF3, iSx-033-TP53e5-bcR4); (iv) TP53 Exon 6 forward and reverse capture oligonucleotides (iSx-050-TP53e6-bcF5, iSx-051-TP53e6-bcR6); (v) TP53 Exon 7 forward and reverse capture oligonucleotides (iSx-060-TP53e7-bcF7, iSx-061-TP53e7-bcR8); and (vi) TP53 Exon 8 forward and reverse capture oligonucleotides (iSx-070-TP53e8-bcF9, iSx-071-TP53e8-bcR10).

Note 9: With the aforementioned products generated using the above primer and linker designs, after cluster or bead amplification, or capture within a well, address, or surface of a flow cell on a commercial instrument, the following primers may be used to initiate sequencing reactions: (i) iLx-003-PEsqP1, Paired End sequencing primer 1; (ii) iLx-004-BrCdR1, Indexing primer, Barcode Read 1; (iii) iLx-001-P5-BrCdR2, Barcode Read 2; and (iv) iLx-005-PEsqP2, Paired End sequencing primer 2 (primer sequences are provided in Table 1 below).

Prophetic Example 2—High Sensitivity Methylation Marker Detection for Promoter Hypermethylation (when Present at 1% to 0.01%) in Plasma DNA Promoter methylation plays an important role in regulating gene expression. Promoters for genes often have regions of high CpG content known as "CpG Islands". When genes, such as tumor suppressor genes, with promoter CpG islands are turned off, this is usually accompanied with methylation of most CpG sequences within the promoter and $1^{st}$ exon regions. There have been two traditional approaches to detecting methylation changes.

The first takes advantage of methyl-sensitive restriction enzymes, wherein genomic DNA is cleaved when unmethylated, and this is followed by a PCR amplification using primers that flank the site(s). If the DNA was methylated, it should amplify, if unmethylated, it should not amplify. This technique has the disadvantage that digestions do not always go to completion, and further, it is not accurate for finding low levels of methylated DNA when the majority of the same sequence is unmethylated, as would be the case with plasma detection.

The second approach is known as "Methyl-specific PCR" and is based on bisulfite treatment of DNA, which converts unmethylated C's to U's. If the base is methylated, then it is not converted. Methyl-specific PCR is based on using primers and TaqMan probes that are specific for the resultant converted sequence if it were methylated, but not unmethylated. Methyl-specific PCR has the advantage of being able to detect very low levels of methylated DNA. A further improvement of this technique employs a blocking oligonucleotide that hybridizes to the sequence for bisulfite-converted unmethylated DNA, thus enriching for amplification of bisulfite-converted methylated DNA. The disadvantage is that bisulfite treatment destroys from 50% to 90% of the original DNA integrity by nicking it. When starting with DNA from the plasma (with average length of about 160 bases), this can be a significant problem. Further, converting C's to U's reduces the complexity of the sequence from 4 bases to 3 bases. Since the converted sequence is now more A:T rich, longer PCR primers are also required. Thus, non-specific amplifications can occur, as primers are more likely to mis-prime at closely related but incorrect sequences. This usually necessitates a nested-PCR approach, this runs the risk of carryover contamination and is generally not ideal for multiplexed amplifications.

Overview of approach: The idea is to faithfully copy every fragment of target DNA that contains methylation at adjacent restriction sites for the regions of interest, append a unique identifier sequence and an optional patient identifier, and circularize them for subsequent sequencing. The oligonucleotide DNA strand is circularized and sequenced. This approach provides the advantage of obtaining both copy number information when needed, and methylation data with the minimum of sequencing required.

Detection of Methylation at Adjacent Sites

Variation 2.1: (See e.g., FIG. 27).

In this variation, DNA is initially cleaved with HinP1I to significantly reduce the amount of unmethylated target. To capture the desired methylated regions, oligonucleotides comprising a 5' probe region complementary to the sequences to the 5' side of the target, a unique identifier sequence, an optional patient identifier sequence, and a 3' probe region complementary to the sequences to the 3' side of the target, are hybridized to the target. The oligonucleotide contains unmethylated HinP1I sequences near both the 3' end of the upstream probe and a blocked 5' or ligation incompetent end of the downstream probe. The 3' end contains mismatches to the target, or is blocked to prevent extension with polymerase. HinP1I will nick the unmethylated strands of the probe target hybrid if the target DNA was methylated, liberating an extension-competent 3'OH end, and a ligation competent 5'-phosphate (left side of FIG. 27). If the target was unmethylated, both strands are cleaved, destroying the target template (right side of FIG. 27). Addition of ligase and polymerase lacking strand displacing activity and both 3'→5' and 5'→3' nuclease activity, enables extension of the liberated 3' end of the probe on the methylated target, followed by ligation to the liberated 5' end of the probe to form a circular product containing both a unique identifier sequence, an optional patient identifier sequence. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Methylation:

2.1a. Cleave isolated cfDNA, or methyl enriched DNA with one or more methyl sensitive enzymes (AciI, HinP1I, Hpy99I, and HpyCH4IV). In this example, HinP1I is used. Heat kill endonuclease(s) (65° C. for 15 minutes) and denature DNA (94° C. 1 minute).

2.1b. Denature target DNA (94° C. 1 minute) in the presence of oligonucleotide probes (comprising a 5' probe region complementary to the sequence of the 5' side of the target, a unique identifier sequence, an optional patient identifier sequence, an optional primer binding site, and a 3' probe region complementary to the sequence of the 3' side of the target), and allow the oligonucleotides to hybridize to their complementary regions on the desired fragments by cooling to a desired temperature (e.g. 40-50° C. for 2 hours). The oligonucleotide contains unmethylated HinP1I sequences near both the 3' and 5' ends of the probes, which are designed to contain either mismatches, blocking groups, or lack phosphorylation, such that they are not substrates for either polymerase or ligase. Cool to 37° C. and add HinP1I, which will nick the unmethylated strands of the probe target hybrid if the target DNA was methylated, liberating an extension-competent 3'OH end, and a ligation competent 5'-phosphate. Heat kill endonuclease(s) (65° C. for 15 minutes). KlenTaq (Taq polymerase lacking nuclease activity), and thermostable ligase (preferably from strain AK16D), dNTPs are either added, subsequent to the annealing step, or subsequent to the restriction endonuclease nicking step. Allow for extension and ligation at 50° C., and optionally raise the temperature (e.g. 60° C.) to assure completion of extension and ligation, to generate circular products.

2.1.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1: Oligonucleotide may lack a 5' phosphate, or contain an optional blocking group on the 5' side, such that the 5' end of the oligonucleotide is not suitable for ligation. Oligonucleotide may contain 3' mismatches, 3' hairpin, or an optional blocking group on the 3' side, such that the 3' end of the oligonucleotide is not suitable for extension on the target. In both cases, the block is only liberated by restriction enzyme nicking of the probe when hybridized to methylated target.

Note 2: The above example use KlenTaq, a polymerase lacking strand displacing activity as well as both 3'→5' and 5'→3' nuclease activity. If the oligonucleotide has a blocking group on the 3' side, then one can use polymerase with 3'→5' nuclease activity, while if the blocking group is on the 5' side, then one can use polymerase with 5'→3' nuclease activity.

Note 3: In the example, the restriction endonuclease (HinP1I) is heat inactivated by incubating at 65° C. for 15 minutes. An alternative approach, (or when using a heat insensitive enzyme like BstUI) is to extend with nucleotide analogues (i.e. 5-methyl-dCTP, or alpha-thiophosphate dCTP) that render a restriction site resistant to re-cleavage with the cognate endonuclease. If the restriction site on the 5' side of the oligonucleotide is not converted to a resistant form by use of nucleotide analogues (i.e. HinP1I), then this case may be solved by using an oligonucleotide with a blocking group on the 5' side, as well as a polymerase containing 5'→3' nuclease activity. Initially, the blocking group is removed by the nicking activity of the restriction endonuclease. Subsequently during the extension step using nucleotide analogues, the polymerase containing 5'→3' nuclease activity nick translates through the recognition site, replacing it with nucleotides that render the site refractory to further cleavage.

Note 4: In the above example, further to minimize nick-translation way past the recognition sequence, the portion of the oligonucleotide directly adjacent to the restriction site of the 5' probe portion may be synthesized to contain thiophosphate linkages. To minimize polymerase displacement of those bases as it extends one base too many (which would make it impossible to ligate to the downstream primer), the target bases at the ligation junction would preferentially be AT rich on the 3' side, and GC rich on the 5' side.

Note 5: The target-specific portions of the oligonucleotide probe are designed such that they will remain hybridized to the target even after liberation of the non-productive 3' and 5' end. If the target contains additional restriction sites that overlap with the probe portions, then the probe may be synthesized with 5-methyl-dC in those positions. Should the target be methylated at those positions, then the site will be methylated at both the target and the oligonucleotide probe, and hence be refractory to nicking. However, should the target be unmethylated at those positions, then the site will be nicked on the target strand, thus interfering with probe hybridization to the (shortened) target.

Note 6. The circular product is suitable for rolling circle amplification (using random hexamer primers with phi-29 polymerase) to create tandem repeats complementary to the desired sequence, and subsequent identification of the targets using next generation sequencing, or alternatively, direct SMRT sequencing on the covalently closed template, using the primer binding sequence as a primer binding site.

Note 7. If the oligonucleotide probes also comprise optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Database of Methylation Status at Adjacent Methyl-Sensitive Restriction Sites.

The current TCGA database contains information on the methylation status of about 450,000 CpG sites on the human genome, both for normal and for tumor of many different tissue sites. However, it does not cover all the methylation status of adjacent HinP1I sites, nor would it distinguish that both sites are methylated on the same piece of genomic DNA.

Consequently, for the above assay method to be most useful, it would be helpful to create a database of methylation status at adjacent methyl-sensitive restriction sites. One such an approach is illustrated in FIG. 28.

Overview of approach: The idea is to generate a library of small fragments that could only have been formed if both ends of the fragment contained restriction sites that were methylated in the original genomic DNA. The fragments have linkers appended with optional unique identifier and optional patient identifier sequences that are now amenable for ligation to create fragment multimers that are then substrates for additional steps and subsequent sequencing.

Variation 2.1.1: (See e.g., FIG. 28).

This approach shows how to discover methylation at adjacent HinP1I sites (GC*GC) throughout genome. The starting material may be either intact genomic DNA or cfDNA with average length of about 160 bp. Cleave genomic DNA with HinP1I to fragment DNA at unmethylated HinP1I sites. Short linkers containing a blocked 5' end at the non-ligating end, are ligated onto both ends of filled in HinP1I cleaved ends and repaired ends of target fragments. (These linkers do not recreate a HinP1I site at the ligation junction). A few rounds of PCR amplification using unmethylated dNTPs and 5' blocked primers generates products that are now unmethylated at the remaining HinP1I sites. These products are then cleaved with HinP1I. Only PCR amplicons containing adjacent HinP1I sites (GCGC) that were methylated in the original target will generate fragments that are unblocked (i.e. ligation competent for linkers) on both ends, when cleaved with HinP1I. Linkers containing optional unique identifier sequence, and optional patient identifier sequence are ligated onto these newly generated filled in HinP1I cleaved ends. These new linkers contain on their non-ligating side either blocked 3' end, or thiophosphate containing backbone (shown as **** in FIG. 28). Upon addition of a double-stranded 3' exonuclease (i.e. Exonuclease III), fragments containing the original short linker on one or both sides will be digested and rendered single-stranded. Only fragments with the new linker ligated to both sides will remain double-stranded, since the 3' blocking group or thiophosphates inhibit digestion with 3' exonuclease. The free ends of the remaining linker-containing fragments are rendered competent for ligation, either by (i) phosphorylating 5' end, (ii) removing blocked 3' group, or (iii) using 5'-nuclease activity to cleave off matching 5'-overlapping base or flap, leaving ligation-competent 5'-phosphate, or any combination thereof. Ligation conditions are designed to favor multimerization, for example by using crowding agents (i.e. 20% PEG), and/or by mixing two sets of ligation products, wherein the non-palindromic 5' linker overhang of the first set is complementary to the non-palindromic 5' linker overhang of the second set. The ligation products comprise of adjacent HinP1I sequences originally methylated in target DNA with optional unique identifier and/or patient identifier sequence. This product is suitable for optional additional steps and subsequent sequencing.

Detailed Protocol for Generating a Database of Methylation Status at Adjacent Methyl-Sensitive Restriction Sites:

2.1.1a. Cleave isolated genomic DNA, or methyl enriched DNA with one or more methyl sensitive enzymes (AciI, HinP1I, Hpy99I, and HpyCH4IV). In this example, HinP1I is used. Optionally, heat kill endonuclease(s) (65° C. for 15 minutes). Ligate on linkers that are blocked on the 5' end of the non-ligating end. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. (See Note 1, below.)

2.1.1b. Add 5' blocked primers, Taq Polymerase, and dNTPs and perform a few cycles of PCR to generate products that are now unmethylated at the remaining HinP1I sites.

2.1.1.c. Add HinP1I to cleave products containing such sites. Only PCR amplicons containing adjacent HinP1I sites (GCGC) that were methylated in the original target will generate fragments that are unblocked (i.e. ligation competent for linkers) on both ends, when cleaved with HinP1I. Residual polymerase from Taq polymerase will fill in 2-base overhang (optionally raise temperature to 60° C.). Remove dNTPs (via a spin column), add back only dATP to generate a single base 3' A overhang.

2.1.1.d. Using T4 ligase, append linkers (containing optional unique identifier sequence, and optional patient identifier sequence) with a single base 3' T overhang on the ligating end to the single base A overhang of the cleaved and filled in target sequences. The 5' non-ligating side of the linker contains a 5' overhang, and optionally is not phosphorylated. The 3' non-ligating side of the linker contains a 3' blocking group and/or thiophosphates to inhibit digestion with 3' exonuclease.

2.1.1.e. Add a 3' exonuclease (i.e. Exonuclease III) and digest at 37° C. Fragments containing the original short linker on one or both sides will be digested and rendered single-stranded. Only fragments with the new linker ligated to both sides will remain double-stranded. Exonuclease will also render the linkers single-stranded. Optionally, remove digestion products from desired fragments with a spin column.

2.1.1.f The free ends of the remaining linker-containing fragments are rendered competent for ligation, either by (i) phosphorylating 5' end using T4 kinase, (ii) removing blocked 3' group, or (iii) using 5'→3' nuclease activity of Taq polymerase to cleave off matching 5'-overlapping base or flap, leaving ligation-competent 5'-phosphate, or any combination thereof. Ligation conditions are designed to favor multimerization. The ligation products comprise of multimers of target fragments with adjacent HinP1I sequences originally methylated in target DNA with optional unique identifier and/or patient identifier sequence. This product is suitable for optional additional steps and subsequent sequencing.

Note 1: Regarding linker ligations: As an alternative for filling in, repairing ends, and A tailing prior to linker ligation with linkers containing a single base T overhang, one can take advantage of the 5' CpG overhang generated by HinP1I. One can generate a single base 3' C overhang using Klenow (exo-) and dCTP. Linkers have a single base 3' C overhang, such that ligation using T4 ligase appends linkers on both ends of the fragment. Alternatively, linkers with a CG overhang may be used directly, with no fill-in of sites, but the linkers are designed, such that if they self ligate, they create an AclI site (AA^CGTT). Thus, genomic DNA is cleaved with Hinp1I (G^CGC), AclI site (AA^CGTT) in the presence of both linkers and T4 ligase at 37° C. Ligation of fragments to each other is cleaved by Hinp1I, ligation of linkers to each other is cleaved by AclI, however ligation of linkers to the ends of fragments is not cleaved by either enzyme, so this 3-enzyme ligation mix serves as a "biochemical selection" to enrich for the desired products.

Note: 2: The 3' end of the blocked linker may be synthesized to contain a Uracil or an apurinic (AP) site at a position internal to the block, and after treatment with UDG and AP endonuclease, liberate a ligation competent 3' end.

Note 3: Fen nuclease may be used instead of polymerase with 5'-3' nuclease activity to generate the ligation-competent 5' phosphate on the 5' side of the target.

Note 4: Ligation will favor formation of multimers by using crowding agents (i.e. 20% PEG), and/or by mixing two sets of ligation products, wherein the non-palindromic 5' linker overhang of the first set is complementary to the non-palindromic 5' linker overhang of the second set.

Detection of Methylation at Adjacent Sites Using Bisulfite Treatment

The above approach is ideal for identifying and enumerating fragments containing adjacently methylated HinP1I sites as a surrogate for methylation within that fragment of DNA. However, for some applications, it is important to identify methylation status of individual CpG sites within a given region. Thus it may be necessary to treat the input DNA with bisulfite, which converts regular C, but not methyl-C, to U.

Overview of approach using bisulfite: The idea is to faithfully copy every fragment of target DNA that is methylated at adjacent AciI restriction sites of the sequence (G*CGG) for the regions of interest, treat with bisulfite, append a unique identifier sequence, an optional primer binding sequence, and an optional patient identifier, and circularize them for subsequent sequencing. The oligonucleotide DNA strand is circularized and sequenced. This approach provides the advantage of obtaining both copy number information when needed, and methylation data with the minimum of sequencing required.

The idea takes advantage of a unique property of the recognition sequence for AciI. The enzyme cleaves the 3.5 base recognition sequence G^CGG in one orientation, and C^CGC in the second orientation. If a methylated AciI site is treated with bisulfite in the first orientation (G*CGG), the site will remain unchanged (G*CGG), while in the second orientation (C*CGC), it will be changed (U*CGU, where *C denotes 5-meC.). After a few rounds of PCR amplification, the 5-methyl C is converted to C, while the U is converted to T. Thus, a methylated AciI site in the first orientation remains as GCGG, an unmethylated AciI site in the first orientation is converted to GTGG, a methylated AciI site in the second orientation is converted to TCGT, and an unmethylated AciI site in the second orientation is converted to TTGT. When cleaved with AciI, only adjacent AciI sites methylated in the original target will create fragments that are ligation competent on both the 3' and 5' ends.

One unique feature of this approach is that bisulfite conversion creates two non-complementary strands. Thus the top strand will have adjacent G*CGG sequences, and even if there is an intervening C*CGC sequence, it doesn't matter because it is converted to U*CGU, which after PCR conversion to TCGT is not recognized as an AciI site. Further, even if there is an intervening G*CGG or GCGG (i.e. unmethylated) site, it will not be nicked by AciI, since it will be in a region that is single-stranded. Even better, sequences on the top strand of the form C*CGC will be G*CGG on the bottom strand. The bottom strand may also be used to query methylation status, and since the two sequences are now very different, the oligonucleotide probes to the top and bottom strand will not hybridize to each other, only to the converted targets. Thus, this approach allows for obtaining detailed methylation status on the promoter using information from both top and bottom strands.

The principle of treating DNA with bisulfite to convert unmethylated DNA into a sequence that is not cleavable by a restriction enzyme, but if methylated, it is still cleavable by that same restriction enzyme may be extended to some additional restriction sites. For example, a BstUI site (CG^CG) retains its same sequence after bisulfite conversion provided both CG sites were methylated (i.e. *CG*CG). Likewise, an Hpy99I site (CGWCG^) also retains its same sequence after bisulfite conversion provided both CG sites were methylated (*CGW*CG). In a different type of example, HpyCH2IV (A^CGT) will cleave both sequences of the form A*CGT and A*CGC after bisulfite conversion, as both become A*CGT. Thus, the variations considered below for AciI are equally valid for, but not limited to, restriction endonucleases BstUI, Hpy99I, HpyCH2IV and their isoschizomers.

Variation 2.2: (See e.g., FIGS. 29-30).

In this variation, short linkers containing 5-methyl C are ligated onto the ends of the DNA. The DNA is then treated with bisulfite, which renders the strands non-complementary so they become single-stranded. A few rounds of PCR amplification generates products that are now unmethylated at the remaining AciI sites. These products are then cleaved with AciI. Only PCR amplicons containing adjacent AciI sites (GCGG) that were methylated in the original target will generate fragments that are now competent for ligation on both ends. To capture the desired regions, oligonucleotide probes comprising a 5' probe region complementary to the sequence of the 5' side of the target, a unique identifier sequence, an optional primer binding sequence, an optional patient identifier sequence, and a 3' probe region complementary to the sequence of the 3' side of the target, are hybridized to the target. Addition of ligase and polymerase lacking strand displacing activity and both 3'→5' and 5'→3' nuclease activity, enables extension of the 3' end of the unmethylated target, followed by ligation to the 5' end of the target to form a circular product containing a unique identifier sequence, an optional patient identifier sequence, and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Methylation:

2.2.a. Ligate on linkers that contain 5-methyl C to retain sequence after bisulfite conversion. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Incubate cfDNA with bisulfite, which converts regular C, but not methyl-C, to U. Bisulfite treatment converts the top and bottom strand differently, such that after treatment, the strands will no longer be complementary to each other, and melt apart.

2.2.b. Add primers, Taq Polymerase, and dNTPs and perform a few cycles of PCR to generate products that are now unmethylated at the remaining AciI sites.

2.2.c. Add AciI to cleave products containing such sites. Only PCR amplicons containing adjacent AciI sites (GCGG) that were methylated in the original target will generate fragments that are unblocked (i.e. ligation competent for linkers) on both ends, when cleaved with AciI. Residual polymerase from Taq polymerase will fill in 2-base overhang (optionally raise temperature to 60° C.).

2.2.d. Denature target DNA (94° C. 1 minute) in the presence of oligonucleotide probes (comprising a 5' probe region complementary to the sequence of the 5' side of the targets, a unique identifier sequence, an optional patient identifier sequence, an optional primer binding site, and a 3' probe region complementary to the sequence of the 3' side of the targets), and allow the oligonucleotides to hybridize to their complementary regions on the desired fragments by cooling to a desired temperature (e.g. 50°-60° C. for 2 hours). KlenTaq (Taq polymerase lacking nuclease activity), and thermostable ligase (preferably from strain AK16D), dNTPs are added to allow for extension and ligation at 50° C., and optionally raise the temperature (e.g. 60° C.) to assure completion of extension and ligation, to generate circular products.

2.2.e. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. Oligonucleotide may lack a 5' phosphate, or contain an optional blocking group on the 5' side, such that the 5' end of the oligonucleotide is not suitable for ligation.

Note 2. The above example use KlenTaq, a polymerase lacking strand displacing activity as well as both 3'→5' and 5'→3' nuclease activity. If the oligonucleotide has a blocking group is on the 5' side, then one can use polymerase with 5'→3' nuclease activity.

Note 3. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 4. If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

In variation 2.2 both a polymerase and a ligase are used to form a covalently closed circle containing a unique identifier sequence, an optional patient identifier sequence, and an optional primer binding site. This may also be accomplished using just a ligase.

Variation 2.3: (See e.g., FIGS. 31-32).

In this variation, short linkers containing 5-methyl C, are ligated onto the ends of the DNA. The DNA is then treated with bisulfite, which renders the strands non-complementary so they become single-stranded. A few rounds of PCR amplification generates products that are now unmethylated at the remaining AciI sites. These products are then cleaved with AciI. Only PCR amplicons containing adjacent AciI sites (GCGG) that were methylated in the original target will generate fragments that are now competent for ligation on both ends. To capture the desired unmethylated regions, a partially double-stranded oligonucleotide pair comprising a first oligonucleotide probe with a 5' probe region complementary to the sequence of the 5' side of the target, an optional primer binding sequence, an optional patient identifier sequence, and a 3' probe region complementary to the sequence of the 3' side of the target, and a second oligonucleotide probe comprising a 5' region complementary to the first oligonucleotide probe strand, a unique identifier sequence and a 3' region complementary to the first oligonucleotide probe strand, are hybridized to the target. Addition of ligase enables ligation of the 3' end of the target to the 5' end of the second oligonucleotide probe, and the 5' end of the target to the 3' end of the second oligonucleotide probe, to form a circular product containing a unique identifier sequence, an optional patient identifier sequence, and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Unmethylation:

2.3.a. Ligate on linkers that contain 5-methyl C to retain sequence after bisulfite conversion. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Incubate cfDNA with bisulfite, which converts regular C, but not methyl-C, to U. Bisulfite treatment converts the top and bottom strand differently, such that after treatment, the strands will no longer be complementary to each other, and melt apart.

2.3.b. Add primers, Taq Polymerase, and dNTPs and perform a few cycles of PCR to generate products that are now unmethylated at the remaining AciI sites.

2.3.c. Add AciI to cleave products containing such sites. Only PCR amplicons containing adjacent AciI sites (GCGG) that were methylated in the original target will generate fragments that are unblocked (i.e. ligation competent for linkers) on both ends, when cleaved with AciI. Residual polymerase from Taq polymerase will fill in 2-base overhang (optionally raise temperature to 60° C.).

2.3.d. Denature target DNA (94° C. 1 minute) in the presence of partially double-stranded oligonucleotide pairs (comprising a first oligonucleotide probe with a 5' probe region complementary to the sequence of the 5' side of the target, an optional primer binding sequence, an optional patient identifier sequence, and a 3' probe region complementary to the sequence of the 3' side of the target, and a second oligonucleotide probe comprising a 5' region complementary to the first oligonucleotide probe, a unique identifier sequence and a 3' region complementary to the first oligonucleotide probe), and allow the oligonucleotides to hybridize to their complementary regions on the desired fragments by cooling to a desired temperature (e.g. 50°-60° C. for 2 hours). A thermostable ligase (preferably from strain AK16D), is added to allow for ligation at 60° C. to generate circular products.

2.3.e. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 2. If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Database of Methylation Status at Adjacent Methyl-Sensitive Restriction Sites (AciI Sites).

The current TCGA database contains information on the methylation status of about 450,000 CpG sites on the human genome, both for normal and for tumor of many different tissue sites. However, it does not cover all the methylation status of adjacent AciI sites, nor would it distinguish that both sites are methylated on the same piece of genomic DNA.

Consequently, for the above assay method to be most useful, it would be helpful to create a database of methylation status at adjacent AciI restriction sites of the same orientation (GCGG). This approach will also include adjacent AciI restriction sites of the other orientation (CCGC), since they will be GCGG on the opposite strand after bisulfite conversion. One such an approach is illustrated in FIG. 33.

Overview of approach: The idea is to generate a library of small fragments that could only have been formed if both ends of the fragment contained restriction sites that were methylated in the original genomic DNA. This idea takes advantage of a unique property of the recognition sequence for AciI. The enzyme cleaves the 3.5 base recognition sequence G^CGG in one orientation, and C^CGC in the other orientation. Start with a methylated AciI site and treat with bisulfite. In the first orientation (G*CGG), the site will remain unchanged, while in the second orientation, it will be changed (U*CGU, where *C denotes 5-meC.). After a few rounds of PCR amplification, the first site is converted to GCGG, which is recognized by AciI, while the second site is converted to TCGT, which is not cleaved. Thus, AciI may be used to identify uniquely methylated sequences after bisulfite treatment. The fragments have linkers appended with optional unique identifier and optional patient identifier sequences that are now amenable for ligation to create fragment multimers that are then substrates for additional steps and subsequent sequencing.

Variation 2.3.1: (See e.g., FIG. 33).

This approach shows how to discover methylation at adjacent AciI sites (GC*GG) throughout genome. The starting material may be either intact genomic DNA or cfDNA with average length of about 160 bp. Short linkers containing a blocked 5' end at the non-ligating end, are ligated onto the ends of the DNA. Bisulfite treat DNA, which converts regular C, but not methyl-C, to U. A few rounds of PCR amplification using unmethylated dNTPs and 5' blocked primers generates products that are now unmethylated at the remaining AciI sites. These products are then cleaved with AciI. Only PCR amplicons containing adjacent AciI sites (GCGG) that were methylated in the original target will generate fragments that are unblocked (i.e. ligation competent for linkers) on both ends, when cleaved with AciI. Linkers containing optional unique identifier sequence, and optional patient identifier sequence are ligated onto these newly generated filled in AciI cleaved ends. These new linkers contain on their non-ligating side either blocked 3' end, or thiophosphate containing backbone (shown as **** in FIG. 33). Upon addition of a double-stranded 3' exonuclease (i.e. Exonuclease III), fragments containing the original short linker on one or both sides will be digested and rendered single-stranded. Only fragments with the new linker ligated to both sides will remain double-stranded, since the 3' blocking group or thiophosphates inhibit digestion with 3' exonuclease. The free ends of the remaining linker-containing fragments are rendered competent for ligation, either by (i) phosphorylating 5' end, (ii) removing blocked 3' group, or (iii) using 5'-nuclease activity to cleave off matching 5'-overlapping base or flap, leaving ligation-competent 5'-phosphate, or any combination thereof. Ligation conditions are designed to favor multimerization, for example by using crowding agents (i.e. 20% PEG), and/or by mixing two sets of ligation products, wherein the non-palindromic 5' linker overhang of the first set is complementary to the non-palindromic 5' linker overhang of the second set. The ligation products comprise of adjacent AciI sequences in the same orientation (i.e. GCGG), originally methylated in target DNA with optional unique identifier and/or patient identifier sequence. This product is suitable for optional additional steps and subsequent sequencing.

Detailed Protocol for Generating a Database of Methylation Status at Adjacent AciI Restriction Sites:

2.3.1.a. Ligate on linkers that are blocked on the 5' end of the non-ligating end. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Incubate cfDNA with bisulfite, which converts regular C, but not methyl-C, to U. Bisulfite treatment converts the top and bottom strand differently, such that after treatment, the strands will no longer be complementary to each other, and melt apart.

2.3.1.b. Add 5' blocked primers, Taq Polymerase, and dNTPs and perform a few cycles of PCR to generate products that are now unmethylated at the remaining AciI sites.

2.3.1.c. Add AciI to cleave products containing such sites. Only PCR amplicons containing adjacent AciI sites (GCGG) that were methylated in the original target will generate fragments that are unblocked (i.e. ligation competent for linkers) on both ends, when cleaved with AciI. Residual polymerase from Taq polymerase will fill in 2-base overhang (optionally raise temperature to 60° C.). Remove dNTPs (via a spin column), add back only dATP to generate a single base 3' A overhang.

2.3.1.d. Using T4 ligase, append linkers (containing optional unique identifier sequence, and optional patient identifier sequence) with a single base 3' T overhang on the ligating end to the single base A overhang of the cleaved and filled in target sequences. The 5' non-ligating side of the linker contains a 5' overhang, and optionally is not phosphorylated. The 3' non-ligating side of the linker contains a 3' blocking group and/or thiophosphates to inhibit digestion with 3' exonuclease.

2.3.1.e. Add a 3' exonuclease (i.e. Exonuclease III) and digest at 37° C. Fragments containing the original short linker on one or both sides will be digested and rendered single-stranded. Only fragments with the new linker ligated to both sides will remain double-stranded. Exonuclease will also render the linkers single-stranded. Optionally, remove digestion products from desired fragments with a spin column.

2.3.1.E The free ends of the remaining linker-containing fragments are rendered competent for ligation, either by (i) phosphorylating 5' end using T4 kinase, (ii) removing blocked 3' group, or (iii) using 5'→3' nuclease activity of Taq polymerase to cleave off matching 5'-overlapping base or flap, leaving ligation-competent 5'-phosphate, or any combination thereof. Ligation conditions are designed to favor multimerization. The ligation products comprise of multimers of target fragments with adjacent AciI sequences originally methylated in target DNA with optional unique identifier and/or patient identifier sequence. This product is suitable for optional additional steps and subsequent sequencing.

Note: 1: The 3' end of the blocked linker may be synthesized to contain a Uracil or an apurinic (AP) site at a position internal to the block, and after treatment with UDG and AP endonuclease, liberate a ligation competent 3' end.

Note 2: Fen nuclease may be used instead of polymerase with 5'-3' nuclease activity to generate the ligation-competent 5' phosphate on the 5' side of the target.

Note 3: Ligation will favor formation of multimers by using crowding agents (i.e. 20% PEG), and/or by mixing two sets of ligation products, wherein the non-palindromic 5' linker overhang of the first set is complementary to the non-palindromic 5' linker overhang of the second set.

Prophetic Example 3—High Sensitivity Unmethylated Marker for Promoter Hypomethylation (when Present at 1% to 0.1%) in Total Plasma DNA The majority of methylation changes in tumors are due to hypomethylation. When such hypomethylation occurs in a promoter region that was previously methylated, it may cause increased expression of a gene, such as an oncogene. Further, repetitive element regions and mobile elements are generally silenced by overall methylation, but such silencing is lost when the tumor becomes hypomethylated.

While methyl-sensitive restriction enzymes may be used to help selectively amplify and identify low levels of methylated sequences, the approach does not work for identifying low levels of unmethylated sequences. Bisulfite treatment and use of PCR primers directed to bisulfite modified unmethylated DNA may be used, although such primers are very AT rich and there may be difficulties amplifying all desired fragments, especially when attempting multiplexed PCR.

Overview of approach: The idea is to faithfully copy every fragment of target DNA that is unmethylated at adjacent restriction sites for the regions of interest, append a unique identifier sequence, an optional primer binding sequence, and an optional patient identifier, and circularize them for subsequent sequencing. The oligonucleotide DNA strand is circularized and sequenced. This approach provides the advantage of obtaining both copy number information when needed, and unmethylation data with the minimum of sequencing required.

Variation 3.1: (See e.g., FIGS. 34 and 35).

In this variation, DNA is cleaved with HinP1I (or other methylation sensitive restriction endonuclease) to generate ligation competent 3' and 5' ends. To capture the desired unmethylated regions, oligonucleotide probes comprising a 5' probe region complementary to the sequence of the 5' side of the target, a unique identifier sequence, an optional primer binding sequence, an optional patient identifier sequence, and a 3' probe region complementary to the sequence of the 3' side of the target, are hybridized to the target. Addition of ligase and polymerase lacking strand displacing activity and both 3'→5' and 5'→3' nuclease activity, enables extension of the 3' end of the unmethylated target, followed by ligation to the 5' end of the target to form a circular product containing both a unique identifier sequence, an optional patient identifier sequence and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Unmethylation:

3.1a. Cleave isolated cfDNA with one or more methyl sensitive enzymes (AciI, HinP1I, Hpy99I, and HpyCH4IV). This example illustrates the use of HinP1I. Heat kill endonuclease(s) (65° C. for 15 minutes) and denature DNA (94° C. 1 minute).

3.1b. Denature target DNA (94° C. 1 minute) in the presence of oligonucleotides (comprising a 5' probe region complementary to the sequence of the 5' side of the targets, a unique identifier sequence, an optional patient identifier sequence, an optional primer binding site, and a 3' probe region complementary to the sequence of the 3' side of the targets), and allow the oligonucleotides to hybridize to their complementary regions on the desired fragments by cooling to a desired temperature (e.g. 50°-60° C. for 2 hours). KlenTaq (Taq polymerase lacking nuclease activity), and thermostable ligase (preferably from strain AK16D), dNTPs are added to allow for extension and ligation at 50° C., and optionally raise the temperature (e.g. 60° C.) to assure completion of extension and ligation, to generate circular products.

3.1.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. Oligonucleotide may lack a 5' phosphate, or contain an optional blocking group on the 5' side, such that the 5' end of the oligonucleotide is not suitable for ligation.

Note 2. The above example use KlenTaq, a polymerase lacking strand displacing activity as well as both 3'→5' and 5'→3' nuclease activity. If the oligonucleotide has a blocking group on the 5' side, then one can use polymerase with 5'→3' nuclease activity.

Note 3. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site. When using direct SMRT sequencing, loss of methylation status of the original template DNA may be directly determined.

Note 4. If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Note 5. The same approach may be used to identify regions that are methylated at promoter regions (see e.g., FIGS. 36 and 37). Cleave isolated cfDNA with a cocktail of methyl sensitive enzymes (AciI, HinP1I, Hpy99I, and HpyCH4IV), as well as by methyl insensitive enzymes (HaeIII and MspI). The figure illustrates this with methylated AciI sites, internal to, and flanked with two HaeIII sites. This approach will work even if there is only one methyl insensitive restriction site (see e.g., FIGS. 39, 40, 42, 43). If the methyl insensitive restriction endonuclease liberates a competent 3' end, then that end would be extended on the oligonucleotide with Taq polymerase (with 5'-3' nuclease activity), and the polymerase would extend and cleave the extra 5' sequence in the target, generating a ligation competent 5' phosphate on the target suitable for ligation to create the circular product (FIG. 39). If the methyl insensitive restriction endonuclease liberates a competent 5' phosphate, then use of a polymerase with 3'-5' nuclease activity would digest the extra 3' sequence in the target (if needed), and then once flush to complementary sequence on the oligonucleotide probe, polymerase would extend the target strand up to the ligation competent 5' phosphate on the target, and the nick sealed by ligase to create the circular product (FIG. 40). After exonuclease digestion, strand survival from methyl-sensitive restriction endonuclease cleavage is a marker for methylation of that region. Further, when using direct SMRT sequencing on the covalently closed template, the methylation status of the original template DNA may be determined.

Note 6. The same approach may be used to identify regions that are methylated at Bsh1236I sites in promoter regions (see e.g., FIGS. 38, 41, 44, 45, 46). Cleave isolated cfDNA with Bsh1236I (CGCG), as well as by methyl insensitive enzymes (HaeIII). FIG. 38 illustrates this with methylated Bsh1236I sites, internal to, and flanked with two HaeIII sites. This approach will work even if there is only one methyl insensitive restriction site (see e.g., 41, 44, 45). If the methyl insensitive restriction endonuclease liberates a competent 3' end, then that end would be extended on the oligonucleotide with Taq polymerase (with 5'-3' nuclease activity), and the polymerase would extend and cleave the extra 5' sequence in the target, generating a ligation competent 5' phosphate on the target suitable for ligation to create the circular product (FIG. 38). If the methyl insensitive restriction endonuclease liberates a competent 5' phosphate, then use of a polymerase with 3'-5' nuclease activity would digest the extra 3' sequence in the target (if needed), and then once flush to complementary sequence on the oligonucleotide probe, polymerase would extend the target strand up to the ligation competent 5' phosphate on the target, and the nick sealed by ligase to create the circular product (FIGS. 41 & 45). After exonuclease digestion, strand survival from methyl-sensitive restriction endonuclease cleavage is a marker for methylation of that region. Rolling circle replication using Bst polymerase in the presence of BstUI (CGCG) assures that sites were methylated in the original sample.

In variation 3.1, both a polymerase and a ligase are used to form a covalently closed circle containing a unique identifier sequence, an optional patient identifier sequence, and an optional primer binding site. This may also be accomplished using just a ligase.

Variation 3.2: (See e.g., FIGS. 47 and 48).

In this variation, DNA is cleaved with HinP1I (or other methylation sensitive restriction endonuclease) to generate ligation competent 3' and 5' ends. To capture the desired unmethylated regions, a partially double-stranded oligonucleotide pair comprising a first oligonucleotide probe with a 5' probe region complementary to the sequence of the 5' side of the target, an optional primer binding sequence, an optional patient identifier sequence, and a 3' probe region complementary to the sequence of the 3' side of the target, and a second oligonucleotide probe comprising a 5' region complementary to the first probe, a unique identifier sequence and a 3' region complementary to the first probe, are hybridized to the target. Addition of ligase enables ligation of the 3' end of the target to the 5' end of the second oligonucleotide probe, and the 5' end of the target to the 3' end of the second oligonucleotide probe to form a circular product containing a unique identifier sequence, an optional patient identifier sequence, and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Unmethylation:

3.2.a. Cleave isolated cfDNA with one or more methyl sensitive enzymes (AciI, HinP1I, Hpy99I, and HpyCH4IV). In this example, HinP1I is used. Heat kill endonuclease(s) (65° C. for 15 minutes) and denature DNA (94° C. 1 minute).

3.2.b. Denature target DNA (94° C. 1 minute) in the presence of partially double-stranded oligonucleotide pairs (comprising a first oligonucleotide probe with a 5' probe region complementary to the sequence of the 5' side of the target, an optional primer binding sequence, an optional patient identifier sequence, and a 3' probe region complementary to the sequence of the 3' side of the target, and a second oligonucleotide probe comprising a 5' region complementary to the first strand, a unique identifier sequence and a 3' region complementary to the first strand), and allow the oligonucleotides to hybridize to their complementary regions on the desired fragments by cooling to a desired temperature (e.g. 50°-60° C. for 2 hours). A thermostable ligase (preferably from strain AK16D), is added to allow for ligation at 60° C. to generate circular products.

3.2.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site. When using direct SMRT sequencing, loss of methylation status of the original template DNA may be directly determined.

Note 2. If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Note 3. The same approach may be used to identify regions that are methylated at promoter regions (see e.g., FIGS. 49 and 51). Cleave isolated cfDNA with a cocktail of methyl sensitive enzymes (AciI, HinP1I, Hpy99I, and HpyCH4IV), as well as by methyl insensitive enzymes (HaeIII and MspI). These figures illustrate methylated AciI sites, internal to, and flanked with two HaeIII sites. Survival of the strand from methyl-sensitive restriction endonuclease cleavage is a marker for methylation of that region. Further, when using direct SMRT sequencing on the covalently closed template, the methylation status of the original template DNA may be determined.

Database of Unmethylation Status at Adjacent Methyl-Sensitive Restriction Sites

The current TCGA database contains information on the methylation status of about 450,000 CpG sites on the human genome, both for normal and for tumor of many different tissue sites. However, it does not cover all the unmethylation status of adjacent HinP1I sites, nor would it distinguish that both sites are unmethylated on the same piece of genomic DNA.

Consequently, for the above assay method to be most useful, it would be helpful to create a database of unmethylation status at adjacent methyl-sensitive restriction sites. One such an approach is illustrated in FIG. 51.

Overview of approach: The idea is to generate a library of small fragments that could only have been formed if both ends of the fragment contained restriction sites that were unmethylated in the original genomic DNA. The fragments have linkers appended with optional unique identifier and optional patient identifier sequences that are now amenable for ligation to create fragment multimers that are then substrates for additional steps and subsequent sequencing.

Variation 3.2.1: (See e.g., FIG. 51).

This approach shows how to discover unmethylation at adjacent HinP1I sites (GCGC) throughout the genome. The starting material may be either intact genomic DNA or cfDNA with average length of about 160 bp. Short linkers containing a blocked 5' end at the non-ligating end, are ligated onto target DNA. Cleave genomic DNA with HinP1I to fragment DNA at unmethylated HinP1I sites. Linkers containing optional unique identifier sequence, and optional patient identifier sequence are ligated onto these newly generated filled in HinP1I cleaved ends. These new linkers contain on their non-ligating side either blocked 3' end, or thiophosphate containing backbone (shown as **** in FIG. 51). Upon addition of a double-stranded 3' exonuclease (i.e. Exonuclease III), fragments containing the original short linker on one or both sides will be digested and rendered single-stranded. Only fragments with the new linker ligated to both sides will remain double-stranded, since the 3' blocking group or thiophosphates inhibit digestion with 3' exonuclease. The free ends of the remaining linker-containing fragments are rendered competent for ligation, either by (i) phosphorylating 5' end, (ii) removing blocked 3' group, or (iii) using 5'-nuclease activity to cleave off matching 5'-overlapping base or flap, leaving ligation-competent 5'-phosphate, or any combination thereof. Ligation conditions are designed to favor multimerization, for example by using crowding agents (i.e. 20% PEG), and/or by mixing two sets of ligation products, wherein the non-palindromic 5' linker overhang of the first set is complementary to the non-palindromic 5' linker overhang of the second set. The ligation products comprise of adjacent HinP1I sequences originally unmethylated in target DNA with optional unique identifier and/or patient identifier sequence. This product is suitable for optional additional steps and subsequent sequencing.

Detailed Protocol for Generating a Database of Methylation Status at Adjacent Methyl-Sensitive Restriction Sites:

3.2.1a. Ligate on linkers that are blocked on the 5' end of the non-ligating end. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Cleave isolated genomic DNA, or methyl enriched DNA with one or more methyl sensitive enzymes (AciI, HinP1I, Hpy99I, and HpyCH4IV). In this example, HinP1I was used. Optionally, heat kill endonuclease(s) (65° C. for 15 minutes).

3.2.1.b. Add HinP1I to cleave products containing such sites. Only target containing adjacent HinP1I sites (GCGC) that were unmethylated in the original target will generate fragments that are unblocked (i.e. ligation competent for linkers) on both ends, when cleaved with HinP1I. Residual polymerase from Taq polymerase will fill in 2-base overhang (optionally raise temperature to 60° C.). Remove dNTPs (via a spin column) and add back only dATP to generate a single base 3' A overhang.

3.2.1.c. Using T4 ligase, append linkers (containing optional unique identifier sequence, and optional patient identifier sequence) with a single base 3' T overhang on the ligating end to the single base A overhang of the cleaved and filled in target sequences. The 5' non-ligating side of the linker contains a 5' overhang, and optionally is not phosphorylated. The 3' non-ligating side of the linker contains a 3' blocking group and/or thiophosphates to inhibit digestion with 3' exonuclease.

3.2.1.d. Add a 3' exonuclease (i.e. Exonuclease III) and digest at 37° C. Fragments containing the original short linker on one or both sides will be digested and rendered single-stranded. Only fragments with the new linker ligated to both sides will remain double-stranded. Exonuclease will also render the linkers single-stranded. Optionally, remove digestion products from desired fragments with a spin column.

3.2.1.1.e. The free ends of the remaining linker-containing fragments are rendered competent for ligation, either by (i) phosphorylating 5' end using T4 kinase, (ii) removing blocked 3' group, or (iii) using 5'→3' nuclease activity of Taq polymerase to cleave off matching 5'-overlapping base or flap, leaving ligation-competent 5'-phosphate, or any combination thereof. Ligation conditions are designed to favor multimerization. The ligation products comprise of multimers of target fragments with adjacent HinP1I sequences originally methylated in target DNA with optional unique identifier and/or patient identifier sequence. This product is suitable for optional additional steps and subsequent sequencing.

Note: 1: The 3' end of the blocked linker may be synthesized to contain a Uracil or an apurinic (AP) site at a position internal to the block, and after treatment with UDG and AP endonuclease, liberate a ligation competent 3' end.

Note 2: Fen nuclease may be used instead of polymerase with 5'-3' nuclease activity to generate the ligation-competent 5' phosphate on the 5' side of the target.

Note 3: Ligation will favor formation of multimers by using crowding agents (i.e. 20% PEG), and/or by mixing two sets of ligation products, wherein the non-palindromic 5' linker overhang of the first set is complementary to the non-palindromic 5' linker overhang of the second set.

Note 4. The same approach may be used to identify regions that are methylated at promoter regions (see e.g., FIG. 52). Cleave isolated cfDNA with a cocktail of methyl sensitive enzymes (AciI, HinP1I, Hpy99I, and HpyCH4IV), and ligate on the short linkers with blocked 5' ends. Then cleave target with methyl insensitive enzymes (HaeIII and MspI). AciI and HaeIII are illustrated in this figure. Survival of the strand from methyl-sensitive restriction endonuclease cleavage is a marker for methylation of that region. Only adjacent HaeIII sites (GGCC) with methylated AciI sites in original target generate unblocked fragments when cleaved with HaeIII. Subsequent ligation of longer linkers is as described above. When using direct SMRT sequencing on the ligated products, the methylation status of the original template DNA may be determined.

Detection of Unmethylated Adjacent Sites in Promoter Region

There may be a desire to determine unmethylation status of CpG sequences in between two methyl sensitive restriction sites in a promoter region. This is similar to the approaches above, and includes an extra bisulfite step.

Overview of approach: The idea is to faithfully copy every fragment of target DNA that is unmethylated at adjacent restriction sites for the regions of interest, treat with bisulfite, append a unique identifier sequence, an optional primer binding sequence, and an optional patient identifier, and circularize them for subsequent sequencing. The oligonucleotide DNA strand is circularized and sequenced. This approach provides the advantage of obtaining both copy number information when needed, and unmethylation data with the minimum of sequencing required.

Variation 3.3: (See e.g., FIGS. 53 and 54).

In this variation, DNA is cleaved with HinP1I (or other methylation sensitive restriction endonuclease) to generate ligation competent 3' and 5' ends. The DNA is then treated with bisulfite, which renders the strands non-complementary so they become single-stranded. To capture the desired unmethylated regions, oligonucleotide probes comprising a 5' probe region complementary to the sequence of the 5' side of the target, a unique identifier sequence, an optional primer binding sequence, an optional patient identifier sequence, and a 3' probe region complementary to the sequence of the 3' side of the target, are hybridized to the target. Addition of ligase and polymerase lacking strand displacing activity and both 3'→5' and 5'→3' nuclease activity, enables extension of the 3' end of the unmethylated target, followed by ligation to the 5' end of the target to form a circular product containing a unique identifier sequence, an optional patient identifier sequence, and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Unmethylation:

3.3.a. Cleave isolated cfDNA with one or more methyl sensitive enzymes (AciI, HinP1I, Hpy99I, and HpyCH4IV). This example describes HinP1I. Heat kill endonuclease(s) (65° C. for 15 minutes) and denature DNA (94° C. 1 minute). Incubate cfDNA with bisulfite, which converts regular C, but not methyl-C, to U. Bisulfite treatment converts the top and bottom strand differently, such that after treatment, the strands will no longer be complementary to each other, and melt apart.

3.3.b. Denature target DNA (94° C. 1 minute, if needed) in the presence of oligonucleotides (comprising a 5' probe region complementary to the sequences to the 5' side of the targets, a unique identifier sequence, an optional patient identifier sequence, an optional primer binding site, and a 3' probe region complementary to the sequences to the 3' side of the targets), and allow the oligonucleotides to hybridize to their complementary regions on the desired fragments by cooling to a desired temperature (e.g. 50°-60° C. for 2 hours). KlenTaq (Taq polymerase lacking nuclease activity), and thermostable ligase (preferably from strain AK16D), dNTPs are added to allow for extension and ligation at 50° C., and optionally raise the temperature (e.g. 60° C.) to assure completion of extension and ligation, to generate circular products.

3.3.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. Oligonucleotide may lack a 5' phosphate, or contain an optional blocking group on the 5' side, such that the 5' end of the oligonucleotide is not suitable for ligation.

Note 2. The above example use KlenTaq, a polymerase lacking strand displacing activity as well as both 3'→5' and 5'→3' nuclease activity. If the oligonucleotide has a blocking group is on the 5' side, then one can use polymerase with 5'→3' nuclease activity.

Note 3. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 4. If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

In variation 3.3 both a polymerase and a ligase were used to form a covalently closed circle containing a unique identifier sequence, an optional patient identifier sequence, and an optional primer binding site. This may also be accomplished using just a ligase.

Variation 3.4: (See e.g., FIGS. 55 and 56).

In this variation, DNA is cleaved with HinP1I (or other methylation sensitive restriction endonuclease) to generate ligation competent 3' and 5' ends, followed by bisulfite treatment. To capture the desired unmethylated regions, a partially double-stranded oligonucleotide pair comprising a first oligonucleotide probe with a 5' probe region complementary to the sequence of the 5' side of the target, an optional primer binding sequence, an optional patient identifier sequence, and a 3' probe region complementary to the sequence of the 3' side of the target, and a second oligonucleotide probe comprising a 5' region complementary to the first probe, a unique identifier sequence and a 3' region complementary to the first probe, are hybridized to the target. Addition of ligase enables ligation to the 3' end of the target to the 5' end of the second oligonucleotide probe, and the 5' end of the target to the 3' end of the second oligonucleotide probe, to form a circular product containing a unique identifier sequence, an optional patient identifier sequence, and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Unmethylation 3.4.a. Cleave isolated cfDNA with one or more methyl sensitive enzymes (AciI, HinP1I, Hpy99I, and HpyCH4IV). This example uses HinP1I. Heat kill endonuclease(s) (65° C. for 15 minutes) and denature DNA (94° C. 1 minute). Incubate cfDNA with bisulfite, which converts regular C, but not methyl-C, to U. Bisulfite treatment converts the top and bottom strand differently, such that after treatment, the strands will no longer be complementary to each other, and melt apart.

3.4.b. Denature target DNA (94° C. 1 minute) in the presence of partially double-stranded oligonucleotide pairs (comprising a first oligonucleotide probe with a 5' probe region complementary to the sequences to the 5' side of the target, an optional primer binding sequence, an optional patient identifier sequence, and a 3' probe region complementary to the sequences to the 3' side of the target, and a second oligonucleotide probe comprising a 5' region complementary to the first strand, a unique identifier sequence and a 3' region complementary to the first strand), and allow the oligonucleotides to hybridize to their complementary regions on the desired fragments by cooling to a desired temperature (e.g. 50°-60° C. for 2 hours). A thermostable ligase (preferably from strain AK16D), is added to allow for ligation at 60° C. to generate circular products.

3.4.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site. When using direct SMRT sequencing, loss of methylation status of the original template DNA may be directly determined.

Note 2. If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Database of Unmethylation Status at Adjacent Methyl-Sensitive Restriction Sites

The current TCGA database contains information on the methylation status of about 450,000 CpG sites on the human genome, both for normal and for tumor of many different tissue sites. However, it does not cover all the unmethylation status of adjacent HinP1I sites, nor the CpG sites between those sites, nor would it distinguish that both sites are unmethylated on the same piece of genomic DNA.

Consequently, for the above assay method to be most useful, it would be helpful to create a database of unmethylation status at adjacent methyl-sensitive restriction sites. One such an approach is illustrated in FIG. 57.

Overview of approach: The idea is to generate a library of small fragments that could only have been formed if both ends of the fragment contained restriction sites that were unmethylated in the original genomic DNA. The fragments have linkers appended with optional unique identifier and optional patient identifier sequences that are now amenable for ligation to create fragment multimers, then treated with bisulfite to reveal positions of methylation or unmethylation, that are then substrates for additional steps and subsequent sequencing.

Variation 3.4.1: (See e.g., FIG. 57).

This approach shows how to discover unmethylation at adjacent HinP1I sites (GCGC) throughout genome. The starting material may be either intact genomic DNA or cfDNA with average length of about 160 bp. Short linkers containing a blocked 5' end at the non-ligating end, are ligated onto target DNA. Cleave genomic DNA with HinP1I to fragment DNA at unmethylated HinP1I sites. Linkers containing optional unique identifier sequence, and optional patient identifier sequence are ligated onto these newly generated filled in HinP1I cleaved ends. These new linkers contain on their non-ligating side either blocked 3' end, or thiophosphate containing backbone (shown as **** in FIG. 57). Upon addition of a double-stranded 3' exonuclease (i.e. Exonuclease III), fragments containing the original short linker on one or both sides will be digested and rendered single-stranded. Only fragments with the new linker ligated to both sides will remain double-stranded, since the 3' blocking group or thiophosphates inhibit digestion with 3' exonuclease. The free ends of the remaining linker-containing fragments are rendered competent for ligation, either by (i) phosphorylating 5' end, (ii) removing blocked 3' group, or (iii) using 5'-nuclease activity to cleave off matching 5'-overlapping base or flap, leaving ligation-competent 5'-phosphate, or any combination thereof. Ligation conditions are designed to favor multimerization, for example by using crowding agents (i.e. 20% PEG), and/or by mixing two sets of ligation products, wherein the non-palindromic 5' linker overhang of the first set is complementary to the non-palindromic 5' linker overhang of the second set. The ligation products comprise of adjacent HinP1I sequences originally unmethylated in target DNA with optional unique identifier and/or patient identifier sequence. The product is then incubated with bisulfite, which converts regular C, but not methyl-C, to U. Bisulfite treatment converts the top and bottom strand differently, such that after treatment, the strands will no longer be complementary to each other, and melt apart. These single-stranded products are suitable for optional additional steps and subsequent sequencing.

Detailed Protocol for Generating a Database of Methylation Status at Adjacent Methyl-Sensitive Restriction Sites:

3.4.1a. Ligate on linkers that are blocked on the 5' end of the non-ligating end. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Cleave isolated genomic DNA, or methyl enriched DNA with one or more methyl sensitive enzymes (AciI, HinP1I, Hpy99I, and HpyCH4IV). In this example, HinP1I is used. Optionally, heat kill endonuclease(s) (65° C. for 15 minutes).

3.4.1.b. Add HinP1I to cleave products containing such sites. Only target containing adjacent HinP1I sites (GCGC) that were unmethylated in the original target will generate fragments that are unblocked (i.e. ligation competent for linkers) on both ends, when cleaved with HinP1I. Residual polymerase from Taq polymerase will fill in 2-base overhang (optionally raise temperature to 60° C.). Remove dNTPs (via a spin column), add back only dATP to generate a single base 3' A overhang.

3.4.1.c. Using T4 ligase, append linkers (containing optional unique identifier sequence, and optional patient identifier sequence) with a single base 3' T overhang on the ligating end to the single base A overhang of the cleaved and filled in target sequences. The 5' non-ligating side of the linker contains a 5' overhang, and optionally is not phosphorylated. The 3' non-ligating side of the linker contains a 3' blocking group and/or thiophosphates to inhibit digestion with 3' exonuclease.

3.4.1.d. Add a 3' exonuclease (i.e. Exonuclease III) and digest at 37° C. Fragments containing the original short linker on one or both sides will be digested and rendered single-stranded. Only fragments with the new linker ligated to both sides will remain double-stranded. Exonuclease will also render the linkers single-stranded. Optionally, remove digestion products from desired fragments with a spin column.

3.4.1.1.e. The free ends of the remaining linker-containing fragments are rendered competent for ligation, either by (i) phosphorylating 5' end using T4 kinase, (ii) removing blocked 3' group, or (iii) using 5'→3' nuclease activity of Taq polymerase to cleave off matching 5'-overlapping base or flap, leaving ligation-competent 5'-phosphate, or any combination thereof. Ligation conditions are designed to favor multimerization. The ligation products comprise of multimers of target fragments with adjacent HinP1I sequences originally methylated in target DNA with optional unique identifier and/or patient identifier sequence. Incubate ligation products with bisulfite, which converts regular C, but not methyl-C, to U. Bisulfite treatment converts the top and bottom strand differently, such that after treatment, the strands will no longer be complementary to each other, and melt apart. These single-stranded products are suitable for optional additional steps and subsequent sequencing.

Note: 1: The 3' end of the longer blocked linker may be synthesized to contain a Uracil or an apurinic (AP) site at a position internal to the block, and after treatment with UDG and AP endonuclease, liberate a ligation competent 3' end. Further, these linkers may be synthesized with 5-methyl C, such that after treatment with bisulfite they retain their original status.

Note 2: Fen nuclease may be used instead of polymerase with 5'-3' nuclease activity to generate the ligation-competent 5' phosphate on the 5' side of the target.

Note 3: Ligation will favor formation of multimers by using crowding agents (i.e. 20% PEG), and/or by mixing two sets of ligation products, wherein the non-palindromic 5' linker overhang of the first set is complementary to the non-palindromic 5' linker overhang of the second set.

Detection of Unmethylation Status of Individual CpG Sites within a Given Region

The above approach is ideal for identifying and enumerating fragments containing adjacently unmethylated HinP1I sites as a surrogate for unmethylation within that fragment of DNA. However, for some applications, it is important to identify unmethylation status of individual CpG sites within a given region. Thus it may be necessary to treat the input DNA with bisulfite, which converts regular C, but not methyl-C, to U.

Overview of approach using bisulfite: The idea is to faithfully copy every fragment of target DNA that is unmethylated at adjacent HphI restriction sites of the sequence (GGTGA) for the regions of interest, treat with bisulfite (convert GGCGA to GGTGA), append a unique identifier sequence, an optional primer binding sequence, and an optional patient identifier, and circularize them for subsequent sequencing. The oligonucleotide DNA strand is circularized and sequenced. This approach provides the advantage of obtaining both copy number information when needed, and methylation data with the minimum of sequencing required.

The idea takes advantage of a unique property of the recognition sequence for HphI. The enzyme cleaves the 4.5 base recognition sequence GGTGA in one orientation, and TCACC in the other orientation. If unmethylated GGCGA site is treated with bisulfite, in the first orientation, the site will become an HphI recognition sequence GGTGA. After a few rounds of PCR amplification, the 5-methyl C is converted to C, while the U is converted to T. When cleaved with HphI, only adjacent sites unmethylated in the original target will create fragments that are ligation competent on both the 3' and 5' ends.

One unique feature of this approach is that bisulfite conversion creates two non-complementary strands. Thus the top strand will have adjacent GGCGA or GGTGA sequences, and even if there is an intervening TCACC sequence, it doesn't matter because it is converted to TUAUU, which is not recognized as an HphI site. Even better, sequences on the top strand of the form TCGCC will be GGCGA on the bottom strand. The bottom strand may also be used to query methylation status, and since the two sequences are now very different, the oligonucleotide probes to the top and bottom strand will not hybridize to each other, only to the converted targets. Thus, this approach allows for obtaining detailed methylation status on the promoter using information from both top and bottom strands.

The principle of treating DNA with bisulfite to convert unmethylated DNA into a sequence that is cleavable by a restriction enzyme, but if methylated, it is not cleavable by that same restriction enzyme may be extended to some additional restriction sites. For example, the sequence CCGTC will be converted to a BccI site (CCATC), provided the internal CG is not methylated. (This results from conversion of the opposite strand, i.e. GACGG into the opposite strand recognition sequence of BccI; i.e. GATGG). Likewise, the sequence GGACG will be converted to a FokI site (GGATG) provided the internal CG is not methylated. Thus, the variations considered below for HphI are equally valid for, but not limited to, restriction endonucleases BccI, FokI, and their isoschizomers.

Variation 3.5: (See e.g., FIGS. 58 and 59).

In this variation, short linkers containing 5-methyl C, are ligated onto the ends of the DNA. The DNA is then treated with bisulfite, which renders the strands non-complementary so they become single-stranded. A few rounds of PCR amplification generates products that are now unmethylated at the HphI sites. These products are then cleaved with HphI. Only PCR amplicons containing adjacent "HphI" sites (GGCGA, or GGTGA) that were unmethylated in the original target will generate fragments that are now competent for ligation on both ends. To capture the desired regions, oligonucleotide probes comprising a 5' probe region complementary to the sequence of the 5' side of the target, a unique identifier sequence, an optional primer binding sequence, an optional patient identifier sequence, and a 3' probe region complementary to the sequence of the 3' side of the target, are hybridized to the target. Addition of ligase and polymerase lacking strand displacing activity and both 3'→5' and 5'→3' nuclease activity, enables extension of the 3' end of the unmethylated target, followed by ligation to the 5' end of the target to form a circular product containing a unique identifier sequence, an optional patient identifier sequence, and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Unmethylation:

3.5.a. Ligate on linkers that contain 5-methyl C to retain sequence after bisulfite conversion. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Incubate cfDNA with bisulfite, which converts regular C, but not methyl-C, to U. Bisulfite treatment converts the top and bottom strand differently, such that after treatment, the strands will no longer be complementary to each other, and melt apart.

3.5.b. Add primers, Taq Polymerase, and dNTPs and perform a few cycles of PCR to generate products that are now unmethylated at the remaining HphI sites.

3.5.c. Add HphI to cleave products containing such sites. Only PCR amplicons containing adjacent HphI sites (GGCGA or GGTGA) that were unmethylated in the original target will generate fragments that are unblocked (i.e. ligation competent for linkers) on both ends, when cleaved with HphI.

3.5.d. Denature target DNA (94° C. 1 minute) in the presence of oligonucleotides (comprising a 5' probe region complementary to the sequences to the 5' side of the targets, a unique identifier sequence, an optional patient identifier sequence, an optional primer binding site, and a 3' probe region complementary to the sequences to the 3' side of the targets), and allow the oligonucleotides to hybridize to their complementary regions on the desired fragments by cooling to a desired temperature (e.g. 50°-60° C. for 2 hours). KlenTaq (Taq polymerase lacking nuclease activity), and thermostable ligase (preferably from strain AK16D), dNTPs are added to allow for extension and ligation at 50° C., and optionally raise the temperature (e.g. 60° C.) to assure completion of extension and ligation, to generate circular products.

3.5.e. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. Oligonucleotide may lack a 5' phosphate, or contain an optional blocking group on the 5' side, such that the 5' end of the oligonucleotide is not suitable for ligation.

Note 2. The above example use KlenTaq, a polymerase lacking strand displacing activity as well as both 3'→5' and 5'→3' nuclease activity. If the oligonucleotide has a blocking group is on the 5' side, then one can use polymerase with 5'→3' nuclease activity.

Note 3. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 4. If the oligonucleotide probe also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

In variation 3.5, a polymerase and a ligase are used to form a covalently closed circle containing a unique identifier sequence, an optional patient identifier sequence, and an optional primer binding site. This may also be accomplished using just a ligase.

Variation 3.6: (See e.g., FIGS. 60 and 61).

In this variation, short linkers containing 5-methyl C, are ligated onto the ends of the DNA. The DNA is then treated with bisulfite, which renders the strands non-complementary so they become single-stranded. A few rounds of PCR amplification generate products that are now unmethylated at the Hph1 sites. These products are then cleaved with Hph1. Only PCR amplicons containing adjacent "Hph1" sites (GGCGA, or GGTGA) that were unmethylated in the original target will generate fragments that are now competent for ligation on both ends. To capture the desired unmethylated regions, a partially double-stranded oligonucleotide pair comprising a first oligonucleotide probe with a 5' probe region complementary to the sequence of the 5' side of the target, an optional primer binding sequence, an optional patient identifier sequence, and a 3' probe region complementary to the sequence of the 3' side of the target, and a second oligonucleotide probe comprising a 5' region complementary to the first strand, a unique identifier sequence and a 3' region complementary to the first strand, are hybridized to the target. Addition of ligase enables ligation of the 3' end of the target to the 5' end of the second oligonucleotide probe, and the 5' end of the target to the 3' end of the second oligonucleotide probe, to form a circular product containing a unique identifier sequence, an optional patient identifier sequence, and an optional primer binding site. Unligated products are eliminated by exonuclease digestion. This circular product is suitable for optional additional steps and subsequent sequencing.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate and will be destroyed by the exonuclease treatment step.

Detailed Protocol for Highly Sensitive Detection of Promoter Unmethylation:

3.6.a. Ligate on linkers that contain 5-methyl C to retain sequence after bisulfite conversion. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Incubate cfDNA with bisulfite, which converts regular C, but not methyl-C, to U. Bisulfite treatment converts the top and bottom strand differently, such that after treatment, the strands will no longer be complementary to each other, and melt apart.

3.6.b. Add primers, Taq Polymerase, and dNTPs and perform a few cycles of PCR to generate products that are now unmethylated at the remaining Hph1 sites.

3.6.c. Add Hph1 to cleave products containing such sites. Only PCR amplicons containing adjacent Hph1 sites (GGCGA or GGTGA) that were unmethylated in the original target will generate fragments that are unblocked (i.e. ligation competent for linkers) on both ends, when cleaved with Hph1.

3.6.d. Denature target DNA (94° C. 1 minute) in the presence of partially double-stranded oligonucleotide pairs (comprising a first oligonucleotide probe with a 5' probe region complementary to the sequence of the 5' side of the target, an optional primer binding sequence, an optional patient identifier sequence, and a 3' probe region complementary to the sequence of the 3' side of the target, and a second oligonucleotide probe comprising a 5' region complementary to the first strand, a unique identifier sequence and a 3' region complementary to the first strand), and allow the oligonucleotides to hybridize to their complementary regions on the desired fragments by cooling to a desired temperature (e.g. 50°-60° C. for 2 hours). A thermostable ligase (preferably from strain AK16D), is added to allow for ligation at 60° C. to generate circular products.

3.6.e. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of a copy of the methylated DNA, the unique identifier sequence, and an optional patient identifier sequence. This circular product is suitable for optional additional steps and subsequent sequencing.

Note 1. The circular product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 2. If the oligonucleotide probe also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Database of Methylation Status at Adjacent Hph1 Restriction Sites

The current TCGA database contains information on the methylation status of about 450,000 CpG sites on the human genome, both for normal and for tumor of many different tissue sites. However, it does not cover all the unmethylation status of adjacent AciI sites, nor would it distinguish that both sites are methylated on the same piece of genomic DNA.

Consequently, for the above assay method to be most useful, it would be helpful to create a database of methylation status at adjacent Hph1 restriction sites of the same orientation (converted GGCGA to GGTGA). This approach will also include adjacent Hph1 restriction sites of the other orientation (TCACC and TCGCC), since they will be GGTGA on the opposite strand after bisulfite conversion. One such an approach is illustrated in FIG. 62.

Overview of approach: The idea is to generate a library of small fragments that could only have been formed if both ends of the fragment contained converted GGCGA (to GGTGA) that were unmethylated in the original genomic DNA. The idea takes advantage of a unique property of the recognition sequence for Hph1. The enzyme cleaves the 4.5 base recognition sequence GGTGA in one orientation, and TCACC in the other orientation. If an unmethylated GGCGA site is treated with bisulfite, in the first orientation, the site will become an Hph1 recognition sequence GGTGA. After a few rounds of PCR amplification, the 5-methyl C is converted to C, while the U is converted to T. When cleaved with Hph1, only adjacent sites unmethylated in the original target will create fragments that are ligation competent on both the 3' and 5' ends. The fragments have linkers appended with optional unique identifier and optional patient identifier sequences that are now amenable for ligation to create fragment multimers that are then substrates for additional steps and subsequent sequencing.

Variation 3.6.1: (See e.g., FIG. 62).

In this variation, short linkers containing 5-methyl C, are ligated onto the ends of the DNA. The DNA is then treated with bisulfite, which renders the strands non-complementary so they become single-stranded. A few rounds of PCR amplification generates products that are now unmethylated at the Hph1 sites. These products are then cleaved with HphI. Only PCR amplicons containing adjacent "Hph1" sites (GGCGA, or GGTGA) that were unmethylated in the original target will generate fragments that are now competent for ligation on both ends. To capture the desired regions, oligonucleotides comprising a 5' probe region complementary to the sequence of the 5' side of the target, a unique identifier sequence, an optional primer binding sequence, an optional patient identifier sequence, and a 3' probe region complementary to the sequence of the 3' side of the target, are hybridized to the target. Addition of ligase and polymerase lacking strand displacing activity and both 3'→5' and 5'→3' nuclease activity, enables extension of the 3' end of the unmethylated target, followed by ligation to the 5' end of the target to form a circular product containing a unique identifier sequence, an optional patient identifier sequence, and an optional primer binding site. Unligated products are eliminated by exonuclease digestion. This circular product is suitable for optional additional steps and subsequent sequencing.

Variation 3.6.1: (See e.g., FIG. 62).

This approach shows how to discover unmethylation at adjacent "Hph1" sites (GGCGA or GGTGA) throughout genome. The starting material may be either intact genomic DNA or cfDNA with average length of about 160 bp. Short linkers containing a blocked 5' end at the non-ligating end, are ligated onto the ends of the DNA. Bisulfite treat DNA, which converts regular C, but not methyl-C, to U. A few rounds of PCR amplification using unmethylated dNTPs and 5' blocked primers generates products that are now unmethylated at the remaining Hph1 sites. These products are then cleaved with Hph1. Only PCR amplicons containing adjacent Hph1 sites (GGCGA and GGTGA) that were unmethylated in the original target will generate fragments that are unblocked (i.e. ligation competent for linkers) on both ends, when cleaved with HphI. Linkers containing optional unique identifier sequence, and optional patient identifier sequence are ligated onto these newly generated Hph1 cleaved ends. These new linkers contain on their non-ligating side either blocked 3' end, or thiophosphate containing backbone (shown as **** in FIG. 62). Upon addition of a double-stranded 3' exonuclease (i.e. Exonuclease III), fragments containing the original short linker on one or both sides will be digested and rendered single-stranded. Only fragments with the new linker ligated to both sides will remain double-stranded, since the 3' blocking group or thiophosphates inhibit digestion with 3' exonuclease. The free ends of the remaining linker-containing fragments are rendered competent for ligation, either by with (i) phosphorylating 5' end, (ii) removing blocked 3' group, or (iii) using 5'-nuclease, or any combination thereof. Ligation conditions are designed to favor multimerization, for example by using crowding agents (i.e. 20% PEG), and/or by mixing two sets of ligation products, wherein the non-palindromic 5' linker overhang of the first set is complementary to the non-palindromic 5' linker overhang of the second set. The ligation products comprise of adjacent AciI sequences in the same orientation (i.e. GCGG), originally methylated in target DNA with optional unique identifier and/or patient identifier sequence. This product is suitable for optional additional steps and subsequent sequencing.

Detailed Protocol for Generating a Database of Unmethylation Status at Adjacent "HphI" Restriction Sites:

3.6.1.a. Ligate on linkers that are blocked on the 5' end of the non-ligating end. Target ends are repaired with T4 polymerase and T4 Kinase, and subsequently a single base 3' A overhang is generated with Klenow (exo-) and dATP. Linkers have a single base 3' T overhang, such that ligation using T4 ligase appends linkers on both ends of the fragment. Incubate cfDNA with bisulfite, which converts regular C, but not methyl-C, to U. Bisulfite treatment converts the top and bottom strand differently, such that after treatment, the strands will no longer be complementary to each other, and melt apart.

3.6.1.b. Add 5' blocked primers, Taq Polymerase, and dNTPs and perform a few cycles of PCR to generate products that are now unmethylated at the remaining Hph1 sites.

3.6.1.c. Add Hph1 to cleave products containing such sites. Only PCR amplicons containing adjacent Hph1 sites (GGCGA or GGTGA) that were unmethylated in the original target will generate fragments that are unblocked (i.e. ligation competent for linkers) on both ends, when cleaved with Hph1. Target ends are repaired with T4 polymerase and T4 Kinase. Remove dNTPs (via a spin column), add back only dATP to generate a single base 3' A overhang.

3.6.1.d. Using T4 ligase, append linkers (containing optional unique identifier sequence, and optional patient identifier sequence) with a single base 3' T overhang on the ligating end to the single base A overhang of the cleaved and filled in target sequences. The 5' non-ligating side of the linker contains a 5' overhang, and optionally is not phosphorylated. The 3' non-ligating side of the linker contains a 3' blocking group and/or thiophosphates to inhibit digestion with 3' exonuclease.

3.6.1.e. Add a 3' exonuclease (i.e. Exonuclease III) and digest at 37° C. Fragments containing the original short linker on one or both sides will be digested and rendered single-stranded. Only fragments with the new linker ligated to both sides will remain double-stranded. Exonuclease will also render the linkers single-stranded. Optionally, remove digestion products from desired fragments with a spin column.

3.6.1.f. The free ends of the remaining linker-containing fragments are rendered competent for ligation, either by (i) phosphorylating 5' end using T4 kinase, (ii) removing blocked 3' group, or (iii) using 5'→3' nuclease activity of Taq polymerase to cleave off matching 5'-overlapping base or flap, leaving ligation-competent 5'-phosphate, or any combination thereof. Ligation conditions are designed to favor multimerization. The ligation products comprise of multimers of target fragments with adjacent AciI sequences originally methylated in target DNA with optional unique identifier and/or patient identifier sequence. This product is suitable for optional additional steps and subsequent sequencing.

Note: 1: The 3' end of the blocked linker may be synthesized to contain a Uracil or an apurinic (AP) site at a position internal to the block, and after treatment with UDG and AP endonuclease, liberate a ligation competent 3' end.

Note 2: Fen nuclease may be used instead of polymerase with 5'-3' nuclease activity to generate the ligation-competent 5' phosphate on the 5' side of the target.

Note 3: Ligation will favor formation of multimers by using crowding agents (i.e. 20% PEG), and/or by mixing two sets of ligation products, wherein the non-palindromic 5' linker overhang of the first set is complementary to the non-palindromic 5' linker overhang of the second set.

Prophetic Example 4—Accurate Quantification of Tumor-Specific Copy Changes in DNA Isolated from Circulating Tumor Cells Copy changes in tumor DNA can be a strong predictor of outcome. Over the last several years, most copy number work has been performed on SNP chips, where bioinformatic approaches average the signal across a region to determine relative copy number. For low numbers of cells, digital PCR approaches are used to obtain an accurate count of starting molecules.

Overview of approach: Generally, copy changes occur over large regions of DNA, such as chromosomal arms. Since there are very low numbers of tumor cells, one could improve accuracy by interrogating multiple regions of a given chromosomal arm simultaneously, and adding or averaging the resultant signal. Likewise, specific genes are amplified in some tumors (i.e. Her2-neu, IGF2), which may predict outcome or guide therapy.

In addition to copy changes, loss of heterozygosity may be followed not only by counting chromosomes, but also by looking for traditional loss of heterozygosity among polymorphic SNPs or markers within the region of interest. The most heterogenous markers are in repetitive sequences. Herein, are illustrated the concepts using tetranucleotide repeat sequences, although tri- and di-nucleotide repeat sequences may also be considered.

Detailed protocol for quantification of tumor-specific copy changes in DNA isolated from circulating tumor cells will be addressed in the next section that scores for mutations from circulating tumor cells, since the overall approach is very similar.

Prophetic Example 5—Detection of Mutations in DNA Isolated from Circulating Tumor Cells or cfDNA Circulating tumor cells provide the advantage of concentrating the mutation-containing DNA, so there is no longer a need to find low-level mutations in an excess of wild-type sequence. However, since there are a low number of starting DNA molecules, it is important to amplify all regions accurately, and verify mutations are truly present.

Overview of approach: The approach here is similar to that for finding known common point mutations, or for sequencing multiple exons, as outlined above. However, when dealing with low amounts of input DNA, there is the potential for polymerase error. This problem is addressed by using circle sequencing or SMRT sequencing.

Since the DNA is being obtained from a few captured tumor cells, if a mutation is present, it should be present in some if not most of the captured cells.

Detailed protocol for detection of mutations in DNA isolated from circulating tumor cells is described below, including quantifying copy number, since the approach is very similar.

Variation 5.1: (See e.g., FIG. 63).

The overall idea here is to convert all cfDNA or CTC DNA into single stranded circles, where each fragment contains a unique identifier sequence, an optional patient identifier sequence, and an optional primer binding sequence. Once that conversion has taken place, the circles are now suitable for raw sequencing, sequence-specific capture of desired targets using biotinylated probes, or for rolling circle amplification and enhanced capture of desired targets using biotinylated probes.

In this variation, the aim is to capture all target and non-target DNA sequence, without using probes to bind to the target. Linkers are ligated to the DNA target (cfDNA of average length of about 160 bases). To capture all sequences, oligonucleotide probes comprising a 5' sequence complementary to the 5' end of the linker, a unique identifier sequence, an optional patient identifier sequence, an optional primer binding sequence, and a sequence complementary to the 3' end of the linker, are hybridized to the target. The oligonucleotide may contain an optional blocking group on one end (5' end shown). Addition of a polymerase allows extension of the 3' end of the oligonucleotide on the target, as well as extension of the 3' end linker through the unique identifier sequence, the optional primer binding sequence, and the optional patient identifier sequence until it is adjacent to the 5' linker on the target.

The 5' end of the linker may be designed to be slightly longer, such that once polymerase extends the 3' linker, it doesn't extend right through the 5' linker complementary sequence until it hits the 5' target portion that is hybridized to the 5' probe region.

This variation requires that the oligonucleotide probe contain sequences complementary to both the 3' and 5' linker strands, with those sequences being separated by only about 20-40 bases. Since the sequences are complementary to the linker strands, which in turn are complementary to each other, it is important to keep the two sequences within the oligonucleotide probe from just forming an internal hairpin with a 20-40 base loop. One solution is to ligate linkers that contain an internal bubble, such that the two linkers retain double stranded character at the low temperature used for linker ligation (16° C. or even 4° C. with T4 ligase). In addition the 5' linker may be designed to be longer than the 3' linker. Finally, the regions of complementarity within the linker may be designed to have subtle mismatches (i.e. G:T and T:G) which are more destabilizing in the complementary oligonucleotide probe (i.e. C:A and A:C) such that the oligonucleotide probe is less likely to form the internal hairpin at the overall hybridization temperature (i.e. 40-50° C.).

Extension of the 3' end of the oligonucleotide on the target enhances association of the probe to the target, and thus increases the ability of the 3' end of the linker to hybridize correctly to its complement and be extended by polymerase. The 5'→3' nuclease cleavage activity of polymerase (or Fen nuclease) cleaves a matching 5'-overlapping base of the 5' linker, leaving ligation-competent 5'-phosphate on the linker. Polymerase also extends oligonucleotide on target, and does not cleave the blocking group on the 5' end of the oligonucleotide.

Ligase covalently seals the extended 3' ends to the ligation-competent 5'-phosphate to create circular ligation products. Blocking group prevents circularization of oligonucleotide probe. Optional addition of Uracil-DNA glycosylase (UDG) and Formamidopyrimidine-DNA glycosylase (Fpg, also known as 8-oxoguanine DNA glycosylase, which acts both as a N-glycosylase and an AP-lyase) may be used to nick targets containing damaged bases. Exonuclease(s) are then added to digest all unligated or nicked products leaving only desired single-stranded circular DNA comprising of original target DNA with unique identifier sequence. This product is suitable for sequence-specific capture of desired targets using biotinylated probes, combined with rolling circle amplification and circle sequencing, or direct SMRT sequencing.

The challenge here is to avoid having polymerase extend the 3' linker in such a way that it destroys the 5' linker without a ligation step (i.e. nick-translation). This may be accomplished by incorporating thiophosphate linkages in the $2^{nd}$ and $3^{rd}$ position from the 5' phosphate end, (which will be liberated by the 5'→3' nuclease activity of the polymerase). To minimize polymerase displacement of those bases as it extends one base too many (which would make it impossible to ligate to the downstream primer), the target bases at the ligation junction would preferentially be AT rich on the 3' side, and GC rich on the 5' side.

An alternative approach is to use a 5' linker containing an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate. When using thermostable EndoIII, the PCR polymerase used would lack the 5'→3' exonuclease activity.

As mentioned above, the nick-translation problem may also be minimized by using a mixture of polymerases, both with and without 5'→3' nuclease cleavage activity (e.g. in a ratio of 1:20) under conditions of distributive extension in the presence of ligase such that most extension is by polymerase without nuclease activity until polymerase with nuclease activity is required to create the ligation competent junction, followed by polymerase dissociation, and a ligation event to generate the desired circular ligation product. Detailed Protocol for Accurate Quantification of Tumor-Specific Copy Changes or Detection of Mutations in Known Genes (e.g. Braf, K-Ras, p53) in DNA Isolated from Circulating Tumor Cells or cfDNA:

5.1.a. Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Optionally, purify target DNA from unligated linker.

5.1.b. Denature target DNA containing linkers on both ends (94° C. 1 minute) in the presence of oligonucleotide probes (comprising a 5' sequence complementary to the 5' end of the linker, a unique identifier sequence, an optional patient identifier sequence, an optional primer binding sequence, and a sequence complementary to the 3' end of the linker), and allow the oligonucleotide probes to hybridize to their complementary regions on the desired fragments by cooling to a desired temperature (e.g. 40-50° C. for 30 min). Oligonucleotide probes may contain an optional blocking group at the 5' end. Taq polymerase and/or KlenTaq (Taq polymerase lacking nuclease activity), and thermostable ligase (preferably from strain AK16D), dNTPs are either added subsequent to the annealing step, or at the start of the procedure. Allow for extension and ligation at the hybridization temperature, and optionally raise the temperature (e.g. 60° C.) to assure completion of extension and ligation, to generate circular products.

5.1.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for sequence-specific capture of desired targets using biotinylated probes, or for rolling circle amplification (using primer complementary to the primer binding sequence with phi-29 polymerase) to create tandem repeats of the desired sequence, followed by enhanced capture of desired targets using biotinylated probes. This may be followed by identification of the targets using next generation sequencing, or alternatively, direct SMRT sequencing on the covalently closed template, using the linker sequence or optional primer binding sequence as a primer binding site.

Note 1: Oligonucleotide may contain an optional blocking group on the 5' side to interfere with subsequent 5'-3' nuclease activity of polymerase, such that the oligonucleotide probe does not circularize.

Note 2: Fen nuclease may be used instead of polymerase with 5'-3' nuclease activity to generate the ligation-competent 5' phosphate on the 5' side of the target.

Note 3: The 5' end linker may be synthesized to contain thiophosphate linkages in the 2nd and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream primer), the target bases at the ligation junction would preferentially be AT rich on the 3' side, and GC rich on the 5' side.

Note: 4: When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate.

Note 5: When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

Note 6: A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Note 7: Capture of tandem repeat copies of the target (generated through rolling circle amplification) provides the unique advantage of multivalent binding to enhance capture of the correct target. This allows for more stringent hybridization/capture conditions resulting in higher efficiencies of capture and less capture of unwanted sequences. This approach may also be used to capture all targets containing repetitive sequences (i.e. AGAT tetra-nucleotide repeat), allowing scoring for loss of heterozygosity, copy number variation, haplotyping, establishing paternity, and other applications.

Note 8: The unique sequence identifier assures that even after rolling circle or other selection/amplification steps, each original target sequence may be uniquely scored, allowing for accurate quantification of the original copy number of each target.

Note 9: The unique identifier sequence may be added on both sides of the linker. If an extra base is not added to the target DNA (i.e. skipping the Klenow step), then a blunt end ligation is used. To avoid linker-to-linker ligation, the blunt end of the linker is un-phosphorylated. Example of linkers containing unique identifiers and blunt ends is provided as oligonucleotides iSx-201-MdAdT (Top strand), and iSx-202-MdLgAdB-bk (Bottom strand) (see Table 1). The top strand is longer, creating a 5' single-stranded overhang on the non-ligating side. The bottom strand has a 5'-OH, and optionally contains a 3' blocking group to avoid extension, as well as internal 5-nitroindole groups to act as universal bases when pairing with the unique identifier sequences of the top strand. After ligation of the blunt end linker, appending unique sequences to the 5' ends of the double-stranded DNA target, those sequences are copied by extending the 3' end with polymerase. Optionally, the top strand contains dU bases for subsequent cleavage with UDG and FPG to liberate a 5' phosphate, suitable for ligation and circularization in subsequent steps. Linker iSx-201-MdAdT (see Table 1) may contain optional thiophosphate groups adjacent to the newly liberate 5' phosphate to prevent nick-translation and facilitate circularization of targets with linker ends.

Note 10: When designing oligonucleotides for use with longer linker sequences, comprising "barcoding" or "indexing" sequences for use with commercial instruments, it may be necessary to assemble the oligonucleotide using PCR, strand-displacement amplification, or a combination thereof. During PCR, use of dUTP instead of TTP incorporates uracil, suitable for subsequent cleavage by UDG. The reverse-strand primer may be phosphorylated, allowing for its digestion using lambda exonuclease or a similar 5'→3' exonuclease. A dA30 sequence may be appended to the 5' end of the forward primer, enabling strand displacement amplification. Example of oligonucleotides for assembly of a reverse complementary sequence, which are suitable for use with the above linkers are: iSx-204-bkA30-Lk-F2, iSx-205-r503-F3, iSx-206-d701-R4, and iSx-207-Lk-R5 (see Table 1).

Note 11: In another variation for appending the unique identifier sequence may be added on both sides of the linker, one strand also comprises a "barcode" or "index" sequence for use with commercial instruments (see e.g., FIG. 64). By dividing the long region between linker and hybridizing oligonucleotide, the different sequences may be synthesized directly and kept to about 100 bases in length. Example of linkers containing index or barcode sequences, unique identifiers and blunt ends is provided as oligonucleotides iSx-211-r702-LgAdT (Top strand), and iSx-202-MdLgAdB-bk (Bottom strand, same as above) (see Table 1). The top strand is considerably longer, creating a 5' single-stranded overhang on the non-ligating side. The bottom strand has a 5'-OH, and optionally contains a 3' blocking group to avoid extension, as well as internal 5-nitroindole groups to act as universal bases when pairing with the unique identifier sequences of the top strand. After ligation of the blunt end linker, appending unique sequences to the 5' ends of the double-stranded DNA target, those sequences are copied by extending the 3' end with polymerase. Optionally, the top strand contains dU bases for subsequent cleavage with UDG and FPG to liberate a 5' phosphate, suitable for ligation and circularization in subsequent steps. The bridging oligonucleotide, iSx-212-r503-R4 (see Table 1), hybridizes to the cleaved 5' phosphate containing linker, as well as the long extended 3' end, allowing for extension with polymerase, and circularization with ligase.

Note 12: With the aforementioned products generated using the above primer and linker designs, after cluster or bead amplification, or capture within a well, address, or surface of a flow cell on a commercial instrument, the following primers may be used to initiate sequencing reactions: (i) iLx-003-PEsqP1, Paired End sequencing primer 1; (ii) iLx-004-BrCdR1, Indexing primer, Barcode Read 1; (iii) iLx-001-P5-BrCdR2, Barcode Read 2; and (iv) iLx-005-PEsqP2, Paired End sequencing primer 2 (Primer sequences provided in Table 1 below).

The above procedure uses linkers with a 5'OH. Variation 5.2 uses linkers with a 5' phosphate to avoid some potential problems associated with using polymerase with a 5'-3' nuclease activity (see e.g., FIG. 63).

Detailed Protocol for Accurate Quantification of Tumor-Specific Copy Changes or Detection of Mutations in Known Genes (e.g. Braf, K-Ras, p53) in DNA Isolated from Circulating Tumor Cells or cfDNA:

5.2.a. Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. The 5' linker contains a phosphate group (optionally added using T4 kinase).

5.2.b. Denature target DNA containing linkers on both ends (94° C. 1 minute) in the presence of oligonucleotide probes (comprising a 5' sequence complementary to the 5' end of the linker, a unique identifier sequence, an optional patient identifier sequence, an optional primer binding sequence, and a sequence complementary to the 3' end of the linker), and allow the oligonucleotide probes to hybridize to their complementary regions on the desired fragments by cooling to a desired temperature (e.g. 40-50° C. for 30 min). Oligonucleotide probe may contain an optional blocking group at the 5' end. KlenTaq (Taq polymerase lacking nuclease activity), and thermostable ligase (preferably from strain AK16D), dNTPs are either added subsequent to the annealing step, or at the start of the procedure. Allow for extension and ligation at the hybridization temperature, and optionally raise the temperature (e.g. 60° C.) to assure completion of extension and ligation, to generate circular products.

5.2.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for sequence-specific capture of desired targets using biotinylated probes, or for rolling circle amplification (using primer complementary to the primer binding sequence with phi-29 polymerase) to create tandem repeats of the desired sequence, followed by enhanced capture of desired targets using biotinylated probes. This may be followed by identification of the targets using next generation sequencing, or alternatively, direct SMRT sequencing on the covalently closed template, using the linker sequence or optional primer binding sequence as a primer binding site.

Note 1: Oligonucleotide may contain an optional blocking group on the 5' side, or a 5' OH, such that the oligonucleotide probe does not circularize.

Note 2: Linkers may be synthesized with 5' phosphate, or the phosphate may be appended using T4 kinase.

Note 3: Capture of tandem repeat copies of the target (generated through rolling circle amplification) provides the unique advantage of multivalent binding to enhance capture of the correct target. This allows for more stringent hybridization/capture conditions resulting in higher efficiencies of capture and less capture of unwanted sequences. This approach may also be used to capture all targets containing repetitive sequences (i.e. AGAT tetra-nucleotide repeat), allowing scoring for loss of heterozygosity, copy number variation, haplotyping, establishing paternity, and other applications.

Note 4: The unique sequence identifier assures that even after rolling circle or other selection/amplification steps, each original target sequence may be uniquely scored, allowing for accurate quantification of the original copy number of each target.

Note 5: Examples of linkers and complementary oligonucleotide to facilitate circularization are: iSx-220-d503-AdT1, iSx-221-pd707-AdB2, and iSx-222-Lk-uRC1, respectively (see Table 1). Linker iSx-220-d503-AdT1 (see Table 1) may contain optional thiophosphate groups at the $2^{nd}$ and $3^{rd}$ position from the 5' end to prevent nick-translation and facilitate circularization of targets with linker ends.

The approaches described in FIGS. 64 and 65 use universal linkers to capture and circularize total genomic DNA, and then later steps, such as capture of desired targets using biotinylated probes to select the targets for sequence analysis. Biotinylated probes are captured on beads either prior to hybridization, or after hybridization, so even though in the second case the hybridization step may be liquid, ultimately there is a liquid to solid step, and these steps may result in lower yields or fragment dropouts.

Variation 5.3 describes an alternative approach, wherein the capture step occurs in liquid, by using probes designed to hybridize near or adjacent to each other on the target, and then create a "landing pad" for the linkers on the ends of the target to hybridize, extend, and ligate to create the covalently closed circular target(s). This approach may be particularly useful when selecting for targets containing repetitive DNA. Detailed Protocol for Accurate Quantification of Tumor-Specific Copy Changes or Detection of Mutations in Known Genes (e.g. Braf, K-Ras, p53) in DNA Isolated from Circulating Tumor Cells or cfDNA:

5.3.a. Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Linkers may be synthesized with 5' phosphate, or the phosphate may be appended using T4 kinase. Optionally, purify target DNA from unligated linker.

5.3.b. Denature target DNA containing linkers on both ends (94° C. 1 minute) in the presence of oligonucleotide probes (comprising a 5' sequence complementary to a unique or repetitive portion (i.e. AGAT repeat) of the target, an optional spacer region, a sequence complementary to the 5' end of the linker, a unique identifier sequence, an optional patient identifier sequence, an optional primer binding sequence, an optional spacer region, a sequence complementary to the 3' end of the linker, and a 3' sequence complementary to a unique or repetitive portion (i.e. AGAT repeat) of the target, and adjacent to the 5' sequence complementary to the target), and allow the oligonucleotides to hybridize to their complementary regions on the desired fragments by cooling to a desired temperature (e.g. 50° C. for 2 hours). Oligonucleotide may contain an optional blocking group on the 5' side. Taq polymerase and/or KlenTaq (Taq polymerase lacking nuclease activity), and thermostable ligase (preferably from strain AK16D), dNTPs are either added subsequent to the annealing step, or at the start of the procedure. In the case where the linker sequence has a 5' phosphate, KlenTaq extends the 3' end until it is directly adjacent to the ligation-competent 5' end (left side of FIG. 70). In the case where the linker sequence has a 5' OH, the 5'→3' nuclease activity of polymerase cleaves the matching 5'-overlapping base to create a ligation competent 5' phosphate (right side of FIG. 70). Allow for extension and ligation at the hybridization temperature, and optionally raise the temperature (e.g. 60° C.) to assure completion of extension and ligation, to generate circular products.

5.3.c. Optionally, cleave the oligonucleotide probe at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for sequence-specific capture of desired targets using biotinylated probes, or for rolling circle amplification (using primer complementary to the primer binding sequence with phi-29 polymerase) to create tandem repeats of the desired sequence, followed by enhanced capture of desired targets using biotinylated probes. This may be followed by identification of the targets using next generation sequencing, or alternatively, direct SMRT sequencing on the covalently closed template, using the linker sequence or optional primer binding sequence as a primer binding site.

Note 1: Oligonucleotide may contain an optional blocking group on the 5' side to interfere with subsequent 5'-3' nuclease activity of polymerase, such that the oligonucleotide probe does not circularize. Alternatively, a cleavable link may be included in the original oligonucleotide.

Note 2: Fen nuclease may be used instead of polymerase with 5'-3' nuclease activity to generate the ligation-competent 5' phosphate on the 5' side of the target.

Note 3: The 5' end linker may be synthesized to contain thiophosphate linkages in the $2^{nd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream primer), the target bases at the ligation junction would preferentially be AT rich on the 3' side, and GC rich on the 5' side.

Note: 4: When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate.

Note 5: When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

Note 6: A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Note 7: Capture of tandem repeat copies of the target (generated through rolling circle amplification) provides the unique advantage of multivalent binding to enhance capture of the correct target. This allows for more stringent hybridization/capture conditions resulting in higher efficiencies of capture and less capture of unwanted sequences. This approach may also be used to capture all targets containing repetitive sequences (i.e. AGAT tetra-nucleotide repeat), allowing scoring for loss of heterozygosity, copy number variation, haplotyping, establishing paternity, and other applications.

Note 8: The unique sequence identifier assures that even after rolling circle or other selection/amplification steps, each original target sequence may be uniquely scored, allowing for accurate quantification of the original copy number of each target.

Note 9: The unique identifier sequence may be added on both sides of the linkers comprising of "index" or "barcode" sequences, using a single base T overhang ligation (see e.g., FIG. 67). Repair target ends with T4 polymerase, phosphorylate 5' end with T4 kinase. Add an A base to 3' end of target using Klenow fragment lacking 3'→5' nuclease activity. Ligate on 3-piece "gap" linkers with 3' T overhang using T4 ligase at 30° C. Use Klenow fragment lacking 3'→5' nuclease activity to fill in gap, and ligate to small linker strand in presence of T4 ligase. Optional, use DNA polymerase lacking 3'→5' nuclease activity to fill in gap, and ligate to small linker strand in presence of T4 ligase. Examples of such 3-piece linker oligonucleotides are: iSx-223-d504-AdT3, iSx-224-pSmAdT4, and iSx-225-pd708-N6AdB5 (see Table 1). Linker iSx-223-d504-AdT3 (see Table 1) may contain optional thiophosphate groups at the $2^{nd}$ and $3^{rd}$ position from the 5' end to prevent nick-translation and facilitate circularization of targets with linker ends.

Note 10: The unique identifier sequence may be added on both sides of the linkers comprising of "index" or "barcode" sequences, using blunt end ligation. Repair target ends with T4 polymerase. Ligate on 3-piece "gap" linkers with 3' phosphate and blunt overhang using T4 ligase at 30° C. Use Klenow fragment lacking 3'→5' nuclease activity to fill in gap at 37° C., heat to 50° C. to denature off small linker. Use Taq DNA polymerase (lacking 3'-5' nuclease activity, but with 5'-3' nuclease activity) to fill in gap, and ligate to target with Thermostable ligase. Examples of such 3-piece linker oligonucleotides are: iSx-226-d505-AdT6, iSx-227-SmAdT7p, and iSx-225-pd708-N6AdB5 (same as above; see Table 1). Linker iSx-226-d505-AdT6 (see Table 1) may contain optional thiophosphate groups at the $2^{nd}$ and $3^{rd}$ position from the 5' end to prevent nick-translation and facilitate circularization of targets with linker ends.

Note 11: The unique identifier sequence may be added on both sides of the linkers comprising of "index" or "barcode" sequences, using reverse transcription. Repair target ends with T4 polymerase, phosphorylate 5' end with T4 kinase (see e.g., FIG. 68). Add 3 C bases to 3' end of target using reverse transcriptase. Hybridize linker pairs where the first linker has rGrG+G on the 3' end (+G is symbol for LNA, rG3), primer binding sites with patient and unique identifier, and 5' phosphate, while the second linker has primer binding sites with patient identifier. Reverse transcriptase undergoes strand switching and copies unique identifier to fill gap. Ligase covalently seals extended target to second linker. RNaseH2 cleaves RNA bases, liberating 3'OH of rG3 (rGrG+G) in first linker sequence. Polymerase fill gaps, and ligase covalently seals the extended ends. Examples of such linker oligonucleotides are: iSx-228-d506-AdT83+G, and iSx-229-pd709-AdB6. Linker iSx-228-d506-AdT83+G (see Table 1) may contain optional thiophosphate groups at the $2^{nd}$ and $3^{rd}$ position from the 5' end to prevent nick-translation and facilitate circularization of targets with linker ends.

Note 12: One variation is to use oligonucleotides comprising multiple cleavable linkages, such that after extension/ligation and treating with the cleaving agent, a unique primer is generated on the target strand, suitable for rolling circle amplification to generate tandem-repeat products. Examples of such oligonucleotides suitable for generating the circular products comprising target regions of KRAS, BRAF, and TP53 exons 5-8 containing hotspot mutations are shown in Table 1 below and include: (i) KRAS forward and reverse target extension/ligation oligonucleotides (iSx-232-KRS-T32, iSx-233-KRS-B33); (ii) BRAF forward and reverse target extension/ligation oligonucleotides (iSx-234-BRF-T34, iSx-235-BRF-B35); (iii) TP53 Exon 5 forward and reverse target extension/ligation oligonucleotides (iSx-241-TP53e5-T41, iSx-242-TP53e5-B42, iSx-243-TP53e5-T43, iSx-244-TP53e5-B44); (iv) TP53 Exon 6 forward and reverse target extension/ligation oligonucleotides (iSx-245-TP53e6-T45, iSx-246-TP53e6-B46); (v) TP53 Exon 7 forward and reverse target extension/ligation oligonucleotides (iSx-247-TP53e7-T47, iSx-248-TP53e7-B48); and (vi) TP53 Exon 8 forward and reverse target extension/ligation oligonucleotides (iSx-249-TP53e8-T49, iSx-250-TP53e8-B50). The above-mentioned extension/ligation oligonucleotides may contain optional thiophosphate groups at the $2^{nd}$ and $3^{rd}$ position from the 5' end to prevent nick-translation and facilitate circularization on complementary targets.

Note 13: Alternatively, after generating the circular products comprising target regions of KRAS, BRAF, and TP53 exons 5-8 containing hotspot mutations, these regions may be subject to rolling circle amplification using newly added target-specific primers to generate tandem-repeat products. These products may be generated either prior to, or after capture of desired targets with target-specific oligonucleotides on a solid support (See note 8 below). Primers may contain an internal cleavable nucleotide base or abasic site such as 1',2'-Dideoxyribose (dSpacer), enabling incorporation of dUTP during rolling circle amplification for protection against carryover contamination. Examples of such primers are shown in Table 1 below and include the following: (i) KRAS forward and reverse primers (iSx-108-KRS-rcF26, iSx-109-KRS-rcR27); (ii) BRAF forward and reverse primers (iSx-118-BRF-rcF26, iSx-119-BRF-rcR27); (iii) TP53 Exon 5 forward and reverse primers (iSx-128-TP53e5-rcF66, iSx-129-TP53e5-rcR67; iSx-130-TP53e5-rcF68, iSx-131-TP53e5-rcR69); (iv) TP53 Exon 6 forward and reverse primers (iSx-138-TP53e6-rcF76, iSx-139-TP53e6- rcR77); (v) TP53 Exon 7 forward and reverse primers (iSx-148-TP53e7-rcF86, iSx-149-TP53e7-rcR87); and (vi) TP53 Exon 8 forward and reverse primers (iSx-158-TP53e8-rcF96, iSx-159-TP53e8-rcR97).

Note 14: After generating the circular products comprising target regions of KRAS, BRAF, and TP53 exons 5-8 containing hotspot mutations, and/or generating tandem-repeat products, these products may be captured by hybridizing to longer oligonucleotides, which contain a capture group suitable for subsequent capture on a solid support. Examples of such capture oligonucleotides, containing biotin groups suitable for capture via streptavidin-coated solid surfaces are shown in Table 1 below and include the following: (i) KRAS forward and reverse capture oligonucleotides (iSx-013-KRS-bcF1, iSx-014-KRS-bcR2); (ii) BRAF forward and reverse capture oligonucleotides (iSx-020-BRF-bcF1, iSx-021-BRF-bcR2); (iii) TP53 Exon 5 forward and reverse capture oligonucleotides (iSx-030-TP53e5-bcF1, iSx-031-TP53e5-bcR2; iSx-032-TP53e5-bcF3, iSx-033-TP53e5-bcR4); (iv) TP53 Exon 6 forward and reverse capture oligonucleotides (iSx-050-TP53e6-bcF5, iSx-051-TP53e6-bcR6); (v) TP53 Exon 7 forward and reverse capture oligonucleotides (iSx-060-TP53e7-bcF7, iSx-061-TP53e7-bcR8); and (vi) TP53 Exon 8 forward and reverse capture oligonucleotides (iSx-070-TP53e8-bcF9, iSx-071-TP53e8-bcR10).

Note 15: With the aforementioned products generated using the above primer and linker designs, after cluster or bead amplification, or capture within a well, address, or surface of a flow cell on a commercial instrument, the following primers may be used to initiate sequencing reactions: (i) iLx-003-PEsqP1, Paired End sequencing primer 1; (ii) iLx-004-BrCdR1, Indexing primer, Barcode Read 1; (iii) iLx-001-P5-BrCdR2, Barcode Read 2; and (iv) iLx-005-PEsqP2, Paired End sequencing primer 2 (primer sequences are provided in Table 1 below).

The approach described in FIG. 70 used ligation of both the oligonucleotide probe as well as the linker-containing target, resulting in circular interlocked ligation products. Subsequently, a nick is introduced at the cleavable link. For repetitive sequences, the 3' end can just be extended using only 3 dNTPs as described below in Variation 5.4, see e.g., FIG. 77.

Detailed Protocol for Accurate Quantification of Tumor-Specific Copy Changes or Detection of Mutations in Known Genes (e.g. Braf, K-Ras, p53) in DNA Isolated from Circulating Tumor Cells or cfDNA:

5.4.a. Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Linkers may be synthesized with 5' phosphate, or the phosphate may be appended using T4 kinase. Optionally, purify target DNA from unligated linker.

5.4.b. Denature target DNA containing linkers on both ends (94° C. 1 minute) in the presence of oligonucleotide probes (comprising a 5' sequence complementary to the 5' end of the linker, a unique identifier sequence, an optional patient identifier sequence, an optional primer binding sequence, an optional spacer region, a sequence complementary to the 3' end of the linker, and a 3' sequence complementary to a unique or repetitive portion (i.e. AGAT repeat) of the target), and allow the oligonucleotide probes to hybridize to their complementary regions on the desired fragments by cooling to a desired temperature (e.g. 50° C. for 2 hours). Oligonucleotide probes may contain an optional blocking group on the 5' side. Taq polymerase and/or KlenTaq (Taq polymerase lacking nuclease activity), and thermostable ligase (preferably from strain AK16D), and for the example of AGAT repeats, only the three complementary nucleotides (i.e. dTTP, dCTP, dATP) are either added subsequent to the annealing step, or at the start of the procedure. In the case where the linker sequence has a 5' phosphate, KlenTaq extends the 3' end until it is directly adjacent to the ligation-competent 5' end (left side of FIG. 77). In the case where the linker sequence has a 5' OH, the 5'→3' nuclease activity of polymerase cleaves the matching 5'-overlapping base to create a ligation competent 5' phosphate (right side of FIG. 77). Allow for extension and ligation at the hybridization temperature, and optionally raise the temperature (e.g. 60° C.) to assure completion of extension and ligation, to generate circular products.

5.4.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for sequence-specific capture of desired targets using biotinylated probes, or for rolling circle amplification (using primer complementary to the primer binding sequence with phi-29 polymerase) to create tandem repeats of the desired sequence, followed by enhanced capture of desired targets using biotinylated probes. This may be followed by identification of the targets using next generation sequencing, or alternatively, direct SMRT sequencing on the covalently closed template, using the linker sequence or optional primer binding sequence as a primer binding site.

Note 1: Oligonucleotide may contain an optional blocking group on the 5' side to interfere with subsequent 5'-3' nuclease activity of polymerase, such that the oligonucleotide probe does not circularize.

Note 2: Fen nuclease may be used instead of polymerase with 5'-3' nuclease activity to generate the ligation-competent 5' phosphate on the 5' side of the target.

Note 3: The 5' end linker may be synthesized to contain thiophosphate linkages in the $2^{nd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream primer), the target bases at the ligation junction would preferentially be AT rich on the 3' side, and GC rich on the 5' side.

Note: 4: When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate.

Note 5: When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

Note 6: A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Note 7: Capture of tandem repeat copies of the target (generated through rolling circle amplification) provides the unique advantage of multivalent binding to enhance capture of the correct target. This allows for more stringent hybridization/capture conditions resulting in higher efficiencies of capture and less capture of unwanted sequences. This approach may also be used to capture all targets containing repetitive sequences (i.e. AGAT tetra-nucleotide repeat), allowing scoring for loss of heterozygosity, copy number variation, haplotyping, establishing paternity, and other applications.

Note 8: The unique sequence identifier assures that even after rolling circle or other selection/amplification steps, each original target sequence may be uniquely scored, allowing for accurate quantification of the original copy number of each target.

To avoid problems with polymerase extension and nick-translation, the procedure may be performed without a polymerase extension step, using just ligase or ligase combined with the 5'-3' nuclease activity of polymerase, as illustrated in FIG. 78 (v5.5). The trick is to append the unique identifier sequence to the linker.

Detailed Protocol for Accurate Quantification of Tumor-Specific Copy Changes or Detection of Mutations in Known Genes (e.g. Braf, K-Ras, p53) in DNA Isolated from Circulating Tumor Cells or cfDNA:

5.5.a. Starting with cfDNA or genomic DNA isolated from CTC, (sheared to about 150 bp), repair ends with T4 polymerase and T4 Kinase, and subsequently a single base 3' A overhang is added with Klenow (exo-) and dATP. Linkers have a single base 3' T overhang, such that ligation using T4 ligase at 4° C. appends linkers on both ends of the fragment. Linkers contain a unique identifier sequence on the 5' single stranded side of the linker, and may be synthesized with 5' phosphate, or the phosphate may be appended using T4 kinase. Optionally, purify target DNA from unligated linker and/or dNTPs.

5.5.b. Denature target DNA containing linkers on both ends (94° C. 1 minute) in the presence of oligonucleotides (comprising a 5' sequence complementary to a unique or repetitive portion (i.e. AGAT repeat) of the target, an optional spacer region, a sequence complementary to the 5' end of the linker, an optional patient identifier sequence, an optional primer binding sequence, an optional spacer region, a sequence complementary to the 3' end of the linker, and a 3' sequence complementary to a unique or repetitive portion (i.e. AGAT repeat) of the target, and directly adjacent to, or overlapping by a single base or flap, the 5' sequence complementary to the target), and allow the oligonucleotides to hybridize to their complementary regions on the desired fragments by cooling to a desired temperature (e.g. 50° C. for 2 hours). Oligonucleotide may contain an optional blocking group on the 5' side. Optionally, Taq polymerase, and thermostable ligase (preferably from strain AK16D), are either added subsequent to the annealing step, or at the start of the procedure. In the case where the linker sequence has a 5' phosphate, the 3' linker is directly adjacent to the ligation-competent 5' end (left side of FIG. 78). In the case where the linker sequence has a 5' OH, the 5'→3' nuclease activity of polymerase cleaves the matching 5'-overlapping base or flap to create a ligation competent 5' phosphate (right side of FIG. 78). Allow for optional flap cleavage, and ligation at the hybridization temperature, and optionally raise the temperature (e.g. 60° C.) to assure completion of ligation, to generate circular products.

5.5.c. Optionally, cleave the oligonucleotide probe at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for sequence-specific capture of desired targets using biotinylated probes, or for rolling circle amplification (using primer complementary to the primer binding sequence with phi-29 polymerase) to create tandem repeats of the desired sequence, followed by enhanced capture of desired targets using biotinylated probes. This may be followed by identification of the targets using next generation sequencing, or alternatively, direct SMRT sequencing on the covalently closed template, using the linker sequence or optional primer binding sequence as a primer binding site.

Note 1: Oligonucleotide may contain an optional blocking group on the 5' side to interfere with subsequent 5'-3' nuclease activity of polymerase, such that the oligonucleotide probe does not circularize. Alternatively, a cleavable link may be included in the original oligonucleotide.

Note 2: Fen nuclease may be used instead of polymerase with 5'-3' nuclease activity to generate the ligation-competent 5' phosphate on the 5' side of the target.

Note 3: Capture of tandem repeat copies of the target (generated through rolling circle amplification) provides the unique advantage of multivalent binding to enhance capture of the correct target. This allows for more stringent hybridization/capture conditions resulting in higher efficiencies of capture and less capture of unwanted sequences. This approach may also be used to capture all targets containing repetitive sequences (i.e. AGAT tetra-nucleotide repeat), allowing scoring for loss of heterozygosity, copy number variation, haplotyping, establishing paternity, and other applications.

Note 4: The unique sequence identifier assures that even after rolling circle or other selection/amplification steps, each original target sequence may be uniquely scored, allowing for accurate quantification of the original copy number of each target.

Prophetic Example 6—Accurate Quantification of Tumor-Specific mRNA or lncRNA Isolated from Exosomes, Circulating Tumor Cells, or Total Blood Cells that Include Circulating Tumor Cells. (e.g. a Dozen Expression Markers that Predict Outcome or Guide Treatment)

Changes in tumor-specific mRNA or lncRNA expression are a powerful tool for classifying disease status in a tissue-specific fashion. This includes accurate detection and quantitation of specific exons of mRNAs or lncRNAs (see e.g., FIGS. 108, 111, 112) or the detection and quantitation of recurrent gene fusions present in mRNAs (see e.g., FIGS. 109 and 110). Total or poly-A mRNA or poly-A lncRNA is isolated from either exosomes or circulating tumor cells and converted into cDNA using reverse transcriptase for use in the process. cDNAs are generated by the use of exon specific primers using standard design rules to obtain maximum specificity of the regions, generally spanning the exon-intron borders of a specific transcript. Alternatively, random hexamer priming may be used to copy the entire transcriptome, or poly dT primers may be used to enrich for the 3' ends of all transcripts.

Oligonucleotides containing sequences complimentary to adjacent but separate regions are hybridized to the cDNA targets. FIGS. 108 and 112 show a an exon detection and quantitation method that uses a gap (i.e. 10-20 nucleotides) between the 5'- and 3'-oligonucleotides in which polymerase is used to extend the 3'-end(s) of the target binding sequences to copy some of the target sequence and close the gap to generate a ligation competent junction suitable for subsequent ligation to form a circular product. In one embodiment, the gap between the 5'- and 3'-ends of the oligonucleotide probes is 10-20 nucleotides. However, the gap to be copied can be tailored to the length of read used in the subsequent sequencing step. FIG. 111 shows an exon detection and quantitation method in which the two target binding sequences are immediately adjacent to each other and no gap exists.

Enumeration of these reporter circles can be carried out by a variety of quantitative methods including but not limited to next generation sequencing. In addition to allowing the simultaneous multiplex detection of many target sequences by circle formation, next generation sequencing as the readout provides additional information (two unique identifiers) about the reporter circles which readily distinguishes legitimate ligation products from ligation artifacts thus increasing the sensitivity of the assay.

FIGS. 109 and 110 describe two variants for the detection and quantitation of recurrent gene fusions found in mRNA. Since the fusion junctions of two genes occurs in an imprecise manner with the deletion of sequence hundreds to thousand of bases in length from between the two 5'-end of one gene and the 3'-end of the other gene, it would be difficult to design an assay that contains dozens of probe pairs upstream and downstream of the indeterminate fusion junction so the method described herein utilizes two half-circular oligonucleotide probes that each have one end in an upstream exon and the other end in a downstream exon. Only upon hybridization of both probes (four ends) adjacent with a gap between them, or immediately adjacent to each other on the cDNA target can a ligation occur to form a single circular product. Subsequent digestion of the unligated oligonucleotide probes (using exonucleases) leaves a circular product that in one variation (see e.g., FIG. 109) contains no additional sequence information (no gap) from the original target cDNA. In another variation (see e.g., FIG. 110), polymerase extends the 3'-ends of each of the probes closing the gap until it encounters each of the 5'-ends of the nearby probes. Both of these reporter circles contain unique identifier sequence, optional patient identifier sequence and one of them, an optional primer binding site. Enumeration of these reporter circles can be carried out by a variety of quantitative methods including but not limited to next generation sequencing. In addition to allowing the simultaneous multiplex detection of many fusion transcripts, next generation sequencing provides additional information (two copies of unique identifiers) about the reporter circles which readily distinguishes legitimate ligation products from ligation artifacts. Each of the two variations (FIGS. 109 and 110) also shows two approaches to the generation of ligation competent 5'-ends. Either the probes possess 5'-phosphates prior to hybridization (left side of the figures) or use the 5'→3' nuclease activity of Taq polymerase to cleave off matching 5'-overlapping base or flap, generating a ligation-competent 5'-phosphate (right side of the figures).

Detailed Protocol for Detection and Quantification of Exons in mRNA or lncRNA Isolated from Exosomes, Circulating Tumor Cells, or Total Blood Cells Including Circulating Tumor Cells.

Variation 6.1, See e.g., FIG. 108:

6.1.a Starting with total or poly-A mRNA or poly-A lncRNA isolated from exosomes, circulating tumor cells, or total blood cells including circulating tumor cells, generate cDNA by the use of reverse transcriptase and exon specific primers.

6.1.b. Denature target cDNA (94° C. 1 minute) in the presence of oligonucleotides (comprising a 5' probe region complementary to a portion of the cDNA towards the 5' side, a unique identifier sequence, an optional patient identifier sequence, an optional primer binding sequence, and a 3' probe region complementary to another portion of the cDNA towards the 3' side), and allow the oligonucleotides to hybridize to their complementary regions on the desired fragments by cooling to a desired temperature (e.g. 40-50° C. for 30 min). Oligonucleotides may contain an optional phosphate group at the 5' end or a matching 5'-overlapping base or flap. Optionally, Taq polymerase and/or KlenTaq (Taq polymerase lacking nuclease activity), and thermostable ligase (preferably from strain AK16D), and optionally dNTPs are either added subsequent to the annealing step, or at the start of the procedure. In the case where the oligonucleotides have a 5' phosphate directly adjacent to the 3'OH at the junction, the two ends may be directly joined using ligase (right side of FIG. 108). In the case where the oligonucleotides have a 5' phosphate with a gap between the 5' and 3' ends, the 3' OH is extended with KlenTaq. In the case where the oligonucleotides have a 5' OH, the 5'→3' nuclease activity of Taq polymerase cleaves the matching 5'-overlapping base or flap to create a ligation competent 5' phosphate (left side of FIG. 108). Allow for extension and ligation at the hybridization temperature, and optionally raise the temperature (e.g. 60° C.) to assure completion of extension and ligation, to generate circular products.

6.1.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising a copy of a short stretch of the original target cDNA, the unique identifier sequence, an optional primer binding sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 1: Fen nuclease may be used instead of polymerase with 5'-3' nuclease activity to generate the ligation-competent 5' phosphate on the 5' side of the target.

Note 2: The 5' end of the oligonucleotide primer may be synthesized to contain thiophosphate linkages in the $2^{nd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream primer), the target bases at the ligation junction would preferentially be AT rich on the 3' side, and GC rich on the 5' side.

Note: 3: When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate.

Note 4: When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

Note 5: A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Note 6: If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Note 7: MMLV reverse transcriptase may be engineered to synthesize cDNA at 50-60° C., from total input RNA (Invitrogen Superscript III). Alternatively, Tth or Tma DNA polymerases have been engineered to improve their reverse-transcriptase activity (may require addition of Mn cofactor). Finally, thermophilic PyroPhage 3173 DNA Polymerase has both strand-displacement and reverse-transcription activity, and may also be used.

Detailed Protocol for Detection and Quantification of Gene Fusions in mRNA Isolated from Exosomes, Circulating Tumor Cells, or Total Blood Cells Including Circulating Tumor Cells:

Variation 6.2 (See e.g., FIG. 109):

6.2.a. mRNA isolated from exosomes or CTCs is first converted into cDNA by a reverse transcriptase in such a manner as to span the junctions of any possible fusion transcripts. In the preferred method, exon-specific primers are used.

6.2.b. Denature target cDNA (94° C. 1 minute) in the presence of two oligonucleotides (the first comprising a 5-' sequence complementary to a unique portion of target exon #1, a unique identifier sequence, an optional patient identifier sequence, an optional primer binding sequence, and a 3'-sequence complementary to a unique portion of target exon #2 and the second comprising a 5'-sequence complimentary to a unique portion of target exon #2, a unique identifier sequence, an optional patient identifier sequence and a 3' sequence complementary to a unique portion of target exon #1), and allow the oligonucleotides to hybridize to their complementary regions on the desired fragments by cooling to a desired temperature (e.g. 50° C. for 2 hours). Thermostable ligase (preferably from strain AK16D), and optionally Taq polymerase and dNTPs are either added subsequent to the annealing step, or at the start of the procedure. In the case where both oligonucleotide sequences have a 5' phosphate, no polymerase is required (left side of FIG. 109). In the case where both oligonucleotide sequences have a 5' OH, the 5'→3' nuclease activity of polymerase cleaves the matching 5'-overlapping base to create a ligation competent 5' phosphate (right side of FIG. 109). Allow for flap cleavage and ligation at the hybridization temperature, and optionally raise the temperature (e.g. 60° C.) to assure completion of flap cleavage and ligation, to generate circular products.

6.2.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 1: Fen nuclease may be used instead of polymerase with 5'-3' nuclease activity to generate the ligation-competent 5' phosphate on the 5' side of the target.

Note 2: If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Note 3: In systems that use two bridging oligonucleotide probes, each containing unique identifier sequence, optional patient identifier sequence and optional primer binding site, it is recommended that only one but not both of the oligonucleotides contain a primer binding site (either the upstream or downstream oligonucleotide). For an additional level of false-positive detection, it is recommended that the unique identifier sequence be different in the upstream and downstream probes.

Note 4: MMLV reverse transcriptase may be engineered to synthesize cDNA at 50-60° C., from total input RNA (Invitrogen Superscript III). Alternatively, Tth or Tma DNA polymerases have been engineered to improve their reverse-transcriptase activity (may require addition of Mn cofactor). Finally, thermophilic PyroPhage 3173 DNA Polymerase has both strand-displacement and reverse-transcription activity, and may also be used.

Detailed Protocol for Another Variation for Detection and Quantification of Gene Fusions in mRNA Isolated from Exosomes, Circulating Tumor Cells, or Total Blood Cells Including Circulating Tumor Cells;

Variation 6.3 (See e.g., FIG. 110):

6.3.a. mRNA isolated from exosomes or CTCs is first converted into cDNA by a reverse transcriptase in such a manner as to span the junctions of any possible fusion transcripts. In the preferred method, exon-specific primers are used.

6.3.b. Denature target cDNA (94° C. 1 minute) in the presence of two oligonucleotides (the first comprising a 5-' sequence complementary to a unique portion of target exon #1, a unique identifier sequence, an optional patient identifier sequence, an optional primer binding sequence, and a 3'-sequence complementary to a unique portion of target exon #2 and the second comprising a 5'-sequence complimentary to a unique portion of target exon #2, a unique identifier sequence, an optional patient identifier sequence and a 3' sequence complementary to a unique portion of target exon #1), and allow the oligonucleotides to hybridize to their complementary regions on the desired fragments by cooling to a desired temperature (e.g. 50° C. for 2 hours). Taq polymerase and/or KlenTaq (Taq polymerase lacking nuclease activity), thermostable ligase (preferably from strain AK16D), and dNTPs are either added subsequent to the annealing step, or at the start of the procedure. In the case where both oligonucleotide sequences have a 5' phosphate, KlenTaq extends the 3' end until it is directly adjacent to the ligation-competent 5' end (left side of FIG. 110). In the case where both oligonucleotide sequences have a 5' OH, the 5'→3' nuclease activity of polymerase cleaves the matching 5'-overlapping base to create a ligation competent 5' phosphate (right side of FIG. 110). Allow for extension and ligation at the hybridization temperature, and optionally raise the temperature (e.g. 60° C.) to assure completion of extension and ligation, to generate circular products.

6.3.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 1: Fen nuclease may be used instead of polymerase with 5'-3' nuclease activity to generate the ligation-competent 5' phosphate on the 5' side of the target.

Note 2: The 5' end of the oligonucleotide primer may be synthesized to contain thiophosphate linkages in the $2^{nd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream primer), the target bases at the ligation junction would preferentially be AT rich on the 3' side, and GC rich on the 5' side.

Note: 3: When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate.

Note 4: When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

Note 5: A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Note 6: If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Note 7: In systems that use two bridging oligonucleotide probes, each containing unique identifier sequence, optional patient identifier sequence and optional primer binding site, it is recommended that only one but not both of the oligonucleotides contain a primer binding site (either the upstream or downstream oligonucleotide). For an additional level of false-positive detection, it is recommended that the unique identifier sequence be different in the upstream and downstream probes.

Note 8: MMLV reverse transcriptase may be engineered to synthesize cDNA at 50-60° C., from total input RNA (Invitrogen Superscript III). Alternatively, Tth or Tma DNA polymerases have been engineered to improve their reverse-transcriptase activity (may require addition of Mn cofactor). Finally, thermophilic PyroPhage 3173 DNA Polymerase has both strand-displacement and reverse-transcription activity, and may also be used.

Detailed Protocol for Detection and Quantification of mRNA Containing Specific Exons (which May not be Adjacent to Each Other) in mRNA Isolated from Exosomes, Circulating Tumor Cells, or Total Blood Cells Including Circulating Tumor Cells;

Variation 6.4 (See e.g., FIG. 111)

6.4.a. mRNA isolated from exosomes or CTCs is first converted into cDNA by a reverse transcriptase in such a manner as to include both exon regions. In the preferred method, exon-specific primers are used.

6.4.b. Denature target cDNA (94° C. 1 minute) in the presence of two oligonucleotides (the first comprising a 5'-sequence complementary to a unique portion of target exon #1, a unique identifier sequence, an optional patient identifier sequence, an optional primer binding sequence, and a 3'-sequence complementary to a unique portion of target exon #2 and the second comprising a 5'-sequence complimentary to a unique portion of target exon #2, a unique identifier sequence, an optional patient identifier sequence and a 3' sequence complementary to a unique portion of target exon #1), and allow the oligonucleotides to hybridize to their complementary regions on the desired fragments by cooling to a desired temperature (e.g. 50° C. for 2 hours). Thermostable ligase (preferably from strain AK16D), and optionally Taq polymerase and dNTPs are either added subsequent to the annealing step, or at the start of the procedure. In the case where both oligonucleotide sequences have a 5' phosphate, no polymerase is required (left side of FIG. 111). In the case where both oligonucleotide sequences have a 5' OH, the 5'→3' nuclease activity of polymerase cleaves the matching 5'-overlapping base to create a ligation competent 5' phosphate (right side of FIG. 111). Allow for flap cleavage and ligation at the hybridization temperature, and optionally raise the temperature (e.g. 60° C.) to assure completion of flap cleavage and ligation, to generate circular products.

6.4.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 1: Fen nuclease may be used instead of polymerase with 5'-3' nuclease activity to generate the ligation-competent 5' phosphate on the 5' side of the target.

Note 2: If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Note 3: In systems that use two bridging oligonucleotide probes, each containing unique identifier sequence, optional patient identifier sequence and optional primer binding site, it is recommended that only one but not both of the oligonucleotides contain a primer binding site (either the upstream or downstream oligonucleotide). For an additional level of false-positive detection, it is recommended that the unique identifier sequence be different in the upstream and downstream probes.

Note 4: MMLV reverse transcriptase may be engineered to synthesize cDNA at 50-60° C., from total input RNA (Invitrogen Superscript III). Alternatively, Tth or Tma DNA polymerases have been engineered to improve their reverse-transcriptase activity (may require addition of Mn cofactor). Finally, thermophilic PyroPhage 3173 DNA Polymerase has both strand-displacement and reverse-transcription activity, and may also be used.

Detailed Protocol for Detection and Quantification of mRNA Containing Specific Exons (which May not be Adjacent to Each Other) in mRNA Isolated from Exosomes, Circulating Tumor Cells, or Total Blood Cells Including Circulating Tumor Cells;

Variation 6.5 (See e.g., FIG. 112):

6.5.a. mRNA isolated from exosomes or CTCs is first converted into cDNA by a reverse transcriptase in such a manner as to include both exon regions. In the preferred method, exon-specific primers are used.

6.5.b. Denature target cDNA (94° C. 1 minute) in the presence of two oligonucleotides (the first comprising a 5-' sequence complementary to a unique portion of target exon #1, a unique identifier sequence, an optional patient identifier sequence, an optional primer binding sequence, and a 3'-sequence complementary to a unique portion of target exon #2 and the second comprising a 5'-sequence complimentary to a unique portion of target exon #2, a unique identifier sequence, an optional patient identifier sequence and a 3' sequence complementary to a unique portion of target exon #1), and allow the oligonucleotides to hybridize to their complementary regions on the desired fragments by cooling to a desired temperature (e.g. 50° C. for 2 hours). Taq polymerase and/or KlenTaq (Taq polymerase lacking nuclease activity) thermostable ligase (preferably from strain AK16D), and dNTPs are either added subsequent to the annealing step, or at the start of the procedure. In the case where both oligonucleotide sequences have a 5' phosphate, KlenTaq extends the 3' end until it is directly adjacent to the ligation-competent 5' end (left side of FIG. 112). In the case where both oligonucleotide sequences have a 5' OH, the 5'→3' nuclease activity of polymerase cleaves the matching 5'-overlapping base to create a ligation competent 5' phosphate (right side of FIG. 112). Allow for extension and ligation at the hybridization temperature, and optionally raise the temperature (e.g. 60° C.) to assure completion of extension and ligation, to generate circular products.

6.5.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 1: Fen nuclease may be used instead of polymerase with 5'-3' nuclease activity to generate the ligation-competent 5' phosphate on the 5' side of the target.

Note 2: The 5' end of the oligonucleotide primer may be synthesized to contain thiophosphate linkages in the $2^{nd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream primer), the target bases at the ligation junction would preferentially be AT rich on the 3' side, and GC rich on the 5' side.

Note: 3: When using KlenTaq polymerase (Taq polymerase without 5'→3' nuclease cleavage activity), the 5' end linker may be synthesized to contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the primer is bound to the target. The endonuclease also cleaves single-stranded primer, but with lower efficiency, and thus primer hybridized to template would be the preferred substrate.

Note 4: When using KlenTaq polymerase (Taq polymerase without 5'→3' nuclease cleavage activity), the 5' end linker may be synthesized to contain a 5' phosphate. Alternatively, the 5' phosphate may be added using T4 kinase either prior to ligating to the target DNA, or after that ligation step.

Note 5: A 1:20 mixture of Taq polymerase (with 5'→3' nuclease activity) and KlenTaq (Taq polymerase without 5'→3' nuclease cleavage activity) may be used under conditions of distributive extension (i.e. higher salt concentration) to minimize degradation of target DNA by nick translation.

Note 6: If the oligonucleotide(s) also comprises optional primer binding sites (i.e. universal primer binding sites), it would be suitable for PCR amplification, followed by subsequent identification of the targets using next generation sequencing, TaqMan assays, UniTaq assays, Real-Time PCR assays, digital PCR, microarray, hybridization, or other detection method.

Note 7: In systems that use two bridging oligonucleotide probes, each containing unique identifier sequence, optional patient identifier sequence and optional primer binding site, it is recommended that only one but not both of the oligonucleotides contain a primer binding site (either the upstream or downstream oligonucleotide). For an additional level of false-positive detection, it is recommended that the unique identifier sequence be different in the upstream and downstream probes.

Note 8: MMLV reverse transcriptase may be engineered to synthesize cDNA at 50-60° C., from total input RNA (Invitrogen Superscript III). Alternatively, Tth or Tma DNA polymerases have been engineered to improve their reverse-transcriptase activity (may require addition of Mn cofactor). Finally, thermophilic PyroPhage 3173 DNA Polymerase has both strand-displacement and reverse-transcription activity, and may also be used.

Prophetic Example 7—Accurate Quantification of Tumor-Specific miRNA Isolated from Exosomes or Argonaut Proteins. (e.g. a Dozen microRNA Markers that Predict Outcome or Guide Treatment)

MicroRNA (miRNA) have been identified as potential tissue-specific markers of the presence of tumors, their classification and prognostication. miRNA exist in serum and plasma either as complexes with Ago2 proteins or by encapsulation as exosomes.

FIGS. 114-117 describe methods for capturing miRNA sequences for subsequent enumeration by high accuracy sequencing. In all methods shown, the process involves making a cDNA copy of the target miRNA sequence which is converted into a circular DNA suitable.

Detailed Protocol for the Capture, Identification, and Quantification of all miRNA Species which are Present in Serum, Plasma or Exosomes without any Selection:

Variation 7.1 (See e.g., FIG. 114)

7.1.a. Isolate miRNA from exosomes or CTCs. Ligate a universal linker to the 3'-end of the miRNA using a DNA linker with a 5'-phosphate and a blocked 3'-end using RNA Ligase 1.

7.1.b. Phosphorylate the 5'-end of the modified miRNA with T4 kinase. Ligate a universal linker to the 5'-end of the modified linker using a DNA linker with a 5'-phosphate and a blocked 3'-end.

7.1.c. After removal of the excess linkers, denature the nucleic acids (94° C. 1 minute) in the presence of oligonucleotides (comprising sequences complementary to the 5'- and 3'-ends of the linkers, a unique identifier sequence, an optional patient identifier sequence, an optional primer binding sequence, and allow the oligonucleotides to hybridize to their complementary regions on the desired fragments by cooling to a desired temperature (e.g. 40-50° C. for 30 min). Add a Reverse Transcriptase lacking 5'-3' activity (i.e. Tth DNA polymerase using Mn2+ cofactor), a thermostable ligase (preferably from strain AK16D) and dNTPs; the components are either added subsequent to the annealing step, or at the start of the procedure. Allow for extension and ligation at the hybridization temperature, and optionally raise the temperature (e.g. 60° C.) to assure completion of extension and ligation, to generate circular products.

7.1.d. Add UDG and AP endonucleases to nick the miRNA in the original target, add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising a copy of the original target miRNA, the unique identifier sequence, an optional primer binding sequence, and an optional patient identifier sequence. This product is suitable for rolling circle amplification (using primer complementary to the primer binding sequence with phi-29 polymerase) to create tandem repeats of the desired sequence. This may be followed by identification of the targets using next generation sequencing, or alternatively, direct SMRT sequencing on the covalently closed template, using the optional primer binding sequence as a primer binding site.

Note 1. If the oligonucleotide(s) also comprise optional primer binding sites (i.e., universal primer binding sites), the circular DNA would be suitable for PCR amplification followed by subsequent identification of the targets using next generation sequencing, TaqMan assays, UniTaq assays, real-time PCR assays, digital PCR, microarray, hybridization or other detection methods.

The next variants of the method (see e.g., FIGS. 115-117) are designed for the capture of specific miRNA sequences from total miRNA isolated form serum, plasma or exosomes. These methods make use of capture probes complementary to all or some part of the target miRNA sequences but subsequently make cDNA copies of the original miRNA sequence and thus are able to detect single base variations in the miRNA or capture due to mis-hybridization.

Detailed Protocol for the Capture, Identification, and Quantification of Specific miRNA Species which are Present in Serum, Plasma or Exosomes without any Selection:

Variation 7.2 (See e.g., FIG. 115)

7.2.a. Isolate miRNA from exosomes or CTCs. Phosphorylate the isolated miRNA using T4 kinase. Hybridize oligonucleotide pairs, the first of which comprising a sequence complementary to the miRNA target, flanked by unique 5'- and 3'-linker sequences while the second oligonucleotide comprising a 5'-phosphorylated end followed by the complement of the unique 3'-linker, a unique identifier sequence, an optional patient identifier sequence, an optional primer binding sequence and a complement of the unique 5'-linker with the last base being a ribonucleotide base. T4 RNA ligase 2 is present to covalently seal the ends of the miRNA creating circular ligation products.

7.2.b. Add Exonuclease I (digests single-stranded DNA in the 3'→5' direction), and Exonuclease III (digests double-stranded DNA in the 3'→5' direction), to digest all unligated oligonucleotides, leaving only the desired single-stranded circular miRNA-DNA chimera. Heat inactivate exonucleases at 80° C. for 20 minutes.

7.2.c. Add a universal 5'-phosphorylated primer to the circular products, hybridize at 37° C. Add Reverse Transcriptase lacking a 5'-3' exonuclease activity (Tth DNA polymerase using Mn2+ cofactor), thermostable ligase (preferably from strain AK16D) and dNTPs; the components are either added subsequent to the annealing step, or at the start of the procedure. Allow for extension and ligation at the hybridization temperature, and optionally raise the temperature (e.g. 60° C.) to assure completion of extension and ligation, to generate circular products now contain a copy of the original target miRNA.

7.2.d. Add UDG and AP endonucleases to nick the miRNA in the original target, add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising a copy of the original target miRNA, the unique identifier sequence, an optional primer binding sequence, and an optional patient identifier sequence. This product is suitable for rolling circle amplification (using primer complementary to the primer binding sequence with phi-29 polymerase) to create tandem repeats of the desired sequence. This may be followed by identification of the targets using next generation sequencing, or alternatively, direct SMRT sequencing on the covalently closed template, using the optional primer binding sequence as a primer binding site.

Note 1. If the oligonucleotide(s) also comprise optional primer binding sites (i.e., universal primer binding sites), the circular DNA would be suitable for PCR amplification followed by subsequent identification of the targets using next generation sequencing, TaqMan assays, UniTaq assays, real-time PCR assays, digital PCR, microarray, hybridization or other detection methods.

The next variation of the method makes use of a C6 or C18 spacer that allows copying of the target miRNA but prevents completion of a circular product and thus eliminating false positive detection of low levels of the desired miRNA. Nick translation of a universal primer containing thiophosphates at the $2^{nd}$ and $3^{rd}$ positions relative to the 5'-end is unable to cross the C6 or C18 spacer in the middle of the target miRNA binding complement sequence enabling destruction of any unligated miRNA probes.

Detailed Protocol for the Capture, Identification, and Quantification of Specific miRNA Species which are Present in Serum, Plasma or Exosomes without any Selection:

Variation 7.3 (See e.g., FIG. 116):

7.3.a. Isolate miRNA from exosomes or CTCs. Phosphorylate the isolated miRNA using T4 kinase. Hybridize oligonucleotide pairs, the first of which comprising a sequence complementary to the miRNA target that contains a single C6 or C18 spacer, flanked by unique 5'- and 3'-linker sequences while the second oligonucleotide comprising a 5'-phosphorylated end followed by the complement of the unique 3'-linker, a unique identifier sequence, an optional patient identifier sequence, an optional primer binding sequence and a complement of the unique 5'-linker with the last base being a ribonucleotide base. Also present in the hybridization mix is a universal primer which contains thiophosphate linkages in the $2^{nd}$ and $3^{rd}$ positions from the 5'-end. T4 RNA ligase 2 is present to covalently seal the ends of the miRNA creating circular ligation products.

7.3.b. Add Reverse Transcriptase possessing a 5'-3' exonuclease activity (Tth DNA polymerase using Mn2+ cofactor) and thermostable ligase (preferably from strain AK16D), dNTPs are either added subsequent to the annealing step, or at the start of the procedure. Allow for extension and ligation at the hybridization temperature, and optionally raise the temperature (e.g. 60° C.) to assure completion of extension and ligation, to generate circular products now contain a copy of the original target miRNA.

7.3.c. Add UDG and AP endonucleases to nick the miRNA in the original target, then add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising a copy of the original target miRNA, the unique identifier sequence, an optional primer binding sequence, and an optional patient identifier sequence. This product is suitable for rolling circle amplification (using primer complementary to the primer binding sequence with phi-29 polymerase) to create tandem repeats of the desired sequence. This may be followed by identification of the targets using next generation sequencing, or alternatively, direct SMRT sequencing on the covalently closed template, using the optional primer binding sequence as a primer binding site.

Note 1. If the oligonucleotide(s) also comprise optional primer binding sites (i.e., universal primer binding sites), the circular DNA would be suitable for PCR amplification followed by subsequent identification of the targets using next generation sequencing, TaqMan assays, UniTaq assays, real-time PCR assays, digital PCR, microarray, hybridization or other detection methods.

Another variant (FIG. 117) takes advantage of a stem-loop capture probe complementary to some portion of the target miRNA. The detailed protocol is as described below:

Detailed Protocol for the Capture, Identification, and Quantification of Specific miRNA Species which are Present in Serum, Plasma or Exosomes without any Selection:

Variation 7.4 (See e.g., FIG. 117):

7.4.a. Isolate miRNA from exosomes or CTCs. Hybridize a stem-loop probe comprised of 5'-end that forms a stem-loop, a protruding 3'-region complementary to some portion of the target miRNA. The loop portion contains a unique identifier sequence, an optional patient identifier sequence, an optional primer binding sequence and an optional cleavable link. Extend the 3'-end of the stem-loop probe with a reverse transcriptase and dNTPs.

7.4.b. Denature the nucleic acids (94° C. 1 minute) in the presence of oligonucleotides (comprising sequences complementary to the 5'-stem-loop sequence and the 3'-ends of the extended cDNA. In addition, the 5'-end is blocked to prevent nick translation.) and allow the oligonucleotides to hybridize to their complementary regions on the desired fragments by cooling to a desired temperature (e.g. 40-50° C. for 30 min).

7.4.c. Add KlenTaq (Taq polymerase lacking nuclease activity) and thermostable ligase (preferably from strain AK16D), dNTPs are either added subsequent to the annealing step, or at the start of the procedure. KlenTaq extends the 3' end until it is directly adjacent to the ligation-competent 5' end. Allow for extension and ligation at the hybridization temperature, and optionally raise the temperature (e.g. 60° C.) to assure completion of extension and ligation, to generate circular products.

7.4.d. Cleave the oligonucleotide probe at a cleavable link (e.g. U cleaved using UDG and AP endonuclease). Add Exonuclease I (digests single-stranded DNA in the 3'→5' direction), and Exonuclease III (digests double-stranded DNA in the 3'→5' direction), to digest all unligated products and excess probes, leaving only the desired single-stranded circular DNA comprising a copy of a short stretch of the original target cDNA, the unique identifier sequence, an optional primer binding sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 1. If the oligonucleotide(s) also comprise optional primer binding sites (i.e., universal primer binding sites), the circular DNA would be suitable for PCR amplification followed by subsequent identification of the targets using next generation sequencing, TaqMan assays, UniTaq assays, real-time PCR assays, digital PCR, microarray, hybridization or other detection methods.

Prophetic Example 8—Clinical Need in Prenatal Diagnosis from Maternal Plasma Sample In the prenatal care field, there is an urgent need to develop non-invasive assays for, common aneuploidies, such as trisomy 21, 18, or 13, small deletions, such as those arising from deletions in the Duchenne muscular dystrophy (DMD) gene, other small copy number anomalies, such as those responsible for autism, balanced translocations to determine potential clinical manifestations, methylation changes, which may result in diseases associated with imprinting, such as Angelman's syndrome or Prader-Willi syndrome, triplet repeat changes, responsible for diseases such as Huntington's disease, point mutations, such as those in the CFTR gene responsible for cystic fibrosis.

Overview: Recent work has shown that fetal DNA as a percentage of maternal DNA in the plasma is at approximately 6%, 20%, and 26% in the $1^{st}$, $2^{nd}$, and $3^{rd}$ trimester respectively. Due to how DNA is degraded, maternal DNA is usually about 160 bases and still associated with the H1 histone, while fetal DNA is about 140 bases and not associated with histone. Depending on the clinical need, and where the knowledge will provide the best care, tests may be developed with sufficient sensitivity to detect fetal DNA in the appropriate trimester.

There are approximately 3,500 recessive genetic disorders where the gene is known. The most common disorders result from DNA copy anomalies, either an extra chromosome such as in Trisomy 21, or deletion of a portion of a gene, such as in the Duchenne muscular dystrophy (DMD) gene. In considering prenatal screening, one needs to balance the probability of a genetic disorder vs. the risk of the procedure. Currently, the standard of care recommends amniocentesis during week 17 for expectant mothers at age 35, since the risk of Trisomy 21 or other chromosomal aneuploidy at 1 in 200 now matches the risk of spontaneous abortion after the procedure.

In considering the use of the methods of nucleic acid sequencing described herein for prenatal screening, two levels of testing are recommended. For low-cost screening of all pregnancies for Trisomy 21, 13, and 18, the sequencing methods of the present invention may be used to rapidly identify differentially expressed genes on chromosomes 21, 13, and 18, e.g., identify those genes that are turned off in the fetus as a consequence of methylation silencing, but are on in the adult. Similar regions are identified on three control chromosomes, i.e. 2, 5, 7. Even when isolating DNA from the serum of a mother in the first trimester, one can rapidly calculate the percentage of DNA arising from the fetus by comparing methylated to unmethylated DNA among control chromosomal regions—in the example herein, that would be 6%. If there is trisomy at any of the other chromosomes, i.e. Trisomy 21, then the promoters from that chromosome will show methylation at about 9%, in other words, some 50% higher than for the normal disomy case. Scoring 1,000 genome equivalents is recommended, such that a count of 90 methylated copies for the trisomy case is easily distinguished from 60 methylated copies for the normal sample.

As a first step in such a procedure, in order to identify those promoter regions which are methylated in fetal DNA during the earliest stages of development, but never methylated in maternal DNA (i.e. WBC). This needs to be performed empirically, by comparing methylation pattern in cfDNA isolated from women who are pregnant with a diploid fetus, a fetus containing a trisomy, and no pregnancy. For a generalized review on using epigenetic markers for NIPD see Patsalis et al., "A New Non-invasive Prenatal Diagnosis of Down syndrome through Epigenetic Markers and Real-time qPCR," *Expert Opin Biol Ther.* 12 Suppl 1:S155-61 (2012), which is hereby incorporated by reference in its entirety. As an example detecting methylation status at a single marker PDE9A, see Lim et al., "Non-invasive Epigenetic Detection of Fetal Trisomy 21 in First Trimester Maternal Plasma," *PLoS One* 6(11):e27709 (2011), which is hereby incorporated by reference in its entirety. The approaches described herein will be able to identify such markers far more rapidly. To identify methylation at adjacent HinP1I sites throughout the genome, the approach outlined in FIG. 28 would be used. Alternatively, when focusing on known genes on the selected chromosomes, probes may be designed for specific target regions and methylation scored as in FIG. 27. This approach would also be used in the final prenatal screening test. For more abundant methylation sites, i.e. at adjacent AciI sites between HaeIII sites, throughout the genome, the approach outlined in FIG. 36 would be used. When focusing on known genes, probes may be designed for specific target regions and methylation scored as in FIGS. 36, 37, 39, and 40. If the above approaches do not yield sufficient markers, methylation sites at adjacent AciI sites throughout the genome may be identified using the approach outlined in FIG. 33 would be used. For these sites, the more targeted approaches outlined in FIGS. 29, and 31 may be used.

Alternatively, there are certain genes that are turned on during fetal development that are off in adult tissue or blood. Under these conditions, it would be important to identify unmethylated promoter regions, by comparing unmethylation pattern in cfDNA isolated from women who are pregnant with a diploid fetus, a fetus containing a trisomy, and no pregnancy. To identify genome-wide loss of methylation patterns, the methods described in FIG. 51, 57, or 62 may be used. To identify unmethylation known genes on the selected chromosomes, probes may be designed for specific target regions and unmethylation scored as in FIGS. 53, 55, 58, 60. This approach would also be used in the final prenatal screening test.

Further, the above approach will be able to accurately quantify methylation changes at other positions in the genome, which may result in diseases associated with imprinting, such as Angelman's syndrome or Prader-Willi syndrome. The ability of the present invention to determine methylation status and at the same time to determine if the deletion is on the paternal or maternal chromosome by SNP or repetitive sequence polymorphisms detection (i.e., detection of upstream or downstream cis-located maternal or paternal identifying SNPs or repetitive sequence polymorphisms) will enhance its diagnostic discrimination of imprinting diseases.

A ligase-based approach to count chromosomal fragments for non-invasive prenatal diagnosis termed DANSR has been recently reported (Sparks et al., "Selective Analysis of Cell-free DNA in Maternal Blood for Evaluation of Fetal Trisomy," *Prenat Diagn.* 32(1):3-9 (2012), which is hereby incorporated by reference in its entirety). This approach is based on using 3 fragments in a ligation reaction on the chromosomal arm: a left fragment containing and upstream universal sequence, a middle fragment, and a right fragment containing a downstream universal sequence. After a ligation reaction, the products are separated from the input primers, PCR amplified, and sequenced. Spurious ligations (i.e. upstream directly to wrong downstream primer, no middle piece) are easily distinguished by sequencing, and were less than 5%. The present invention can also use this approach, either by capturing specific targets from the ligated products of the entire genome, as described in FIGS. 63-69, or by using target-specific probes during the initial ligation event, as described in FIGS. 13-26, or FIGS. 70-78.

Since the above approach depends on counting chromosomal regions, the accuracy of the technique may be improved by taking advantage of polymorphisms in such regions. FIGS. 70, 77, and 78, describe a set of techniques for capturing fragments containing repeat sequence polymorphisms. These polymorphisms will allow for identification of copy number differences either across the genome, or at defined places, either for copy gains or copy loss—this is also relevant for cancer genome analysis. Trisomy may arise from non-disjunction during the initial meiosis, or during the second meiosis. Let's take the case of spermatogenesis. If the non-disjunction occurs at the first meiotic division, then homologous chromosomes move to the same pole during anaphase. When these then split to form gametes, two will be disomic (containing 1 of each parental chromosomes) and two will be null-somic. If these gametes fertilize a euploid egg, the resultant zygotes would be 2 trisomic (1+1+1), and two monosomic. If on the other hand, the non-disjunction occurs at the second meiotic division, then sister chromatids move to the same pole during anaphase. When these then split to form gametes, one will be disomic (containing 2 of the same parental chromosomes) and one will be null-somic, and two will euploid (1 chromosome each). If these gametes fertilize a euploid egg, the resultant zygotes would be 1 trisomic (2+1), and one monosomic, and two euploid (disomic). The same holds true for the maternal chromosomes. Thus, a trisomy fetus may have a number of different combinations of paternal and maternal chromosomes.

The example of 1,000 genome equivalents for the maternal DNA, and 100 genome equivalents for the fetal DNA can be used to illustrate the difference in distinguishing by scoring for presence of copy vs. presence of polymorphism. When using highly polymorphic markers such as with tetranucleotide repeats, it is not unusual for 3 or all 4 of the polymorphisms to be different. Results will be compared with these cases, where either the markers for the maternal or paternal chromosome are the same or different. Chromosome 2 will be used as the control, and 21 as the example for trisomy Case 1 (Copy Number Only)

|  | Maternal | Fetus | Total |
| --- | --- | --- | --- |
| Chrm 2 | 2,000 | 200 | 2,200 |
| Chrm 21 | 2,000 | 300 | 2,300 |

Case 2 (Maternal Markers Homozygous, Maternal Non-Disjunction, First Meiosis)

|  | Maternal | Fetus | Total |
| --- | --- | --- | --- |
| Chrm 2M1 | 1,000 | 0 | + |
| Chrm 2M2 | 1,000 | 100 | 2,100* |
| Chrm 2P1 | 0 | 100 | 100 |
| Chrm 2P2 | 0 | 0 | 0 |
| Chrm 21M1 | 1,000 | 100 | + |
| Chrm 21M2 | 1,000 | 100 | 2,200* |
| Chrm 21P1 | 0 | 100 | 100 |
| Chrm 21P2 | 0 | 0 | 0 |

*Note: Since alleles 2M1 and 2M2 are the same, total = 2,100. Likewise, since alleles 21M1 and 21M2 are the same, total = 2,200. Paternal alleles may be either heterozygous or homozygous Case 3 (Maternal Markers Homozygous, Maternal Non-Disjunction, Second Meiosis)

|  | Maternal | Fetus | Total |
| --- | --- | --- | --- |
| Chrm 2M1 | 1,000 | 0 | + |
| Chrm 2M2 | 1,000 | 100 | 2,100* |
| Chrm 2P1 | 0 | 100 | 100 |
| Chrm 2P2 | 0 | 0 | 0 |
| Chrm 21M1 | 1,000 | 0 | + |
| Chrm 21M2 | 1,000 | 200 | 2,200* |
| Chrm 21P1 | 0 | 100 | 100 |
| Chrm 21P2 | 0 | 0 | 0 |

*Note: Since alleles 2M1 and 2M2 are the same, total = 2,100. Likewise, since alleles 21M1 and 21M2 are the same, total = 2,200. Paternal alleles may be either heterozygous or homozygous Case 4 (Maternal Markers Heterozygous, Maternal Non-Disjunction, First Meiosis)

|  | Maternal | Fetus | Total |
| --- | --- | --- | --- |
| Chrm 2M1 | 1,000 | 0 | 1,000 |
| Chrm 2M2 | 1,000 | 100 | 1,100 |
| Chrm 2P1 | 0 | 100 | 100 |
| Chrm 2P2 | 0 | 0 | 0 |
| Chrm 21M1 | 1,000 | 100 | 1,100 |
| Chrm 21M2 | 1,000 | 100 | 1,100 |
| Chrm 21P1 | 0 | 100 | 100 |
| Chrm 21P2 | 0 | 0 | 0 |

Case 5 (Maternal Markers Heterozygous, Maternal Non-Disjunction, Second Meiosis)

|  | Maternal | Fetus | Total |
| --- | --- | --- | --- |
| Chrm 2M1 | 1,000 | 0 | 1,000 |
| Chrm 2M2 | 1,000 | 100 | 1,100 |
| Chrm 2P1 | 0 | 100 | 100 |
| Chrm 2P2 | 0 | 0 | 0 |
| Chrm 21M1 | 1,000 | 0 | 1,000 |
| Chrm 21M2 | 1,000 | 200* | 1,200 |
| Chrm 21P1 | 0 | 100 | 100 |
| Chrm 21P2 | 0 | 0 | 0 |

*Note: There is an additional combination of trisomy wherein 2 copies of allele 21M1 are in the fertilized egg.

Case 6 (Maternal Markers Homozygous, Paternal Non-Disjunction, First Meiosis)

|  | Maternal | Fetus | Total |
| --- | --- | --- | --- |
| Chrm 2M1 | 1,000 | 0 | + |
| Chrm 2M2 | 1,000 | 100 | 2,100* |
| Chrm 2P1 | 0 | 100 | 100 |
| Chrm 2P2 | 0 | 0 | 0 |
| Chrm 21M1 | 1,000 | 0 | + |
| Chrm 21M2 | 1,000 | 100 | 2,100* |
| Chrm 21P1 | 0 | 100 | 100 |
| Chrm 21P2 | 0 | 100 | 100 |

*Note: Since alleles 2M1 and 2M2 are the same, total = 2,100. Likewise, since alleles 21M1 and 21M2 are the same, total = 2,100. Paternal alleles may be either heterozygous or homozygous Case 7 (Maternal Markers Homozygous, Paternal Non-Disjunction, Second Meiosis)

|  | Maternal | Fetus | Total |
| --- | --- | --- | --- |
| Chrm 2M1 | 1,000 | 0 | + |
| Chrm 2M2 | 1,000 | 100 | 2,100* |
| Chrm 2P1 | 0 | 100 | 100 |
| Chrm 2P2 | 0 | 0 | 0 |
| Chrm 21M1 | 1,000 | 0 | + |
| Chrm 21M2 | 1,000 | 100 | 2,100* |
| Chrm 21P1 | 0 | 200 | 200 |
| Chrm 21P2 | 0 | 0 | 0 |

*Note: Since alleles 2M1 and 2M2 are the same, total = 2,100. Likewise, since alleles 21M1 and 21M2 are the same, total = 2,100. Paternal alleles may be either heterozygous or homozygous Case 8 (Maternal Markers Heterozygous, Paternal Non-Disjunction, First Meiosis)

|  | Maternal | Fetus | Total |
|---|---|---|---|
| Chrm 2M1 | 1,000 | 0 | 1,000 |
| Chrm 2M2 | 1,000 | 100 | 1,100 |
| Chrm 2P1 | 0 | 100 | 100 |
| Chrm 2P2 | 0 | 0 | 0 |
| Chrm 21M1 | 1,000 | 0 | 1,000 |
| Chrm 21M2 | 1,000 | 100 | 1,100 |
| Chrm 21P1 | 0 | 100 | 100 |
| Chrm 21P2 | 0 | 100 | 100 |

Case 9 (Maternal Markers Heterozygous, Paternal Non-Disjunction, Second Meiosis)

|  | Maternal | Fetus | Total |
|---|---|---|---|
| Chrm 2M1 | 1,000 | 0 | 1,000 |
| Chrm 2M2 | 1,000 | 100 | 1,100 |
| Chrm 2P1 | 0 | 100 | 100 |
| Chrm 2P2 | 0 | 0 | 0 |
| Chrm 21M1 | 1,000 | 0 | 1,000 |
| Chrm 21M2 | 1,000 | 100 | 1,100 |
| Chrm 21P1 | 0 | 200 | 200 |
| Chrm 21P2 | 0 | 0 | 0 |

*Note: There is an additional combination of trisomy wherein 2 copies of allele 21P2 are in the fertilized egg.

From this analysis, it is clear that to distinguish trisomy, the most useful markers are those where the maternal loci is polymorphic, and the paternal loci is different from both maternal alleles. The paternal loci does not need to be polymorphic. For X-linked deletions, such as found in Duchenne's muscular dystrophy, the approach is simpler, since the disease is mostly manifest in boys. Again, comparing chromosome 2 with the X chromosome in the area of the deletion would yield:

Case 10 (Maternal Markers Heterozygous, Inherited X-Linked Deletion)

|  | Maternal | Fetus | Total |
|---|---|---|---|
| Chrm 2M1 | 1,000 | 0 | 1,000 |
| Chrm 2M2 | 1,000 | 100 | 1,100 |
| Chrm 2P1 | 0 | 100 | 100 |
| Chrm 2P2 | 0 | 0 | 0 |
| Chrm XM1 | 1,000 | 0 | 1,000 |
| Chrm XM2 | 0* | 0* | 0 |
| Chrm XP1 | 0 | 0 | 0 |
| Chrm YP2 | 0 | 100 | 100 |

*Note: deletion of inherited region

Case 11 (Maternal markers heterozygous, fetus does not contain X-linked deletion)

|  | Maternal | Fetus | Total |
|---|---|---|---|
| Chrm 2M1 | 1,000 | 0 | 1,000 |
| Chrm 2M2 | 1,000 | 100 | 1,100 |
| Chrm 2P1 | 0 | 100 | 100 |
| Chrm 2P2 | 0 | 0 | 0 |
| Chrm XM1 | 1,000 | 100 | 1,100 |
| Chrm XM2 | 0* | 0* | 0 |
| Chrm XP1 | 0 | 0 | 0 |
| Chrm YP2 | 0 | 100 | 100 |

*Note: deletion of inherited region

Case 11 (Maternal Markers Heterozygous, Sporadic X-Linked Deletion)

|  | Maternal | Fetus | Total |
|---|---|---|---|
| Chrm 2M1 | 1,000 | 0 | 1,000 |
| Chrm 2M2 | 1,000 | 100 | 1,100 |
| Chrm 2P1 | 0 | 100 | 100 |
| Chrm 2P2 | 0 | 0 | 0 |
| Chrm XM1 | 1,000 | 0 | 1,000 |
| Chrm XM2 | 1,000 | 0* | 1,000 |
| Chrm XP1 | 0 | 0 | 0 |
| Chrm YP2 | 0 | 100 | 100 |

*Note: deletion of inherited region

Case 10 shows inherited Duchenne's muscular dystrophy, where the mother is a carrier. Under these conditions, the amount of the total amount of two X-chromosome alleles appears half of other positions. In case 11, the fetus does not have the disease, and in case 12 the disease is a sporadic mutation that appears in the fetus. The Y chromosome marker confirms the fetus in male. The above shows how genotyping would be performed at the DMD locus. If there is prior knowledge that the mother is a carrier, than phasing of the deletion with neighboring polymorphisms can be determined (see below), and then these neighboring polymorphisms may also be used to verify if the fetus also carries the deletion, and if the fetus is male, and susceptible to the disease. This approach may be used to find both X-linked and autosomal dominant changes.

To determine if the fetus contains an inherited or sporadic mutation on one of the roughly 3,500 other disorders, including deletions, point mutations, or abnormal methylation, a more sophisticated analysis would be recommended. Sequence analysis readily determines presence of the recessive allele in both parents. If the mutation is different in the parents, it is possible to determine if the child is a compound heterozygote for the disease by evaluating cell-free DNA from the maternal serum. To obtain the full answer from analysis of fetal DNA in the maternal serum may require two parts to this assay. The first is to establish phase for the maternal SNPs or polymorphisms in repeat regions that surround the disease gene. This may be accomplished by isolating high molecular weight DNA from white blood cells of the mother, or from saliva of the father.

Determining accurate haplotype or phase may be accomplished by using a variation of an approach developed by Complete Genomics (see Peters et al., "Accurate Whole-genome Sequencing and Haplotyping from 10 to 20 Human Cells," Nature 487(7406):190-5 (2012), which is hereby incorporated by reference in its entirety). For the present application HMW DNA is distributed into 96 or 384 well plates such that there is less than one chromosome per well. Subsequently, whole genome amplification is used to determine which wells contain the chromosome, and then the phase of 96 neighboring SNPs or repetitive sequence polymorphisms to the maternal disease allele are determined for the gene in question. Once this is accomplished, one scores for presence of the disease allele from the father (as described in approach 4 above), and using sequencing, verifies that the chromosome that is inherited from the mother also contains a disease allele. Multiple approaches for capturing repetitive sequences of DNA throughout the genome are described herein, which may be used to identify polymorphisms from original or whole-genome-amplified DNA.

The ability to determine haplotypes from diploid genomes remains a very technically challenging and expensive task that essentially relies on the physical isolation of chromosomes or sub-chromosomal fragments prior to genotyping by sequencing or some other technology. The following describes a rapid and easy procedure for capturing two regions on the same strand of genomic DNA to allow determination of the haplotype structure defined by the two regions.

For each potential target, two oligonucleotides are hybridized simultaneously, each containing sequences complementary to upstream and downstream portions flanking each of two polymorphisms on the target. These polymorphisms may be tetranucleotide, trinucleotide, or dinucleotide repeats, or SNPs. The most informative polymorphisms are ones that are polymorphic in both the maternal chromosomes, as well as polymorphic in the father's chromosome that is transferred to the fetus. Polymerase is used to extend from each of the two 3'-ends to close the gap and determine the genotype of the polymorphisms located between the two pairs of flanking binding sequences. The two targeted polymorphisms need not necessarily be adjacent to each other, and can be separated by other polymorphisms. The distance between the two polymorphism of interest is limited only by the probability of being bridged by the four binding sequences contained in the two oligonucleotides. Each of the oligonucleotides contains unique identifier sequence, optional patient identifier sequence, optional primer binding sequence, and optional phosphate on 5' end.

Detailed Protocol for Determining the Haplotype Between Two Known Polymorphisms:

Variation 8.1 (See e.g., FIG. 113):

8.1.a. Genomic DNA is isolated by a method that yields high (>15 kb) molecular weight material.

8.1.b. Denature target DNA (94° C. 1 minute) in the presence of two oligonucleotides (the first comprising a 5-' sequence complementary to a unique region upstream of target Polymorphism #1, a unique identifier sequence, an optional patient identifier sequence, an optional primer binding sequence, and a 3'-sequence complementary to a unique region downstream of target Polymorphism #2 and the second comprising a 5'-sequence complimentary to a unique region upstream of target Polymorphism #2, a unique identifier sequence, an optional patient identifier sequence and a 3' sequence complementary to a unique region downstream of target Polymorphism #1), and allow the oligonucleotides to hybridize to their complementary regions on the desired fragments by cooling to a desired temperature (e.g. 50° C. for 2 hours). Taq polymerase and/or KlenTaq (Taq polymerase lacking nuclease activity), and thermostable ligase (preferably from strain AK16D), dNTPs are either added subsequent to the annealing step, or at the start of the procedure. In the case where both oligonucleotide sequences have a 5' phosphate, KlenTaq extends the 3' end until it is directly adjacent to the ligation-competent 5' end (left side of FIG. 113). In the case where both oligonucleotide sequences have a 5' OH, the 5'→3' nuclease activity of polymerase cleaves the matching 5'-overlapping base to create a ligation competent 5' phosphate (right side of FIG. 113). Allow for extension and ligation at the hybridization temperature, and optionally raise the temperature (e.g. 60° C.) to assure completion of extension and ligation, to generate circular products.

8.1.c. Add Exonuclease I (digests single-stranded DNA in the 3'→5' direction), and Exonuclease III (digests double-stranded DNA in the 3'→5' direction), to digest all unligated or nicked products, leaving only the desired single-stranded circular DNA comprising of the original target DNA, the linker sequence, the unique identifier sequence, an optional primer binding sequence, and an optional patient identifier sequence. This product is suitable for rolling circle amplification (using random hexamer primers with phi-29 polymerase) to create tandem repeats of the desired sequence, and subsequent identification of the targets using next generation sequencing, or alternatively, direct SMRT sequencing on the covalently closed template, using the primer binding sequence as a primer binding site.

Note 1: This approach also easily allows establishing haplotype (i.e. phase) with the actual disease causing mutation. Primers are designed such that one of the polymorphic site is the actual disease gene.

Note 2: In systems that use two bridging oligonucleotide probes, each containing unique identifier sequence, optional patient identifier sequence and optional primer binding site, it is recommended that only one but not both of the oligonucleotides contain a primer binding site (either the upstream or downstream oligonucleotide. For an additional level of false-positive detection, it is recommended that the unique identifier sequence be different in the upstream and downstream probes.

Note 3: It is important to maximize formation of ligation products where the two oligo binding sequences are actually joined by a contiguous stretch of DNA, and minimize formation of ligation products where the bridged fragments are not contiguous.

Consider the following example for illustrative purposes. Upstream region is designated "X" and has an AGAT tetranucleotide repeat, while downstream region is designated "Y" and has a CA dinucleotide repeat. The upstream region X is illustrated below as "X-up", the upstream primer binding site, AGAT (n), the tetranucleotide repeat region, and "X-dn", the downstream primer binding site. The downstream region Y is illustrated below as "Y-up", the upstream primer binding site, CA (n), the dinucleotide repeat region, and "Y-dn", the downstream primer binding site. In this example, the two regions are 10 kb apart, and the two Maternal chromosomes are of the form:

X-up AGAT(12) X-dn . . . (10 kb) . . . Y-up CA(23) Y-dn
X-up AGAT(16) X-dn . . . (10 kb) . . . Y-up CA(18) Y-dn

Then add Ligation-extension primers that bind to the lower strand (as in FIG. 113).

They will be of the form:
(Left) 5' X-dn-primer site-Identifier #1-Y-up 3'
(Right) 5' Y-dn-identifier #2-X-up 3'
(In this example, the primer binding site is only in the left primer.)

Then the 2 possible ligation products defined by the haplotypes (linearized at the primer binding site so it's easier to follow) would be of the form:
primer site-Identifier #1-Y-up CA(23) Y-dn-identifier #2-X-up AGAT(12) X-dn
primer site-Identifier #1-Y-up CA(18) Y-dn-identifier #2-X-up AGAT(16) X-dn One can maximize formation of the correct products arising from contiguous sites on the same chromosomal fragments by diluting the reaction, such that the probability of products arising from non-contiguous sites becomes infinitesimally small. Further, since the primer is in vast excess of the chromosomal DNA, if two fragments are not contiguous, then there is a far higher probability that each fragment will already have a "Left" and "Right" composite primer-binding to it (i.e. 4 primers binding to two separate fragments). Only when the two fragments are contiguous is there a higher probability the two regions will be bound together by one each of the "Left" and "Right" composite primers. It is a straightforward experiment to optimize yield of correct ligation products by generating a matrix of conditions of different target concentrations vs. different dilutions of ligation-extension primers.

If there are an incorrect ligation products arising from two different chromosomal regions coming together, then it would erroneously create a product where CA(23) is together with AGAT(16), and CA(18) is together with AGAT(12).

As an example, consider a worst case scenario, where 80% of the ligation product arises from bridged fragments that are not contiguous. For simplicity, assume 1,000 genome equivalents. Note, if the product arises from bridged fragments, then there is an equal chance they will come from the same maternal chromosome as from the opposite ones (i.e. 400 each). But those products arising from contiguous DNA will only arise from the same maternal chromosome (i.e. 200 each). Thus, there should be the following combinations:

| | |
|---|---|
| CA(23) and AGAT(12) | 600 (= 400 + 200) |
| CA(23) and AGAT(16) | 400 |
| CA(18) and AGAT(12) | 400 |
| CA(18) and AGAT(16) | 600 (= 400 + 200) |

Even if these numbers fluctuated by 50 in the least favorable direction (equivalent to 90% of the ligation products arising from bridged fragments it would still be straightforward to distinguish the haplotype at each chromosome as CA(23) and AGAT(12); as well as CA(18) and AGAT(16).

| | |
|---|---|
| CA(23) and AGAT(12) | 550 (= 400 − 50 + 200) |
| CA(23) and AGAT(16) | 450 (= 400 + 50) |
| CA(18) and AGAT(12) | 450 (= 400 + 50) |
| CA(18) and AGAT(16) | 550 (= 400 − 50 + 200) |

Alternatively, in a second approach, the disease genes may be divided into the 20 most common inherited diseases, as well as autosomal dominant diseases, and then divided into 17 groups of less commonly mutated sequences covering an average of 200 genes each. Each group of genes would be covered by sets of capture probes, and then depending on the results from the parental sequencing analysis, the maternal blood would be given proper patient identifiers and evaluated on one or more of the 17 specialty probe capture sets.

The first of the above approaches will identify both inherited and sporadic mutations, as well as determine if the fetus inherited a mutation-bearing region from the mother. This approach should also be able to determine the presence of deletions for x-linked inherited diseases, other chromosomal deletions, aberrant methylation in the fetus, diseases arising from triplet repeats, and diseases arising from chromosomal translocations or other rearrangements.

The second approach will identify disease conditions for the genes interrogated. The key issue will be how important is it for the family to get the right answer. It is straightforward to determine if both parents are carriers, and if the mutations are different, relatively straightforward to determine if the father's disease allele is present in the fetus. If it is absent, then the fetus will be either disease free or a carrier. If it is present, then the chances of inheriting the maternal allele and getting the disease are 50%. If haplotype for the maternal allele has been determined, then haplotype markers may be used to verify presence or absence of the inherited maternal allele. It may also be prudent to do an amniocentesis and directly test for the presence of the maternal allele. The current recommendation is to sequence the gene as outlined above, and score for the paternal disease allele. If present, or if the paternal and maternal disease-specific mutations are identical, then the physician recommends amniocentesis.

The methods of the present invention can also be used for non-invasive prenatal diagnosis and preimplantation genetic diagnosis (PGD) of unbalanced chromosomal translocations. Individuals that carry chromosomal translocations are at increased risk for infertility, miscarriage, stillbirth, and/or having a child with birth defects. Preimplantation genetic diagnosis is able to distinguish between embryos that have the correct amount of genetic material (balanced/normal) and embryos that are missing genetic material as a result of the translocation (unbalanced). Many couples in which one member is a translocation carrier have experienced miscarriages or have had to face difficult decisions when learning about a pregnancy with an unbalanced set of chromosomes. The methods of the present invention based PGD would reduce the likelihood of having to deal with these particular circumstances by knowing prior to conception that the embryo(s) transferred have balanced chromosomal translocations.

The approach of scoring chromosome-specific SNPs or repetitive sequence polymorphisms may also be employed in pre-implantation screening. In contrast to pregnancy, where only trisomy 21, 18, and 13 come to term (as well as X and Y chromosome anomalies), with in vitro fertilization, other chromosomal abnormalities may still allow for growth at the 16, 32, or higher cell number stage. Consequently, polymorphisms throughout the genome will be needed to account for both proper copy number and loss or gain of chromosomal regions. The higher the number of polymorphisms being interrogated, the finer copy number changes can be determined.

Prophetic Example 9—Paternity Testing of the Fetus (e.g. Prenatal Care Support)

Overview: The basic approach is to look for presence of alleles present in the father, but absent in the mother. There are two general ways to approach this. One can start with SNPs where the common allele has a frequency around 70-75%, so that there is about a 50% chance the mother is homozygous for the major allele. One starts with about 48 SNPs of which about half of them (24) the mother will be homozygous for the common allele, and there is a 50% chance the father will be either heterozygous or homozygous for the minority allele. One simply scores for the presence of the minority allele in the maternal blood, similar to looking for mutations, but one also quantifies the amount present just to confirm it's a minority allele from the father. A second approach is to start with alleles with frequency around 50%, then there is a 50% chance the mother is homozygous for one of the alleles, and then there is a 75% chance the father will have the other allele at that position. It is a little less informative in differentiating the fathers, but more positions will be informative. An third approach is to use repetitive sequence polymorphisms, where there is a high degree of polymorphism, such that the father's allele has a high probability of being different from either of the mother's allele at a given position. This would require the least amount of alleles. Under all these conditions, care must be taken by the physician to respect the mother's privacy in case the husband is not the father of the fetus (non-paternity).

TABLE 1

Oligonucleotide Sequences of the Disclosure

| Name | Description | Sequence | SEQ ID NO |
|---|---|---|---|
| iLx-003-PEsqP1 | PE sequencing primer 1 | ACACTCTTTCCCTACACGACGCTCTTCCGATCT | 1 |
| iLx-004-BrCdR1 | Indexing primer | GATCGGAAGAGCACACGTCTGAACTCCAGTCAC | 2 |
| iLx-001-P5-BrCdR2 | Indexing primer | AATGATACGGCGACCACCGAGATCTACAC | 3 |
| iLx-005-PEsqP2 | PE sequencing primer 2 | GTGACTGGAGTTCAGACGTGTGCTCTTCCGATCT | 4 |
| iSx-001-bkA30 | Universal dA30 primer | /5SpC3/AAAAAAAAAAAAAAAAAAAAAAAAAAAAAA | 5 |
| iSx-003-ShAdT | Short linker T Overhang | TGC*T*CTTCCGATCT | 6 |
| iSx-004-pShAdB | Bottom linker T overhang | /5Phos/GATCGGAAGA*G*C | 7 |
| iSx-005-ShAdB | Short linker blunt end | AGATCGGAAGAGC | 8 |
| iSx-006-MdAdT | Medium linker T overhang | TCG*A*CGCTCTTCCGATCT | 9 |
| iSx-007-pMdAdB | Medium linker T overhang | /5Phos/GATCGGAAGAGCAC*A*C | 10 |
| iSx-015-pKRSF10 | KRAS forward primer | /5Phos/AGGCAAGAGTGCCTTGACGATACAGCTAA | 11 |
| iSx-016-bkA30-KRSF11 | KRAS forward primer for isothermal replication | /5SpC3/AAAAAAAAAAAAAAAAAAAAAAAAAAAAAAAGGCAAGAGTGCCTTGACGATACAGCTAA | 12 |
| iSx-017-pKRSF12 | KRAS bridge primer 1 | /5Phos/AGGCAAGAGTGCCTTGACGATACAGCTAATTCAGAATCATTTTGTGGACGAGATCGGAAGAGCACACGTCTGAACTCCAGTCAC | 13 |
| iSx-008-701F | D701 primer | /5Phos/GAGCACACGTCTGAACTCCAGTCACCGAGTAATATCTCGTAUGCCGTCTUCTGCTTGACACACUCGCAATGAUACGG | 14 |
| iSx-009-501R | D501 primer | /5Phos/GAGCGTCGTGTAGGGAAAGAGTGTAGGCTATAGTGTAGATCUCGGTGGTCGCCGUATCATTGCGAGUGTGTCAAGCAG | 15 |
| iSx-018-pKRSF13 | KRAS bridge primer 2 | /5Phos/ACACTCTTTCCCTACACGACGCTCTTCCGATCTTTATTATAAGGCCTGCTGAAAATGACTGAATATAAACTTGTGGTAGTTGG | 16 |
| iSx-018-pKRSR14 | KRAS reverse primer | /5Phos/CCAACTACCACAAGUTTATATUCAGTCATTTTCAGCA | 17 |
| iSx-019-bkA30-KRSR15 | KRAS reverse primer for isothermal replication | /5SpC3/AAAAAAAAAAAAAAAAAAAAAAAAAAAAAACCAACTACCACAAGUTTATATUCAGTCATTTTCAGCA | 18 |
| iSx-022-pBRF-F10 | BRAF forward primer | /5Phos/CTCGATGGAGUGGGTCCCAUCAGTTTGAAC | 19 |
| iSx-023-bkA30-BRF-F11 | BRAF forward primer for isothermal replication | /5SpC3/AAAAAAAAAAAAAAAAAAAAAAAAAAAAAACTCGATGGAGUGGGTCCCAUCAGTTTGAAC | 20 |
| iSx-024-pBRF-F12 | BRAF bridge primer 1 | /5Phos/CTCGATGGAGTGGGTCCCATCAGTTTGAACAGTTGTCTGGATCCATTTTGAGATCGGAAGAGCACACGTCTGAACTCCAGTCAC | 21 |

TABLE 1-continued

Oligonucleotide Sequences of the Disclosure

| Name | Description | Sequence | SEQ ID NO |
|---|---|---|---|
| iSx-025-pBRF-F13 | BRAF bridge primer 2 | /5Phos/ACACTCTTTCCCTACACGACGCTCTTCCGATCTT TTCTTCATGAAGACCTCACAGTAAAAATAGGTGATTT TGGTCTAGCTAC | 22 |
| iSx-026-pBRF-R14 | BRAF reverse primer | /5Phos/GTAGCTAGACCAAAAUCACCTATTTTUACTGTG AGGTCTTC | 23 |
| iSx-027-bkA30-pBRF-R15 | BRAF reverse primer for isothermal replication | /5SpC3/AAAAAAAAAAAAAAAAAAAAAAAAAAAAAA GTAGCTAGACCAAAAUCACCTATTTTUACTGTGAGGT CTTC | 24 |
| iSx-034-pTP53e5F10 | TP53 Exon 5.1 forward primer | /5Phos/GTGCAGCTGUGGGTTGAUTCCACAC | 25 |
| iSx-035-bkA30-pTP53e5F11 | TP53 Exon 5.1 forward primer for isothermal replication | /5SpC3/AAAAAAAAAAAAAAAAAAAAAAAAAAAAAA GTGCAGCTGUGGGTTGAUTCCACAC | 26 |
| iSx-036-pTP53e5F12 | TP53 Exon 5.1 bridge primer 1 | /5Phos/GTGCAGCTGTGGGTTGATTCCACACCCCCGCCC GGCACCCGCGTCCGCGAGATCGGAAGAGCACACGTCT GAACTCCAGTCAC | 27 |
| iSx-037-pTP53e5F13 | TP53 Exon 5.1 bridge primer 2 | /5Phos/ACACTCTTTCCCTACACGACGCTCTTCCGATCTT CCTACAGTACTCCCCTGCCCTCAACAAGATGTTTTGCC AACTGGCCAAG | 28 |
| iSx-038-pTP53e5R14 | TP53 Exon 5.1 reverse primer | /5Phos/C1TGGCCAGTGGCAAAACAUCTTGTTGA | 29 |
| iSx-039-bkA30-TP53e5R15 | TP53 Exon 5.1 reverse primer for isothermal replication | /5SpC3/AAAAAAAAAAAAAAAAAAAAAAAAAAAAAA CTTGGCCAGTUGGCAAAACAUCTTGTTGA | 30 |
| iSx-042-pTP53e5F20 | TP53 Exon 5.2 forward primer | /5Phos/GAGCGCTGCUCAGAUAGCGATGGTGA | 31 |
| iSx-043-bkA30-TP53e5F21 | TP53 Exon 5.2 forward primer for isothermal replication | /5SpC3/AAAAAAAAAAAAAAAAAAAAAAAAAAAAAA GAGCGCTGCUCAGAUAGCGATGGTGA | 32 |
| iSx-044-pTP53e5F22 | TP53 Exon 5.2 bridge primer 1 | /5Phos/GAGCGCTGCTCAGATAGCGATGGTGAGCAGCT GGAGCTGGAGAGACGACAAGATCGGAAGAGCACACG TCTGAACTCCAGTCAC | 33 |
| iSx-045-pTP53e5F23 | TP53 Exon 5.2 bridge primer 2 | /5Phos/ACACTCTTTCCCTACACGACGCTCTTCCGATCTT CCGCGCCATGGCCATCTACAAGCAGTCACAGCACATG ACGGAGGTTGTG | 34 |
| iSx-046-pTP53e5R24 | TP53 Exon 5.2 reverse primer | /5Phos/CACAACCTCCGUCATGTGCUGTGACTG | 35 |
| iSx-047-bkA30-TP53e5R25 | TP53 Exon 5.2 reverse primer for isothermal replication | /5SpC3/AAAAAAAAAAAAAAAAAAAAAAAAAAAAAA CACAACCTCCGUCATGTGCUGTGACTG | 36 |
| iSx-052-pTP53e6F30 | TP53 Exon 6 forward primer | /5Phos/GAAACACTTUCGACATAGTGUGGTGGTGCC | 37 |
| iSx-053-bkA30-TP53e6F31 | TP53 Exon 6 forward primer for isothermal replication | /5SpC3/AAAAAAAAAAAAAAAAAAAAAAAAAAAAAA GAAACACTTUCGACATAGTGUGGTGGTGCC | 38 |
| iSx-054-pTP53e6F32 | TP53 Exon 6 bridge primer 1 | /5Phos/GAAACACTTTTCGACATAGTGTGGTGGTGCCCT ATGAGCCGCCTGAGGTCAGATCGGAAGAGCACACGT CTGAACTCCAGTCAC | 39 |

TABLE 1-continued

Oligonucleotide Sequences of the Disclosure

| Name | Description | Sequence | SEQ ID NO |
|---|---|---|---|
| iSx-055-pTP53e6F33 | TP53 Exon 6 bridge primer | /5Phos/ACACTCTTTCCCTACACGACGCTCTTCCGATCT GGCCCCTCCTCAGCATCTTATCCGAGTGGAAGGAAAT TTGCGTGTGGAGT | 40 |
| iSx-056-pTP53e6R34 | TP53 Exon 6 reverse primer | /5Phos/ACTCCACACGCAAAUTTCCUTCCACTC | 41 |
| iSx-057-bkA30-TP53e6R35 | TP53 Exon 6 reverse primer for isothermal replication | /5SpC3/AAAAAAAAAAAAAAAAAAAAAAAAAAAAAA ACTCCACACGCAAAUTTCCUTCCACTC | 42 |
| iSx-062-pTP53e7F40 | TP53 Exon 7 forward primer | /5Phos/CCTCACCATCAUCACACUGGAAGACTCC | 43 |
| iSx-063-bkA30-TP53e7F41 | TP53 Exon 7 forward primer for isothermal replication | /5SpC3/AAAAAAAAAAAAAAAAAAAAAAAAAAAAAA CCTCACCATCAUCACACUGGAAGACTCC | 44 |
| iSx-064-pTP53e7F42 | TP53 Exon 7 bridge primer 1 | /5Phos/CCTCACCATCATCACACTGGAAGACTCCAGGTC AGGAGCCACTTGCCACCAGATCGGAAGAGCACACGT CTGAACTCCAGTCAC | 45 |
| iSx-065-pTP53e7F43 | TP53 Exon 7 bridge primer 2 | /5Phos/ACACTCTTTCCCTACACGACGCTCTTCCGATCT GCTCTGACTGTACCACCATCCACTACAACTACATGTG TAACAGTTCCTGC | 46 |
| iSx-066-pTP53e7R44 | TP53 Exon 7 reverse primer | /5Phos/GCAGGAACTGTUACACATGUAGTTGTAGTGGA TG | 47 |
| iSx-067-pTP53e7R45 | TP53 Exon 7 reverse primer for isothermal replication | /5SpC3/AAAAAAAAAAAAAAAAAAAAAAAAAAAAAA GCAGGAACTGTUACACATGUAGTTGTAGTGGATG | 48 |
| iSx-072-pTP53e8F50 | TP53 Exon 8 forward primer | /5Phos/GGGAGAGACCGGCGUACAGAGGAA | 49 |
| iSx-073-bkA30-TP53e8F51 | TP53 Exon 8 forward primer for isothermal replication | /5SpC3/AAAAAAAAAAAAAAAAAAAAAAAAAAAAAA GGGAGAGACCGGCGUACAGAGGAA | 50 |
| iSx-074-pTP53e8F52 | TP53 Exon 8 bridge primer 1 | /5Phos/GGGAGAGACCGGCGUACAGAGGAAGAGAATC TCCGCAAGAAAGGAGAGCCAGATCGGAAGAGCACAC GTCTGAACTCCAGTCAC | 51 |
| iSx-075-pTP53e8F53 | TP53 Exon 8 bridge primer 2 | /5Phos/ACACTCTTTCCCTACACGACGCTCTTCCGATCT CTCTTTTCCTATCCTGAGTAGTGGTAATCTACTGGGAC GGAACAGCTTTG | 52 |
| iSx-076-pTP53e8R54 | TP53 Exon 8 reverse primer | /5Phos/CAAAGCUG1TCCGUCCCAGTAGATTACC | 53 |
| iSx-077-bkA30-TP53e8R55 | TP53 Exon 8 reverse primer for isothermal replication | /5SpC3/AAAAAAAAAAAAAAAAAAAAAAAAAAAAAA CAAAGCUGTTCCGUCCCAGTAGATTACC | 54 |
| iSx-102-pKRSF20 | KRAS forward primer | /5Phos/GTAGGCAAGAGUGCTTUGACGATAC | 55 |
| iSx-103-bkA30-KRSF21 | KRAS forward primer for isothermal replication | /5SpC3/AAAAAAAAAAAAAAAAAAAAAAAAAAAAAA GTAGGCAAGAGUGCTTUGACGATAC | 56 |
| iSx-104-pKRSF22 | KRAS bridge primer 1 | /5Phos/GTAGGCAAGAGTGCTTTGACGATACAGCTGATT CAGAATCATTTCGTGGACGAATATGACCCAACAATAG AGGTAGATCTNNNNNAGATCGGAAGAGCACACGTCT GAACTCCAGTCAC | 57 |

TABLE 1-continued

Oligonucleotide Sequences of the Disclosure

| Name | Description | Sequence | SEQ ID NO |
|---|---|---|---|
| iSx-100-705F | D705 primer | /5Phos/GAGCACACGTCTGAACTCCAGTCACTTCTGAAT ATCTCGTAUGCCGTCTUCTGCTTGACACACUCGCAAT GAUACGG | 58 |
| iSx-101-502R | D502 primer | /5Phos/GAGCGTCGTGTAGGGAAAGAGTGTGCCTCTAT GTGTAGATCUCGGTGGTCGCCGUATCATTGCGAGUGT GTCAAGCAG | 59 |
| iSx-105-pKRSF23 | KRAS bridge primer 2 | /5Phos/ACACTCTTTCCCTACACGACGCTCTTCCGATCT NNNNNCTAATATGGTCACATTTTCATTGTTTTTATTAT AAGGTCTGCTGAAAATGACCGAATATAAACTTGTAGT AGTTGGAGCT | 60 |
| iSx-106-pKRSR24 | KRAS reverse primer | /5Phos/AGCTCCAACUACUACAAGUTUATATTCGGTC | 61 |
| iSx-107-bkA30-KRSR25 | KRAS reverse primer for isothermal replication | /5SpC3/AAAAAAAAAAAAAAAAAAAAAAAAAAAAAA AGCTCCAACUACUACAAGUTUATATTCGGTC | 62 |
| iSx-112-pBRF-F20 | BRAF forward primer | /5Phos/AAAUCTCGAUGGAGCGGGTCC | 63 |
| iSx-113-bkA30-BRF-F21 | BRAF forward primer for isothermal replication | /5SpC3/AAAAAAAAAAAAAAAAAAAAAAAAAAAAAA AAAUCTCGAUGGAGCGGGTCC | 64 |
| iSx-114-pBRF-F22 | BRAF bridge primer 1 | /5Phos/AAATCTCGATGGAGCGGGTCCCATCAGTTCGA ACAGTTGTCTGGGTCCATTTTGTGGATAGTAAGAATT GAGGCTGTTTTNNNNNAGATCGGAAGAGCACACGTCT GAACTCCAGTCAC | 65 |
| iSx-115-pBRF-F23 | BRAF bridge primer 2 | /5Phos/ACACTCTTTCCCTACACGACGCTCTTCCGATCT NNNNNTTTCCTTCACTTACTACACCTCGGATATATTTC TTCACGAAGACCTCACAGTGAAAATAGGTGATTTCGG TCTAGCTACA | 66 |
| iSx-116-pBRF-R24 | BRAF reverse primer | /5Phos/TGTAGCUAGACCGAAAUCACCTATTTTCAC | 67 |
| iSx-117-bkA30-BRF-R25 | BRAF reverse primer for isothermal replication | /5SpC3/AAAAAAAAAAAAAAAAAAAAAAAAAAAAAAT GTAGCUAGACCGAAAUCACCTATTTTCAC | 68 |
| iSx-122-pTP53e5F60 | TP53 Exon 5 forward primer | /5Phos/AGGCGCUGCCCCCAUCAT | 69 |
| iSx-123-bkA30-TP53e5F61 | TP53 Exon 5 forward primer for isothermal replication | /5SpC3/AAAAAAAAAAAAAAAAAAAAAAAAAAAAAA AGGCGCUGCCCCCAUCAT | 70 |
| iSx-124-pTP53e5F62 | TP53 Exon 5 bridge primer 1 | /5Phos/AGGCGCTGCCCCCATCATGAGCGCTGCTCGGAT AGCGATGGTGAACAGCTGGAGCTGGAAAGACGACAG GGCTGGCTGCCNNNNNAGATCGGAAGAGCACACGTC TGAACTCCAGTCAC | 71 |
| iSx-125-pTP53e5F63 | TP53 Exon 5 bridge primer 2 | /5Phos/ACACTCTTTCCCTACACGACGCTCTTCCGATCT NNNNNTGTGGGTCGATTCCACACCCCCACCCGGCACC CGCGTTCGCGCCATGGCCATTTACAAGCAGTCACAAC ACATGACGGAG | 72 |
| iSx-126-pTP53e5R64 | TP53 Exon 5 reverse primer | /5Phos/CTCCGTCATGUGTTGTGACUGCTTGTAAA | 73 |
| iSx-127-bkA30-TP53e5F65 | TP53 Exon 5 reverse primer for isothermal replication | /5SpC3/AAAAAAAAAAAAAAAAAAAAAAAAAAAAAA CTCCGTCATGUGTTGTGACUGCTTGTAAA | 74 |

TABLE 1-continued

Oligonucleotide Sequences of the Disclosure

| Name | Description | Sequence | SEQ ID NO |
|---|---|---|---|
| iSx-132-pTP53e6F70 | TP53 Exon 6 forward primer | /5Phos/AACACTTUTCGACACAGUGTGGTGGT | 75 |
| iSx-133-bkA30-TP53e6F71 | TP53 Exon 6 forward primer for isothermal replication | /5SpC3/AAAAAAAAAAAAAAAAAAAAAAAAAAAAAA AACACTTUTCGACACAGUGTGGTGGT | 76 |
| iSx-134-pTP53e6F72 | TP53 Exon 6 bridge primer 1 | /5Phos/AACACTTTTCGACACAGTGTGGTGGTGCCTTAT GAGCCGCCTGAAGTCTGGTTTGCAACCGGAGTCTCTG GGAGGAAGGGNNNNNAGATCGGAAGAGCACACGTCT GAACTCCAGTCAC | 77 |
| iSx-135-pTP53e6F73 | TP53 Exon 6 bridge primer 2 | /5Phos/ACACTCTTTCCCTACACGACGCTCTTCCGATCT NNNNNCTCACTGACTGCTCTTAGGTCTAGCCCCTCCTC AGCACCTTATCCGAGTGGAGGGAAATTTGCGTGTAGA GTATTTGGAT | 78 |
| iSx-136-pTP53e6R74 | TP53 Exon 6 reverse primer | /5Phos/ATCCAAATACUCTACACGCAAAUTTCCCTCC | 79 |
| iSx-137-bkA30-TP53e6F75 | TP53 Exon 6 reverse primer for isothermal replication | /5SpC3/AAAAAAAAAAAAAAAAAAAAAAAAAAAAAA ATCCAAATACUCTACACGCAAAUTTCCCTCC | 80 |
| iSx-142-pTP53e7F80 | TP53 Exon 7 forward primer | /5Phos/GGCGGCAUGAACCGAAGACCC | 81 |
| iSx-143-bkA30-TP53e7F81 | TP53 Exon 7 forward primer for isothermal replication | /5SpC3/AAAAAAAAAAAAAAAAAAAAAAAAAAAAAA GGCGGCAUGAACCGAAGACCC | 82 |
| iSx-144-pTP53e7F82 | TP53 Exon 7 bridge primer 1 | /5Phos/GGCGGCATGAACCGAAGGCCCATCCTCACTAT CATCACACTGGAGGACTCCAGGTCAGGAACCACTTGC CACCCTGTACANNNNNAGATCGGAAGAGCACACGTC TGAACTCCAGTCAC | 83 |
| iSx-145-pTP53e7F83 | TP53 Exon 7 bridge primer 2 | /5Phos/ACACTCTTTCCCTACACGACGCTCTTCCGATCT NNNNNTGGCCTCACCTTGGGCCTGTGTCATCTCCTAG GTTGGTTCTGACTGTACCACTATCCACTACAACTATAT GTGTAACAGT | 84 |
| iSx-146-pTP53e7R84 | TP53 Exon 7 reverse primer | /5Phos/ACTGTTACACAUATAGTTGTAGUGGATAGTGGT AC | 85 |
| iSx-147-bkA30-TP53e7R85 | TP53 Exon 7 reverse primer for isothermal replication | /5SpC3/AAAAAAAAAAAAAAAAAAAAAAAAAAAAAA ACTGTTACACAUATAGTTGTAGUGGATAGTGGTAC | 86 |
| iSx-152-pTP53e8F90 | TP53 Exon 8 forward primer | /5Phos/AGAGACCGUCGCACGGAGGAA | 87 |
| iSx-153-bkA30-TP53e8F91 | TP53 Exon 8 forward primer for isothermal replication | /5SpC3/AAAAAAAAAAAAAAAAAAAAAAAAAAAAAA AGAGACCGUCGCACGGAGGAA | 88 |
| iSx-154-pTP53e8F92 | TP53 Exon 8 bridge primer 1 | /5Phos/AGAGACCGUCGCACGGAGGAAGAGAATCTTCG CAAGAAAGGAGAACCTCACCACGAGCTACCCCCAGG GAGCACCAAGCGNNNNNAGATCGGAAGAGCACACGT CTGAACTCCAGTCAC | 89 |
| iSx-155-pTP53e8F93 | TP53 Exon 8 bridge primer 2 | /5Phos/ACACTCTTTCCCTACACGACGCTCTTCCGATCT NNNNNTTACTGCTTCTTGCTTCTCTTCTCCTATCCTGA GTAATGGTAATCTACTGGAACGGAACAGCTTTGAAGT GCGTGTTTGT | 90 |
| iSx-156-pTP53e8R94 | TP53 Exon 8 reverse primer | /5Phos/ACAAACACGCACUTCAAAGCUGTTCC | 91 |

TABLE 1-continued

Oligonucleotide Sequences of the Disclosure

| Name | Description | Sequence | SEQ ID NO |
|---|---|---|---|
| iSx-157-bkA30-TP53e8R95 | TP53 Exon 8 reverse primer for isothermal replication | /5SpC3/AAAAAAAAAAAAAAAAAAAAAAAAAAAAAA ACAAACACGCACUTCAAAGCUGTTCC | 92 |
| iSx-108-KRS-rcF26 | KRAS top primer | AAGGCCTGCTGAAAATG/idSp/CTGAATATAAACrUTGT A/3SpC3/ | 93 |
| iSx-109-KRS-rcR27 | KRAS bottom primer | CGTCCACAAAATGATTC/idSp/GAATTAGCTGTATCrGT CAG/3SpC3/ | 94 |
| iSx-118-BRF-rcF26 | BRAF top primer | TCAGATATATTTCTTCATGA/idSp/GACCTCACAGTAAA rAATAA/3SpC3/ | 95 |
| iSx-119-BRF-rcR27 | BRAF bottom primer | ACAAAATGGATCCAG/idSp/CAACTGTTCAAACrTGATA /3SpC3/ | 96 |
| iSx-128-TP53e5-rcF66 | TP53 Exon 5.2 top primer | CGCCATGGCCATC/idSp/ACAAGCAGTCACrAGCAT/ 3SpC3/ | 97 |
| iSx-129-TP53e5-rcR67 | TP53 Exon 5.2 bottom primer | GCTGCTCACCATC/idSp/CTATCTGAGCArGCGCA/ 3SpC3/ | 98 |
| iSx-130-TP53e5-rcF68 | TP53 Exon 5.1 top primer | CTTCCTACAGTACTCC/idSp/CTGCCCTCAACrAAGAC/ 3SpC3/ | 99 |
| iSx-131-TP53e5-rcR69 | TP53 Exon 5.1 bottom primer | GGCGGAGGTGTG/idSp/AATCAACCCACArGCTGT/ 3SpC3/ | 100 |
| iSx-138-TP53e6-rcF76 | TP53 Exon 6 top primer | CCTCAGCATCTTATC/idSp/GAGTGGAAGGAAArTTTGT/ 3SpC3/ | 101 |
| iSx-139-TP53e6-rcR77 | TP53 Exon 6 bottom primer | CGGCTCATAGGG/idSp/ACCACCArCACTG/3SpC3/ | 102 |
| iSx-148-TP53e7-rcF86 | TP53 Exon 7 top primer | CTCTGACTGTACCACCA/idSp/CCACTACAACTACrATG TA/3SpC3/ | 103 |
| iSx-149-TP53e7-rcR87 | TP53 Exon 7 bottom primer | CTGACCTGGAGTCTT/idSp/CAGTGTGATGArTGGTA/ 3SpC3/ | 104 |
| iSx-158-TP53e8-rcF96 | TP53 Exon 8 top primer | TGAGTAGTGGTAATCTACT/idSp/GGACGGAACrAGCTC /3SpC3/ | 105 |
| iSx-159-TP53e8-rcR97 | TP53 Exon 8 bottom primer | GCTCCCCTTTCTTG/idSp/GGAGATTCTCTTCrCTCTA/ 3SpC3/ | 106 |
| iSx-013-KRS-bcF 1 | KRAS top strand capture oligo | /52-Bio/ TTTTTTTTTTGCTGGTGGCGTAGGCAAGAGTGCCTTGA CGATACAGCTAATTCAGAATCATTTTGTGGAC | 107 |
| iSx-014-KRS-bcR2 | KRAS bottom strand capture oligo | /52-Bio/ TTTTTTTTTTACGCCACCAGCTCCAACTACCACAAGTT TATATTCAGTCATTTTCAGCAGGCCTTATAAT | 108 |
| iSx-020-BRF-bcF1 | BRAF top strand capture oligo | /52-Bio/ TTTTTTTTTTGCTACAGTGAAATCTCGATGGAGTGGGT CCCATCAGTTTGAACAGTTGTCTGGATCCATT | 109 |
| iSx-021-BRF-bcR2 | BRAF bottom strand capture oligo | /52-Bio/ TTTTTTTTTTGATTTCACTGTAGCTAGACCAAAATCAC CTATTTTTACTGTGAGGTCTTCATGAAGAAAT | 110 |
| iSx-030-TP53e5-bcF1 | TP53 Exon 5.1 top strand capture oligo | /52-Bio/ TTTTTTTTTTAAGACCTGCCCTGTGCAGCTGTGGGTTG ATTCCACACCCCCGCCCGGCACCCGCGTCCGC | 111 |
| iSx-031-TP53e5-bcR2 | TP53 Exon 5.1 bottom strand capture oligo | /52-Bio/ TTTTTTTTTTCACAGGGCAGGTCTTGGCCAGTTGGCAA AACATCTTGTTGAGGGCAGGAGAGTACTGTAG | 112 |
| iSx-032-TP53e5-bcF3 | TP53 Exon 5.2 top strand capture oligo | /52-Bio/ TTTTTTTTTTAGGCGCTGCCCCCACCATGAGCGCTGCT CAGATAGCGATGGTGAGCAGCTGGAGCTGGAG | 113 |

TABLE 1-continued

Oligonucleotide Sequences of the Disclosure

| Name | Description | Sequence | SEQ ID NO |
|---|---|---|---|
| iSx-033-TP53e5-bcR4 | TP53 Exon 5.2 bottom strand capture oligo | /52-Bio/TTTTTTTTTTGGGCAGCGCCTCACAACCTCCGTCATGTGCTGTGACTGCTTGTAGATGGCCATGGCGCGG | 114 |
| iSx-050-TP53e6-bcF5 | TP53 Exon 6 top strand capture oligo | /52-Bio/TTTTTTTTTTTGGATGACAGAAACACTTTTCGACATAGTGTGGTGGTGCCCTATGAGCCGCCTGAGGTC | 115 |
| iSx-051-TP53e6-bcR6 | TP53 Exon 6 bottom strand capture oligo | /52-Bio/TTTTTTTTTTGTCATCCAAATACTCCACACGCAAATTTCCTTCCACTCGGATAAGATGCTGAGGAGGAGC | 116 |
| iSx-060-TP53e7-bcF7 | TP53 Exon 7 top strand capture oligo | /52-Bio/TTTTTTTTTTGGCGGCATGAACCGGAGGCCCATCCTCACCATCATCACACTGGAAGACTCCAGGTCAGGA | 117 |
| iSx-061-TP53e7-bcR8 | TP53 Exon 7 bottom strand capture oligo | /52-Bio/TTTTTTTTTTCATGCCGCCCATGCAGGAACTGTTACACATGTAGTTGTAGTGGATGGTGGTACAGTCAGA | 118 |
| iSx-070-TP53e8-bcF9 | TP53 Exon 8 top strand capture oligo | /52-Bio/TTTTTTTTTTTGTCCTGGGAGAGACCGACGCACAGAGGAAGAGAATCTCCGCAAGAAAGGAGAGCCTCAC | 119 |
| iSx-071-TP53e8-bcR10 | TP53 Exon 8 bottom strand capture oligo | /52-Bio/TTTTTTTTTTCCCAGGACATGCACAAACACGCACCTCAAAGCTGTTCCGTCCCAGTAGATTACCACTACT | 120 |
| iSx-201-MdAdT | Blunt end linker | GTGACUGGAGTUCAGACGTGUG*C*TCTTCCGATCTNNNNNGCC | 121 |
| iSx-202-MdLgAdB-bk | Blunt end linker | GGC/i5NitInd//i5NitInd//i5NitInd//i5NitInd//i5NitInd/AGAUCGGAAGAGC/3SpC3/ | 122 |
| iSx-203-Lk-F1 | Linker bridge forward primer | /5Phos/AGAUCGGAAGAGCGUCGTGTAGGGAAA | 123 |
| iSx-204-bkA30-Lk-F2 | Linker bridge forward primer for isothermal replication | /5SpC3/AAAAAAAAAAAAAAAAAAAAAAAAAAAAAAAGAUCGGAAGAGCGUCGTGTAGGGAAA | 124 |
| iSx-205-r503-F3 | Linker D503 bridge primer 1 | /5Phos/AGAUCGGAAGAGCGUCGTGTAGGGAAAGAGUGTAGGATAGGGTGTAGAUCTCGGTGGTCGCCGUATCATTGCGAGTGTGUCAAGCAGAAGAC | 125 |
| iSx-206-d701-R4 | Linker D701 bridge reverse primer 2 | /5Phos/AAAAGGAAGAGCACACGUCTGAACTCCAGUCACCGAGTAATATCTCGUATGCCGTCTTCTGCTUGACACACTCGCAATGAT | 126 |
| iSx-207-Lk-R5 | Linker bridge reverse primer | /5Phos/AAAAGGAAGAGCACACGUCTGAACTC | 127 |
| iSx-208-bkA30-Lk-R6 | Linker bridge reverse primer for isothermal replication | /5SpC3/AAAAAAAAAAAAAAAAAAAAAAAAAAAAAAGGAAGAGCACACGUCTGAACTC | 128 |
| iSx-211-r702-LgAdT | Long D702 blunt end Linker | GCGAGTGTGUCAAGCAGAAGACGGCAUACGAGATUCCGGAGAGTGACUGGAGTUCAGACGTGUG*C*TCTTCCGATCTNNNNNGCC | 129 |
| iSx-212-r503-R4 | Linker D503 reverse bridge primer | AGATCGGAAGAGCGTCGUGTAGGGAAAGAGTGUAGGATAGGGTGTAGATCUCGGTGGTCGCCGUATCATTGCGAGTGTGUCAAGCAGAAGACGGCUTTTT | 130 |
| iSx-220-d503-AdT1 | D503 thiophosphate Linker | AA*T*GATACGGCGACCACCGAGATCTACACCCTATCCTACACTCTTTCCCTACACGACGCTCTTCCGATCT | 131 |
| iSx-221-pd707-AdB2 | D707 Linker | /5Phos/GATCGGAAGAGCACACGTCTGAACTCCAGTCACAGCTTCAGATCTCGTATGCCGTCTTCTGCTTG | 132 |

TABLE 1-continued

Oligonucleotide Sequences of the Disclosure

| Name | Description | Sequence | SEQ ID NO |
|---|---|---|---|
| iSx-222-Lk-uRC1 | Universal reverse linker bridge | TGTAGATCUCGGTGGTCGCCGUATCATTGCGAGTGTG UCAAGCAGAAGACGGCAUACGAGATTTTTT | 133 |
| iSx-223-d504-AdT3 | D504 thiophosphate Linker | AA*T*GATACGGCGACCACCGAGATCTACACGGCTCT GAACACTCTTTCCCTACACGACGCTCTTCCGATCT | 134 |
| iSx-224-pSmAdT4 | Small 5'-phos Linker | /5Phos/CCTCCGACCGT | 135 |
| iSx-225-pd708-N6AdB5 | D708 modified Linker | /5Phos/CGGTCGGAGGNNNNNNAGATCGGAAGAGCAC ACGTCTGAACTCCAGTCACGCGCATTAATCTCGTATG CCGTCTTCTGCTTG | 136 |
| iSx-226-d505-AdT6 | D505 thiophosphate Linker | AA*T*GATACGGCGACCACCGAGATCTACACAGGCGA AGACACTCTTTCCCTACACGACGCTCTTCCGATCT | 137 |
| iSx-227-SmAdT7p | Small 3'-Phos primer | CTCCGACCG/3Phos/ | 138 |
| iSx-228-d506-AdT83+G | D506-2rG-LNA Linker | AA*T*GATACGGCGACCACCGAGATCTACACTAATCTT AACACTCTTTCCCTACACGACGCTCTTCCGATCTNNNN NNrGrG+G | 139 |
| iSx-229-pd709-AdB6 | D709 Linker | /5Phos/GATCGGAAGAGCACACGTCTGAACTCCAGTCA CCATAGCCGATCTCGTATGCCGTCTTCTGCTTG | 140 |
| iSx-232-KRS-T32 | KRAS top circle primer | CG*A*TACAGCTAATTCAGAAUCATTTTGTGGACGAAT TTTUAGGTCGCCGUATCATTGCGAGTGTGUCAAGCAG AAGACGUTTTTTGCTGGTGGCGUAGGCAAGAGTG | 141 |
| iSx-233-KRS-B33 | KRAS bottom circle primer | TT*A*TATTCAGTCATTTTCAGCAGGCCUTATAATAAA AATAATGATTTTTAGGTCGCCGUATCATTGCGAGTGT GUCAAGCAGAAGACGUTTTTTACGCCACCAGCUCCAA CTACC | 142 |
| iSx-234-BRF-T34 | BRAF top circle primer | GT*T*TGAACAGTTGUCTGGAUCCATTTTGTGGTTTTU AGGTCGCCGUATCATTGCGAGTGTGUCAAGCAGAAG ACGUTTTTTGCTACAGTGAAAUCTCGAUGGAGTGGGT C | 143 |
| iSx-235-BRF-B35 | BRAF bottom circle primer | GT*C*TTCATGAAGAAAUATATCTGAGGTGUAGTAAG TAAAGGATTTTUAGGTCGCCGUATCATTGCGAGTGTG UCAAGCAGAAGACGUTTTTTGATTTCACTGTAGCUAG ACCAAAATCACCTATTTTTAC | 144 |
| iSx-241-TP53e5-T41 | TP53 Exon 5.1 top circle primer | TG*A*TTCCACACCUCCGCCCTTTTUAGGTCGCCGUAT CATTGCGAGTGTGUCAAGCAGAAGACGUTTTTTAAGA CCUGCCCUGTGCAGCTGTG | 145 |
| iSx-242-TP53e5-B42 | TP53 Exon 5.1 bottom circle primer | CA*T*CTTGTTGAGGGUAGGAGAGTACTGTAGTTTTUA GGTCGCCGUATCATTGCGAGTGTGUCAAGCAGAAGA CGUTTTTTCACAGGGUAGGTCTTGGCCAGTTG | 146 |
| iSx-243-TP53e5-T43 | TP53 Exon 5.2 top circle primer | GC*T*CAGATAGCGATGGUGAGCAGCTGTTTTUAGGT CGCCGUATCATTGCGAGTGTGUCAAGCAGAAGACGU TTTTTAGGCGCUGCCCCCACCATG | 147 |
| iSx-244-TP53e5-B44 | TP53 Exon 5.2 bottom circle primer | GT*G*CTGTGACTGCTTGTAGAUGGCCATTTTUAGGTC GCCGUATCATTGCGAGTGTGUCAAGCAGAAGACGUTT TTTGGGUAGCGCCUCACAACCTC | 148 |
| iSx-245-TP53e6-T45 | TP53 Exon 6 top circle primer | CC*C*TATGAGCCGCCUGAGGTCTTTTTUAGGTCGCCG UATCATTGCGAGTGTGUCAAGCAGAAGACGUTTTTTT TGGAUGACAGAAACACTTTTCGACATAGTGTG | 149 |
| iSx-246-TP53e6-B46 | TP53 Exon 6 bottom circle primer | TC*G*GATAAGATGCTGAGGAGGUGCCAGTTTTUAGG TCGCCGUATCATTGCGAGTGTGUCAAGCAGAAGACG UTTTTTGTCATCCAAAUACTCCACACGCAAATTTCC | 150 |

TABLE 1-continued

Oligonucleotide Sequences of the Disclosure

| Name | Description | Sequence | SEQ ID NO |
|---|---|---|---|
| iSx-247-TP53e7-T47 | TP53 Exon 7 top circle primer | AC*C*ATCATCACACTGGAAGACUCCAGGTTTTUAGG TCGCCGUATCATTGCGAGTGTGUCAAGCAGAAGACG UTTTTTGGCGGCAUGAACCGGAGACCC | 151 |
| iSx-248-TP53e7-B48 | TP53 Exon 7 bottom circle primer | AT*G*TAGTTGTAGTGGATGGTGGUACAGTCAGTTTTU AGGTCGCCGUATCATTGCGAGTGTGUCAAGCAGAAG ACGUTTTTTCATGUCGCCCATGCAGGAACTG | 152 |
| iSx-249-TP53e8-T49 | TP53 Exon 8 top circle primer | GG*A*AGAGAATCTCCGCAAGAAAGGUGAGCTTTTUA GGTCGCCGUATCATTGCGAGTGTGUCAAGCAGAAGA CGUTTTTTTGTCCUGGGAGAGACCGGCG | 153 |
| iSx-250-TP53e8-B50 | TP53 Exon 8 bottom circle primer | GT*T*CCGTCCCAGTAGAUTACCACTACTCAGTTTTUA GGTCGCCGUATCATTGCGAGTGTGUCAAGCAGAAGA CGUTTTTTCCCAGGACAUGCACAAACACGCACCTC | 154 |

/3Phos/ = 3' Phosphate
/3SpC3/ = 3' C3 spacer (blocks 3' end)
/5Phos/ = 5' Phosphate
/5SpC3/ = 5' C3 spacer (blocks 5' end)
/52-Bio/ = 5' Dual Biotin
/idSp/ = Internal 1',2'-Dideoxyribose (dSpacer)
/i5NitInd/ = Internal 5-Nitroindole
+G = LNA (locked nucleic acid) guanidine
N = Any base
rG = ribo-guanidine
U = Deoxyuridine
* = thiophosphate backbone Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A system comprising:
   a collection of different circular chimeric single-stranded nucleic acid constructs, each construct comprising:
   a first single-stranded segment of original genomic DNA from a host organism and
   a second single-stranded nucleic acid segment that is linked to the first single-stranded segment and comprises a nucleotide sequence that is exogenous to the host organism, said nucleotide sequence comprising a first solid support primer-specific portion, a second solid support primer-specific portion, and a patient identifier sequence, whereby said chimeric single-stranded nucleic acid constructs of the collection are suitable for rolling circle amplification and/or sequencing;
   one or more oligonucleotide amplification primers, each amplification primer comprising at least a first nucleotide sequence that is complementary to a portion of the chimeric single-stranded nucleic acid constructs of the collection, wherein at least one of the one or more oligonucleotide amplification primers further comprises (i) a 3' portion comprising a cleavable nucleotide or nucleotide analogue and a blocking group that blocks 3' polymerase extension of said oligonucleotide amplification primer, (ii) a 5' portion comprising a cleavable nucleotide or nucleotide analogue and a capture group, said capture group capable of being immobilized to a solid support, or both (i) and (ii); and
   a polymerase suitable for rolling circle amplification.

2. The system of claim 1, wherein the one or more oligonucleotide amplification primers comprise a first nucleotide sequence that is complementary to the second solid support primer-specific portion of the chimeric single-stranded nucleic acid constructs of the collection, and said one or more amplification primers are immobilized on a solid support.

3. The system of claim 1, wherein the one or more oligonucleotide amplification primers comprise (i) a first nucleotide sequence that is complementary to the first solid support primer-specific portion of the chimeric single-stranded nucleic acid constructs of the collection and (ii) a second nucleotide sequence that is complementary to the second solid support primer-specific portion of the chimeric single-stranded nucleic acid constructs of the collection.

4. The system of claim 1, wherein the one or more oligonucleotide amplification primers comprise (a) a first oligonucleotide amplification primer having (i) a first nucleotide sequence that is complementary to a first portion of the original genomic DNA segment of the chimeric single-stranded nucleic acid constructs of the collection, and (ii) a 3' portion comprising a cleavable nucleotide or nucleotide analogue and a blocking group that blocks 3' polymerase extension of said first oligonucleotide amplification primer, and (b) a second oligonucleotide amplification primer having (i) a first nucleotide sequence that is complementary to a second portion of the original genomic DNA segment of the chimeric single-stranded nucleic acid constructs of the collection, and (ii) a 5' portion comprising a cleavable nucleotide or nucleotide analogue and a capture group, said capture group capable of being immobilized to a solid support.

5. The system of claim 1, wherein the one or more amplification primers comprise a portion that is capable of being tethered to a solid support.

6. The system of claim 1 further comprising:
a solid support on which a plurality of first oligonucleotide primers is immobilized, each first oligonucleotide primer comprising a nucleotide sequence that is the same as the nucleotide sequence of the first solid support primer-specific portion of the chimeric single stranded nucleic acid constructs of the collection.

7. The system of claim/wherein the solid support further comprises:
a plurality of immobilized second oligonucleotide primers, each second oligonucleotide primer comprising a nucleotide sequence that is complementary to the nucleotide sequence of the second solid support primer-specific portion of the chimeric single-stranded nucleic acid constructs of the collection.

8. The system of claim 1 further comprising:
a collection of crosslinking oligonucleotides, each crosslinking oligonucleotide comprising two or more repeats of a nucleotide sequence, wherein said nucleotide sequence is the same as at least a portion of the nucleotide sequence of the second single-stranded nucleic acid segment of the chimeric single-stranded nucleic acid constructs of the collection.

9. The system of claim 1, wherein the polymerase is a strand-displacing polymerase.

10. A method for sequencing a plurality of nucleic acid molecules, said method comprising:
providing the system of claim 1;
blending one or more oligonucleotide amplification primers hybridized to circular chimeric single-stranded nucleic acid constructs of the collection with the polymerase to form a rolling circle amplification reaction mixture;
subjecting the rolling circle amplification reaction mixture to an extension treatment where the polymerase extends the one or more hybridized oligonucleotide amplification primers to produce a plurality of primary extension products, each primary extension product comprising one or more tandem linear sequences, wherein each tandem linear sequence is complementary to a circular chimeric single-stranded nucleic acid construct in the collection; and sequencing the circular chimeric single-stranded nucleic acid constructs directly or said plurality of primary extension products thereof.

11. The method of claim 10, wherein the rolling circle amplification reaction mixture further comprises:
a methyl-sensitive restriction endonuclease, wherein during said subjecting the rolling circle amplification reaction mixture to the extension treatment, the endonuclease cleaves double-stranded DNA at a recognition sequence if said recognition sequence is unmethylated thereby selectively forming primary extension products only from chimeric single-stranded nucleic acid constructs comprising a first single-stranded segment of original methylated genomic DNA.

12. The method of claim 10 further comprising:
providing a solid support on which a plurality of first oligonucleotide primers is immobilized, each first oligonucleotide primer comprising a nucleotide sequence that is the same as the nucleotide sequence of the first solid support primer-specific portion of the chimeric single-stranded nucleic acid constructs of the collection and
hybridizing the plurality of primary extension products to one or more of the plurality of first oligonucleotide primers on the solid support prior to said sequencing.

13. The method of claim 12, wherein two or more first oligonucleotide primers on the solid support hybridize to two or more tandem linear sequences of a primary extension product, said method further comprising:
extending the two or more hybridized first oligonucleotide primers using a polymerase to form a plurality of immobilized secondary extension products, each secondary extension product comprising a nucleotide sequence that is complementary to one tandem linear sequence of the hybridized primary extension product; and
denaturing the primary extension products from the first oligonucleotide primers on the solid support, whereby said sequencing involves sequencing the immobilized secondary extension products.

14. The method of claim 10, wherein the one or more amplification primers comprise (i) a first nucleotide sequence portion that is complementary to the first solid support primer-specific portion of the chimeric single-stranded nucleic acid constructs and (ii) a second nucleotide sequence portion that is complementary to the second solid support primer-specific portion of the chimeric single-stranded nucleic acid constructs.

15. The method of claim 11, wherein the one or more amplification primers comprise a further portion, said further portion capable of being tethered to the solid support, said method further comprising:
capturing the further portion of the primary extension products on the solid support prior to or during said subjecting.

16. The method of claim 10 further comprising:
providing a collection of crosslinking oligonucleotides, each crosslinking oligonucleotide comprising two or more repeats of a nucleotide sequence, wherein said nucleotide sequence is the same as at least a portion of the nucleotide sequence of the second single-stranded nucleic acid segment of the circular chimeric single-stranded nucleic acid constructs of the collection; and
capturing one or more tandem linear sequences of a primary extension product on a crosslinking oligonucleotide of the collection, thereby condensing the primary extension product into a compact structure prior to said sequencing.

17. The method of claim 10, wherein the circular chimeric single-stranded nucleic acid constructs of the collection are prepared by a method comprising:
   providing a sample containing one or more target genomic DNA segments;
   providing one or more first oligonucleotide probes, each first oligonucleotide probe comprising (a) a 5' target-specific portion, (b) a 3' target-specific portion, and (c) a further portion, said further portion comprising (i) the patient identifier sequence, (ii) the first solid support primer-specific portion, and (iii) the second solid support primer-specific portion;
   contacting the sample and the one or more first oligonucleotide probes under conditions effective for the 3' target-specific portion of a first oligonucleotide probes to hybridize in a base specific manner to a complementary 3' end of a target genomic DNA segment and for the 5' target-specific portion of the first oligonucleotide probe to hybridize in a base specific manner to a complementary 5' end of the target genomic DNA segment, if present in the sample;
   generating a ligation competent junction between the 3' and 5' ends of each target genomic DNA segment hybridized to the first oligonucleotide probe; and
   ligating the ligation junction of each target genomic DNA segment to form different circular chimeric single-stranded nucleic acid constructs of the collection.

18. The method of claim 10, wherein the different circular chimeric single-stranded nucleic acid constructs of the collection are prepared by a method comprising:
   providing a sample containing one or more target genomic DNA segments, wherein said target genomic DNA segments potentially contain one or more base differences or one or more methylated residues;
   appending nucleotide linkers to 3' and 5' ends of the target genomic DNA segments to form linker-appended target genomic DNA segments;
   providing one or more first oligonucleotide probes, each first oligonucleotide probe comprising (a) a 3' portion complementary to the 3' nucleotide linker of the target genomic DNA segment, (b) a 5' portion complementary to the 5' nucleotide linker of the target genomic DNA segment, and (c) a further portion, said further portion comprising (i) the patient identifier sequence, (ii) the first solid support primer-specific portion, and/or (iii) the second solid support primer-specific portion;
   contacting the sample and the one or more first oligonucleotide probes under conditions effective for the first oligonucleotide probes to hybridize in a base specific manner to complementary nucleotide linker sequences of the linker-appended target genomic DNA segments, if present in the sample;
   generating one or more ligation competent junctions suitable for coupling the 3' and 5' ends of the target genomic DNA segments hybridized to the first oligonucleotide probes; and
   ligating the target genomic DNA segments at the one or more ligation junctions to form different circular chimeric single-stranded nucleic acid constructs of the collection.

19. The method of claim 10, wherein the different circular chimeric single-stranded nucleic acid constructs of the collection are prepared by a method comprising:
   providing a sample containing one or more target genomic DNA segments, wherein said target genomic DNA segments have 3' and 5' ends;
   appending linker sequences to the 3' and 5' ends of the target genomic DNA segments, wherein said linker sequences comprise (i) one or more patient identifier sequences, (ii) the first solid support primer-specific portion, and (iii) the second solid support primer-specific portion to form linker appended target genomic DNA segments;
   providing one or more first oligonucleotide probes, each first oligonucleotide probe comprising (a) a portion complementary to the 3' linker sequence of the linker appended target genomic DNA segment, and (b) a portion complementary to the 5' linker sequence of the linker appended target genomic DNA segment; and
   contacting the sample and the one or more first oligonucleotide probes under conditions effective for the first oligonucleotide probes to hybridize in a base specific manner to complementary 3' and 5' linker sequences of the linker appended target genomic DNA segments, if present in the sample;
   generating one or more ligation competent junctions suitable for coupling 3' and 5' ends of the linker appended target genomic DNA segments hybridized to the first oligonucleotide probes; and
   ligating the linker appended target genomic DNA segments at the one or more ligation junctions to form different circular chimeric single-stranded nucleic acid constructs of the collection.

* * * * *